US012558099B2

(12) United States Patent
Mathis et al.

(10) Patent No.: US 12,558,099 B2
(45) Date of Patent: Feb. 24, 2026

(54) DEVICES, TREATMENTS AND METHODS TO RESTORE TISSUE ELASTIC RECOIL

(71) Applicant: Free Flow Medical, Inc., Fremont, CA (US)

(72) Inventors: Mark L. Mathis, Fremont, CA (US); Michael W. Lau, Menlo Park, CA (US); Kevin Mitz, Campbell, CA (US); Ryan Braxtan, Newark, CA (US)

(73) Assignee: Free Flow Medical, Inc., Fremont, CA (US)

( * ) Notice: Subject to any disclaimer, the term of this patent is extended or adjusted under 35 U.S.C. 154(b) by 629 days.

(21) Appl. No.: 17/836,262

(22) Filed: Jun. 9, 2022

(65) Prior Publication Data

US 2022/0387046 A1 Dec. 8, 2022

Related U.S. Application Data

(63) Continuation of application No. PCT/US2020/063755, filed on Dec. 8, 2020.

(Continued)

(51) Int. Cl.
| | |
|---|---|
| *A61B 17/12* | (2006.01) |
| *A61B 17/04* | (2006.01) |
| *A61B 17/00* | (2006.01) |

(52) U.S. Cl.
CPC .... *A61B 17/12172* (2013.01); *A61B 17/0401* (2013.01); *A61B 2017/00867* (2013.01)

(58) Field of Classification Search
CPC .......... A61B 17/12172; A61B 17/0401; A61B 2017/00867; A61B 1/018; A61B 1/05;

(Continued)

(56) References Cited

U.S. PATENT DOCUMENTS

| | | | | |
|---|---|---|---|---|
| 3,425,411 A | * | 2/1969 | Robinson | ................ A61F 6/144 |
| | | | | 128/839 |
| 3,490,456 A | * | 1/1970 | Kortum | ................ A61M 25/04 |
| | | | | 604/106 |

(Continued)

FOREIGN PATENT DOCUMENTS

| | | |
|---|---|---|
| EP | 3727195 A1 | 10/2020 |
| EP | 4072467 | 10/2022 |

(Continued)

OTHER PUBLICATIONS

"European Application Serial No. 20899675.1, Extended European Search Report mailed Nov. 28, 2023", 9 pgs.

(Continued)

*Primary Examiner* — Dianne Dornbusch
(74) *Attorney, Agent, or Firm* — Schwegman, Lundberg & Woessner, P.A.

(57) ABSTRACT

Pulmonary treatment devices, systems and methods of use are provided which take into account the vast tissue damage of advanced COPD sufferers and provide treatments designed specifically to treat the particularly compromised lung tissues that are present in these patients. These treatments reduce trapped air volume, tension lung tissue and enhance lung elastic recoil. In particular, a variety of embodiments of invertible pulmonary treatment devices are provided. The devices are comprised of a shape memory material wherein the devices are able to be expanded under tension, and then are able to recoil back toward an original relaxed or resting shape. In these embodiments, a portion of the device is invertible. Thus, each device is able to store energy at least in the inversion, wherein the energy is utilized to continually tension the lung as the device relaxes toward its original shape.

20 Claims, 116 Drawing Sheets

Related U.S. Application Data

(60) Provisional application No. 62/945,510, filed on Dec. 9, 2019.

(58) Field of Classification Search
CPC ................ A61B 1/0684; A61B 1/2676; A61B 17/12104; A61B 17/1214; A61B 17/12145; A61B 2017/00809; A61B 17/068; A61F 2002/043; A61F 2/88; A61F 2/962; A61F 2/04
See application file for complete search history.

(56)         References Cited

U.S. PATENT DOCUMENTS

| | | | |
|---|---|---|---|
| 5,980,554 A * | 11/1999 | Lenker | A61B 17/12118 606/198 |
| 6,113,611 A * | 9/2000 | Allen | A61B 17/068 606/151 |
| 6,117,157 A | 9/2000 | Tekulve | |
| 6,174,323 B1 | 1/2001 | Biggs et al. | |
| 6,419,696 B1 * | 7/2002 | Ortiz | A61F 2/2409 623/2.37 |
| 6,458,092 B1 * | 10/2002 | Gambale | A61F 2/06 604/93.01 |
| 6,599,311 B1 | 7/2003 | Biggs et al. | |
| 6,616,675 B1 * | 9/2003 | Evard | A61B 18/1445 606/155 |
| 7,914,527 B2 * | 3/2011 | Malecki | A61B 17/0057 606/41 |
| 7,992,567 B2 * | 8/2011 | Hirotsuka | A61B 17/24 600/375 |
| 8,632,605 B2 | 1/2014 | Thompson et al. | |
| 8,668,704 B2 * | 3/2014 | Rothstein | A61B 17/0057 606/151 |
| 8,740,921 B2 | 6/2014 | Mathis et al. | |
| 8,753,362 B2 * | 6/2014 | Widomski | A61B 17/0057 606/151 |
| 8,828,026 B2 * | 9/2014 | Ishioka | A61B 17/068 606/139 |
| 8,832,605 B2 | 9/2014 | Choi | |
| 8,858,576 B2 | 10/2014 | Takahashi et al. | |
| 8,968,393 B2 * | 3/2015 | Rothstein | A61F 2/2466 623/2.11 |
| 10,786,257 B2 | 9/2020 | Mathis et al. | |
| 11,285,003 B2 * | 3/2022 | Duffy | A61F 2/2454 |
| 2003/0018351 A1 | 1/2003 | Kaji et al. | |
| 2003/0070683 A1 * | 4/2003 | Deem | A61B 17/12172 128/207.16 |
| 2003/0088256 A1 * | 5/2003 | Conston | A61B 17/11 623/1.36 |
| 2004/0073237 A1 | 4/2004 | Leinsing | |
| 2004/0078054 A1 | 4/2004 | Biggs et al. | |
| 2005/0055050 A1 | 3/2005 | Alfaro | |
| 2005/0143763 A1 | 6/2005 | Ortiz et al. | |
| 2005/0187564 A1 * | 8/2005 | Jayaraman | A61B 17/12172 606/141 |
| 2005/0197594 A1 | 9/2005 | Burbank et al. | |
| 2005/0251154 A1 * | 11/2005 | Chanduszko | A61B 17/0057 606/151 |
| 2006/0052821 A1 * | 3/2006 | Abbott | A61B 17/064 606/213 |
| 2006/0135947 A1 | 6/2006 | Soltesz et al. | |
| 2007/0060858 A1 * | 3/2007 | Sogard | A61B 17/0057 604/8 |
| 2007/0186933 A1 | 8/2007 | Domingo et al. | |
| 2007/0221230 A1 | 9/2007 | Thompson et al. | |
| 2007/0244553 A1 | 10/2007 | Rafiee et al. | |
| 2008/0015627 A1 | 1/2008 | Devore | |
| 2008/0072914 A1 | 3/2008 | Hendricksen et al. | |
| 2008/0221582 A1 | 9/2008 | Gia et al. | |
| 2009/0012626 A1 | 1/2009 | Thompson et al. | |
| 2010/0070050 A1 | 3/2010 | Mathis et al. | |
| 2010/0100196 A1 | 4/2010 | Thompson et al. | |

| | | | |
|---|---|---|---|
| 2011/0301587 A1 * | 12/2011 | Deem et al. | |
| 2012/0172927 A1 * | 7/2012 | Campbell | A61B 17/12172 606/213 |
| 2012/0179086 A1 * | 7/2012 | Shank | A61F 2/04 604/8 |
| 2013/0006352 A1 * | 1/2013 | Yaron | A61F 2/2427 623/2.37 |
| 2013/0096603 A1 | 4/2013 | Mathis et al. | |
| 2015/0045612 A1 | 2/2015 | Ostrovsky et al. | |
| 2015/0051709 A1 | 2/2015 | Vasquez et al. | |
| 2015/0057695 A1 | 2/2015 | Mathis et al. | |
| 2015/0119920 A1 * | 4/2015 | Mathis | A61B 17/12131 606/191 |
| 2015/0272662 A1 | 10/2015 | Shuman et al. | |
| 2015/0366556 A1 | 12/2015 | Khairkhahan et al. | |
| 2016/0015394 A1 | 1/2016 | Cedro, Jr. et al. | |
| 2016/0113657 A1 | 4/2016 | Mathis et al. | |
| 2016/0278845 A1 | 9/2016 | Mayse | |
| 2016/0374689 A1 | 12/2016 | Tanaka et al. | |
| 2017/0367810 A1 | 12/2017 | Tanaka et al. | |
| 2018/0291522 A1 | 10/2018 | Rokicki | |
| 2019/0307458 A1 * | 10/2019 | Mathis | A61B 1/00148 |
| 2019/0328400 A1 | 10/2019 | Mathis et al. | |
| 2019/0336131 A1 | 11/2019 | Mathis et al. | |
| 2021/0186512 A1 | 6/2021 | Mathis et al. | |

FOREIGN PATENT DOCUMENTS

| | | | |
|---|---|---|---|
| JP | 2016526472 A | 9/2016 | |
| JP | 2023506485 | 2/2023 | |
| JP | 7671512 B2 | 4/2025 | |
| WO | WO-2016115193 A1 | 7/2016 | |
| WO | WO-2019126683 A1 | 6/2019 | |
| WO | WO-2021118983 A1 | 6/2021 | |

OTHER PUBLICATIONS

"International Application Serial No. PCT/US2020/063755, International Preliminary Report on Patentability mailed Jun. 23, 2022", 13 pgs.

"International Application Serial No. PCT/US2020/063755, International Search Report mailed Apr. 30, 2021", 4 pgs.

"International Application Serial No. PCT/US2020/063755, Written Opinion mailed Apr. 30, 2021", 11 pgs.

"European Application Serial No. 20899675.1, Response to Communication pursuant to Rules 161(2) and 162 EPC filed Jan. 27, 2023", 16 pgs.

"Japanese Application Serial No. 2022-535589, Notification of Reasons for Refusal mailed Sep. 30, 2024", w/ English translation, 8 pgs.

"U.S. Appl. No. 16/444,835, Examiner Interview Summary mailed May 7, 2020", 3 pgs.

"U.S. Appl. No. 16/444,835, Non Final Office Action mailed Jan. 8, 2020", 15 pgs.

"U.S. Appl. No. 16/444,835, Notice of Allowance mailed Jun. 1, 2020", 11 pgs.

"U.S. Appl. No. 16/444,835, Response filed Apr. 8, 2020 to Non Final Office Action mailed Oct. 8, 2020", 16 pgs.

"U.S. Appl. No. 16/444,835, Response filed Sep. 25, 2019 to Restriction Requirement mailed Aug. 29, 2019", 1 pg.

"U.S. Appl. No. 16/444,835, Restriction Requirement mailed Aug. 29, 2019", 9 pgs.

"U.S. Appl. No. 16/444,849, Examiner Interview Summary mailed Jul. 23, 2020", 4 pgs.

"U.S. Appl. No. 16/444,849, Final Office Action mailed Oct. 2, 2020".

"U.S. Appl. No. 16/444,849, Non Final Office Action mailed Apr. 15, 2020", 23 pgs.

"U.S. Appl. No. 16/444,849, Response filed Jan. 6, 2020 to Restriction Requirement mailed Nov. 5, 2019", 1 pg.

"U.S. Appl. No. 16/444,849, Response filed Jul. 15, 2020 to Non Final Office Action mailed Apr. 15, 2020", 11 pgs.

"U.S. Appl. No. 16/444,849, Restriction Requirement mailed Nov. 5, 2019", 8 pgs.

(56)          References Cited

OTHER PUBLICATIONS

"U.S. Appl. No. 17/249,473, Advisory Action mailed Jan. 29, 2025", 10 pgs.

"U.S. Appl. No. 17/249,473, Advisory Action mailed Sep. 27, 2023", 4 pgs.

"U.S. Appl. No. 17/249,473, Examiner Interview Summary mailed Jun. 20, 2024", 4 pgs.

"U.S. Appl. No. 17/249,473, Examiner Interview Summary mailed Sep. 21, 2023", 2 pgs.

"U.S. Appl. No. 17/249,473, Examiner Interview Summary mailed Oct. 6, 2021", 2 pgs.

"U.S. Appl. No. 17/249,473, Final Office Action mailed Apr. 5, 2022", 25 pgs.

"U.S. Appl. No. 17/249,473, Final Office Action mailed Jun. 13, 2023", 20 pgs.

"U.S. Appl. No. 17/249,473, Final Office Action mailed Oct. 16, 2024", 42 pgs.

"U.S. Appl. No. 17/249,473, Non Final Office Action mailed Jan. 10, 2024", 23 pgs.

"U.S. Appl. No. 17/249,473, Non Final Office Action mailed Feb. 1, 2023", 28 pgs.

"U.S. Appl. No. 17/249,473, Non Final Office Action mailed Aug. 2, 2021", 15 pgs.

"U.S. Appl. No. 17/249,473, Notice of Non-Compliant Amendment mailed Feb. 10, 2022", 4 pgs.

"U.S. Appl. No. 17/249,473, Notice of Non-Compliant Amendment mailed Nov. 22, 2021", 4 pgs.

"U.S. Appl. No. 17/249,473, Response filed Jan. 12, 2022 to Notice of Non-Compliant Amendment mailed Nov. 22, 2021", 11 pgs.

"U.S. Appl. No. 17/249,473, Response filed Feb. 25, 2022 to Notice of Non-Compliant Amendment mailed Feb. 10, 2022", 13 pgs.

"U.S. Appl. No. 17/249,473, Response filed May 1, 2023 to Non Final Office Action mailed Feb. 1, 2023", 13 pgs.

"U.S. Appl. No. 17/249,473, Response filed Jun. 10, 2024 to Non Final Office Action mailed Jan. 10, 2024", 23 pgs.

"U.S. Appl. No. 17/249,473, Response filed Jun. 23, 2021 to Restriction Requirement mailed Apr. 29, 2021", 6 pgs.

"U.S. Appl. No. 17/249,473, Response filed Sep. 13, 2023 to Final Office Action mailed Jun. 13, 2023", 12 pgs.

"U.S. Appl. No. 17/249,473, Response filed Oct. 4, 2022 to Final Office Action mailed Apr. 5, 2022", 12 pgs.

"U.S. Appl. No. 17/249,473, Response filed Oct. 19, 2021 to Non Final Office Action mailed Aug. 2, 2021", 10 pgs.

"U.S. Appl. No. 17/249,473, Response filed Dec. 16, 2024 to Final Office Action mailed Oct. 16, 2024", 16 pgs.

"U.S. Appl. No. 17/249,473, Restriction Requirement mailed Apr. 29, 2021", 9 pgs.

"U.S. Appl. No. 19/180,544, Non Final Office Action mailed Jul. 23, 2025", 16 pgs.

"European Application Serial No. 18891953.4, Communication Pursuant to Article 94(3) EPC mailed May 21, 2024", 5 pgs.

"European Application Serial No. 18891953.4, Extended European Search Report mailed Feb. 9, 2021", 11 pgs.

"European Application Serial No. 18891953.4, Response filed Sep. 8, 2021 to Extended European Search Report mailed Feb. 9, 2021", 3 pgs.

"European Application Serial No. 18891953.4, Response filed Sep. 13, 2021 to Extended European Search Report mailed Feb. 9, 2021", 3 pgs.

"European Application Serial No. 18891953.4, Response filed Nov. 21, 2024 to Communication Pursuant to Article 94(3) EPC mailed May 21, 2024", 10 pgs.

"International Application Serial No. PCT/US2018/067160, International Preliminary Report on Patentability mailed Jun. 23, 2020", 11 pgs.

"International Application Serial No. PCT/US2018/067160, International Search Report mailed May 8, 2019", 4 pgs.

"International Application Serial No. PCT/US2018/067160, Written Opinion mailed May 8, 2019", 10 pgs.

* cited by examiner

Working channel and light source

208

202

210

Lens and CCD chip

Light source connection

Processor connection

206

Suction port

200

204

208

202

Working length (typically 600 mm)

Total length (typically 900mm)

20

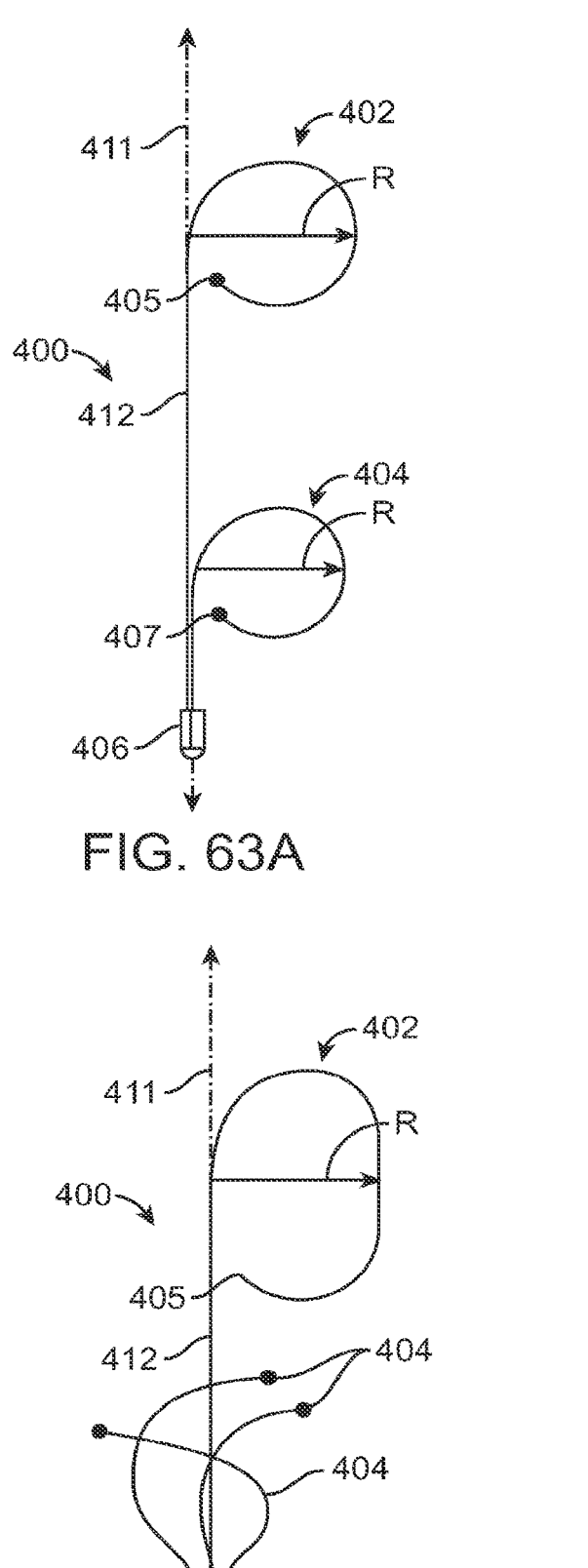
FIG. 63A
FIG. 63C
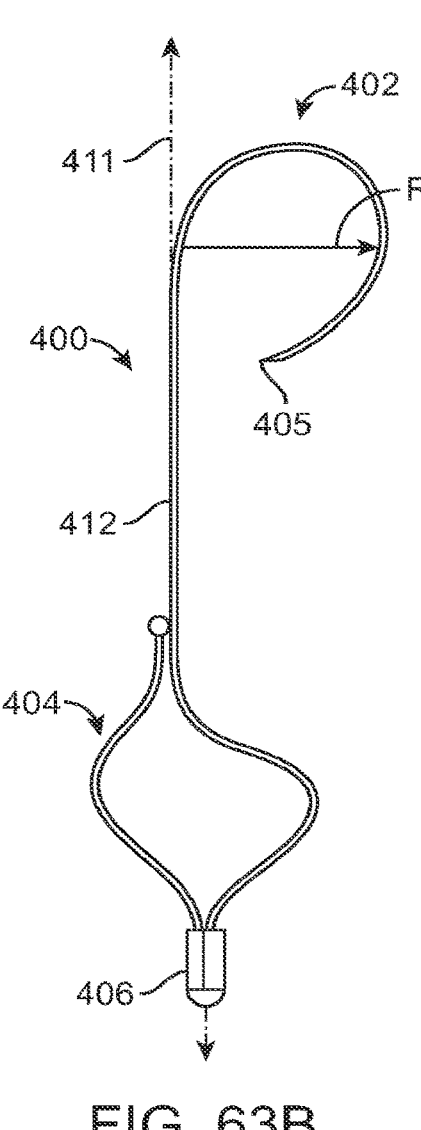
FIG. 63B

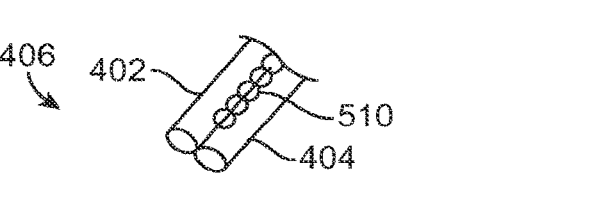
FIG. 75
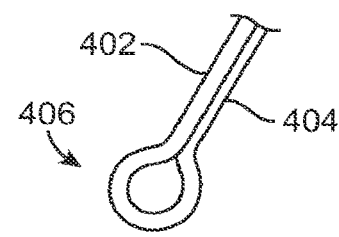
FIG. 76A
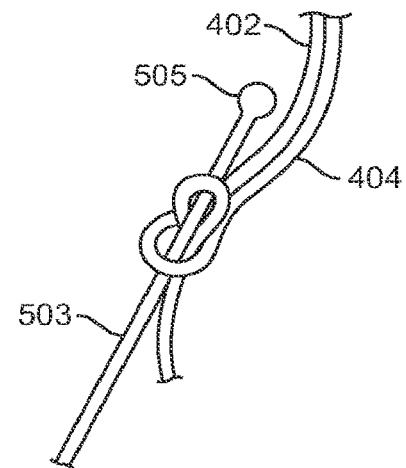
FIG. 76B
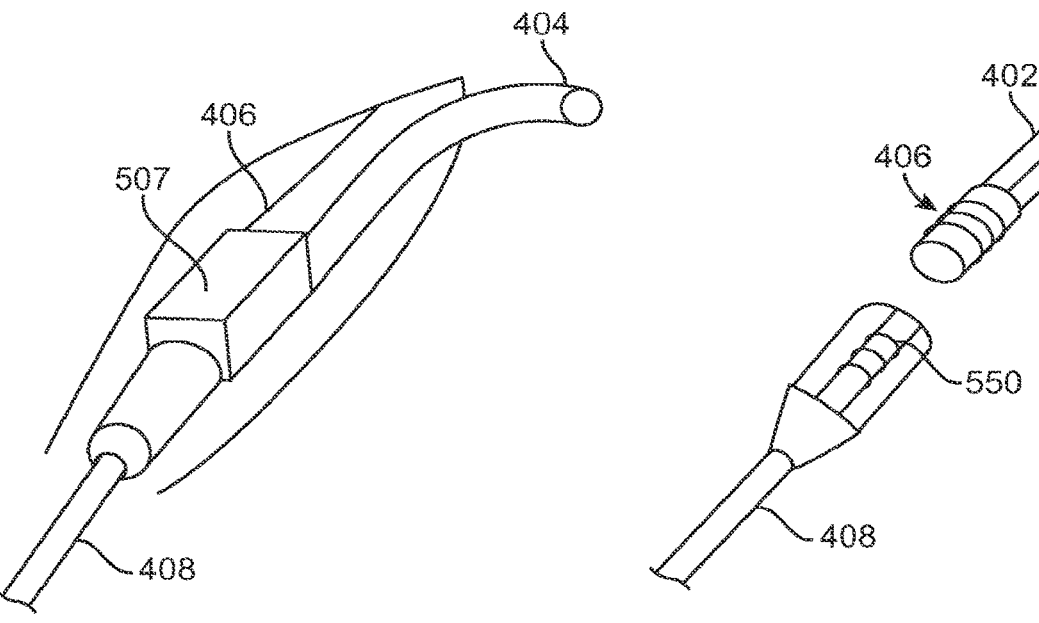
FIG. 77
FIG. 78

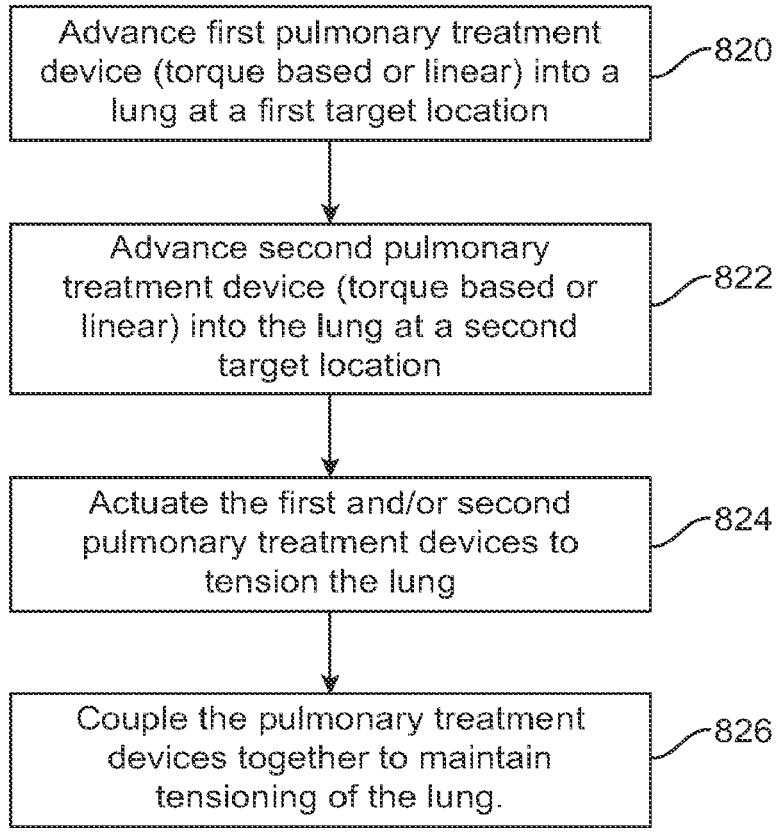

Advance first pulmonary treatment device (torque based or linear) into a lung at a first target location — 820

Advance second pulmonary treatment device (torque based or linear) into the lung at a second target location — 822

Actuate the first and/or second pulmonary treatment devices to tension the lung — 824

Couple the pulmonary treatment devices together to maintain tensioning of the lung. — 826

FIG. 94

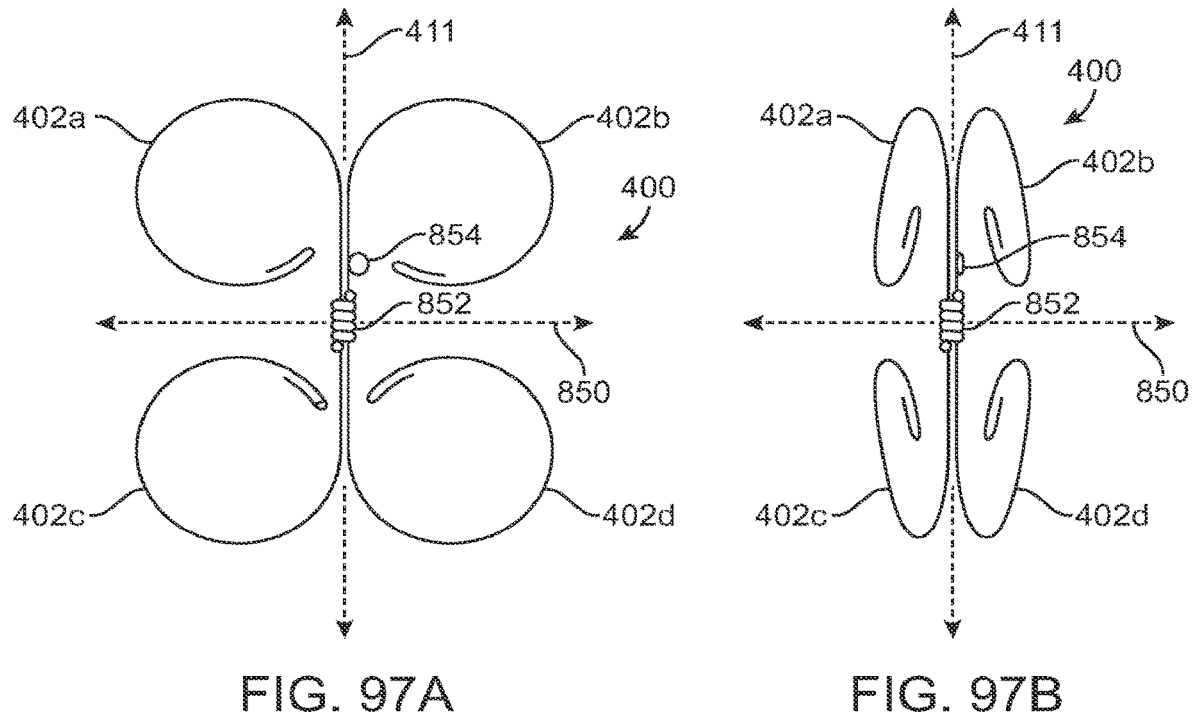
FIG. 97A                    FIG. 97B
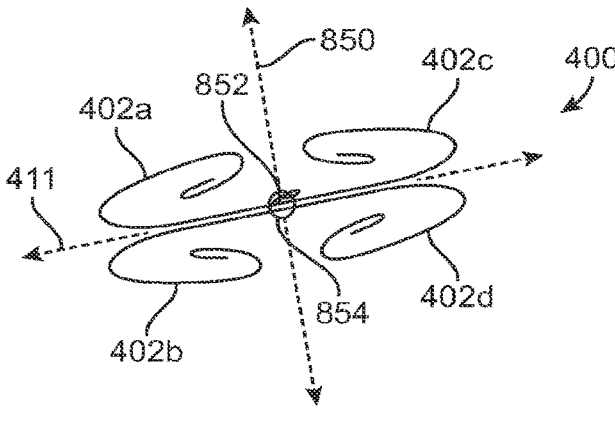
FIG. 97C

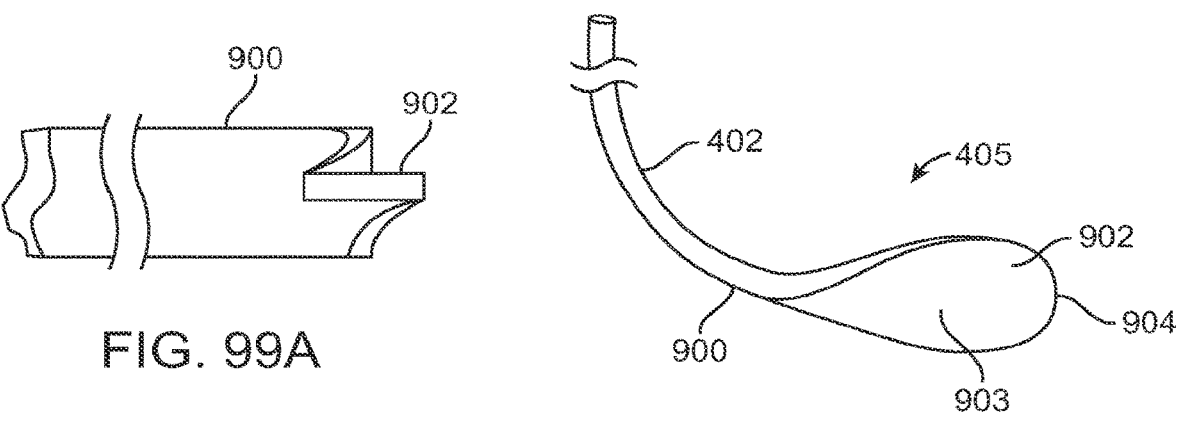
FIG. 99A
FIG. 99B
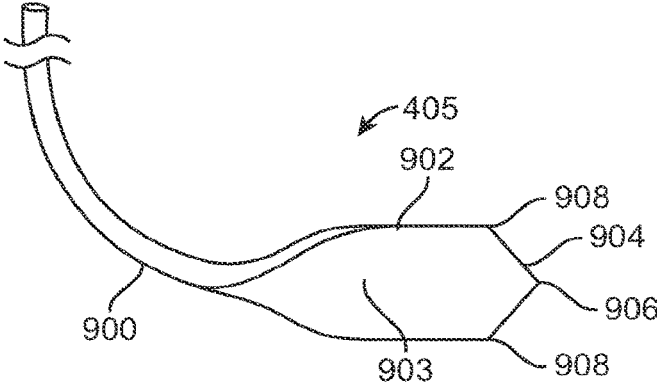
FIG. 99C
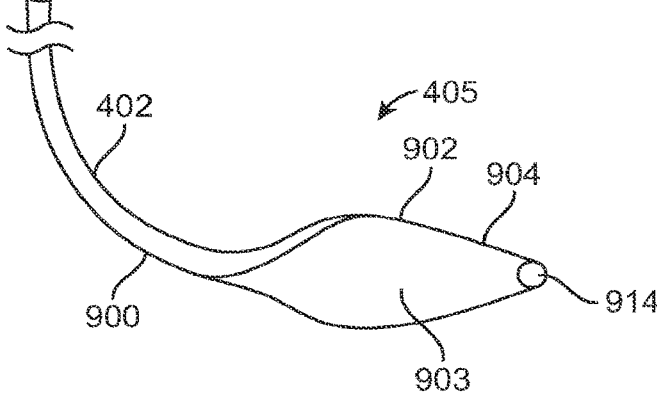
FIG. 99D

DEVICES, TREATMENTS AND METHODS TO RESTORE TISSUE ELASTIC RECOIL

CROSS-REFERENCE TO RELATED APPLICATIONS

This application is a continuation of PCT Application No. PCT/US20/63755, filed Dec. 8, 2020, which claims the benefit of U.S. Provisional No. 62/945,510, filed Dec. 9, 2019, the entire content of which is incorporated herein by reference.

BACKGROUND OF THE INVENTION

Chronic obstructive pulmonary disease (COPD) is a common progressive, debilitating lung disease that is often fatal. COPD patients are diagnosed with either emphysema, chronic bronchitis or more commonly, a combination of both. The symptoms of COPD include a persistent cough, particularly one that produces excessive of mucus, shortness of breath (especially during exercise), a wheezing sound while breathing, a barrel-chest deformity, and tightness in the chest muscles due to expansion of the chest with the barrel-chest deformation. Late stages of COPD manifest in symptoms that relate more closely to slow persistent suffocation as the disease eventually nearly totally obstructs any outflow of gas from the lungs. Such symptoms may start as a minor impediment to daily life, but they often lead to difficulty in talking or basic breathing. COPD reduces oxygen and carbon dioxide gas exchange which leads to circulatory problems, such as low oxygen levels in the blood, brain and heart muscles. This negatively affects mental alertness and contributes to a very rapid heartbeat, due to increased strain on the heart.

According to the National Institutes of Health, COPD is the third leading cause of death in the United States. The American Lung Association reports that more than 11 million people in the United States have been diagnosed with COPD. However, about 24 million more people may have the disease and not know it. Globally, COPD affects approximately 65 million people.

COPD can occur in people suffering from an inherited genetic condition called Alpha-1 Antitrypsin Deficiency (A1AT Deficiency) and from breathing air in environmental conditions such as air pollution, contaminated air, in work environments that are not ideal etc. However, COPD most commonly occurs in people who are over age 40 and who have a history of smoking. Cigarette smoke is composed of over 4000 different chemicals, many of which are toxic. Both smoke that the smoker inhales (through the filter) and the smoke from the burning end are toxic. There are three main components that are hazardous to health: tar, nicotine and carbon monoxide. Tar settles in the lungs and stimulates a series of changes that lead to obstructive lung disease and lung cancer. Nicotine is an addictive element in cigarettes and also stimulates the nervous system to reduce arteriole diameter and release adrenaline, increasing heart rate and blood pressure. Nicotine also causes increased stickiness of blood platelets, which increases the risk of blood clotting. Carbon monoxide combines irreversibly with hemoglobin so that oxygen cannot bind effectively. This causes a strain on the heart muscle because it must pump more to provide the same amount of oxygen.

Tobacco smoke and secondhand smoke travel down through the windpipe and into the bronchial tubes. The toxic smoke then moves into the bronchioles, which contain the small clusters of air sacs known as alveoli. Within the alveoli are the capillaries. In a healthy person, oxygen moves through the alveoli and into the capillaries and bloodstream during inhalation, allowing oxygen rich blood to be distributed to the rest of the body via the arterial system. Simultaneously, carbon dioxide is transported from blood along venous pathways to the capillaries and into the alveoli so it can be removed from the body during exhalation. This process is known as gas exchange. The elasticity of healthy air sacs enables this exchange to occur during lung volume change with breathing cycles. However, the inhalation of smoke ultimately destroys this elasticity and lung tissue itself.

The effect of tobacco smoke on lung elastin is extremely complicated, affecting many facets of connective tissue metabolism. Inhalation of cigarette smoke causes an accumulation in the respiratory bronchi of alveolar macrophages, which appear to be filled with pigments and are metabolically and morphologically activated. The activated macrophage has the ability to secrete chemo attractants and secretagogues for neutrophils, as well as secrete a metalloprotease capable of digesting elastin and al antiprotease. The end result is a clustering of large numbers of neutrophils and macrophages, poised to release considerable amounts of elastolytic enzymes at the site where the earliest signs of centrilobular emphysema are detected. This is seen, in X-ray images of the lung as small pockets of dissolved tissue known as blebs. In addition to this, the alveolar macrophages, as well as cigarette smoke, are rich sources of oxidizing agents. One potential action of these oxidants would be to oxidize the methionine residue found at the active site of al proteinase inhibitor. This has been shown by selective chemical oxidation to yield a relatively ineffective inhibitor that associates with elastase some 2000 times more slowly than the native protein. This results in oxidant damage to lung cells and cellular components such as lipids, cofactors, and nucleic acids. Endogenous antioxidant systems within the lung, such as ceruloplasmin, vitamin C, or methionine sulphoxide-peptide reductase, are adversely affected by cigarette smoke, lowering the lung's defense against oxidants. The elastin maturation process is impaired by cigarette smoke.

Such damage affects the walls between the alveolar sacs. As the air sacs weaken, their walls break open or "melt", creating one large air sac instead of many smaller ones. The total surface area of the air sacs is reduced, and this reduces that amount of gas that can be exchanged across the walls of the air sacs. These gasses are transported across the thin air sac membrane surfaces using a diffusion process. By reducing the majority of air sacs, the total surface area of the sacs is limited causing gas exchange to be reduced. This makes it more difficult for the capillaries to absorb enough oxygen and for the body to expel carbon dioxide, making it progressively harder to breathe. In addition, the air sacs lose their elasticity making it harder to recoil and expel air. The walls of the airways thicken and become swollen while making more mucus than normal which can clog the airways that lead to the air sacs. The thickening and mucus plugging are the chronic bronchitis component of COPD. All of these factors contribute to the symptoms of COPD.

Another common COPD symptom is air trapping which causes breathing disfunction as well as lobar and lung hyperinflation. The reduced volume reached by the lungs after exhalation is determined by the balance of forces between the inward elastic recoil pressure, or inward pulling tension of the lung tissue that lifts the diaphragm and the outward recoil pressure or outward pulling of the chest wall. The lung is suspended in an expanded state due to negative pressure or vacuum between the chest wall and the exterior lining of the lung. This vacuum keeps the lung expanded and pinned to the chest wall. Because the lungs are held in a generally expanded state, interior lung tissue (parenchyma) is stressed in tension (creating lung elastic resistance to stretching, commonly referred to as lung elastic recoil). This tension, throughout the lung, pulls radially outward on the airways to hold these airways open and the tension helps to allow air to be squeezed out of the lungs during the expiration breathing cycle. During expiration, the diaphragm muscle is relaxed, and the lung's internal elastic recoil lifts the diaphragm and lung floor up which reduces the lung volume and squeezes air out of the lung. During inspiration, the diaphragm muscle contracts to pull the diaphragm down which increase lung volume which draws air back into the lungs. Static hyperinflation occurs when the lungs exert less recoil pressure to counter the recoil pressure of the chest wall due to the destruction of elastin. This results in an equilibrium of recoil forces at a higher resting volume than normal. In other words, there is less recoil so the diaphragm cannot be lifted as far and the lungs ability to expel air is reduced. This creates a chronic increase in lung volume, also known as increased total lung capacity (TLC). Dynamic hyperinflation occurs when air is trapped within the lungs after each breath due to a disequilibrium between the volumes inhaled and exhaled. This most commonly occurs during exercise and inspiration is more efficient than expiration. With each breath, hyperinflation is increased. The ability to fully exhale depends on the degree of airflow limitation and the time available for exhalation. Both types of air trapping causes 1) lung gas congestion, preventing new oxygen from being inspired, 2) retainment of $CO_2$ in the lung and blood stream (hypoxemia) and 3) crushing of better functioning lobes making them incapable of inspiration or expiration. The last phenomenon occurs because the trapping often occurs in places with the most lung tissue destruction (regions with the greatest reduction of recoil). As more air is trapped in this area and the lobe hyperinflates, it expands into regions where tissue is better preserved and still performing well but the added pressure of the inflated tissue restricts air flow in and out of the healthier region.

Ultimately, enzymes destroy and eliminate airways and alveoli tissue. Large holes are formed in alveoli beds forming pulmonary blebs and bullae. Pulmonary blebs are small subpleural thin walled air pockets, not larger than 1-2 cm in diameter. Their walls are less than 1 mm thick. If they rupture, they allow air to escape into the pleural space between the lung and chest wall, which is normally holding the lungs expanded and pinned to the chest wall with vacuum, resulting in a spontaneous pneumothorax or collapse of the lung. Pulmonary bullae, like blebs, are cystic air spaces or pockets that have an imperceptible wall (less than 1 mm). The difference between blebs and bullae is generally considered to be their size, with the cross-over being around 2 cm in diameter. Blebs may, over time, coalesce to form bullae.

Smoking cessation continues to be an important therapeutic intervention for COPD. Approaches to management by stage include the following:

Stage I (mild obstruction): Short-acting bronchodilator as needed;

Stage II (moderate obstruction): Short-acting bronchodilator as needed; long-acting bronchodilator(s); cardiopulmonary rehabilitation;

Stage III (severe obstruction): Short-acting bronchodilator as needed; long-acting bronchodilator(s); cardiopulmonary rehabilitation; inhaled glucocorticoids if repeated exacerbations;

Stage IV (very severe obstruction or moderate obstruction with evidence of chronic respiratory failure): Short-acting bronchodilator as needed; long-acting bronchodilator(s); cardiopulmonary rehabilitation; inhaled glucocorticoids if repeated exacerbation; long-term oxygen therapy (if criteria met); interventions such as lung transplantation, lung volume reduction surgery (LVRS), or implantable therapeutic devices.

Lung volume reduction surgery (LVRS) is a surgical procedure to remove diseased, emphysematous lung tissue. The surgery removes up to ⅓ of the lung to attempt to remove non-gas exchanging portions of lung. This is intended to remove sections of non-performing tissue that can no longer exchange gas to and from the blood stream. It is also intended to remove blood vessels that would otherwise shunt under oxygenated blood with high levels of $CO2$ (vessels traveling through portions of the lung where gas cannot be exchanged) back to the heart and blood circulatory system. However, this surgery presents patients with high risk of surgery related morbidity and mortality. Patients who already have distressed breathing due to the disease are further stressed with severe orthopedic trauma due to a sternotomy, which presents difficulty in reviving these patients from general anesthesia. LVRS related mortality and morbidity is a common result as was published in the National Emphysema Treatment Trial (NETT) report. NETT was a multicenter, randomized, controlled clinical trial, comparing the efficacy of lung volume reduction surgery (LVRS) plus medical management with rehabilitation to medical management with rehabilitation in 1,218 patients with severe emphysema.

LVRS is performed with a long simple excision to remove a large portion of lung volume. Thus, it is not discriminative in the tissue that is removed. LVRS also removes portions of remaining intact lung that would otherwise exchange gas. This reduces lung capacity that patients need to exchange gas. LVRS is also not effective for homogenous disease, which is the type that most COPD patients suffer from. In homogenous disease, the disease is spread evenly in all lobes without a discrete target lung volume that can be sacrificed to enhance lung elastic recoil. Homogenous patients need therapy because they suffer from an insufficient lung capacity to exchange gas. Removing more lung tissue only reduces their capacity. Therefore, the surgery actually degrades these patient's ability to breathe.

A variety of implantable therapeutic devices have been developed to assist in treating COPD sufferers. One such device is an endobronchial valve. An endobronchial valve is minimally invasive alternative to lung volume reduction surgery (LVRS). Endobronchial valves were designed to replicate the effects of that procedure without requiring incisions by allowing the most diseased lobe of a lung to be pneumatically blocked off so air can be evacuated to cause the treatment lobe to collapse. An endobronchial valve is a small, one-way valve that is typically implanted such that when a patient exhales, air is able to flow through the valve and out of the lobe, but when the patient inhales, the valve closes and blocks air from entering that lobe. Thus, a set of implanted endobronchial valves can help a lobe to empty itself of air. This has been shown to be beneficial in the treatment of a very small population of patients suffering from heterogenous emphysema, however such endobronchial valves suffer from some of the same limitations as LVRS. Endobronchial valves that succeed to collapse lobes in homogenous patients reduce their already insufficient lung capacity. Homogeneous disease is the type that most COPD patients suffer from. Thus, the valves may actually degrade these patient's ability to breathe. Another limitation with the valves is the fact that approximately 80% of patients present with additional flow paths that lead into the lobe in addition to the major airway tree that is typically shown in anatomy texts. The valves are designed to block flow in airways but in the majority of patients, total blockage or perfect pneumatic isolation can never be achieved and the lobe never collapses. Many times, the alternate flow paths are created by enzyme destruction due to the disease itself. This is particularly true in heterogenous patients where tissue damage is concentrated.

A similar type of therapy involves an endoscopic volume reduction using lung sealant. The lung sealant foam is instilled into the peripheral airways and alveoli where it polymerizes and functions as tissue glue on the lungs inner surfaces in order to seal the target region to cause durable irreversible absorption atelectasis or collapse of the lung tissue. Such treatment by a biological sealant produces an irreversible change in emphysematous tissue. The biological sealant is delivered to the alveolar compartment as separate liquid components via a dual lumen catheter passed through the instrument channel of a flexible bronchoscope. A common side effect is a systemic flu-like inflammatory reaction after the foam sealant application accompanied by transient fever, cough, bronchospasm, chest pain, leukocytosis, malaise, and elevated C-reactive protein levels. This side effect is sometimes self-limited and resolves within 24-96 h spontaneously. Other times, the inflammation can cause long term morbidity and even mortality. Other serious pulmonary side effects within 6 months after the procedure include repetitive COPD exacerbations, pneumonia, bronchitis, and hemoptysis. Over a period of several weeks, the treated lung region will start to shrink, reducing lung volume by atelectasis. However, such treatment again ultimately suffers from some of the same limitations as LVRS. In particular, lung sealants destroy lung tissue and reduce lung capacity so they are not effective for homogenous disease, which is the type that most COPD patients suffer from. Thus, these techniques actually degrade these patient's ability to breathe.

Endobronchial coils are another type of therapeutic device developed to assist in treating COPD sufferers and act as a minimally invasive alternative to lung volume reduction surgery (LVRS). Endobronchial coils are nitinol devices implanted bronchoscopically under fluoroscopic guidance. The coils are straightened so they can be passed through a bronchoscope and into airways for deployment and then they are pushed out of the catheter and allowed to recover to a programmed shape that bends the airway they are deployed into. The device bends the airway to compress adjacent tissue to cause a small lung volume reduction effect. As multiple coils revert to their original double-loop shape within the airways, targeted pockets of lung tissue are compressed between features of the coil to replicate the effects of the LVRS in a minimally invasive treatment. Multiple coils implanted throughout a lobe attempt to achieve mechanical volume reduction. However, such bending and folding of the airways increases resistance to gas flow which blocks the airways from flowing efficiently to exchange gas. The bending also compresses tissue by permanently freezing motion in portions of the lung volume and preventing those portions from efficiently contributing to exchanging gas. Thus, there is limited inspiration and expiration in those regions which reduces the patient's capacity to breathe. In addition, the coil design and dimensions provide a very small contact area which produces high pressure and compressive stress on the lung tissue. This potentially allows for a kind of "cheese wire" cutting effect that limits the effective time that a treatment remains effective, even if initial results are positive. The coils are strong enough to bend thick collagenous airways with substantial walls that would not be easily abraded or subject to device related tissue erosion or migration. However, due to the nature of the disease and the enzymatic destruction in COPD patients, substantial, thick walled airways are nearly absent beyond the 4th airway generation in patients with the requisite degree of disease that would require this type of intervention. The typical disease related tissue destruction leaves only fragile segments of thin tissue in areas in contact with the coils and this can only accelerate the "cheese wire" effect which may reduce the potential for treatment success substantially. In addition, blood vessels run parallel to most lung airways and they are of comparable size with respect to the airway. It is inadvisable to bend central airways (2nd-4th generation) as a blood vessel could easily be pinched closed or ruptured. Since the patient's entire cardiac pumping capacity is routed through the lungs and these vessels, the use of such coils on these airways would present the patient with extreme risk.

Devices such as the endobronchial coils and endobronchial valves that are mechanical structures suffer from fatigue related failure due to the high number of breathing cycles that these products endure and the nature of the flexure that lung airways present on these devices. In order to clear mucus, airways compress flat during coughing to reduce the cross-sectional area of the airway which increases the velocity of expelled gas and this increases the effectiveness of a cough event in clearing unwanted materials from the lung. In many cases, device failure occurs where metallic or stiff biocompatible materials are placed in the lungs where coughing presents the devices with repeated high force flexure and airway collapse. Another cause for device failure is tissue irritation and granular buildup of airway wall tissue and the formation of bacterial colonies that are commonly found on implanted polymers in the lung. Most devices that have been previously proposed to treat COPD in the past have included one or more design flaws to cause granulation tissue formations or bacterial colonization's which are nearly impossible to remove or otherwise treat.

Thus, additional treatment options are desired, particularly for treatment of homogenous COPD where LVRS is particularly ineffective and potentially harmful. Such treatment options should avoid blocking off, rendering nonfunctioning or removing segments of the lung in the manner of LVRS. In addition, such treatment options should avoid deleterious compression of tissue. Compression of lung tissue can compress and block blood vessels leading to tissue necrosis and cell death, which in turn causes chronic air leaks and eventual lung collapse due to breaching of the vacuum seal between the lungs and chest wall. Such treatment options should also be suitable for patients with late stage COPD. These patients typically do not have any anatomically normal airways past the 4th generation where the anatomy is comprised of extremely weak, destroyed alveoli tissue which continues to degrade. The ideal solution will be a device made using materials and using methods that minimizes the potential for bacterial colonization and the formation of granulation tissue in airways. At least some of these objectives will be met by the present invention.

SUMMARY OF THE INVENTION

The present invention generally relates to medical systems, devices and methods, and more particularly relates to treatment of patients suffering from COPD. Likewise, the present invention relates to the following numbered clauses:

In addition, the present invention relates to the following aspects:

In an aspect of the present invention, the pulmonary treatment devices, methods and systems contained herein treat COPD and COPD symptoms by tensioning lung tissue in patients who have been diagnosed with emphysema whereas lung tissue destruction has been determined to present between zero and 70% volume of destroyed tissue, preferably at least 30% destruction, determined by calculating the percent of destroyed low density lung volume tissue that presents in CT images with a Hounsfield unit score at or higher than 850 (HU) Hounsfield units.

In another aspect of the present invention, the pulmonary treatment devices, methods and systems contained herein treat COPD and COPD symptoms by tensioning lung tissue in patients who have been diagnosed with emphysema whereas the patient has also been determined to be trapping air sufficiently so that retained residual volume is determined to be between 100% and 400% of normal but most preferably residual volume is determined to be in excess of 175% of normal for the patients gender, age and height.

In another aspect of the present invention, the pulmonary treatment devices, methods and systems contained herein treat COPD and COPD symptoms by tensioning lung tissue in patients who have been diagnosed with emphysema whereas the treatment may be performed in each of the four major lobes of the lungs, in a single or separate procedures, if the volume of damaged lung tissue in each lobe, defined as the volume of low density tissue greater that 850 (HU), falls within a range of zero to 70% but preferably is in excess of 30% in each lobe.

In another aspect of the present invention, the pulmonary treatment devices, methods and systems contained herein treat COPD and COPD symptoms by compressing lung tissue as the tissue is wrapped around an implant device that has been fixed to lung tissue and torqued to be rotated so lung tissue is drawn to the device and then anchored to another portion of lung tissue, to prevent the implant from counter-rotating which would allow lung tissue to be unwound from the implant.

In another aspect of the present invention, the pulmonary treatment devices, methods, systems and structures that may be considered implant systems contained herein treat COPD and COPD symptoms by tensioning lung tissue and reducing lung volume to make at least one of the following measurable physiologic changes to improve breathing in COPD patients:

1) Lift the diaphragm with respect to a reference rib location
2) Measure diaphragm lift with respect to a reference rib location while the patient maintains expiration, as a result of treatment
3) Elevate the base of at least one lung towards the patient's upper chest
4) Reduce coughing
5) Reduce mucus production
6) Reduce coughing caused by trapped air and mucus
7) Reduce glottis closure sensitivity
8) Increase the patient's ability to clear mucus from the lungs
9) Increase arterial blood oxygen levels in the blood stream
10) Increase arterial blood oxygen percent in the blood stream
11) Decrease arterial CO2 levels in the blood stream
12) Decrease arterial CO2 percentage in the blood stream
13) Increase mobility as measured by the currently standard 6-minute walk test
14) Increase the number of meters a patient can walk in 6 minutes
15) Increase lung airway caliber as measured using high resolution CT
16) Increase airway diameter
17) Increase lung emptying volume during expiration
18) Increase airway lumen diameter
19) Provide radial outward support to airways
20) Assist reduction of lung volume during exhalation
21) Reduce the volume of at least one lung
22) Reduce the volume of a lobe
23) Reduce the volume of both lungs
24) Reduce the volume of a lung pair
25) Reduce TLC of a lung pair
26) Perform tissue compression
27) Compress tissue in a lobe
28) Remove slack in the lung tissue
29) Restore lung tissue elastic recoil back to a physiologic performance between 2 and 200 cm*H2O of pressure to expand the lung
30) Increase lung elastic recoil
31) Decrease lung compliance
32) Change the shape of the pressure volume curve generated by measuring patient breathing
33) Increase the area within a pressure vs. volume curve describing a patient's breathing
34) Displace fissures as seen using CT image post processed images comparing inspiration and expiration data
35) Delay airway closure during expiration, by using post processed CT image data to compare pre-treatment versus post treatment airway volumes of a similar region in the lung
36) Cause a volume of the lung to be reduced
37) Reduce airway resistance
38) Reduce the volume of one or more lungs in a patient
39) Reduce inspiratory effort using pulse transit time or respiratory inductance plethysmography methods
40) Reduce dynamic hyperinflation as measured by CT or 6-minute walk testing or plethysmography
41) Reduce end-expiratory lung volume
42) Reduce functional residual capacity
43) Reduce the incidence of respiratory failure
44) Increase time between COPD exacerbation events
45) Increase time that airways stay open during expiration
46) Increase the forced expiratory volume in the first second (FEV1)
47) Increase the forced vital capacity volume (FVC)
48) Increase the ratio FEV1/FVC
49) Reduce dysthymia
50) Reduce pressure on the heart
51) Reduce pressure on coronary arteries
52) Reduce blood hypertension
53) Reduce hypertension in the lungs
54) Reduce hypertension in blood vessels that supply the heart muscle
55) Reduce systolic and/or diastolic blood pressure
56) Reduce heart rate
57) Reduce systolic blood pressure
58) Increase the heart's ejection fraction
59) Reduce pulmonary artery pressure
60) Reduce lung tissue density (from 800 to 810-1000 HU, that's Hounsfield units)

61) Make lung tissue density more uniform (adjust the difference between lobes of average lobar density between 1-200 Hounsfield Units)

62) Increase forced expiratory volume during expiration

63) Reduce residual volume that is left in the lung during or after expiration (RV)

64) Reduce the volume of gas that is trapped in the lung during or after expiration 65) Reduce the volume of gas that is trapped in a lobe during or after expiration 66) Increase tidal expiratory volume change during tidal breathing at rest 67) Increase the inspiratory reserve volume during tidal breathing at rest 68) Decrease the patient's breathing rate 69) Decrease the patient's heart rate 70) Increase the patient's cardiac blood ejection fraction 71) Decrease the patient's total lung capacity 72) Decrease lung compliance 73) Decrease compliance in lobes or regions of lung tissue 74) Increase lung tissue compliance uniformity between upper versus lower lobes 75) Increase lung tissue compliance uniformity between lung lobes in a patient 76) Increase lung tissue compliance uniformity between lobar segments 77) Decrease inspiratory effort 78) Decrease the total lung capacity (TLC)

79) Reduce the RV/TLC ratio

80) Increase the volume of airways in a lobe during inspiration

81) Increase the volume of airways in a lobe during expiration

82) Reduce the difference in volume of lung airways in a lobe during breathing

83) Increase the total blood volume in a patient's lung or lobe by performing a treatment 84) Reduce regional blood volume in severely compromised lung tissue to reduce the volume of reduced oxygenated blood being mixed with normal blood in emphysema patients 85) Increase the change in lobar volume between an inspiration and expiration breathing cycle 86) Reduce the volume of trapped air in a lobe after expiration 87) Reduce expiratory volume of lungs after treatment 88) Increase volume of one or more lobes during inspiration 89) Increase the volume within distal airways in one or more lobes 90) Increase the volume within central airways in one or more lobes 91) Reduce impedance of central airways in one or more lobes 92) Reduce impedance in one or both lungs 93) Reduce resistance to flow in one or more lobes 94) Reduce resistance to flow in one or more lungs 95) Increase blood vessel density in one or more lobes 96) Increase the number of blood vessels per liter of lobar volume 97) Increase the volume of airway wall in one or more lobes 98) Increase the volume of airway wall in central airways of one or more lobes 99) Decrease the percentage of damaged tissue per liter of lung volume in one or more lobes 100) Hold airways open longer to increase the rate of aerosol transport in one or more lobes 101) Hold airways open longer to increase regional concentration of aerosol delivered drugs in one or more lobes 102) Measure one or more fissures that have moved more than 2 mm to indicate lobar volume has changed 103) Measure one or more fissures that have moved with respect to a chest wall rib more than 2 mm to indicate lung volume has changed 104) Reduce the percentage of low attenuation lung tissue in one lobe or more 105) Reduce the volume of low attenuation lung tissue in one lobe or more 106) Reduce the percentage of low-density tissue that is 950 HU or higher in one lobe or more 107) Reduce the volume of low-density tissue that is 950 HU or higher in one lobe or more.

In another aspect of the present invention, a pulmonary treatment device is provided comprising: a distal end that efficiently attaches to lung tissue that has been degraded by enzymatic destruction.

In another aspect of the present invention, a pulmonary treatment device is provided comprising: a pulmonary treatment device with proximal a distal end that anchors to an airway in the lung.

In another aspect of the present invention, a pulmonary treatment device is provided comprising: a pulmonary treatment device with a distal end that attaches to tissue primarily comprised of alveoli.

In another aspect of the present invention, a pulmonary treatment device is provided comprising: a treatment device, method or system that tensions lung tissue, parenchyma, alveoli, tissue with enzyme damage, distended, slackened or stretched tissue.

In another aspect of the present invention, a pulmonary treatment device is provided comprising: a pulmonary treatment device that is produced from round wire shaft material that presents minimal sharp edges to soft tissues in the lung, that would otherwise cause the formulation of granulation tissue In another aspect of the present invention, a COPD treatment device is provided comprising: a lung treatment device that is produced from round wire shaft material with a distal end and a proximal end, whereas at least the distal or proximal end is formed to make a blunt atraumatic end without the benefit of recasting material.

In another aspect of the present invention, a COPD treatment device is provided comprising: a lung treatment device that is produced from round wire shaft material with a distal end, a proximal end and a midsection whereas the distal end is connected to the midsection and the proximal end is connected to the midsection without the benefit of a connection to join components.

In another aspect of the present invention, a COPD treatment device is provided comprising: a lung treatment device that is produced and coated with an anti-bacterial coating such as silver or some other material that bacteria is repelled from.

In one aspect of the present invention, a pulmonary treatment device is provided comprising: an elongate shaft coiled into a helical shape around a longitudinal axis to form a tissue gathering end, an extendable midsection and a stabilizing end, wherein the tissue gathering end includes at least one loop which curves at least partially around the longitudinal axis and is configured to engage loose damaged alveolar sac tissue, wherein the stabilizing end includes at least one loop which curves at least partially around the longitudinal axis and is configured to engage a lung passageway proximal to the loose damaged alveolar sac tissue, and wherein the extendable midsection is configured to extend along the longitudinal axis while the tissue gathering end engages the loose damaged alveolar sac tissue so that the loose damaged alveolar sac tissue is pulled toward the lung passageway and the stabilizing end seats in the lung passageway in a manner that maintains the loose damaged alveolar sac tissue in a pulled position.

In another aspect of the present invention, a device is provided for treating a lung comprising: a tissue engaging end configured to engage loose damaged alveolar sac tissue; and a stabilizing end configured to engage a lung passageway proximal to the loose damaged alveolar sac tissue, wherein the device is configured to re-tension a portion of the lung by pulling the tissue engaging end toward the stabilizing end seated in the lung passageway and maintaining such pulling by recoil force.

In another aspect of the present invention, a lung treatment device is provided for treating a lung; comprising a tissue gathering distal end, a stabilizing proximal end and an elastic midsection whereas at least a portion of the device is configured to be positioned around the exterior of a bronchoscope in a configuration that is suitable for advancement into the lung. The device is configured so that at least a portion of the tissue gathering end or a portion of the mid-section or a portion of the stabilizing end is configured to circle at least partially around the longitudinal axis of the bronchoscope during advancement into the lung and is configured to displace lung tissue, wherein the extendable midsection is configured to be lengthened while the tissue gathering end is anchored to lung tissue in a way that allows lung tissue to be pulled toward the midsection of the device and the stabilizing end seats in lung tissue in a manner so lung tissue at the proximal end of the treatment device is pulled towards the midsection of the treatment device, after the bronchoscope is removed from the lung.

In another aspect of the present invention, a lung treatment device is provided for treating a lung comprising: a tissue gathering end configured to be fixed to lung tissue; a stabilizing proximal end configured to be fixed to lung tissue that is proximal to the tissue the tissue gathering end is fixed to, wherein the device is configured to re-tension a portion of the lung by pulling the tissue gathering end towards the stabilizing end seated in the lung.

In another aspect of the present invention, a lung treatment device is provided for treating a lung comprising: a tissue gathering end configured to be fixed to lung tissue; a stabilizing proximal end configured to be fixed to lung tissue that is proximal to the tissue the tissue gathering end is fixed to, wherein the device is configured to re-tension a portion of the lung by pulling the tissue that the tissue gathering end is fixed to toward the tissue that the stabilizing end is fixed to in the lung.

In another aspect of the present invention, a pulmonary treatment device is provided for treating a lung comprising: a tissue gathering end configured to be fixed to lung tissue; a stabilizing proximal end configured to be fixed to lung tissue that is proximal to the tissue the tissue gathering end is fixed to, wherein the device is configured to re-tension a portion of the lung by pulling the tissue that the tissue engaging end is fixed to toward the tissue that the stabilizing end is fixed to in the lung while the midsection of the lung treatment device is configured to maintain a patent lumen through the lung treatment device.

In another aspect of the present invention, a lung treatment device is provided for treating a lung comprising: a tissue gathering end configured to be fixed to lung tissue; a stabilizing proximal end configured to be fixed to lung tissue that is proximal to the tissue the tissue gathering end is fixed to, wherein the device is configured to be advanced into the lung and then stretched to a longer configuration before fixing the tissue gathering end to tissue and before fixing the proximal stabilizing end to tissue to more effectively re-tension a portion of the lung by pulling the tissue engaging end towards the stabilizing end which is fixed to tissue in the lung.

In another aspect of the present invention, a pulmonary treatment device is provided comprising: an elongate shaft coiled into a helical shape around a longitudinal axis to form a tissue gathering end, an extendable midsection and a stabilizing end, wherein the tissue gathering end includes at least one loop that is configured to engage loose damaged alveolar sac tissue or the wall of an airway, wherein the stabilizing end includes at least one loop which curves at least partially around the longitudinal axis and is configured to engage a lung passageway proximal to the loose damaged alveolar sac tissue, and wherein the extendable midsection is configured to extend along the longitudinal axis while the tissue gathering end engages the loose damaged alveolar sac tissue so that the loose damaged alveolar sac tissue is pulled toward the lung passageway and the stabilizing end seats in the lung passageway in a manner that maintains the loose damaged alveolar sac tissue in a pulled position.

In another aspect of the present invention, a pulmonary treatment device is provided comprising: an implant made from polymer or metal that behaves in at least a partially elastic manor that is shaped to form a tissue gathering anchor end, an extendable midsection and a stabilizing end, wherein the tissue gathering end can be advanced distally to cause the extendable midsection to be extended with increased length and strained elastically after which the tissue gathering end may be deployed to be fixed or anchored to the wall of the airway, wherein the stabilizing end includes at least one loop which curves at least partially around the longitudinal axis and is configured to engage a lung passageway proximal to the midsection, and wherein the extendable midsection is configured to provide elastic recoil force that tensions lung tissue and provides lumen patency maintaining support to stent the airway and prevent airway collapse while the tissue gathering end and the proximal stabilizing ends are pulled towards each other.

In another aspect of the present invention, a pulmonary treatment device is provided that reduces the length of airway segments to enhance lung elastic recoil.

In another aspect of the present invention, a pulmonary treatment device is provided that is configured to be mounted to the outside of a bronchoscope while it is delivered to a location in the lung.

In another aspect of the present invention, a pulmonary treatment device is provided that configured to be advanced into the lung in a length unconstrained configuration. This allows the system to be flexible while being delivered along a tortuous path. Most of these devices are delivered to the upper lobes and that typically requires the scope and device to go through at least one small radius bend in the lungs.

In another aspect of the present invention, a pulmonary treatment device is provided that can be advanced into the lung in a condition that is unstressed to allow the delivery system to be flexible while the device is being delivered along a tortuous path.

In another aspect of the present invention, a pulmonary treatment device is provided for treating a lung that has not been stressed to lengthen or shorten the device length so as to allow the delivery system to be as flexible as possible while being delivered along a tortuous path.

In another aspect of the present invention, a pulmonary treatment device is provided that is configured so that the length can be lengthened or shorted before deploying the device into the lung to stress lung tissue.

In another aspect of the present invention, a pulmonary treatment device is provided that can be advanced along a tortuous path to a treatment location in the lung and configured in a flexible unstressed condition that allows the length to be unconstrained but configured to be elongated at the treatment location before being deployed to distort lung tissue.

In another aspect of the present invention, a pulmonary treatment device is provided that can be advanced along a tortuous path to a treatment location in the lung, configured in a flexible unstressed condition, but configured to be strained to a longer configuration to store strain energy that may be applied to lung tissue after deployment of the treatment device.

In another aspect of the present invention, a pulmonary treatment device is provided that can be advanced into the lung and the device length can be adjusted to change length after a portion of the device is placed in contact with lung tissue.

In another aspect of the present invention, a pulmonary treatment device is provided comprising a distal anchor, a proximal anchor and spring coil midsection.

In another aspect of the present invention, a pulmonary treatment device is provided comprising a central lumen and a constrained distal anchor feature that is unconstrained by retracting a delivery device component from the central lumen of the treatment device.

In another aspect of the present invention, a pulmonary treatment device is provided comprising a central longitudinal axis, a distal end, a proximal end and a lumen running coaxial along the central longitudinal axis that is configured to be guided by a guidewire that is advanced through the lumen along the central longitudinal axis.

In another aspect of the present invention, a pulmonary treatment device is provided comprising a central longitudinal axis, a distal end, a proximal end and a lumen running coaxial along the central longitudinal axis that is configured to be guided by a bronchoscope that is advanced through the lumen along the central longitudinal axis.

In another aspect of the present invention, a pulmonary treatment device is provided comprising distal and proximal anchors and a midsection that can be elongated to store fully elastic strain energy in the midsection.

In another aspect of the present invention, a pulmonary treatment device is provided comprising distal and proximal anchors and a midsection that can be elongated to store fully elastic strain energy in the treatment device before the device is coupled to lung tissue.

In another aspect of the present invention, a pulmonary treatment device is provided comprising a tissue gathering distal end, a stabilizing proximal end and a midsection that can be elongated to store fully elastic strain energy.

In another aspect of the present invention, a pulmonary treatment device is provided comprising a tissue gathering distal end, a stabilizing proximal end and a midsection that can be elongated to store fully elastic strain energy before the device is coupled to lung tissue so the device causes length compression of the lung tissue.

In another aspect of the present invention, a pulmonary treatment device is provided comprising a tissue gathering distal end, a stabilizing proximal end and a midsection that can be elongated to store fully elastic strain energy after the stabilizing proximal end is seated in lung tissue.

In another aspect of the present invention, a pulmonary treatment device is provided comprising a distal end, a proximal end and a midsection that can be elongated to store fully elastic strain energy that can be deployed in a lung to restore tension in lung tissue.

In another aspect of the present invention, a pulmonary treatment device is provided comprising a distal end, a proximal end and a midsection that can be elongated to store fully elastic strain energy that can be deployed in a lung to restore lung elastic recoil in the lung.

In another aspect of the present invention, a pulmonary treatment device is provided comprising a proximal end, a distal end and a midsection configured such that the midsection is cylindrical and the proximal end is flared.

In another aspect of the present invention, a pulmonary treatment device is provided comprising a proximal end, a distal end and a midsection configured such that the midsection is tapered so the diameter varies along the length of the midsection of the device.

In another aspect of the present invention, a pulmonary treatment device is provided comprising a proximal end, a distal end and a midsection configured such that the distal end comprises a spring element that can be constrained by the exterior surfaces of a bronchoscope.

In another aspect of the present invention, a pulmonary treatment device is provided comprising a proximal end, a distal end and a midsection configured such that the device comprises a spring element that can be expanded to a larger diameter by a balloon.

In another aspect of the present invention, a pulmonary treatment device is provided that is configured to be mounted around the outside of a bronchoscope while it is delivered to a location in the lung to increase tension in lung tissue.

In another aspect of the present invention, a pulmonary treatment device is provided having a distal anchor, a proximal anchor and a midsection that can be elongated to store elastic strain energy to tension lung tissue.

In another aspect of the present invention, a pulmonary treatment device is provided that can be advanced into the lung in a condition that is unstressed to allow the system to be flexible while being delivered along a tortuous path, configured with a distal anchor, a proximal anchor and a midsection that is made from single wire shaft.

In another aspect of the present invention, a pulmonary treatment device is provided comprising a distal anchor, a proximal anchor and a midsection that is made from continuous wire shaft.

In another aspect of the present invention, a pulmonary treatment device is provided comprising a distal anchor, a proximal anchor and a midsection that is made from single element with no connections to join features of the device.

In another aspect of the present invention, a pulmonary treatment device is provided comprising a distal anchor, a proximal anchor and a midsection; the treatment device is configured in a way that may be elongated to store elastic strain energy to tension lung tissue comprising at least one weldment to connect features of the device.

In another aspect of the present invention, a pulmonary treatment device is provided comprising a distal anchor, a proximal anchor and a midsection; the treatment device is configured in a way that may be elongated to store elastic strain energy to tension lung tissue comprising at least one crimped sleeve to connect features of the device.

In another aspect of the present invention, a pulmonary treatment device is provided comprising a distal anchor, a proximal anchor and a midsection; the treatment device is configured in a way that may be elongated to store elastic strain energy to tension lung tissue comprising at least one glue bonded joint to connect features of the device.

In another aspect of the present invention, a pulmonary treatment device is provided that is made from a continuous wire shaft whereas the wire shaft ends are terminated to be blunt atraumatic tips.

In another aspect of the present invention, a pulmonary treatment device is provided that is made from a continuous wire shaft whereas at least one wire shaft end is recast to be shaped into a blunt atraumatic blunt end.

In another aspect of the present invention, a pulmonary treatment device is provided that is made from a continuous wire shaft that may be delivered while at least partially encircling a bronchoscope and at least one wire shaft end is recast to be shaped into a ball shaped tip.

In another aspect of the present invention, a pulmonary treatment device is provided comprising a distal end, a proximal end and a midsection; the treatment device is made from one or more wire shaft components and at least one proximal end or one distal end or both ends are recast to be shaped into ball shaped blunt tip.

In another aspect of the present invention, a pulmonary treatment device is provided comprising a distal end, a proximal end and a midsection; the treatment device is configured to be delivered at least partially mounted to the outside of a bronchoscope and at least one proximal end or one distal end or both ends are recast to be shaped into ball shaped blunt tips.

In another aspect of the present invention, a pulmonary treatment device is provided comprising a distal anchor, a proximal anchor and a midsection; the treatment device is configured in a way that may be elongated to store elastic strain energy to tension lung tissue whereas the distal end has been melted to form a blunt ball end.

In another aspect of the present invention, a pulmonary treatment device is provided that is configured in a way that may be elongated to store elastic strain energy to tension lung tissue whereas the distal end has been melted to form a blunt ball end.

In another aspect of the present invention, a pulmonary treatment device is provided comprising a distal anchor, a proximal anchor and a midsection; the treatment device is configured in a way that may be elongated to store elastic strain energy to tension lung tissue whereas the distal end has been melted to form a blunt end.

In another aspect of the present invention, a pulmonary treatment device is provided that is configured in a way that may be elongated to store elastic strain energy to tension lung tissue whereas the distal end has been melted to form a blunt end.

In another aspect of the present invention, a pulmonary treatment device is provided comprising a distal anchor, a proximal anchor and a midsection; the treatment device is configured in a way that may be elongated to store elastic strain energy to tension lung tissue whereas the distal end has had material joined to it to form an atraumatic end.

In another aspect of the present invention, a pulmonary treatment device is provided that is configured in a way that may be elongated to store elastic strain energy to tension lung tissue whereas the distal end has had material joined to it to form an atraumatic end.

In another aspect of the present invention, a pulmonary treatment device is provided comprising a distal anchor, a proximal anchor and a midsection; the device being configured so it can be advanced into the lung in a delivery configuration that has not been stressed to lengthen or shorten the device length and the device is configured in such a way that the device may be elongated to store elastic strain energy and anchored to lung tissue such that lung tissue is tensioned in a delivered treatment configuration.

In another aspect of the present invention, a pulmonary treatment device is provided comprising a distal anchor, a proximal anchor and a midsection that may be delivered to a treatment site in a delivery configuration and made to perform work on lung tissue in a treatment configuration. In the delivery configuration, the device may be advanced into the lung free from stress that would otherwise lengthen or shorten the device; in the treatment configuration the device may be elongated to store elastic strain energy to beneficially tension lung tissue.

In another aspect of the present invention, a pulmonary treatment device is provided comprising a distal anchor, a proximal anchor and a midsection; the device being configured so it can be elongated to store elastic strain energy whereby the distal anchor is anchored to a location in a lung, the proximal anchor is anchored in a proximal location in the lung that is distant from the location of the distal anchor and the elastic strain energy is allowed to reduce the distance between the distal anchor and the proximal anchor to bring the distal and proximal anchors closer together in the lung.

In another aspect of the present invention, a pulmonary treatment device is provided comprising a distal anchor, a proximal anchor and a midsection that may be delivered to a treatment site in a delivery configuration and made to perform work on lung tissue in a treatment configuration. In the delivery configuration, the device may be elongated to store elastic strain energy; in the treatment configuration the device may use the elastic strain energy to shorten the device to beneficially tension lung tissue.

In another aspect of the present invention, a pulmonary treatment device is provided comprising a distal anchor, a proximal anchor and a midsection that may be delivered to a treatment site in a delivery configuration and made to perform work on lung tissue in a treatment configuration. In the delivery configuration, the device may be mounted around the exterior of a bronchoscope; in the treatment configuration the device may benefit by the use of pneumatic pressure to shorten the device to beneficially tension lung tissue. Shortening may be accomplished by pneumatically expanding the device diameter, using a balloon, while allowing device foreshortening to shorten the device to cause lung tissue tensioning.

In another aspect of the present invention, a pulmonary treatment device is provided comprising a distal anchor, a proximal anchor and a midsection that may be delivered to a treatment site in a delivery configuration and made to perform work on lung tissue in a treatment configuration. In the delivery configuration, the device may be mounted around the exterior of a bronchoscope; in the treatment configuration the device may benefit by the use of hydraulic pressure to shorten the device to beneficially tension lung tissue.

In another aspect of the present invention, a pulmonary treatment device is provided that can be advanced along a tortuous path to a treatment location in the lung, configured in a flexible unstressed condition that allows the length to be unchanged from its unstressed state, but configured to be elongated at the treatment location before being deployed to distort lung tissue.

In another aspect of the present invention, a pulmonary treatment device is provided that can be advanced along a tortuous path to a treatment location in the lung, configured in a flexible condition whereas the length is unchanged from its unstressed state, but configured to be elongated at the treatment location before being deployed to distort lung tissue.

In another aspect of the present invention, a pulmonary treatment device is provided that can be advanced along a tortuous path to a treatment location in the lung, configured in a flexible condition whereas the length is unchanged from its unstressed state but configured to shorten in an unassisted way, after being deployed in tissue, to beneficially tension lung tissue.

In another aspect of the present invention, a pulmonary treatment device is provided that can be advanced along a tortuous path to a treatment location in the lung, configured in a flexible condition configured to shorten in an unassisted way, after being deployed in tissue, to beneficially tension lung tissue.

In another aspect of the present invention, a pulmonary treatment device is provided, configured with a distal end, a proximal end and a midsection that can be advanced along a tortuous path to a treatment location in the lung, configured to shorten in an unassisted way, after being deployed in tissue, to beneficially tension lung tissue.

In another aspect of the present invention, a pulmonary treatment device is provided, configured with a distal end, a proximal end and a midsection that can be advanced along a tortuous path to a treatment location in the lung, configured to shorten in an unassisted way, after being elongated to store elastic strain energy, to beneficially tension lung tissue.

In another aspect of the present invention, a pulmonary treatment device is provided, configured with a distal anchor, a proximal anchor and a midsection that can be advanced along a tortuous path to a treatment location in the lung, configured to shorten in an unassisted way, after being elongated to store elastic strain energy, to beneficially tension lung tissue.

In another aspect of the present invention, a pulmonary treatment device is provided, configured with a distal anchor that anchors a first location in a lung, a proximal anchor that anchors a second location in a lung that is distant to the first location and a midsection, connected to the proximal and distal anchors; the device is configured so it can be advanced along a tortuous path to a treatment location in the lung, the midsection is configured to be lengthened before the proximal and distal anchors are deployed to beneficially tension lung tissue.

In another aspect of the present invention, a pulmonary treatment device is provided, configured with a distal anchor that anchors a first location in a lung, a proximal anchor that anchors a second location in a lung that is distant to the first location and a midsection, connected to the proximal and distal anchors; the device is configured so it can be advanced along a tortuous path to a treatment location in the lung, the midsection is configured to shorten after the proximal and distal anchors are deployed, to beneficially tension lung tissue.

In another aspect of the present invention, a pulmonary treatment device is provided, configured with a distal anchor that anchors a first location in a lung, a proximal anchor that anchors a second location in a lung that is distant to the first location and a midsection, connected to the proximal and distal anchors; the device is configured to be mounted at least partially around the outside of a bronchoscope so it can be advanced along a tortuous path to a treatment location in the lung, the midsection is configured to shorten after the proximal and distal anchors are deployed, to beneficially tension lung tissue.

In another aspect of the present invention, a pulmonary treatment device is provided, configured with a distal anchor that anchors a first location in a lung, a proximal anchor that anchors a second location in a lung that is distant to the first location and a midsection, connected to the proximal and distal anchors; the device is configured to be mounted at least partially around the outside of a bronchoscope so it can be advanced along a tortuous path to a treatment location in the lung, the midsection is configured to shorten after the proximal and distal anchors are deployed, to beneficially tension lung tissue.

In another aspect of the present invention, a pulmonary treatment device is provided, configured with a distal anchor that anchors a first location in a lung, a proximal anchor that anchors a second location in a lung that is distant to the first location and a midsection, connected to the proximal and distal anchors; the device is configured to be mounted at least partially around the outside of a bronchoscope so it can be advanced along a tortuous path to a treatment location in the lung, the midsection is configured to be shortened after the proximal and distal anchors are deployed, to beneficially tension lung tissue.

In another aspect of the present invention, a pulmonary treatment device is provided that acts in a stent-like manner to maintain lung airway patency and straighten the airway path between its proximal and distal ends.

In another aspect of the present invention, a pulmonary treatment device is provided that acts in a stent-like manner that supports the airway to open the airway lumen and also to act as a tensioning device along the longitudinal axis of the airway.

In another aspect of the present invention, a pulmonary treatment device is provided that is advanceable into the lung in a non-strained state.

In another aspect of the present invention, a pulmonary treatment device is provided that is advanceable into the lung while maintaining an unstretched length.

In another aspect of the present invention, a pulmonary treatment device is provided that at least partially encircles the bronchoscope used to deliver the pulmonary treatment device.

In another aspect of the present invention, a pulmonary treatment device is provided with a distal anchor feature, configured to beneficially use a bronchoscope shaft to hold the distal anchor from being deployed while the device is being advanced into the lung.

In another aspect of the present invention, a pulmonary treatment device is provided, configured to encircle the bronchoscope so the scope shaft strength is used to beneficially modify the treatment device dimensions.

In another aspect of the present invention, a pulmonary treatment device is provided that may be lengthened by advancing the bronchoscope.

In another aspect of the present invention, a pulmonary treatment device is provided that may be elongated by advancing the bronchoscope.

In another aspect of the present invention, a pulmonary treatment device is provided that may be elongated by retracting the bronchoscope.

In another aspect of the present invention, a pulmonary treatment device is provided that may be elongated by retracting a bronchoscope guide sleeve.

In another aspect of the present invention, a pulmonary treatment device is provided, configured to deploy the proximal end to engage tissue first before being lengthened to enhance lung elastic recoil.

In another aspect of the present invention, a pulmonary treatment device is provided that may be advanced into the lung in a state whereby the device has not been strained to be lengthened or shortened from a zero-strain length, whereby the device length may be increased, using delivery system components at the treatment site before any portion of the device is released from the delivery system.

In another aspect of the present invention, a pulmonary treatment device is provided that can be pulled and lengthened after partial deployment.

In another aspect of the present invention, a pulmonary treatment device is provided that can be pulled and lengthened after deploying its distal end.

In another aspect of the present invention, a pulmonary treatment device is provided that may be tensioned along the longitudinal direction but the device length is maintained after deploying the distal end.

In another aspect of the present invention, a pulmonary treatment device is provided that can be longitudinally tensioned to pull distal end and adjacent lung tissue more proximally after deploying the distal end.

In another aspect of the present invention, a pulmonary treatment device is provided with flared ends for treating emphysema (end diameter is larger than midsection).

In another aspect of the present invention, a pulmonary treatment device is provided that acts in a stent-like manner with flared ends for treating emphysema (end diameter is larger than central body).

In another aspect of the present invention, a pulmonary treatment device is provided that tensions lung tissue that can be deployed in every anatomical lumen in lung that is either anatomical or made by disease or created by a device as shown as RB1 through LB10 on conventional airway charts.

In another aspect of the present invention, a pulmonary treatment device is provided that acts in a stent-like manner that is delivered by advancing a bronchoscope.

In another aspect of the present invention, a pulmonary treatment device is provided that stents lung tissue that is delivered by advancing a catheter (without the use of a scope).

In another aspect of the present invention, a pulmonary treatment device is provided to stent lung tissue wherein the device is delivered by guiding a bronchoscope in position using a guidewire.

In another aspect of the present invention, a pulmonary treatment device is provided to stent lung tissue wherein the device is delivered by guiding a catheter in position using a guidewire.

In another aspect of the present invention, a pulmonary treatment device is provided that straightens airways.

In another aspect of the present invention, a pulmonary treatment device is provided that straightens 2 or more airways at the same time.

In another aspect of the present invention, a pulmonary treatment device is provided that straightens 2 or more airways while laterally urging them closer together.

In another aspect of the present invention, a pulmonary treatment device is provided that urges 2 or more airways together to cause lung tissue tension.

In another aspect of the present invention, a pulmonary treatment device is provided that urges 2 or more airways together to cause any one of the beneficial changes listed above as items (1) through (107) above.

In another aspect of the present invention, a pulmonary treatment device is provided that straightens an airway while shortening the length of the airway.

In another aspect of the present invention, a pulmonary treatment device is provided that displaces lung tissue closer to the trachea.

In another aspect of the present invention, a pulmonary treatment device is provided that pulls tissue farther from the pleura.

In another aspect of the present invention, a pulmonary treatment device is provided that shifts lung tissue closer to the heart.

In another aspect of the present invention, a pulmonary treatment device is provided that urges 2 or more airways together to displaces lung tissue closer to the trachea. In another aspect of the present invention, a pulmonary treatment device is provided that urges 2 or more airways together to pull tissue farther from the pleura.

In another aspect of the present invention, a pulmonary treatment device is provided that urges 2 or more airways together to shift lung tissue closer to the heart.

In another aspect of the present invention, a pulmonary treatment device is provided that shortens an airway length while tensioning tissue that is distal to its distal end.

In another aspect of the present invention, a pulmonary treatment device is provided that is tensioned while supporting airway patency.

In another aspect of the present invention, a pulmonary treatment device is provided that is tensioned while supporting airway patency between its ends.

In another aspect of the present invention, a pulmonary treatment device is provided that stents lung tissue to provide support to keep airways open while also providing tension in the longitudinal axis of the airway.

In another aspect of the present invention, a pulmonary treatment device is provided that is resilient enough to change dimension during breathing.

In another aspect of the present invention, a pulmonary treatment device is provided, comprising a curvilinear shape that maintains a fixed length as measured down the curvilinear path before and after deployment, that tensions lung tissue.

In another aspect of the present invention, a pulmonary treatment device is provided that straightens an airway while allowing gas to flow through in at least one direction.

In another aspect of the present invention, a pulmonary treatment device is provided that deploys into an airway while the device also straightens the gas flow path through the airway where the pulmonary treatment device is deployed.

In another aspect of the present invention, a pulmonary treatment device is provided, comprising a distal end designed to couple to low density lung tissue that is known to be greater than 800 HU in density.

In another aspect of the present invention, a pulmonary treatment device is provided, comprising an optimized design with high tissue contact area to reduce lung tissue stress, In another aspect of the present invention, a pulmonary treatment device is provided that tensions lung tissue distal to the pulmonary treatment device and shortens the length of the airway the pulmonary treatment device occupies.

In another aspect of the present invention, a pulmonary treatment device is provided that tensions lung tissue distal to the pulmonary treatment device and shortens the length of the airway the pulmonary treatment device occupies and supports the airway wall to maintain airway patency.

In another aspect of the present invention, a pulmonary treatment device is provided that tensions lung tissue distal to the pulmonary treatment device whereas the device length is increased as tension is applied to the device.

In another aspect of the present invention, a pulmonary treatment device is provided, comprising an anchor that tensions lung tissue whereas the device length is increased as the proximal end of the device is moved closer to the trachea.

In another aspect of the present invention, a pulmonary treatment device is provided, comprising an anchor that tensions lung tissue whereas the device length is increased as a portion of the device is moved closer to the trachea.

In another aspect of the present invention, a pulmonary treatment device is provided that tensions lung tissue longitudinally along the axis the device occupies while also supporting the airway wall to maintain airway patency.

In another aspect of the present invention, a pulmonary treatment device is provided that tensions lung tissue and reduces elastic recoil adjacent the airway that the pulmonary treatment device occupies.

In another aspect of the present invention, a pulmonary treatment device is provided that tensions lung tissue distal or proximal to the pulmonary treatment device and supports the airway wall to maintain airway patency.

In another aspect of the present invention, a pulmonary treatment device is provided that straightens at least a portion of airway wall.

In another aspect of the present invention, a tensioning pulmonary treatment device is provided, comprising at least one end that forms a circular shape.

In another aspect of the present invention, a tensioning pulmonary treatment device is provided, comprising at least one end that forms a helical shape.

In another aspect of the present invention, a tensioning pulmonary treatment device is provided, comprising at least one end that penetrates lung tissue.

In another aspect of the present invention, a tensioning pulmonary treatment device is provided, comprising at least one end that deploys in a shape that contacts itself.

In another aspect of the present invention, a tensioning pulmonary treatment device is provided, comprising at least one end that does not compress tissue.

In another aspect of the present invention, a tensioning pulmonary treatment device is provided, comprising a design which is axisymmetric.

In another aspect of the present invention, a tensioning pulmonary treatment device is provided that changes the lung volume sufficiently to move the heart laterally.

In another aspect of the present invention, a pulmonary treatment device is provided that stents lung tissue to hold at least a portion of an airway lumen open while providing longitudinal tension.

In another aspect of the present invention, a pulmonary treatment device is provided, comprising a proximal or distal end that straightens as tension is applied to the device during deployment.

In another aspect of the present invention, a lung tissue tensioning pulmonary treatment device is provided that does not compress tissue.

In another aspect of the present invention, a lung tissue tensioning pulmonary treatment device is provided that selectively tensions tissue regions.

In another aspect of the present invention, a lung tissue tensioning pulmonary treatment device is provided that increases tension in lung tissue to a uniform magnitude.

In another aspect of the present invention, a pulmonary treatment device is provided that tensions lung tissue in a portion of a lung while relieving tension in another portion of the same lung.

In another aspect of the present invention, a pulmonary treatment device is provided that is delivered in a delivery configuration and deployed in a deployed configuration, comprising a proximal end; a distal end and a midsection which is connected to the proximal end and the distal end; configured to a delivery length in a delivery configuration and a deployed length that is longer than the delivery length.

In another aspect of the present invention, a pulmonary treatment device is provided that tensions lung tissue in a way that is compliant during breathing.

In another aspect of the present invention, a pulmonary treatment device is provided that tensions lung tissue and elongates during the inspiration portion of the breathing cycle.

In another aspect of the present invention, a pulmonary treatment device is provided that tensions lung tissue and contracts to a shorter length during the expiration portion of the breathing cycle.

In another aspect of the present invention, a COPD treatment device is provided that lengthens during the inspiration portion of the breathing cycle.

In another aspect of the present invention, a COPD treatment device is provided that shortens during the exhalation portion of the breathing cycle.

In another aspect of the present invention, a COPD treatment device is provided that acts as a stent device, comprising: a tubular shaped member having first and second open end and a lumen running therethrough, said member is sized for placement within a lung airway, said member is comprised of a shape memory material that exhibits a shape recovery transition temperature in a temperature range below normal body temperature such that after placement within the lung, having a temperature at or near normal body temperature, said member expands radially and contracts longitudinally so at least a portion of said member becomes firmly anchored to lung tissue.

In another aspect of the present invention, a COPD treatment device is provided that acts as a stent device, comprising: a tubular shaped member having first and second open end and a lumen running therethrough, said member is sized for placement within a lung airway, said member is comprised of a shape memory material that exhibits a shape recovery transition temperature in a temperature range below normal body temperature such that after placement within the lung, having a temperature at or near normal body temperature, said member expands radially and contracts longitudinally so at least a portion of said member straightens the lung airway.

In another aspect of the present invention, a COPD treatment device is provided comprising a helically wound coil spring, wherein the spring has a tubular shaped member having first and second open end and a lumen running therethrough, said member sized for placement within a lung airway, said member comprised of a shape memory material that exhibits a shape recovery transition temperature in a temperature range below normal body temperature such that after placement within the lung, having a temperature at or near normal body temperature, said member expands radially and contracts longitudinally so at least a portion of said member straightens the lung airway.

In another aspect of the present invention, a COPD treatment device is provided that acts as a stent device, comprising: a tubular shaped member having first and second open end and a lumen running therethrough, said member is sized for placement within a lung airway, said member is comprised of a shape memory material that exhibits a shape recovery transition temperature in a temperature range below normal body temperature such that after placement within the lung, having a temperature at or near normal body temperature, said member expands radially and contracts longitudinally so at least a portion of said member tensions the lung tissue.

In another aspect of the present invention, a COPD treatment device is provided that acts as a helically wound coil spring, comprising: a tubular shaped member having first and second open end and a lumen running therethrough, said member is sized for placement within a lung airway, said member is comprised of a shape memory material that exhibits a shape recovery transition temperature in a temperature range below normal body temperature such that after placement within the lung, having a temperature at or near normal body temperature, said member expands radially and contracts longitudinally so at least a portion of said member tensions lung tissue.

In another aspect of the present invention, a COPD treatment device is provided that acts as a stent device, comprising: a tubular shaped member having first and second open end and a lumen running therethrough, said member is sized for placement within a lung airway, said member is comprised of a nitinol material that exhibits a shape recovery transition temperature in a temperature range below normal body temperature such that after placement within the lung, having a temperature at or near normal body temperature, said member expands radially and contracts longitudinally so at least a portion of said member tensions the lung tissue.

In another aspect of the present invention, a COPD treatment device is provided that acts as a helically wound coil spring, comprising: a tubular shaped member having first and second open end and a lumen running therethrough, said member is sized for placement within a lung airway, said member is comprised of nitinol material that exhibits a shape recovery transition temperature in a temperature range below normal body temperature such that after placement within the lung, having a temperature at or near normal body temperature, said member expands radially and contracts longitudinally so at least a portion of said member tensions lung tissue.

In another aspect of the present invention, a COPD treatment device is provided that acts as a stent device, comprising a proximal end, a distal end and a midsection that joins the ends and a lumen running therethrough, said member is sized for placement within a lung airway, said member is comprised of a nitinol material that exhibits a shape recovery transition temperature in a temperature range below normal body temperature such that after placement within the lung, having a temperature at or near normal body temperature, said member contracts longitudinally so at least a portion of said member tensions the lung tissue.

In another aspect of the present invention, a COPD treatment device is provided that acts as a stent device, comprising a proximal end, a distal end and a midsection that joins the ends and a lumen running therethrough, said member is sized for placement within a lung airway, said member is comprised of a nitinol material that exhibits a shape recovery transition temperature in a temperature range below normal body temperature such that after placement within the lung, having a temperature at or near normal body temperature, said member contracts longitudinally so at least a portion of said member tensions the lung tissue; whereas the distal end is configured to anchor to loose lung tissue.

In another aspect of the present invention, a COPD treatment device is provided comprising a helically wound coil spring, comprising: a tubular shaped member having first and second open end and a lumen running therethrough, said member is sized for placement within a lung airway, said member is comprised of nitinol material that exhibits a shape recovery transition temperature in a temperature range below normal body temperature such that after placement within the lung, having a temperature at or near normal body temperature, said member contracts longitudinally so at least a portion of said member tensions lung tissue.

In another aspect of the present invention, a COPD treatment device is provided comprising a helically wound coil spring, comprising: a tubular shaped member having first and second open end and a lumen running therethrough, said member is sized for placement within a lung airway, said member is comprised of nitinol material that exhibits a shape recovery transition temperature in a temperature range below normal body temperature such that after placement within the lung, having a temperature at or near normal body temperature, said member contracts longitudinally so at least a portion of said member tensions lung tissue; whereas the distal end is configured to anchor in loose lung tissue.

In another aspect of the present invention, a COPD treatment device is provided comprising a helically wound coil spring, comprising: a tubular shaped member having first and second open end and a lumen running therethrough, said member is sized for placement within a lung airway, said member is comprised of nitinol material that exhibits a shape recovery transition temperature in a temperature range below normal body temperature such that after placement within the lung, having a temperature at or near normal body temperature, said member contracts longitudinally so at least a portion of said member tensions lung tissue; whereas the proximal end is configured to anchor in reinforced lung tissue.

In another aspect of the present invention, a COPD treatment device is provided comprising a first coil shaped end and second coil shaped end and a lumen running therethrough, said device is sized for placement within a lung airway, said device is comprised of nitinol material that exhibits a shape recovery transition temperature in a temperature range below normal body temperature such that after placement within the lung, having a temperature at or near normal body temperature, said device contracts longitudinally so at least a portion of said device tensions lung tissue.

In another aspect of the present invention, a COPD treatment device is provided that straightens the airway comprising a single helical component with an arc length that is not changed during deployment.

In another aspect of the present invention, a COPD treatment device is provided that does not cause lung volume reduction.

In another aspect of the present invention, a COPD treatment device is provided that causes minimal lung volume reduction.

In another aspect of the present invention, a COPD treatment device is provided that does not cause lung volume compression.

In another aspect of the present invention, a COPD treatment device is provided that causes minimal lung volume compression.

In another aspect of the present invention, a COPD treatment device is provided that does not cause lung tissue compression.

In another aspect of the present invention, a COPD treatment device is provided that causes minimal lung tissue compression.

In another aspect of the present invention, a COPD treatment device is provided comprising: a resilient stent device for straightening lung airways comprising a wire formed into a plurality of bends to generally form a helical shape having a longitudinal axis that is lengthened before being decoupled from a delivery system to apply longitudinal tension to lung tissue in a patient when said stent device is disposed within said airway.

In another aspect of the present invention, a COPD treatment device is provided comprising: a medical device for straightening a lung airway, comprising: a tissue gathering end, a stabilizing end, and a tether extending between the tissue gathering end and stabilizing end, the device configured so that the distance between the ends measured along the tether is fixed and maintained after being released from a delivery device but the distance between the ends can be lengthened by moving the delivery device before releasing the medical device from the delivery device.

In another aspect of the present invention, a COPD treatment device is provided that tensions lung tissue and a tension indicator feature.

In another aspect of the present invention, a COPD treatment device is provided that tensions lung tissue and a displacement indicator feature.

In another aspect of the present invention, a COPD treatment device is provided that straightens airways in the lung that includes a tension indicator feature.

In another aspect of the present invention, a COPD treatment device is provided that straightens airways in the lung and includes a displacement indicator feature.

In another aspect of the present invention, a COPD treatment device is provided that straightens airways in the lung when tension is applied to the lung tissue.

In another aspect of the present invention, a COPD treatment device is provided that dilates airways in the lung when the device is used to apply tension to lung tissue.

In another aspect of the present invention, a COPD treatment device is provided comprising: a medical device for straightening a lung airway, comprising: a tissue gathering end, a stabilizing end, and a tether extending between the tissue gathering end and stabilizing end, whereas the tether is shaped to form a coil and the coil is straightened as the distance between the tissue gathering end and the stabilizing end of the device is lengthened.

In another aspect of the present invention, a COPD treatment device is provided comprising: a medical device used to tension lung tissue; having a tissue gathering end, a stabilizing end and a tether joining the two ends that is made from a single continuous length of plastic, metal, tubing, wire, or extrusion.

In another aspect of the present invention, a COPD treatment device is provided comprising: a first portion having a first bearing surface and defining a first local axis, the first portion of the treatment device configured to engage a first portion of the airway with the first bearing surface; and the treatment device further comprising a second portion coupled to the first portion of the treatment device, the second portion of the treatment device having a second bearing surface and defining a second local axis, the second portion of the treatment device configured to engage a second portion of the airway with the second bearing surface, the second portion of the airway being axially spaced apart from the first portion of the airway; wherein, in a deployed configuration within the lung, the first portion of the treatment device presses against the first portion of the airway to urge it to a more coaxial orientation relative to the second local axis, and the second portion of the treatment device presses against the second portion of the airway to urge it to a more coaxial orientation relative to the first local axis, thereby straightening the path through the airway in contact with the first and second portions of the treatment device.

In another aspect of the present invention, a COPD treatment device is provided comprising: a first portion having a structure with a centroid defining a first local axis and a first bearing surface, the first portion of the treatment device configured to engage a first portion of the airway with the first bearing surface; and the treatment device further comprising a second portion coupled to the first portion of the treatment device, the second portion of the treatment device having a structure with a centroid defining a second local axis and a second bearing surface, the second portion of the treatment device configured to engage a second portion of the airway with the second bearing surface, the second portion of the airway being axially spaced apart from the first portion of the airway; wherein, in a deployed configuration within the lung, the first portion of the treatment device presses against the first portion of the airway to urge it to a more coaxial orientation relative to the second local axis, and the second portion of the treatment device presses against the second portion of the airway to urge it to a more coaxial orientation relative to the first local axis, thereby straightening the path through the airway in contact with the first and second portions of the treatment device In another aspect of the present invention, a pulmonary treatment device is provided, configured to be deployed within an airway of a lung of a patient for treating the lung of the patient, the treatment device comprising: a first portion having a structure with a centroid defining a first local axis and a first bearing surface, the first portion of the treatment device configured to engage a first portion of the airway with the first bearing surface; and a second portion coupled to the first portion of the treatment device, the second portion of the treatment device having a structure with a centroid defining a second local axis and a second bearing surface, the second portion of the treatment device configured to engage a second portion of the airway with the second bearing surface, the second portion of the airway being axially spaced apart from the first portion of the airway; wherein, in a deployed configuration within the lung, the first portion of the treatment device presses against the first portion of the airway to urge it to a more coaxial orientation relative to the second local axis, and the second portion of the treatment device presses against the second portion of the airway to urge it to a more coaxial orientation relative to the first local axis, thereby straightening the path through the airway in contact with the first and second portions of the treatment device.

In another aspect of the present invention, a pulmonary treatment device is provided, configured to be deployed within more than one airway of a lung of a patient for treating the lung of the patient, the treatment device comprising: a first portion having a first bearing surface and defining a first local axis, the first portion of the treatment device configured to engage a first portion of a first airway with the first bearing surface; and the treatment device further comprising a second portion (can be a portion of a proximal v clip) coupled to the first portion of the treatment device, a second portion of the treatment device having a second bearing surface and defining a second local axis, the second portion of the treatment device configured to engage a second portion of the first airway with the second bearing surface, the second portion of the airway being axially spaced apart from the first portion of the first airway; a third portion coupled to the second portion of the treatment device having a third bearing surface and defining a third local axis, the third portion of the treatment device configured to engage a first portion of a second airway with the third bearing surface; and a fourth portion (can be another tissue gathering end) coupled to the third portion of the treatment device, the fourth portion of the treatment device having a fourth bearing surface and defining a fourth local axis, the fourth portion of the treatment device configured to engage a second portion of the second airway with the fourth bearing surface, the second portion of the second airway being axially spaced apart from the first portion of the second airway; wherein, in a deployed configuration within the lung, the first portion of the treatment device presses against the first portion of the first airway to urge it to a more coaxial orientation relative to the second local axis in the first airway, and the second portion of the treatment device presses against the second portion of the first airway to urge it to more a coaxial orientation relative to the first local axis, thereby straightening the path through the first airway in contact with the first and second portions of the treatment device and the third portion of the treatment device presses against the first portion of the second airway to urge it to a more coaxial orientation relative to the fourth local axis in the second airway, and the fourth portion of the treatment device presses against the second portion of the second airway to urge it to more a coaxial orientation relative to the third local axis, thereby straightening the path through the second airway in contact with the third and fourth portions of the treatment device.

In another aspect of the present invention, a pulmonary treatment device is provided, configured to be deployed within more than one airway of a lung of a patient for treating the lung of the patient, the treatment device comprising: a first portion having a first bearing surface having a structure with a centroid defining a first local axis, the first portion of the treatment device configured to engage a first portion of a first airway with the first bearing surface; a second portion (can be a portion of a proximal v clip) coupled to the first portion of the treatment device, the second portion of the treatment device having a second bearing surface having a structure with a centroid defining a second local axis, the second portion of the treatment device configured to engage a second portion of the first airway with the second bearing surface, the second portion of the first airway being axially spaced apart from the first portion of the first airway; a third portion coupled to the second portion of the treatment device having a third bearing surface having a structure with a centroid defining a third local axis, the third portion of the treatment device configured to engage a first portion of a second airway with the third bearing surface; and a fourth portion (can be another distal end) coupled to the third portion of the treatment device, the fourth portion of the treatment device having a fourth bearing surface having a structure with a centroid defining a fourth local axis, the fourth portion of the treatment device configured to engage a second portion of the second airway with the fourth bearing surface, the second portion of the second airway being axially spaced apart from the first portion of the second airway; wherein, in a deployed configuration within the lung, the first portion of the treatment device presses against the first portion of the first airway to urge it to a more coaxial orientation relative to the second local axis in the first airway, and the second portion of the treatment device presses against the second portion of the first airway to urge it to more a coaxial orientation relative to the first local axis, thereby straightening the path through the first airway in contact with the first and second portions of the treatment device and the third portion of the treatment device presses against the first portion of the second airway to urge it to a more coaxial orientation relative to the fourth local axis in the second airway, and the fourth portion of the treatment device presses against the second portion of the second airway to urge it to more a coaxial orientation relative to the third local axis, thereby straightening the path through the second airway in contact with the third and fourth portions of the treatment device.

In another aspect of the present invention, a pulmonary treatment device is provided, configured to be deployed within more than one airway of a lung of a patient for treating the lung of the patient, the treatment device comprising: a first portion having a first bearing surface having a structure with a centroid defining a first local axis, the first portion of the treatment device configured to engage a first portion of a first airway with the first bearing surface; a second portion (can be a portion of a proximal v clip) coupled to the first portion of the treatment device, the second portion of the treatment device having a second bearing surface having a structure with a centroid defining a second local axis, the second portion of the treatment device configured to engage a second portion of the first airway with the second bearing surface, the second portion of the first airway being axially spaced apart from the first portion of the first airway; a third portion coupled to the second portion of the treatment device having a third bearing surface having a structure with a centroid defining a third local axis, the third portion of the treatment device configured to engage a first portion of a second airway with the third bearing surface; and a fourth portion (can be another distal end) coupled to the third portion of the treatment device, the fourth portion of the treatment device having a fourth bearing surface having a structure with a centroid defining a fourth local axis, the fourth portion of the treatment device configured to engage a second portion of the second airway with the fourth bearing surface, the second portion of the second airway being axially spaced apart from the first portion of the second airway; wherein, in a deployed configuration within the lung, the first portion of the treatment device presses against the first portion of the first airway to urge it to a more coaxial orientation relative to the second local axis in the first airway, and the second portion of the treatment device presses against the second portion of the first airway to urge it to more a coaxial orientation relative to the first local axis, thereby straightening the path through the first airway in contact with the first and second portions of the treatment device and the third portion of the treatment device presses against the first portion of the second airway to urge it to a more coaxial orientation relative to the fourth local axis in the second airway, and the fourth portion of the treatment device presses against the second portion of the second airway to urge it to more a coaxial orientation relative to the third local axis, thereby straightening the path through the second airway in contact with the third and fourth portions of the treatment device; whereas the first and second portions of the treatment device are urged closer to the third and fourth portions of the treatment device in a deployed configuration within the lung.

In another aspect of the present invention, a pulmonary treatment device is provided, configured to be deployed within more than one airway of a lung of a patient for treating the lung of the patient, the treatment device comprising: a first portion having a first bearing surface having a structure with a centroid defining a first local axis, the first portion of the treatment device configured to engage a first portion of a first airway with the first bearing surface; a second portion (can be a portion of a proximal v clip) coupled to the first portion of the treatment device, the second portion of the treatment device having a second bearing surface having a structure with a centroid defining a second local axis, the second portion of the treatment device configured to engage a second portion of the first airway with the second bearing surface, the second portion of the first airway being axially spaced apart from the first portion of the first airway; a third portion coupled to the second portion of the treatment device having a third bearing surface having a structure with a centroid defining a third local axis, the third portion of the treatment device configured to engage a first portion of a second airway with the third bearing surface; and a fourth portion (can be another distal end) coupled to the third portion of the treatment device, the fourth portion of the treatment device having a fourth bearing surface having a structure with a centroid defining a fourth local axis, the fourth portion of the treatment device configured to engage a second portion of the second airway with the fourth bearing surface, the second portion of the second airway being axially spaced apart from the first portion of the second airway; wherein, in a deployed configuration within the lung, the first portion of the treatment device presses against the first portion of the first airway to urge it to a more coaxial orientation relative to the second local axis in the first airway, and the second portion of the treatment device presses against the second portion of the first airway to urge it to more a coaxial orientation relative to the first local axis, thereby straightening the path through the first airway in contact with the first and second portions of the treatment device and the third portion of the treatment device presses against the first portion of the second airway to urge it to a more coaxial orientation relative to the fourth local axis in the second airway, and the fourth portion of the treatment device presses against the second portion of the second airway to urge it to more a coaxial orientation relative to the third local axis, thereby straightening the path through the second airway in contact with the third and fourth portions of the treatment device; whereas the first and second portions of the treatment device are urged closer to the third and fourth portions of the treatment device in a deployed configuration within the lung; whereas the treatment device increases tension in lung tissue in a deployed configuration within the lung.

In another aspect of the present invention, a pulmonary treatment device is provided, configured to be deployed within more than one airway of a lung of a patient for treating the lung of the patient, the treatment device comprising: a first portion having a first bearing surface having a structure with a centroid defining a first local axis, the first portion of the treatment device configured to engage a first portion of a first airway with the first bearing surface; a second portion (can be a portion of a proximal v clip) coupled to the first portion of the treatment device, the second portion of the treatment device having a second bearing surface having a structure with a centroid defining a second local axis, the second portion of the treatment device configured to engage a second portion of the first airway with the second bearing surface, the second portion of the first airway being axially spaced apart from the first portion of the first airway; a third portion coupled to the second portion of the treatment device having a third bearing surface having a structure with a centroid defining a third local axis, the third portion of the treatment device configured to engage a first portion of a second airway with the third bearing surface; and a fourth portion (can be another distal end) coupled to the third portion of the treatment device, the fourth portion of the treatment device having a fourth bearing surface having a structure with a centroid defining a fourth local axis, the fourth portion of the treatment device configured to engage a second portion of the second airway with the fourth bearing surface, the second portion of the second airway being axially spaced apart from the first portion of the second airway; wherein, in a deployed configuration within the lung, the first portion of the treatment device presses against the first portion of the first airway to urge it to a more coaxial orientation relative to the second local axis in the first airway, and the second portion of the treatment device presses against the second portion of the first airway to urge it to more a coaxial orientation relative to the first local axis, thereby straightening the path through the first airway in contact with the first and second portions of the treatment device and the third portion of the treatment device presses against the first portion of the second airway to urge it to a more coaxial orientation relative to the fourth local axis in the second airway, and the fourth portion of the treatment device presses against the second portion of the second airway to urge it to more a coaxial orientation relative to the third local axis, thereby straightening the path through the second airway in contact with the third and fourth portions of the treatment device; whereas the first and second portions of the treatment device are urged closer to the third and fourth portions of the treatment device in a deployed configuration within the lung; whereas the second and third portions of the treatment device are coupled by a resilient spring material.

In another aspect of the present invention, a pulmonary treatment device is provided, configured to be deployed within more than one airway of a lung of a patient for treating the lung of the patient, the treatment device comprising: a first portion having a first bearing surface having a structure with a centroid defining a first local axis, the first portion of the treatment device configured to engage a first portion of a first airway with the first bearing surface; a second portion (can be a portion of a proximal v clip) coupled to the first portion of the treatment device, the second portion of the treatment device having a second bearing surface having a structure with a centroid defining a second local axis, the second portion of the treatment device configured to engage a second portion of the first airway with the second bearing surface, the second portion of the first airway being axially spaced apart from the first portion of the first airway; a third portion coupled to the second portion of the treatment device having a third bearing surface having a structure with a centroid defining a third local axis, the third portion of the treatment device configured to engage a first portion of a second airway with the third bearing surface; and a fourth portion (can be another distal end) coupled to the third portion of the treatment device, the fourth portion of the treatment device having a fourth bearing surface having a structure with a centroid defining a fourth local axis, the fourth portion of the treatment device configured to engage a second portion of the second airway with the fourth bearing surface, the second portion of the second airway being axially spaced apart from the first portion of the second airway; wherein, in a deployed configuration within the lung, the first portion of the treatment device presses against the first portion of the first airway to urge it to a more coaxial orientation relative to the second local axis in the first airway, and the second portion of the treatment device presses against the second portion of the first airway to urge it to more a coaxial orientation relative to the first local axis, thereby straightening the path through the first airway in contact with the first and second portions of the treatment device and the third portion of the treatment device presses against the first portion of the second airway to urge it to a more coaxial orientation relative to the fourth local axis in the second airway, and the fourth portion of the treatment device presses against the second portion of the second airway to urge it to more a coaxial orientation relative to the third local axis, thereby straightening the path through the second airway in contact with the third and fourth portions of the treatment device; whereas the first and second portions of the treatment device are urged closer to the third and fourth portions of the treatment device in a deployed configuration within the lung; whereas the second and third portions of the treatment device are coupled by a resilient spring material; whereas at least one of the portions of the treatment device is covered with a jacket to increase the area that is engaged with a portion of an airway.

In another aspect of the present invention, a pulmonary treatment device is provided, configured to be deployed within more than one airway of a lung of a patient for treating the lung of the patient, the treatment device comprising: a first portion having a first bearing surface having a structure with a centroid defining a first local axis, the first portion of the treatment device configured to engage a first portion of a first airway with the first bearing surface; a second portion (can be a portion of a proximal v clip) coupled to the first portion of the treatment device, the second portion of the treatment device having a second bearing surface having a structure with a centroid defining a second local axis, the second portion of the treatment device configured to engage a second portion of the first airway with the second bearing surface, the second portion of the first airway being axially spaced apart from the first portion of the first airway; a third portion coupled to the second portion of the treatment device having a third bearing surface having a structure with a centroid defining a third local axis, the third portion of the treatment device configured to engage a first portion of a second airway with the third bearing surface; and a fourth portion (can be another distal end) coupled to the third portion of the treatment device, the fourth portion of the treatment device having a fourth bearing surface having a structure with a centroid defining a fourth local axis, the fourth portion of the treatment device configured to engage a second portion of the second airway with the fourth bearing surface, the second portion of the second airway being axially spaced apart from the first portion of the second airway; wherein, in a deployed configuration within the lung, the first portion of the treatment device presses against the first portion of the first airway to urge it to a more coaxial orientation relative to the second local axis in the first airway, and the second portion of the treatment device presses against the second portion of the first airway to urge it to more a coaxial orientation relative to the first local axis, thereby straightening the path through the first airway in contact with the first and second portions of the treatment device and the third portion of the treatment device presses against the first portion of the second airway to urge it to a more coaxial orientation relative to the fourth local axis in the second airway, and the fourth portion of the treatment device presses against the second portion of the second airway to urge it to more a coaxial orientation relative to the third local axis, thereby straightening the path through the second airway in contact with the third and fourth portions of the treatment device; whereas the first and second portions of the treatment device are urged closer to the third and fourth portions of the treatment device in a deployed configuration within the lung; whereas the second and third portions of the treatment device are coupled by a resilient spring material; whereas at least one of the portions of the treatment device is covered with a jacket to increase the area that is engaged with a portion of an airway; whereas the first and fourth portions of the treatment device are covered with a jacket to increase the area that is engaging the first portion of the first airway and second portion of the second airway.

In another aspect of the present invention, a pulmonary treatment device is provided, configured to be deployed within more than one airway of a lung of a patient for treating the lung of the patient, the treatment device comprising: a first portion having a first bearing surface having a structure with a centroid defining a first local axis, the first portion of the treatment device configured to engage a first portion of a first airway with the first bearing surface; a second portion (can be a portion of a proximal v clip) coupled to the first portion of the treatment device, the second portion of the treatment device having a second bearing surface having a structure with a centroid defining a second local axis, the second portion of the treatment device configured to engage a second portion of the first airway with the second bearing surface, the second portion of the first airway being axially spaced apart from the first portion of the first airway; a third portion coupled to the second portion of the treatment device having a third bearing surface having a structure with a centroid defining a third local axis, the third portion of the treatment device configured to engage a first portion of a second airway with the third bearing surface; and a fourth portion (can be another distal end) coupled to the third portion of the treatment device, the fourth portion of the treatment device having a fourth bearing surface having a structure with a centroid defining a fourth local axis, the fourth portion of the treatment device configured to engage a second portion of the second airway with the fourth bearing surface, the second portion of the second airway being axially spaced apart from the first portion of the second airway; wherein, in a deployed configuration within the lung, the first portion of the treatment device presses against the first portion of the first airway to urge it to a more coaxial orientation relative to the second local axis in the first airway, and the second portion of the treatment device presses against the second portion of the first airway to urge it to more a coaxial orientation relative to the first local axis, thereby straightening the path through the first airway in contact with the first and second portions of the treatment device and the third portion of the treatment device presses against the first portion of the second airway to urge it to a more coaxial orientation relative to the fourth local axis in the second airway, and the fourth portion of the treatment device presses against the second portion of the second airway to urge it to more a coaxial orientation relative to the third local axis, thereby straightening the path through the second airway in contact with the third and fourth portions of the treatment device; whereas the first and second portions of the treatment device are urged closer to the third and fourth portions of the treatment device in a deployed configuration within the lung; whereas the second and third portions of the treatment device are coupled by a resilient spring material; whereas at least one of the portions of the treatment device is covered with a jacket, selected from the materials defined as jacket materials in this specification, to increase the area that is engaged with a portion of an airway; whereas the first and fourth portions of the treatment device are covered with a jacket to increase the area that is engaging the first portion of the first airway and second portion of the second airway.

In another aspect of the present invention, a pulmonary treatment device is provided, configured with a jacket to increase the area that is engaged with lung tissue.

In another aspect of the present invention, a pulmonary treatment device is provided, configured with a jacket, made from material listed in this specification defined as jacket materials, to increase the area that is engaged with lung tissue.

In another aspect of the present invention, a pulmonary treatment device is provided, configured with a jacket to increase the area that is engaged with lung tissue.

In another aspect of the present invention, a pulmonary treatment device is provided, configured with a jacket, made from a polymer, to increase the area that is engaged with lung tissue.

In another aspect of the present invention, a pulmonary treatment device is provided, configured with a jacket, made from a polymer material, that regulates the rate of release of a therapeutic drug.

In another aspect of the present invention, a pulmonary treatment device is provided, configured with a jacket, made from a polymer material, that regulates the rate of release of a therapeutic drug; whereas the therapeutic drug reduces the rate of wound healing, tissue remodeling, inflammation, generation of granular tissue or a combination of these.

In another aspect of the present invention, a pulmonary treatment device is provided, configured to be deployed within an airway of a lung of a patient for treating the lung of the patient, the treatment device comprising: an elongate body having a proximal end and a distal end; the elongate body configured to transition between a delivery configuration and a deployed configuration; and wherein the deployed configuration of the elongate body exerts force on the airway to straighten a portion of the airway that is axially spaced between the proximal and distal end of the treatment device for reducing air flow resistance in the lung; and wherein the elongate body is configured to increases tension in lung tissue to bring benefits related to increasing lung tension.

In another aspect of the present invention, a pulmonary treatment device is provided, configured to be deployed within an airway of a lung of a patient for treating the lung of the patient, the treatment device comprising: an elongate body having a proximal end and a distal end; the elongate body configured to transition between a delivery configuration and a deployed configuration; and wherein the deployed configuration of the elongate body exerts force on the airway to straighten a portion of the airway that is axially spaced between the proximal and distal end of the treatment device for reducing air flow resistance in the lung; and wherein the elongate body is configured to increases tension in lung tissue to bring benefits related to increasing lung tension; and wherein the elongate body is configured to elute a therapeutic drug.

In another aspect of the present invention, a pulmonary treatment device is provided, configured to be deployed within an airway of a lung of a patient for treating the lung of the patient, the treatment device comprising: an elongate body having a proximal end and a distal end; the elongate body configured to transition between a delivery configuration and a deployed configuration; and wherein the deployed configuration of the elongate body exerts force on the airway to straighten a portion of the airway that is axially spaced between the proximal and distal end of the treatment device for reducing air flow resistance in the lung; and wherein the elongate body is configured to increases tension in lung tissue to bring benefits related to increasing lung tension; and wherein the elongate body is configured to elute a therapeutic drug; wherein the therapeutic drug is configured to locally reduce a wound healing rate.

In another aspect of the present invention, a pulmonary treatment device is provided, configured to be deployed within an airway of a lung of a patient for treating the lung of the patient, the treatment device comprising: an elongate body having a proximal end and a distal end; the elongate body configured to transition between a delivery configuration and a deployed configuration; and wherein the deployed configuration of the elongate body exerts force on the airway to straighten a portion of the airway that is axially spaced between the proximal and distal end of the treatment device for reducing air flow resistance in the lung; and wherein the elongate body is configured to increases tension in lung tissue to bring benefits related to increasing lung tension; and wherein the elongate body is configured to elute a therapeutic drug; wherein the therapeutic drug is configured to locally reduce tissue remodeling.

In another aspect of the present invention, a pulmonary treatment device is provided, configured to be deployed within an airway of a lung of a patient for treating the lung of the patient, the treatment device comprising: an elongate body having a proximal end and a distal end; the elongate body configured to transition between a delivery configuration and a deployed configuration; and wherein the deployed configuration of the elongate body exerts force on the airway to straighten a portion of the airway that is axially spaced between the proximal and distal end of the treatment device for reducing air flow resistance in the lung; and wherein the elongate body is configured to increases tension in lung tissue to bring benefits related to increasing lung tension; and wherein the elongate body is configured to elute a therapeutic drug; wherein the therapeutic drug is configured to locally reduce inflammation.

In another aspect of the present invention, a pulmonary treatment device is provided, configured to be deployed within an airway of a lung of a patient for treating the lung of the patient, the treatment device comprising: an elongate body having a proximal end and a distal end; the elongate body configured to transition between a delivery configuration and a deployed configuration; and wherein the deployed configuration of the elongate body exerts force on the airway to straighten a portion of the airway that is axially spaced between the proximal and distal end of the treatment device for reducing air flow resistance in the lung; and wherein the elongate body is configured to increases tension in lung tissue to bring benefits related to increasing lung tension; and wherein the elongate body is configured to elute a therapeutic drug; wherein the therapeutic drug is configured to reduce granular tissue formation.

In another aspect of the present invention, a pulmonary treatment device is provided, configured to be deployed within an airway of a lung of a patient for treating the lung of the patient, the treatment device comprising: an elongate body having a proximal end and a distal end; the elongate body configured to transition between a delivery configuration and a deployed configuration; and wherein the deployed configuration of the elongate body exerts force on the airway to straighten a portion of the airway that is axially spaced between the proximal and distal end of the treatment device for reducing air flow resistance in the lung; and wherein the elongate body is configured to increases tension in lung tissue to bring benefits related to increasing lung tension; and wherein the elongate body is configured to elute a therapeutic drug; wherein the therapeutic drug is configured to reduce hyperplasia.

In another aspect of the present invention, a pulmonary treatment device is provided, configured to be deployed within an airway of a lung of a patient for treating the lung of the patient, the treatment device comprising: an elongate body having a proximal end and a distal end; the elongate body configured to transition between a delivery configuration and a deployed configuration; and wherein the deployed configuration of the elongate body exerts force on the airway to straighten a portion of the airway that is axially spaced between the proximal and distal end of the treatment device for reducing air flow resistance in the lung; and wherein the elongate body is configured to increases tension in lung tissue to bring benefits related to increasing lung tension; and wherein the elongate body is configured to elute a therapeutic drug; wherein the elongate body comprises a polymer material and wherein the polymer material regulates a release of the therapeutic drug.

In another aspect of the present invention, a method is provided for treating a lung comprising: deploying an implantable pulmonary treatment device to the airway of the lung, the treatment device comprising an elongate body having a proximal end and a distal end that can be repositioned; wherein the distal end of the elongate body is deployed to anchor to lung tissue, the proximal end of the elongate body is deployed to an initial position to anchor to lung tissue in a repositionable way, the proximal end is repositioned to a position farther from the distal end of the treatment device than the proximal end initial deployed position so that the elongate body and airway are urged to a more straight configuration.

In another aspect of the present invention, a method is provided for treating a lung comprising: deploying an implantable pulmonary treatment device to the airway of the lung, the treatment device comprising an elongate body having a proximal end and a distal end that can be repositioned; wherein the distal end of the elongate body is deployed to anchor to lung tissue, the proximal end of the elongate body is deployed to an initial position to anchor to lung tissue in a repositionable way, the proximal end is repositioned to a position farther from the distal end of the treatment device than the proximal end initial deployed position so that the elongate body and airway are urged to a more straight configuration; wherein the elongate body of the treatment device is configured to tension lung tissue to bring benefits related to increasing lung tension.

In another aspect of the present invention, a method is provided for treating a lung comprising: deploying an implantable pulmonary treatment device to the airway of the lung, the treatment device comprising an elongate body having a proximal end and a distal end that can be repositioned; wherein the distal end of the elongate body is deployed to anchor to lung tissue, the proximal end of the elongate body is deployed to an initial position to anchor to lung tissue in a repositionable way, the proximal end is repositioned to a position farther from the distal end of the treatment device than the proximal end initial deployed position so that the elongate body and airway are urged to a more straight configuration; wherein the elongate body of the treatment device is configured to increase tension of lung tissue that lie along directional vectors between the treatment device and chest wall.

In another aspect of the present invention, a method is provided for treating a lung comprising: deploying a pulmonary treatment device to the airway of the lung, the treatment device comprising an elongate body having a proximal end and a distal end that can be repositioned; wherein the distal end of the elongate body is deployed to anchor to lung tissue, the proximal end of the elongate body is deployed to an initial position to anchor to lung tissue in a repositionable way, the proximal end is repositioned to a position farther from the distal end of the treatment device than the proximal end initial deployed position so that the elongate body and airway are urged to a more straight configuration; wherein the elongate body of the treatment device is configured to increase tension of lung tissue that lies between the treatment device and the chest wall.

In another aspect of the present invention, a method is provided for treating a lung comprising: deploying a pulmonary treatment device to the airway of the lung, the treatment device comprising an elongate body having a proximal end and a distal end that can be repositioned; wherein the distal end of the elongate body is deployed to anchor to lung tissue, the proximal end of the elongate body is deployed to an initial position to anchor to lung tissue in a repositionable way, the proximal end is repositioned to a position farther from the distal end of the treatment device than the proximal end initial deployed position so that the elongate body and airway are urged to a more straight configuration; wherein the elongate body of the treatment device is configured to elute a therapeutic drug.

In another aspect of the present invention, a method is provided for treating a lung comprising: deploying a tissue engaging end of a pulmonary treatment device into loose damaged alveolar sac tissue distal to a lung passageway; pulling the tissue engaging end toward the lung passageway so that a portion of the lung associated with the loose damaged alveolar sac tissue is re-tensioned; and seating a stabilizing end of the pulmonary treatment device into the lung passageway so as to maintain re-tensioning of the portion of the lung.

In another aspect of the present invention, a method is provided to treat a lung comprising: providing a pulmonary treatment device with a proximal end configured to be a stabilizing end, a distal end configured to be a tissue gathering end and an elastic midsection that is connected to the stabilizing end and the tissue gathering ends and a delivery device configured to seat the stabilizing end of the pulmonary treatment device into the lung passageway; apply force to stress the elastic midsection of the treatment device so it is strained to a longer length and the distal tissue gathering end of the lung treatment device is advanced further within the lung; fix the tissue engaging end of the treatment device to the lung and then remove the delivery device to allow the elastic midsection to stent the lumen of the lung passageway while applying compressive stress on the lung tissue near the treatment device and to tension portions of the lung that are adjacent to the treatment device.

In another aspect of the present invention, a method is provided for reducing the distance between two locations in a lung to increase tension in locations in the lung that are not between the two locations. The method includes the steps of providing a device with at least two anchors and an elastic midsection that can be elongated to store elastic recoil strain energy, anchoring at a first location in the lung a first anchor, elongating the midsection to store elastic recoil strain energy, anchoring at a second location a second anchor where the second location is distant from the first location, allow the midsection with stored elastic recoil strain energy to reduce the distance between the anchored first location and the anchored second location to decrease the distance between the two locations to increase tension in locations in the lung that are not between the two anchored locations.

In another aspect of the present invention, a method is provided for reducing the distance between two locations in a lung to increase tension in locations in the lung that are not between the two locations. The method includes the steps of providing a device with at least two anchors and an elastic midsection that can store elastic recoil strain energy, anchoring at a first location in the lung a first anchor, anchoring at a second location a second anchor where the second location is distant from the first location, reducing the distance between the anchored first location and the anchored second location to decrease the distance between the two locations to increase tension in locations in the lung that are not between the two anchored locations.

In another aspect of the present invention, a method is provided for reducing the distance between two locations in a lung to increase tension in locations in the lung that are not between the two locations. The method includes the steps of providing a device with at least two anchors and an elastic midsection that can store elastic recoil strain energy, anchoring at a first location in the lung a first anchor, anchoring at a second location a second anchor where the second location is distant from the first location, reducing the distance between the anchored first location and the anchored second location to decrease the distance between the two locations to increase tension in locations in the lung that are not between the two anchored locations using stored elastic recoil strain energy.

In another aspect of the present invention, a method is provided for treating a lung comprising: advancing a lung treatment device comprising a tissue gathering distal end, a stabilizing proximal end, both connected to an elastic midsection; a delivery device comprising a bronchoscope, a deployment sleeve and a guidewire into a lung airway; advancing the treatment device through a lung airway until the stabilizing end or proximal end of the treatment device seats in the lung airway whereby the user continues to advance the non-stabilizing proximal end portion of the treatment device until the mid-section is extended or lengthened; deploying a tissue anchoring feature of the distal end of the pulmonary treatment device to allow the elastic midsection of the treatment device to pull lung tissue towards the center of the elastic midsection to increase tension in adjacent lung tissue. After removing the delivery system, the lung elastic recoil tension would be enhanced in the lung. By performing this method of treatment, one end of the treatment device is fixed to lung tissue, the treatment device is lengthened to store strain energy to fully elastically lengthen the device and the distal portion is then fixed to lung tissue. After removing the bronchoscope and related delivery system components such as a guidewire and deployment sleeve, the lung treatment device utilizes the stored strain energy to recover back to an original unstressed length and this pulls the tissue engaging end toward the lung passageway so that a portion of the lung associated with the distal or loose damaged alveolar sac tissue is re-tensioned and the seated stabilizing end of the pulmonary treatment device is pulled into the lung tissue so as to maintain re-tensioning of a large portion of the lung. The elastic midsection of the treatment device may be configured to stent the lung airway while enhancing lung tension as the airway tissue that is in contact with the elastic mid-section may be compressed over time and prone to allow lumen collapse during breathing. The elastic midsection of the treatment device may be made from a laser cut tube or a coiled or braided wire.

In another aspect of the invention, a method is provided to advance and deploy a pulmonary treatment device using a guidewire a deployment sleeve and a bronchoscope guide sleeve to 1) seat the proximal anchor of the treatment device which has been described as the stabilizing end of the treatment device, 2) advance the distal anchor structure that has been defined in as the tissue gathering end portion of the treatment device so that the midsection of the treatment device is elongated in a fully reversibly elastic way, 3) the deployment sleeve applies compressive force against the tissue gathering end portion of the treatment device to maintain the extended length of the mid-section while the bronchoscope is removed, 4) withdrawing the bronchoscope activates the anchor feature that is attached to the tissue gathering end so the distal portion of the treatment device is fixed to the lung tissue while 5) the guidewire, deployment sleeve and bronchoscope are fully removed from the lung to 6) allow the elastic recoil properties of the pulmonary treatment device to re-tension the area of loose damaged alveolar sac tissue, 7) pull the distal and proximal ends of the treatment device closer together 8) reduce compliance of the lung and 9) maintain the re-tension of the area of loose damaged alveolar sac tissue to enhance radial outward force to airways so symptoms of COPD are reduced or eliminated.

In another aspect of the present invention, a method is provided for treating a lung comprising the steps of: advancing a lung treatment system to a treatment location comprising a delivery system element with a distal end, a proximal end and a lung treatment device configured to at least partially encircle the delivery system element while the system is used to treat a patient, elongating the treatment device and deploying the device into the lung to tension lung tissue.

In another aspect of the present invention, a method is provided for treating a lung comprising the steps of: advancing a lung treatment system to a treatment location comprising a delivery system element with a distal end, a proximal end and a length which is longer than 2 times the largest transverse dimension of the element, a pulmonary treatment device configured to at least partially encircle the delivery system element while the system is advanced into a patient and elongating the treatment device and deploying the device into the lung to enhance lung elastic recoil.

In another aspect of the present invention, a method is provided for treating a lung comprising the steps of: advancing a lung treatment system comprising a delivery system element with a distal end, a proximal end and a length which is longer than 2 times the largest transverse dimension of the element, a pulmonary treatment device configured to at least partially encircle the delivery system element while the system is advanced into a patient to deliver the treatment device to a treatment location in the lung, elongating the treatment device and deploying the device into the lung to pull lung tissue towards the treatment device centroid.

In another aspect of the present invention, a method is provided for treating a lung comprising the steps of: advancing a lung treatment system comprising a delivery system element with a distal end, a proximal end and a length which is longer than 2 times the largest transverse dimension of the element and an implantable pulmonary treatment device configured to at least partially encircle the delivery system element while the system is advanced into a patient to deliver the treatment device to a treatment location in the lung, elongating the treatment device and deploying the treatment device in the lung to beneficially stress tissue in the lung.

In another aspect of the present invention, a method is provided for treating a lung comprising the steps of: advancing a lung treatment system comprising a delivery system canula with a distal end, a proximal end and a length which is longer than 2 times the largest transverse dimension of the canula, a pulmonary treatment device configured to at least partially encircle the delivery system canula while the system is advanced into a patient to deliver the treatment device to a treatment location in the lung and implant the treatment device in the lung to enhance lung elastic recoil and reduce symptoms of COPD.

In another aspect of the present invention, a method is provided for treating a lung comprising the steps of: advancing a lung treatment system comprising a delivery system canula with a distal end, a proximal end and a length which is longer than 2 times the largest transverse dimension of the canula, a pulmonary treatment device configured to at least partially encircle the delivery system canula while the system is advanced into a patient to deliver the treatment device to a treatment location in the lung, elongate the treatment device and deploy the treatment device in the lung to tension lung tissue.

In another aspect of the present invention, a method is provided for treating a lung comprising the steps of: advancing a lung treatment system comprising a bronchoscope with a distal end, a proximal end and a length which is longer than 2 times the largest transverse dimension of working length portion of the bronchoscope, a pulmonary treatment device configured to at least partially encircle the bronchoscope while the system is advanced into a patient to deliver the treatment device to a treatment location in the lung, elongate the treatment device and implanted it in the lung to treat COPD.

In another aspect of the present invention, a lung treatment method is provided for treating a lung comprising the steps of; providing a bronchoscope with a distal end, a proximal end and a length which is longer than 5 inches and a pulmonary treatment device with a distal tissue gathering end, a proximal tissue stabilizing end and a midsection. The treatment device is configured to at least partially encircle the bronchoscope while the system is advanced into a patient to deliver the treatment device to a lung. The method includes anchoring the tissue gathering end at a first location, anchoring the tissue stabilizing end at a second location which is distant from the first location and reducing the distance between the first and second locations to increase tension in a portion of the lung that is not between the first and second locations.

In another aspect of the present invention, a lung treatment method is provided, comprising the steps of providing a bronchoscope with a distal end, a proximal end and a length which is longer than 5 inches, a pulmonary treatment device with a distal tissue gathering end, a proximal tissue stabilizing end and a midsection which is configured to be able to store elastic strain energy. Additionally, the treatment device is configured to at least partially encircle the bronchoscope while the system is advanced into a patient to deliver the treatment device to a lung. The method includes anchoring the tissue gathering end at a first location, anchoring the tissue stabilizing end at a second location which is distant from the first location and allowing stored elastic strain energy to reduce the distance between the first and second locations to increase tension in a portion of the lung that is not between the first and second locations.

In another aspect of the present invention, a lung treatment method is provided, comprising the steps of providing a bronchoscope with a distal end, a proximal end and a length which is longer than 5 inches, a lung treatment device with a distal tissue gathering end, a proximal tissue stabilizing end and a midsection which is configured to be able to store elastic strain energy. The method includes anchoring the tissue gathering end at a first location, anchoring the tissue stabilizing end at a second location which is distant from the first location and allowing stored elastic strain energy to reduce the distance between the first and second locations to increase tension in a portion of the lung that is not between the first and second locations.

In another aspect of the present invention, a lung treatment method is provided, comprising the steps of providing an elongate delivery system shaft with a distal end, a proximal end and a length which is longer than 5 inches, a lung treatment device with a distal tissue gathering end, a proximal tissue stabilizing end and a midsection which is configured to be able to store elastic strain energy. The method includes anchoring the tissue gathering end at a first location, anchoring the tissue stabilizing end at a second location which is distant from the first location and allowing stored elastic strain energy to reduce the distance between the first and second locations to increase tension in a portion of the lung that is not between the first and second locations.

In another aspect of the present invention, a lung treatment method is provided, comprising the steps of providing an elongate delivery system shaft with a distal end, a proximal end and a length which is longer than 5 inches, a pulmonary treatment device with a distal tissue gathering end, a proximal tissue stabilizing end and a midsection which is configured to be able to store elastic strain energy. Additionally, the pulmonary treatment device is configured to at least partially encircle the elongate delivery system shaft. The method includes anchoring the tissue gathering end at a first location, anchoring the tissue stabilizing end at a second location which is distant from the first location and allowing stored elastic strain energy to reduce the distance between the first and second locations to increase tension in a portion of the lung that is not between the first and second locations.

In another aspect of the present invention, a lung treatment method is provided, comprising the steps of providing an elongate delivery system shaft with a distal end, a proximal end and a length which is longer than 5 inches, a pulmonary treatment device with a distal tissue gathering end, a proximal tissue stabilizing end and a midsection which is configured to be able to store elastic strain energy. Additionally, the treatment device is configured to at least partially encircle the elongate delivery system shaft. The method includes anchoring the tissue gathering end at a first location, anchoring the tissue stabilizing end at a second location which is distant from the first location and reducing the distance between the first and second locations to increase tension in a portion of the lung that is not between the first and second locations.

In another aspect of the present invention, a lung treatment method is provided, comprising the steps of providing an elongate delivery system shaft with a distal end, a proximal end and a length which is longer than 5 inches, a pulmonary treatment device with a distal tissue gathering end, a proximal tissue stabilizing end and a midsection which is configured to be able to store elastic strain energy.

The method includes anchoring the tissue gathering end at a first location, anchoring the tissue stabilizing end at a second location which is distant from the first location and reducing the distance between the first and second locations to increase tension in a portion of the lung that is not between the first and second locations.

In another aspect of the present invention, a lung treatment method is provided, comprising the steps of providing a pulmonary treatment device, a bronchoscope and a bronchoscope guide sleeve whereas the treatment device is configured with a proximal end, a distal end and a midsection that incorporates a lumen running through the treatment device proximal end and midsection along the central axis between the distal end and the proximal ends, a bronchoscope guide sleeve is configured with a proximal end, a distal end and a lumen running through the full length of the bronchoscope guide sleeve along the central axis between the distal end and proximal end; a bronchoscope that is configured to be advanced through the bronchoscope guide sleeve and through the proximal end and midsection of the treatment device in a way that allows the lung treatment device length to be lengthened or shortened by sliding the bronchoscope guide sleeve, which has been attached to the lung treatment device, along the axis of the coaxial bronchoscope. Further, the treatment device distal end is anchored to a first location in the lung, the treatment device proximal end is anchored to a second location in the lung which is distant from the first location and the treatment device is shortened to reduce the distance between the two locations in the lung to increase tension in areas in the lung that are not between the two locations.

In another aspect of the present invention, a lung treatment method is provided, comprising the steps of providing a pulmonary treatment device, a bronchoscope and a bronchoscope guide sleeve whereas the lung treatment device is configured with a proximal end, a distal end and a midsection. The treatment device can be elongated to store elastic strain energy. The treatment device may also be attached to the bronchoscope and the bronchoscope guide sleeve. The bronchoscope guide sleeve is configured with a proximal end, a distal end and a lumen running therethrough along its longitudinal axis. The bronchoscope is configured to be advanced through the bronchoscope guide sleeve and through the treatment device in a way that allows the lung treatment device length to be lengthened or shortened by sliding the bronchoscope guide sleeve along the axis of the coaxial bronchoscope. Further, the treatment device distal end is anchored to a first location in the lung, the treatment device proximal end is anchored to a second location in the lung which is distant from the first location and the treatment device is shortened to reduce the distance between the two locations in the lung to increase tension in areas in the lung that are not between the first or second anchored locations.

In another aspect of the present invention, a lung treatment method is provided, comprising the steps of providing a pulmonary treatment device, a bronchoscope and a bronchoscope guide sleeve whereas the treatment device is configured with a proximal end, a distal end and a midsection. The treatment device can be elongated to store elastic strain energy. The treatment device may also be attached to the bronchoscope and the bronchoscope guide sleeve. The bronchoscope guide sleeve is configured with a proximal end, a distal end and a lumen running therethrough along its longitudinal axis. The bronchoscope is configured to be advanced through the bronchoscope guide sleeve and through the treatment device in a way that allows the treatment device length to be lengthened or shortened by sliding the bronchoscope guide sleeve along the axis of the coaxial bronchoscope. Further, the treatment device is elongated to store elastic strain energy, distal end is anchored to a first location in the lung, the treatment device proximal end is anchored to a second location in the lung which is distant from the first location and the treatment device is shortened to reduce the distance between the two locations in the lung to increase tension in areas in the lung that are not between the first or second anchored locations.

In another aspect of the present invention, a lung treatment method is provided, comprising the steps of providing a pulmonary treatment device, a bronchoscope and a bronchoscope guide sleeve whereas the treatment device is configured with a proximal end, a distal end and a midsection. The treatment device can be elongated to store elastic strain energy. The treatment device may also be attached to the bronchoscope and the bronchoscope guide sleeve. The bronchoscope guide sleeve is configured with a proximal end, a distal end and a lumen running therethrough along its longitudinal axis. The bronchoscope is configured to be advanced through the bronchoscope guide sleeve and through the lung treatment device in a way that allows the lung treatment device length to be lengthened or shortened by sliding the bronchoscope guide sleeve along the axis of the coaxial bronchoscope. Further, the treatment device is elongated to store elastic strain energy, distal end is anchored to a first location in the lung, the lung treatment device proximal end is anchored to a second location in the lung which is distant from the first location and the stored elastic strain energy is allowed to shorten the lung treatment device to reduce the distance between the two locations in the lung to increase tension in areas in the lung that are not between the first or second anchored locations.

In another aspect of the present invention, a lung treatment method is provided, comprising the steps of deploying the tissue gathering end of a pulmonary treatment device in an airway at a location more distal from a bifurcation than the length of the pulmonary treatment device, pulling the undeployed portion of the device proximally and then deploying the stabilizing end at the bifurcation.

In another aspect of the present invention, a lung treatment method is provided, comprising the steps of deploying the tissue gathering end of a pulmonary treatment device in an airway at a location more distal from a stabilizing end target location than the length of the device, pulling the undeployed portion of the device proximally and then deploying the stabilizing end at the proximal stabilizing end target location.

In another aspect of the present invention, a lung treatment method is provided, comprising the steps of deploying the tissue gathering end of a pulmonary treatment device in an airway at a location more distal from a bifurcation than the length of the device, deploying the rest of the device and then tensioning the stabilizing end of the device to place the stabilizing end at the airway ostium or bifurcation.

In another aspect of the present invention, a lung treatment method is provided, comprising the steps of deploying the tissue gathering end of a pulmonary treatment device in an airway at a location more distal from a stabilizing end target location than the length of the device, deploying the rest of the device and then tensioning the stabilizing end of the device to place the stabilizing end at the stabilizing end target location.

In another aspect of the present invention, a lung treatment method is provided, comprising the steps of deploying the tissue gathering end of a pulmonary treatment device in an airway at a location more distal from a bifurcation than the length of the pulmonary treatment device, deploying the rest of the pulmonary treatment device and then tensioning a portion of the pulmonary treatment device to allow the stabilizing end to be placed at the airway ostium or bifurcation.

In another aspect of the present invention, a lung treatment method is provided, comprising the steps of deploying the tissue gathering end of a pulmonary treatment device in an airway at a location more distal from a stabilizing end target location than the length of the pulmonary treatment device, deploying the rest of the pulmonary treatment device and then tensioning a portion of the pulmonary treatment device to allow the stabilizing end to be placed at the stabilizing end target location.

In another aspect of the present invention, a lung treatment method is provided, comprising the steps of installing a shape-memory alloy medical device within a human lung so that the device is substantially at body temperature wherein the shape-memory alloy medical device displays reversible stress-induced or strain induced martensite at body temperature to straighten a lung airway, the method further comprising: deforming the medical device into a deformed shape different from a final shape; restraining the deformed shape of the medical device by the application of a restraining mechanism; positioning the medical device and restraining mechanism within the lung; and removing the restraining mechanism to allow the device to recover from the deformed shape into the final shape.

In another aspect of the present invention, a lung treatment method is provided, comprising the steps of installing a shape-memory alloy medical device within a human lung so that the device is substantially at body temperature wherein the shape-memory alloy medical device displays reversible stress-induced or strain induced martensite at body temperature to straighten a lung airway, the method further comprising: deforming the medical device into a deformed shape different from a final shape; restraining the deformed shape of the medical device by the application of a restraining mechanism; positioning the medical device and restraining mechanism within the lung; and removing the restraining mechanism to allow the device to recover from the deformed shape into the final shape; whereby the device tensions lung tissue.

In another aspect of the present invention, a lung treatment method is provided, comprising the steps of tensioning lung tissue by: delivering to the lung a resilient medical device with a distal end, a proximal end and a connected midsection; anchoring at least a portion of the distal end at a first position in the lung; displacing at least a portion of the proximal end to a position that is distant from the anchored at least portion of the distal end; anchoring at least a portion of the proximal end at a second position in the lung.

In another aspect of the present invention, a lung treatment method is provided, comprising the steps of tensioning lung tissue by: delivering to the lung a resilient medical device with a distal end, a proximal end and a connected midsection; anchoring at least a portion of the distal end at a first position in the lung; displacing at least a portion of the proximal end to a position that is distant from the anchored at least portion of the distal end; anchoring at least a portion of the proximal end at a second position in the lung, whereas displacing the proximal end lengthens the device.

In another aspect of the present invention, a lung treatment method is provided, comprising the steps of tensioning lung tissue by: delivering to the lung a resilient medical device with a distal end, a proximal end and a connected midsection; anchoring a at least portion of the distal end at a first position in the lung; displacing a at least portion of the proximal end to a position that is distant from the anchored at least portion of the distal end to tension the device; anchoring at least a portion of the proximal end at a second position in the lung.

In another aspect of the present invention, a lung treatment method is provided, comprising the steps of straightening a lung airway by: delivering to the lung a resilient medical device with a distal end, a proximal end and a connected midsection; anchoring at least a portion of the distal end at a first position in the lung; displacing at least a portion of the proximal end to a position that is distant from the anchored at least portion of the distal end in a way that straightens the lung airway; anchoring at least a portion of the proximal end at a second position in the lung.

In another aspect of the present invention, a lung treatment method is provided, comprising the steps of tensioning a lung airway by: delivering to the lung a resilient medical device a with distal end, a proximal end and a connected midsection; anchoring at least a portion of the distal end at a first position in a lung airway; displacing at least a portion of the proximal end to a position that is distant from the anchored at least portion of the distal end in a way that tensions the lung airway; anchoring at least at least a portion of the proximal end at a second position in another lung airway.

In another aspect of the present invention, a lung treatment method is provided, comprising the steps of tensioning a lung airway by: delivering to the lung a resilient medical device with a distal end, a proximal end and a connected midsection; anchoring at least a portion of the distal end at a first position in a lung airway; displacing at least a portion of the proximal end to a position that is distant from the anchored at least portion of the distal end in a way that tensions the lung airway; anchoring at least at least a portion of the proximal end at a second position in another at least portion of the same lung airway.

In another aspect of the present invention, a lung treatment method is provided, comprising the steps of tensioning lung tissue without causing lung volume reduction, the steps include: delivering to the lung a resilient medical device a with distal end, a proximal end and a connected midsection; anchoring at least a portion of the distal end at a first position in a lung; displacing at least a portion of the proximal end to a position in the lung that is distant from the anchored at least portion of the distal end to cause the midsection of the device to be elongated; anchoring at least a portion of the proximal end at the distant position in the lung, whereas all adjacent lung tissue has been tensioned and no lung tissue has been compressed to cause lung volume reduction.

In another aspect of the present invention, a lung treatment method is provided, comprising the steps of tensioning lung tissue without causing lung volume reduction, the steps include: delivering to the lung a resilient medical device with a distal end, a proximal end and a connected midsection; anchoring at least a portion of the proximal end at a first position in the lung; displacing a portion of the distal end to a position in the lung that is distant from the anchored at least portion of the proximal end to cause the midsection of the device to be elongated; anchoring at least a portion of the distal end at the distant position in the lung, whereas all adjacent lung tissue has been tensioned and no lung tissue has been compressed to cause lung volume reduction.

In another aspect of the present invention, a lung treatment method is provided, comprising the steps of deploying a resilient airway straightening medical device comprising an elongate body and at least one end that can be attached to lung tissue; attaching the end to at least a portion of a lung and; pulling the device to cause the attached end to pull on lung tissue to straighten a portion of a lung airway.

In another aspect of the present invention, a lung treatment method is provided, comprising the steps of deploying a resilient airway straightening medical device comprising an elongate body and at least one end that can be attached to lung tissue; attaching the end to at least a portion of a lung and; pulling the device to cause the attached end to pull on lung tissue to straighten a portion of a lung airway in a way that causes no lung volume reduction or tissue compression to occur.

In another aspect of the present invention, a lung treatment method is provided, comprising the steps of deploying a resilient airway straightening medical device comprising an elongate body and at least one end configured to be attached to lung tissue; attaching the end to at least a portion of a lung; and pulling the device to cause the attached end to pull on lung tissue to straighten a portion of a lung airway.

In another aspect of the present invention, a lung treatment method is provided, comprising the steps of deploying a pulmonary treatment device from a delivery device within a lung airway; the pulmonary treatment device comprising a tissue gathering end, a stabilizing end, and a resilient tether extending between the tissue gathering end and stabilizing end; the device configured such that the distance between the ends is increased then the ends are attached to lung tissue before releasing the pulmonary treatment device from a delivery device.

In another aspect of the present invention, a lung treatment method is provided, comprising the steps of deploying a pulmonary treatment device from a delivery device within a lung airway; the pulmonary treatment device comprising a tissue gathering end, a stabilizing end, and a resilient tether extending between the tissue gathering end and stabilizing end, the device configured such that the distance between the ends is increased and the ends are attached to a lung airway before releasing the pulmonary treatment device from a delivery device; thus straightening the lung airway.

In another aspect of the present invention, a lung treatment method is provided, comprising the steps of deploying a pulmonary treatment device from a delivery device within a lung airway; the pulmonary treatment device comprising a tissue gathering end, a stabilizing end, and a resilient tether extending between the tissue gathering end and stabilizing end, the device configured such that the distance between the ends is increased; the ends are attached to lung tissue; the pulmonary treatment device is released from the delivery device to increase tension between the ends.

In another aspect of the present invention, a lung treatment method is provided, comprising the steps of deploying a pulmonary treatment device from a delivery device within a lung airway; the pulmonary treatment device comprising a tissue gathering end, a stabilizing end, and a resilient tether extending between the tissue gathering end and stabilizing end, the device configured such that the distance between the ends is increased; and the ends are attached to lung tissue before releasing the pulmonary treatment device from a delivery device; allowing the tissue to maintain the increased distance.

In another aspect of the present invention, a lung treatment method is provided, comprising the steps of enhancing a breathing efficiency of a patient with a lung having an airway, the method comprising: advancing a treatment device distally through the airway to a portion of the lung of the patient while the treatment device is in a delivery configuration, the treatment device having a proximal end and a distal end; deploying the treatment device in a portion of the lung by transitioning the treatment device from the delivery configuration to a deployed configuration, the deployed configuration of the treatment device comprising at least two helical sections with a transition section disposed between the at least two helical sections; wherein the transition section is configured to straighten lung tissue disposed between the at least two helical sections when the device is in the second configuration.

In another aspect of the present invention, a lung treatment method is provided, comprising the steps of enhancing a breathing efficiency of a patient with a lung having an airway, the method comprising: advancing a treatment device distally through the airway to a portion of the lung of the patient while the treatment device is in a delivery configuration, the treatment device having a proximal end and a distal end; deploying the treatment device in a portion of the lung by transitioning the treatment device from the delivery configuration to a deployed configuration, the deployed configuration of the treatment device comprising at least two helical sections with a transition section disposed between the at least two helical sections; wherein the distal end is configured to straighten lung tissue disposed more distal to the at least two helical sections when the treatment device is transitioned to the deployed configuration.

In another aspect of the present invention, a lung treatment method is provided, comprising the steps of enhancing a breathing efficiency of a patient with a lung having an airway, the method comprising: advancing a treatment device distally through the airway to a portion of the lung of the patient while the treatment device is in a delivery configuration, the treatment device having a proximal end and a distal end; deploying the treatment device in a portion of the lung by transitioning the treatment device from the delivery configuration to a deployed configuration, the deployed configuration of the treatment device comprising at least two helical sections with a transition section disposed between the at least two helical sections; wherein the distal end is configured to straighten lung tissue disposed more distal to the at least two helical sections when the treatment device is transitioned to the deployed configuration.

In another aspect of the present invention, a lung treatment method is provided, comprising the steps of enhancing a breathing efficiency of a patient with a lung having an airway, the method comprising: advancing a treatment device distally through the airway to a portion of the lung of the patient while the treatment device is in a delivery configuration, the treatment device having a proximal end and a distal end; deploying the treatment device in a portion of the lung by transitioning the treatment device from the delivery configuration to a deployed configuration, the deployed configuration of the treatment device comprising at least two helical sections with a transition section disposed between the at least two helical sections; wherein the distal end is configured to straighten lung tissue disposed more distal to the distal end when the treatment device is transitioned to the deployed configuration and the proximal end is repositioned more proximally, relative to the deployed distal end.

In another aspect of the present invention, a system is provided for treating a lung comprising: a delivery device having a proximal end, a distal end and lumen therethrough, wherein the distal end is configured to be advanced through a tracheobronchial tree of the lung to an area of loose damaged alveolar sac tissue; a pulmonary treatment device advanceable through the lumen of the delivery device, wherein the pulmonary treatment device includes a tissue gathering end and a stabilizing end; a deployment element removably attached to the pulmonary treatment device and insertable into the lumen of the delivery device, wherein together the delivery device and deployment element 1) deploy the tissue gathering end into the area of loose damaged alveolar sac tissue while maintaining attachment of the pulmonary treatment device to the deployment element, 2) pull the deployed tissue gathering end so as to re-tension the area of loose damaged alveolar sac tissue, and 3) deploy the stabilizing end within a lung passageway so as to maintain the re-tension of the area of loose damaged alveolar sac tissue.

In another aspect of the present invention, a system is provided for treating a lung comprising: a delivery device having a proximal end, a distal end and lumen therethrough, wherein the distal end is configured to be advanced through a tracheobronchial tree of the lung to an airway in the lung; a deployment sleeve comprising a distal end and a proximal end and a lumen therethrough which is sized to be advanced through the delivery device lumen, a guidewire which may be passed through the lumen of the deployment sleeve; a pulmonary treatment device having a distal tissue gathering end, a proximal stabilizing end and a midsection spring element that is mounted around the outside of the delivery device in a configuration that allows the system to be advanceable through the trachea and into lung airways and lung passageways, wherein the pulmonary treatment device is configured to be advanced so that the proximal stabilizing end is wedged into lung tissue; the delivery device is configured to continue to advance the non-stabilizing portion of the treatment device so that the midsection spring element is strained to a longer state; the deployment sleeve is configured to be advanced and held against distal end of the treatment device to hold it in place in the patient while the delivery device is removed. The system includes a guidewire which is configured to hold the treatment device aligned in the same axis as the delivery device lumen. The delivery device may be a bronchoscope.

In another aspect of the present invention, a system is provided for treating a COPD patient's lung comprising: a delivery system element with a distal end, a proximal end and a lung treatment device configured to at least partially encircle the delivery system element while the system is used to treat a patient.

In another aspect of the present invention, a system is provided for treating a COPD patient's lung comprising: a delivery system element with a distal end, a proximal end and a length which is longer than 2 times the largest transverse dimension of the element, a lung treatment device configured to at least partially encircle the delivery system element while the system is advanced into a patient.

In another aspect of the present invention, a system is provided for treating a COPD patient's lung comprising: a delivery system element with a distal end, a proximal end and a length which is longer than 2 times the largest transverse dimension of the element, a lung treatment device configured to at least partially encircle the delivery system element while the system is advanced into a patient to deliver the treatment device to a treatment location in the lung.

In another aspect of the present invention, a system is provided for treating a COPD patient's lung comprising: a delivery system element with a distal end, a proximal end and a length which is longer than 2 times the largest transverse dimension of the element, a lung treatment device configured to at least partially encircle the delivery system element while the system is advanced into a patient to deliver the treatment device to a treatment location in the lung.

In another aspect of the present invention, a system is provided for treating a COPD patient's lung comprising: a delivery system canula with a distal end, a proximal end and a length which is longer than 2 times the largest transverse dimension of the canula, a lung treatment device configured to at least partially encircle the delivery system canula while the system is advanced into a patient to deliver the treatment device to a treatment location in the lung, whereas the lung treatment device is implanted in the lung to enhance lung elastic recoil.

In another aspect of the present invention, a system is provided for treating a lung comprising: a delivery system canula with a distal end, a proximal end and a length which is longer than 2 times the largest transverse dimension of the canula, a pulmonary treatment device configured to at least partially encircle the delivery system canula while the system is advanced into a patient to deliver the treatment device to a treatment location in the lung, whereas the treatment device is implanted in the lung to tension lung tissue.

In another aspect of the present invention, a system is provided for treating a lung comprising: a bronchoscope with a distal end, a proximal end and a length which is longer than 2 times the largest transverse dimension of working length portion of the bronchoscope, a pulmonary treatment device configured to at least partially encircle the bronchoscope while the system is advanced into a patient to deliver the treatment device to a treatment location in the lung, whereas the treatment device is implanted in the lung to treat COPD.

In another aspect of the present invention, a system is provided for treating a lung comprising: a bronchoscope with a distal end, a proximal end and a length which is longer than 2 times the largest transverse dimension of working length portion of the bronchoscope, a pulmonary treatment device configured to at least partially encircle the bronchoscope while the system is advanced into a patient to deliver the treatment device to a treatment location in the lung, whereas the treatment device is implanted in the lung to treat the symptoms relating to COPD.

In another aspect of the present invention, a system is provided for treating a lung comprising: a bronchoscope with a distal end, a proximal end and a length which is longer than 2 times the largest transverse dimension of working length portion of the bronchoscope, a pulmonary treatment device configured to at least partially encircle the bronchoscope while the system is advanced into a patient to deliver the treatment device to a treatment location in the lung, whereas the treatment device is implanted in the lung to by making one or more of the beneficial changes in the patient that are listed herein above.

In another aspect of the present invention, a system is provided for treating a lung comprising: a bronchoscope with a distal end, a proximal end and a length which is longer than 2 times the largest transverse dimension of working length portion of the bronchoscope, a pulmonary treatment device configured to at least partially encircle the bronchoscope while the system is advanced into a patient to deliver the treatment device to a treatment location in the lung, whereas the treatment device is elongated before it is implanted in the lung to make one or more of the beneficial changes in the patient that are listed herein above.

In another aspect of the present invention, a system is provided for treating a lung comprising: a bronchoscope with a distal end, a proximal end and a length which is longer than 2 times the largest transverse dimension of working length portion of the bronchoscope, a pulmonary treatment device configured to at least partially encircle the bronchoscope while the system is advanced into a patient to deliver the treatment device to a treatment location in the lung, whereas the treatment device is elongated to store elastic strain energy to be released in tissue to make one or more of the beneficial changes in the patient that are listed herein above.

In another aspect of the present invention, a system is provided for treating a lung comprising: a bronchoscope with a distal end, a proximal end and a lumen miming therethrough, a pulmonary treatment device configured to at least partially encircle the bronchoscope while the system is advanced into a patient to deliver the treatment device to a treatment location in the lung, whereas the treatment device is elongated to store elastic strain energy to be released in tissue to make one or more of the beneficial changes in the patient that are listed herein above.

In another aspect of the present invention, a system is provided for treating a lung comprising: a bronchoscope with a distal end, a proximal end and a lumen running therethrough, a pulmonary treatment device configured to at least partially encircle the bronchoscope while the system is advanced into a patient to deliver the treatment device to a treatment location in the lung, whereas the treatment device is elongated to store elastic strain energy to be used to tension lung tissue.

In another aspect of the present invention, a system is provided for treating a lung comprising: a bronchoscope with a distal end, a proximal end and a lumen running therethrough, a pulmonary treatment device configured to at least partially encircle the bronchoscope while the system is advanced into a patient to deliver the treatment device to a treatment location in the lung and a bronchoscope guide sleeve with a distal end, a proximal end and a lumen configured to allow the bronchoscope to be advanced through the bronchoscope guide sleeve; whereas the treatment device is elongated by the bronchoscope guide sleeve and the bronchoscope to store elastic strain energy in the treatment device to be used to tension lung tissue.

In another aspect of the present invention, a system is provided for treating a lung comprising: a pulmonary treatment device, a bronchoscope and a bronchoscope guide sleeve whereas the treatment device is configured with a proximal end, a distal end and a midsection and a lumen running through the treatment device proximal end and midsection along the central axis between the distal end and the proximal ends, the bronchoscope guide sleeve is configured with a proximal end, a distal end and an open lumen running through the full length of the bronchoscope guide sleeve along the central axis between the distal end and proximal end; the bronchoscope is configured to be advanced through the bronchoscope guide sleeve and through the proximal end and midsection of the lung treatment device so the treatment device length may be adjusted by sliding the bronchoscope guide sleeve along the axis of the coaxial bronchoscope.

In another aspect of the present invention, a system is provided for treating a lung comprising: an assembly for straightening a portion of a lung airway, the assembly comprising:

a straightening element; a first end configured for fixing to a first portion of the lung, the straightening element attached to the first end; a second end configured for fixing to a second portion of the lung, the straightening element being attached to the second end; a delivery device for delivering the first end to the first portion of the lung and for delivering the second end to the second portion of the lung.

In another aspect of the present invention, a system is provided for treating a lung comprising: an assembly for straightening a portion of a lung airway, the assembly comprising:

a straightening element; a first end configured for fixing to a first portion of the lung, the straightening element attached to the first end; a second end configured for fixing to a second portion of the lung, the straightening element being attached to the second end; a delivery device for delivering the first end to the first portion of the lung and for delivering the second end to the second portion of the lung; whereas the delivery device is a bronchoscope.

In another aspect of the present invention, a system is provided for treating a lung comprising: an assembly for straightening a portion of a lung airway, the assembly comprising:

a straightening element; a first end configured for fixing to a first portion of the lung, the straightening element attached to the first end; a second end configured for fixing to a second portion of the lung, the straightening element being attached to the second end; a delivery device for delivering the first end to the first portion of the lung and for delivering the second end to the second portion of the lung; whereas the delivery device is a tube.

In another aspect of the present invention, a system is provided for treating a lung comprising: an assembly for straightening a portion of a lung airway, the assembly comprising: a straightening element; a first end configured for fixing to a first portion of the lung, the straightening element attached to the first end; a second end configured for fixing to a second portion of the lung, the straightening element being attached to the second end; a delivery device for delivering the first end to the first portion of the lung and for delivering the second end to the second portion of the lung; whereas the straightening element is tensioned after at least one end is deployed.

In another aspect of the present invention, a system is provided for treating a lung comprising: an assembly for straightening a portion of a lung airway, the assembly comprising: a straightening element; a first end configured for fixing to a first portion of the lung, the straightening element attached to the first end; a second end configured for fixing to a second portion of the lung, the straightening element being attached to the second end; a delivery device for delivering the first end to the first portion of the lung and for delivering the second end to the second portion of the lung; whereas the straightening element and ends are made more co-axial before being released from the delivery device than they are while being delivered to the airway.

In another aspect of the present invention, a system is provided for treating a lung comprising: an assembly for straightening a portion of a lung airway, the assembly comprising: a straightening element; a first end configured for fixing to a first portion of the lung, the straightening element attached to the first end; a second end configured for fixing to a second portion of the lung, the straightening element being attached to the second end; a delivery device for delivering the first end to the first portion of the lung and for delivering the second end to the second portion of the lung; whereas the first end is a deformable spring.

In another aspect of the present invention, a system is provided for treating a lung comprising: an assembly for straightening a portion of a lung airway, the assembly comprising: a straightening element; a first end configured for fixing to a first portion of the lung, the straightening element attached to the first end; a second end configured for fixing to a second portion of the lung, the straightening element being attached to the second end; a delivery device for delivering the first end to the first portion of the lung and for delivering the second end to the second portion of the lung; whereas the second end is a deformable spring.

In another aspect of the present invention, a system is provided for treating a lung comprising: an assembly for straightening a portion of a lung airway, the assembly comprising: a straightening element; a first end configured for fixing to a first portion of the lung, the straightening element attached to the first end; a second end configured for fixing to a second portion of the lung, the straightening element being attached to the second end; a delivery device for delivering the first end to the first portion of the lung and for delivering the second end to the second portion of the lung; whereas the straightening element is a helix.

In another aspect of the present invention, a system is provided for straightening more than one lung airway, the assembly comprising: a first straightening element having a first end for attaching to a first airway in the lung; a second straightening element having a second end for attaching to a second airway in the lung; a connector that connects the first straightening element to the second straightening element; and a delivery device for delivering the first end to the first airway in the lung and for delivering the second end to the second airway in the lung.

In another aspect of the present invention, a system is provided for straightening more than one lung airway, the assembly comprising: a first straightening element having a first end for attaching to a first airway in the lung; a second straightening element having a second end for attaching to a second airway in the lung; a connector that connects the first straightening element to the second straightening element; and a delivery device for delivering the first end to the first airway in the lung and for delivering the second end to the second airway in the lung; whereas the delivery device is a bronchoscope In another aspect of the present invention, a system is provided for straightening more than one lung airway, the assembly comprising: a first straightening element having a first end for attaching to a first airway in the lung; a second straightening element having a second end for attaching to a second airway in the lung; a connector that connects the first straightening element to the second straightening element; and a delivery device for delivering the first end to the first airway in the lung and for delivering the second end to the second airway in the lung; whereas the delivery device is a tube.

In another aspect of the present invention, a system is provided for straightening more than one lung airway, the assembly comprising: a first straightening element having a first end for attaching to a first airway in the lung; a second straightening element having a second end for attaching to a second airway in the lung; a connector that connects the first straightening element to the second straightening element; and a delivery device for delivering the first end to the first airway in the lung and for delivering the second end to the second airway in the lung; whereas the first straightening element is tensioned after at least one end is deployed.

In another aspect of the present invention, a system is provided for straightening more than one lung airway, the assembly comprising: a first straightening element having a first end for attaching to a first airway in the lung; a second straightening element having a second end for attaching to a second airway in the lung; a connector that connects the first straightening element to the second straightening element; and a delivery device for delivering the first end to the first airway in the lung and for delivering the second end to the second airway in the lung; whereas the first straightening element and first end is made more co-axial before being released from the delivery system than they are while being delivered to the airway.

In another aspect of the present invention, a system is provided for straightening more than one lung airway, the assembly comprising: a first straightening element having a first end for attaching to a first airway in the lung; a second straightening element having a second end for attaching to a second airway in the lung; a connector that connects the first straightening element to the second straightening element; and a delivery device for delivering the first end to the first airway in the lung and for delivering the second end to the second airway in the lung; whereas the second straightening element and second end is made more co-axial before being released from the delivery device than they are while being delivered to the airway.

In another aspect of the present invention, a system is provided for straightening more than one lung airway, the assembly comprising: a first straightening element having a first end for attaching to a first airway in the lung; a second straightening element having a second end for attaching to a second airway in the lung; a connector that connects the first straightening element to the second straightening element; and a delivery device for delivering the first end to the first airway in the lung and for delivering the second end to the second airway in the lung; whereas the first tissue gathering end is a deformable spring.

In another aspect of the present invention, a system is provided for straightening more than one lung airway, the assembly comprising: a first straightening element having a first end for attaching to a first airway in the lung; a second straightening element having a second end for attaching to a second airway in the lung; a connector that connects the first straightening element to the second straightening element; and a delivery device for delivering the first end to the first airway in the lung and for delivering the second end to the second airway in the lung; whereas the first straightening element is a helix.

In another aspect of the present invention, a system is provided for straightening more than one lung airway, the assembly comprising: a first straightening element having a first end for attaching to a first airway in the lung; a second straightening element having a second end for attaching to a second airway in the lung; a connector that connects the first straightening element to the second straightening element; and a delivery device for delivering the first end to the first airway in the lung and for delivering the second end to the second airway in the lung; whereas the second straightening element is a helix.

In another aspect of the present invention, a system is provided for straightening more than one lung airway, the assembly comprising: a first straightening element having a first end for attaching to a first airway in the lung; a second straightening element having a second end for attaching to a second airway in the lung; a connector that connects the first straightening element to the second straightening element; and a delivery device for delivering the first end to the first airway in the lung and for delivering the second end to the second airway in the lung; whereas the connector that connects the first straightening element to the second straightening element is a v shaped spring.

In another aspect of the present invention, a system is provided for straightening more than one lung airway, the assembly comprising: a first straightening element having a first end for attaching to a first airway in the lung; a second straightening element having a second end for attaching to a second airway in the lung; a connector that connects the first straightening element to the second straightening element; and a delivery device for delivering the first end to the first airway in the lung and for delivering the second end to the second airway in the lung; whereas the connector that connects the first straightening element to the second straightening element is a v shaped spring.

In another aspect of the present invention, a system is provided for straightening more than one lung airway, the assembly comprising: a first straightening element having a first end for attaching to a first airway in the lung; a second straightening element having a second end for attaching to a second airway in the lung; a connector that connects the first straightening element to the second straightening element; and a delivery device for delivering the first end to the first airway in the lung and for delivering the second end to the second airway in the lung; additionally, more components may be included to be used to straighten a 3rd or 4th, 5th or 6th airway with a single device.

In another aspect of the present invention, a lung airway straightening system is provided for enhancing breathing efficiency of a patient with an airway, the system comprising: an implantable device configured to impart a straightening force on a lung airway, the implantable device including a proximal end, and a distal end with a transition section connecting the two ends that includes at least one helical loop structure; furthermore, the device has a first delivery configuration and a second deployed configuration, the first configuration of the implantable device corresponds to a deliverable length constrained condition, the second configuration is configured so the distance between the start and end of at least one of the helical loop structurer can be increased to straighten the airway.

In another aspect of the present invention, a lung airway straightening system is provided for enhancing breathing efficiency of a patient with an airway, the system comprising: an implantable device configured to impart tension on lung tissue, the implantable device including a proximal stabilizing end, and a distal tissue gathering end with a transition section connecting the two ends that includes at least one helical loop structure with a start and an end to the helical loop; furthermore, the device has a first delivery configuration and a second deployed configuration, the first configuration of the implantable device corresponds to a deliverable condition and a finite distance between the start and end of at least one of the helical loop structures, the second configuration is configured so the distance between the start and end of the same helical loop structures may be elastically strained longer to apply tension to lung tissue.

In another aspect of the present invention, a lung airway straightening system is provided for enhancing breathing efficiency of a patient with an airway, the system comprising: an implantable device configured to impart tension on lung tissue, the implantable device including a proximal stabilizing end, and a distal tissue gathering end with a transition section connecting the two ends that includes at least one helical loop structure with a start and an end to the helical loop; furthermore, the device has a first delivery configuration and a second deployed configuration, the first configuration of the implantable device corresponds to a deliverable condition and a finite distance between the start and end of at least one of the helical loop structures, the second configuration is configured so the distance between the start and end of the same helical loop structures may be elastically strained longer to apply tension to lung tissue; wherein at least one of the ends comprise a circular helical section when the implantable device is in the second configuration.

In another aspect of the present invention, a lung airway straightening system is provided for enhancing breathing efficiency of a patient with an airway, the system comprising: an implantable device configured to impart tension on lung tissue, the implantable device including a proximal stabilizing end, and a distal tissue gathering end with a transition section connecting the two ends that includes at least one helical loop structure with a start and an end to the helical loop; furthermore, the device has a first delivery configuration and a second deployed configuration, the first configuration of the implantable device corresponds to a deliverable condition and a finite distance between the start and end of at least one of the helical loop structures, the second configuration is configured so the distance between the start and end of the same helical loop structures may be elastically strained longer to apply tension to lung tissue; wherein both of the ends comprise a circular helical section when the implantable device is in the second configuration.

In another aspect of the present invention, a lung airway straightening system is provided for enhancing breathing efficiency of a patient with an airway, the system comprising: an implantable device configured to impart tension on lung tissue, the implantable device including a proximal stabilizing end, and a distal tissue gathering end with a transition section connecting the two ends that includes at least one helical loop structure with a start and an end to the helical loop; furthermore, the device has a first delivery configuration and a second deployed configuration, the first configuration of the implantable device corresponds to a deliverable condition and a finite distance between the start and end of at least one of the helical loop structures, the second configuration is configured so the distance between the start and end of the same helical loop structures may be elastically strained longer to apply tension to lung tissue; wherein the implantable device further comprises a jacket (jacket can be metallic, plastic, coating, coil or extrusion made from a variety of materials, such as metals (e.g. stainless steel, titanium, nitinol, nickel, cobalt chrome, or a combination of these) or polymers (e.g. polycarbonate urethane, polytetrafluoroethylene (PTFE), ethylene tetrafluoroethylene (ETFE). fluorinated ethylene propylene (FEP), polyimide film (e.g. Kapton®), polyimide, polyether ether ketone (PEEK), polyethylene, ethylene-vinyl acetate (EVA) (also known as poly (ethylene-vinyl acetate) (PEVA)), polypropylene, polyvinyl alcohol (PVA), polyurethane, nylon, polyether block amides (PEBA), acrylonitrile butadiene styrene (ABS), polybutyrate, butyrate, polyethylene terephthalate (PET), polysulfone (PES), ethylene tetrafluoroethylene (ETFE), polyvinylidene fluoride (PVDF), thermoplastic polyurethane elastomers (e.g. Pellethane®), aliphatic polyether-based thermoplastic polyurethanes (TPUs) (e.g. Tecoflex®), metallocenes or a combination of these) which covers a portion of the implantable device, the jacket configured to reduce erosion into the airway by a deployed implantable device (by maximizing the bearing area in contact with the tissue to be greater than 9.81E−7 inches squared of bearing area per linear inch of the implantable device).

In another aspect of the present invention, a lung airway straightening system is provided for enhancing breathing efficiency of a patient with an airway, the system comprising: an implantable device configured to impart tension on lung tissue, the implantable device including a proximal stabilizing end, and a distal tissue gathering end with a transition section connecting the two ends that includes at least one helical loop structure with a start and an end to the helical loop; furthermore, the device has a first delivery configuration and a second deployed configuration, the first configuration of the implantable device corresponds to a deliverable condition and a finite distance between the start and end of at least one of the helical loop structures, the second configuration is configured so the distance between the start and end of the same helical loop structures may be elastically strained longer to apply tension to lung tissue; wherein a jacket covers the at least one helical sections.

In another aspect of the present invention, a lung airway straightening system is provided for enhancing breathing efficiency of a patient with an airway, the system comprising: an implantable device configured to impart tension on lung tissue, the implantable device including a proximal stabilizing end, and a distal tissue gathering end with a transition section connecting the two ends that includes at least one helical loop structure with a start and an end to the helical loop; furthermore, the device has a first delivery configuration and a second deployed configuration, the first configuration of the implantable device corresponds to a deliverable condition and a finite distance between the start and end of at least one of the helical loop structures, the second configuration is configured so the distance between the start and end of the same helical loop structures may be elastically strained longer to apply tension to lung tissue; wherein a jacket covers the distal end of the implantable device.

In another aspect of the present invention, a lung airway straightening system is provided for enhancing breathing efficiency of a patient with an airway, the system comprising: an implantable device configured to impart tension on lung tissue, the implantable device including a proximal stabilizing end, and a distal tissue gathering end with a transition section connecting the two ends that includes at least one helical loop structure with a start and an end to the helical loop; furthermore, the device has a first delivery configuration and a second deployed configuration, the first configuration of the implantable device corresponds to a deliverable condition and a finite distance between the start and end of at least one of the helical loop structures, the second configuration is configured so the distance between the start and end of the same helical loop structures may be elastically strained longer to apply tension to lung tissue; wherein the distal end of the implantable device is configured to couple with the airway.

In another aspect of the present invention, a lung airway straightening system is provided for enhancing breathing efficiency of a patient with an airway, the system comprising: an implantable device configured to impart tension on lung tissue, the implantable device including a proximal stabilizing end, and a distal tissue gathering end with a transition section connecting the two ends that includes at least one helical loop structure with a start and an end to the helical loop; furthermore, the device has a first delivery configuration and a second deployed configuration, the first configuration of the implantable device corresponds to a deliverable condition and a finite distance between the start and end of at least one of the helical loop structures, the second configuration is configured so the distance between the start and end of the same helical loop structures may be elastically strained longer to apply tension to lung tissue; wherein the proximal end of the implantable device is atraumatic.

A method for treating a lung of a patient, the lung including a lung passageway system having a first lung passageway elongate axial region with an associated first local lung passageway central axis and a second lung passageway elongate axial region with an associated second local lung passageway central axis, the method comprising: introducing an elongate body of an implant system axially into the lung passageway system so that a proximal portion of the elongate body is disposed within the first axial lung passageway region and so that a distal implant portion of the elongate body is disposed within the second axial lung passageway region; tensioning a lung tissue volume disposed at least in part distal to at least one of the lung passageway axial regions by bending the elongate body between the proximal and distal portions so as to urge the first local lung passageway axis of the first lung passageway axial region laterally toward the second lung passageway axial region while the proximal and distal portions of the elongate body extend axially within the first and second lung passageway axial regions, respectively.

A method for treating a lung of a patient, the lung including a lung passageway system having a first lung passageway elongate axial region with an associated first local lung passageway central axis, and a second lung passageway elongate axial region with an associated second local lung passageway central axis, the method comprising: introducing an elongate body of an implant system axially into the lung passageway system so that a proximal portion of the elongate body is disposed within the first axial lung passageway region and so that a distal implant portion of the elongate body is disposed within the second axial lung passageway region; tensioning a lung tissue volume disposed at least in part distal to at least one of the lung passageway axial regions by releasing strain energy that has been previously stored in the elongate body to compress the elongate body between the proximal and distal portions so as to urge the first local lung passageway axis of the first lung passageway axial region laterally toward the second lung passageway axial region while the proximal and distal portions of the elongate body extend within the first and second lung passageway axial regions, respectively.

A method for treating a lung of a patient, the lung including a lung passageway system having a first lung passageway elongate axial region with an associated first local lung passageway central axis, and a second lung passageway elongate axial region with an associated second local lung passageway central axis, the method comprising: introducing an elongate body of an implant system axially into the lung passageway system so that a proximal portion of the elongate body is disposed within the first axial lung passageway region and so that a distal implant portion of the elongate body is disposed within the second axial lung passageway region; tensioning a lung tissue volume by releasing strain energy that has been previously stored in the elongate body so as to urge the first local lung passageway axis of the first lung passageway axial region laterally toward the second lung passageway axial region while the proximal and distal portions of the elongate body extend axially within the first and second lung passageway axial regions, respectively.

A method for treating a lung of a patient, the lung including an lung passageway system having a first lung passageway elongate axial region with an associated first local lung passageway central axis, and a second lung passageway elongate axial region with an associated second local lung passageway central axis, the method comprising: introducing an elongate body of an implant system axially into the lung passageway system so that a proximal portion of the elongate body is disposed within the first axial lung passageway region and so that a distal implant portion of the elongate body is disposed within the second axial lung passageway region; tensioning a lung tissue volume by rotating the elongate body.

In another aspect of the present invention, a lung airway straightening system is provided for enhancing breathing efficiency of a patient with an airway, the system comprising: an implantable device configured to impart tension on lung tissue, the implantable device including a proximal stabilizing end, and a distal tissue gathering end with a transition section connecting the two ends that includes at least one helical loop structure with a start and an end to the helical loop; furthermore, the device has a first delivery configuration and a second deployed configuration, the first configuration of the implantable device corresponds to a deliverable condition and a finite distance between the start and end of at least one of the helical loop structures, the second configuration is configured so the distance between the start and end of the same helical loop structures may be elastically strained longer to apply tension to lung tissue; wherein the proximal end of the implantable device comprising one or more features selected from the following: a ball, loop, break away link, threaded hole or shaft, friction fit taper or hole, that is reversibly coupled to a delivery system.

In another aspect of the present invention, a lung airway straightening system is provided for enhancing breathing efficiency of a patient with an airway, the system comprising: an implantable device configured to impart tension on lung tissue, the implantable device including a proximal stabilizing end, and a distal tissue gathering end with a transition section connecting the two ends that includes at least one helical loop structure with a start and an end to the helical loop; furthermore, the device has a first delivery configuration and a second deployed configuration, the first configuration of the implantable device corresponds to a deliverable condition and a finite distance between the start and end of at least one of the helical loop structures, the second configuration is configured so the distance between the start and end of the same helical loop structures may be elastically strained longer to apply tension to lung tissue; wherein the implantable device is made of a metal alloy that contains nickel and titanium.

In another aspect of the present invention, a lung airway straightening system is provided for enhancing breathing efficiency of a patient with an airway, the system comprising: an implantable device configured to impart tension on lung tissue, the implantable device including a proximal stabilizing end, and a distal tissue gathering end with a transition section connecting the two ends that includes at least one helical loop structure with a start and an end to the helical loop; furthermore, the device has a first delivery configuration and a second deployed configuration, the first configuration of the implantable device corresponds to a deliverable condition and a finite distance between the start and end of at least one of the helical loop structures, the second configuration is configured so the distance between the start and end of the same helical loop structures may be elastically strained longer to apply tension to lung tissue; wherein the implantable device is made from a stainless-steel alloy.

In another aspect of the present invention, a lung airway straightening system is provided for enhancing breathing efficiency of a patient with an airway, the system comprising: an implantable device configured to impart tension on lung tissue, the implantable device including a proximal stabilizing end, and a distal tissue gathering end with a transition section connecting the two ends that includes at least one helical loop structure with a start and an end to the helical loop; furthermore, the device has a first delivery configuration and a second deployed configuration, the first configuration of the implantable device corresponds to a deliverable condition and a finite distance between the start and end of at least one of the helical loop structures, the second configuration is configured so the distance between the start and end of the same helical loop structures may be elastically strained longer to apply tension to lung tissue; wherein the implantable device is made from a steel alloy containing chromium.

In another aspect of the present invention, a lung airway straightening system is provided for enhancing breathing efficiency of a patient with an airway, the system comprising: an implantable device configured to impart tension on lung tissue, the implantable device including a proximal stabilizing end, and a distal tissue gathering end with a transition section connecting the two ends that includes at least one helical loop structure with a start and an end to the helical loop; furthermore, the device has a first delivery configuration and a second deployed configuration, the first configuration of the implantable device corresponds to a deliverable condition and a finite distance between the start and end of at least one of the helical loop structures, the second configuration is configured so the distance between the start and end of the same helical loop structures may be elastically strained longer to apply tension to lung tissue; wherein the implantable device is made from an alloy containing cobalt.

In another aspect of the present invention, a lung airway straightening system is provided for enhancing breathing efficiency of a patient with an airway, the system comprising: an implantable device configured to impart tension on lung tissue, the implantable device including a proximal stabilizing end, and a distal tissue gathering end with a transition section connecting the two ends that includes at least one helical loop structure with a start and an end to the helical loop; furthermore, the device has a first delivery configuration and a second deployed configuration, the first configuration of the implantable device corresponds to a deliverable condition and a finite distance between the start and end of at least one of the helical loop structures, the second configuration is configured so the distance between the start and end of the same helical loop structures may be elastically strained longer to apply tension to lung tissue; wherein the stabilizing end comprises more helical loops than the tissue gathering end when the implantable device is in the second configuration.

In another aspect of the present invention, a lung airway straightening system is provided for enhancing breathing efficiency of a patient with an airway, the system comprising: an implantable device configured to impart tension on lung tissue, the implantable device including a proximal stabilizing end, and a distal tissue gathering end with a transition section connecting the two ends that includes at least one helical loop structure with a start and an end to the helical loop; furthermore, the device has a first delivery configuration and a second deployed configuration, the first configuration of the implantable device corresponds to a deliverable condition and a finite distance between the start and end of at least one of the helical loop structures, the second configuration is configured so the distance between the start and end of the same helical loop structures may be elastically strained longer to apply tension to lung tissue; wherein the tissue gathering end comprises less than one loop when the implantable device is in the second configuration.

In another aspect of the present invention, a lung airway straightening system is provided for enhancing breathing efficiency of a patient with an airway, the system comprising: an implantable device configured to impart tension on lung tissue, the implantable device including a proximal stabilizing end, and a distal tissue gathering end with a transition section connecting the two ends that includes at least one helical loop structure with a start and an end to the helical loop; furthermore, the device has a first delivery configuration and a second deployed configuration, the first configuration of the implantable device corresponds to a deliverable condition and a finite distance between the start and end of at least one of the helical loop structures, the second configuration is configured so the distance between the start and end of the same helical loop structures may be elastically strained longer to apply tension to lung tissue; wherein the helical section transitions into the proximal end via a bend that is disposed between the proximal portion of the helical section and the proximal end such that the helical section is straightened when proximal end is repositioned more proximally relative to the proximal portion of the helical section when the device is in the second configuration.

In another aspect of the present invention, a lung airway straightening system is provided for enhancing breathing efficiency of a patient with an airway, the system comprising: an implantable device configured to impart tension on lung tissue, the implantable device including a proximal stabilizing end, and a distal tissue gathering end with a transition section connecting the two ends that includes at least one helical loop structure with a start and an end to the helical loop; furthermore, the device has a first delivery configuration and a second deployed configuration, the first configuration of the implantable device corresponds to a deliverable condition and a finite distance between the start and end of at least one of the helical loop structures, the second configuration is configured so the distance between the start and end of the same helical loop structures may be elastically strained longer to apply tension to lung tissue; wherein the implant comprises a spring element and wherein the implant is constrained to the delivery configuration during delivery and wherein the implant is configured to naturally recover from the constrained delivery configuration to the deployed configuration during deployment.

In another aspect of the present invention, a lung tensioning device is provided that tensions lung tissue with the application of a rotating motion to turn the implant after a portion of the implant has engaged tissue.

In another aspect of the present invention, a lung tensioning device is provided that tensions lung tissue with the application of a combination of rotating motion and longitudinal translation motion to turn the implant and to apply longitudinal translation of the implant after a portion of the implant has engaged tissue.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 63A-63C illustrates embodiments of treatment devices with a variety of tissue gathering and anchoring element shapes.

FIG. 75 illustrates an embodiment of a treatment device section made from two joined wires.

FIG. 76A-76B illustrates embodiments of treatment device attachment end configurations.

FIG. 77 illustrates an embodiment of a treatment device socketing attachment end.

FIG. 78 illustrates an embodiment of a treatment device threaded attachment end.

FIG. 94 illustrates steps of an embodiment of a method to deploy two treatment devices in branching airways.

FIGS. 97A-97C illustrates an embodiment of a torsion-based treatment device that is surgically installed.

FIGS. 99A-99D illustrate embodiments of distal tips having twisted ends.

FIG. 123 illustrates an embodiment of a delivery device having a deployment device that is coupleable to a clip in a manner that allows transmission of torque to the clip by rotation of the deployment device.

Figures 123, 124:
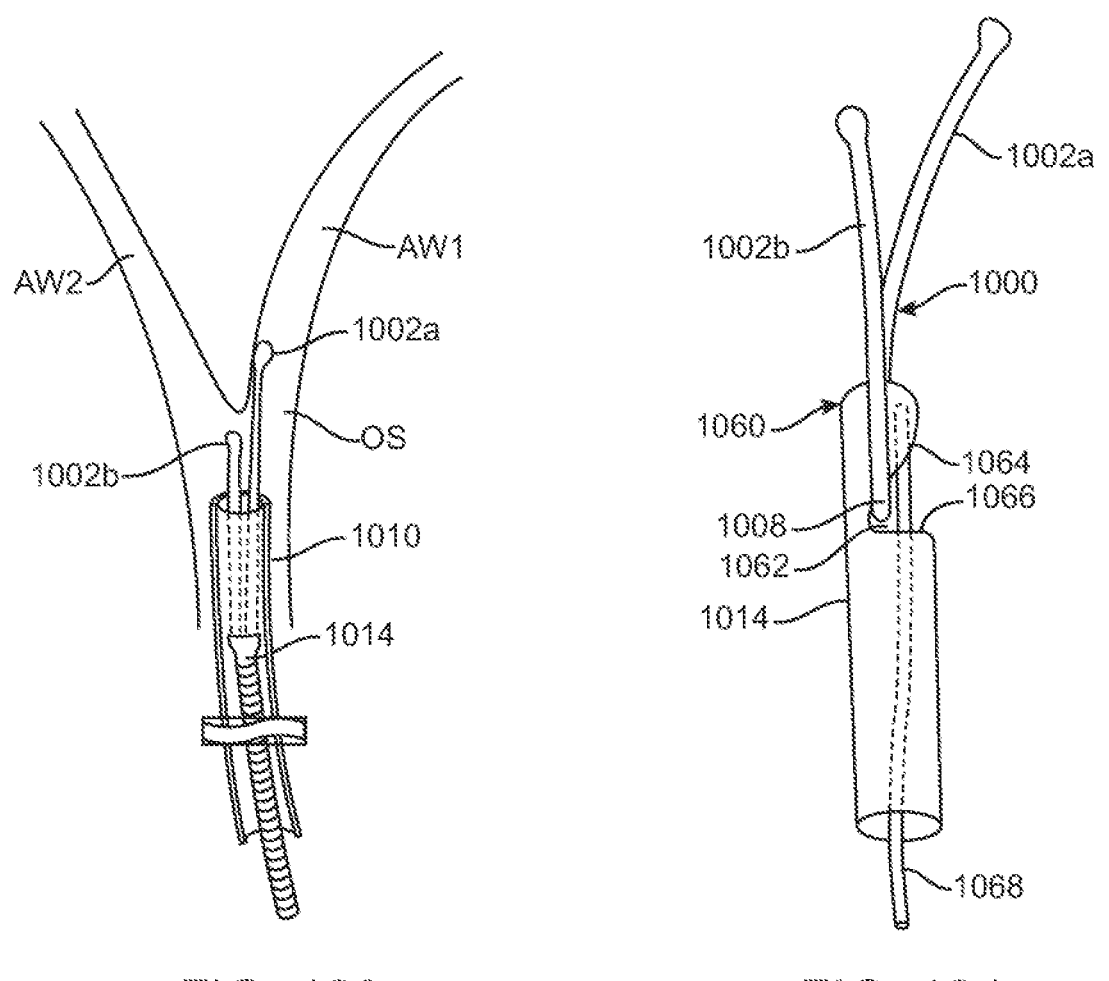

FIG. 124 provides a close-up view of an embodiment of a deployment device that is coupleable to a clip in a manner that allows transmission of torque.

Figure 125:
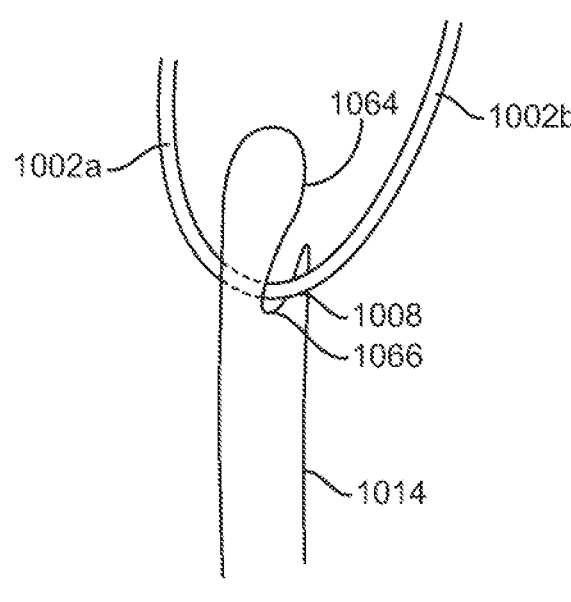

FIG. 125 illustrates an embodiment deployment device having a window of a spiral shape.

Figure 126:
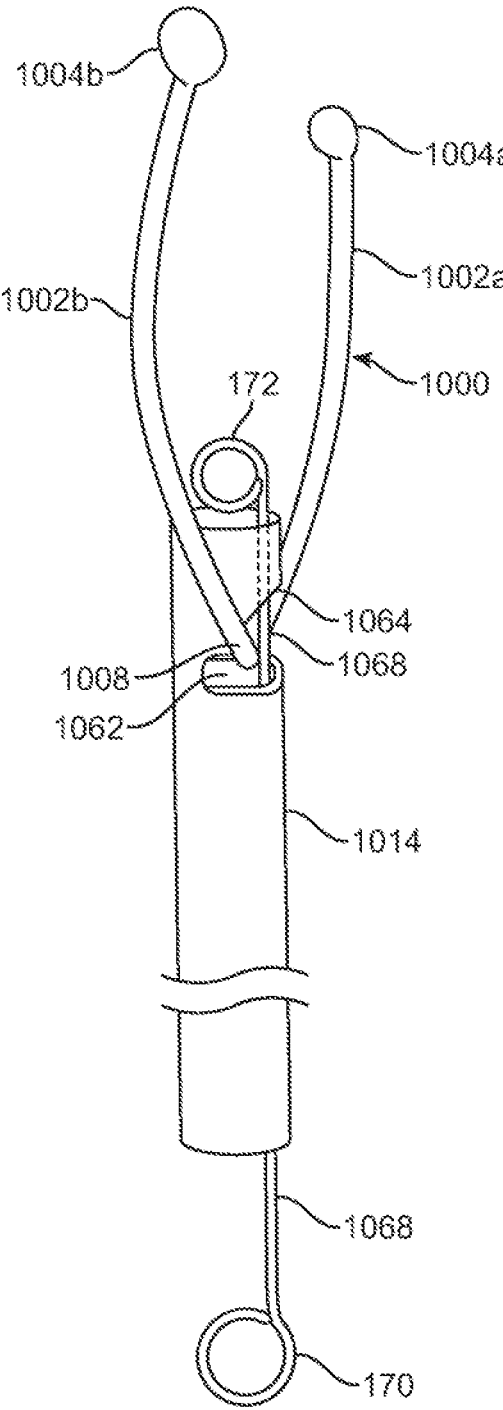

FIG. 126 illustrates an embodiment of a deployment device similar to FIG. 124, however here the hitch wire has a configured proximal end and distal end.

Figure 127:
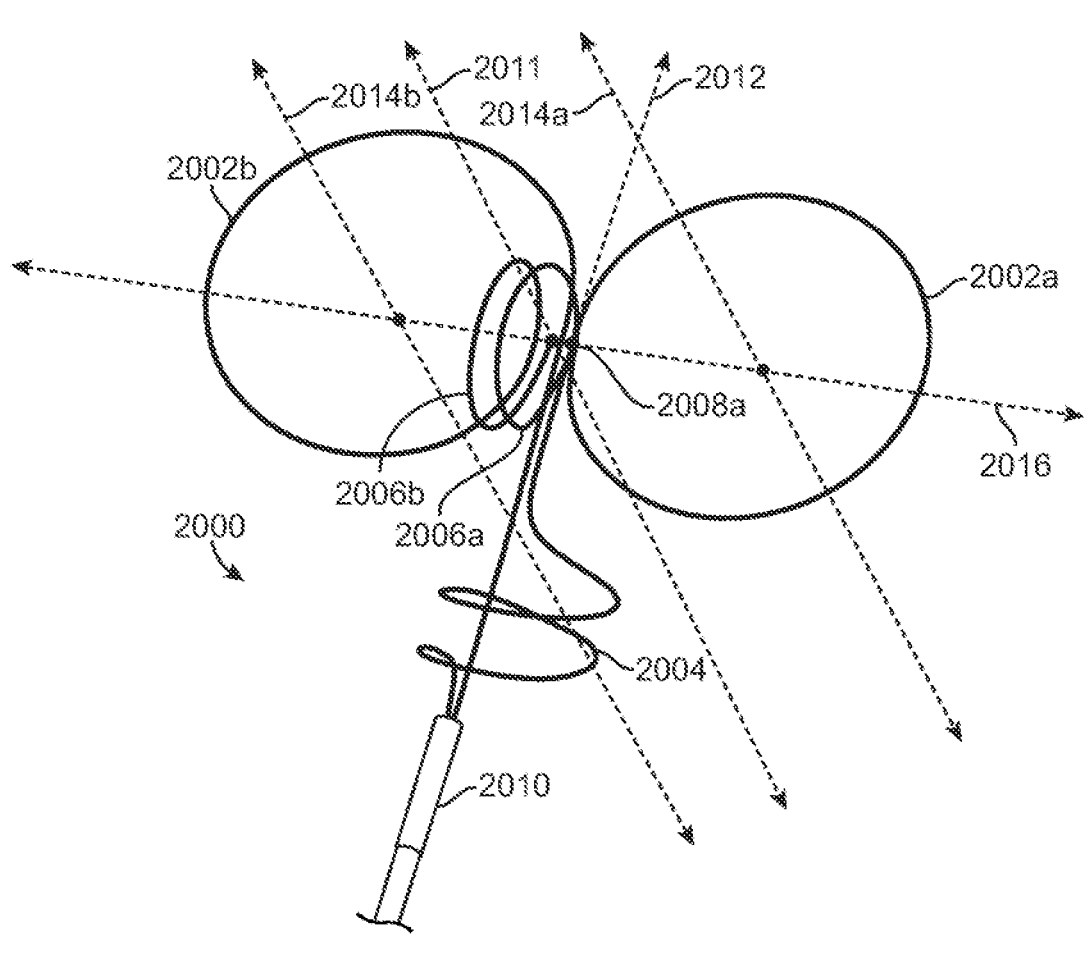

FIG. 127 illustrates an embodiment of an invertible pulmonary treatment device emerging from a delivery device.

Figure 128:
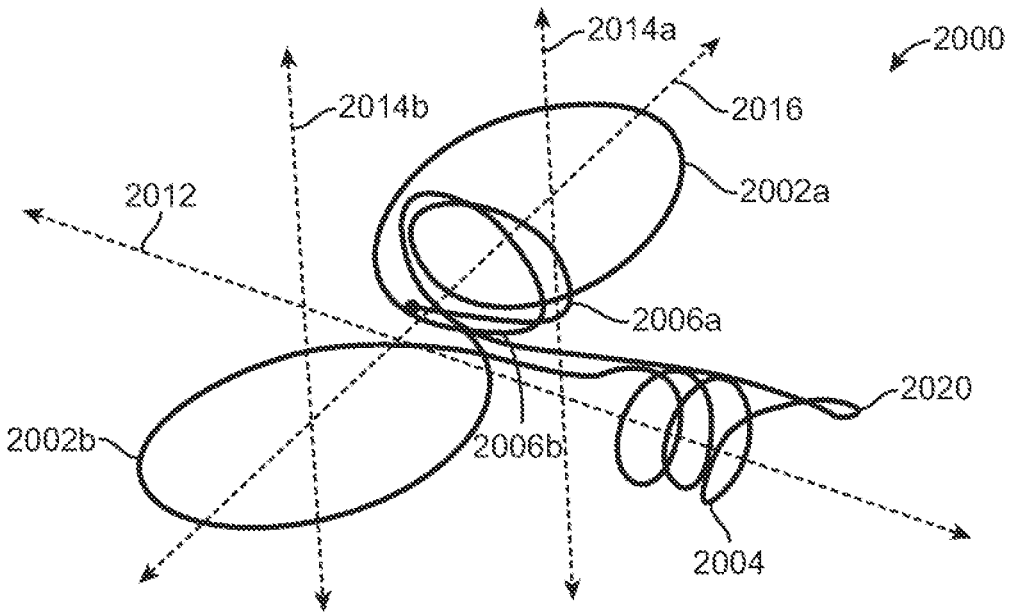

FIG. 128 illustrates an embodiment of an invertible pulmonary treatment device that is similar to that illustrated in FIG. 127.

Figure 129:
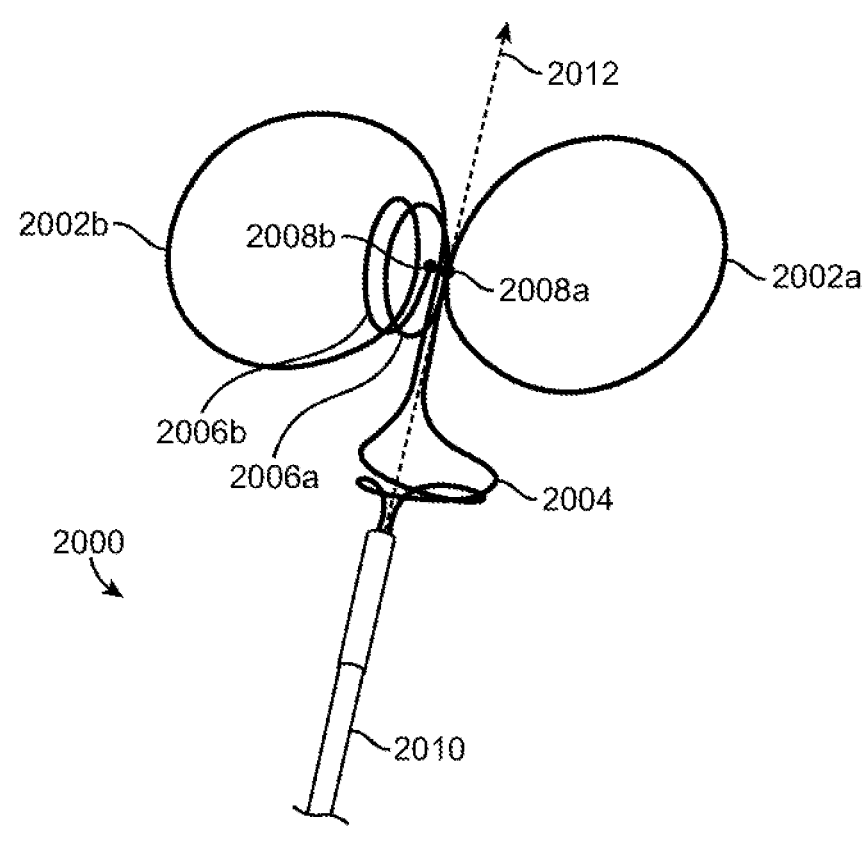

FIG. 129 illustrates another embodiment of an invertible pulmonary treatment device.

Figure 130:
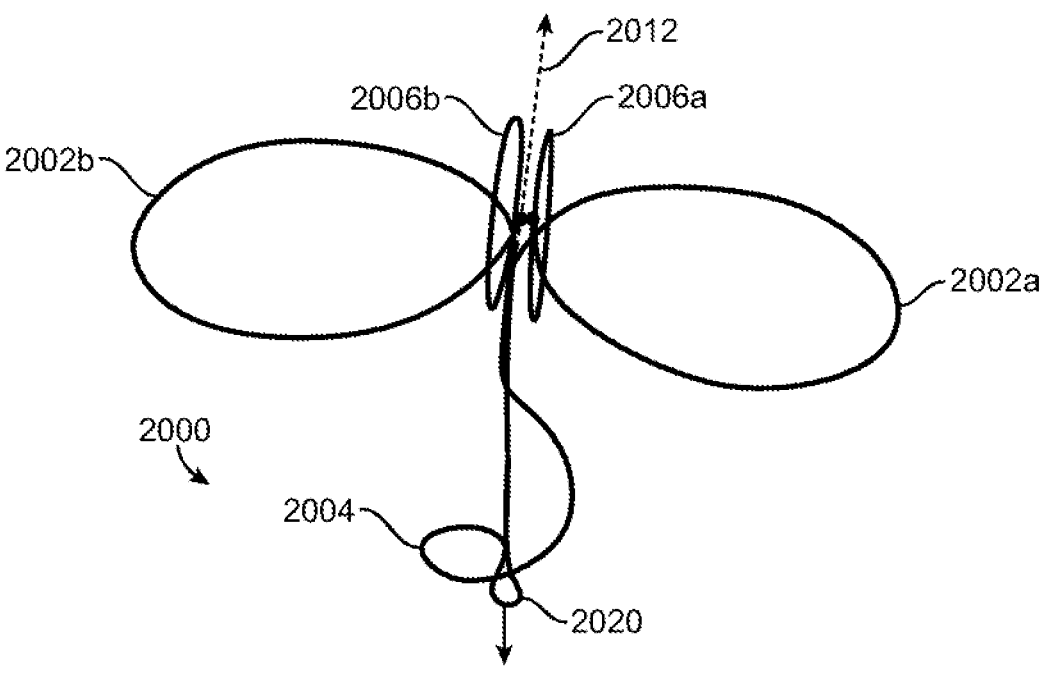

FIG. 130 illustrates yet another embodiment of an invertible pulmonary treatment device.

Figure 131:
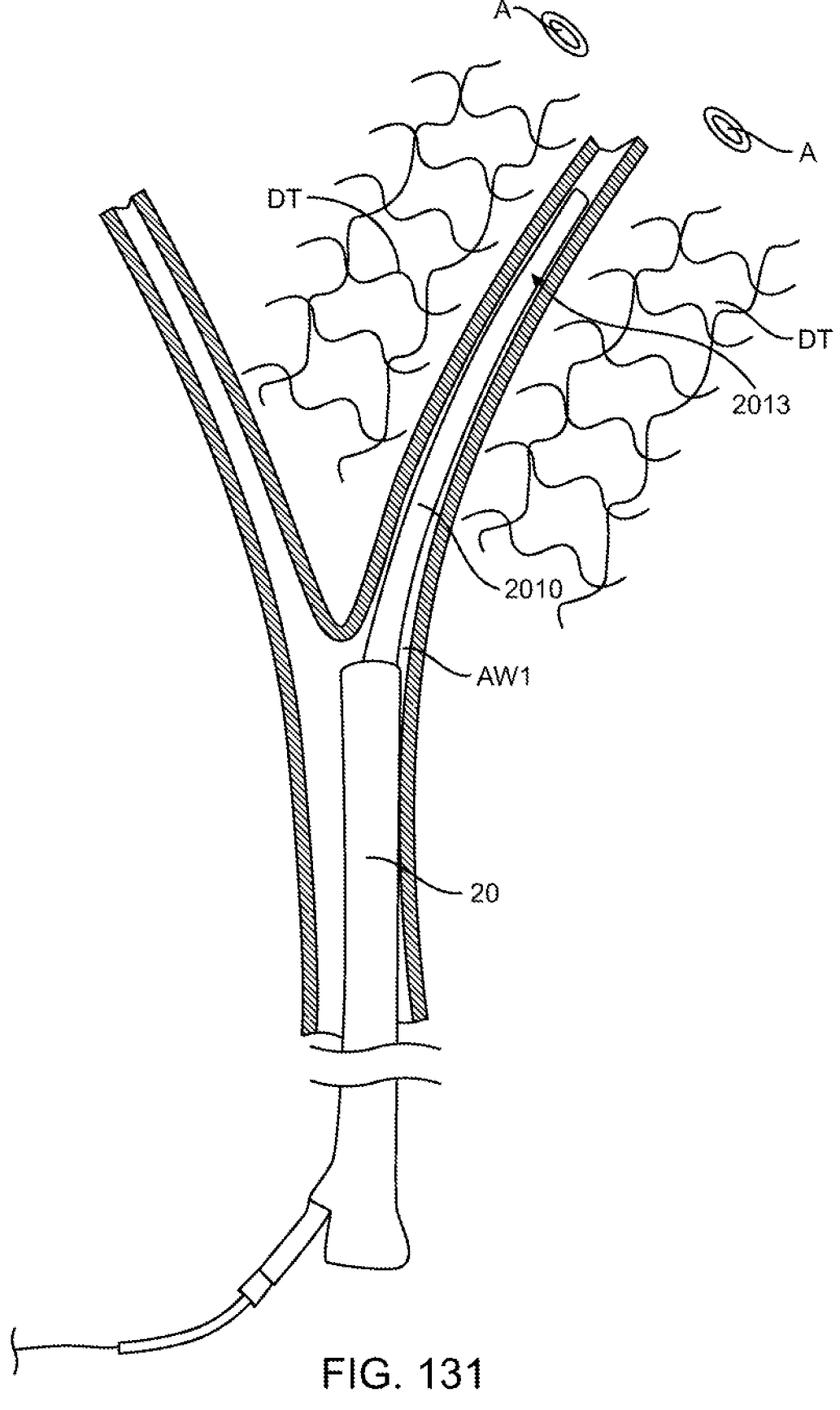

FIG. 131 illustrates a branched lung passageway comprising a first airway that extends into damaged tissue, along with a delivery device positioned therein.

Figure 132:
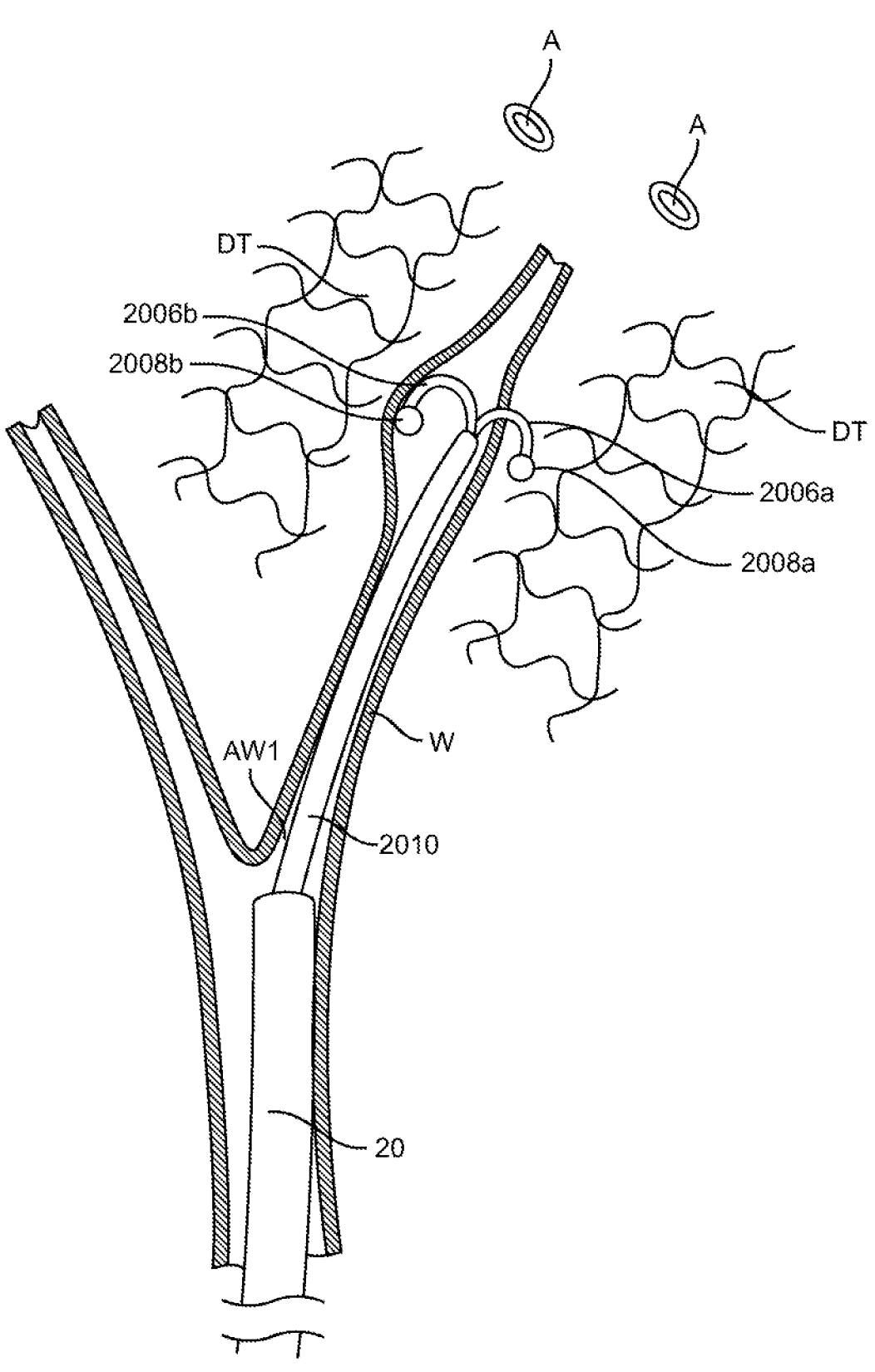

FIG. 132 illustrates an early step in a process of deployment of an invertible pulmonary treatment device wherein the distal tips have emerged from the distal end of the delivery device.

Figure 133:
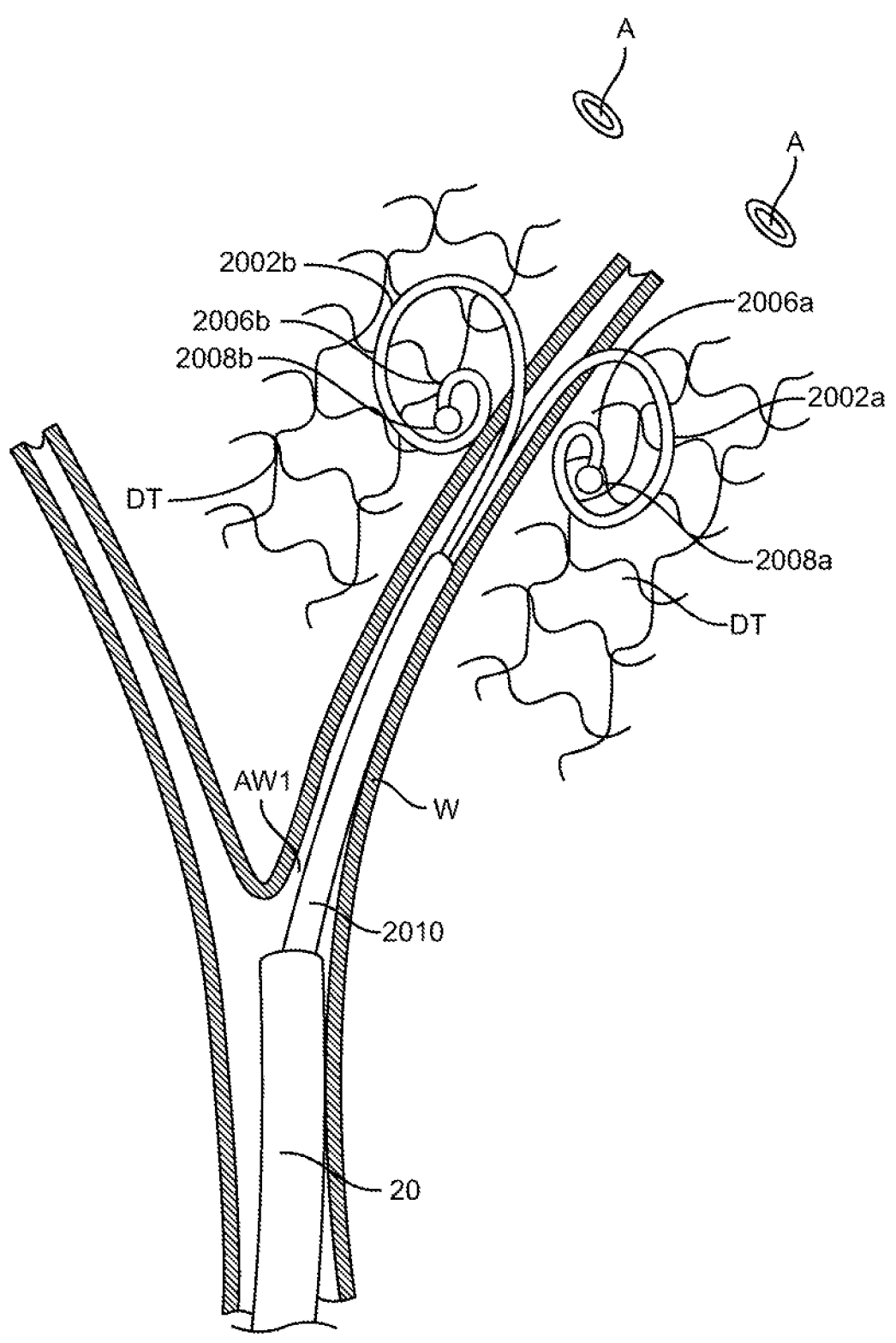

FIG. 133 illustrates tissue gathering elements extending into damaged tissue and holding elements grasping damaged tissue.

Figure 134:
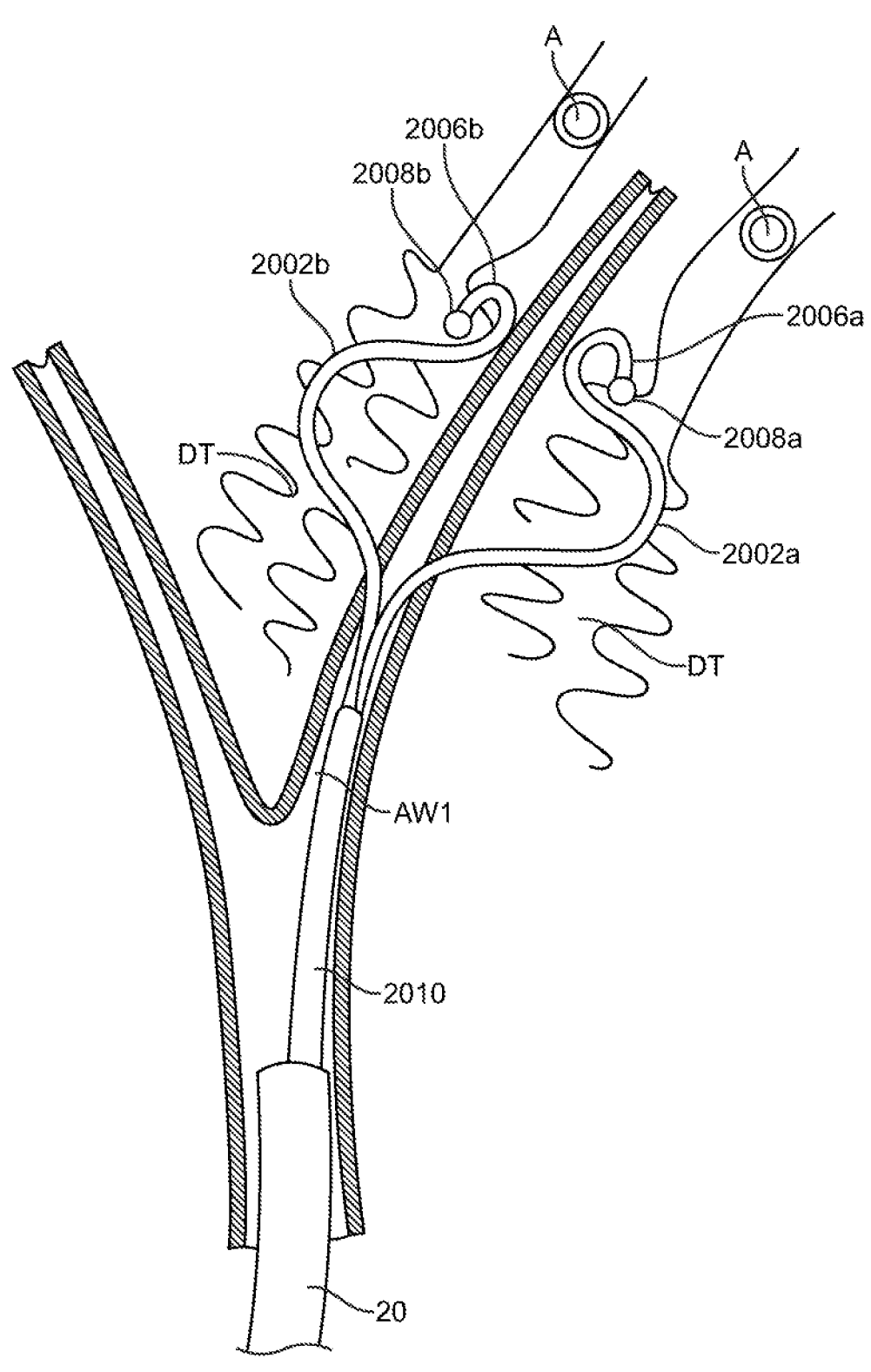

FIG. 134 illustrates an invertible pulmonary treatment device that has been pulled so that the tissue gathering elements have inverted.

Figure 135:
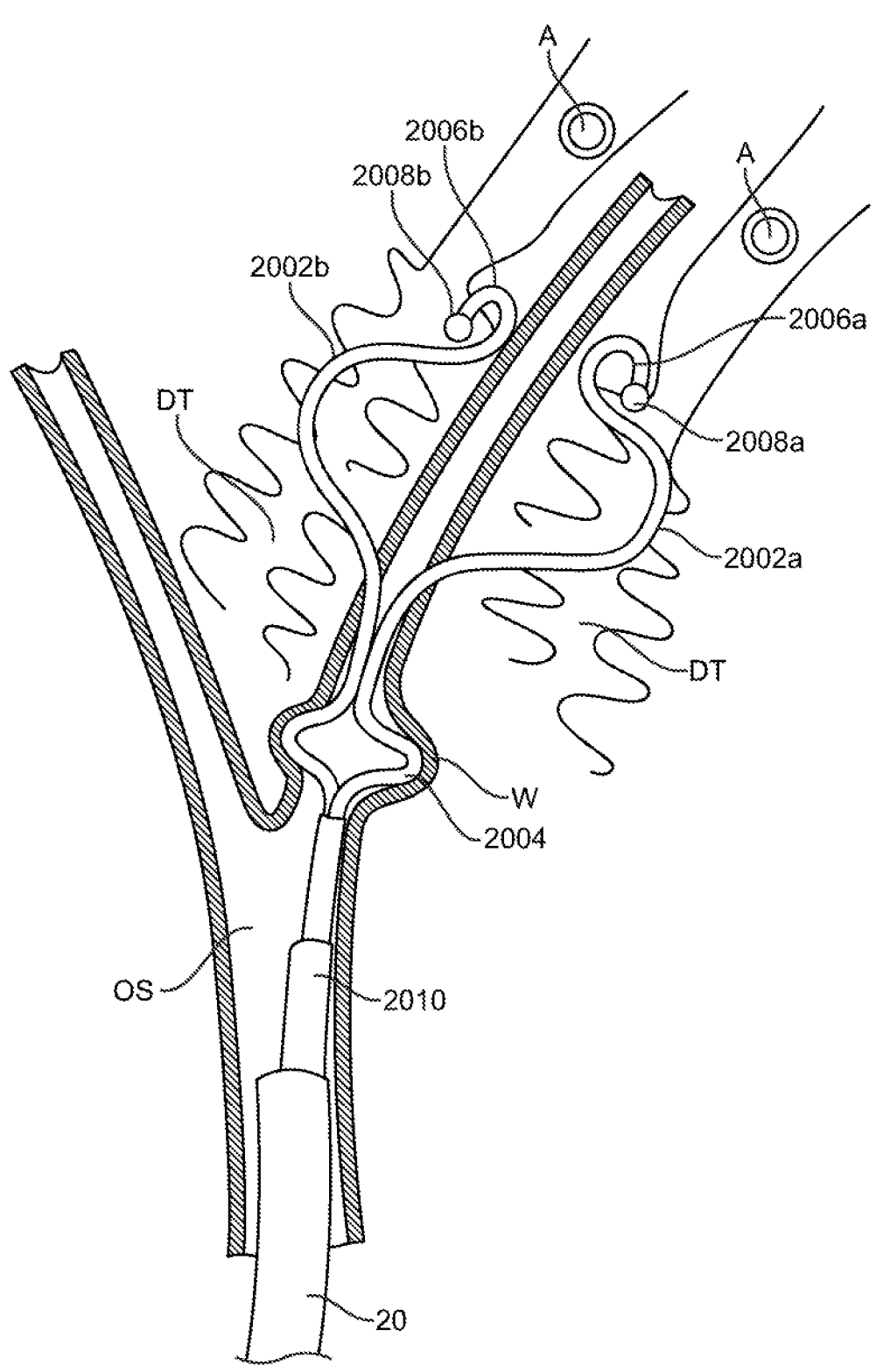

FIG. 135 illustrates an embodiment of an anchoring element deployed by retraction of a delivery device and optionally a bronchoscope.

Figure 136:
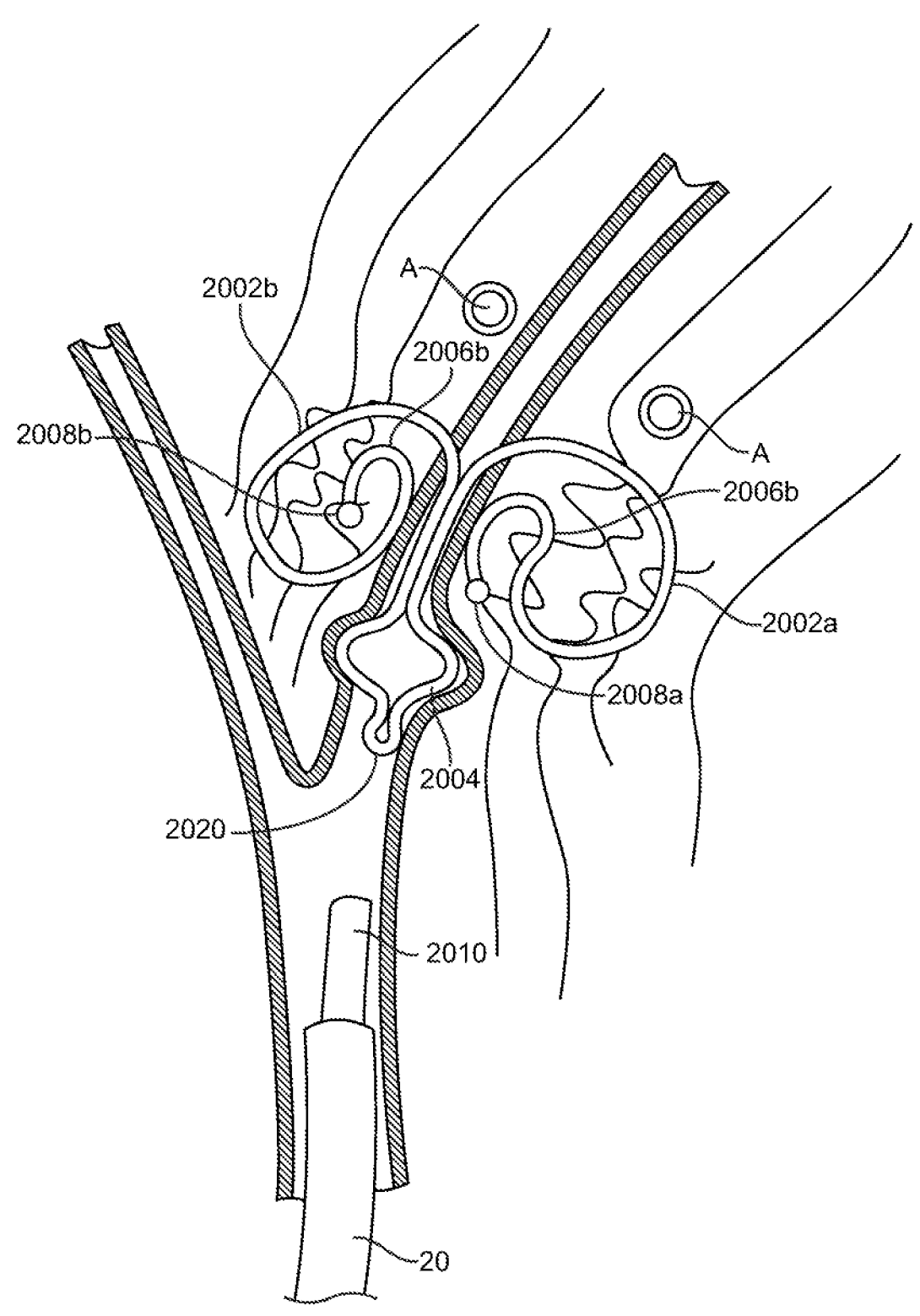

FIG. 136 illustrates an embodiment of an invertible pulmonary treatment device decoupled from a delivery device, revealing an attachment feature.

Figure 137A:
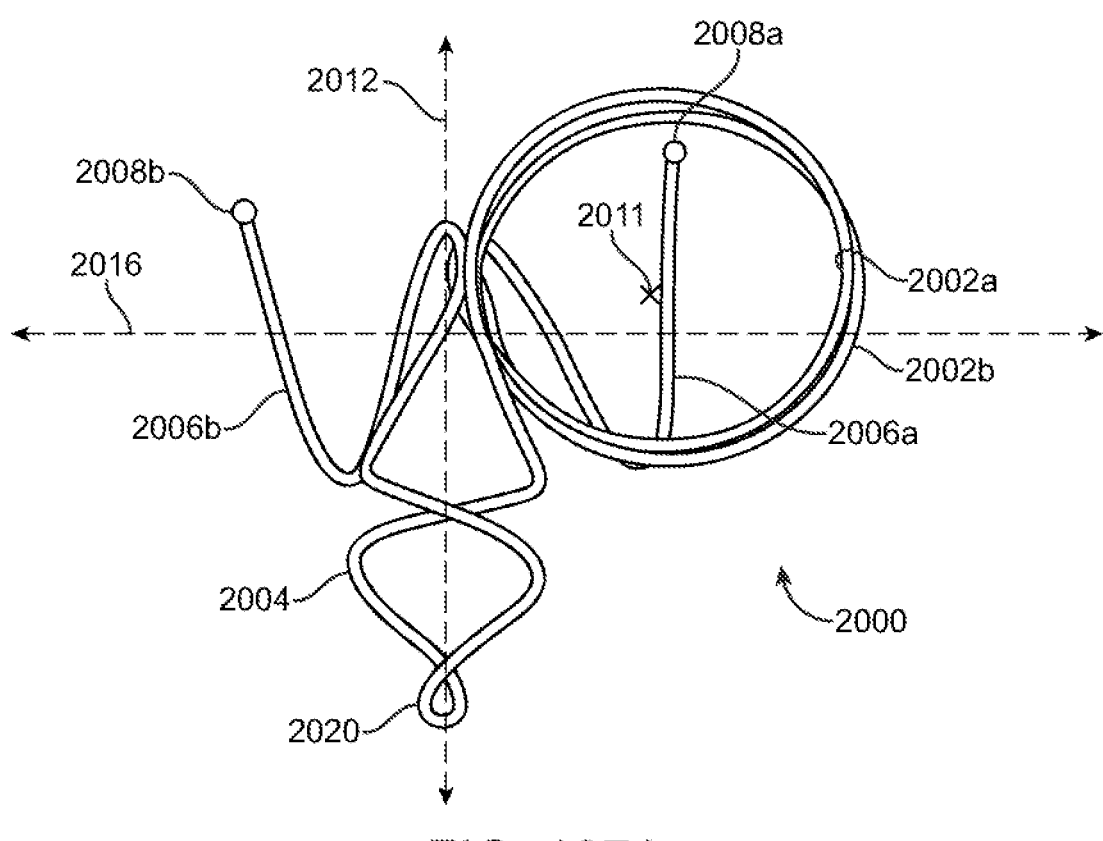

FIG. 137A illustrates another embodiment of an invertible pulmonary treatment device.

Figure 137B:
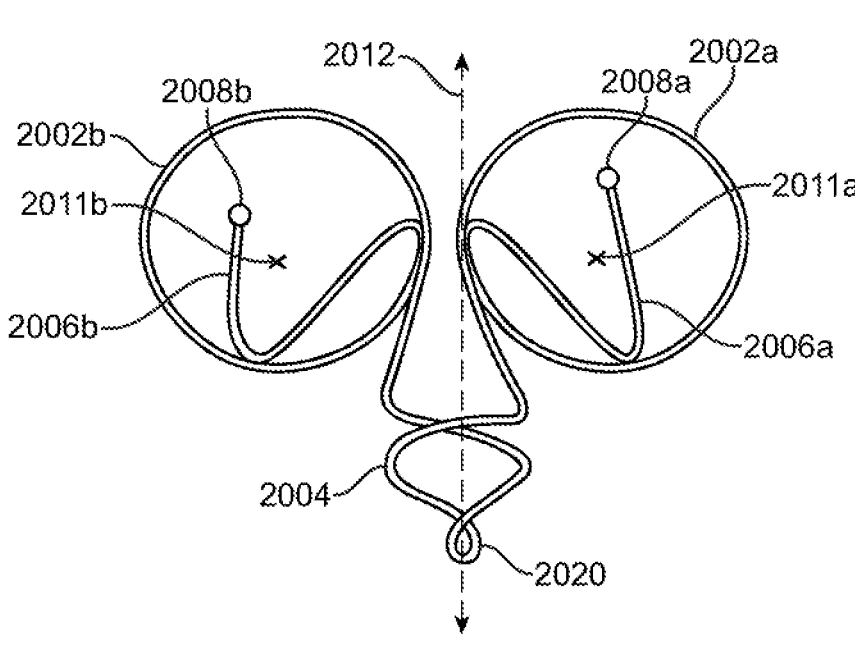

FIG. 137B illustrates a variation of the embodiment of FIG. 137A wherein the inversion elements curve radially outwardly away from the longitudinal axis and each other.

Figure 138:
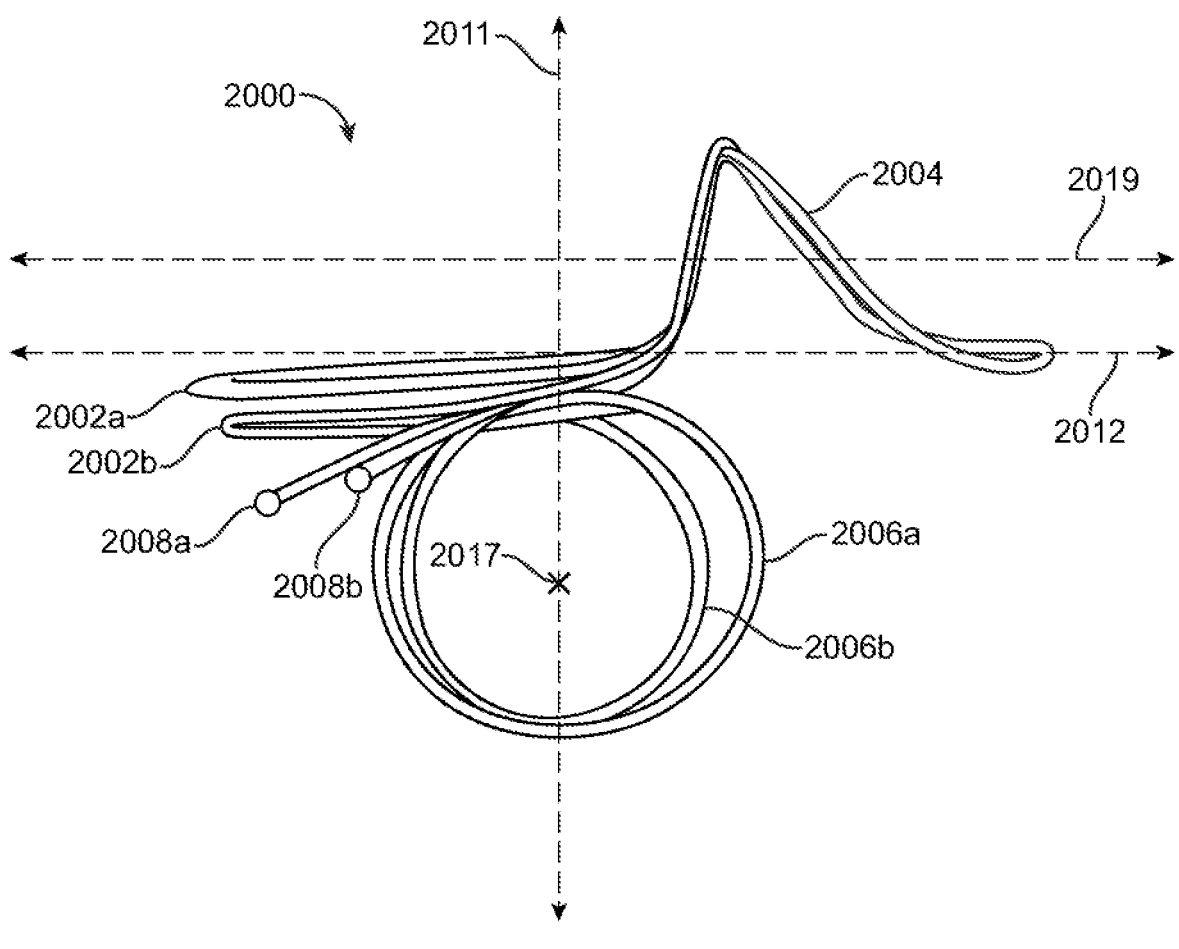

FIG. 138 provides a side view of the invertible pulmonary treatment device of FIG. 137A

FIGS. 139A-139D illustrate an embodiment of a delivery system of an invertible pulmonary treatment device.

Figures 140, 141:
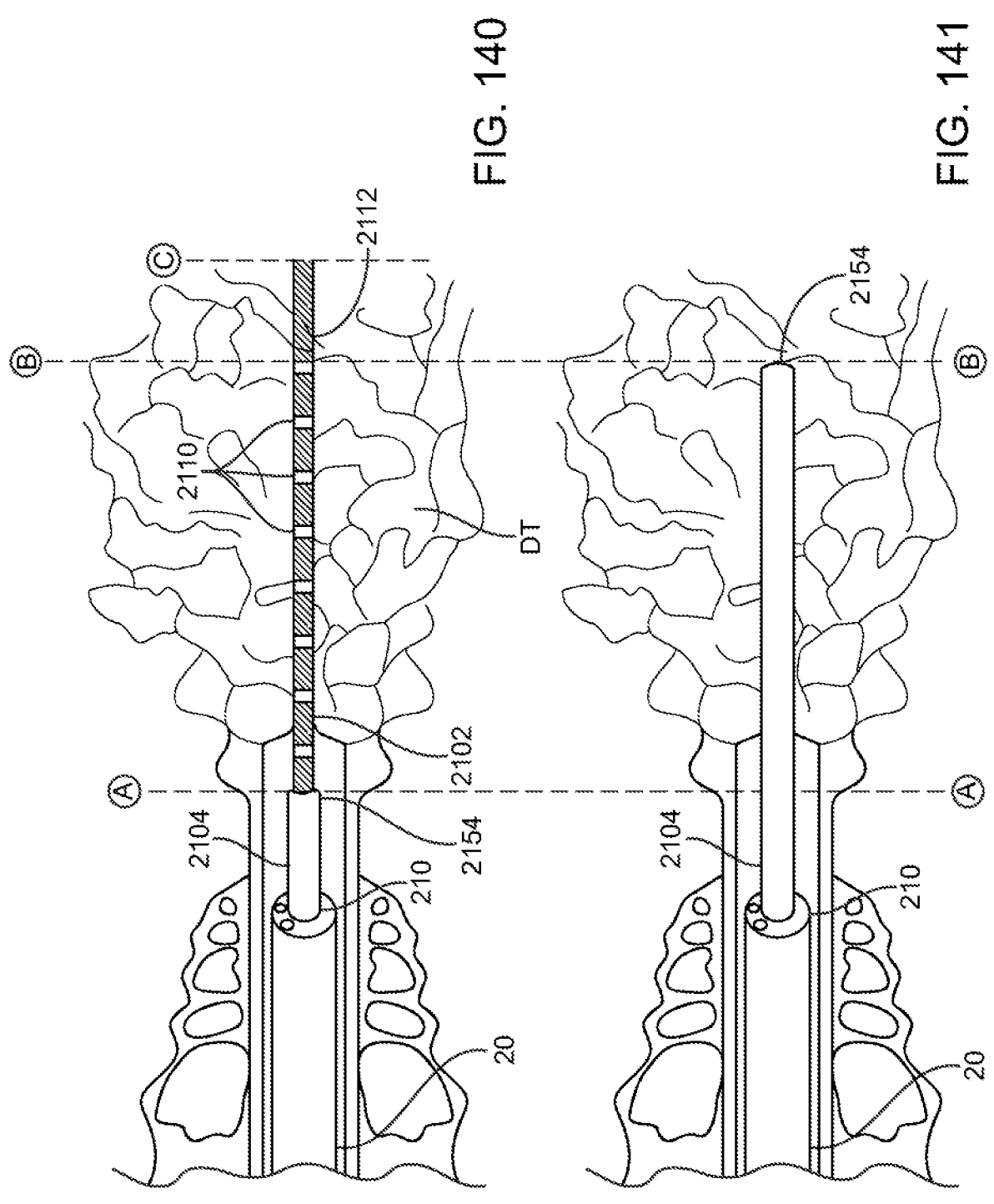

FIG. 140 illustrates the insertion cord tip of the bronchoscope inserted into a lung passageway, wherein the distal end of the catheter extends a short distance from the bronchoscope and the guidewire extends into the lung anatomy.

FIG. 141 illustrates the catheter advanced further into the working channel of the bronchoscope so that the distal end of the catheter is advanced further.

Figure 142:
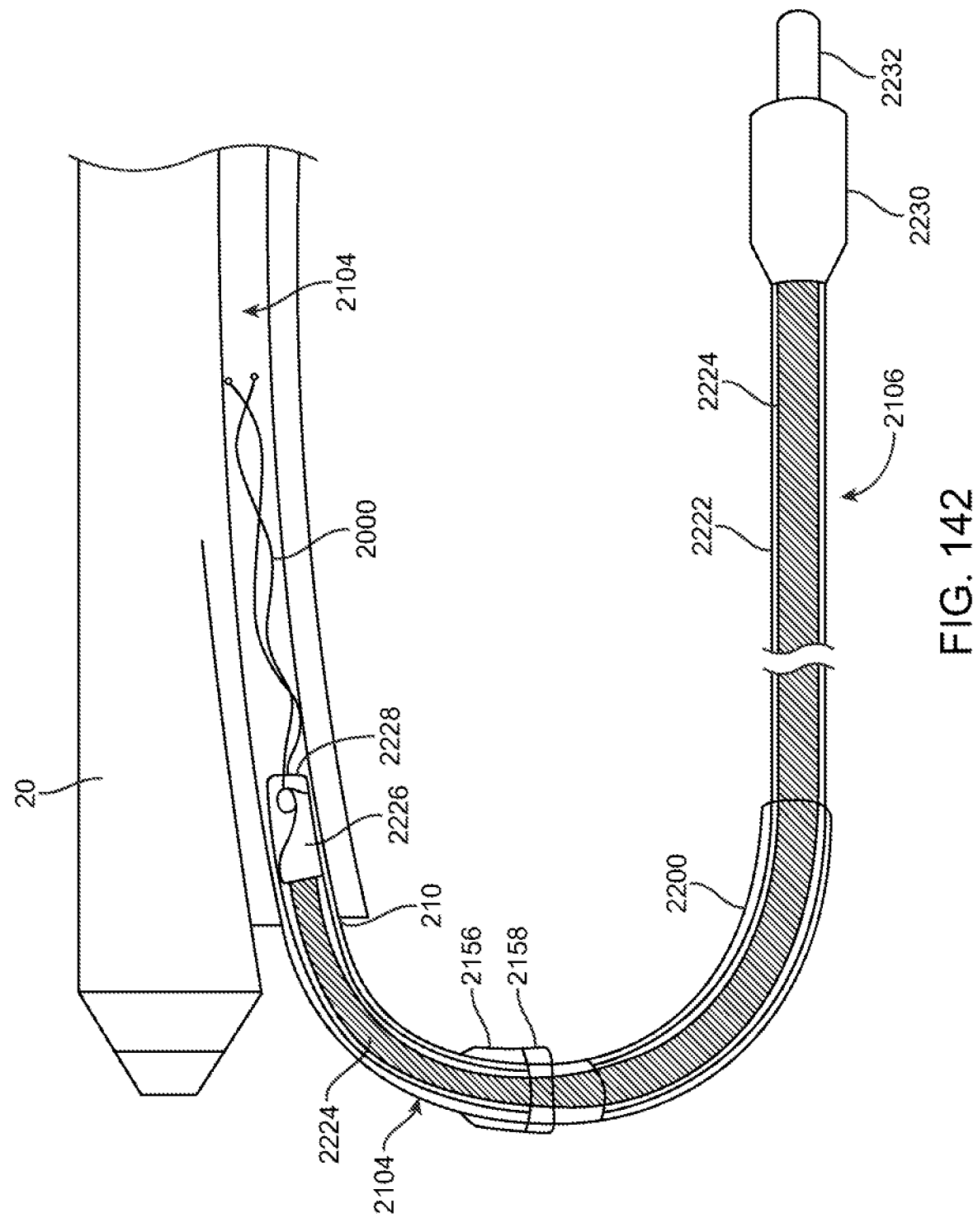

FIG. 142 illustrates the catheter inserted into the working channel of the bronchoscope so that its proximal end emerges from the working channel.

Figures 143, 144, 145:
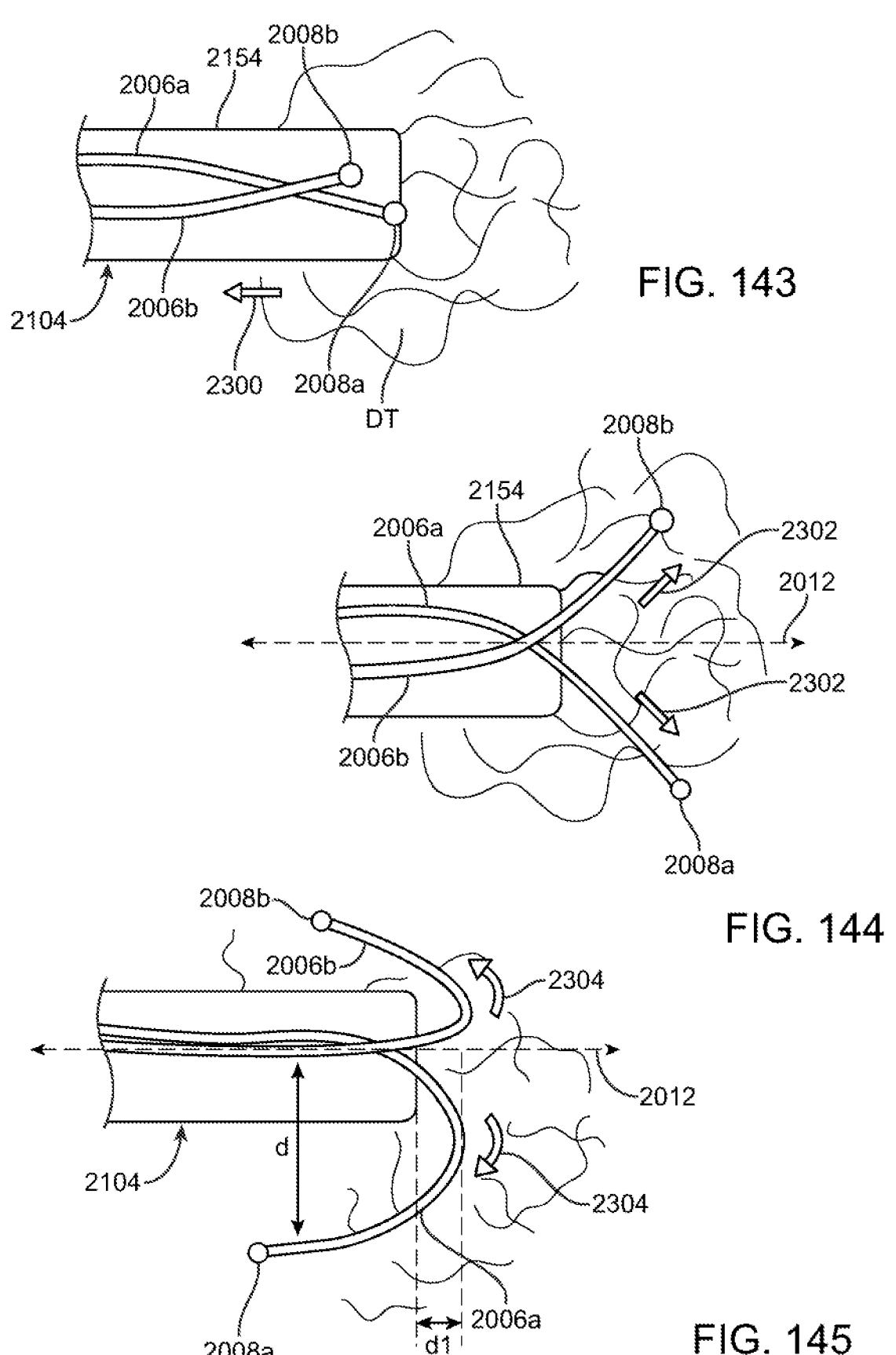

FIG. 143 illustrates an embodiment of an invertible pulmonary treatment device reaching the distal end of the catheter.

FIG. 144 illustrates an embodiment of an invertible pulmonary treatment device as it is emerged further from the catheter.

FIG. 145 illustrates further advancement of the tissue gathering elements into damaged tissue, wherein their pre-curvature bends distal tips toward the proximal direction.

Figure 146:
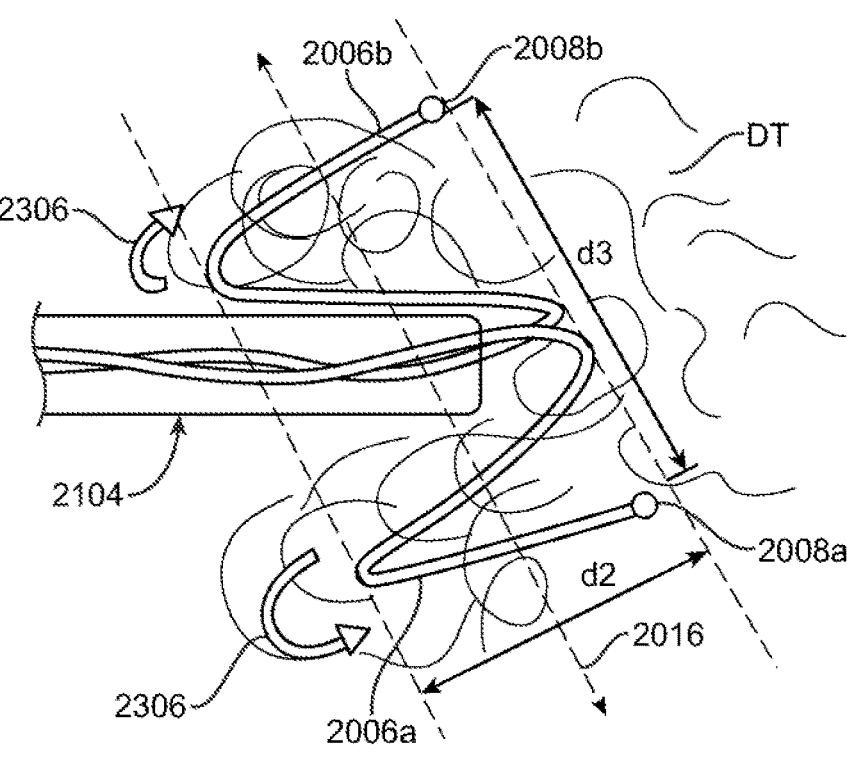

FIG. 146 illustrates still further advancement of the tissue gathering elements into the damaged tissue wherein their pre-curvature bends distal tips back around toward the distal direction.

Figure 147:
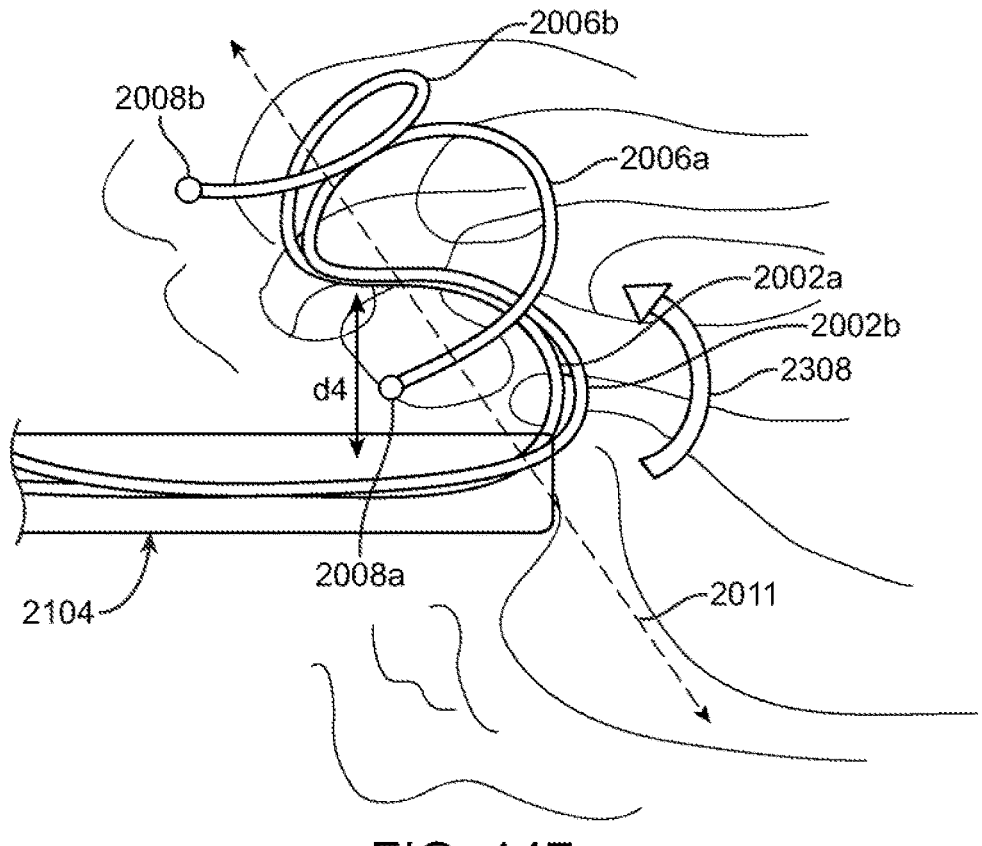

FIG. 147 illustrates emerging of the inversion elements from the distal end of the catheter.

Figure 148:
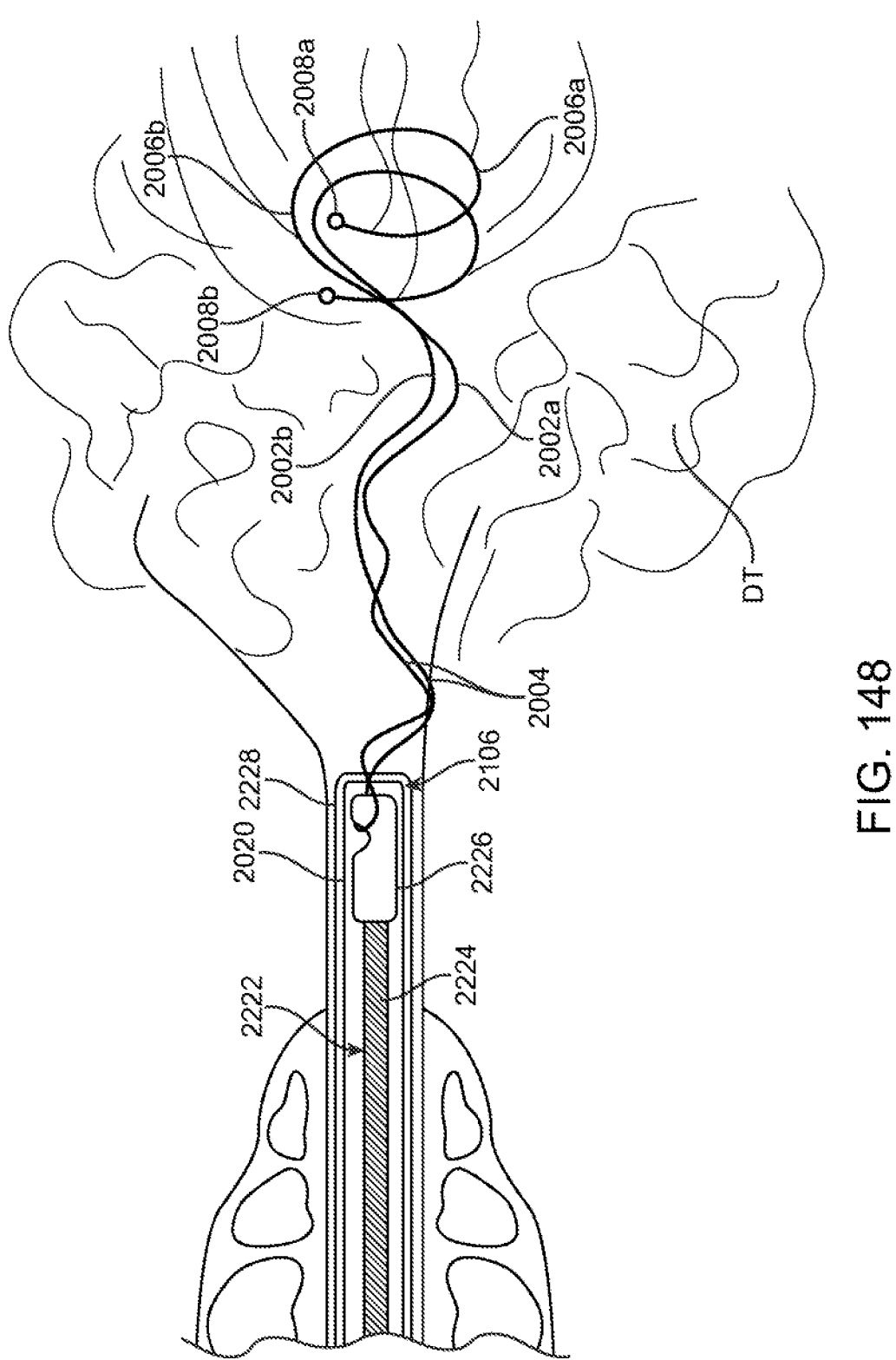

FIG. 148 illustrates the catheter and plunger having been pulled together in the proximal direction.

Figure 149:
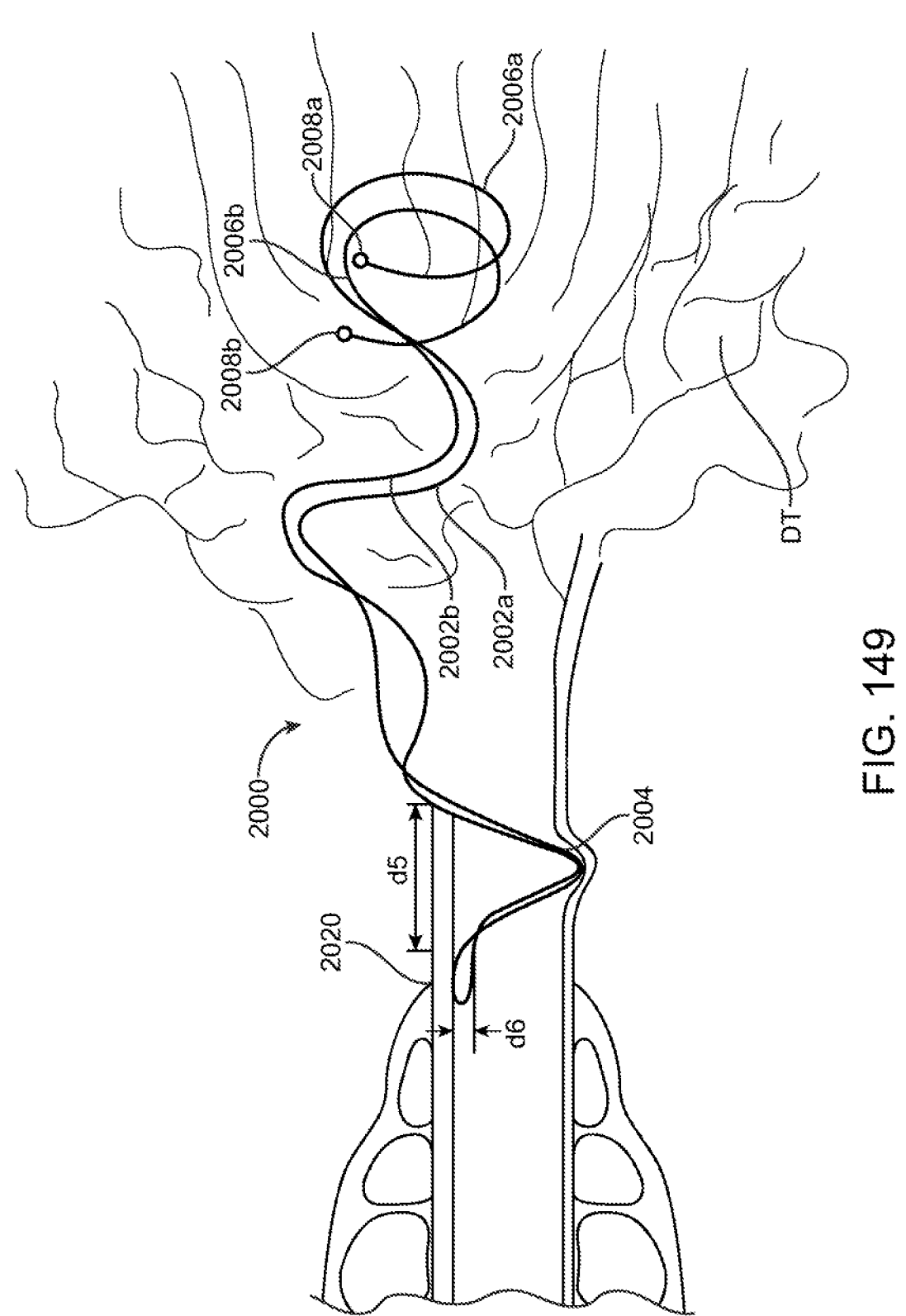

FIG. 149 illustrates the anchoring element released from the plunger.

Figure 150:
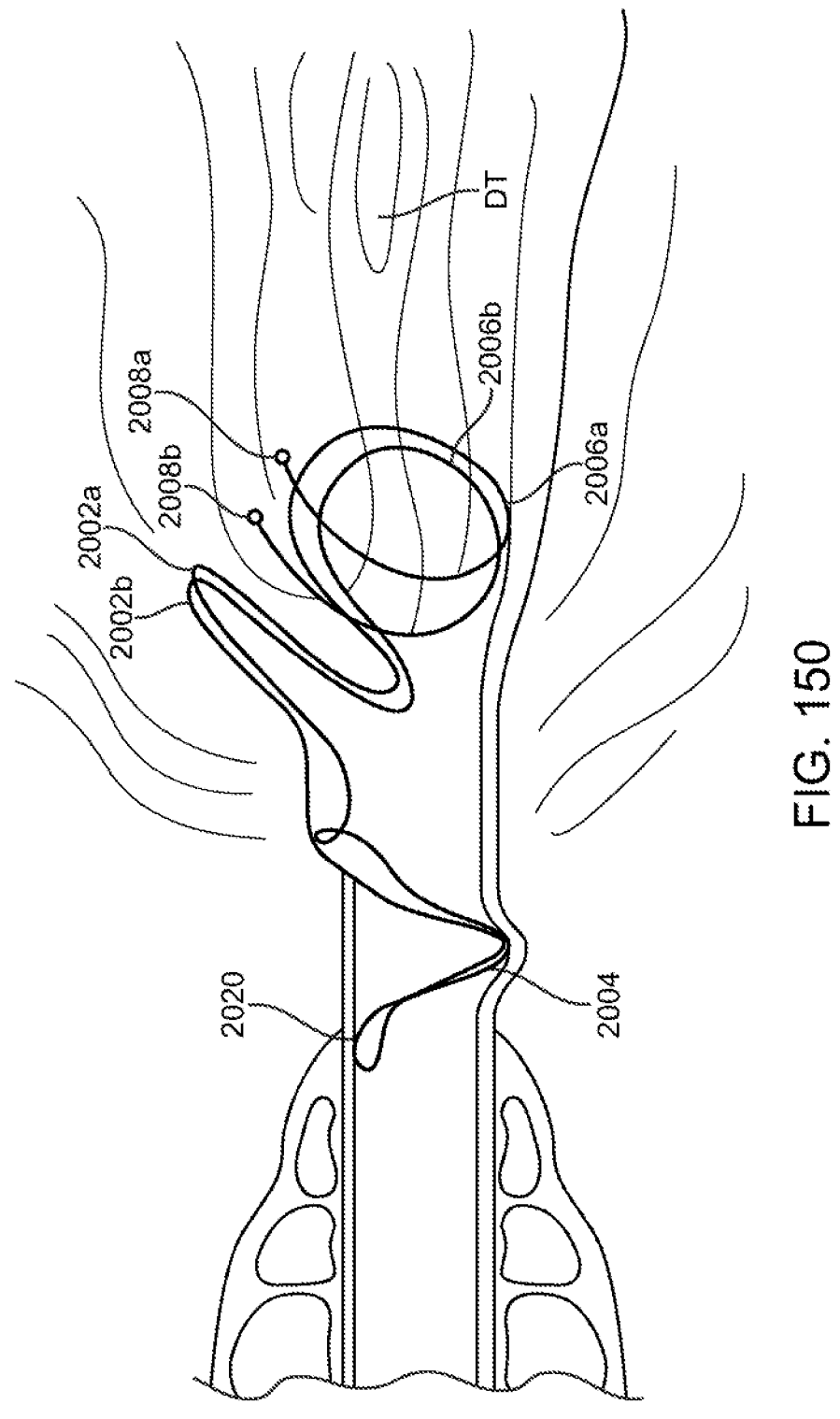
Figure 151:
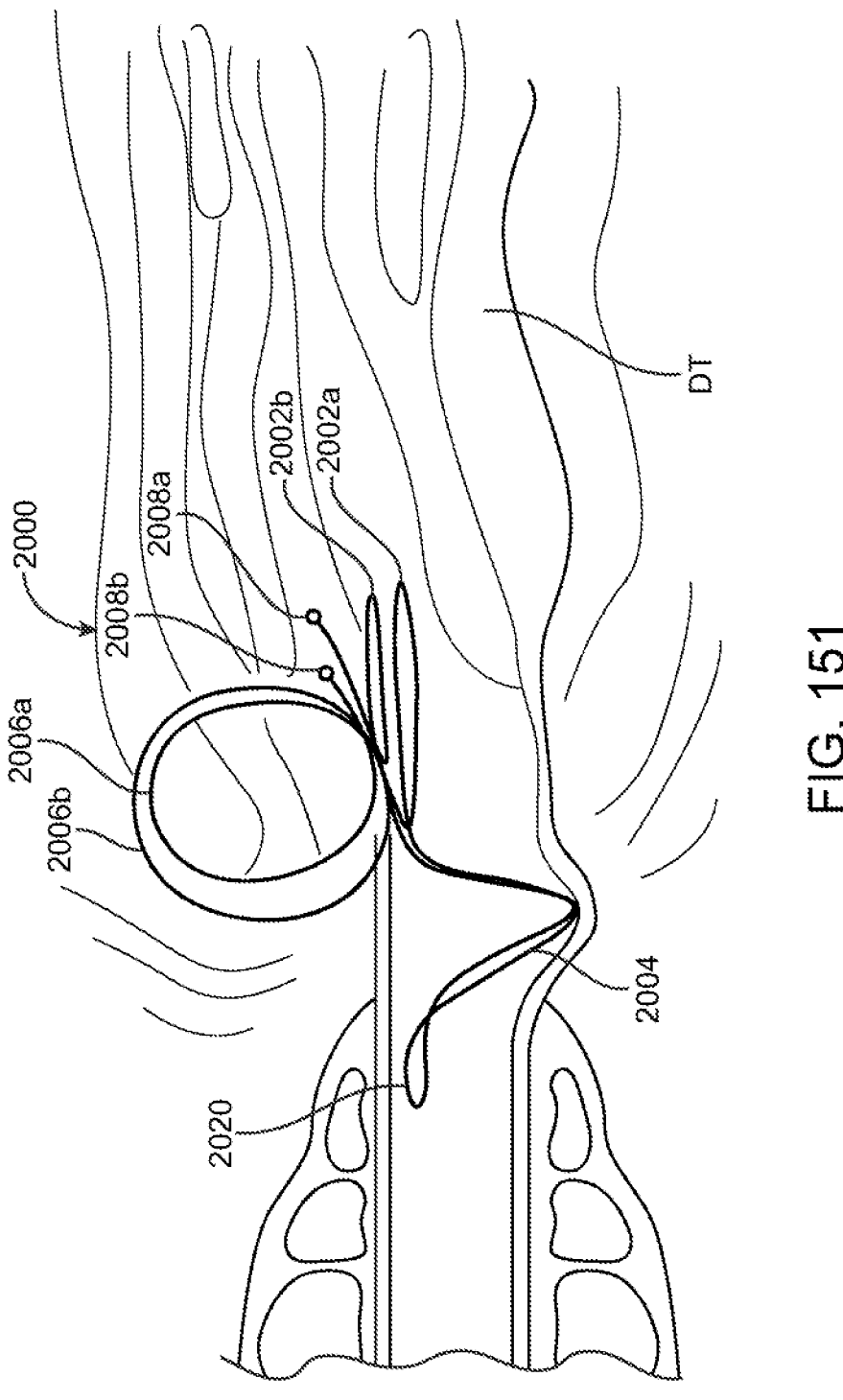

FIG. 150 illustrates the inversion elements having been recovered toward its original pre-formed shape FIG. 151 illustrates the inversion elements have fully retracted to its original pre-formed shape.

DETAILED DESCRIPTION OF THE INVENTION

Specific embodiments of the disclosed device, delivery system, and method will now be described with reference to the drawings. Nothing in this detailed description is intended to imply that any particular component, feature, or step is essential to the invention.

Anatomical Changes in COPD

Figure 1:
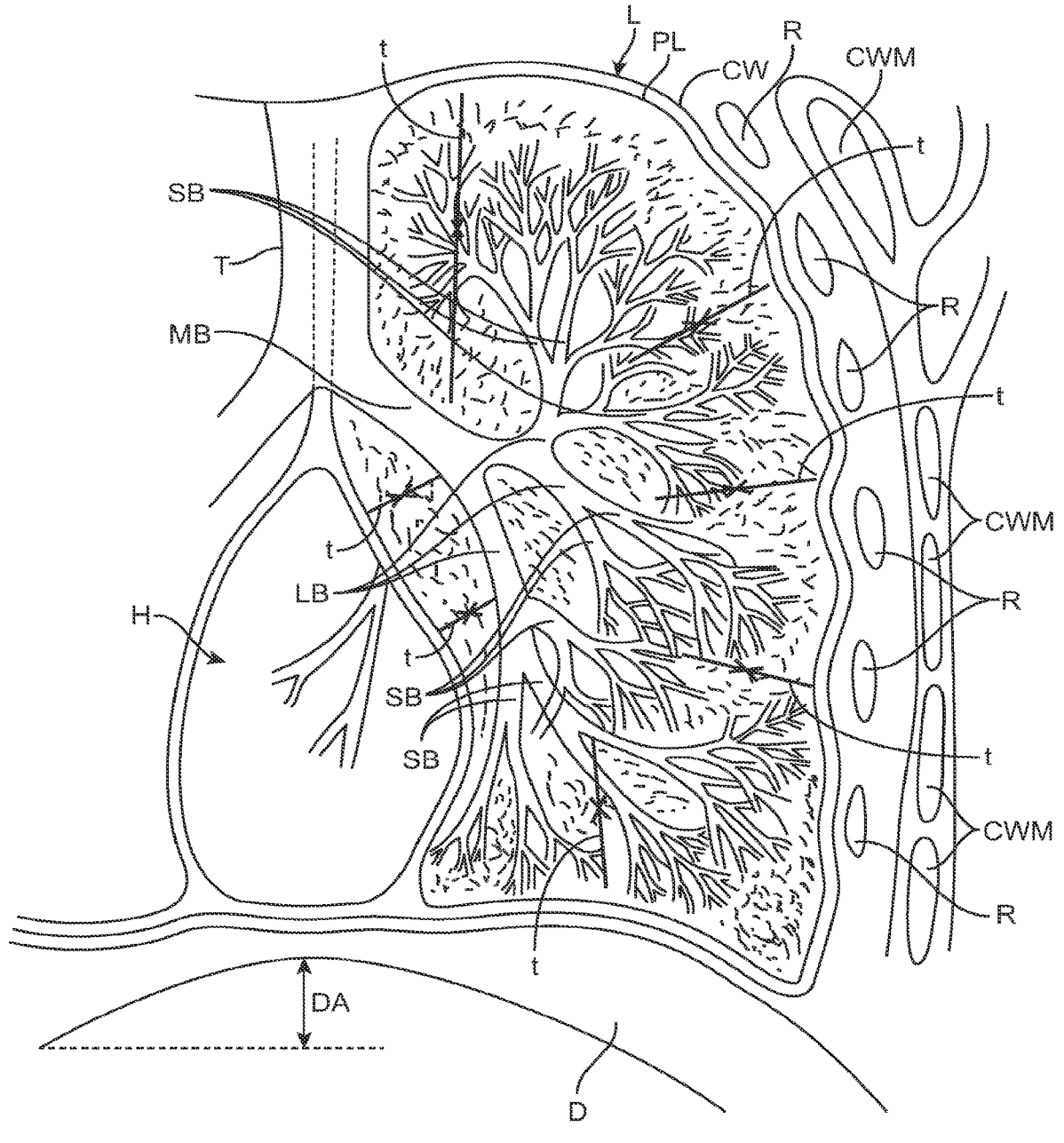
FIG. 1 illustrates a healthy lung of a patient.

FIG. 1 illustrates a healthy lung L of a patient. As shown, the lung L includes a tracheobronchial tree which is the anatomical and functional segment of the respiratory system that conducts air from the larger upper airways to the lung parenchyma. It is comprised of the trachea T and various intrapulmonary airways, including the bronchi, bronchioles and terminal bronchioles. The trachea and bronchi have cartilaginous walls which makes them thick, fibrous and this allows them to maintain patency during breathing Bronchi undergo multiple divisions and eventually give rise to the terminal bronchioles, which by definition, lack cartilage. The most distal respiratory bronchioles and alveoli are where gas exchanges into and out of the blood stream.

The trachea T is also referred to as the zero-generation airway and it extends distally 10-12 cm and it then divides into the right and left mainstem bronchi MB, commonly referred to as the first-generation airways. The left mainstem bronchus MB (shown in FIG. 1) is about 5 cm in length. The mainstem bronchus MB divides into the lobar bronchi LB (secondary or second-generation airways) and subsequently into the segmental bronchi SB (tertiary or third generation). Subsegmental airways (fourth generation airways) branch off from the segmental airways and they lead to the numerous subsegmental portions that are found in each lobar segment. Bronchi undergo multiple divisions (on average 23) along the bronchial tree. The initial 16-17 generations of bronchi make up the conducting zone of the airways and these do not normally participate in gas exchange in healthy lungs. However, with the progression of COPD and particularly with Emphysema, many of the traditional pathways beyond about the fourth generation commonly get destroyed and collateral pathways are formed that allow gas to communicate and get trapped in places in the lung that can no longer exchange gas as well as alveolar tissue in the lung that can exchange gas.

As bronchi divide into smaller airways, the respiratory epithelium undergoes histological changes and gives rise to terminal bronchioles. The 17th to 19th generations of bronchioles constitute the transitional zone. These bronchioles enter pyramid-shaped pulmonary lobules separated from one another by a thin septum, with the apex directed toward the hilum, comprising 5-7 terminal bronchioles. The last 2-3 generations of bronchioles have some alveoli in their walls and make up the respiratory zone. The area of the lung that is distal to a terminal bronchiole is termed the acinus. The final division is called the respiratory bronchiole, which further branches into multiple alveolar ducts. Alveoli, the functional units of the respiratory system, start appearing at the level of the respiratory bronchioles. This is where the majority of gas is exchanged. It is important to note that the majority of the healthy lung volume is comprised of alveoli tissue. The airway network branches from the trachea through the various portions of the lung to supply a volume of oxygen and to expel carbon dioxide from alveoli that are positioned almost everywhere within the lung. Only a small volume of the lung is occupied by the airway tree and the arterial network that transports blood from the right side of the heart through the lung to the left side of the heart.

In a healthy lung L, the intrapulmonary airways are held open by tension t (indicated by lines with facing arrows) between the airways and the chest wall CW. The elastic nature of healthy connective lung tissue and alveoli tissue communicates the tension. The tension is required to hold airways open during normal breathing as the airways experience higher external pressure, relative to the internal air pressure, during exhalation breathing cycles. Without this radial outward lung elastic recoil tension holding the airways open, the airways would collapse during exhalation which would not allow air to exit the lung. The lung L is suspended in an expanded state due to negative pressure or vacuum between the chest wall CW and the exterior lining of the lung, or pleura PL, of the lung L. As a person inhales, the chest wall CW and ribs R are expanded by the chest wall muscle CWM and the diaphragm muscle D contracts to lower the diaphragm and reduce the diaphragm arch DA which expands the lung L and its volume. By expanding the volume, a negative pressure is created in the alveoli which draws fresh oxygen into the airways and alveoli. Such expansion causes the interior lung tissue to be stressed with increased tension which dilates the airways and increases lung elastic recoil. This increased lung elastic recoil greatly enhances alveoli and airway contraction during exhalation. This ability to stretch and undergo extreme elastic strain elongation with the ability to fully recoil back to an original shape is made possible by a fibrous protein called elastin. Elastin fibers are present in virtually all vertebrate tissues, although it is only found in abundance within a few structures, such as arteries, some ligaments, and the lung. In these organs, elastin comprises an appreciable percentage of the total protein.

In many respects, elastin is a perfectly designed protein for its role in normal lung function. The unusual amino acid composition and lysine derived crosslinks provide the elastin fiber with great distensibility and recoil properties. They also lend chemical stability to the fiber, which is susceptible to few proteolytic enzymes and chemical injuries. Complications arise in conjunction with this inherent stability. Mature elastin has an extremely low turnover rate. Once the delicate architecture of the alveolar walls has been constructed and the continuum of connective tissue fibers is established, the components are meant to remain in that configuration. After the fetal and early perinatal stages of lung development there is no ability to initiate a new and architecturally correct alveolus if the original structure has been destroyed.

The introduction of tobacco smoke and other pollutants signals macrophages and neutrophils to respond. As the neutrophils degranulate and release their enzymes there is disparity between the finely tuned ratio of elastase to antiprotease which perpetuates destruction of the lung tissue and lung elastic properties. Every injury sustained by alveolar elastin that is not repaired hastens the inevitable cleavage of the alveolar wall. If the injury is perpetuated, as is the case with cigarette smoke, alveolar walls are slowly cleaved, leaving greatly enlarged air spaces and a lung without elastic recoil properties. Coalescence of damage leaves structural gaps in the tissue that further reduces the lungs ability to maintain tissue integrity and lung elastic recoil properties.

Figures 2, 3:
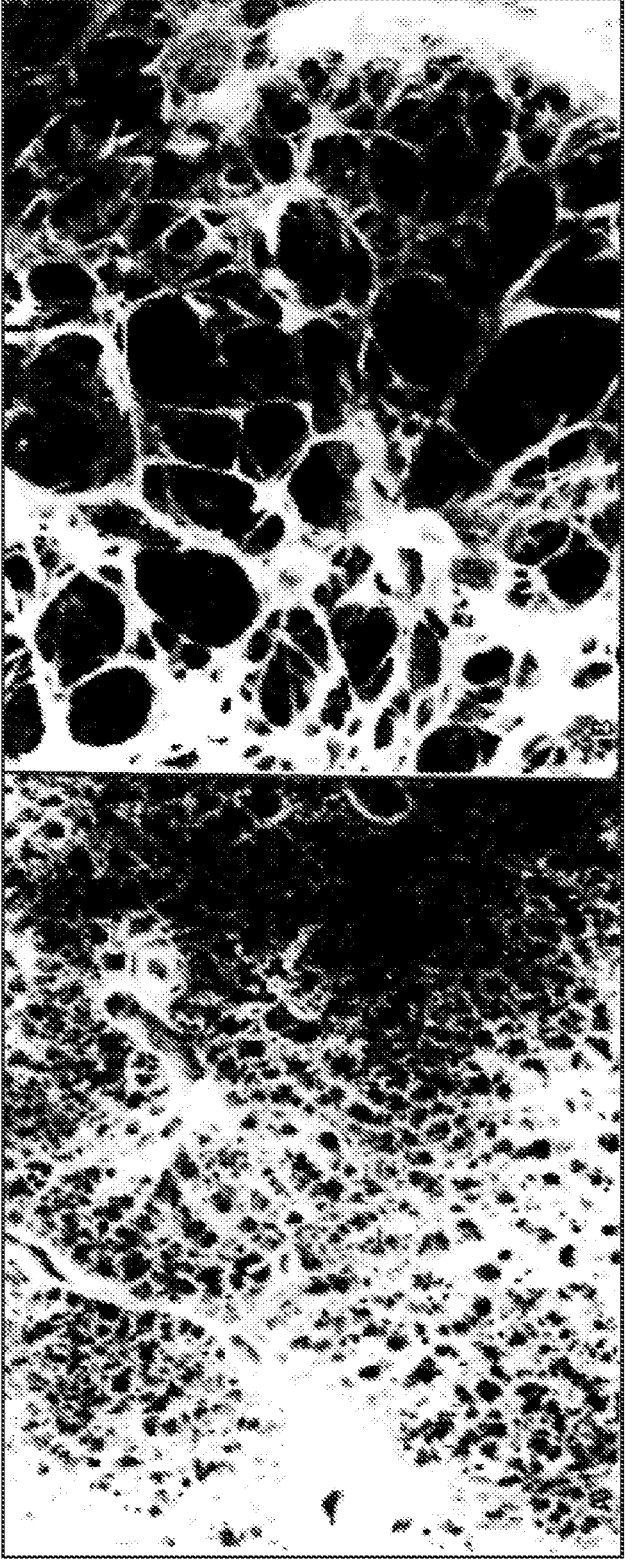
FIGS. 2-3 illustrates damaged lung tissue.
Figure 4:
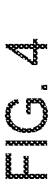
FIG. 4 illustrates a cross-sectional slice under computed tomography (CT) of the lungs of a patient suffering from COPD.

FIGS. 2-3 illustrate this change in lung composition. As the alveolar sacs are destroyed, large open spaces form called pulmonary blebs, bullae and giant bullae which can exceed several centimeters in length, width or length. Pulmonary blebs are small subpleural thin walled air containing spaces, not larger than 1-2 cm in diameter. Their walls are less than 1 mm thick. Pulmonary bullae are, like blebs, cystic air spaces that have an imperceptible wall (less than 1 mm). The difference between blebs and bullae is generally considered to be their size, with the cross-over being around 2 cm in diameter. Blebs may, over time, coalesce to form bullae or giant bullae. FIG. 2 illustrates damage that is typically seen in patients with early stage of severe emphysema while FIG. 3 is more typical of tissue that would be seen in a late stage emphysema patient who would typically present with 30% annual mortality rate. FIG. 4 illustrates a cross-sectional slice acquired using computed tomography (CT) of the lungs of a patient suffering from COPD. CT is a noninvasive, painless procedure that uses low-dose x-ray images to visualize the lung tissue. As shown, a large portion of the lung parenchyma has been destroyed and the majority of the lungs are now mostly air pockets, consisting of blebs and bullae.

Figure 5:
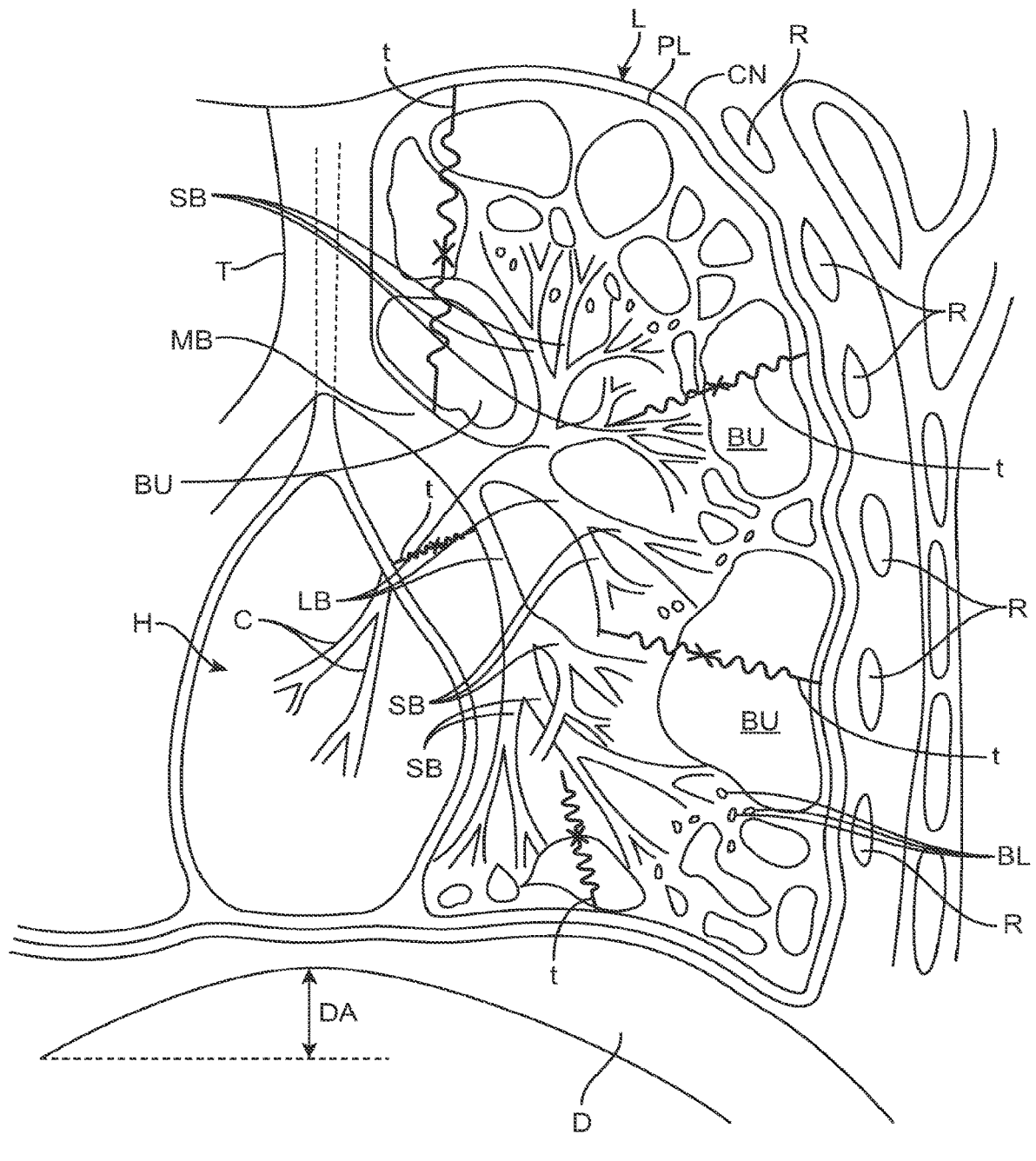
FIG. 5 illustrates a lung of a patient suffering from advanced COPD.

FIG. 5 illustrates a lung L of a patient suffering from advanced COPD. As in most COPD sufferers, this example shows homogenous destruction of the lung parenchyma. This can be easily identified by the fact that there is a similar amount of damage in the upper, middle and lower portion of the lung. If only the upper most portion of the lung was damaged, it would be considered a lung with heterogeneous upper lobe predominant damage. Predominant damage in the lower portion would be heterogeneous lower lobe predominant. Some patients present with heterogeneous disease but it may be upper lobe predominant in one lung and lower lobe predominant in the other lung but the vast majority of heterogenous patients present with upper lobe damage in both lungs or lower lobe damage in both lungs. Over 60% to 75% of all patients present with homogenous disease with a generally even distribution of damage throughout the lung volumes. Visible damage in some patients may be not be easily visible, even utilizing high resolution CT images where the image slice thickness is less than 1.0 mm thick. However, most patients present with damage that can be easily seen in these images such as the pockets BU shown in FIG. 5. There is vast tissue destruction beyond the $4^{th}$ generation airways wherein diffuse blebs BL and bullae BU fill the area of the lung L. Thus, late stage COPD sufferers often do not have any anatomically normal airways past the $4^{th}$ generation. This is a discovery based on the review of thousands of three-dimensionally reconstructed computed tomography files that were acquired to study severe emphysema patient's lungs. Basic medical and specialized pulmonology education teachings indicate that medium to small collagenous walled airways are preserved in late stage emphysema patients and this is simply not true. CT reconstructions are typically referred to as post processed CT files that show more than just two-dimensional visual images of cross-sectional slices of the lung. These detailed images of the inner structures of the body can be reconstructed (post-processed) in a three-dimensional format so tissue density and changes of density can reveal lung tissue condition, anatomical boundaries as well as physiologic data and dimensions. This data can be analyzed to summarize anatomical and physiologic changes such as airway lumen diameter change during breathing and airway volume change. Post processing can also be used to measure the volume and density of blood vessels that remain intact in damaged lungs. This is particularly useful to determine the over-all gas exchange activity in lobes or regions of the lung. Regions of lung tissue that trap gas or otherwise don't exchange oxygen and CO2 efficiently experience accommodation which is vascular contraction that prevents the flow of blood that is not being properly prepared to be sent back into the vascular system. By using post processing software, it's possible to measure dynamic and static blood volumes in lungs, lobes and segments to evaluate where to treat the patient, recommended dose and to determine if additional treatments may be required later to maintain the patients breathing mechanics. Effective treatment recruits additional blood volume where it is otherwise insufficient or lower than typically physiologically normal. Post processing can also measure airway volume within areas of the lung during the respiration cycle. The volume during inspiration can be compared to the volume during expiration and the magnitude of airway collapse can be calculated by subtracting the difference. This is a good indicator of where air trapping occurs and it also indicates where lung elastic recoil is suboptimal as the elastic recoil is what normally holds the airways patent with volume. Areas with a greater difference in airway volume during the breathing cycle need treatment more than areas with less.

Emphysema related destruction severely reduces lung elastic recoil and it eliminates or dramatically reduces gas exchanging tissue surface area. The reduction of lung elastic recoil leads to airway collapse during exhalation, air trapping and hyperinflation. As previously mentioned, lung elastic recoil and its associated outward radial pulling is necessary to hold airways open during exhalation as the external pressure on and around the airways are higher than the internal airway pressure. With reduced lung elastic recoil, the outward radial pulling on the airway is reduced and the airway collapses during exhalation. Air is still allowed to enter the lungs during inhalation but no air is allowed to flow out during exhalation. This leads to classic air trapping and hyperinflation. The lung volume may increase but the patients breathing capacity is reduced due to the lack of flow of fresh oxygen. With these patients undergoing any form of exercise, the airways collapse and trap air in the lung due to diminished tension t (indicated by wavy lines with facing arrows) between the airways and the chest wall CW. The air trapping and resulting increase in lung volume increases pressure on the heart H and the coronary arteries C. This in turn can lead to increased blood pressure, increased heart rate and decreased blood ejection fraction from the heart to the patient's arterial system.

It may be appreciated that in some instances there is no obvious visual sign of tissue destruction in low or high-resolution CT images, however there may still be numerous uniform small pockets of damage throughout the parenchyma which can reduce the surface area of the alveoli and therefor reduce gas exchange by as much as 50% or sometimes more. In addition, there can be severe damage to the elastin and loss of lung elastic recoil without the presence of destruction that can be seen in CT images in the form of blebs, bullae or other visual indicators of bulk enzymatic tissue destruction. This renders a normal looking lung dysfunctional due to airway collapse during breathing, etc. Most patients, however, present with a combination of symptoms that indicate a reduction of lung elastic recoil and also present with lung tissue damage that can be seen in CT image reconstructions.

Treatment Overview

Methods, systems and devices are provided which take into account the vast tissue damage of advanced COPD sufferers and provides treatment designed specifically to treat the particularly compromised lung tissues that are present in these patients. Such tissue damage has not been identified or acknowledged by previous treatment plans which has led to insufficient treatment and undesired outcomes in many cases. In particular, in some embodiments, the degree of tissue damage is assessed and the locations that the damage manifests in a lobe or lobes is utilized in the determination of the treatment plan. Thus, the extent and distribution of tissue damage is utilized in determining the number of devices that may be desired to treat the patient and the most optimal locations that the devices should be placed. These same data may also be used to assess the patient over time to determine if more devices should be implanted at the same locations as was targeted in a previous procedure to enhance or restore the improvement brought on in the first procedure or if implants might be best deployed in new locations that were not previously treated in order to restore the benefit brought on by an original treatment. In some embodiments, damage that can be seen by looking at CT image file reconstructions or post-processed CT image files is used as an indicator for loss of tissue recoil properties, compromised blood vessel communication or perfusion, hyper-inflation, air trapping, airway lumen collapse, clogged or congested airways. The extent and distribution of such tissue loss is determined by a variety of comparisons, such as comparisons between upper and lower lobes, comparisons between volumes of affected tissue per lobe, and comparisons of areas of destruction per CT slice integrated across number of slices. In some embodiments, damage is quantified by analyzing CT files (CT post-processing) and used to plan treatment or dose of therapeutic implant. For example, in some embodiments, such analysis of CT files utilizes software that analyzes and compares CT scans and summarized detailed physiologic data that is acquired during a patient's inspiration portion of a breath versus data acquired during expiration, to measure the change in density and additional metrics which indicate degree of airway collapse, blood flow patterns through the breathing cycle, locations of trapped air, regional lung volume changes, lobar lung volume changes, total lung volume changes, diaphragm motion, vectors of motion and displacement of motion of various regions of the lung which can be used to evaluate levels of compliance in the lungs or regions of the lungs. Areas with high compliance (large magnitudes of tissue displacement during breathing) need treatment to restore elastic recoil force that reduces compliance.

Blood vessel volume and total blood volume within a lung, lobe, segment and sub-segments can be calculated using CT data files and post-processing technology. Since blood vessels contract where oxygen transfer is less than normal (below physiologic levels, commonly called blood vessel accommodation) blood volume reduction or signals such as data indicating that blood volume is lower than normal can be used to determine where lung elastic recoil needs to be improved, where the airways are collapsing and trapping air, where lung elastic recoil is suboptimal, where enzymatic activity is high and many other things that would indicate that the devices should be placed in those regions. Differences between lobes of more than 10% blood volume is significant and less blood volume indicates more damage has been done by the disease. Changes of more than 10% of lobar blood volume over time indicates significant ongoing destruction and this signals a target for minimally invasive therapy such as the treatment described herein. Successful treatment increases the lobar blood volume in most cases.

Pre-treatment versus post treatment CT analysis that indicates an increase of lobar blood volume of 5% or more is considered significant.

In some instances, CT images that are acquired during inhalation and others acquired during exhalation can be compared to determine what regions or lobes experience the greatest amount of volume expansion and contraction. High levels of motion and relative volume change indicates that these regions perform with a high level of compliance. Again, areas with high compliance is a target where treatment can benefit the patient. Computational CT analysis may be performed to measure the relative change in position of thousands of easily identifiable points in the lungs such as the many Corina branch points of the blood vessels and airways during inhalation versus exhalation. If the distance between 2 points moves more than the rest of the points in the lung (on % basis or gross length change), the region between the points is more compliant than other regions in the lung. Additionally, the compliant regions may comprise elongated and slack tissue so the distance between the two points move freely during chest expansion. It may be appreciated that slack tissue is typically referred to as high compliance or high compliance tissue. High compliance is a strong indicator of slack tissue with low tissue elasticity and patients will benefit from placement of devices that incorporate strong spring elements where the compliance is highest. Thus, devices may be deployed in parts of the lung that are the most compliant as these devices are designed to reduce compliance to bring the patients lung breathing mechanics closer to physiologic breathing performance.

In some instances, CT images are acquired while the patient inhales and others acquired while the patient exhales wherein they are compared to determine what regions or lobes experience air trapping. The volume of the lungs, lobes, segments or even sub-segments of a lobe may be measured using CT quantitative analysis to measure these volumes during inhalation and compare to the same region during exhalation. If the volume of a region, as measured while the patient exhales, is less than 40% of the measured volume of the same region while the patient inhales, the region is considered to be not trapping air. However, if the exhale volume is more than 40% of the volume of the same region while the patient inhales, the region is considered to be trapping air. This is a strong indicator that the lung elastic recoil in the region has been compromised and the tissue requires therapy to increased tissue tensioning. The total volume of lung that is measured that traps air indicates how much dose the patient needs. For instance, therapy is recommended if the patient is found to trap air in 50 cc's of lung volume or more. Therapy that reduces more than 50 cc's of lung volume improves breathing and this can be measured using any of the measurable outcomes listed herein. The therapy devices described herein provide lung volume reduction of at least 50 cc. The therapies described herein may provide at least a 50 cc reduction of lung volume that traps air, as measured by quantitative CT analysis. The device embodiments described herein are typically designed to provide at least 10 cc of volume reduction or reduction of lung that traps air. Again, areas with high compliance trap air during exhale and present a measurable and quantitative parameter to use as a threshold to indicate treatment, to recommend therapy dose and such areas also provide a target to determine where treatment should be placed to most beneficially treat the patient.

If the patient presents with homogenous destruction, the pulmonary treatment devices can be delivered to the most severely damaged regions, if they can be identified, or the devices can be delivered to every major lobe so as to tension the entire lung system uniformly. If the patient presents with strongly heterogenous destruction, the pulmonary treatment devices can be delivered to low attenuation (low density) or high compliance areas of the lung, commonly the two upper lobes only. These areas exchange gas less efficiently and therefore present as lower risk locations to place implants rather than always placing devices in all lobes, in order to preserve maximum lung and breathing capacity. Devices may also be placed in high attenuation portions of the lung (high density tissue) to gain additional traction if the low attenuation portions are so destroyed that there is minimal to no tissue for the device to engage. This is possible because the devices restore the airway lumens and minimal tissue is being compromised with device placement. If this is done, the high-density tissue that has a significant amount of preserved elastic recoil will not easily expand or elongate with tension but the entire region of relatively preserved tissue will simply be pulled to a new location and the adjacent low attenuation tissue with low elastic recoil properties will still be tensioned. Sometimes this involves pulling an entire lobe to a new position and using the negative pressure in the fissure that separate the lobes to communicate the tension to another lobe. This allows tension and lung elastic recoil to be enhanced or created in places that may not be ideal for implant placement. Device placement and tensioning also lifts the diaphragm to restore basic diaphragm movement to enhance breathing mechanics. By deploying the device in a lung to cause tensioning, the lowest compliance tissues that are connected in a serial fashion will be strained more than the higher compliance areas and the lung tissue will be brought to equilibrium with more uniform compliance and elastic recoil performance. This strain also pulls airways radially outward and holds them open so they cannot collapse during exhale events. This reduces air trapping in the lung tissue.

Once the type and extent of damage has been accessed, the treatment plan is devised, including choice and placement of various treatment devices of the present invention designed specifically for use in damaged lung tissue.

Figure 6:
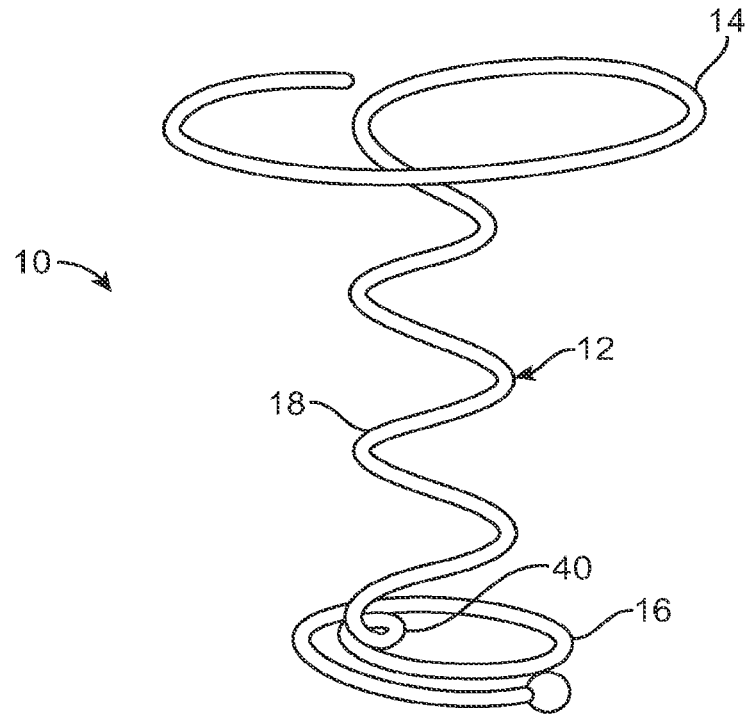
FIG. 6 illustrates an embodiment of a pulmonary treatment device comprising an elongate shaft coiled into a helical shape to form a tissue gathering end, a stabilizing end and an extendable midsection therebetween.
Figure 7:
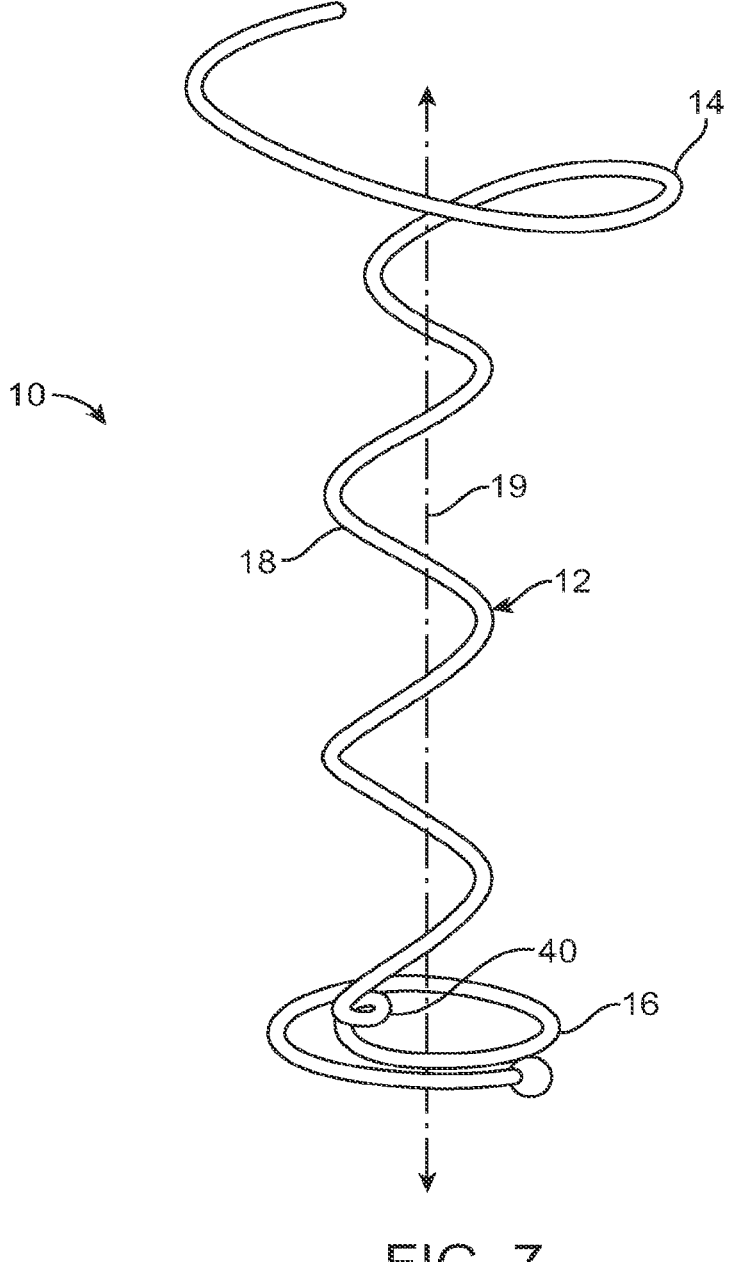
FIG. 7 illustrates an embodiment of the pulmonary treatment device expanding along its longitudinal axis.

FIG. 6 illustrates an embodiment of a pulmonary treatment device 10 of the present invention. In this embodiment, the device 10 comprises an elongate shaft 12 coiled into a helical shape to form a tissue gathering element or tissue gathering end 14, an anchoring element or stabilizing end 16 and an extendable midsection 18 therebetween. Typically, each end 14, 16 is comprised of 1-2 coil turns, however any suitable number of turns may be used. The pulmonary treatment device 10 is configured to expand along a longitudinal axis 19, as illustrated in FIG. 7, wherein the bulk of the expansion occurs along the extendable midsection 18. In some embodiments, the device 10 has a diameter of 2-50 mm and a length of 0.25-10 inches, preferably 0.5-1 inch, in resting free space. In such embodiments, the device 10 typically has a potential longitudinal elongation of between 0.25 and 10 inches, but most preferably 2-4 inches of potential elongation beyond the devices original length. However, the dimensions of the device 10 after deployment in the body may vary due to constraints of the airways and pattern of disease. Devices 10 deployed into smaller airways will have smaller diameters due to anatomical constraints. Likewise, the extension of the midsection 18 may vary depending on the location of the target treatment site within the tracheobronchial tree. A brief overview of deployment will be provided followed by a more detailed description of various elements and features.

Figure 8:
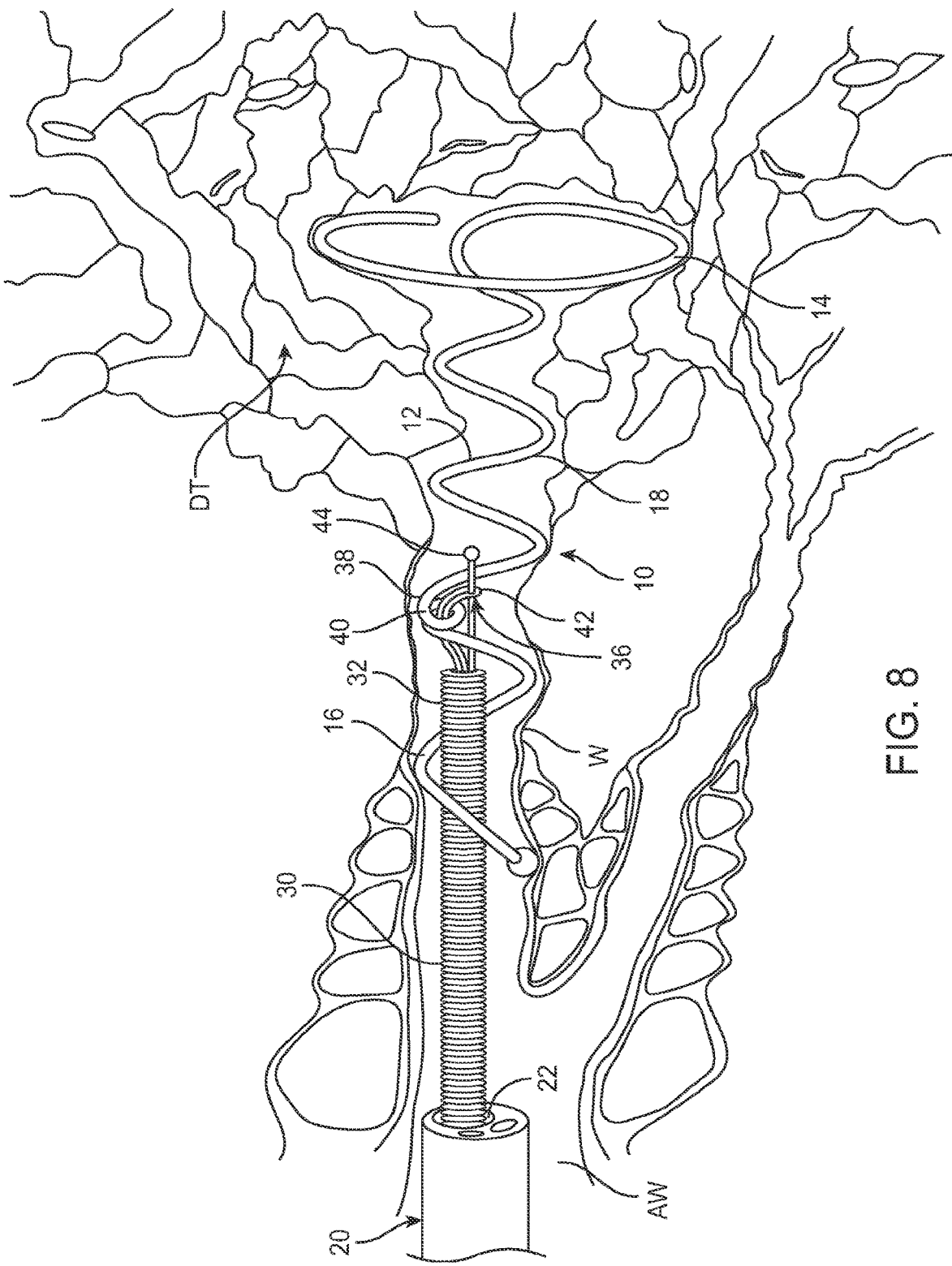
FIG. 8 illustrates a pulmonary treatment device delivered by a delivery device configured to be advanced to an area of loose damaged alveolar sac tissue.

The pulmonary treatment device 10 is sized and configured to be delivered by a delivery device configured to be inserted into the lung, such as a steerable scope (e.g. bronchoscope 20), such as illustrated in FIG. 8. In some embodiments, the pulmonary treatment device 10 is configured to be delivered through a lumen in the delivery device, such as by pushing the treatment device through a lumen of a scope, catheter, introducer, sheath, sleeve or similar device. In other embodiments, the pulmonary treatment device 10 is configured to be delivered by mounting it on the outside of a delivery device, such as on the outside of a scope, catheter (e.g. a balloon catheter), introducer, sheath, sleeve, guidewire or similar device. In some embodiments, when mounting on the outside of a delivery device, the treatment device 10 freely slide along the length of the delivery device. It may be appreciated that the pulmonary treatment device 10 may be configured to be delivered using a combination of these delivery device components such as mounting the treatment device 10 on a guidewire or balloon catheter shaft and delivering the assembly through the channel of the bronchoscope. It may be appreciated that when using a guidewire, the delivery system may be configured to be Over-The-Wire (OTW) or Rapid Exchange (RX) wherein the guidewire exits the delivery system at a particular location for the configuration. For example, in an OTW design, the guidewire exits the delivery system at its proximal end so that the guidewire that tracks along the full length of the delivery device. In contrast, in the RX design, the guidewire only tracks along a short section (about 25 cm) of the delivery device and then exists at a side port. This design saves time compared with advancing a guidewire through the full length of the delivery device.

In some embodiments, the device 10 is loaded into a bronchoscope port 22 and the bronchoscope 20 is advanced through the tracheobronchial tree to a target location within the lung. In patients with advanced COPD, lung tissue and airways are inflamed, bleed easily and react to even slight trauma, such as by advancement of a guidewire or catheter. Therefore, unlike conventional endobronchial valves and coils, in these embodiments, the device 10 may be deliverable without the use of a guidewire and/or catheter. In this embodiment, the device 10 is loaded within the bronchoscope port 22 so that the tissue gathering end 14 is directed distally. The bronchoscope 20 is then steered through the airways AW atraumatically, without digging its distal tip into the airway walls W. Typically, the distal end of the bronchoscope 20 is advanced into or well beyond the 4$^{th}$ generation airways, often into the areas of the lung containing highly damaged tissue DT. This is easily accomplished when the bronchoscope outer diameter is less than 4.5 mm diameter. This is typically a bronchoscope with a 2.0 mm diameter channel and port. In these areas of damaged tissue, large portions of parenchyma are often loose or missing, forming coalesced blebs and bullae. Thus, normal lung passageways with supportive walls are typically not available, and any existing tissue is sponge-like and very weak. The tissue gathering end 14 of the pulmonary treatment device 10 is deployed in this damaged tissue DT, as illustrated in FIG. 8. This is typically achieved by advancement of a deployment element 30 that extends through the bronchoscope port 22 or by retraction of the bronchoscope 20 while the deployment element 30 maintains its position relative to the damaged tissue DT. The deployment element 30 comprises an elongate shaft 32 having an attachment mechanism 36 near its distal end. The attachment mechanism 36 engages an attachment feature 38 on the device 10 so as to maintain connection between the deployment element ment 30 and the device 10 during deployment. In this embodiment, the attachment feature 38 comprises a loop 40 formed by the shaft 12 of the device 10. The loop 40 is disposed near or within the stabilizing end 16, as more clearly illustrated in FIGS. 6-7. Referring back to FIG. 8, in this embodiment, the attachment mechanism 36 comprises a tether 42 (e.g. suture, metallic wire (such as comprised of stainless steel, titanium, nitinol or other nickel based alloy), monofilament or multifilament fiber, braid, polymer or ceramic or glass fiber (such as comprised of Kevlar®, carbon fiber, nylon, polyurethane, polypropylene or other durable material)) and a support rod 44 (such as comprised of polymer, metal, ceramic or another durable material). The tether 42 extends through the loop 40 and around the support rod 44 so as to secure the loop 40 to the support rod 44. Thus, the stabilizing end 16 of the device 10 is able to remain attached to the deployment element 30 during deployment by the attachment mechanism 36. It may be appreciated that other attachment features 38 include a ball, a breakaway link, a threaded hole or shaft, or a friction fit taper or hole, to name a few.

Figure 9:
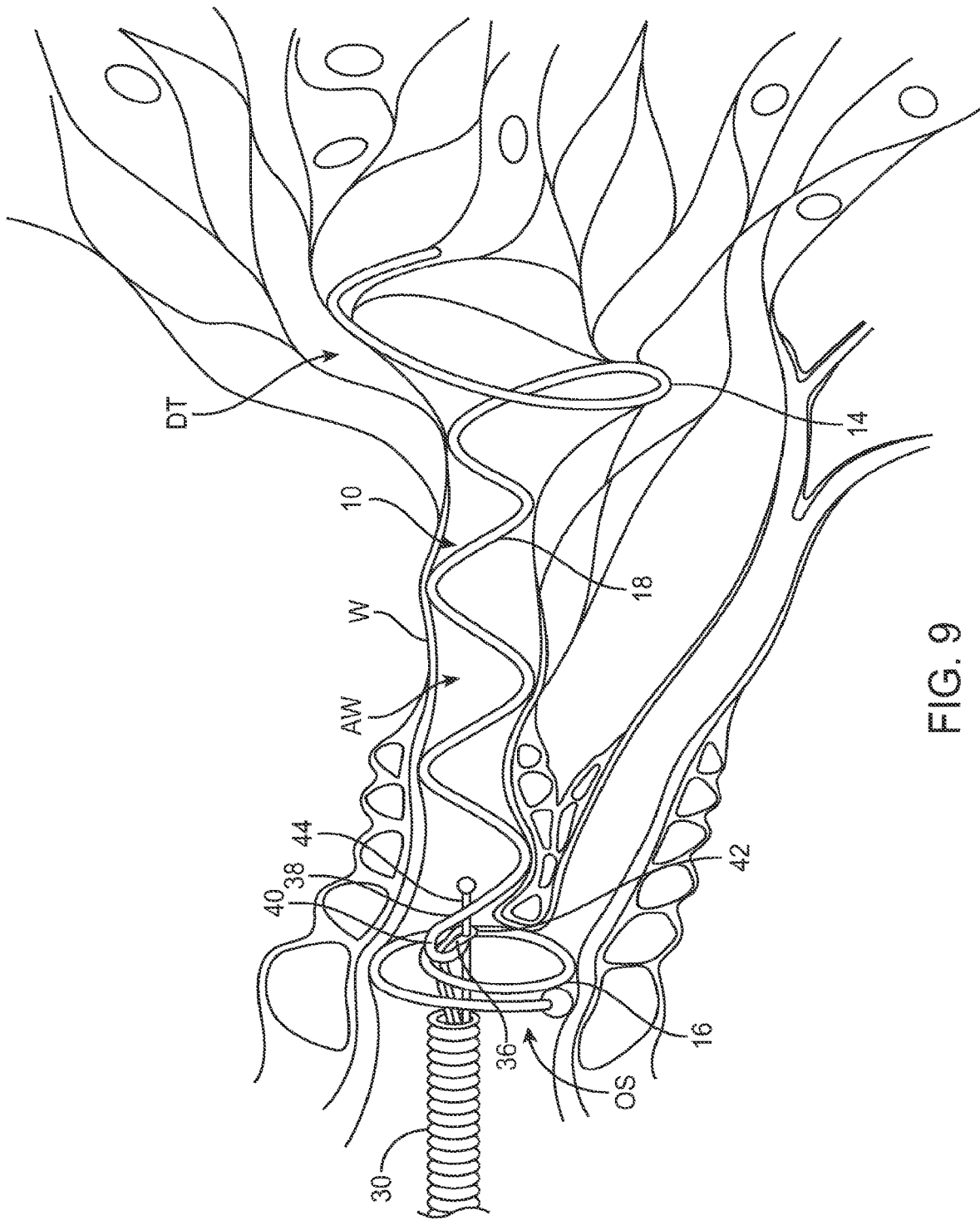
FIG. 9 illustrates retraction of the deployment element which straightens and extends the surrounding airway.
Figure 10:
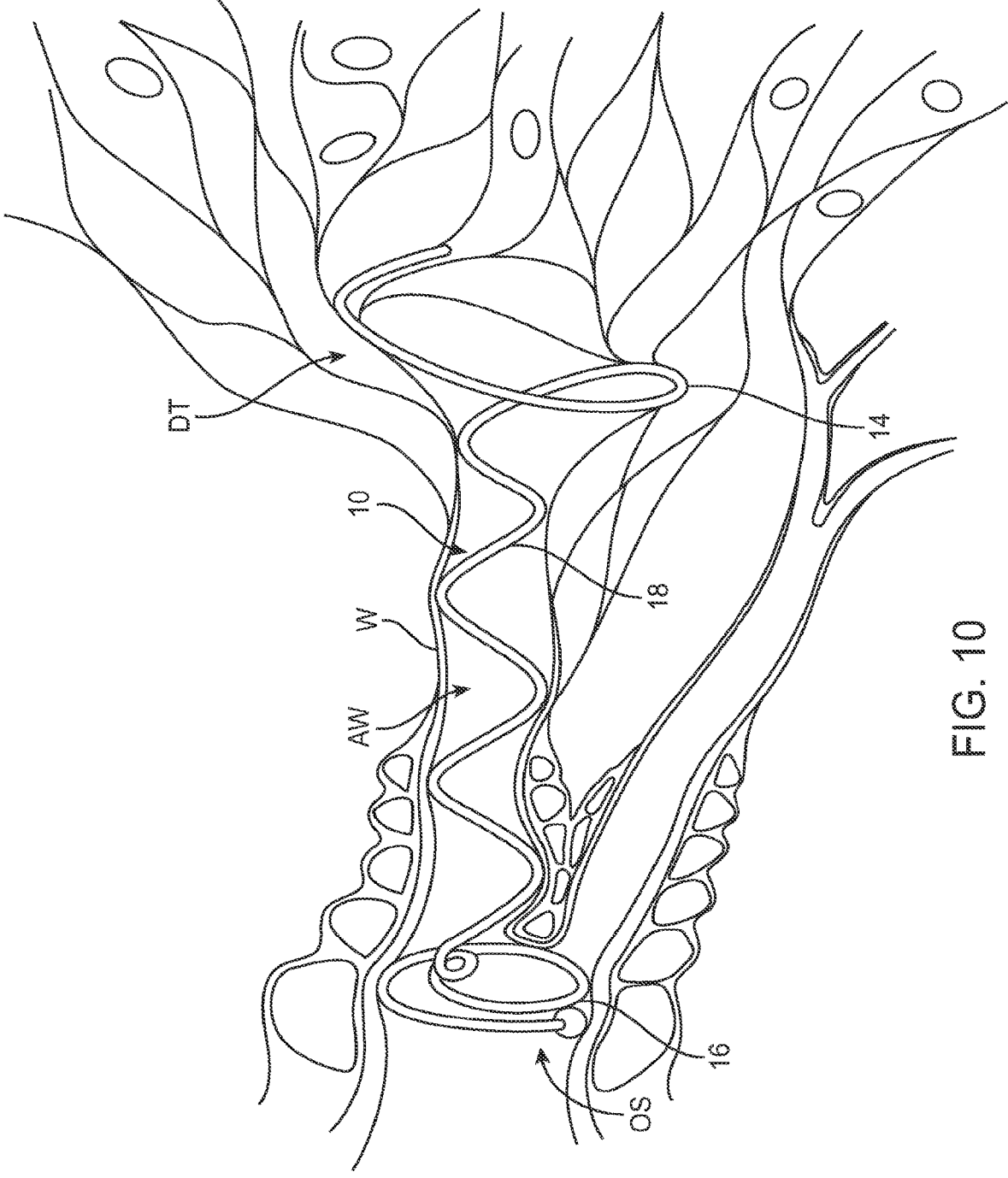
FIG. 10 illustrates the pulmonary treatment device left in place to maintain re-tensioning of the lung.

In some embodiments, as the tissue gathering end 14 is released into the area of loose damaged DT, the tissue gathering end 14 expands and rotates, gathering up the loose, damaged tissue in a manner that fixedly engages the end 14 with the damaged tissue DT. In other embodiments, the tissue gathering end 14 expands and dilates the airway or passageway through the damaged tissue DT so as to be effective in gathering tissue when the tissue gathering end 14 is pushed or pulled longitudinally along the axis 19. Once the tissue gathering end 14 has fixedly engaged within the damaged tissue DT, the deployment element 30 is retracted into the bronchoscope port 22. Since the deployment element 30 is attached to the attachment feature 38 of the device 10, such retraction tugs the device 10. This causes extension of the midsection 18 and pulling of the damaged tissue DT engaged by the tissue gathering end 14. Such pulling continues until a desired level of resistance occurs or the damaged tissue DT has been pulled a desired amount. This retraction may be observed using an integrated bronchoscope camera or using one of many possible forms of X-ray imaging and equipment such as real time fluoroscopic imaging, fluoroscopic CT (computed tomography), biplane X-ray or other methods. The retraction and tissue gathering magnitude may be measured by observing the distance that the tissue gathering feature is moved. In some embodiments, movement in a range of 1 cm to 25 cm, preferably 7-8 cm, indicates substantial and adequate gathering of tissue and axial pulling to cause lung tissue tensioning to increase lung elastic recoil. Pulling force of 0.005 to 0.30 pounds force are beneficial to the patient but preferably 0.01-0.20 pounds force are applied to the tissues of the lung. The deployment element 30 is then additionally retracted which further extends the midsection 18. This straightens and extends the surrounding airway AW, as illustrated in FIG. 9. By observing the increased length of the midsection 18, using imaging methods, the user can observe and adjust the amount of length change imparted on the midsection which will ensure adequate recoil energy is stored in the midsection 18 of the device 10. It is important to store potential energy in the device 10 so it remains in tension to continue to enhance lung elastic recoil, even if the lung tissue relaxes and elongates over time. Retraction of the deployment element 30 continues until the stabilizing end 16 reaches a suitable airway for holding and maintaining the stabilizing end 16. Typically, the deployment element 30 is retracted until the stabilizing end 16 is positioned within an ostium OS or point of branching within the tracheobronchial tree. The larger diameter of the ostium OS allows the stabilizing end 16 to expand and exert stabilizing radial force against the walls W of the ostium OS, holding the expanded device 10 in place. If the midsection 18 is not desirably elongated, such as 1-5 cm longer than it presents prior to retraction of the stabilizing end 16, the device may be recaptured and redeployed more distally so the midsection 18 may be elongated enough to preserve the treatment effect over time. Once the stabilizing end 16 is secured within the airway AW, the attachment mechanism 36 is released from the attachment feature 38. In this embodiment, the tether 42 is severed which allows removal from the support rod 44. The tether 42 is then removed along with the support rod 44. The bronchoscope 20 is then removed, along with the deployment element 30, leaving the device 10 in place, as illustrated in FIG. 10.

Since the device 10 remains in an expanded configuration, the coiled configuration holds potential energy and creates tension between the damaged tissue DT and the ostium OS. This newly acquired tension replaces the loss of tension caused by COPD. Thus, the airway AW and tissue that is more distal and more proximal to the device 10 is re-tensioned, providing renewed recoil strength. This improves breathing and reduces air trapping and resultant hyperinflation which is common in advanced COPD. In addition, the stored potential energy provides continued tension as the damaged tissue DT and/or airway AW naturally relaxes due to progression of COPD. Thus, such re-tensioning continues even during disease progression.

Thus, the pulmonary treatment device 10 provides a variety of features which improve lung function and quality of life for COPD sufferers, particularly those in advanced stages with few treatment options. Since the device 10 has a coiled configuration with an open central lumen, the device 10 does not obstruct airflow when implanted. This is in contrast to many of the existing implantable devices used to treat COPD, such as endobronchial valves. Such valves are intended to obstruct the airway, blocking off a portion of the lung so as to mimic LVRS. Thus, any functioning alveolar sacs are obstructed and are unable to be used. In contrast, the pulmonary treatment device 10 maintains access to the damaged tissue DT so that remaining functioning alveolar sacs can be utilized. The ends 14, 16 of the device 10 are coaxially biased so that positioning of the device 10 within a tortuous airway naturally straightens the airway AW along the longitudinal axis 19 of the device 10. In addition, the elongation of the midsection 18 of the device 10, elongates the airway AW providing a more direct pathway with less resistance to airflow. This is in contrast to endobronchial coils which are intended to bend and fold airways, compressing tissue and creating resistance to airflow. This blocks off regions of the lung so as to mimic LVRS.

In addition, at least some portions of the coiled configuration are radially expandable. Thus, the pulmonary treatment device 10 acts in a stent-like manner, supporting airway walls W and improving airflow. In addition to providing tensioning of the lung tissues to radially pull on airways to maintain patency during exhalation (when airway collapse is common in these patients), the stenting feature of the pulmonary treatment device internally supports the inside diameter of the airways to maintain patency during breathing. The act of deploying the device 10 (thereby re-tensioning the airways) holds the small airways, that are smaller than 2.0 mm in diameter, open, further increasing airflow. This act also displaces lung tissue closer to the trachea and pulls tissue farther from the pleura, shifting lung tissue closer to the heart. The trachea and central airways, such as the first, second, third and fourth generation airways, are much better reinforced by a pulmonary treatment device configured to be anchored in airways comprising mostly cartilage as compared to airways beyond the 4th generation so the tissues closer to the heart function as a foundational support for device 10. As the device 10 is elongated and anchored in the reinforced support region, the distal tissue gathering end 14 can efficiently pull and tension tissue that lies between the tissue gathering end 14 and the chest wall. Most of the lung volume adjacent to the chest wall comprises small airways and alveoli. This is a particularly fertile region to retention in order to improve breathing mechanics as a large percentage of air trapping happens in the beds of small airways (commonly referred to as small airways disease). The coiled configuration provides a spring-like or resilient quality to the device 10 during breathing During inhalation, the device 10 lengthens or elongates, and, during exhalation, the device 10 shortens or contracts. This ability to change dimension during breathing while maintaining relatively uniform tension levels in the lung allows device 10 to behave similar to normal healthy lung tissue. The tension does not dramatically change during the breath cycle.

It is important to point out that this type of lung elastic recoil enhancing treatment device 10 can beneficially be made from a single continuous element such as a single length of wire or fiber. This single element design enjoys the benefit of not comprising joints or links that may fail due to strain or bending during the high number of breathing cycles the device may encounter during the remainder of the patient's life. The single element may be made with varying diameter sections or it can be made from tapered diameter material as well as material that has totally non-uniform size or cross section along its length. A single component implant design is ideal. The treatment device 10 may also be made from a number of components if different diameter shaft material or if different materials are desired in the different sections such as the mid-section versus the stabilizing end or the mid-section versus the tissue gathering end. The mid-section is most ideal if it's made from resilient material whereas the tissue gathering distal end 14 and the stabilizing proximal end 16 may be made from more rigid material. The difference in modulus between the two portions may be as much as 500% or more different and they would still be suitable. A single component structure may be configured with tuned material properties in different locations of the single element. Nitinol material may be adjusted by using local heat treatment techniques to increase or decrease the stiffness or modulus of elasticity in local portions of the wire. This is beneficial in that the tissue gathering ends may be tuned to be stiff to be most effective to engage tissue and the central spring portion may be tuned to be less stiff to be ideally matched with the stiffness of healthy lung tissue.

Figure 11:
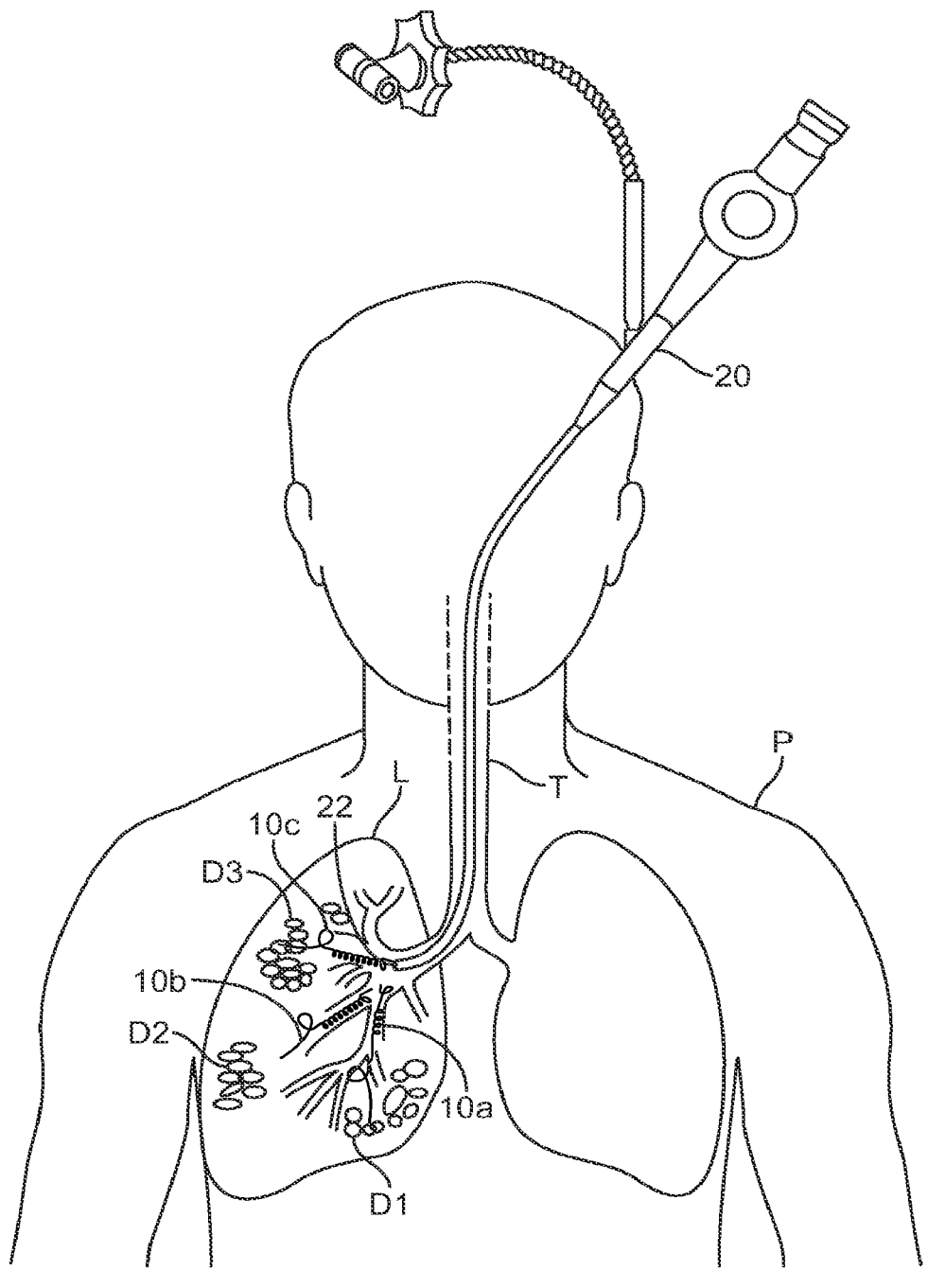
FIG. 11 illustrates the positioning of three pulmonary treatment devices within the lung of a patient.

It may be appreciated that any number of pulmonary treatment devices 10 may be positioned within a lung of a patient. FIG. 11 illustrates the positioning of three pulmonary treatment devices 10a, 10b, 10c within the lung L of a patient P. As shown, a bronchoscope 20 is advanced down the trachea T and into the bronchial tree of the lung L. A first pulmonary treatment device 10a is loaded within a port 22 and the bronchoscope 20 is advanced through the airways of the bronchial tree to a first area of damaged tissue DT1. The first pulmonary treatment device 10a is deployed as described above so that the first area of damaged tissue DT1 is drawn toward the trachea T and lung tissue in the vicinity is re-tensioned. The bronchoscope 20 may then be retracted and removed from the patient P. This allows the broncho-scope 20 to be cleansed so as to avoid transferring bacteria and contaminating other airways when re-introducing the bronchoscope 20. The second pulmonary treatment device 10*b* is then loaded within the port 22 and the bronchoscope 20 is advanced through the airways of the bronchial tree to a second area of damaged tissue DT2. The second pulmo-nary treatment device 10*b* is deployed as described above so that the second area of damaged tissue DT2 is drawn toward the trachea T and lung tissue in the vicinity is re-tensioned. The bronchoscope 20 may then again be retracted and removed from the patient P. Again, the bronchoscope 20 may be cleansed and third pulmonary treatment device 10*c* is loaded within the port 22 and the bronchoscope 20 is advanced through the airways of the bronchial tree to a third area of damaged tissue DT3. The third pulmonary treatment device 10*c* is deployed as described above so that the third area of damaged tissue DT3 is drawn toward the trachea T and lung tissue in the vicinity is re-tensioned. The broncho-scope 20 is then retracted and removed from the patient P. Alternatively, the bronchoscope 20 may be left in the lung throughout the delivery of the three devices 10*a*, 10*b*, 10*c* through the bronchoscope channel to the locations shown in FIG. 11. Or, the devices 10*a*, 10*b*, 10*c* may be delivered into the lung via a catheter that has been advanced through the bronchoscope channel. As many as 25 devices may be placed within each lobe. Pulmonary treatment devices may be placed in a single lobe during a single procedure, in two or more lobes during a single procedure or in all 4 major lobes during a single procedure. Alternatively, one, two, three or 4 of the major lobes may be treated over a sequence of several procedures with typically 1-4 weeks of recovery time between procedures. Lastly, one or more pulmonary treatment devices may be placed in one or more lobes during a single procedure and additional pulmonary treatment devices may be implanted in sequential additional proce-dures.

Figure 12:
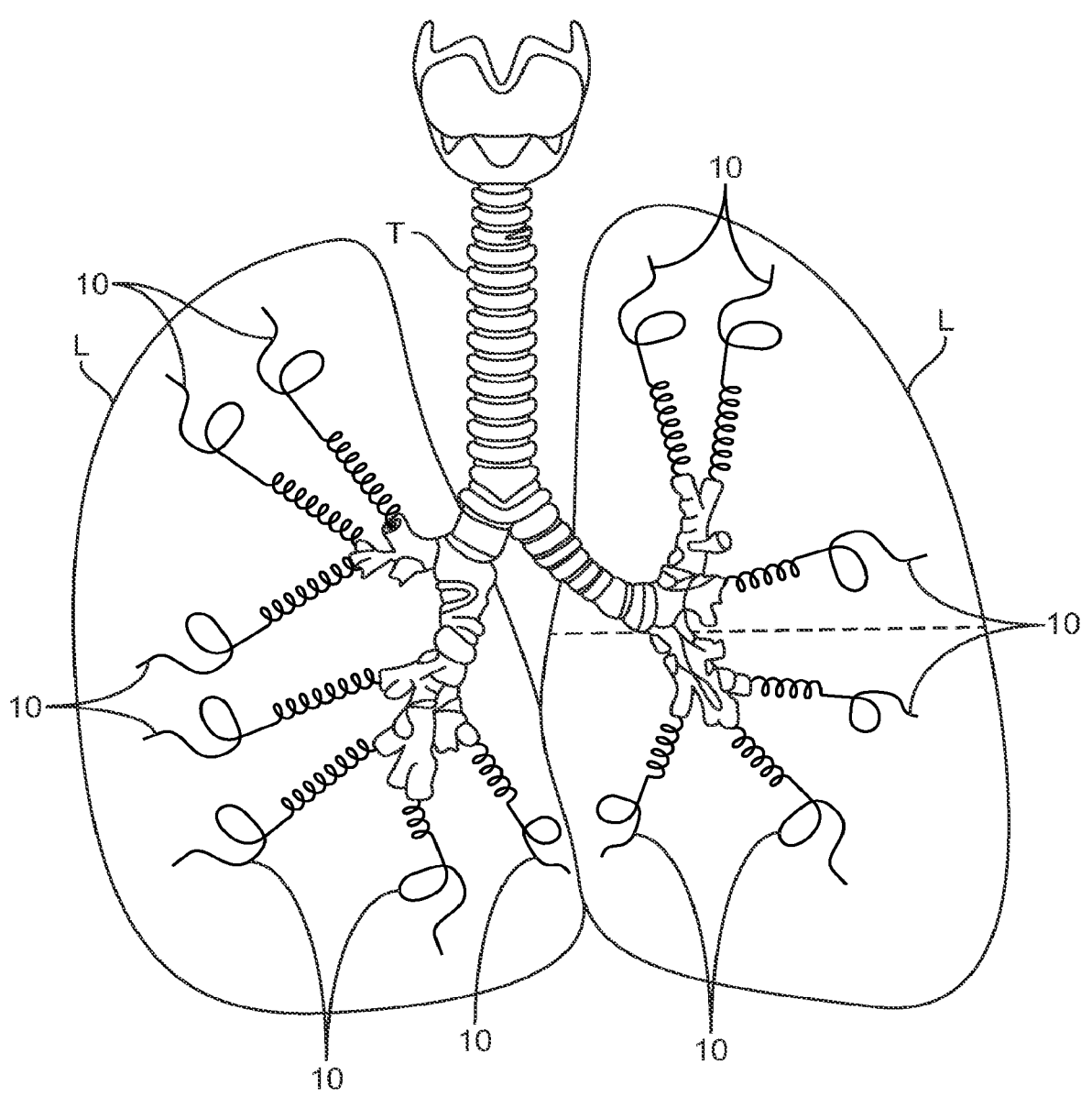
FIG. 12 illustrates a plurality of pulmonary treatment devices positioned in both lungs of a patient.

FIG. 12 illustrates a plurality of pulmonary treatment devices 10 positioned in both lungs L. The devices 10 are preferably delivered into regions of the lung with the most tissue destruction. If the patient suffers from upper lobe predominant heterogenous disease, the upper lobes in the left and right lungs are preferably treated. If the patient suffers from homogenous disease where the tissue destruc-tion is diffuse throughout every major lobe of both lungs, devices 10 are preferably placed in all five lobes of the lung. This "total lung" treatment is ideal because each device 10 is designed to restore and preserve lung elastic recoil. Homogeneous patients need this enhancement in all major lobes of the lung and unlike nearly every alternative treat-ment, the devices 10 will not block or otherwise render lung tissue non-functioning. By simply pulling tissue sufficiently to eliminate slack in the lung tissue and restoring lung elastic recoil without compromising gas exchange function of the tissue, the devices 10 can be placed in locations throughout the lungs to additively enhance breathing mechanics in these patients.

It may be appreciated that each pulmonary treatment device 10 may impart differing levels of re-tensioning in a lung L. But, overall, the impact on the lung L is such that a variety of clinical goals have been achieved. Such goals include returning physiologic tension to make the lung perform in a more physiologic way. The human lung nor-mally behaves in a fully elastic manner in which it expands between approximately 200 milliliters with the application of pressure relating to approximately 20 centimeters of $H_2O$ or 0.02 Bar or 0.02 atmospheres and 1200 milliliters with the application of 40 centimeters of $H_2O$ pressure. The pulmo-nary treatment device removes slack in the tissue, minimizes tissue compression, restores lung elastic recoil, enhances breathing mechanics by providing an elastic link to enhance spring properties in the tissue, radially outwardly supports airways to maintain airway lumen patency, internally stents airways to maintain lumen patency and lifts the diaphragm to restore diaphragm motion. This also increases the lumen diameter or caliber of the airways and increases the radial outward support to the airways so that the support is sufficient to hold the airways open. Airway closure during expiration is delayed and the time that airways stay open during expiration is increased. Likewise, airway resistance is reduced along with air trapping in the lung. Such tensioning reduces hyperinflation and the related increase in lung volume. This has a variety of beneficial effects on the heart and circulation, including reducing pressure on the heart because hyperinflated lungs push on the heart, reducing pressure on coronary arteries, reducing pulmonary artery pressure, reducing systolic and/or diastolic blood pressure, reducing blood hypertension, reducing heart rate, increasing blood oxygen percent, decreasing CO2 levels in blood stream and increasing blood ejection fraction as relieving lung inflation related pressure on the heart allows it to contract and refile more efficiently. Additionally, treating patients with the pulmonary treatment device will reduce the amount of Dyspnea, otherwise known as shortness of breath, and quality of life is improved. Quality of life is normally measured using validated patient surveys such as SGRQ scoring surveys. As the patient's quality of life is improved, the SGRQ survey score is decreased. Appropriate patients who a have been treated with the pulmonary treatment devices described herein will typically survey with reduced SGRQ scores of at least 1 point but more preferably a reduction of 4 or more points will be experienced.

In addition, beneficial effects of pulmonary treatment in the lung can be measured by monitoring one or more of a number of possible pulmonary indicators, including mea-suring benefit by measuring increased forced expiratory volume during expiration, increased lung emptying during expiration, reduced end-expiratory lung volume, reduced functional residual capacity, reduced residual volume left in the lung during or after expiration (RV), reduced volume of gas that is trapped in the lung during or after expiration reduced volume of gas that is trapped in a lobe during or after expiration, reduced dynamic hyperinflation, decrease total lung capacity, reduce RV/TLC ratio, increased tidal expiratory volume change during tidal breathing at rest, increased inspiratory reserve volume during tidal breathing at rest, increased forced expiratory volume in the first second (FEV1), increased forced vital capacity volume (FVC), and increase ratio FEV1/FVC, to name a few.

Additionally, the beneficial effects of pulmonary treat-ment in the lung can be measured by monitoring one or more of the following measures, including reduced lung tissue density (e.g. more than 5 HU (Hounsfield units) change in average lung tissue density due to a treatment procedure), measuring lobar lung tissue density in which more than 2% change is measured, measuring the difference between lobes of lobar damage volume using a 950 HU filter in which the volume difference between lobes is reduced and a reduction of more than 3% volume of damaged tissue due to the treatment is significant, measuring displacement of more than 2 mm of fissure shift during the same portion of the breathing cycle is significant, or reduction of folds of pleura that demarcate the lobes in the lung, decreased lung com-pliance, decreased compliance in lobes or regions of lung tissue, increased lung tissue compliance uniformity between upper versus lower lobes, increased lung tissue compliance uniformity between lung lobes in a patient, and increased lung tissue compliance uniformity between lobar segments, to name a few.

Overall, the patient typically has a variety of symptomatic improvements, including reduced coughing (e.g. due to trapped air and mucus), increased ability to clear mucus due to passageways opening larger and for longer periods of time, increased mobility (e.g. as measured by currently standard 6-min walk test), reduced inspiratory effort, reduced dysthymia, decreased breathing rate, reduced glottis closure sensitivity (by clearing mucus, inflammation is reduced and coughing is reduced), reduced incidence of respiratory failure and increase time between COPD exacerbation events, to name a few.

Pulmonary Treatment Device Embodiments

Embodiments of the pulmonary treatment device 10 have various features and design elements to achieve the above described treatment effects and clinical goals. In addition, such features and design elements may have varying alternatives, a variety of which will be set forth herein.

Overall, the pulmonary treatment device 10 has a relatively short length of between approximately 1 cm and 20 cm but preferably 2-3 cm in an unstrained condition so as to minimize its length within the bronchoscope 20. This allows the bronchoscope 20 to be advanced to or as close to the target area within the lung L for deployment of the tissue gathering end 14. In some embodiments, the distal end of the bronchoscope 20 positioned at the target area and the tissue gathering end 14 is deployed by retraction of the bronchoscope 20. Delivering the tissue gathering end 14 and allowing it to recover to its deployed configuration at the target area avoids pushing of the device 10 forward within the lung tissue which causes tissue trauma.

Herein various aspects of the pulmonary treatment device 10 are described in more detail. It may be appreciated that although a variety of aspects and features are described, embodiments of the device 10 may include any combination of these aspects and features. Likewise, some embodiments may not include all of the aspects and features described. For example, in some embodiments, the device 10 comprises a tissue gathering end 14 and a stabilizing end 16 without an extendible midsection 18 therebetween.

A. Tissue Gathering End

As described previously, the tissue gathering end 14 of the pulmonary treatment device 10 is designed to be deployed into intact airways or the damaged tissue DT, comprised of loose, sponge-like, weakened tissue and open areas of blebs and bullae, so as to effectively engage the damaged tissue DT while minimizing any trauma. A variety of design features are provided to achieve these goals. In some embodiments, the tissue gathering end 14 expands and is rotatable so as to gather up the loose, damaged tissue in a manner that fixedly engages the end 14 with the damaged tissue DT. Thus, the tissue gathering end 14 is configured to gather, connect or hook into as much damaged soft tissue as possible. In some embodiments, this involves rotating the tissue gathering end 14 which threads the end 14 into place, such as through existing holes in the tissue. Due to the specialized design of the tissue gathering end 14, such rotation does not twist or bend airways in the lung.

Figure 13:
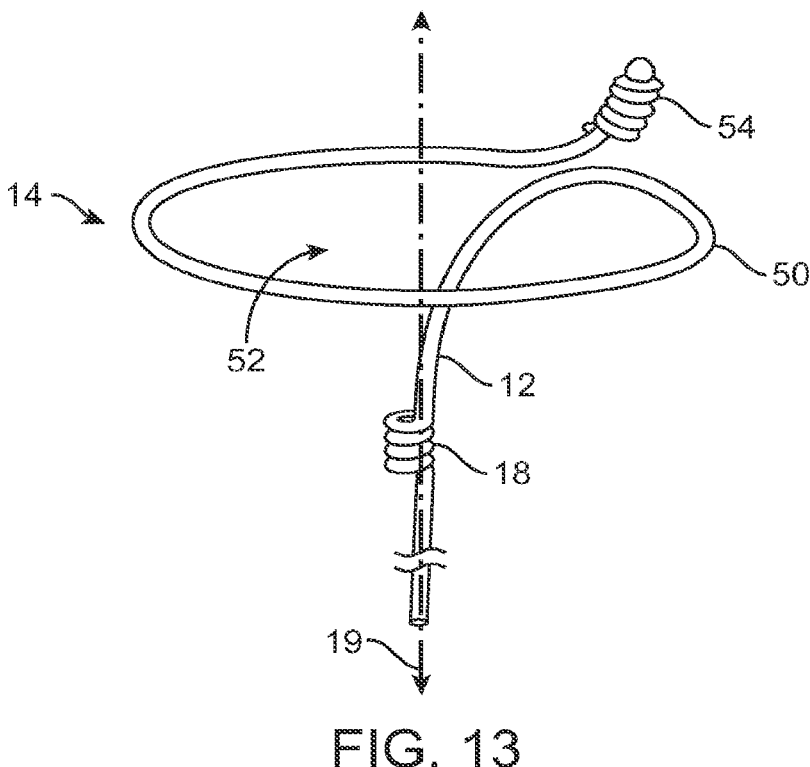
FIG. 13 illustrates an embodiment of a tissue gathering end of a pulmonary treatment device.
Figure 14:
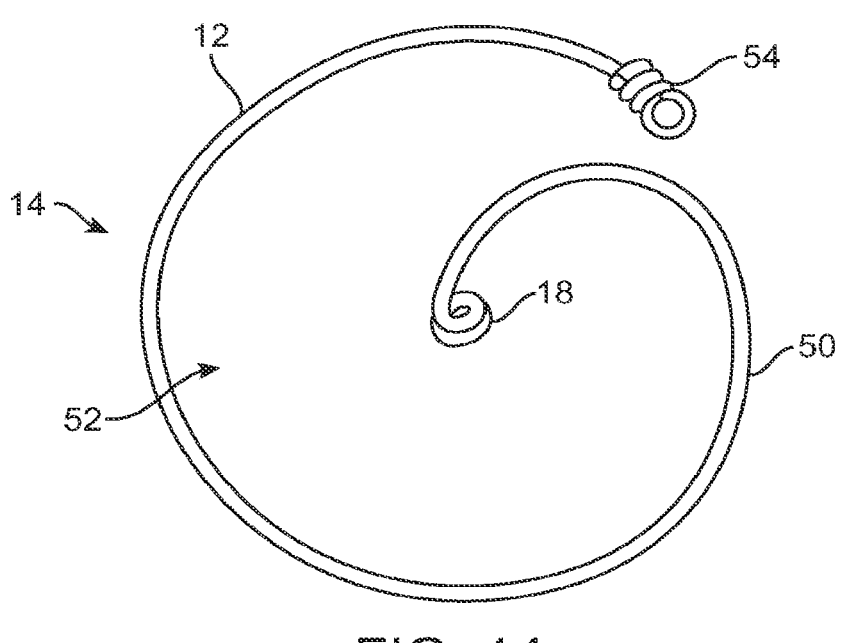
FIG. 14 illustrates a top view of the embodiment of FIG. 13.

FIG. 13 illustrates an embodiment of a tissue gathering end 14 of a pulmonary treatment device 10 of the present invention. In this embodiment, the tissue gathering end 14 comprises a portion of the elongate shaft 12 coiled into a helical shape, particularly having a single coil turn to form a loop shape. In this embodiment, the shaft 12 extends along the longitudinal axis 19 through the extendible midsection 18 and then bends radially outwardly distal to the extendible midsection 18, such as perpendicularly or at a 90 degree angle to the longitudinal axis, forming a loop 50 in the same plane. Thus, the loop 50 has an opening 52 perpendicular to the longitudinal axis 19. FIG. 14 illustrates a top view of the embodiment of FIG. 13. Thus, as illustrated, the opening of the loop 50 is perpendicular to the longitudinal axis 19, having a circular shape. Likewise, in this embodiment, the loop extends nearly 360 degrees around the longitudinal axis 19. In this embodiment, the shaft 12 has a distal tip 54 which is "turned-up" or facing in the distal direction. In some embodiments, the distal tip 54 is aligned with the longitudinal axis 19 and in other embodiments the distal tip 54 is offset from the longitudinal axis 19. In any case, the turned-up configuration aligns the distal tip 54 with or parallel with the direction of tension so as to avoid or reduce any trauma to the surrounding tissue. The distal tip 54 may have a variety of shapes including an end loop, coil, ball, bullet, tear drop, cone or taper shape to minimize tissue trauma.

In this embodiment, the tissue gathering end 14 comprises a single loop 50. However, it may be appreciated that the tissue gathering end 14 may comprise any suitable number of loops 50 or partial loops, including a quarter loop, a half loop, a three-quarter loop, one loop, two loops, three loops, four loops, five loops, six loops, more than six loops or any combination of these. The loops 50 may have any suitable diameter, typically in the range of 10 mm to 50 mm. Each of the loops 50 may have the same diameter or differing diameters. In some embodiments, the loop diameters taper, such as in a funnel or cone shape, wherein loop diameters incrementally decrease in size along the tissue gathering end 14. In such embodiments, the taper may be in the distal direction or the proximal direction. In some embodiments, the tissue gathering end 14 comprises a series of loops 50 having the same diameter and then transitions into a taper, typically in the distal direction, to the distal tip 54 or to a series of loops 50 having the same diameter which is smaller than the loops 50 disposed proximally. In some situations, these arrangements reduce trauma to the tissue.

In some embodiments the tissue gathering end 14 comprises more than one loop 50 to act as a spring that limits peak tensioning force on the fragile lung tissue, like a tension fuse between the tissue and the user. Typically, total pull force applied to the tissue gathering end 14 during placement of the device 10 is less than or equal to 9 Newtons. In preferred embodiments, the total pull force is less than or equal to 0.9 Newtons but patients may utilize a range of force between 0.005 and 10 Newtons but preferably near 0.07 Newtons, depending on the density of the tissue that is to be re-tensioned. The lower forces are required for low density tissue and more force is required in tissue that is denser and better preserved with more lung elastic recoil. In any case, the tissue gathering end 14 is shaped to optimize contact area to reduce lung tissue stress or pressure.

In some embodiments, the tissue gathering end 14 is comprised of heavy gage core wire, such as core wire having a diameter of 0.10-2.5 mm but most preferably between 0.25 mm and 0.30 mm. In some instances, the preferred diameter depends on the shape and configuration of the tissue gathering end 14. For example, if the tissue gathering end 14 comprises a loop shape having a diameter of less than 25 mm, the preferred core wire diameter may be 1 mm. If the tissue gathering end 14 comprises a loop shape having a diameter of greater than or equal to 25 mm, the preferred core wire diameter may be 1-2 mm.

Figure 15:
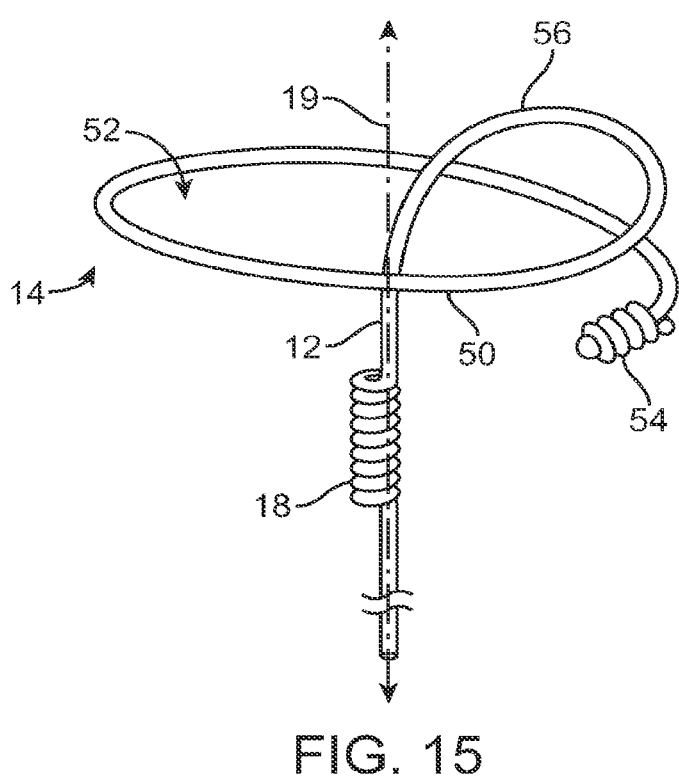
FIG. 15 illustrates another embodiment of a tissue gathering end of a pulmonary treatment device.
Figure 16:
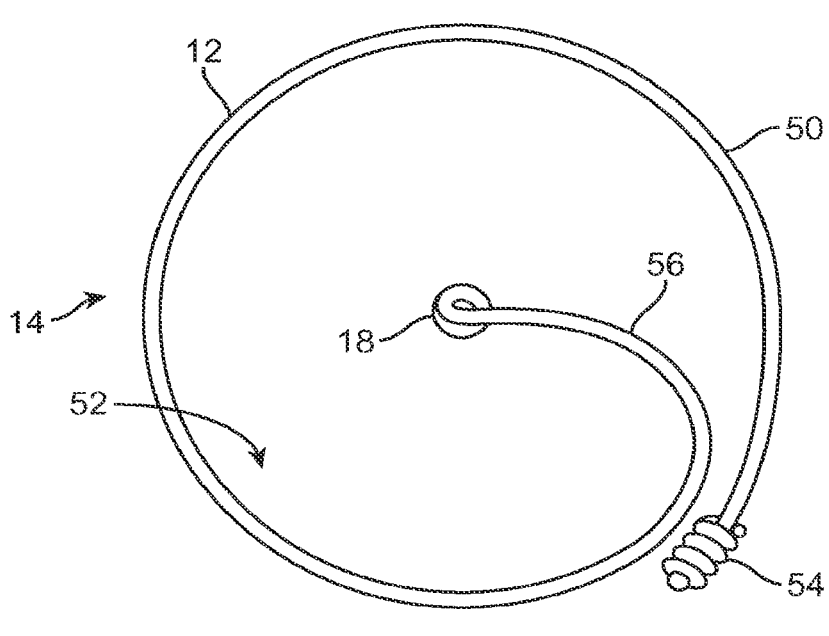
FIG. 16 illustrates a top view of the embodiment of FIG. 15.

FIG. 15 illustrates a similar embodiment of a tissue gathering end 14 of a pulmonary treatment device 10. In this embodiment, the shaft 12 extends along the longitudinal axis 19 through the extendible midsection 18 and then gradually bends radially outwardly distal to the extendible midsection 18. Rather than bending at a 90 degree angle to the longitudinal axis 19, the shaft 12 bends at an angle less than 90 degrees, such as a 30-45 degree angle to the longitudinal axis 19. This creates an arch 56, wherein the shaft 12 then bends downward at a distance from the longitudinal axis 19 and ultimately forms a loop 50 in a plane perpendicular to the longitudinal axis 19. Thus, the tissue gathering end 14 comprises a distal facing arch 56 with a loop 50 extending around the longitudinal axis 19 proximal of the arch 56. As the shaft 12 is retracted to tension lung tissue, arch 56 pulls loop 50 down against distal tip 54 to create a shape that emulates a concentric ring that gathers tissue. FIG. 16 illustrates a top view of the embodiment of FIG. 15. As shown, the opening 52 of the loop 50 is perpendicular to the longitudinal axis 19 having a circular shape. Likewise, in this embodiment, the loop 50 extends nearly 360 degrees around the longitudinal axis 19. In this embodiment, the shaft 12 has a distal tip 54 which is not "turned-up"; rather the distal tip 54 is disposed in the plane of the loop 50.

Figure 17:
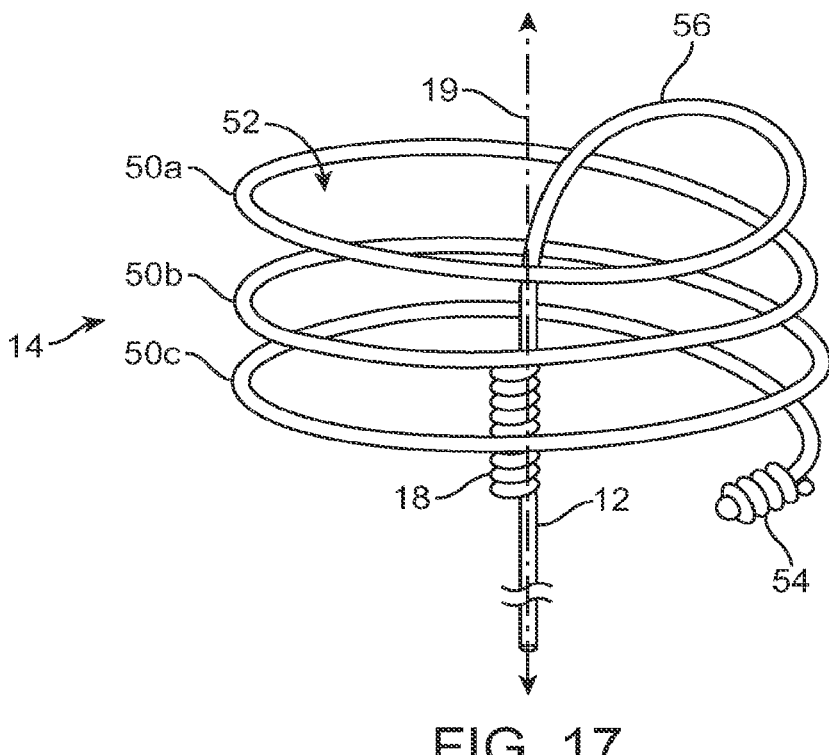
FIG. 17 illustrates an embodiment of a tissue gathering end of a pulmonary treatment device having multiple loops.

FIG. 17 illustrates an embodiment of a tissue gathering end 14 of a pulmonary treatment device 10 having multiple loops 50. In this embodiment, the shaft 12 extends along the longitudinal axis 19 through the extendible midsection 18 and then gradually bends radially outwardly distal to the extendible midsection 18. Again, rather than bending at a 90 degree angle to the longitudinal axis 19, the shaft 12 bends at an angle less than 90 degrees, such as a 30-45 degree angle to the longitudinal axis 19. This creates an arch 56, wherein the shaft 12 then bends downward at a distance from the longitudinal axis 19 and ultimately forms a first loop 50*a* in a plane perpendicular to the longitudinal axis 19. The shaft 12 then bends to form additional loops, such as a second loop 50*b* and a third loop 50*b*, each in a plane perpendicular to the longitudinal axis 19 and parallel to each other. Thus, the tissue gathering end 14 comprises a distal facing arch 56 with a plurality of loops 50*a*, 50*b*, 50*c* extending around the longitudinal axis 19 proximal of the arch 56. In some instances, the plurality of loops 50*a*, 50*b*, 50*c* allows the grabbing of more damaged tissue DT and the entire anchor may be pulled together to bind the tissue and trap tissue between the loops to cause tissue traction that wouldn't otherwise be achievable with a single loop shape. This configuration also stores potential energy in the plurality of loops 50*a*, 50*b*, 50*c* that acts to maintain tissue tension even after the lung disease continues with elongation of tissue over time.

Figure 18:
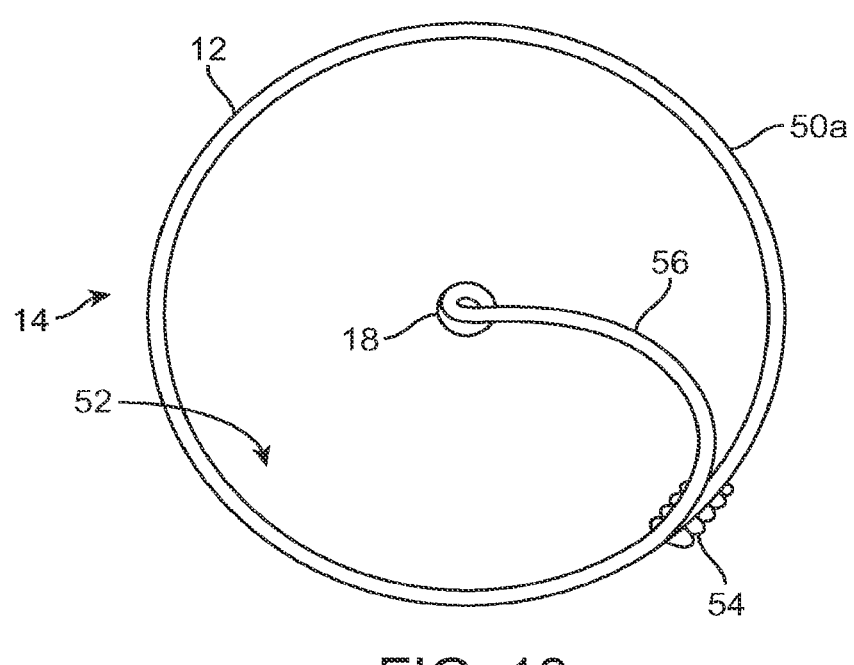
FIG. 18 illustrates a top view of the embodiment of FIG. 17.

FIG. 18 illustrates a top view of the embodiment of FIG. 17. Since the loops 50*a*, 50*b*, 50*c* have the same diameter, they are not individually visible from the top view as they are overlaid. As shown, the opening 52 of the loops 50*a*, 50*b*, 50*c* are perpendicular to the longitudinal axis 19 and have a circular shape. Likewise, in this embodiment, the loops 50*a*, 50*b*, 50*c* extend nearly 360 degrees around the longitudinal axis 19. Again, in this embodiment, the shaft 12 has a distal tip 54 which is not "turned-up"; rather the distal tip 54 is disposed in a plane parallel to the planes of the loops 50*a*, 50*b*, 50*c*.

Figure 19:
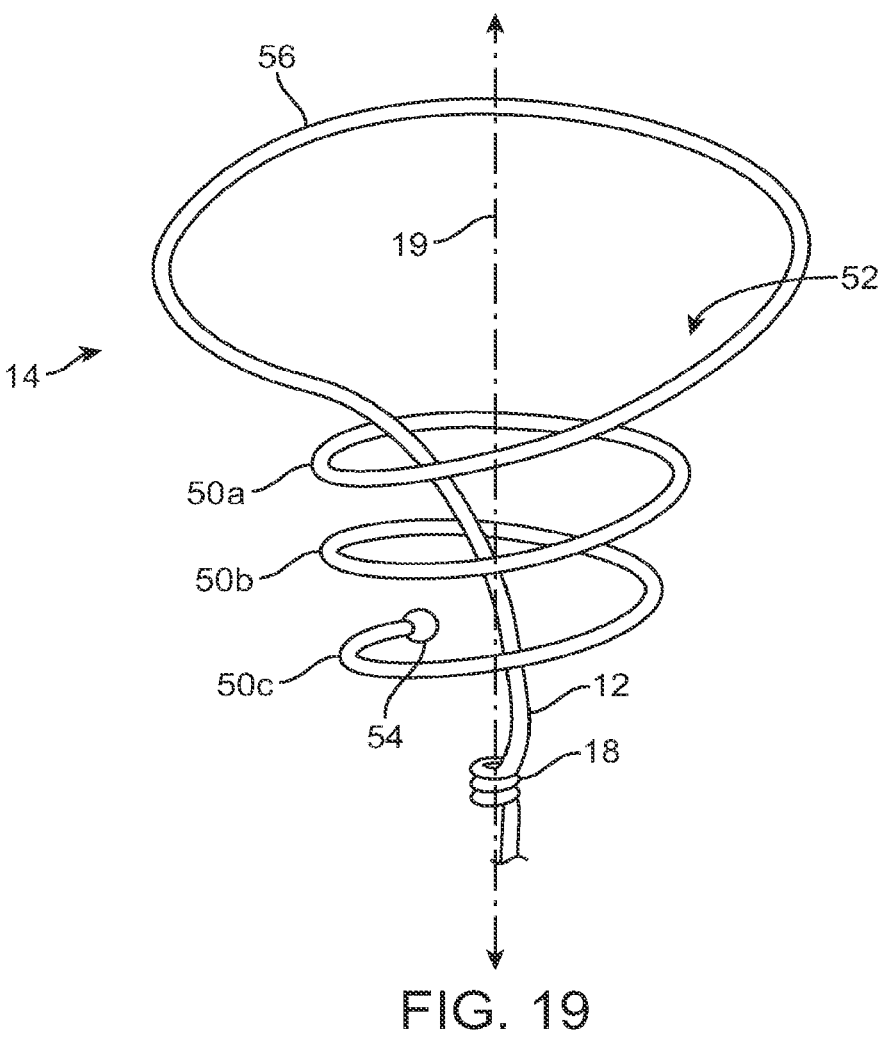
FIG. 19 illustrates another embodiment of a tissue gathering end of a pulmonary treatment device.

FIG. 19 illustrates another embodiment of a tissue gathering end 14 of a pulmonary treatment device 10 having multiple loops 50. In this embodiment, the shaft 12 extends along the longitudinal axis 19 through the extendible midsection 18 and then gradually bends radially outwardly distal to the extendible midsection 18. In this embodiment, the bending is in a first direction at a 90 degree or lesser angle to the longitudinal axis 19. The shaft 12 then bends in a second direction which is opposite to the first direction and ultimately bends downward at a distance from the longitudinal axis 19 on the opposite side of the extendible midsection 18. This creates an arch 56 which straddles the extendible midsection 18. The shaft 12 then forms a first loop 50*a* in a plane perpendicular to the longitudinal axis 19 and bends to form additional loops, such as a second loop 50*b* and a third loop 50*b*, each in a plane perpendicular to the longitudinal axis 19 and parallel to each other. Thus, the tissue gathering end 14 comprises a distal facing arch 56 with a plurality of loops 50*a*, 50*b*, 50*c* extending around the longitudinal axis 19 proximal of the arch 56. In this embodiment, the radius of the arch 56 is such that the arch 56 extends beyond the diameter of the loops 50*a*, 50*b*, 50*c*. This configuration resists movement of the arch 56 through the loops 50*a*, 50*b*, 50*c* while positioning the device 10, such as when tugging on the device 10 to re-tension the lung tissue.

Figure 20:
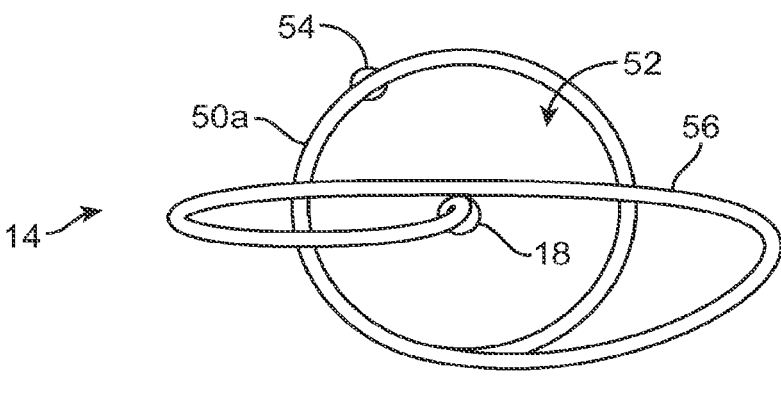
FIG. 20 illustrates a top view of the embodiment of FIG. 19.

FIG. 20 illustrates a top view of the embodiment of FIG. 19. Since the loops 50*a*, 50*b*, 50*c* have the same diameter, they are not individually visible from the top view as they are overlaid. As shown, the opening 52 of the loops 50*a*, 50*b*, 50*c* are perpendicular to the longitudinal axis 19 and have a circular shape. Likewise, in this embodiment, the loops 50*a*, 50*b*, 50*c* extend nearly 360 degrees around the longitudinal axis 19. This top view also illustrates that the arch 56 extends beyond the diameters of the loops 50*a*, 50*b*, 50*c*. Again, in this embodiment, the shaft 12 has a distal tip 54 which is not "turned-up"; rather the distal tip 54 is disposed in a plane parallel to the planes of the loops 50*a*, 50*b*, 50*c*.

Figure 21:
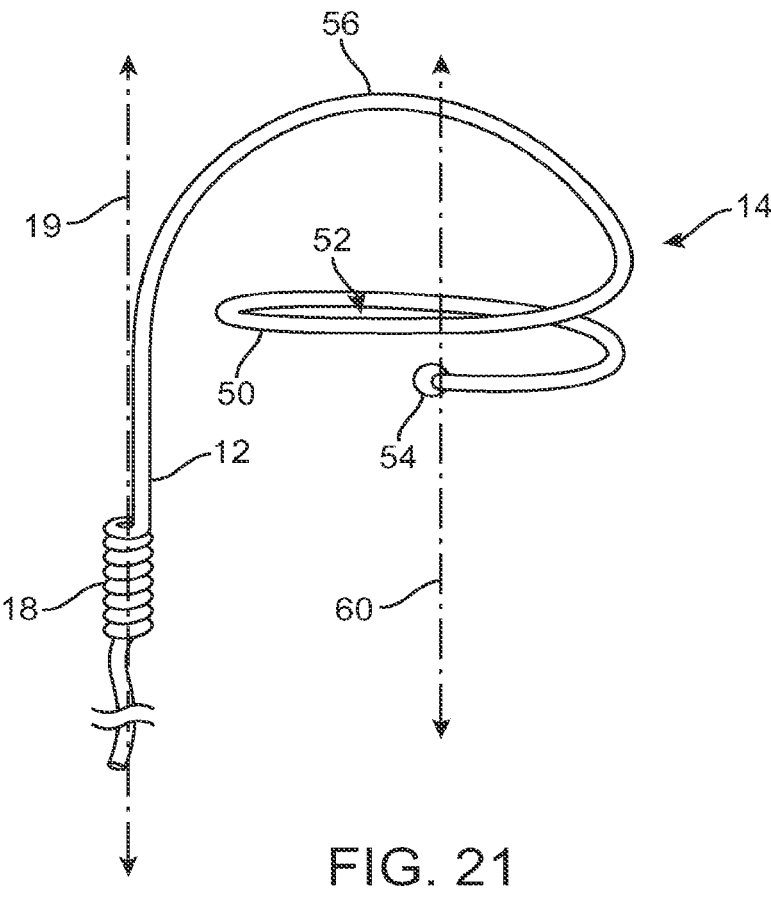
FIG. 21 illustrates an embodiment of a tissue gathering end wherein the shaft extends along the longitudinal axis through the extendible midsection and then gradually bends radially outwardly distal to the extendible midsection.
Figure 22:
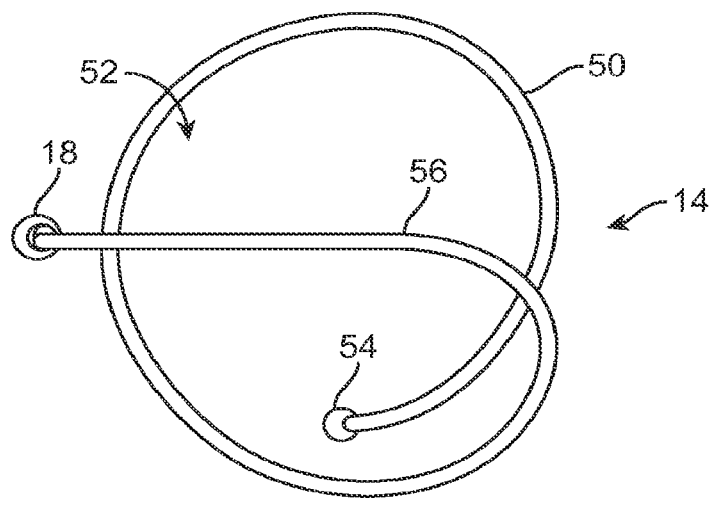
FIG. 22 illustrates a top view of the embodiment of FIG. 21.

In each of the above embodiments, the openings 52 of the one or more loops 50 of the tissue gathering end 14 are substantially concentric with the longitudinal axis 19. However, in other embodiments, the openings 52 of the one or more loops 50 are not substantially concentric with the longitudinal axis 19 and are offset from the longitudinal axis 19. For example, FIG. 21 illustrates an embodiment wherein the shaft 12 extends along the longitudinal axis 19 through the extendible midsection 18 and then gradually bends radially outwardly distal to the extendible midsection 18. Rather than bending at a 90 degree angle to the longitudinal axis 19, the shaft 12 bends at an angle less than 90 degrees, such as a 30-45 degree angle to the longitudinal axis 19. This creates an arch 56, wherein the shaft 12 then bends downward at a distance from the longitudinal axis 19 and ultimately forms a loop 50 in a plane perpendicular to the longitudinal axis 19. In this embodiment, the loop 50 is extends over 360 degrees but does not encircle the longitudinal axis 19. Instead, the loop 50 is concentric with an axis 60 which is parallel to the longitudinal axis 19 and offset by 3-30 mm, preferably 13 mm. FIG. 22 illustrates a top view of the embodiment of FIG. 21. As shown, the opening 52 of the loop 50 is perpendicular to the longitudinal axis 19 and shifted to one side of the extendable midsection 18. Likewise, in this embodiment, the loop 50 extends more than 360 degrees. In this embodiment, the shaft 12 has a distal tip 54 which is not "turned-up"; rather the distal tip 54 is disposed in the plane of the loop 50.

This offset configuration allows the extendable midsection 18 to be positioned against the wall of a lung passageway rather than extending through the center of the lung passageway lumen. This may reduce any potential accumulation of mucus within the lung passageway lumen, providing an open pathway for airflow. It may be appreciated that when the tissue gathering end 14 is positioned within damaged tissue DT, the loop 50 is not disposed within a natural lung passageway having structured walls. Therefore, contact between the loop 50 and the shaft 12 above the extendable midsection 18 is not problematic as the tissue gathering end 14 is not compressing the walls of a lung passageway.

Figure 23:
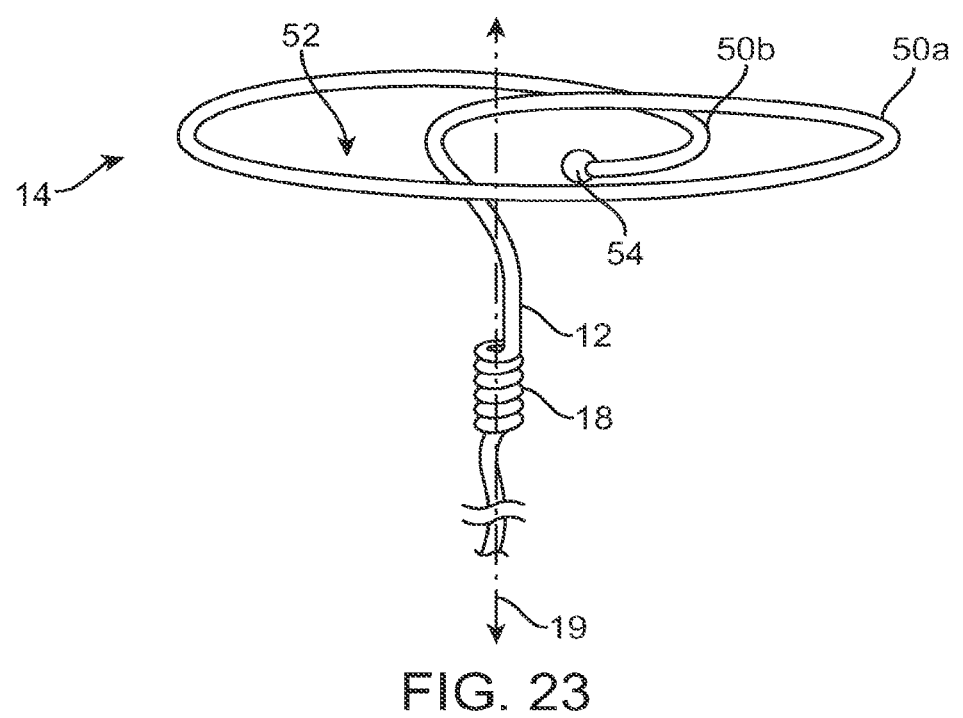
FIG. 23 illustrates an embodiment of a tissue gathering end wherein at least one of the loops of the tissue gathering end cross at least a portion of another loop.
Figure 24:
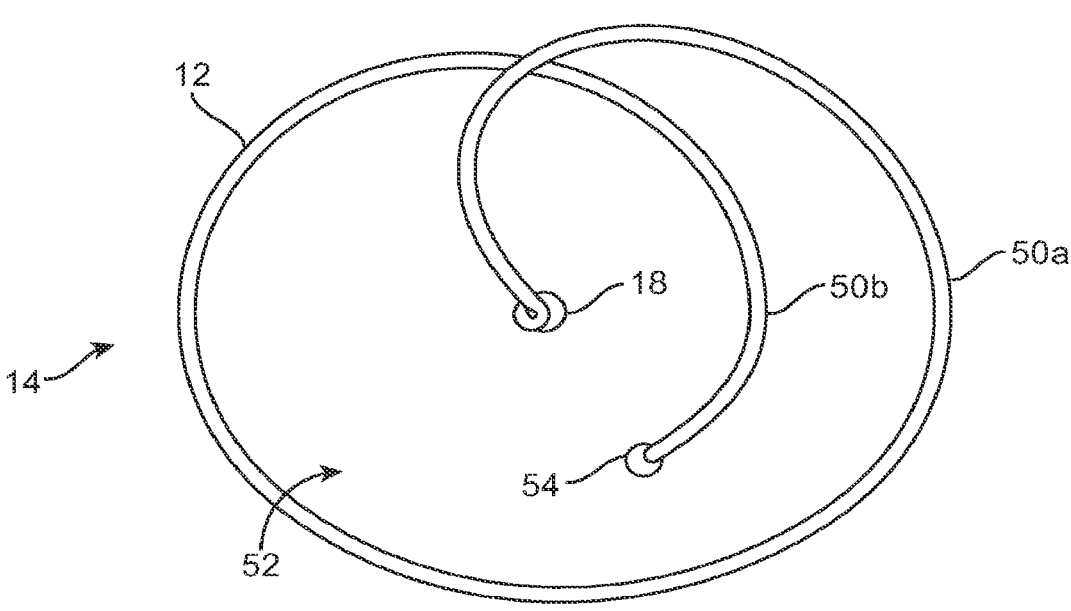
FIG. 24 illustrates a top view of the embodiment of FIG. 23.

In some embodiments, at least one of the loops 50 of the tissue gathering end 14 crosses at least a portion of another loop as illustrated in FIGS. 23-24. In particular, FIG. 23 illustrates an embodiment wherein the shaft 12 extends along the longitudinal axis 19 through the extendible midsection 18 and then bends radially outwardly distal to the extendable midsection 18, such as perpendicularly or at a 90 degree angle to the longitudinal axis, forming a first loop 50a in the same plane. Thus, the first loop 50a has an opening 52 perpendicular to the longitudinal axis 19. In this embodiment, the shaft 12 continues bending circumferentially to form at least a portion of a second loop 50b, wherein the second loop 50b has a smaller diameter than the first loop 50a. In addition, the second loop 50b is disposed proximally to the first loop 50a. FIG. 24 illustrates a top view of the embodiment of FIG. 23. Thus, as illustrated, the opening of the loops 50a, 50b are perpendicular to the longitudinal axis 19. Likewise, in this embodiment, the second loop 50b portion extends under the first loop 50a. Thus, when the device 10 is tugged in the proximal direction, during the re-tensioning step, the first loop 50a captures the second loop 50b, applying the total area of the combined length of both coils times the width of the shaft 12 material to present a broad efficient tissue gathering anchor to be pulled in the proximal direction. This large area of contact reduces the bearing pressure that is imparted on the tissue which minimizes or eliminates the tendency for the device to grow through or migrate through the tissue over time. With minimal migration, the advantageous effect of the treatment is prolonged. It may be appreciated that any number of loops 50 may be present, the distal-most loop applying force to the more proximal loops.

B. Extendable Midsection

Figure 25:
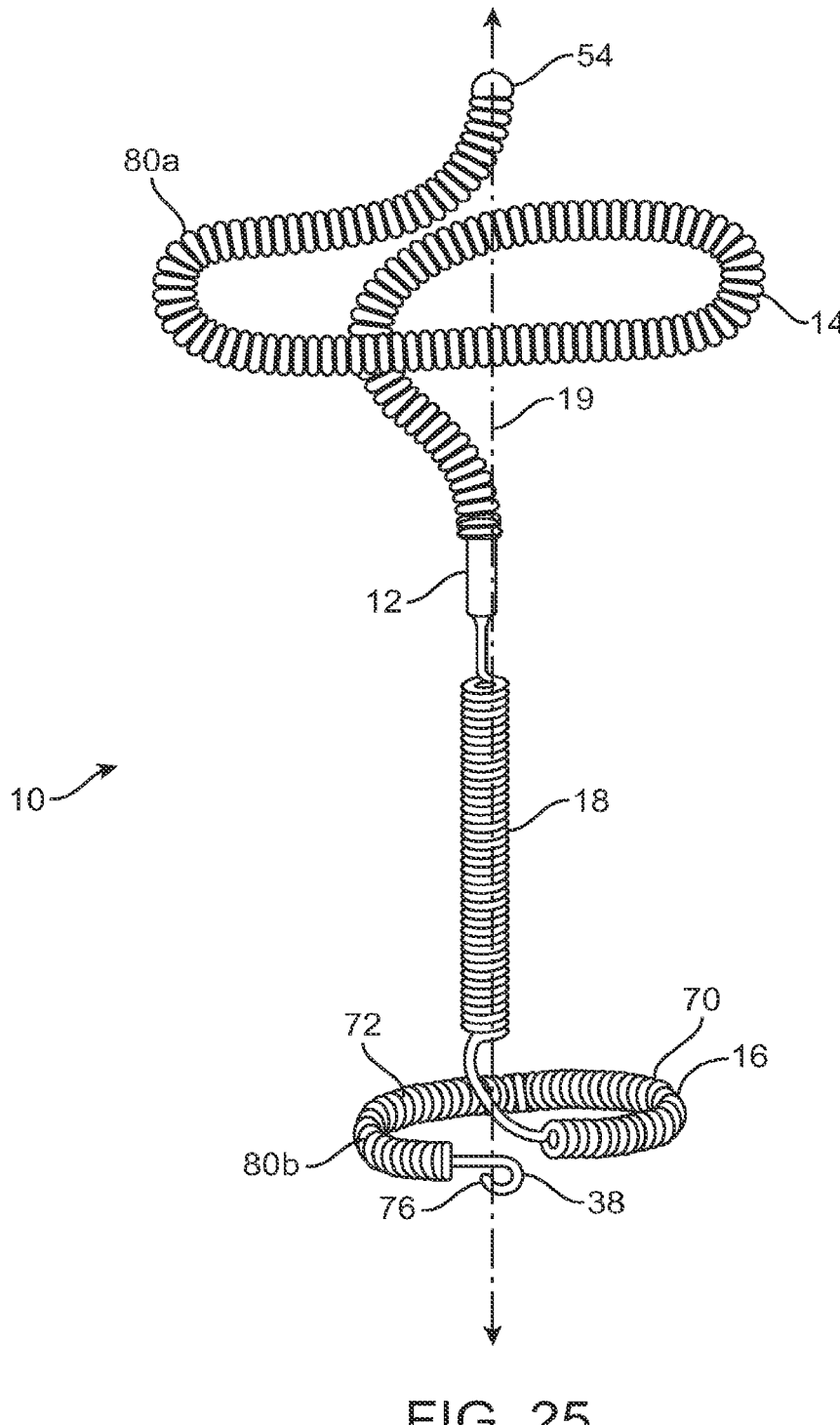
FIG. 25 illustrates an embodiment of a pulmonary treatment device having an extendible midsection connecting the tissue gathering end with the stabilizing end.

The extendible midsection 18 connects the tissue gathering end 14 with the stabilizing end 16, as illustrated in FIG. 25. In some embodiments, the tissue gathering end 14, extendible midsection 18 and stabilizing end 16 are formed by shaping a single shaft to form the desired configurations. However, it may be appreciated that each or some of the parts may be formed individually and joined together. In any case, the midsection 18 is configured to be extendible from at least a relaxed state to an extended state, wherein the midsection 18 stores potential energy. As described previously, once the tissue gathering end 14 has fixedly engaged the damaged tissue DT, the deployment element 30 is retracted into the bronchoscope port 22 which tugs the device 10 in the proximal direction. This causes extension of the midsection 18 and pulling of the damaged tissue DT engaged by the tissue gathering end 14. Such pulling continues until a desired level of resistance occurs or the damaged tissue DT has been pulled a desired amount. The deployment element 30 is then additionally retracted which further extends the midsection 18. This straightens and extends the surrounding airway AW. Retraction of the deployment element 30 continues until the stabilizing end 16 reaches a suitable airway for holding and maintaining the stabilizing end 16. Thus, the bulk of the expansion occurs along the extendable midsection 18.

In some embodiments, the extendible midsection 18 has the shape of an elastic spring or coil. Typically, the shaft 12 is coiled into a helical shape to form the elastic spring or coil. In some embodiments, the midsection 18 has a length in the range of 5-75 mm but preferably a length of less than 25 mm in resting free space and a potential longitudinal elongation in the range of 10-200 mm but preferably more than 75 mm. However, the extension of the midsection 18 while the device 10 is in use depends on the location of the target treatment site within the tracheobronchial tree, the extent of damage to the tissue and the desired level of re-tensioning. In any event, in some embodiments the midsection 18 comprises at least 3 complete coils.

In some embodiments, the coiled extendible midsection 18 has a diameter in the range of 0.5-10 mm, such as 2.5 mm, particularly when the shaft 12 is comprised of a wire having a diameter in the range of 0.10-0.75 mm, preferably 0.25-0.3 mm. It may be appreciated that in some embodiments, the diameter of the shaft 12 forming the extendible midsection 18 is smaller than the diameter of the shaft 12 forming the tissue gathering end 14 or the stabilizing end 16. This may be achieved by necking down the shaft 12 in the area of the extendible midsection 18, such as by grinding. In any case, the overall diameter of the extendible midsection 18 is typically smaller than both the tissue gathering end 14 and the stabilizing end 16.

In some embodiments, the extendible midsection 18 additionally supports the airway wall. In use, the device 10 draws the loose damaged tissue DT inward toward the lung passageways that have a maintained structure. Therefore, the extendible midsection 18 is located within an airway having structured walls when the device 10 is implanted. However, such walls are often weakened and benefit from the additional internal support offered by the extendible midsection 18, particularly under the new level of lung tensioning. As the midsection 18 of device 10 is elongated to store energy, the adjacent airway wall, along the length of the midsection, may be longitudinally compressed which will weaken it and possibly allow it to collapse more easily. This is more than offset by the coil of the midsection providing radial strength and radial stenting support enough to prevent the airway, along this midsection 18 length from collapsing. Likewise, the extendible midsection 18 straightens the airway or the general path of the overall airway system.

In some embodiments, the extendible midsection 18 is axisymmetric with the tissue gathering end 14 and/or the stabilizing end 16, such as illustrated in FIGS. 6-7. In such embodiments, the midsection 18 typically has an open lumen forming a tunnel to allow passage of air therethrough. However, it may be appreciated that in some embodiments the extendible midsection 18 may not be axisymmetric and is disposed to one side of the tissue gathering end 14, such as illustrated in FIG. 21, and/or the stabilizing end 16. Thus, in these embodiments, the midsection 18 extends along the side of the airway (e.g. adjacent to the wall).

In some embodiments, the extendible midsection 18 is joined to a feature along the tissue gathering end 14 to keep the tissue gathering end 14 from rotating.

C. Stabilizing End

As described previously, the stabilizing end 16 of the pulmonary treatment device 10 is designed to hold the device 10, and therefore the lung tissue, in tension by seating in an appropriate portion of the tracheobronchial tree. As mentioned, after the tissue gathering end 14 has been desirably positioned, the deployment element 30 retracts and pulls the stabilizing end 16, which in turn pulls the extendable midsection 18 and tissue gathering end 14. Such pulling continues and increasingly applies tension to the lung, along with other physical benefits such as straightening the airway and increasing airflow. Once the stabilizing end 16 reaches a suitable airway for holding and maintaining the stabilizing end 16, the stabilizing end 16 is seated and released. Typically, the stabilizing end 16 is positioned within an airway or ostium OS or point of branching within the tracheobronchial tree. The larger diameter of the ostium OS allows the stabilizing end 16 to expand and exert stabilizing radial force against the walls W of the ostium OS, holding the expanded device 10 in place. The end 16 stabilizes the device 10, providing a base or anchor for the applied tension which is then maintained throughout treatment of the patient as the device 10 is left behind.

In some embodiments, the stabilizing end 16 comprises a portion of the elongate shaft 12 coiled into a helical shape, particularly having multiple coil turns, each having a loop shape. In some embodiments, the stabilizing end 16 comprises single loop 70, as illustrated in FIG. 25. However, the stabilizing end 16 may have additional loops, such as two loops, three loops, four loops or any combination with partial loops, such as a half loop, one and a half loops, two and a half loops or three and a half loops, to name a few. The wire end at the far proximal end of the stabilizing end 16 may be terminated using a crimp, compression sleeve, weld, glue joint or tether to connect it to the previous loop. By connecting the proximal loose end of the stabilizing end to the previous loop, the hoop strength of the stability end is greatly enhanced. This brings benefit in two ways. It reduces the likeliness that the stabilizing end will be forced into a smaller diameter and be pulled into the airway. By preventing this, the odds of bringing long term benefit for the patient are greatly increased. Also, there are circumstances in which the treatment devices may need to be removed, such as times when the patient may have severe lung infection or lung cancer. In order to recapture and remove a device, large bronchoscope must be utilized to provide a large bore channel and lumen for a forceps or other instrument that will be used to connect to the treatment device. These scopes typically provide a 2.0 mm channel and the scope outside diameter normally exceeds 6 mm. Large scopes such as the one we are describing cannot be guided past the 3rd generation airways so it is ideal that the stabilizing end of the treatment device can be reliably fixed at the ostium that joins 3rd generation airways. Most other devices that intend to treat these patients tend to migrate deeper in the lung and they present the physician who is charged to remove them with great difficulties.

In one embodiment, the shaft 12 forms the extendible midsection 18 along the longitudinal axis 19 and then bends radially outwardly distal to the extendible midsection 18, such as perpendicularly or at a 90 degree angle to the longitudinal axis 19, forming a loop 70 in the same plane. Thus, the loop 70 has an opening 72 perpendicular to the longitudinal axis 19 and has a circular shape. Likewise, in this embodiment, the loop 70 extends nearly 360 degrees around the longitudinal axis 19.

The loops 70 may have any suitable diameter, typically in the range of 10 mm to 12 mm, particularly when formed from a shaft 12 having a diameter of 0.3 mm. Thus, the overall diameter of the stabilizing end 16 is typically smaller than the diameter of the tissue gathering end 14. When the stabilizing end 16 comprises a plurality of loops 70, each of the loops 70 may have the same diameter or differing diameters. Typically, the loops 70 are expandable so as to enlarge within an ostium OS or other suitable portion of the tracheobronchial tree.

Typically, the stabilizing end 16 is the portion of the device 10 which is pulled to re-tension the lung and locate the final placement of the device 10 for implantation. Therefore, in such embodiments, the stabilizing end 16 includes an attachment feature 38 to which the deployment element 30 of the bronchoscope 20 is coupled. In the embodiment of FIG. 25, the attachment feature 38 comprises a loop 40 formed by the proximal tip of the shaft 12 of the device 10. Such a loop-shaped attachment feature 38 may be utilized with a compatible attachment mechanism 36 on the deployment element 30, such as a tether 42 and a support rod 44, as previously illustrated in FIGS. 8-9. The tether 42 extends through the loop 40 and around the support 42 so as to secure the loop 40 to the support rod 44. Thus, the stabilizing end 16 of the device 10 is able to remain attached to the deployment element 30 during deployment by the attachment mechanism 36.

Figure 26:
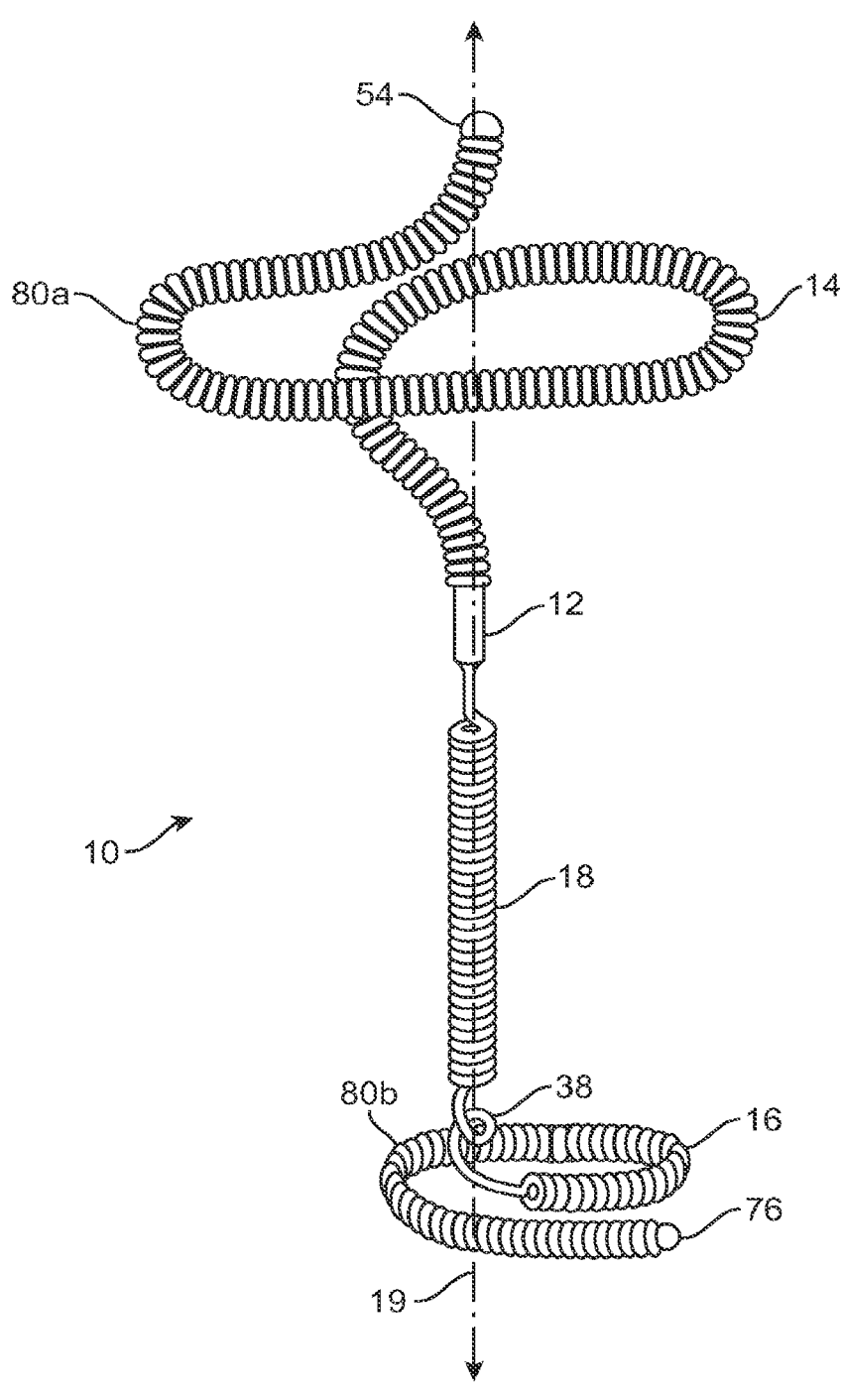
FIG. 26 illustrates an embodiment of a pulmonary treatment device having an attachment feature located distally of the stabilizing end.

In other embodiments, the attachment feature 38 is located distally of the stabilizing end 16, such as illustrated in FIG. 26. Here, the attachment feature 38 comprises a loop 40 formed by the shaft 12 between the extendible midsection 18 and the stabilizing end 16. Again, such a loop-shaped attachment feature 38 may be utilized with a compatible attachment mechanism 36 on the deployment element 30, such as a tether 42 and a support rod 44, as previously illustrated in FIGS. 8-9. Since the attachment feature 38 is distal to the stabilizing end 16, the attachment feature 38 may be pulled proximally in a way that allows the stabilizing end 16 to expand and anchor freely in the ostium. Thus, the stabilizing end 16 will be free to expand into the ostium OS while pulling on the device 10 in the proximal direction during delivery.

It may be appreciated that other types of attachment features 38 may be used, such as threaded couplers, hook like wire forms, snap lock connections etc.

In some embodiments, the shaft 12 has a separate proximal tip which is "turned-down" or facing in the proximal direction. In some embodiments, the proximal tip is aligned with the longitudinal axis 19 and in other embodiments the proximal tip is offset from the longitudinal axis 19. In any case, the turned-down configuration aligns the proximal tip 76 with or parallel with the direction of tension so as to avoid or reduce any trauma to the surrounding tissue, such as blunt end agitation on the airway wall or bleeding or coughing that this brings. The proximal tip 76 may have a variety of shapes including a coil, ball, end loop, cone shape or other blunt end shape that will minimize tissue agitation during breathing related motion.

D. Shaft Materials

The pulmonary treatment device 10 may be formed from a single element, such as a continuous shaft 12, or from individual parts that are joined together. When parts are joined together, they may ultimately appear as a continuous shaft 12, however the device 10 will include various transition zones where the parts are joined. In some embodiments, the parts are comprised of differing materials, etc. Thus, the shaft 12 will be described herein and may refer to a single continuous shaft forming the tissue gathering end 14, extendible midsection 18 and stabilizing end 16, or a shaft forming any one or more of these parts.

In some embodiments, the shaft 12 is comprised of a shape-memory alloy, such as nickel titanium (nitinol). Nitinol alloys exhibit two closely related and unique properties: shape memory effect and super-elasticity or pseudo-elasticity. Shape memory is the ability of nitinol to undergo deformation at one temperature, then recover its original, undeformed shape upon heating above its "transformation temperature". Super-elasticity occurs at a temperature range above its transformation temperature; in this case, the transformation temperature should be set under that of body temperature so no heating is necessary to cause the undeformed shape to recover, and the material exhibits enormous elasticity, some 10-30 times that of ordinary metal.

Thus, the desired configuration of the shaft 12 (e.g. bends, loops, etc.) is set during manufacturing of the device 10. The device 10 is then able to be elongated, restrained, compressed or deformed, such that when loaded within the delivery device, the pulmonary treatment device recovers to its original shape in free space. When the device 10 is delivered to a confined space, the device 10 is able to recover toward its original shape, with modifications according to the confined space. Recovery force is tuned by adjusting Austenite final ($A_f$) temperature using heat treating of the alloy during manufacturing. An $A_f$ temperature closer to body temperature (37° C.) lowers recovering force. An $A_f$ temperature farther below body temperature increases recovery force. Thus, in some embodiments, an $A_f$ temperature that is 5-50 degrees below body temperature is preferred. In other embodiments, the pulmonary treatment device my beneficially be produced with a gradation of $A_f$ temperatures. For instance, a large wire may be used to produce the device so the distal and proximal structures are strong, tuned with an $A_f$ of 15 degrees C. to allow them to anchor into tissue reliably but the extendable midsection, also constructed using the same large wire, may be thermally tuned so the $A_f$ is 30 degrees C. (closer to 37 degrees C., typical body temperature) so the extendable midsection is weaker and the spring stress versus strain ratio is lower. Any number of $A_f$ temperatures may be set at any location on the implant in order to enhance performance.

In some embodiments, the metallic surface of the nitinol is stripped of contaminants and oxides to native metal. The nitinol is then passivated to form a thin layer of titanium dioxide on the surface for optimal biocompatibility. In some embodiments, the thin layer is 0.5-10 μm thick, preferably 2 μm thick.

In some embodiments, the shaft 12 is comprised of a metal, such as stainless steel, steel containing chromium, steel containing cobalt, steel containing chrome, a metal alloy with nickel and/or titanium, a biocompatible metal that is fully elastic after being strained, or a combination of these, to name a few. In some embodiments, the metallic surface of the metal is stripped of contaminants and oxides to native metal. The metal is then passivated to form a thin layer of chromium oxide (when the metal is steel-based) on the surface for optimal biocompatibility. In some embodiments, the thin layer is 0.5-10 μm thick, preferably 2 μm thick.

In some embodiments, the shaft 12 is comprised of other materials, such as composites (e.g. carbon fiber) or ceramics, polymers, polyimide film (e.g. Kapton®), para-aramid synthetic fiber (e.g. Kevlar®), nylons, polyimides, metals such as titanium, nickel alloys, nitinol, memory shape alloys such as martensite nitinol or super-elastic forms of nitinol.

In some embodiments, the shaft 12 is comprised of wire, such as round-section wire, or square or rectangular section ribbon. The shaft 12 may be solid or hollow, such as comprised of tubing. All edges of the shaft 12 are free of sharp edges to minimize inflammation and the related granulation tissue that is formed from cyclic agitation of the soft tissues in the lung.

In some embodiments, the shaft 12 has a diameter between 0.010 inches-0.080 inches, but preferably between 0.009 and 0.023 inches.

E. Shaft Tips

As mentioned, the shaft 12 has a distal tip 54 and a proximal tip 76. In some embodiments, such tips 54, 76 are optimized to assist in advancement of the device 10 from the delivery device. Typically, the tips 54, 76 have a blunt surface to reduce any potential injury or inflammation of tissue due to delivery. In addition, in some embodiments, the tips 54, 76 include a feature which assists in resisting relative motion between the tips 54, 76 and the surrounding tissue. This helps to resist sliding or movement of the tips 54, 76 towards the center of the implant, such as toward the extendible midsection 18. Such resistance to tip migration bolsters storage of potential energy in the device 10 rather than losing energy during migration. Thus, for example, the distal tip 54 can advance but resists moving backwards, in the proximal direction, and the proximal tip 76 can be pulled proximally but resists moving in the distal direction.

Figure 27A:
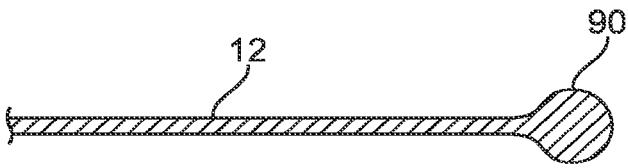
FIGS. 27A-27D illustrate example tips suitable for either the distal tip or proximal tip.

FIGS. 27A-27D illustrate example tips 90 suitable for either the distal tip 54 or proximal tip 76. Each of the tips 90 are formed at the end of the shaft 12. FIGS. 28A-28B illustrate example methods of forming such tips 90. To begin, FIG. 27A illustrates an embodiment of a tip 90 having a ball shape. Such a ball shape may be formed by melting the distal-most portion 92 of the shaft 12, as illustrated in FIG. 28A. Here, a forming tool, such as a copper mold 96 is positioned a distance d from the end of the shaft 12. The copper mold 96 serves as a heat sink. The distal-most portion 92 of the shaft 12 is then melted while the copper mold 96 stops the melt-back, forming the ball. Thus, the length of distance d determines the size of the ball shaped tip 90.

Figure 27B:
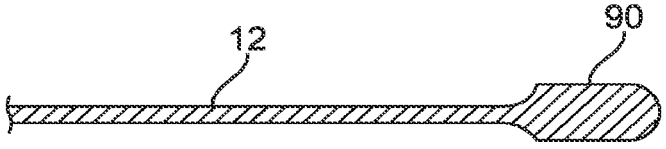
Figure 28A:
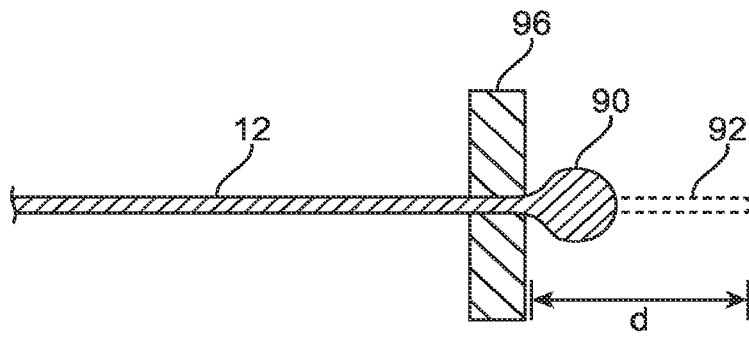
FIGS. 28A-28D illustrate example methods of forming the tips of FIGS. 27A-27D.
Figure 28B:
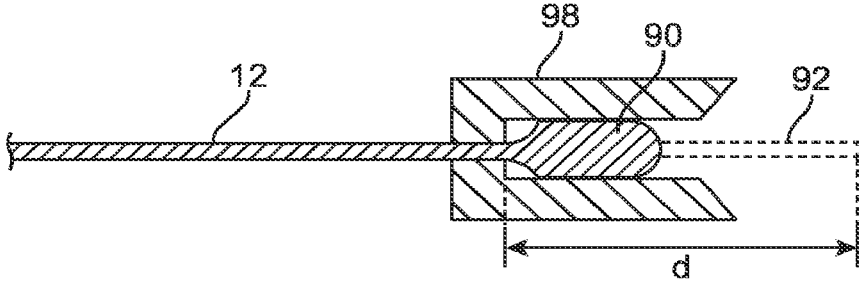
Figure 28C:
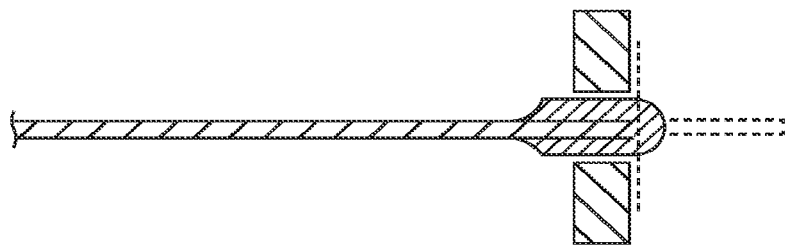
Figure 28D:
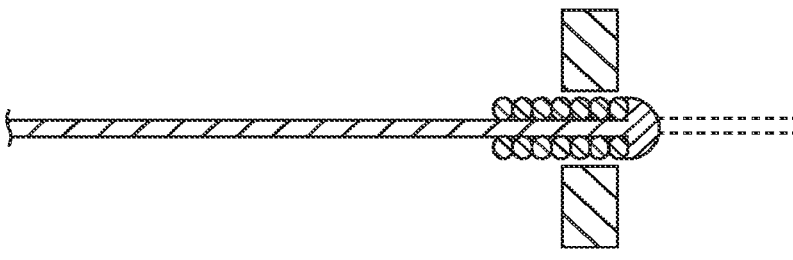
Figure 29A:
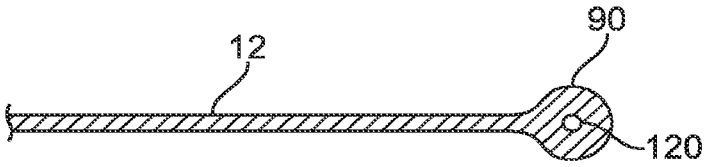
FIGS. 29A-29D illustrate example tips having an attachment feature.
Figure 29B:
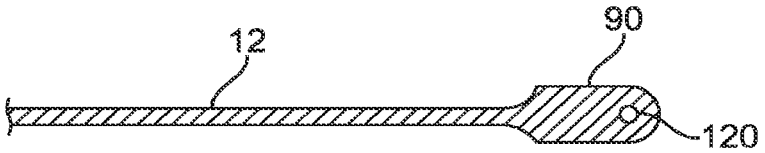
Figure 29C:
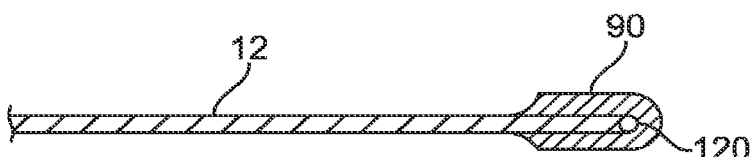
Figure 29D:
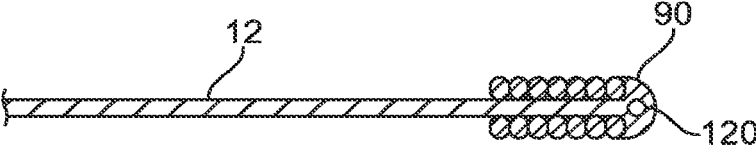

FIG. 27B illustrates an embodiment of a tip 90 having a cylindrical shape. Such a cylindrical shape may be formed by melting the distal-most portion 92 of the shaft 12, as illustrated in FIG. 28B. Here, a forming tool, such as a copper casting tool 98 or welding arc, is positioned a distance d from the end of the shaft 12. The copper casting tool 98 serves as a heat sink and a mold. The distal-most portion 92 of the shaft 12 is then melted into the casting tool 98 forming a cylindrical shape. Again, the length of distance d determines the size of the cylindrical shaped tip 90.

Figure 27C:
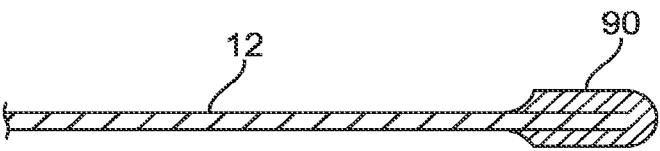

FIG. 27C illustrates an embodiment of a tip 90 having a blunt large bore shape. A tube is placed over wire and the wire and tube are welded together, to yield a hemisphere tip and tube with a chamfer or straight cut back edge to grab tissue.

Figure 27D:
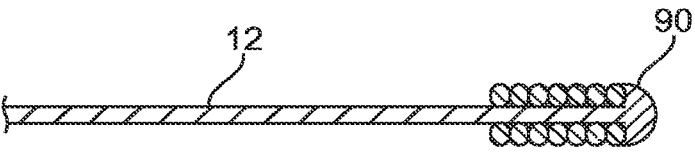

FIG. 27D illustrates an embodiment of a tip 90 having a coil spring and spherical end shape. By placing a coil over the wire, positioning the coil end coincident with the wire end and striking a welding arch at the end, a hemispherical weldment is created that joins the coil and wire that is blunt and larger diameter than the bare wire would be without the benefit of the coil. The wire coil or tube used to make the tips can be made from titanium, nitinol or a more radiopaque material such as tungsten, tantalum, gold or platinum.

In each of these embodiments, the tip 90 is smooth to allow removal of the device 10 if desired, but the increase in diameter compared to the shaft 12 allows the tip 90 to catch on a portion of tissue, particularly in an area of damaged tissue DT, which assists in anchoring the tip the place.

It may be appreciated that in some embodiments, the tip 90 functions as an attachment feature 38. In such embodiments, the tip 90 includes a hole or opening 120, as illustrated in FIGS. 29A-29D, which is used to connect with an attachment mechanism 36. Thus, a tether 42 can be passed through the opening 120 and around a support rod 44, so as to secure the tip 90 to the support rod 44. This allows the device 10 to be attached to the deployment element during delivery, as described previously.

F. Jacket

In some embodiments, the pulmonary treatment device 10 includes one or more jackets 80. A jacket 80 is a covering that extends over the shaft 12, such as to increase the diameter of the shaft 12, increase engagement quality with surrounding tissue, increase surface area of the shaft 12, and/or to provide drug delivery, to name a few. The jacket 80 may be formed from a variety of materials, such as metals (e.g. stainless steel, titanium, nitinol, nickel, cobalt chrome, or a combination of these) or polymers (e.g. polycarbonate urethane, polytetrafluoroethylene (PTFE), fluorinated ethylene propylene (FEP), polyimide film (e.g. Kapton®), polyimide, polyether ether ketone (PEEK), polyethylene, ethylene-vinyl acetate (EVA) (also known as poly (ethylene-vinyl acetate) (PEVA)), polypropylene, polyvinyl alcohol (PVA), polyurethane, nylon, polyether block amides (PEBA), acrylonitrile butadiene styrene (ABS), polybutyrate, polyethylene terephthalate (PET), polysulfone (PES), ethylene tetrafluoroethylene (ETFE), polyvinylidene fluoride (PVDF), thermoplastic polyurethane elastomers (e.g. Pellethane®), aliphatic polyether-based thermoplastic polyurethanes (TPUs) (e.g. Tecoflex®), or a combination of these). Likewise, the jacket 80 may be formed from a metallocene. A metallocene is a compound typically comprising two cyclopentadienyl anions (Cp, which is $C_5H^-_5$) bound to a metal center (M) in the oxidation state II, with the resulting general formula $(C_5H_5)_2M$.

The jacket 80 may take a variety of forms. In some embodiments, the jacket 80 comprises a wire, extrusion or sleeve that is welded to, over-molded, shrunk to, glued to, adhered to, compression fit to or otherwise joined with the shaft 12. In some embodiments, the jacket 80 has the form of a coil which is advanced over the shaft 12 in the desired area. In such embodiments, a ball or other feature may be welded to the shaft 12 to hold the jacket 80 on the shaft 12. In other embodiments, the jacket 80 comprises a coating.

Both FIG. 25 and FIG. 26 illustrate a pulmonary treatment device 10 having a plurality of jackets 80. For example, the device 10 includes a first jacket 80a positioned over the tissue gathering end 14. In some embodiments, the first jacket 80a covers the entire tissue gathering end 14, as shown, and in other embodiments, the first jacket 80a covers a portion of the tissue gathering end 14. An example of such a first jacket 80a is a 2.0 mm diameter nitinol coil; such a jacket may be suitable for positioning over, for example, a shaft 12 comprising a 1.0 mm diameter wire. This allows passage of the tissue gathering end 14 through a 2.0 mm channel of a bronchoscope 20. However, it may be appreciated that other sized jackets may be used, particularly in the range of 0.5-3.0 mm diameter. For example, if a therapeutic scope is used as a delivery device (having a 2.8 mm channel), a jacket having a 2.8 mm diameter may be used. Increasing the cross sectional area of the tissue gathering end increases the bearing area imparted on the tissue which reduces the pressure imparted on the tissue and this reduces implant migration or implant ingrowth through the tissue. These benefits are important as they increase the durability of the treatment.

In FIG. 25 and FIG. 26, the device 10 includes also includes a second jacket 80b positioned over the stabilizing end 16. In some embodiments, the second jacket 80b covers the entire stabilizing end 16 (FIG. 25), and in other embodiments, the second jacket 80b covers a portion of the stabilizing end 16 (FIG. 26). An example of such a second jacket 80b is a 0.50-4 mm diameter nitinol coil but most preferably a 2.5-2.8 mm diameter coil; such a jacket may be suitable for positioning over, for example, a shaft 12 comprising a 0.2-0.3 mm diameter wire. This also allows passage of the stabilizing end 16 through a 2.8 mm channel of a bronchoscope 20. Again, it may be appreciated that other sized jackets may be used, particularly in the range of 0.5-4.0 mm diameter. For example, if a therapeutic scope is used as a delivery device (having a 2.8 mm channel), a jacket having a 2.8 mm diameter may be used.

The second jacket 80b increases the area that is engaging tissue. By maximizing the bearing area in contact with the tissue to be greater than 9.81E-8 square inches but preferably more than 10E-7 square inches of bearing area per linear inch along the implantable device centroid+, the potential for device migration through tissue is nearly eliminated. This reduces erosion into the airway by the device 10 to increase treatment effect durability. In addition, the second jacket 80b prevents the stabilizing end 16 from "cheese wiring" or cutting through the soft ostium tissue.

In some embodiments, the jacket 80 provides controlled delivery of an agent, such as a drug. In some instances, such delivery reduces the rate of wound healing, tissue remodeling, inflammation, generation of granular tissue, and hyperplasia, to name a few.

Alternative Embodiments

Figure 30:
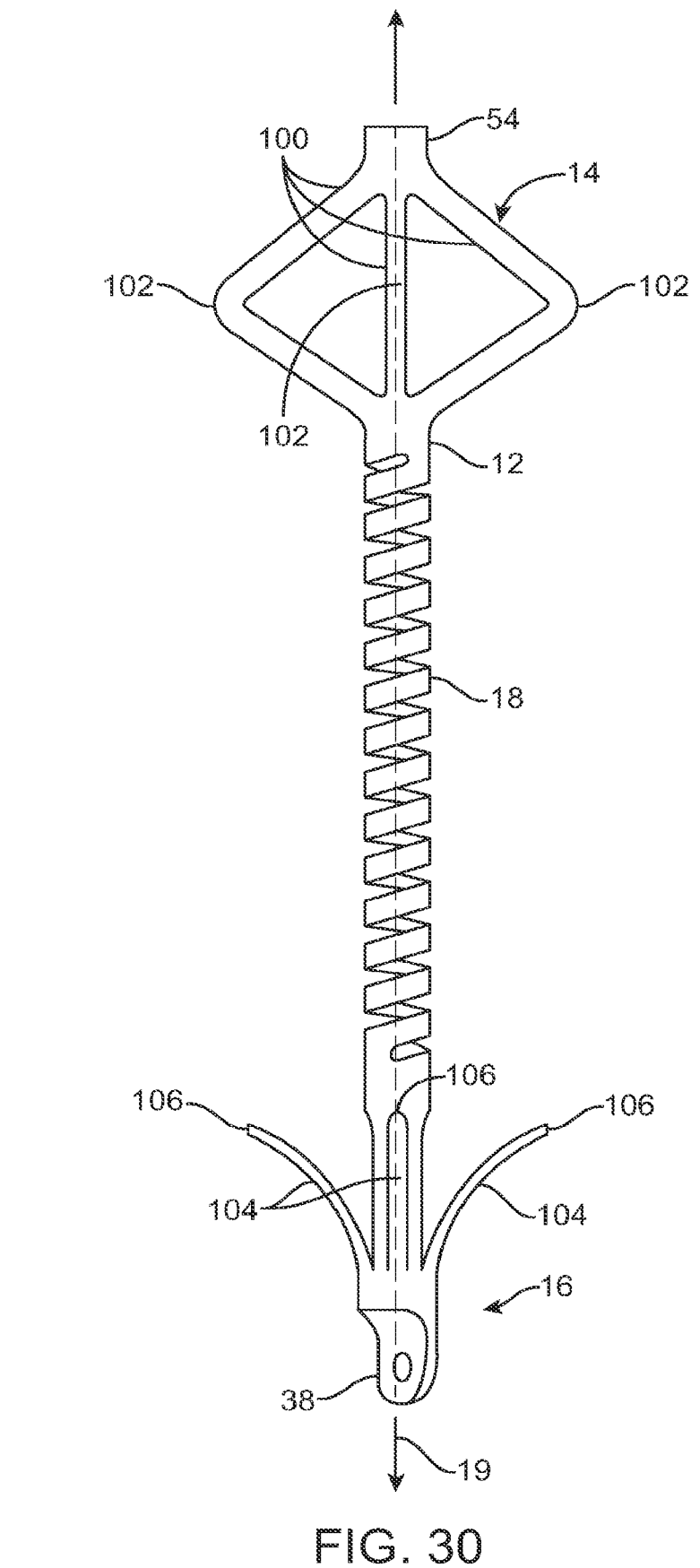
FIG. 30 illustrates an embodiment of a device configured from a shaft comprising a hollow tube.

It may be appreciated that the pulmonary treatment device 10 may take a variety of alternative forms. In such embodiments, the device 10 may include elements similar in function but differing in form. Or, the embodiments may include features which function differently but still satisfactorily treat the lung. FIG. 30 illustrates an embodiment of a device 10 configured from a shaft 12 comprising a hollow tube. In this embodiment, the device 10 includes a tissue engaging end 14, an extendible midsection 18, and a stabilizing end 16, each laser cut from the hollow tube. Here, the tissue engaging end 14 includes one or more wings 100 which extend radially outwardly from the longitudinal axis 19 when deployed. Each wing 100 has an elongate shape formed from the shaft 12, such as by laser cutting longitudinal slits in the shaft 12 from the extendible midsection 18 to the distal tip 54. Thus, the tissue engaging end 14 is configured to have a slim profile, wherein the wings 100 extend in parallel to the longitudinal axis 19, while the tissue engaging end 14 is disposed within the delivery device. Each wing 100 also has a predetermined bend location 102, typically midway along the length of the wing 100. Upon deployment, each wing 100 juts radially outwardly, perpendicular to the longitudinal axis 19, by bending at its bend location 102. This creates an expanded profile which allows the end 14 to engage the damaged tissue DT of the lung. As each wing 100 bends radially outwardly, the expandable midsection 18 and distal tip 54 are drawn toward each other.

In this embodiment, the extendible midsection 18 is also laser cut from the hollow tube shaft 12. Here, the hollow tube is cut in a helical or spiral shape to form a spring or coil. Further, in this embodiment, the stabilizing end 16 is also cut from the hollow tube shaft 12. Here, the stabilizing end 16 includes at least one prong 104 cut from the shaft 12. Each prong 104 may have any suitable shape but is typically elongate having a free end with an atraumatic tip 106. The stabilizing end 16 is configured to have a slim profile, wherein the prongs 104 extend in parallel to the longitudinal axis 19, while the stabilizing end 16 is disposed within the delivery device. Each prong 104 also has a pre-curvature which causes the prong 104 to bend radially outwardly, away from the longitudinal axis, upon deployment. This allows the stabilizing end 16 to expand in a desired lung area, such as an ostium, to stabilize the position of the device 10 when implanted. In this embodiment, the stabilizing end 16 also includes an attachment feature 38 for attaching to an attachment mechanism 36 on the deployment element 30 during deployment. In this embodiment, the attachment feature 38 comprises a hole cut into the tubular shaft 12.

Delivery Device Embodiments

Figures 31A, 31B:
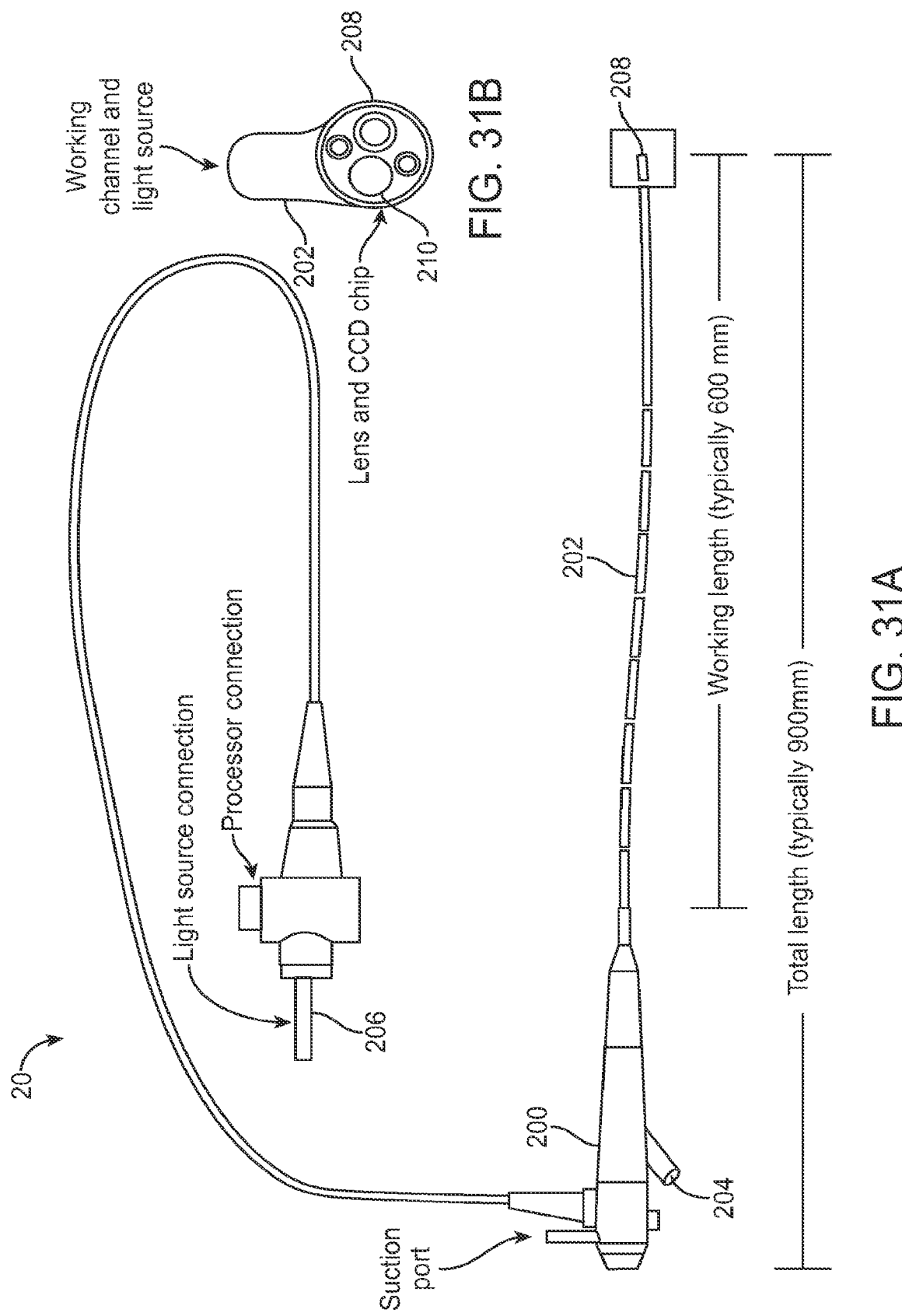
FIGS. 31A-31B illustrate an embodiment of a bronchoscope used as a delivery device for delivering the pulmonary treatment device.

As mentioned previously, the pulmonary treatment device 10 is sized and configured to be delivered by a delivery device that is insertable into the lung, such as a steerable scope (e.g. bronchoscope 20), catheter or other delivery system. The delivery device is configured to be advanced within any anatomical lumen in the lung that is either innate or created within the lung, either by disease or with the use of an instrument. An example delivery device is a bronchoscope 20, an embodiment of which is illustrated in FIG. 31A-31B. In this example, the bronchoscope 20 includes a bronchoscope body 200 and an insertion cord 202. The insertion cord 202 is advanced into the endobronchial tree of the patient and the bronchoscope body 200 remains outside of the patient, typically grasped by the operator's non-dominant hand. The insertion cord 202 contains a fiberoptic bundle for light and image transmission, tip bending control wires and a working channel. The average length of the insertion cord 202 is 600 mm (range 500-650 mm). The working channel continues into the bronchoscope body 200, exiting at the working channel port 204. The bronchoscope body 200 also includes an eye piece (which can be attached to a camera for display on a screen-fiberoptic scopes have an eye piece; video scopes do not), diopter ring (for focusing), and control lever. The control lever is used to control the distal tip of the insertion cord 202. Typically, the control lever is used to move the insertion cord tip 208 up/down and/or side-to-side, whereas rotation is typically achieved by rotation of the bronchoscope body 200 with the operator's wrist and shoulder. The bronchoscope 20 also includes a light source which can be supplied via a cable 206 or a portable battery powered source. The light source may be halogen, incandescent or LED, to name a few. FIG. 31B illustrates an end view of the insertion cord tip 208. As shown, the working channel 210 extends through the tip 208, allowing delivery of the pulmonary treatment device 10 therefrom.

As mentioned previously, in some embodiments, the pulmonary treatment device 10 is configured to be delivered through a lumen in the delivery device, such as by pushing the treatment device through a lumen of a scope, catheter, introducer, sheath, sleeve or similar device. For example, in some embodiments, the pulmonary treatment device 10 is loaded directly into the working channel port 204 and advanced through the working channel 210 for delivery from the insertion cord tip 208.

However, in other embodiments, the device 10 is pre-loaded into an introducer which is advanceable into the working channel 210 for delivery therefrom. In other embodiments, the treatment device 10 is mounted on a guidewire which constrains portions of the device 10, preventing these portions from expanding radially. The device 10 and guidewire are advanced together into the working channel 210 for delivery therefrom. In another embodiment, the device is pre-loaded on the guidewire which is advanceable into the working channel 210 for delivery therefrom.

Figure 32:
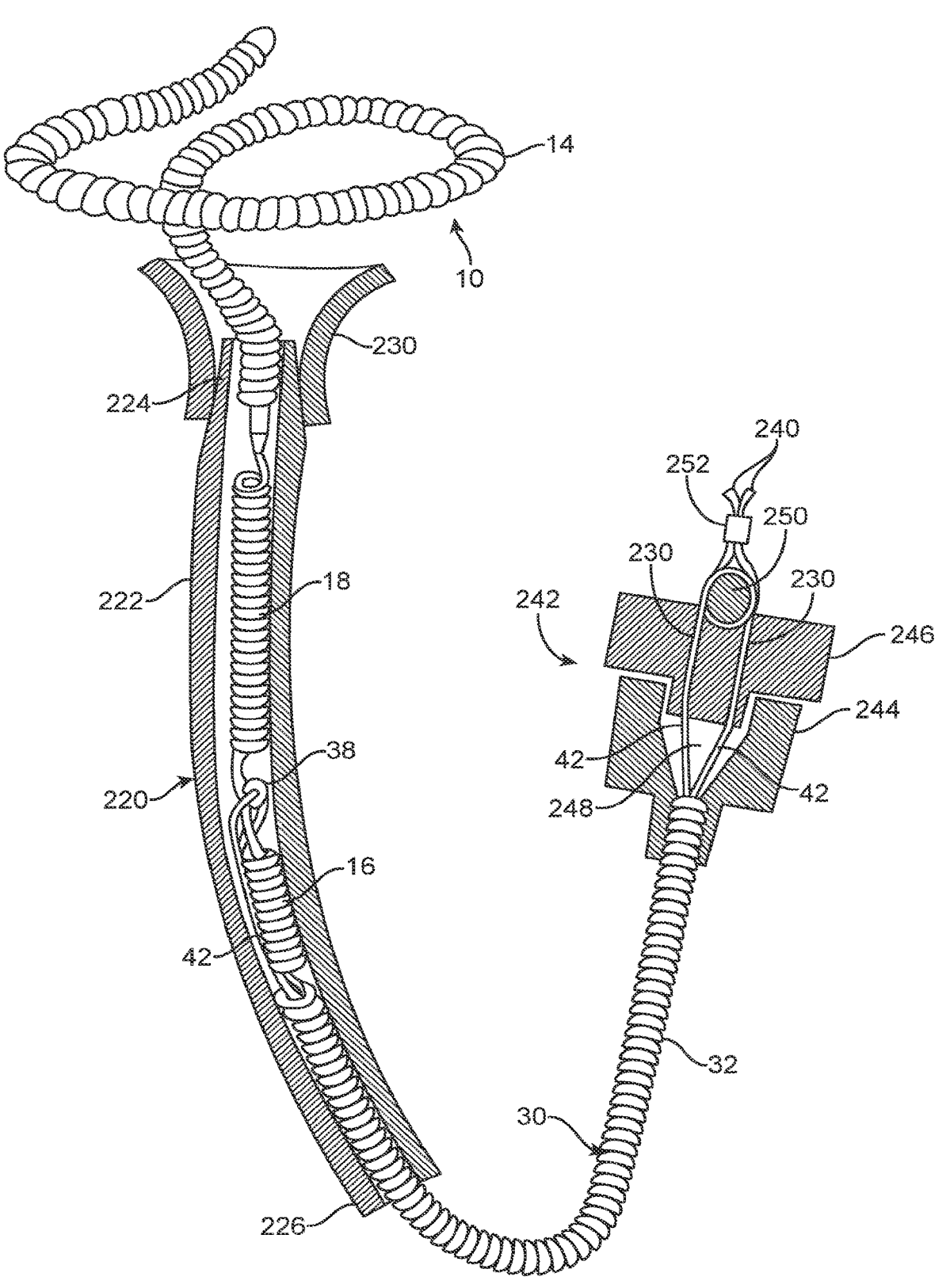
FIG. 32 illustrates an embodiment of an introducer having a pre-loaded pulmonary treatment device.

FIG. 32 illustrates an embodiment of an introducer 220 having a pre-loaded pulmonary treatment device 10. In this embodiment, the introducer 220 comprises an elongate tube 222 having a first end 224 and a second end 226. The elongate tube 222 is comprised of any suitable material, such as metal, stainless steel, polymer or composite tubing. Typically, the elongate tube 222 has a bend to assist in insertion into the working channel port 204 or is bendable to both assist in insertion and to allow for compact packaging (such as positioning into round track or square track packaging without kinking). In any case, the introducer 220 should be strong enough to keep the device 10 from distorting from a straight configuration and hard enough that the device 10 cannot indent into the wall of the introducer 220, particularly during the sterilization process that involves heating to 130-180° C. The introducer 220 can be any suitable length, such as a minimum of 2 inches longer than the device 10 therein and a maximum of half the length of the deployment element 30. In some embodiments, the introducer 220 has a length of 4 to 20 inches, preferably 10 inches.

FIG. 32 illustrates the stabilizing end 16 and the extendible midsection 18 loaded within the introducer 220. Here, the tissue gathering end 14 is disposed outside of the introducer 220 and allowed to coil into its expanded state. In some embodiments, the tissue gathering end 14 is packaged in this configuration to reduce stress on the end 14 during transport and sterilization. In such embodiments, the tissue gathering end 14 is then retracted into the introducer 220 prior to use. In this embodiment, the first end 224 of the introducer 220 is removably joined with a funnel 230 to assist in retracting the tissue gathering end 14 into the introducer 220. Thus, the funnel 230 has a tapered shape which gradually draws the tissue gathering end 14 radially inward toward the interior lumen of the introducer 220. Once the tissue gathering end 14 resides within the introducer 220, the funnel 230 is removed.

In this embodiment, the device 10 is attached to a deployment element 30 by tether 42. The deployment element 30 comprises an elongate shaft 32, typically having an interior lumen extending therethrough. The elongate shaft 32 may take various forms, including a coiled shape, as shown and may be comprised of a variety of materials, such as metal or polymer. In some embodiments, the shaft 32 is comprised of a wire or polymer coil having a flexible exterior sheath or liner that minimizes kinking as it is advanced through the working channel 210 of the bronchoscope 20. Likewise, in some embodiments, the shaft 32 includes an interior liner, such as of polytetrafluoroethylene or other polymer, to protect the tether 42 passing therethrough from breaking. In other embodiments shaft 32 is comprised of a braided frame with a liner (such as comprised of polytetrafluoroethylene) and an outer jacket (such as comprised of thermoplastic elastomer or flexible polyamide). It may be appreciated that in some embodiments, the elongate shaft 32 has a solid center rather than a hollow center. It may also be appreciated that the deployment element 30 may have any suitable length, such as 13-45 inches, preferably 34 inches.

When the elongate shaft 32 is hollow or has an interior lumen, the tether 42 passes through the interior lumen, through the attachment feature 38 and then back through the interior lumen of the deployment element 30 creating two free ends 240 of the tether 42. The tether 42 may be comprised of any suitable material such as a monofilament or braided high strength polymer, a carbon fiber, or a thread or braid comprising metal, stainless steel, nitinol, titanium, steel alloyed with chrome or cobalt, polytetrafluoroethylene, and/or material from a family of ultra-high molecular weight polymers, to name a few.

In this embodiment, the deployment element 30 extends out of the second end 226 of the introducer 220 and culminates in a hub 242 which holds the free ends 240 of the tether 42. Thus, the device 10 is able to remain attached to the deployment element 30 by tether 42 during deployment. In this embodiment, the hub 242 of the deployment element 30 comprises a base 244 and a top 246. Here, each of the base 244 and top 246 are thumb knob shaped for ease of use. In this embodiment, the base 244 is crimped, glued or welded to the shaft 32 of the deployment element 30. The free ends 240 of the tether 42 extend from the shaft 32 and then pass through the base 244, typically within a cavity 248 therein. Such passage through the cavity 248 ensures that the tether 42 is not abraded by the base 244. In this embodiment, the cavity 248 has tapered walls leading to the shaft 32 so as to minimize the size of the cavity 248 while ensuring adequate space for the tether 42. The free ends 240 then pass through the top 246 where they are separated into individual lumens 230. The lumens 230 are spaced apart to impart a moment while twisting to make length reduction related tightening more effective. In this embodiment, the free ends 240 then wrap around a support 250 which reduces stress on the tether 42. Typically, the support 250 has an atraumatic shape, such as a cylinder or ball. The free ends 240 are then held together with a clip 252.

Figure 33:
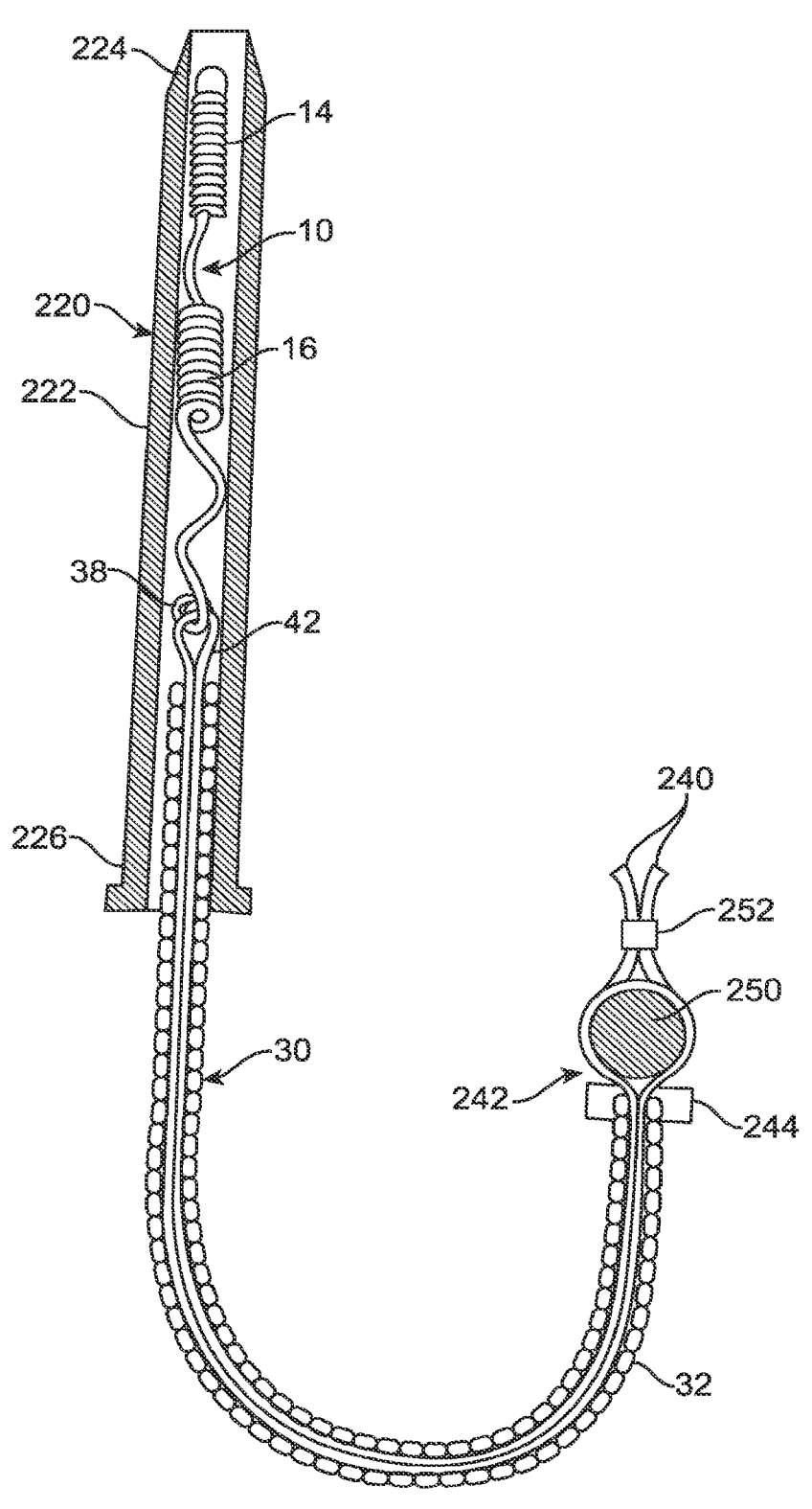
FIG. 33 illustrates another embodiment of an introducer having a pre-loaded pulmonary treatment device.

FIG. 33 illustrates another embodiment of an introducer 220 having a pre-loaded pulmonary treatment device 10. In this embodiment, the introducer 220 again comprises an elongate tube 222 having a first end 224 and a second end 226. The elongate tube 222 is comprised of any suitable material, such as metal or polymer. In this embodiment, the device 10 comprises a tissue gathering end 14 and a stabilizing end 16, without an extendible midsection 18. FIG. 33 illustrates the tissue gathering end 14 and stabilizing end 16 loaded within the introducer 220.

In this embodiment, the deployment element 30 is attached to the attachment feature 38 of the device 10 by tether 42. The deployment element comprises an elongate shaft 32 having an interior lumen extending therethrough. The elongate shaft 32 may take various forms, including a coiled shape, as shown. The tether 42 passes through the interior lumen of the deployment element 30, through the attachment feature 38 and then back through the interior lumen of the deployment element 30 creating two free ends 240 of the tether 42. In this embodiment, the deployment element 30 extends out of the second end 226 of the introducer 220 and culminates in a hub 242 which holds the free ends 240 of the tether 42. Thus, the device 10 is able to remain attached to the deployment element 30 by tether 42 during deployment. In this embodiment, the hub 242 of the deployment element 30 comprises a base 244. In this embodiment, the base 244 is crimped, glued or welded to the shaft 32 of the deployment element 30. In this embodiment, the free ends 240 then wrap around a support 250 which reduces stress on the tether 42. Typically, the support 250 has an atraumatic shape, such as a cylinder or ball. The free ends 240 are then held together with a clip 252.

In any case, the use of a pre-loaded introducer 220 allows for ease in loading of the bronchoscope 20 for delivery of the device 10 therethrough. The introducer 220 holds the device 20 in a relatively straight configuration so it can easily be introduced into the bronchoscope 20. In some embodiments, the introducer 220 also holds the device 20 in a radially compressed configuration so that it can be advanced through the working channel 210 of a bronchoscope 20 having a conventional inner diameter (e.g. 2.0 mm). Thus, the operator is relieved from any manipulation of the device 10 during loading of the bronchoscope 20 and is ensured proper orientation and delivery.

Figure 34:
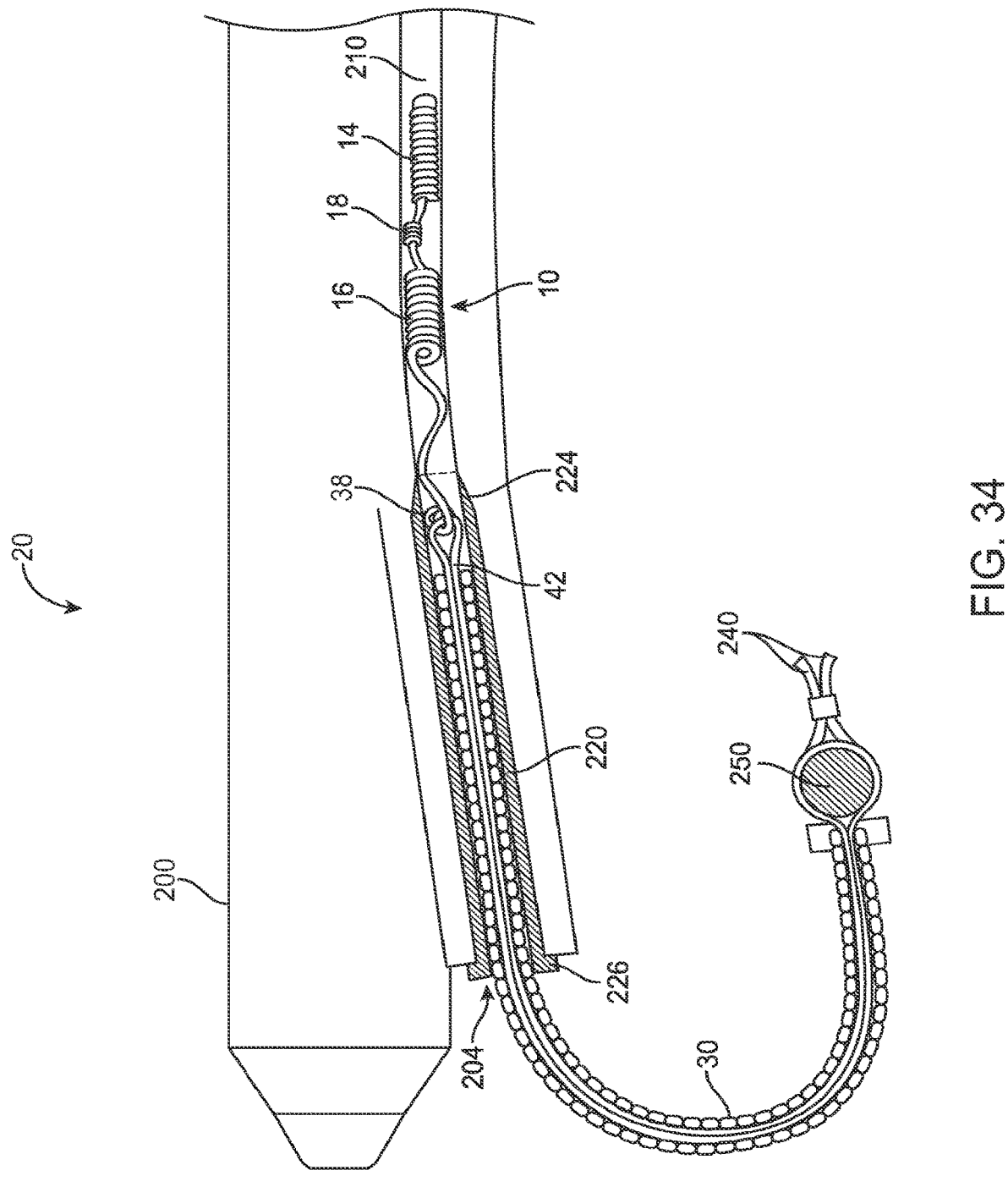
FIG. 34 illustrates a pre-loaded introducer advanceable into the working channel port of a bronchoscope.

As illustrated in FIG. 34, the pre-loaded introducer 220 is advanceable into the working channel port 204 of the bronchoscope 20, typically once the bronchoscope 20 has been desirably positioned within the lung. In some embodiments, the introducer 220 has a shape, such as a male luer taper, that sockets into the working channel port 204. Such advancement into the port 204 relieves the operator from holding the device 10 during delivery. As shown, the device 10 is advanced from the first end 224 of the introducer 220 and into the working channel 210 by advancement of the deployment element 30. Thus, the deployment element 30 pushes the device 10 through the introducer 220 and through the working channel 210 of the bronchoscope 20.

Figure 35:
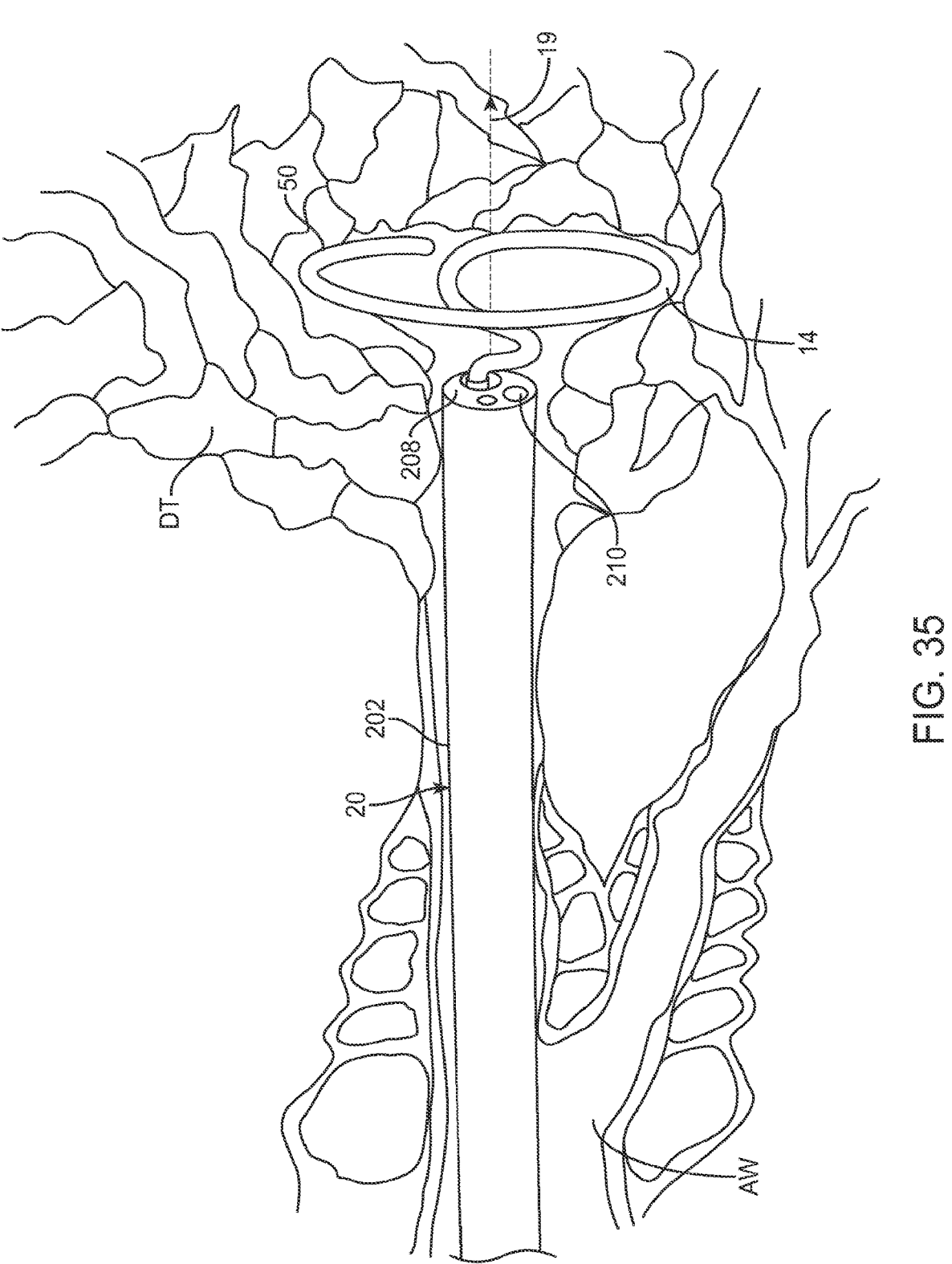
FIG. 35 illustrates the insertion cord tip of the bronchoscope positioned in the damaged tissue of the patient's lung.

FIG. 35 illustrates the insertion cord tip 208 of the bronchoscope 20 positioned in the damaged tissue DT of the patient's lung. The position of the insertion cord tip 208 indicates the delivery location of the tissue gathering end 14. The tissue gathering end 14 is deployed at this delivery location by retraction of the bronchoscope 20 while holding the deployment element 30 fixed. Thus, the deployment element 30 and attached device 10 remain fixed in relation to the anatomy while the bronchoscope 20 is retracted. This exposes the tissue gathering end 14, allowing the tissue gathering end 14 to expand into a deployed configuration. In this embodiment, the tissue gathering end 14 comprises a loop 50 deployed in a plane perpendicular to the longitudinal axis 19 of the device 10.

Once the tissue gathering end 14 is deployed, the lung is ready for re-tensioning. This can be achieved by a variety of methods. In one embodiment, the deployment element 30 is fixed relative to the bronchoscope 20 and together the deployment element 30 and bronchoscope 20 are retracted. Such retraction pulls the tissue gathering end 14 toward the larger bronchioles and trachea, which in turn pulls the damaged tissue DT, because the device 10 is connected to the deployment element 30. This is continued until a desired level of re-tensioning of the lung, has been achieved. It may be appreciated that the deployment element 30 and bronchoscope 20 can be advanced and retracted together as needed to adjust the level of re-tensioning, if desired.

As mentioned, other methods of delivery and re-tensioning can be achieved with the pulmonary treatment device 10. In some embodiments, the tissue gathering end 14, optional midsection 18, and stabilizing end 16 are all deployed prior to the re-tensioning step. Thus, once the device 10 has been deployed, re-tensioning can be achieved by retracting the deployment element 30 and bronchoscope 20 together as described previously. The retraction pulls the device 10 toward the larger bronchioles and trachea, which in turn pulls the damaged tissue DT. Retraction continues until the stabilizing end 16 is seated in a desired portion of the airway.

Once the operator is satisfied with the placement of the device 10, the device 10 is detached from the deployment element 30.

It may be appreciated that the device 10 may alternatively be deployed from the bronchoscope 20 by advancing the deployment element 30, thereby pushing the device 10 out of the working channel 210 of the bronchoscope 20. In such embodiments, the deployment element 30 typically has a low compressibility. Such deployment of the device 10 can be achieved all at once or in separate steps. Since the deployment element 30 is attached to the device 10, re-tensioning can be achieved by the same methods as described above (i.e. retraction of the deployment element 30 and bronchoscope 20). Once the operator is satisfied with the placement of the device 10, the device 10 is detached from the deployment element 30.

It may be appreciated that in some embodiments, the device 10 is delivered to the desired location within the lung with the use of a guidewire and/or catheter, passed through the working channel 210 of a bronchoscope 20 or alone.

When more than one device 10 is to be implanted into the patient during a procedure with the use of a bronchoscope 20, the bronchoscope 20 is typically exchanged or cleaned before implanting the next device 10. Since bronchoscopes 20 typically not disposable, they are designed for such cleaning protocols. The ability to easily exchange or clean the delivery device between uses reduces any risk of cross-contamination from one portion of the lung to another and/or from one lung to another. Previously, when using conventional devices and treatment protocols, both lungs of a patient could not be treated during the same procedure due to risks of cross contamination between both lungs which could prove fatal to the patient. However, the delivery methods and devices of the present invention reduce or eliminate this risk.

It may be appreciated that an additional device 10' can be implanted into the same airway as a previous implanted device 10. In some embodiments, the additional device 10' is passed through the previously implanted device 10 to reach a more distally located area of the lung.

In some embodiments, the device 10, attached deployment element 30 and introducer 220 are packaged or pouched as a single unit. Each unit is used to treat a particular target location in the lung. In some embodiments, the units are sold individually since the number of devices 10 implanted in a single lung will vary depending on the patient's disease state and a variety of other features. In other embodiments, the units are sold by the box wherein each box contains a plurality of units. In some embodiments, 6-14 devices are delivered to a single lung during a treatment session. If two lungs are treated during a single treatment session, upwards of 30 devices may be used. It may be appreciated that in some embodiments, the procedure has a flat cost wherein an unlimited number of devices 10 may be used during the procedure for the same cost. This allows the operator to focus on the technical aspects of the procedure rather than on the cost of using additional units.

Figure 36:
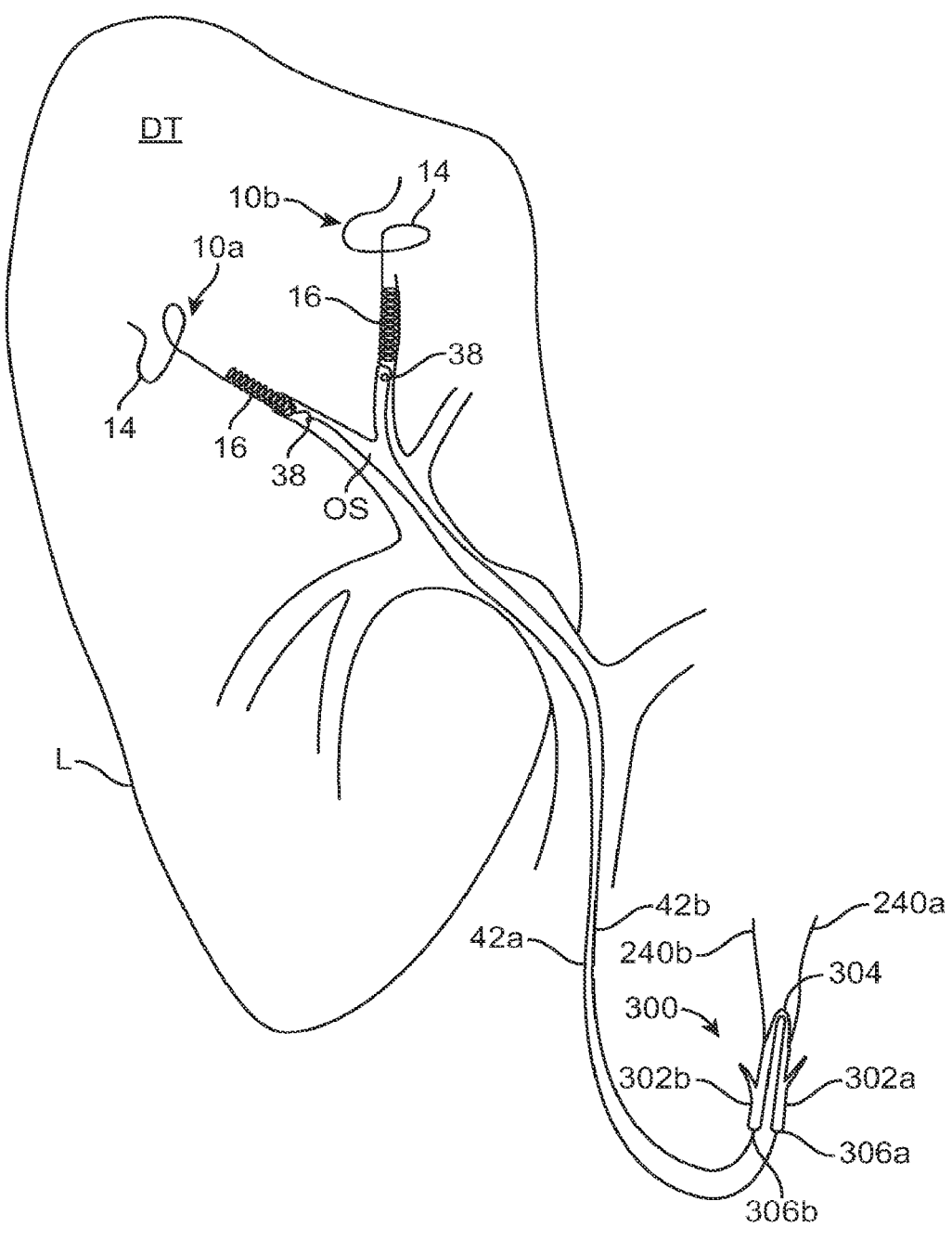
FIGS. 36-37 illustrate an embodiment wherein two devices are joined with the use of a joining device.
Figure 37:
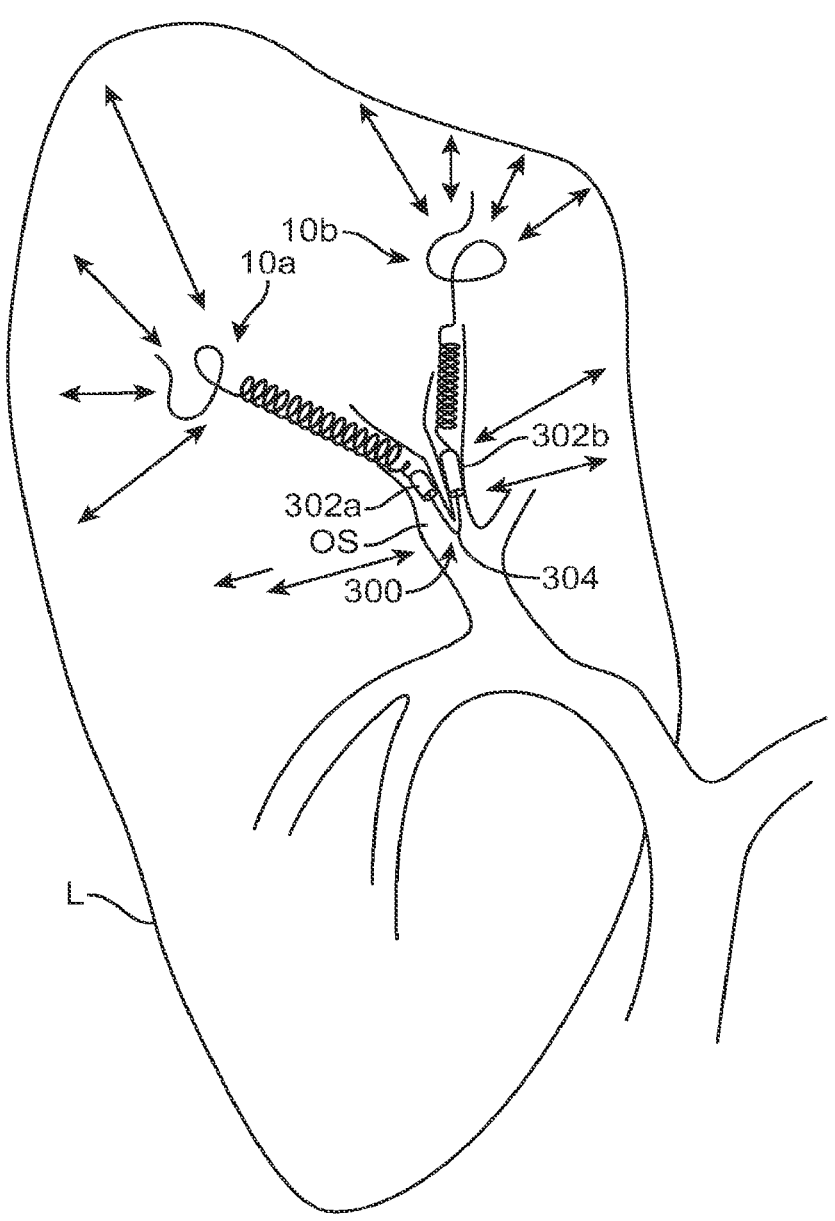

It may be appreciated that in some embodiments, two or more devices 10 are joined or fixed together within the lung anatomy. FIGS. 36-37 illustrate an embodiment wherein two devices 10 are joined with the use of a joining device 300. FIG. 36 illustrates a first device 10a implanted at a first location within a lung L and a second device 10b implanted at a second location within lung L. In this embodiment, the first and second locations are along lung passageways branching from the same ostium OS. As shown, the tissue gathering ends 14 are disposed in damaged tissue DT and the stabilizing ends 16 are located more proximal along the respective lung passageways. In addition, each device 10a, 10b has a respective tether 42a, 42b attached to its attachment feature 38. The tethers 42a, 42b extend from the devices 10a, 10b to the exterior of the patient. The delivery device is not shown in FIG. 36 for clarity, however the tethers 42a, 42b extend through the delivery device to the exterior of the patient. The joining device 300 is then advanced over the free ends 240a, 240b of the tethers 42a, 42b. In this embodiment, the joining device 300 comprises a clip having a first arm 302a and a second arm 302b, wherein the arms 302a, 302b are connected by a connector 304. Each arm 302a, 302b has a respective lumen 306a, 306b through which an individual tether passes. Thus, joining device 300 is advanced over the free ends 240a, 240b so that the first tether 42a passes through the lumen 306a of the first arm 302a and the second tether 42b passes through the lumen 306b of the second arm 302b. The joining element 300 is then advanced along the tethers 42a, 42b until the arms 302a, 302b reach the devices 10a, 10b. As illustrated in FIG. 37, the joining device 300 is then advanced so as to attach the first arm 240a to the first device 10 and the second arm 240b to the second device 10b. In this embodiment, the joining device 300 resides within the ostium OS, each arm 302a, 302b extending toward a separate lung passageway, thereby creating a V or U shape. The tethers 42a, 42b are removed and the joining device 300 is left in place.

It may be appreciated that in some embodiments, the clip having the first arm 302a and the second arm 302b is configured to apply compression force to tissue between the arms 302a, 302b when tissue is inserted therebetween. For example, in some embodiments, the arms 302a, 302b are configured to be advanced a sufficient distance within the separate lung passageways of the bifurcation so as to apply force to the inner walls of the lung passageways. Such force pushes the lung passageways toward each other, straightening the passageways while compressing the tissue therebetween.

In other embodiments of the invention, the pulmonary treatment device 10 is mounted on the outside of the bronchoscope 20. Mounting the device 10 on the outside of the bronchoscope 20 avoids packing the device 10 within a bronchoscope working channel 210 or catheter within a bronchoscope channel which involves restraining the device 10 in a high strain configuration. Once restrained, the device 10 would then transition to a more relaxed configuration upon deployment. However, by mounting the device 10 on the outside of the bronchoscope 20, device 10 can be delivered into the patient in a non-stressed and non-strained state. This configuration provides the benefit of reliably delivering the treatment device 10 along the delivery path in substantially the same shape as it will be when it is inserted into the target airway. In addition, the device 10 may be comprised of a broader selection of materials, including high strength materials that would typically be unsuitable for such restraint and relaxation. In some embodiments, the treatment device 10 may be comprised of titanium, steel, a stainless-steel alloy, one or more ferrous metals, one or more non-ferrous metals, metals that contain nickel, iron, and/or manganese, or any combination of these listed materials. In other embodiments, the treatment device 10 may also be comprised of a polymer material, a ceramic material or a composite material that is made from any combination of plastic, metal, carbon, carbon fiber or any other material that exhibits resilience and biocompatibility performance, such as nitinol or an alloy made from nickel and titanium. It may be appreciated that, in some embodiments, materials that can perform in a fully reversible elastic way up to a minimum of 1% strain are very suitable.

Figure 38:
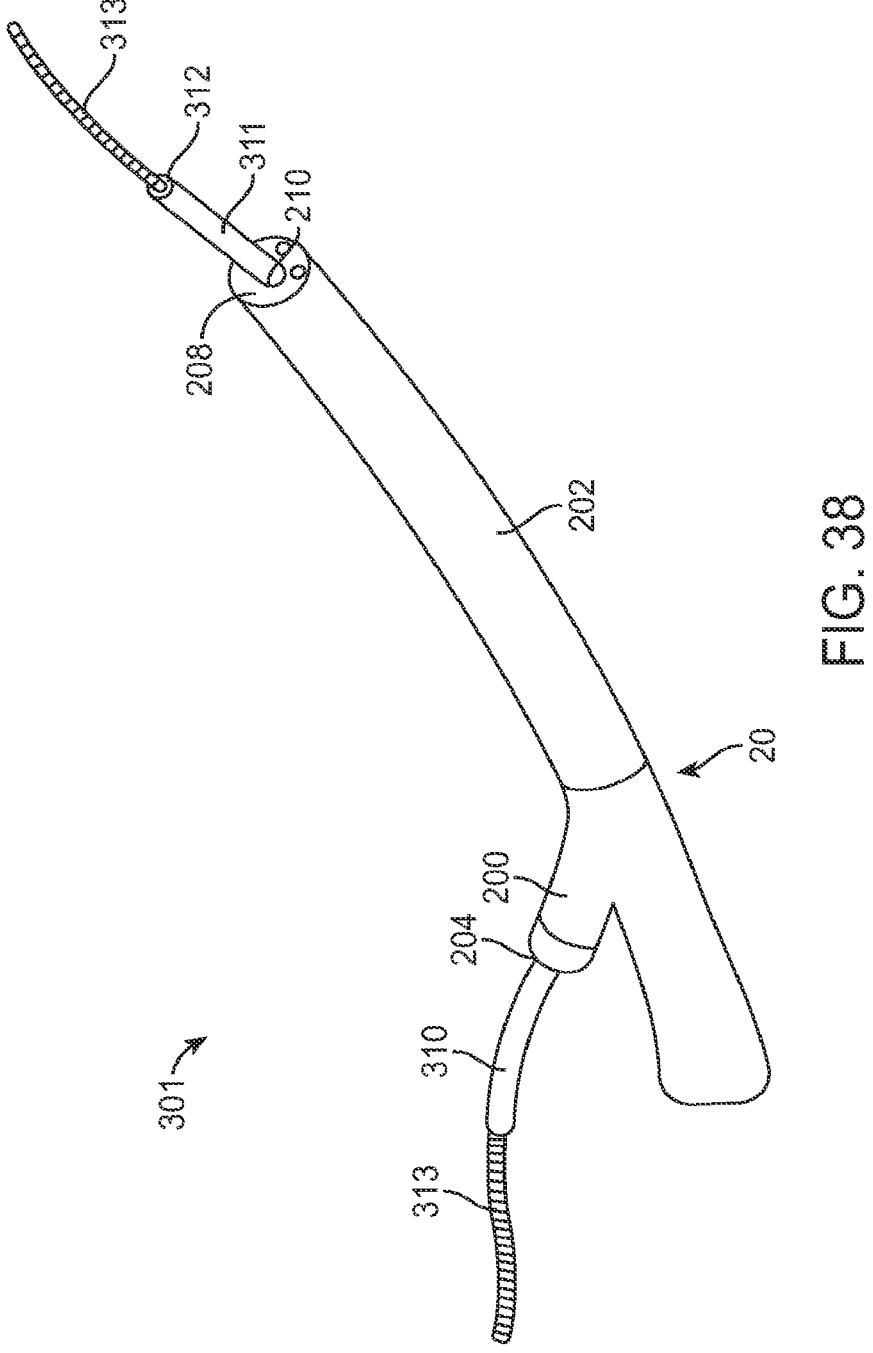
FIG. 38 illustrates an embodiment of a delivery system for delivering a pulmonary treatment device of the present invention.
Figure 39:
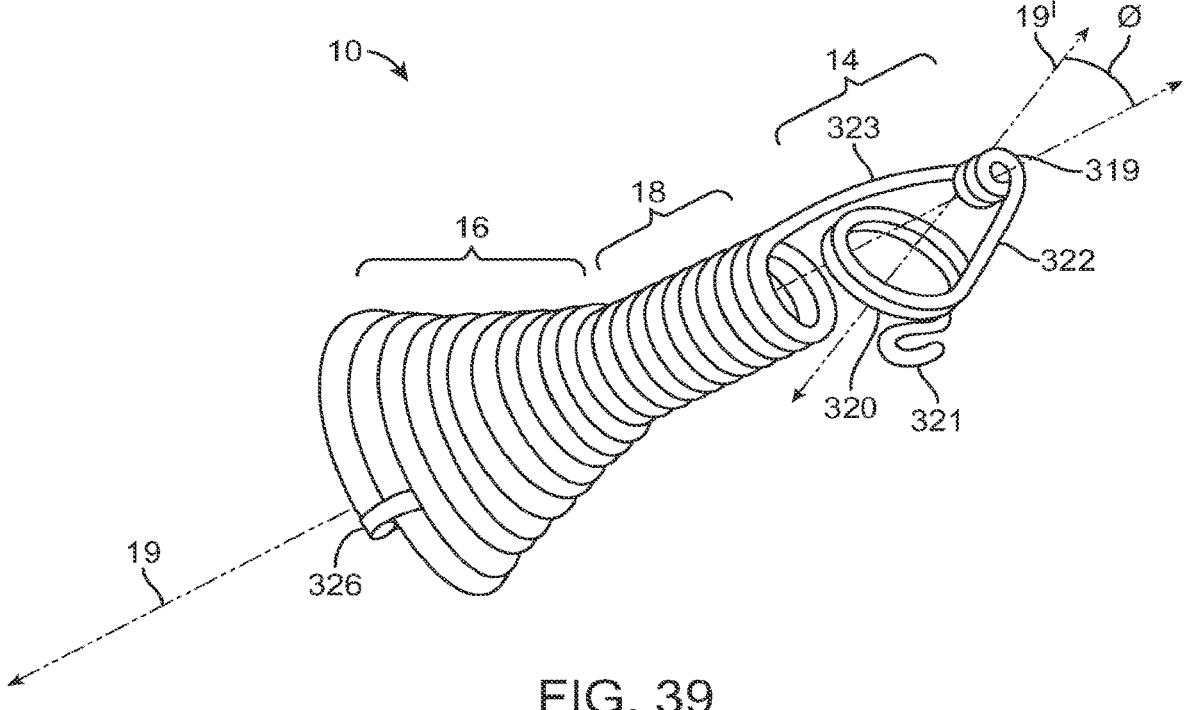
FIG. 39 illustrates an embodiment of a pulmonary treatment device that is deliverable by the system of FIG. 38 and has a flared stabilizing end.

FIG. 38 illustrates an embodiment of a delivery system 301 for delivering a treatment device 10. In this embodiment, the system 301 includes a bronchoscope 20 having a bronchoscope body 200 and an insertion cord 202 with an insertion cord tip 208. Suitable bronchoscope outer diameters may be as large as 10 mm in diameter but they may also be as small as 1 mm diameter. More typically, the bronchoscope is between 2 mm and 3 mm outer diameter. In this embodiment, the delivery system 301 further includes a deployment sleeve 311 and a guidewire 313, both of which may be utilized in delivering particular embodiments of the treatment device 10. As shown, the deployment sleeve 311 includes a proximal end 310 and a distal end 312. The deployment sleeve 311 is advanceable through the working channel 210 of the bronchoscope 20, such as extending through the working channel port 204 and beyond the insertion cord tip 208, as shown. In some embodiments, the deployment sleeve 311 is comprised of a polymer tube, a polymer or metallic round wire coil, a ribbon coil, a braid reinforced sleeve, an extrusion or any combination of these. In some embodiments, the deployment sleeve 311 has an outer diameter of up to 5 mm but preferably its outer diameter is between 2 mm and 4 mm with an inside diameter as small as 0.010", but more preferably it has an inside diameter of 0.018-0.040 inches. Additionally, in some embodiments, a guidewire 313 is advanceable through the deployment sleeve 311, as illustrated in FIG. 38. In some embodiments, the guidewire 313 is comprised of a stainless steel or nitinol core wire with a stainless-steel or nitinol wound coil outer jacket. The guidewire diameter may be as small as 0.010" and as large as 3 mm, ideally but it's ideally between 0.025-0.040 inches in diameter. In some embodiments, the guidewire 313 and deployment sleeve 311 are longer than 60 cm, preferably 90 to 110 cm. Other embodiments include a much longer guidewire that is 90 cm to 250 cm long, with sufficient length so that pulmonary treatment devices may be removed from the patient or exchanged on and off of the guidewire with enough excess guidewire length to allow the maneuvers to be accomplished without ever needing to let go of the guidewire. This insures that the guidewire stays in an appropriate position while exchanges are being made FIG. 39 illustrates an embodiment of a pulmonary treatment device 10 that is deliverable by the system 301 of FIG. 38. In this embodiment, the pulmonary treatment device 10 comprises a tissue gathering end 14, an extendible midsection 18 and a stabilizing end 16. In this embodiment, the stabilizing end 16 comprises a coil having a flared configuration, as illustrated in FIG. 39. Here, the outer diameter of the stabilizing end 16 generally matches that of the extendible midsection 18 and then gradually expands moving away from the midsection 18 forming the flared configuration. The flared configuration can assist in seating the stabilizing end 16 within the airway, particularly within an ostium. In this embodiment, the stabilizing end 16 also includes a connector 326 which assists in maintaining the shape of the stabilizing end 16. When the stabilizing end 16 is comprised of a coil, the free end of the coil is connected with the remainder of the coil by the connector 326 to ensure that the free end does not cause trauma to tissue, such as during delivery and deployment. Such connection of the free end to the remainder of the coil forms a complete hoop which increases the hoop strength of the most proximal portion of the stabilizing end 16. In some instances, the increased hoop strength assists in anchoring the stabilizing end 16 in a portion of the lung airway.

In this embodiment, the extendible midsection 18 also comprises a coil, however the midsection 18 typically has a uniform diameter. The diameter is typically chosen so as to be mountable on a bronchoscope 20 or other delivery device, such as a guidewire. The extendible midsection 18 is able to be elongated to store elastic strain energy which urges the treatment device 10 to recover back to a non-elongated length.

In this embodiment, the tissue gathering end 14 comprises an anchor strut 322 which is extendable radially outwardly from the longitudinal axis 19 to assist in anchoring the device 10 within a lung passageway or within damaged tissue. Anchor strut 322 may extend 1 mm to more than 30 mm but 6-12 mm is preferable. The anchor strut 322 terminates in an anchor strut end 321, which may have a variety of shapes including a coil, ball, sharp end barb, L shaped pad, strain relief long coil or tapered coil. The anchor strut 322 is configured to extend radially outwardly upon deployment so at least the anchor strut end 321 engages an airway wall W or damaged tissue DT, such as in the area of the alveolar sacs. However, in some instances, the anchor strut 322 itself additionally engages the airway wall W or damaged tissue DT.

During delivery and prior to deployment, the anchor strut 322 is held in a retracted or un-extended position so as to avoid dragging along the airway walls W or traumatizing tissue. Such retraction is maintained by an alignment element 320. In this embodiment, the alignment element 320 has the form of a loop, however it may be appreciated that the element 320 may have the form of a partial loop or snap locking structure, partial loop, hook shaped lock or spring lock mechanism. When the center of the loop is aligned with the longitudinal axis 19, the anchor strut 322 is held parallel to or at a small angle in relation to the longitudinal axis 19. Such alignment may be maintained by passing a device, such as the bronchoscope 20 or guidewire, catheter, balloon catheter, hitch lock wire, or other accessories related thereto, through the center of the treatment device 10 and through the alignment element 320 (as will be illustrated in later sections). The tissue gathering end 14 is configured so as to bias the alignment element 320 and attached anchor strut 322 radially outwardly. Therefore, withdrawal of devices from the alignment element 320 frees the alignment element 320 and allows the alignment element 320 to rotate away from alignment with the longitudinal axis 19. This, in turn, causes the anchor strut 322 to extend radially outwardly, as illustrated in FIG. 39. Thus, in the extended position, the alignment element 320 has an axis 19 which is at an angle θ to the longitudinal axis 19. Typically, the angle θ is in the range of 1 to 90 degrees but it's preferably 20-65 degrees. In some embodiments, additional portions of the tissue gathering end 14 are also biased to assist in extension of the anchor strut 322 radially outwardly. For example, in some embodiments, the tissue gathering end 14 includes a body strut 323 which is connected to the anchor strut 322. In such embodiments, the body strut 323 is biased so as to further extend the anchor strut 322 radially outwardly. In the embodiment of FIG. 39, the body strut 323 is disposed opposite the anchor strut 322 so that the alignment element 320 is disposed therebetween. Thus, when the center of the alignment element 320 is aligned with the longitudinal axis 19, the body strut 323 and anchor strut 322 reside on opposite sides of the longitudinal axis 19. In some instances, release of the alignment element 320 allows both the body strut 323 and anchor strut 322 to bias toward their relaxed configurations (such as pushing both the body strut 323 and anchor strut 322 outwardly in the same radial direction). This can allow the body strut 323 and anchor strut 322 to spread fully elastically at least 5 degrees but up to 90 degrees, and preferably 20 to 65 degrees, to push the anchor strut end 321 into or through the wall of an airway or the diseased tissue to anchor the tissue gathering end 14 in the lung tissue.

In some embodiments, the tissue gathering end 14 further includes a guide element 319, such as illustrated in FIG. 39. In this embodiment, the guide element 319 comprises a coil, however the element 319 may have any suitable shape including a single loop. In some embodiments, the guide element 319 helps keep the device 10 centered on the end of the bronchoscope 20 or other delivery device such as a guidewire, catheter or balloon catheter. In some embodiments, the guide element 319 is arranged so that a guidewire emerging from the insertion cord tip 208 of the bronchoscope 20 passes through the guide element 319. This assists in aligning the tissue gathering end 14 with the longitudinal axis 19 and holding the body strut 323 and anchor strut 322 in its retracted position during delivery, prior to deployment. In some embodiments, the guide element 319 comprises a coil partial coil, hook, hitch lock system or snap lock geometry. In some instances, the coil dictates the strength of the spreading force of the anchor strut 322 radially outwardly.

Figure 40:
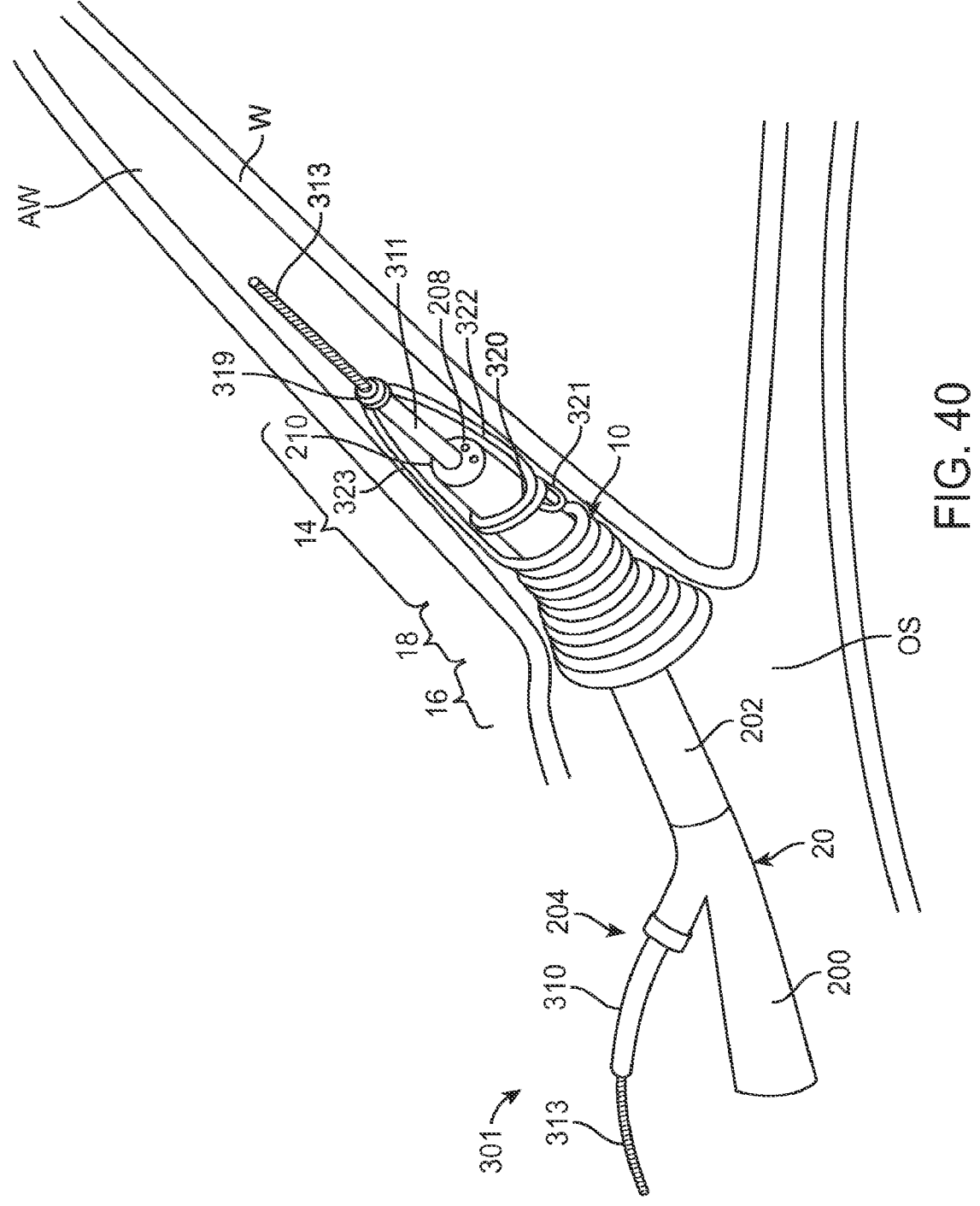
FIG. 40 illustrates the treatment device of FIG. 39 mounted on the delivery system of FIG. 38.

FIG. 40 illustrates the treatment device 10 of FIG. 39 mounted on the delivery system 301 of FIG. 38. As shown, the treatment device 10 is mountable on the bronchoscope 20, deployment sleeve 311 and guidewire 313. In particular, the most distal portion of the system 301 is advanced through the central lumen of the treatment device 10, from the stabilizing end 16 toward the tissue gathering end 14. Thus, the tissue gathering end 14 of the treatment device 10 faces distally. In some embodiments, the stabilizing end 16 and midsection 18 are mounted on the exterior of the bronchoscope 20. In some embodiments, portions of the tissue gathering end 14 are also mounted on the exterior of the bronchoscope 20. For example, in some embodiments the alignment element 320 is mounted on the bronchoscope 20, as shown in FIG. 40. In this embodiment, portions of the tissue gathering end 14 extend beyond the insertion cord tip 208 of the bronchoscope 20. In particular, the guide element 319 is mounted on the guidewire 313 and held in place by the deployment sleeve 311. This is achieved by having the inner diameter of the guide element 319 smaller than the outer diameter of the deployment sleeve 311 so that the guide element 319 abuts the deployment sleeve 311.

The delivery system 301 and mounted treatment device 10 are then advanceable into the lung anatomy, the guidewire 313 guiding the system 301 through the lung passageways. Once the target location has been reached, the delivery system 301 is positioned so as to seat the stabilizing end 16 at a desired location, such as within an ostium OS. FIG. 40 illustrates the tissue stabilizing end 16 within an ostium OS at a bifurcation of two lung airways AW. Here, at least a portion of the stabilizing end 16 resides in the ostium OS while the midsection 18 and tissue gathering end 14 extend into the target airway AW. Thus, the flared configuration of the stabilizing end 16 anchors the stabilizing end 16 within the ostium OS by pressing against the walls W of the airway AW.

Figure 41:
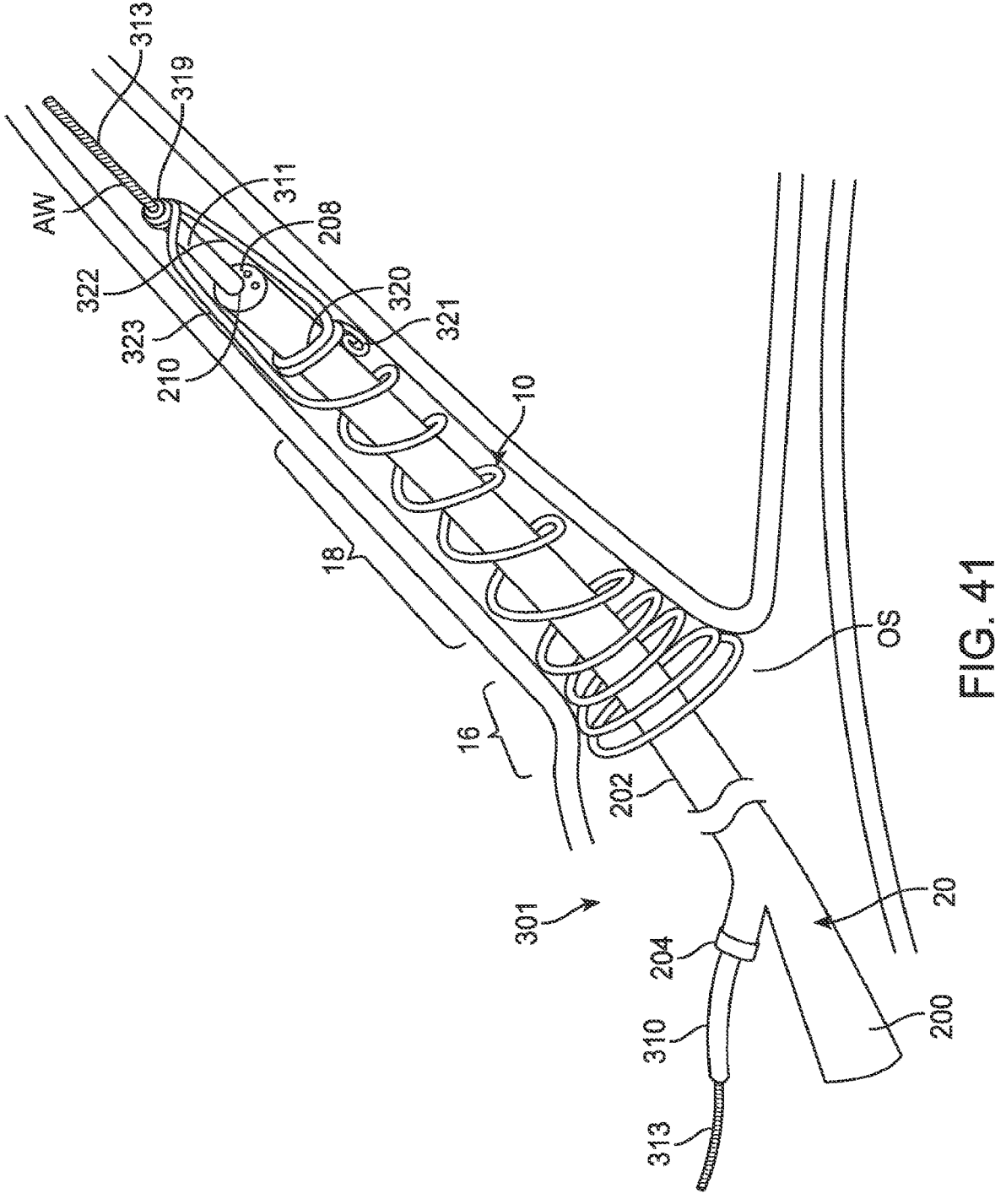
FIG. 41 illustrates deployment of the treatment device within the target airway by advancing the delivery system so as to push the tissue gathering end further along the target airway while the extendible midsection expands, elongating the treatment device.

The treatment device 10 is then deployed within the target airway AW by advancing the delivery system 301, as illustrated in FIG. 41. Since the stabilizing end 16 is anchored within the ostium OS and the treatment device 10 has a structure which allows elongation along its longitudinal axis 19, advancement of the delivery system 301 pushes the tissue gathering end 14 further along the target airway AW while the treatment device 10 expands. In particular, the extendible midsection 18 length elongates and stores elastic recoil strain energy in its helix structure; the elastic strain energy will be used to urge the treatment device 10 to recover to its original shorter length after the device 10 has been fully deployed and the delivery system 301 has been decoupled from the device 10.

Figure 42:
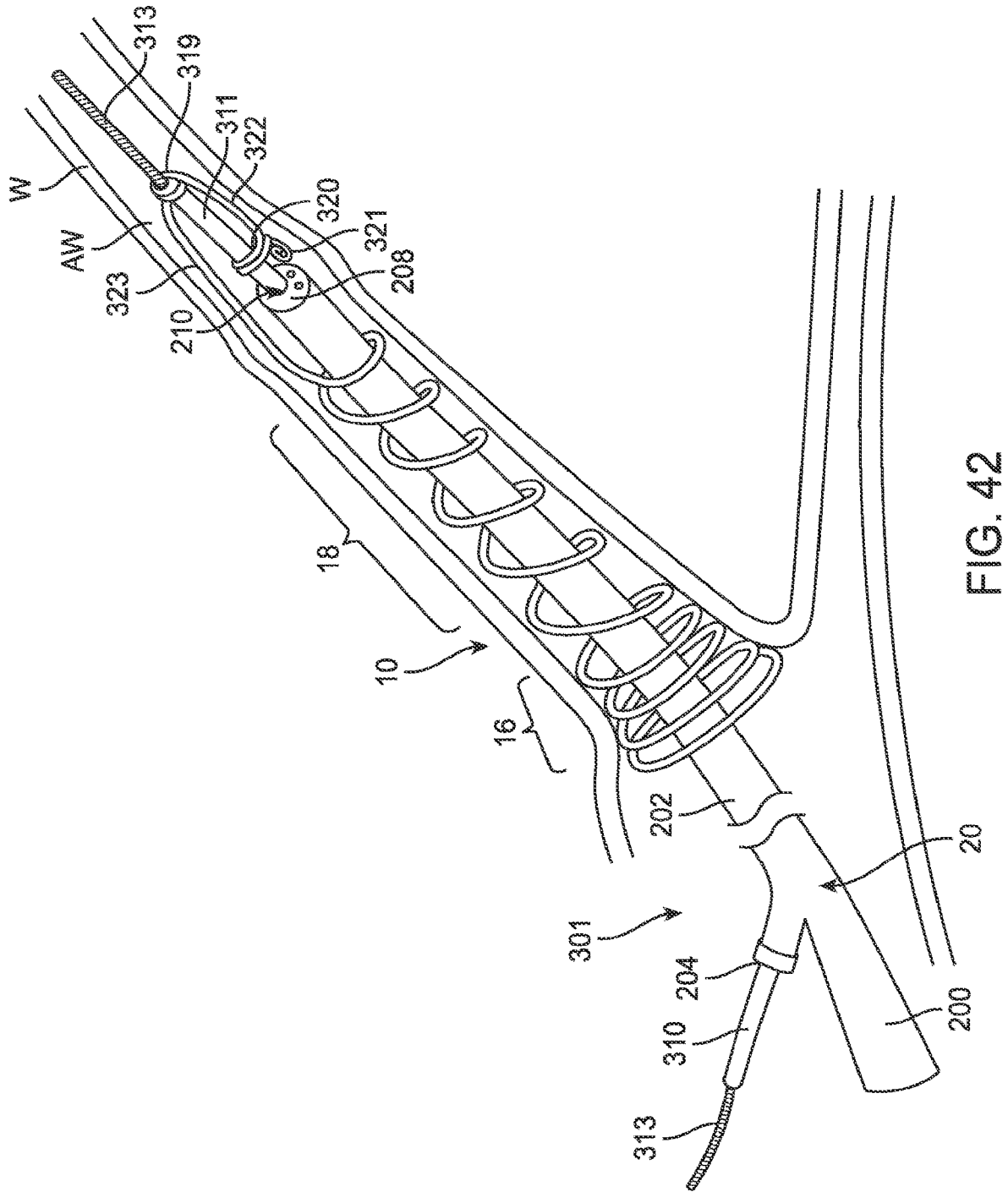
FIG. 42 illustrates the beginning stages of decoupling the device from the delivery system wherein the tissue gathering end is unmounted from the bronchoscope.

FIG. 42 illustrates the beginning stages of decoupling the device 10 from the delivery system 301. To begin, the tissue gathering end 14 is unmounted from the bronchoscope 20. In particular, the alignment element 320 is released from the bronchoscope 20, such as by retracting the bronchoscope 20 or by advancing the deployment sleeve 311 which in turn advances the anchor strut 322 which pulls the alignment element 320 off the insertion cord tip 208. The guidewire 313, and optionally the deployment sleeve 311, are held in a fixed position within the airway AW so as to maintain the elongated configuration of the treatment device 10. Release of the alignment element 320 allows the anchor strut 322 to extend radially outwardly toward its biased configuration. Thus, as shown in FIG. 42, the anchor strut end 321 engages with the wall W of the airway AW in an anchoring manner. In this embodiment, at least the anchor strut end 321 deforms a portion of the wall W to make purchase at a location that is distant from the stabilizing end 16.

Figure 43:
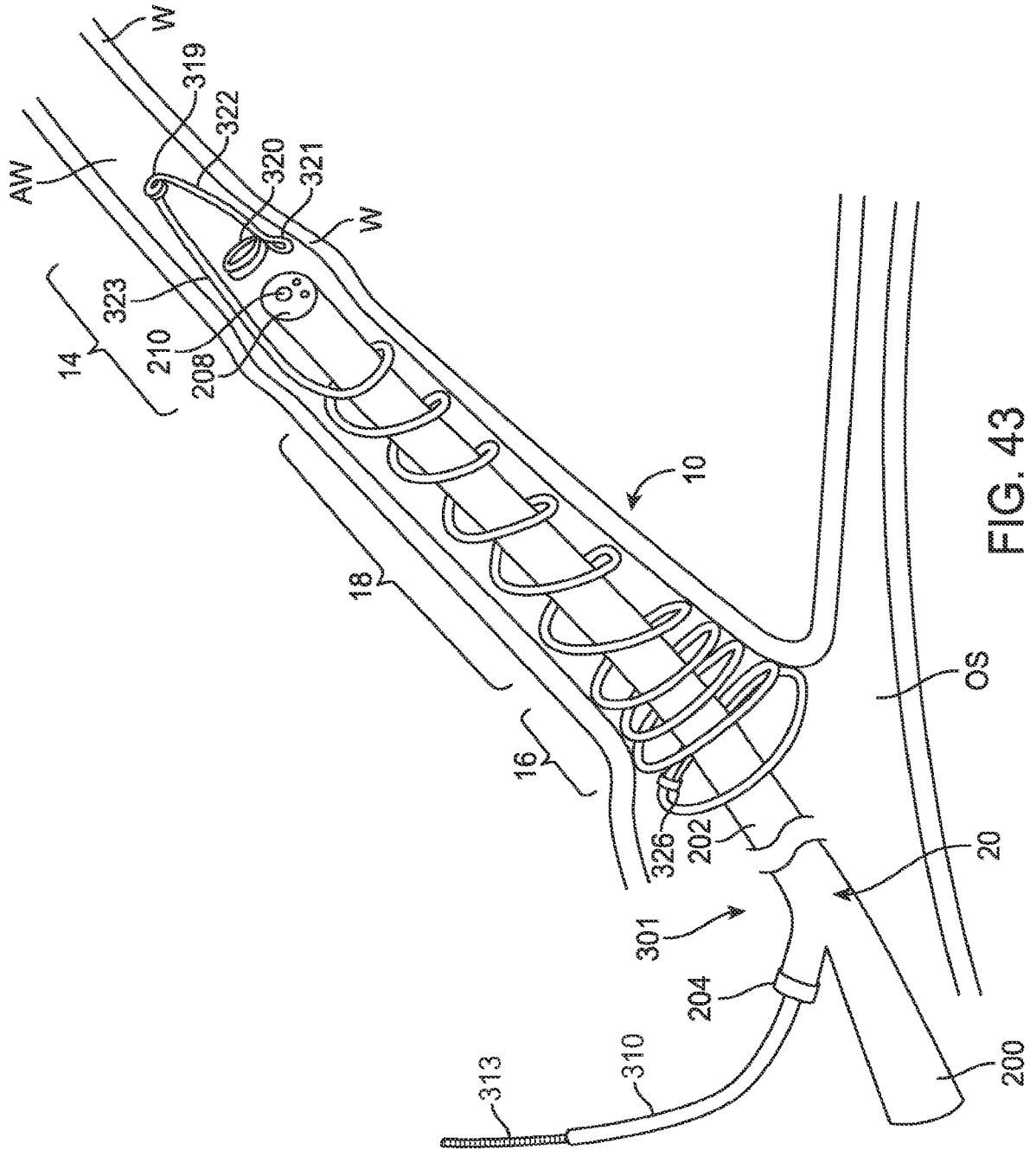
FIG. 43 illustrates further steps of decoupling the device from the delivery system, wherein the deployment sleeve and guidewire have been removed from the bronchoscope allowing the tissue gathering end to fully engage with the wall of the airway.
Figure 44:
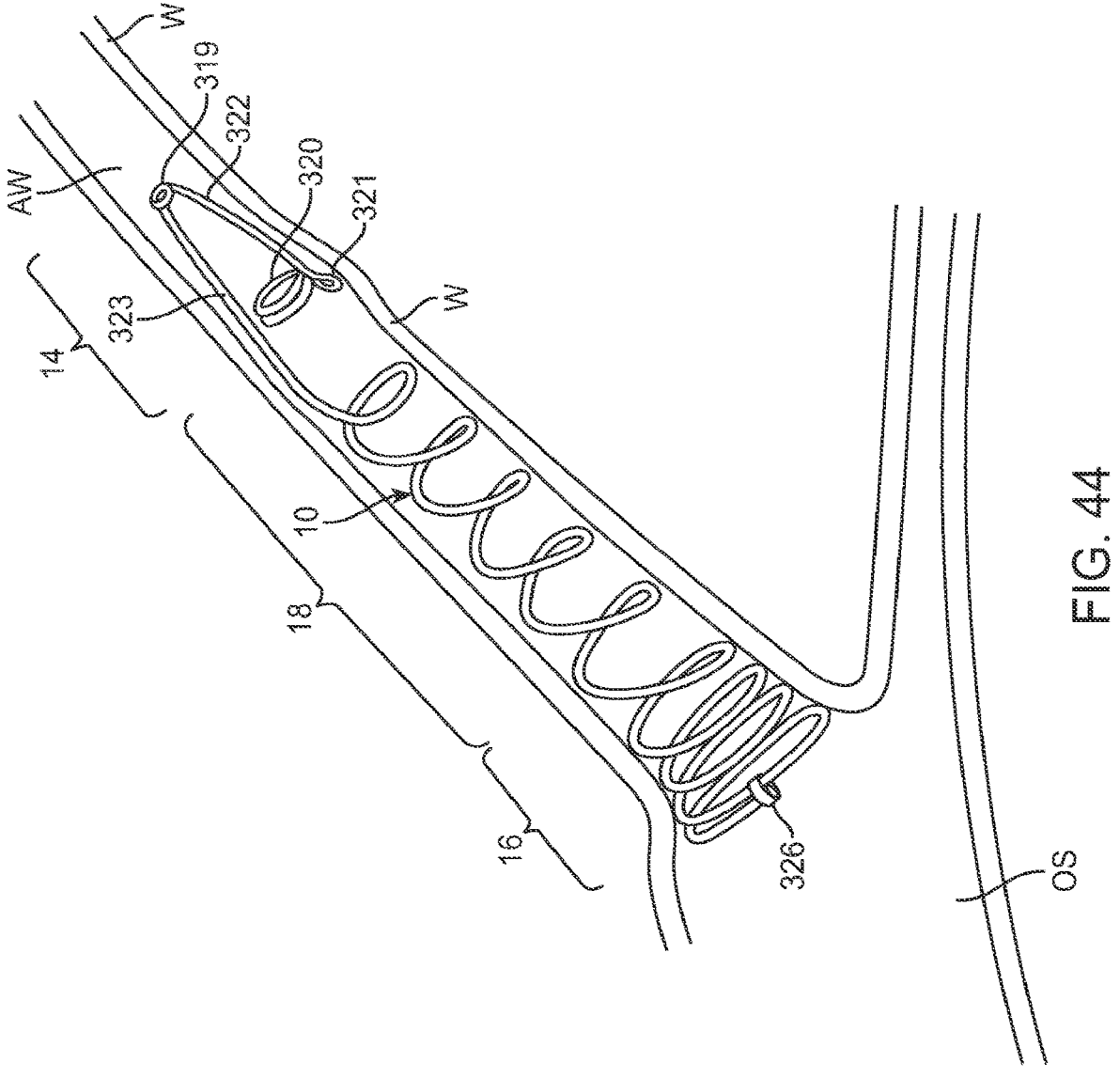
FIG. 44 illustrates retraction and removal of the delivery device from the lung anatomy, leaving the treatment device behind.

FIG. 43 illustrates further steps of decoupling the device 10 from the delivery system 301. Here, the deployment sleeve 311 and guidewire 313 have been removed from the bronchoscope 20 allowing the tissue gathering end 14 to fully engage with the wall W of the airway AW. Thus, the tissue gathering end 14 is fixed to lung tissue within the target airway at a position distant from the stabilizing end 16 within the ostium OS. The bronchoscope 20 can then be fully retracted and removed from the lung anatomy, leaving the treatment device 10 behind, as illustrated in FIG. 44.

Figure 45:
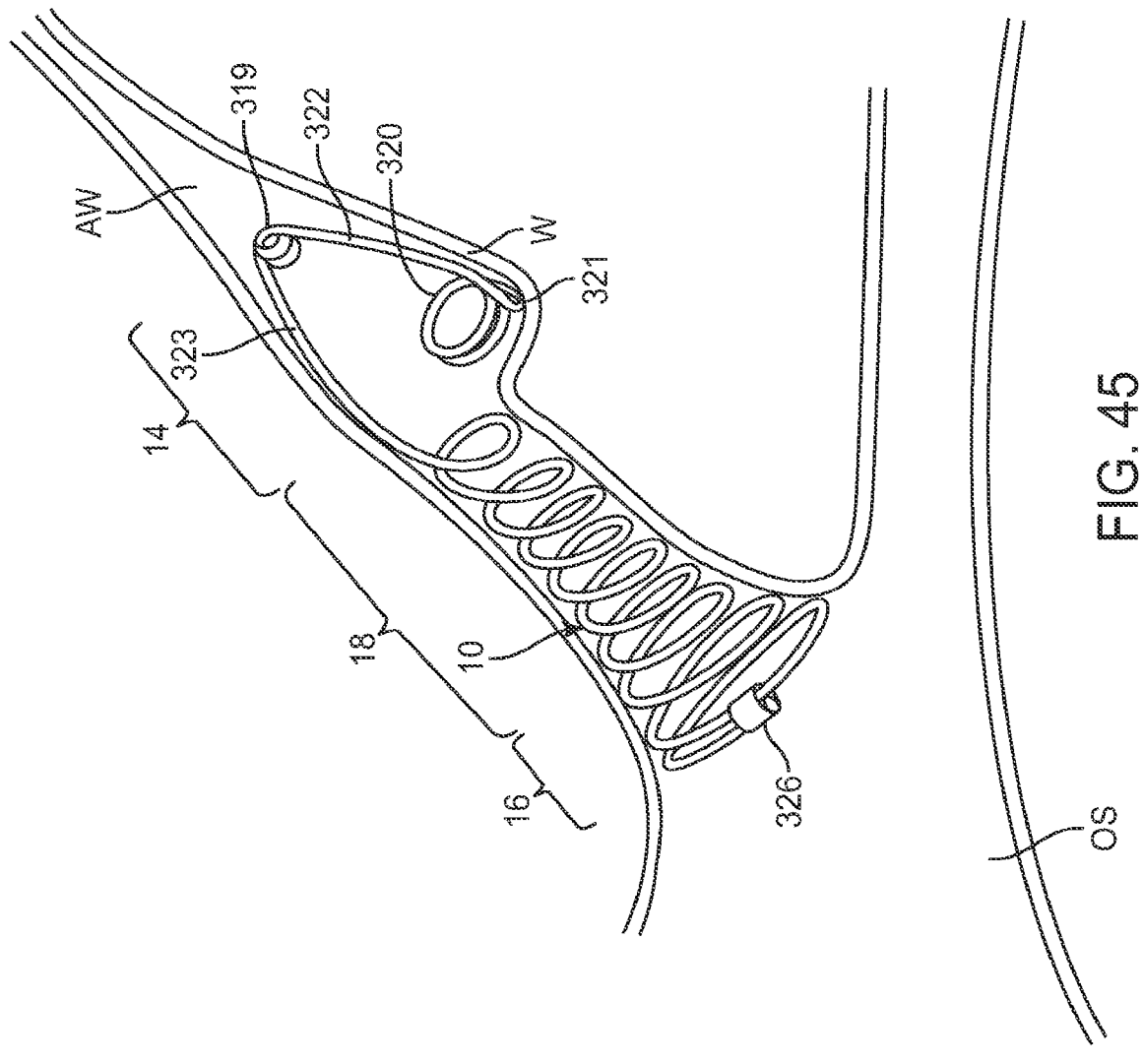
FIG. 45 illustrates the treatment device after the stored elastic strain energy that has been stored in at least the midsection of the treatment device has urged the device to shorten and recover elastically more closely to its original pre-elongated length.

The stored elastic strain energy of the extendible midsection 18, and optionally any stored energy in the stabilizing end 16 and/or tissue gathering end 14, creates an urging force to recoil and shorten the treatment device 10 toward its original configuration and length. Since the strength of the airway AW is compromised, the walls W are unable to overcome this urging force. Thus, the wall W, at least at the point of purchase or engagement by the tissue gathering end 14, is carried with the tissue gathering end 14 toward the stabilizing end 16. This retensions the airway distal to the treatment device 10. FIG. 45 illustrates the treatment device 10 after the stored elastic strain energy that has been stored in at least the midsection 18 of the treatment device 10 has urged the device 10 to shorten and recover elastically more closely to its original pre-elongated length. As described, this shortens the length of the airway along the treatment device 10 yet elongates the length of the airway distal to the treatment device 10 to cause restoration of lung tissue tension and elastic recoil in the tissue that is distal, proximal and adjacent to the treatment device 10. By tensioning the lung tissue, the device 10 has tensioned the entire bronchial tree that is distal to this single airway which in turn expands the associated alveoli tissue. By tensioning the airways and alveoli, the involved airways are held in a dilated arrangement. In some instances, this simulates the effects of bronchodilator drugs in patients who still respond to this family of drugs (unfortunately, these late stage severe emphysema and COPD patients typically no longer respond to these drugs).

It may be appreciated that the delivery system 301 of FIG. 38 may be used to deliver treatment devices 10 in a variety of ways. One such way, which was illustrated in FIGS. 40-43, involves seating the stabilizing end 16 in an ostium, or other stable portion of the lung anatomy, and advancing the stabilizing end 14 further along the airway. It may be appreciated that the treatment devices 10 may be delivered by alternative methods. For example, the tissue gathering end 14 may be positioned at a target location and the stabilizing end 16 retracted to an ostium, or other stable portion of the lung anatomy. This may be achieved with the use another embodiment of the delivery system 301, such as illustrated in FIG. 46.

Figure 46:
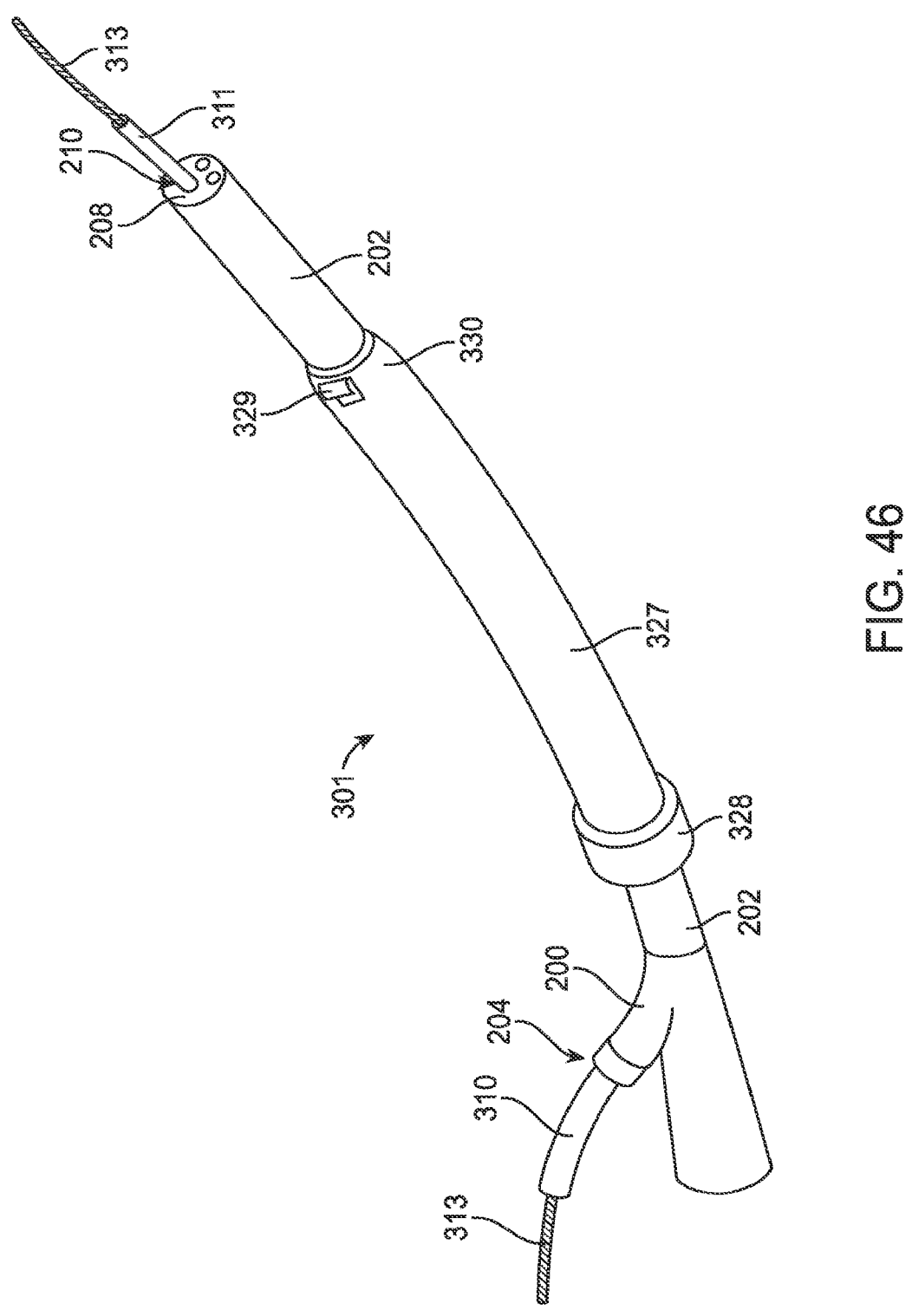
FIG. 46 illustrates another embodiment of a delivery system for delivery of a treatment device, the delivery system comprises a bronchoscope having a bronchoscope body and an insertion cord, a guidewire, a deployment sleeve and a guide sleeve.

FIG. 46 illustrates another embodiment of a delivery system 301 for delivery of a treatment device 10. In this embodiment, the delivery system comprises a bronchoscope 20 (having a bronchoscope body 200 and an insertion cord 202), a guidewire 313, a deployment sleeve 311 and a guide sleeve 327. In some embodiments, the guide sleeve 327 has a proximal end 328, a distal end 330 and length extender catch feature 329 near its distal end 330. In this embodiment, the catch feature 329 comprises a protrusion which extends radially outwardly from the guide sleeve 327. The protrusion may have a variety of shapes including a flap, a hook, a knob, a nub, a clasp or any suitable shape for attaching to the treatment device 10 itself or a corresponding feature on the treatment device 10. The guide sleeve 327 is position able over the insertion cord 202 of the bronchoscope 20 as shown and is able to slide longitudinally over the insertion cord 202. In addition, the catch feature 329 is configured to removably attach to the treatment device 10, such as the stabilizing end 16 of the treatment device 10, so that translation of the guide sleeve 327 along the insertion cord 202 of the bronchoscope 20 adjusts the treatment device 10 length. For example, retraction of the guide sleeve 327 (toward the proximal end of the bronchoscope 20) increases the length of the device 10 by pulling the stabilizing end 16 proximally. This in turn increases the stress and strain on the treatment device 10. Such retraction can be undertaken to achieve any desired treatment device stress, strain and length configurations before advancing the treatment device 10 into the lung, while advancing the treatment device 10 in the lung, just before deployment of the treatment device 10 in the lung, after anchoring the stabilizing end 16, after anchoring the tissue gathering end 14, after anchoring both the stabilizing end 16 and the tissue gathering end 14, or before or after any combination of these actions to deploy the treatment device 10 in lung tissue. It may be appreciated that in other embodiments the guide sleeve 327 may be advanced to push the treatment device 10 off of the insertion cord 202 or the guide sleeve 327 may be held fixed to support the stabilizing end 16 of the treatment device 10 to keep the treatment device 10 from binding with the insertion cord 202. Further, it may be appreciated that the guide sleeve 327 may be used to pull the treatment device 10 out of the airway while the insertion cord 202 is being withdrawn from the treatment device.

Figure 47:
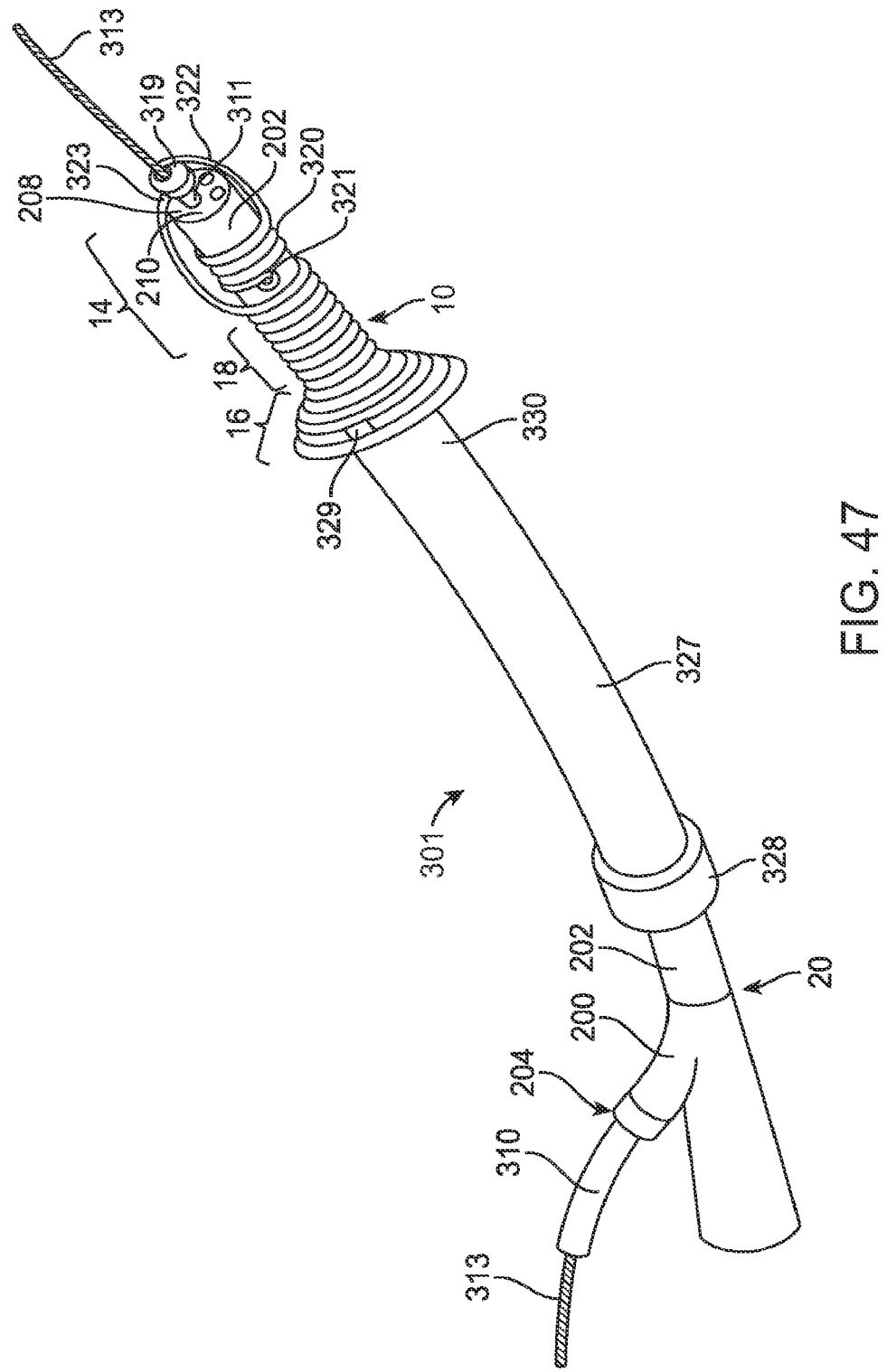
FIG. 47 illustrates an embodiment of a treatment device releasably mounted on the delivery system of FIG. 46.

FIG. 47 illustrates an embodiment of a treatment device 10 releasably mounted on the delivery system of FIG. 46. As shown, the guide sleeve 327 is advanced over the insertion cord 202 and disposed proximal to the insertion cord tip 208. The treatment device 10 is mounted on the bronchoscope 20 so that the tissue gathering end 14 is disposed over the insertion cord tip 208 and the stabilizing end 16 is disposed over a portion of the guide sleeve 327. Here, the catch feature 329 engages the stabilizing end 16, such as by hooking on to one or more turns of the coil forming the stabilizing end 16. This constrains the stabilizing end 16 so it cannot use stored elastic spring energy to open and increase the longitudinal dimension of the treatment device 10. In addition, a guidewire 313 has been advanced through the working channel port 204 of the bronchoscope 20 and through the guide coil 319 to guide the advancement of the system 301. Likewise, the deployment sleeve 311 has been advanced through the working channel 210 of the broncho-scope 20 and it is butted against the guide coil 319. As mentioned, the guide sleeve 327 and catch feature 329 has been connected to the stabilizing end 16 and adjusted relative to the bronchoscope 20 so the midsection 18 is fixed in an unstressed and unstrained configuration to allow the delivery system 301 and the treatment device 10 to remain unstressed and flexible during delivery for easy advancement to a treatment location.

Once the delivery system 301 has been advanced to the treatment location within the lung anatomy, the tissue gathering end 14 is desirably positioned within the treatment location. The tissue gathering end 14 will substantially remain in this desired position while the stabilizing end 16 is retracted. To accomplish this, the tissue gathering end 14 is unmounted or deployed from the bronchoscope 20. In particular, the alignment element 320 is released from the bronchoscope 20, such as by retracting the bronchoscope 20 or by advancing the deployment sleeve 311 which in turn advances the anchor strut 322 which pulls the alignment element 320 off the insertion cord tip 208. The guidewire 313, and optionally the deployment sleeve 311, are held in a fixed position within the airway AW so as to maintain the elongated configuration of the treatment device 10. Release of the alignment element 320 allows the anchor strut 322 to extend radially outwardly toward its biased configuration. Thus, the anchor strut end 321 engages with the wall W of the airway AW in an anchoring manner. In this embodiment, at least the anchor strut end 321 deforms a portion of the wall W to make purchase at the desired location.

Figure 48:
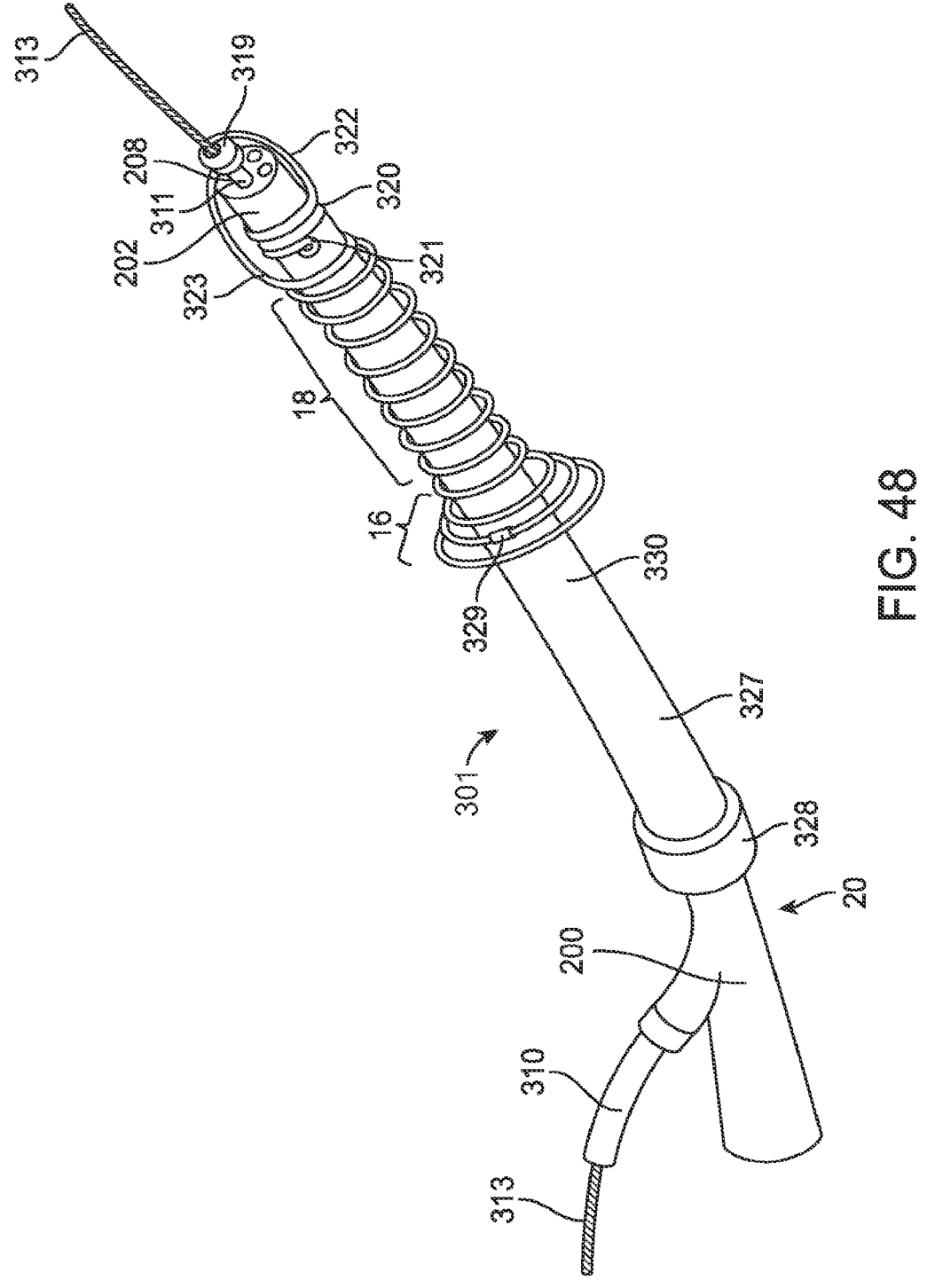
FIG. 48 illustrates elongation of the extendible midsection due to retraction of the stabilizing end by the guide sleeve and catch feature.

The stabilizing end 16 is then retracted, as illustrated in FIG. 48. Here, the guide sleeve 327 and catch feature 329 has been retracted relative to the insertion cord 202, pulling the stabilizing end 16 proximally so that the extendible midsection 18 is elongated. This allows the stabilizing end 16 to be positioned within an ostium or other stable area within the airway. The treatment device 10 is then released from the delivery system 301. The stored elastic strain energy of the extendible midsection 18, and optionally any stored energy in the stabilizing end 16 and/or tissue gathering end 14, creates an urging force to recoil and shorten the treatment device 10 toward its original configuration and length. Since the strength of the airway AW is compromised, the walls W are unable to overcome this urging force. Thus, the wall W at least the point of purchase or engagement by the tissue gathering end 14 is carried with the tissue gathering end 14 toward the stabilizing end 16. This re-tensions the airway distal to the treatment device 10. By tensioning the lung tissue, the device 10 has tensioned the entire bronchial tree that is distal to this single airway which in turn expands the associated alveoli tissue.

Figure 49:
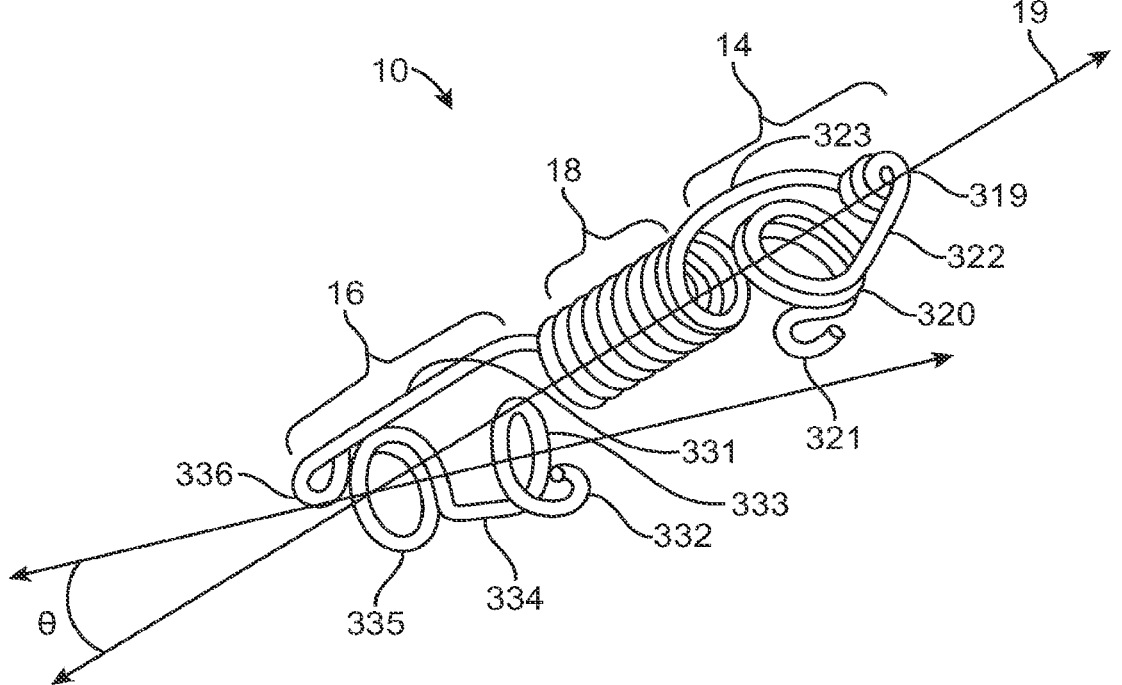
FIG. 49 illustrates another embodiment of a treatment device, wherein the treatment device has a tissue gathering end and extendible midsection which is similar to the device of FIG. 39, however in this embodiment the stabilizing end differs.

FIG. 49 illustrates another embodiment of a treatment device 10. In this embodiment, the treatment device 10 has a tissue gathering end 14 and extendible midsection 18 which is similar to the device 10 of FIG. 39, however in this embodiment the stabilizing end 16 differs. In this embodiment, the stabilizing end 16 is configured to resist movement relative to the lung tissue in the distal direction. The stabilizing end 16 is comprised of elastic material that is capable of storing elastic strain energy and recovering to its initial stable shape. In this embodiment, the initial shape of the stabilizing end 16, illustrated in FIG. 49, comprises a plurality of loops which splay or deploy radially outwardly due to stored elastic strain energy. In this embodiment, the stabilizing end 16 comprises a body strut 331, an extension loop 336, a spring loop 335, an anchor strut 334, an actuation loop 333, and an anchor strut end 332. The body strut 331 is generally aligned with the longitudinal axis 19 of the device 10. The extension loop 336 is used to tether the device 10 to the delivery device 301. Alternatively, the delivery device may be a guidewire. The anchor strut 334 is joined with the body strut 331 by the spring loop 335 which biases the anchor strut 334 radially outward at an angle θ, such as between 5 and 90 degrees, preferably about 45 degrees. The stabilizing end 16 is strained, against its stable shape configuration, during delivery with the delivery device 301 retaining the spring loop 335 and the actuation loop 333 in a condition that is coaxial with the longitudinal axis 19. This keeps the anchor strut end 332 from being forced against lung tissue until the user is ready to deploy the stabilizing end 16.

Figure 50:
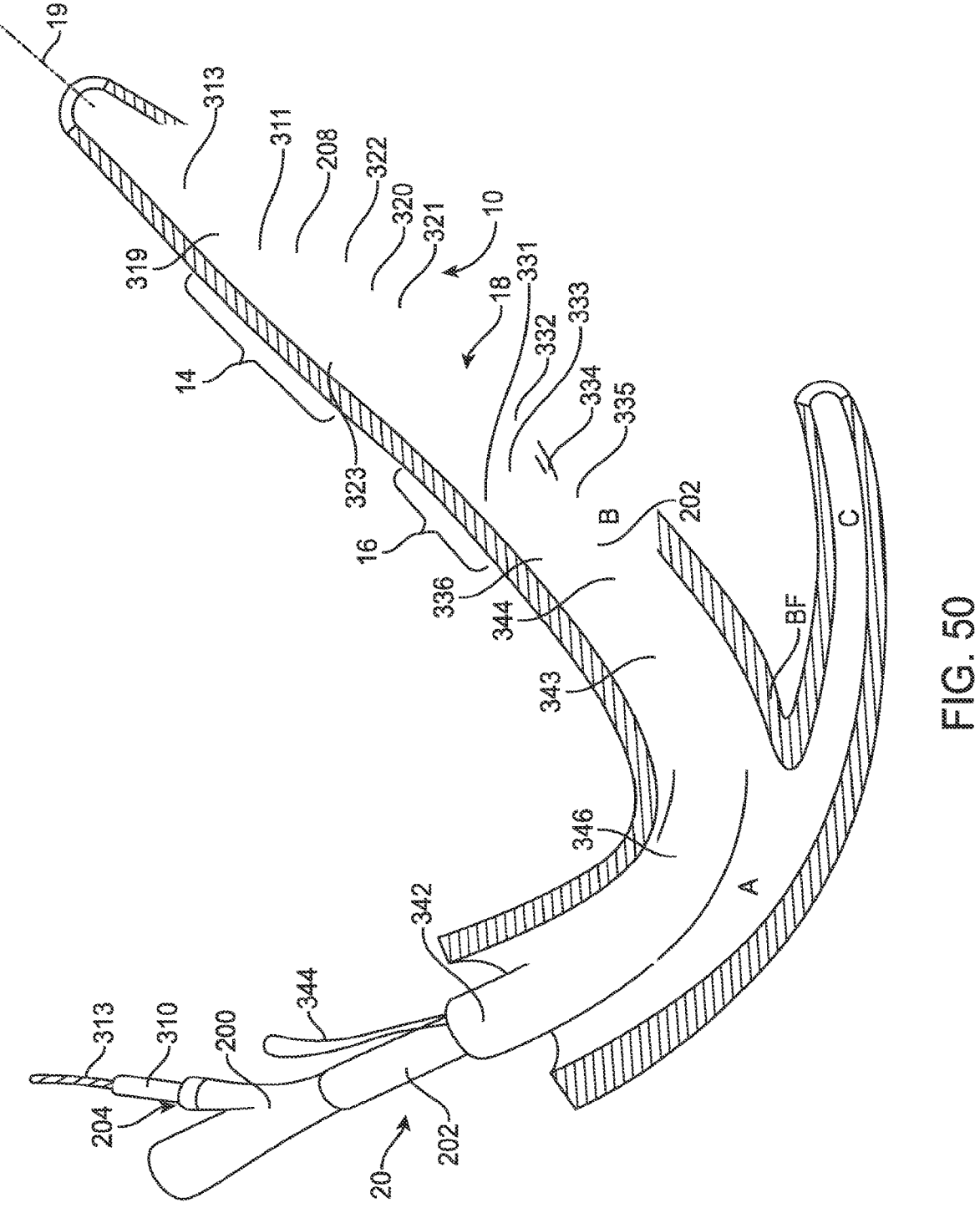
FIG. 50 illustrates the treatment device of FIG. 49 loaded onto a delivery system.

FIG. 50 illustrates the treatment device 10 of FIG. 49 loaded onto a delivery system 301. In this embodiment, the delivery system 301 comprises a bronchoscope 20 (including a bronchoscope body 200 and an insertion cord 202), a guidewire 313, a deployment sleeve 311 and a guide sleeve 346. The guide sleeve 346 has a proximal end 342 and a distal end 343. The guide sleeve 346 is position able over the insertion cord 202 of the bronchoscope 20 as shown and is able to slide longitudinally over the insertion cord 202. FIG. 50 illustrates the delivery system 301 advanced into lung anatomy so that the treatment device 10 has been advanced through airway A and into airway B via a bifurcation BF which also leads to airway C. The tissue gathering end 14 and stabilizing end 16 are constrained from actuating by the insertion cord 202 which is holding the alignment element 320 and the actuation loop 333 coaxial with the longitudinal axis 19.

Figure 51:
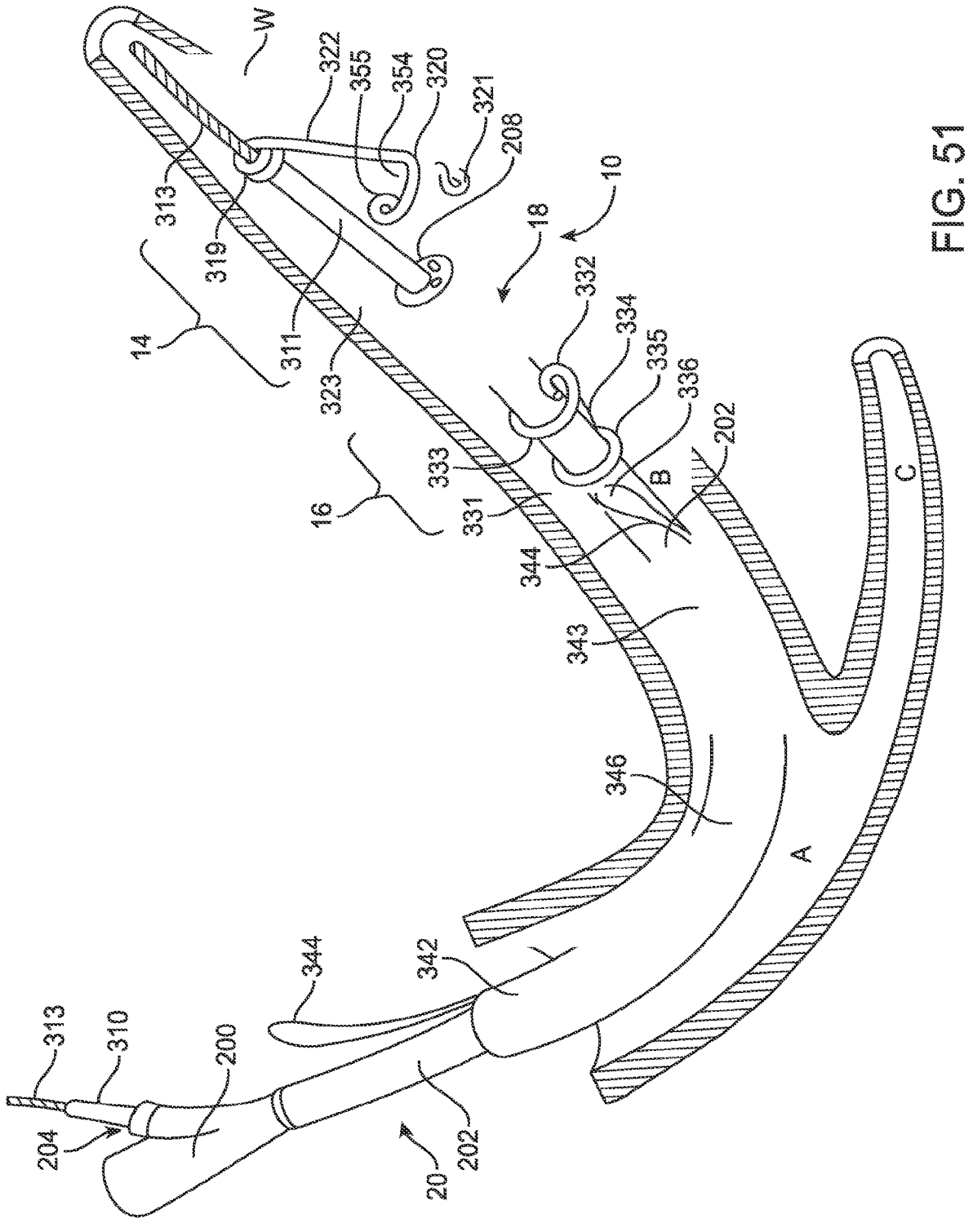
FIG. 51 illustrates deployment of the tissue gathering end of the treatment device of FIG. 49 within an airway.

FIG. 51 illustrates deployment of the tissue gathering end 14 within airway B. In this embodiment, deployment is achieved by advancing the deployment sleeve 311 so as to contact the guide coil 319. Additional advancement causes guide coil 319 and attached anchor strut 322 to pull the alignment element 320 off of the insertion cord tip 208 of the bronchoscope 20. Alternatively, in other embodiments, deployment is achieved by retracting the insertion cord tip 208 while maintaining position of the deployment sleeve 311 so that the alignment element 320 is pulled off of the insertion cord tip 208. In either situation, this releases the stored elastic strain energy in the tissue gathering end 14 driving the anchor strut end 321 into the airway wall W to anchor the distal end of the treatment device 10 at the desired location in airway B, as described previously in relation to the embodiment of FIG. 39. It may be appreciated that in some embodiments the alignment element 320 is configured as a structure that only partially encircles the bronchoscope shaft 202 as shown in FIG. 51 wherein the anchor loop 320 has an opening 354 and the loop 320 is then turned back around to form a blunt partial loop termination 355. It may be appreciated that the proximal anchor spring loop 335 and the proximal anchor actuation loop 333 may be similarly formed so as to not fully encircle the bronchoscope and still be effective. This allows for a bronchoscope or other delivery cannula or delivery device shaft, such as a guidewire, that may have diameter variation down the length to be translated to activate or unlock these anchor assemblies without actually removing the bronchoscope or delivery canula or delivery element. The proximal extension loop 336 is utilized for connection to a wire, link or tether 344 which may be pulled to move the device 10 or the stabilizing end 16 more proximally so as to extend the length of the midsection 18 while the device 10 is anchored into the lung tissue. The tissue gathering end 14 is configured to resist moving proximally in relation to the airway wall W, but it is configured to easily be moved more distally relative to the airway wall W. The stabilizing end 16 is configured to resist being advanced distally in relation to the airway wall W but it is configured to be able to be moved proximally relative to the airway wall W thereby extending the midsection 18.

Figure 52:
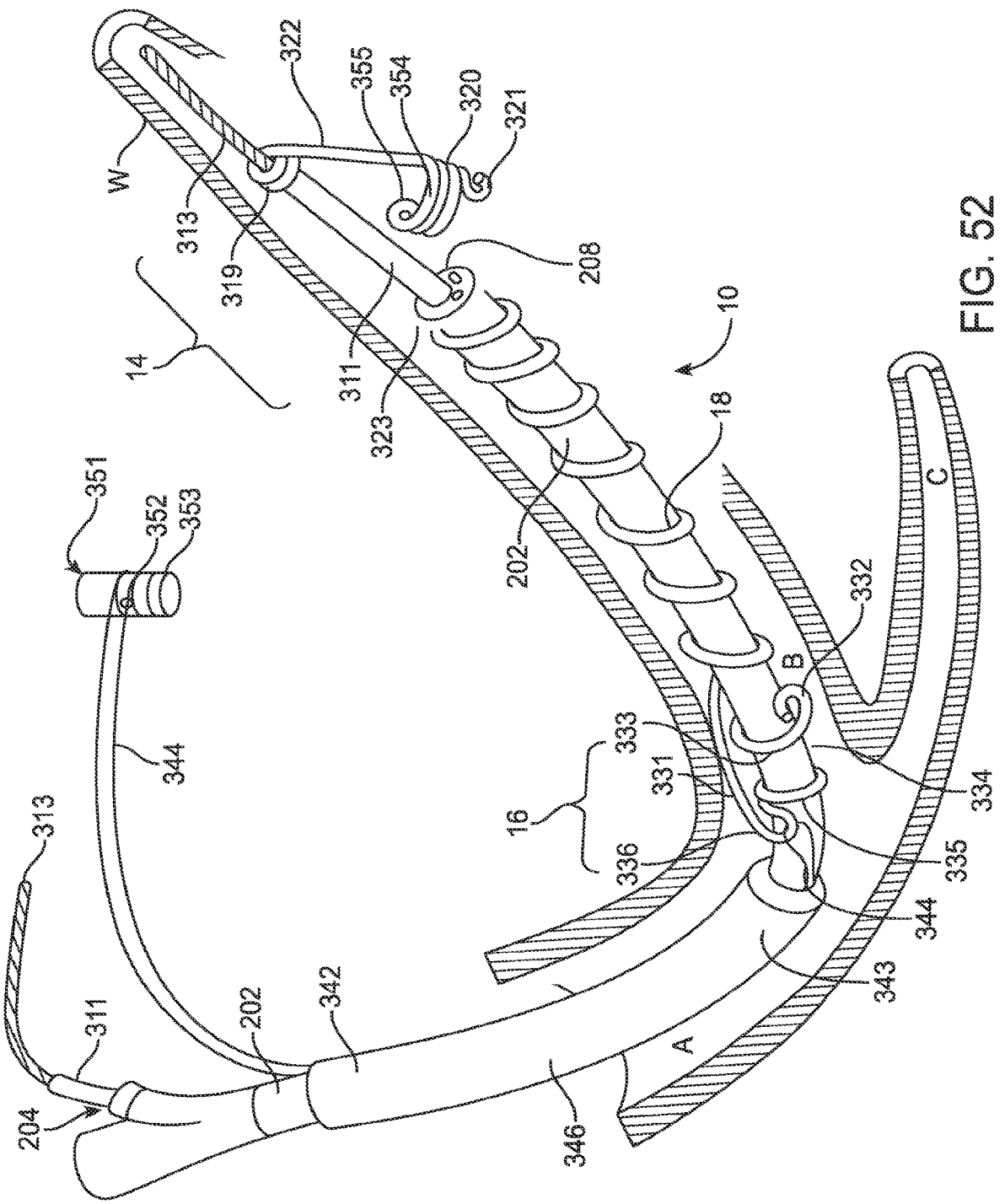
FIG. 52 illustrates extension of the midsection of the treatment device of FIG. 49 by retracting the guide sleeve which has a tether extending therethrough removably attached to the extension loop of the device.

The midsection 18 is extended, as illustrated in FIG. 52. In some embodiments, such extension is achieved by retracting the guide sleeve 346 which has a tether 344 extending therethrough. The tether 344 is removably attached to the extension loop 336 of the device 10, as mentioned previously. Retraction of the guide sleeve 346 pulls the tether 344 which in turn pulls the stabilizing end 16 of the device 10. In other embodiments, the guide sleeve 346 remains in place and the tether 344 is retracted into or through the guide sleeve 346. In some embodiments, this is achieved by pulling a handle 351 which is attached to the tether 344. FIG. 52 illustrates an embodiment of such a handle 351. Here, the handle 351 comprises a shaft 353 having a hole 352 therethrough. The tether 344 has two free ends which extend through or along the guide sleeve 346, exiting the proximal end 342 of the guide sleeve 346. The free ends wrap around the shaft 353 of the handle 351 and through the hole 352 to increase traction and efficiency when pulling the tether 344. Thus, as the handle 351 is pulled away from the patient, the tether 344 is tensioned and pulls on the extension loop 336 of the device 10. By tensioning the tether 344, the tether 344, treatment device 10 and airway wall W become a tensile member which straightens the tether 344, the treatment device 10 and the airway wall W.

The pulling force is translated through the device 10 to the tissue gathering end 14. If the tissue gathering end 14 is anchored in stable lung tissue, the tissue gathering end 14 will remain in place and the midsection 18 will expand longitudinally as the stabilizing end 16 moves in the proximal direction. If the tissue gathering end 14 is anchored in unstable or weakened lung tissue, the tissue gathering end 14 will pull the weakened airway wall W along with it in the proximal direction as the stabilizing end 16 moves in the proximal direction. This will continue until stronger lung tissue is reached wherein the tissue gathering end 14 will cease movement and the midsection 18 will expand longitudinally as the stabilizing end 16 moves in the proximal direction. The midsection 18 is extended until the stabilizing end 16 is desirably positioned within the airway. The stabilizing end 16 is then released and anchored in place.

Figure 53:
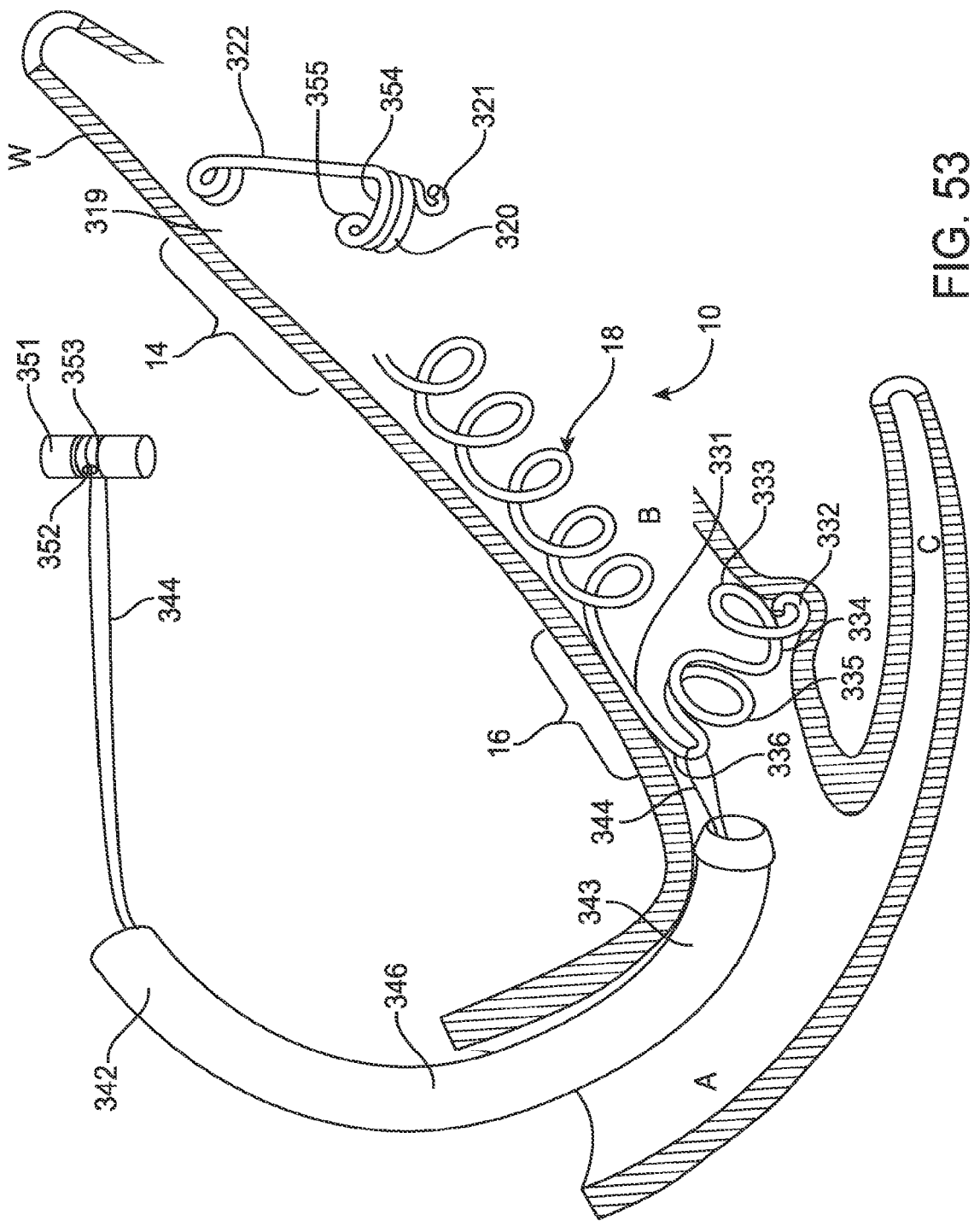
FIG. 53 illustrates anchoring of the stabilizing end of the treatment device of FIG. 49 by retracting the bronchoscope from the device.

FIG. 53 illustrates anchoring of the stabilizing end 16 within the airway B, just beyond the branch to airway C. This is achieved by retracting the bronchoscope 20 from the device 10. Such retraction releases the spring loop 335 of the device 10. As mentioned previously, the spring loop 335 joins the body strut 331 with the anchor strut 334 which is biased radially outward. Thus, release of the spring loop 335 allows the anchor strut 334 to extend radially outwardly, toward the airway wall W, such as shown. The anchor strut end 332 engages the airway wall W, anchoring the stabilizing end 16 in place.

Figure 54:
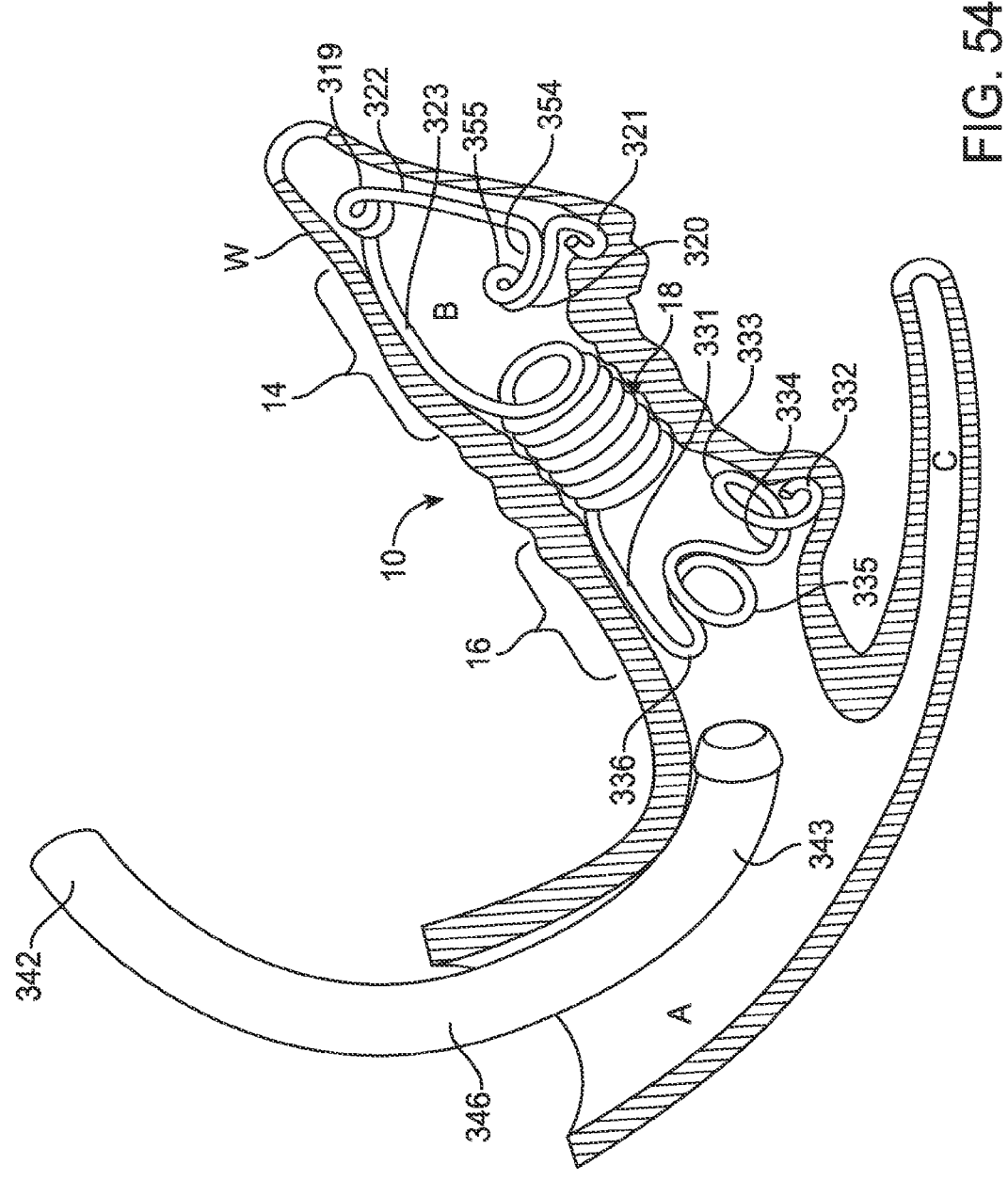
FIG. 54 illustrates the treatment device of FIG. 49 after the tether has been cut and removed, thereby allowing the midsection to recoil toward its natural configuration over time.

FIG. 54 illustrates the treatment device 10 after the tether 344 has been cut and removed. Removal of the pulling force from the tether 344 allows the midsection 18 to recoil toward its natural configuration over time. Since the stabilizing end 16 and the tissue gathering end 14 are engaged with the airway walls W, the engaged portions of the airway walls W travel along with the ends 14, 16. In some embodiments, both ends 14, 16 travel toward each other as the longitudinal length of the midsection 18 shortens. Thus, the lung tissue along the airway between the ends 14, 16 becomes minimally compressed, as illustrated in FIG. 54, and the volume of the lung along the airway B becomes minimally reduced. The airway between the ends 14, 16 is supported by the helical structure of the midsection 18, acting as a stent to keep the airway patent. Thus, COPD symptoms are reduced rather than increased, which is the result when the airways are compressed without internal support, exasperating the original problem in the lung particularly during expiration breathing cycles. In addition, the more proximal airway A structure and the proximal end of airway B structure is now stronger and provides a better foundation and base to stabilize lung tissue and lung treatment devices than the distal end of airway B.

It may be appreciated that in some embodiments the ends 14, 16 travel equal distance toward the center of the midsection 18. In other embodiments, the ends 14, 16 travel differing distances, such as influenced by the stability of the portions of the airway wall W engaged by the ends 14, 16. For example, the stabilizing end 16 is typically positioned more proximally than the tissue gathering end 14, within a portion of the airway that is stronger and more stable. In such instances, the stabilizing end 16 would travel a smaller distance than the tissue gathering end 14 which is engaged with weaker tissue. It may also be appreciated that in some embodiments, only one of the ends 14, 16 moves while the other remains stationary. In such instances, typically the tissue gathering end 14 moves toward the stabilizing end 16. However, the outcome would vary depending on the characteristics of the airway and the treatment device 10. It may also be appreciated that as the health of the patient changes over time, such as a progression of the disease state, the device 10 will continue to shorten so as to maintain tension in the lung.

Figure 55:
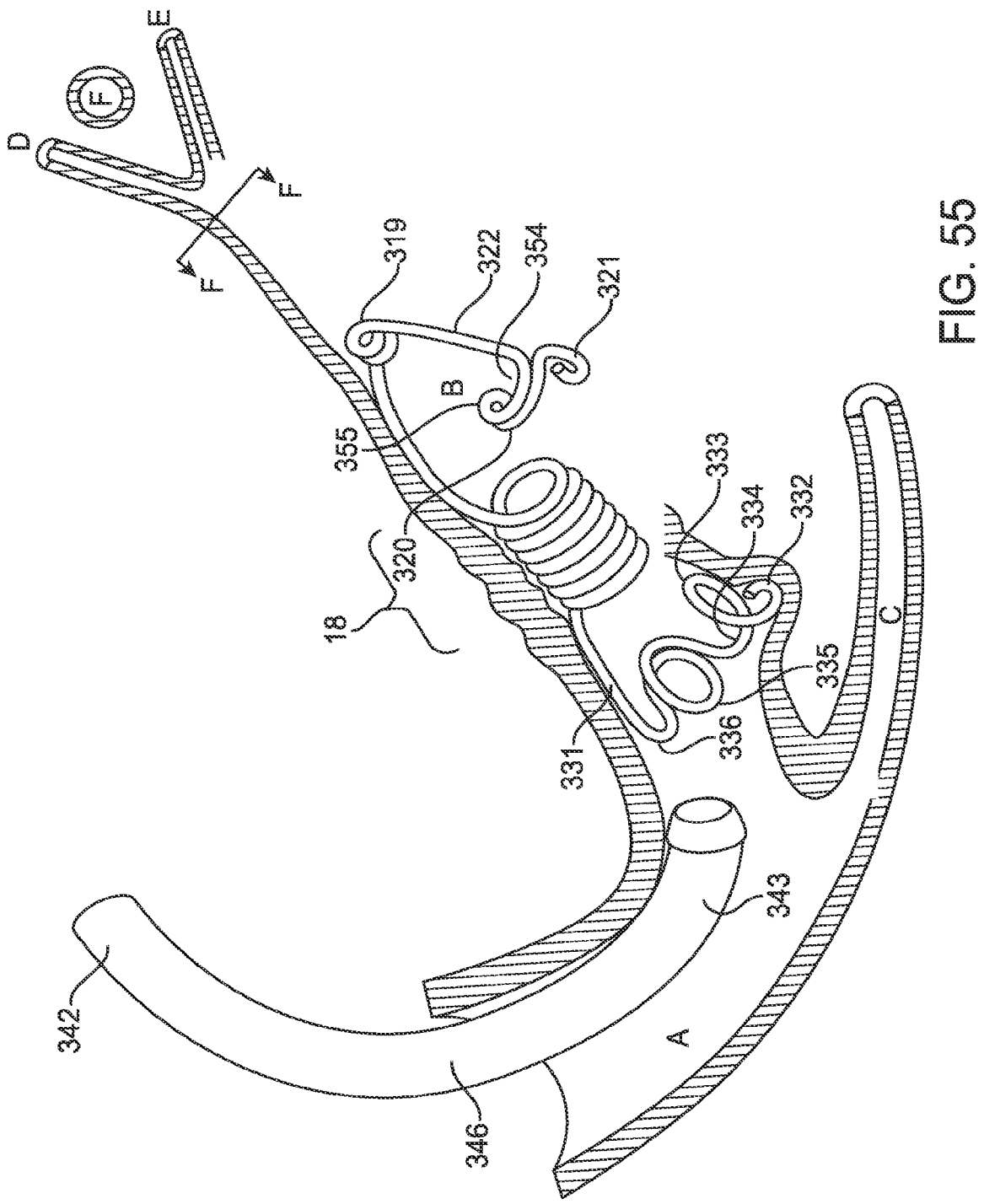
FIG. 55 illustrates the elastic recoil of the treatment device of FIG. 54 supporting the airway tree A, B, C, D, E and F in tension.
Figure 56:
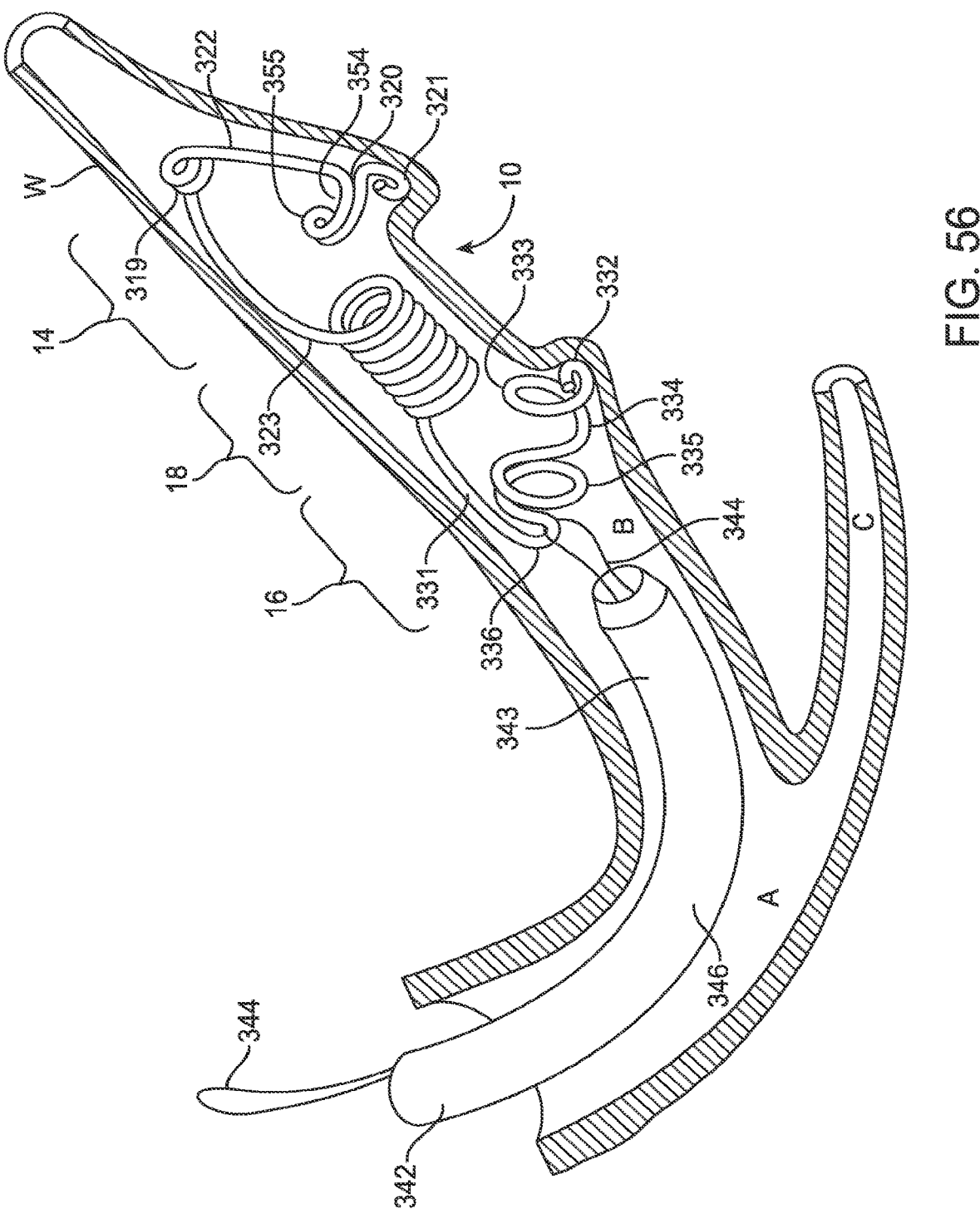
FIG. 56 illustrates an alternative method of treating a patient wherein the pulmonary treatment device is deployed in the lung anatomy and then expanded thereafter.

FIG. 55 illustrates the elastic recoil of the treatment device 10 causing midsection 18 shortening as has been previously discussed. FIG. 55 also illustrates the branching of the distal portion of airway B into an attached network of airways D, E (F is the cross-section of the distal portion of airway B). The airways B, D, E that are longitudinally tensioned and affected by the deployment, elongation and tensioning of the treatment device 10. The distal portion of airway B is shown to be supported and made to remain round and patent as the patient successfully expires air as connective tissue between the distal airways D and E connect to the distal portion of airway B to hold the distal portion of airway B more open and round (as shown in F) as tension is applied to the entire lung airway system. By tensioning the lung tissue to support the airway tree A, B, C, D, and E in tension, the symptoms listed herein are reduced and one or more of the physiologic changes that are listed in herein are changed to beneficially affect and treat COPD patients who may suffer from emphysema. FIG. 56 illustrates an alternative method to treating the patient wherein the device 10 is deployed in the lung anatomy and then expanded thereafter. In this embodiment, the treatment device 10 is similar to that of FIG. 49 and is deployable by a delivery device 301 into an airway of the lung. In this embodiment, the device 10 is partially deployed according to FIGS. 50-51, wherein the tissue engaging end 14 is deployed and engaged with the airway wall W. However, in this embodiment, the stabilizing end 16 is also deployed without extending the midsection 18. This may be achieved by retracting the bronchoscope 20 while the guide sleeve 346 is held against the stabilizing end 16 so that the stabilizing end 16 is released and deployed. Thus, the device 10 is deployed into the airway in a substantially relaxed configuration, as illustrated in FIG. 56.

The device 10 maintains connection with the tether 344 which extends through or along the guide sleeve 346. It may be appreciated that the configuration of the tissue gathering end 14 and its engagement with the wall W creates resistance to movement of the device 10 along the airway in the proximal direction. In particular, the anchor strut 322 extends radially outwardly from the longitudinal axis 19 forming an angle θ which faces the proximal direction or midsection 18. Likewise, anchor strut end 321 faces the proximal direction or midsection 18 as it engages the wall W. This creates an indent in the wall W and a tissue ledge which impedes movement of the anchor strut end 321 along the wall W in the proximal direction. Likewise, the configuration of the stabilizing end 16 and its engagement with the wall W creates resistance to movement of the device 10 along the airway in the distal direction. In particular, the anchor strut 334 extends radially outwardly from the longitudinal axis 19 forming an angle θ which faces the distal direction or midsection 18. Likewise, anchor strut end 332 faces the distal direction or midsection 18 as it engages the wall W. This creates an indent in the wall W and a tissue ledge which impedes movement of the anchor strut end 332 along the wall W in the distal direction. However, it may be appreciated that either or both of the tissue gathering end 14 and stabilizing end 16 are able to move along the airway away from the midsection 18. In this embodiment, the stabilizing end 16 is tethered to the delivery device 301, particularly the guide sleeve 346. Therefore, the stabilizing end 16 is able to be pulled in the proximal direction by pulling the tether 344. However, the tissue gathering end 14 resists movement along the wall W in the proximal direction at least due to the tissue ledge impeding the anchor strut end 321. If the wall W is weak, the wall W itself moves in the proximal direction, being pulled by the anchor strut end 321. This continues until a stronger portion of the wall W is reached which is able to resist longitudinal compression. At that point, the tissue gathering end 14 anchors in place and the midsection 18 expands, increasing the overall longitudinal length of the device 10. This continues incrementally as the stabilizing end 16 is pulled along the airway. At any time, pulling may cease and the stabilizing end 16 remains engaged at the new location along the wall W due to resistance in the distal direction at least due to the tissue ledge impeding the anchor strut end 332. Such extension of the midsection 18 stores elastic strain energy in the device 10. Since the wall W has compressed and adjusted during positioning of the stabilizing end 16, the device 10 will likely maintain its length and position upon release of pulling force. However, over time, the stored elastic strain energy may cause the midsection to contract, along with movement of the tissue gathering end 14 and/or stabilizing end 16 toward the midsection 18.

It may be appreciated that such capability may allow the length of the device 10 to be adjusted throughout the procedure to achieve the desired re-tensioning of the airway. Once this has been achieved, the tether 344 is removed along with the delivery device 301. It may be appreciated that in some embodiments the device 10 may be re-accessed and repositioned. This may be achieved by re-tethering or re-connecting a device, such as a delivery device 301, to the stabilizing end 16 and further pulling the stabilizing end so as to position the stabilizing end 16 at a new more proximal location. This pulling motion further tensions the airway. Again, once the desired effect has been achieved, the delivery device 301 is removed leaving the device 10 in place.

It may be appreciated that the pulmonary treatment devices 10 may be removed from the lung anatomy either during the procedure, for repositioning or replacement, or at a later time during a secondary procedure. Removal may be achieved by threading a delivery device through the appropriate portions of the device 10, such as through the actuation loop 333 and/or alignment element 320, so as to re-engage the device 10. The device 10 is then pulled proximally by the delivery device and extracted from the body. It may also be appreciated that the device 10 may be pulled from the anatomy by attachment to any suitable portion, such as the stabilizing end 16, and applying sufficient force in the proximal direction to withdraw the device 10. The same device 10 can then be sanitized and reloaded on the delivery device for re-delivery to the target treatment area or a new device 10 may be utilized.

Likewise, it may be appreciated that previously positioned devices 10 may be adjusted at a later time during a secondary procedure. This may be achieved by accessing a previously positioned device 10 with a delivery device and attaching thereto. This can be achieved by threading a delivery device through the appropriate portions of the device 10, such as through the actuation loop 333 and/or alignment element 320, so as to re-engage the device 10. Typically, the actuation loop 333 is re-engaged so as to attach to the stabilizing end 16 of the device 10. Or, the stabilizing end 16 is grasped such as with the use of a catch feature 329. In such instances, the stabilizing end 16 is pulled proximally so as to further re-tension the airway AW. This may be desired if the disease has progressed over time beyond the ability of the device 10 to compensate. The stabilizing end 16 is then secured in a new location to maintain the re-tensioning. The delivery device is then disengaged from the pulmonary treatment device 10 which is left behind as an implant.

It may be appreciated that a variety of approaches have been described herein, including treatment devices 10 which are introduced through a lumen in a delivery device (including being pushed or pulled through the lumen by itself, within an introducer or mounted on an additional device such as a catheter or guidewire which is advanceable within the lumen), and treatment devices 10 which are introduced by mounting on an exterior portion of a delivery device, such as the insertion cord tip 208 of a bronchoscope 20 or on a catheter, wherein the treatment device 10 is pushed or pulled from the mounted position by an external or internal sleeve or device. It may be appreciated that in some embodiments the treatment device 10 is deployed as it is released from the delivery device and in other embodiments, the treatment device 10 is released from the delivery device and then deployed, such as by the removal of an element or device which holds the treatment device 10 in a constrained configuration (e.g. a guidewire or sleeve). It may be appreciated that in some embodiments, a single treatment device 10 is deliverable from a delivery device at a time and in other embodiments multiple treatment devices 10 (including two, three, four, five, six or more) are deliverable from the delivery device at a time. It may be appreciated that the treatment devices 10 may be pre-loaded on or within the delivery device or may be loaded by the user. It may also be appreciated that in some embodiments the tissue gathering end 14 is anchored initially in the lung passageway and the stabilizing end 16 is pulled so as to re-tension the airway. In other embodiments, the stabilizing end 16 is anchored initially in the lung passageway and the tissue gathering end 14 is pushed so as to re-tension the airway. It may be appreciated that pulling of the stabilizing end 16 or pushing of the tissue gathering end 14 may be achieved while the end 14, 16 is held in a contracted state for ease of movement or after the end 14, 16 has been deployed (wherein the end 14,16 has been specially designed to allow such movement).

Figure 57:
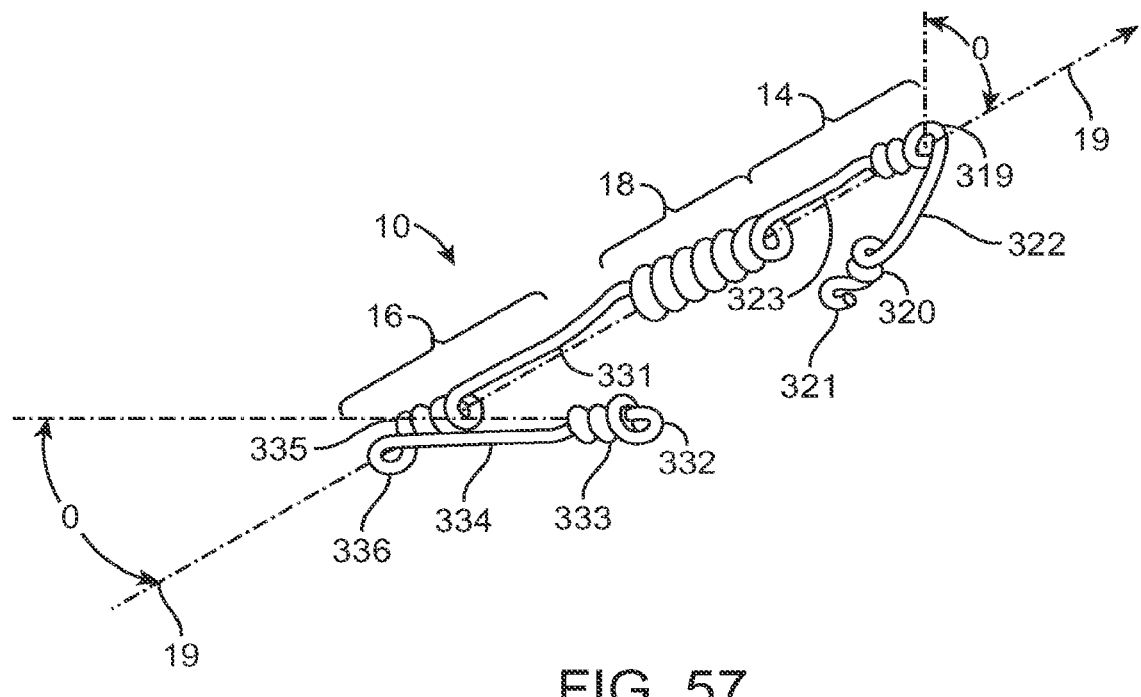
FIG. 57 illustrates an embodiment of a treatment device that is collapsible into a small profile for optional delivery through a lumen in a delivery device.

FIG. 57 illustrates another embodiment of a treatment device 10. In this embodiment, the treatment device 10 is optionally introduce able through a lumen in a delivery device. Thus, it is collapsible into a small profile. It is held in the collapsed or constrained configuration by the use of a catheter or guidewire which holds the treatment device 10 in the constrained configuration. In some embodiments, a guidewire is preferred due to its small diameter and ability to be advanced into distant branches of the lung passageways. Once the treatment device 10 is desirably positioned within the lung passageway, the guidewire is removed, thereby allowing the device 10 to deploy either at once or in stages.

FIG. 57 illustrates the treatment device 10 in its deployed or expanded state. In this embodiment, the treatment device 10 has a tissue gathering end 14, unextendible midsection 18 and a stabilizing end 16. The treatment device 10 may have a single component structure or may be comprised of a number of components. In any case, individual stiffnesses of the tissue gathering end 14, extendible midsection 18 and stabilizing end 16 may be tuned to maximize effectiveness of both anchoring and supporting likeness to healthy lung tissue. Likewise, the tissue gathering end 14 and stabilizing end 16 are flexible so as to collapse along longitudinal axis 19 and deploy or expand to the relaxed configuration shown in FIG. 57. Such expansion is typically achieved by self-expansion due to spring loading.

Figure 58:
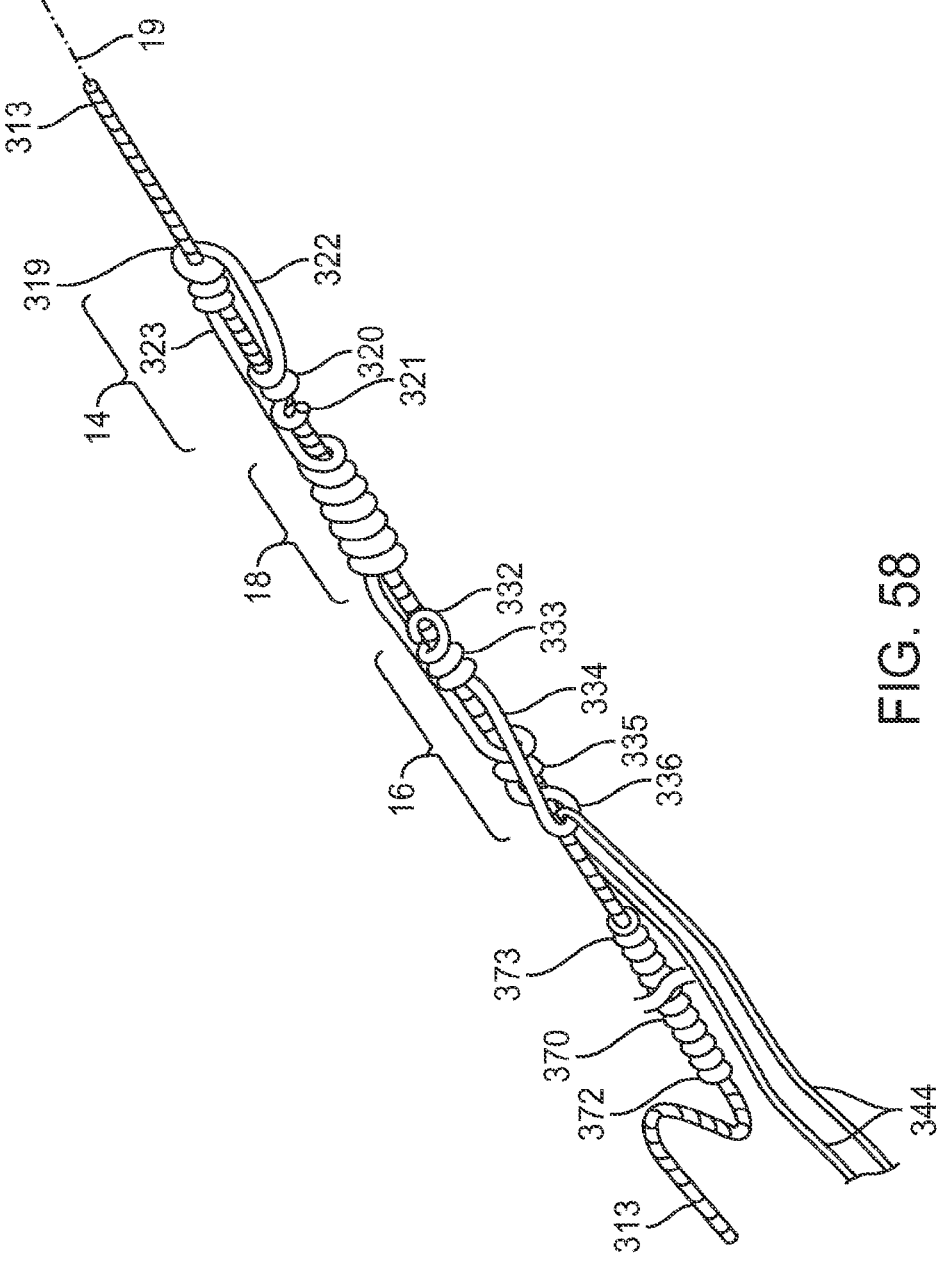
FIG. 58 illustrates the treatment device of FIG. 57 in a collapsed configuration mounted on a guidewire.

FIG. 58 illustrates the treatment device 10 of FIG. 57 in a collapsed configuration. Here, the device 10 is mounted on a guidewire 313. Thus, each of the tissue gathering end 14, midsection 18 and stabilizing end 16 form at least one loop or partial loop through which the guidewire 313 is passable so that the treatment device 10 is mountable on the guidewire 313 and the tissue gathering end 14 and stabilizing end 16 are held in a constrained configuration (storing elastic strain energy). In this collapsed or constrained configuration, the guidewire 313 and treatment device 10 are passable through a lumen in a delivery device, such as a working channel 210 of a bronchoscope 20. In some embodiments, the guidewire 313 and treatment device 10 are passable through a working channel 210 having an inner diameter that is sized between 1.3 and 3.2 mm. In this embodiment, the extendible midsection 18 comprises a coil wherein the guidewire 313 is passable therethrough. Thus, the extendible midsection 18 is able to be elongated to store elastic strain energy which urges the treatment device 10 to recover back to a non-elongated length. In some embodiments, the midsection 18 has a uniform diameter. However, in other embodiments, the midsection 18 has a tapering diameter, particularly tapering downward toward the stabilizing end 14 of the treatment device 10. Such tapering may mimic the tapering diameter of a lung passageway within which the device 10 is implanted.

As more easily visualized in FIG. 58, the tissue gathering end 14 comprises a body strut 323, a guide element 319, an anchor strut 322, an alignment element 320 and an anchor strut end 321. In this embodiment, the body strut 323 extends from the flexible midsection 18 and is generally parallel to the longitudinal axis 19. The body strut 323 is connected with a guide element 319 which typically forms the distal-most portion of the treatment device 10. In this embodiment, the guide element 319 comprises a coil, however the element 319 may have any suitable shape including a single loop. In this embodiment, the guide element 319 is arranged so that the guidewire 313 coaxially passes through the guide element 319. The guide element 319 also stores the strain energy which allows the anchor strut 322 to deploy and extend outwardly. In some instances, the coil dictates the strength of the spreading force of the anchor strut 322 radially outwardly. During delivery and prior to deployment, the anchor strut 322 is held in a retracted or un-extended position so as to avoid dragging along the airway walls W or traumatizing tissue. Such retraction is maintained by alignment element 320. In this embodiment, the alignment element 320 has the form of a coil, however it may be appreciated that the element 320 may have the form of a single loop, a partial loop or snap locking structure, a hook shaped lock or spring lock mechanism, to name a few. When the center of the element 320 is aligned with the longitudinal axis 19, the anchor strut 322 is held parallel to or at a small angle in relation to the longitudinal axis 19. Such alignment is maintained by passing the guidewire 313 or similar device through the center of the treatment device 10 and through the alignment element 320 (as illustrated in FIG. 58). The tissue gathering end 14 is configured so as to bias the alignment element 320 and attached anchor strut 322 radially outwardly. Therefore, withdrawal of guidewire 313 from the alignment element 320 frees the alignment element 320 and allows the alignment element 320 to rotate away from alignment with the longitudinal axis 19. This, in turn, causes the anchor strut 322 to extend radially outwardly. In some embodiments, the anchor strut 322 extends 1 mm to more than 30 mm but 6-12 mm is preferable. The anchor strut 322 terminates in an anchor strut end 321, which may have a variety of shapes including a coil, ball, sharp end barb, L shaped pad, strain relief long coil or tapered coil, to name a few. The anchor strut 322 is configured to extend radially outwardly upon deployment so at least the anchor strut end 321 engages an airway wall W or damaged tissue DT, such as in the area of the alveolar sacs. However, in some instances, the anchor strut 322 itself additionally engages the airway wall W or damaged tissue DT.

In the extended position, the alignment element 320 has an axis which is at an angle θ to the longitudinal axis 19. Typically, the angle θ is in the range of 1 to 90 degrees, preferably 20-65 degrees. In some embodiments, additional portions of the tissue gathering end 14 are also biased to assist in extension of the anchor strut 322 radially outwardly. For example, in some embodiments, the body strut 323 is biased so as to further extend the anchor strut 322 radially outwardly. In the embodiment of FIG. 39, the body strut 323 is disposed opposite the anchor strut 322 so that the alignment element 320 is disposed therebetween. Thus, when the center of the alignment element 320 is aligned with the longitudinal axis 19, the body strut 323 and anchor strut 322 reside on opposite sides of the longitudinal axis 19. In some instances, release of the alignment element 320 allows both the body strut 323 and anchor strut 322 to bias toward their relaxed configurations (such as pushing both the body strut 323 and anchor strut 322 outwardly in the same radial direction). This can allow the body strut 323 and anchor strut 322 to spread fully elastically at least 5 degrees but up to 90 degrees, and preferably 20 to 65 degrees, to push the anchor strut end 321 into or through the wall of an airway or the diseased tissue to anchor the tissue gathering end 14 in the lung tissue.

In this embodiment, the stabilizing end 16 comprises a body strut 331, a spring loop 335, an extension loop 336, an anchor strut 334, an actuation loop 333, and an anchor strut end 332. The body strut 331 and spring loop 335 are generally aligned with the longitudinal axis 19 of the device 10 in both the relaxed and constrained configurations. The anchor strut 334 is joined with the body strut 331 by the spring loop 335 which biases the anchor strut 334 radially outward at an angle θ, such as between 5 and 90 degrees, preferably about 45 degrees. The spring loop 335 also allows the anchor strut 334 to be moved toward the longitudinal axis 19 so that the actuation loop 333 is aligned coaxially with the longitudinal axis 19 for passage of the guidewire 313 therethrough. This keeps the anchor strut end 332 from being forced against lung tissue until the user is ready to deploy the stabilizing end 16.

Referring again to FIG. 58, the treatment device 10 of FIG. 57 is shown loaded onto a guidewire 313. In this embodiment, the delivery system comprises the guidewire 313, a pusher coil 370 and a tether 344 that is looped, tied, attached (such as with a hitch knot) or otherwise removably attached to the pulmonary treatment device 10, such as to extension loop 336. The pusher coil 370 has a proximal end 372 and a distal end 373. The coil shape allows the pusher coil 370 to bend and flex easily through the anatomy. The pusher coil 370 Is typically comprised of a metal material to assist in cleaning and steam sterilization however other materials may be used such as polymers. The pusher coil 370 is positionable over the guidewire 313, proximal to the treatment device 10, as shown, and is able to slide longitudinally over the guidewire 313. To deploy the treatment device 10, the pusher coil 370 is advanced over the guidewire 313 so as to push the treatment device 10 in the distal direction while the guidewire 313 remains in place. Consequently, the treatment device 10 is pushed off of the guidewire 313 wherein it deploys to its relaxed and expanded configuration. This may be achieved in stages or all at once. For example, in some embodiments, the tissue gathering end 14 is pushed off the distal end of the guidewire 313 with the use of the pusher coil 370 so that the anchor strut 322 expands and at least the anchor strut end 321 engages the lung passageway wall. This is achieved while the remainder of the treatment device 10 remains mounted on the guidewire 313. The proximal end of the treatment device 10 is then pulled in the proximal direction by applying pulling force to the tether 344. Since the tissue anchoring end 14 is anchored in the lung passageway, the lung passageway is pulled proximally, re-tensioning the airway, while the midsection 18 also expands. Once airway is desirably re-tensioned, the stabilizing end 16 is deployed by advancing the pusher coil 370, thereby pushing the stabilizing end 16 off of the guidewire 313. This allows the stabilizing end 16 to anchor in place. The guidewire 313 and pusher coil 370 are then removed from the patient. In addition, the tether 344 is removed from the treatment device 10.

It may be appreciated that the delivery system of FIG. 58 and treatment device 10 mounted thereon may be passed through a lumen of a scope or other instrument, particularly through a working lumen of a bronchoscope 20. Or, the delivery system of FIG. 58 and treatment device 10 mounted thereon can be advanced through the trachea and into the lung by itself, without the use of a bronchoscope.

Torque-Based Pulmonary Treatment Device Embodiments

Torque-Based Treatment Overview

The above described embodiments rely primarily on linear or curvilinear pulling and pushing of lung tissue to re-tension the lung in patients suffering from COPD, particularly advanced COPD where tissue is highly damaged. Here, methods and devices are provided which rely primarily on torque, twisting and rotation to re-tension the lung, optionally in addition to linear or curvilinear pulling and pushing. Such embodiments are particularly suitable for patients with advanced emphysema, such as patients who are diagnosed as GOLD stage II, III, and IV, where the lung contains highly damaged tissue, particularly into and well beyond the lobar airways and typically beyond the bifurcations that lead to regions of the lung that would normally contain the 3rd generation airways or more distal generations of airways in a healthy person. Lung airways and bronchi are comprised of smooth muscle, submucosa, mucosa, connective tissue made of collagen, a subepithelial basement membrane and epithelium. Among other things, the COPD disease progresses to allow enzymes to dissolve bronchi, airway components and complete airways. The disease also destroys elastin in tissue that survives the enzymatic bulk reduction of airways and lung tissue. Late stage Emphysema patient lungs are compromised to the point that these patients commonly communicate gases through paths or passageways that are largely without airways. In these areas of damaged tissue, large portions of parenchyma are often loose or missing, forming coalesced blebs and bullae. Thus, normal lung passageways with supportive walls are typically not available, and any existing tissue is sponge-like. These pulmonary treatment devices and methods consider the vast tissue damage of advanced COPD sufferers and are designed specifically to treat these patients. It may be appreciated that although the previously described pulmonary treatment devices rely primarily on linear or curvilinear pulling and pushing of lung tissue to treat the lung, particular embodiments may also be used to apply torque to the lung tissue in such treatment.

Figures 59A, 59B:
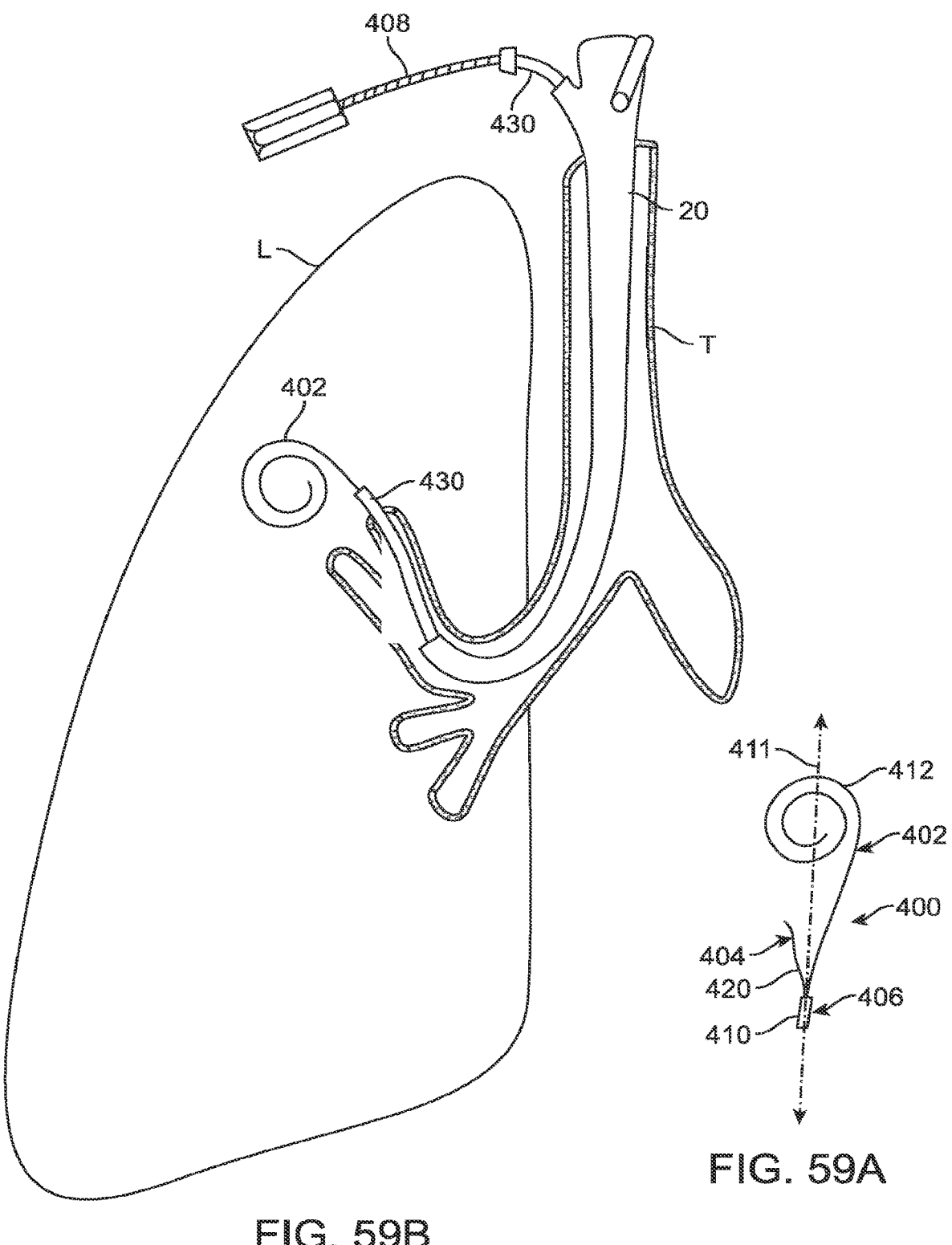
FIG. 59A illustrates the treatment device in a non-stressed configuration
FIG. 59B illustrates the treatment device and delivery system in a lung with the treatment device partially deployed in the lung

FIG. 59A illustrates an example of a torque-based pulmonary treatment device 400 and FIG. 59B illustrates the treatment device 400 deployed into a lung L. Referring to FIG. 59A, in this embodiment the device 400 comprises a tissue gathering element 402 and an anchoring element 404, both of which join with an attachment end 406. The attachment end 406 may be used to attach a delivery device thereto, such as a torqueing tool 408. Thus, the attachment end 406 typically has a non-round cross-section shape, such as a square, rectangular, polygonal or oval shape, to assist in maintaining rotational torque coupling and torque transmission during rotational or torqueing motion of the torqueing tool 408. It may be appreciated that in some embodiments the attachment end 406 is formed from portions of the tissue gathering element 402 and anchoring element 404 themselves, such the joining of their respective proximal ends. In other embodiments, the attachment end 406 includes an attachment element 410 to assist in joining the elements 402, 404 and forming a desired shape for attachment and torqueing. And yet in other embodiments, the attachment end 406 resides at the proximal end of the tissue gathering element 402 or the anchoring element 404 and the elements 402, 404 are joined to each other distally of the attachment end 406.

In this embodiment, the tissue gathering element 402 is comprised of a shaft 412 extending in a first direction from the attachment end 406 and then bending laterally outwardly in a second direction to form a circular, inwardly spiraled shape. The shaft 412 may reside in a single plane (e.g. x-y plane) or may pass through additional planes throughout the spiral shape (e.g. in the z direction) so that portions of the shaft 412 reside out of the x-y plane. Typically, the tissue gathering element 402 has a shape which is approximately 0.25 to 3 inches in diameter, preferably approximately 0.5 to 1.5 inches in diameter. In this embodiment, the shaft 412 is comprised of wire, such as metal (e.g. nitinol, austenite or martensite nitinol, spring steel, stainless steel, cobalt steel alloys, titanium etc.) or polymeric compounds, ceramic, carbon fiber and/or other biocompatible materials. Such wire is typically extruded, drawn or sintered into near net shapes or wire form shapes, wherein the wire has a constant diameter between 0.005 inches up to 0.200 inches but preferably round wire between 0.013 and 0.070 inches in diameter or ribbon wire that is 0.005 to 0.040 inches thick and 0.010 to 0.100 wide. The ribbon width or thickness may be different at the distal tissue gathering element 402 as compared to the proximal anchoring element 404. In some embodiments, the distal tissue gathering element 402 is made from ribbon that is 0.015 to 0.030 inches thick and 0.045 to 0.080 inches wide while the and the proximal anchoring element 404 is made from ribbon that is 0.010 to 0.030 inches thick and 0.010 to 0.030 wide. In some embodiments, the shaft 412 is comprised of a single wire and in other embodiments, the shaft 412 is comprised of more than one wire (such as twisted together) and/or includes additional features and/or elements to increase its diameter and/or increase its ability to gather lung tissue, as will be described in later sections. It may be appreciated that the one or more wires may have any suitable cross-sectional shape including round, oval, square, rectangular, etc. Further, the one or more wires may have a cross-sectional shape which changes along the length of the shaft 412. Likewise, the one or more wires may be made from tapered wire or wire that varies in diameter at different locations along the tissue gathering element 402. It may be appreciated that the tissue gathering element 402 may be comprised of any combination of these materials and geometries. In other embodiments, the shaft 412 includes additional features and/or elements to increase its diameter and/or increase its ability to gather lung L tissue, as will be described in later sections.

In this embodiment, the anchoring element 404 is comprised of a shaft 412 which extends from the attachment end 406, as shown in FIG. 59A, in the same direction as the tissue gathering element 402, generally along a longitudinal axis 411. In this embodiment, the shaft 420 of the anchoring element 404 bows outwardly, away from the longitudinal axis 411 and tissue gathering element 404, such as to form the shape of a bifurcation. This bifurcation typically mimics the bifurcations found in the airway network branches from the trachea through the various portions of the lung L. In some embodiments, this aspect allows the anchoring element 404 to anchor the device 400 in the lung anatomy.

Referring to FIG. 59B, the treatment device 400 is sized and configured to be delivered through a delivery device which is insertable into the lung L, such as a steerable scope (e.g. bronchoscope 20). In this embodiment, the device 400 is loaded within a catheter 430 or similar delivery device which is advanceable through a lumen in the bronchoscope 20. During such advancement, the device 400 is constrained within the catheter 430 to allow for ease of movement. In this embodiment, such constraint is achieved by retraction of the device 400 of FIG. 59A into a lumen in the catheter 430 so that the anchoring element 404 and tissue gathering element 402 are drawn together and the tissue gathering element 402 is uncoiled and straightened. The device 400 remains within the catheter 430 until the distal tip of the catheter 430 is desirably positioned within the lung L.

In some embodiments, the distal tip of the catheter 430 is advanced beyond the distal tip of the bronchoscope 20. This allows the catheter 430 to reach locations that are beyond the reach of the bronchoscope 20 due to size constraints (i.e. the smaller diameter of the catheter 430 can pass through small diameter or contorted passageways that the larger diameter bronchoscope is restricted from entering). Thus, in some instances, the catheter 430 is able to reach far distal portions of the lung L, such as the apical portions of the upper lobes and the lateral corners of the lower lobes, which are typically unreachable by the bronchoscope alone.

In some embodiments, the catheter 430 is advanced with the use of a guidewire. This may be within an airway or beyond the natural airways into damaged tissue, parenchyma, alveoli, artificially created passageways or other types of lung tissue. In such instances, the device 400 is not pre-loaded into the catheter 430, rather the device 400 is inserted at a later time once the catheter 430 is desirably positioned. This is because the guidewire typically fills the catheter lumen. The guidewire fills the catheter lumen so as to minimize digging of the catheter leading edge into tissue during advancement and to provide a flexible, blunt, atraumatic tip. The guidewire then acts as a rail or support shaft to further advance the catheter 430. Alternating advancement of the guidewire and catheter in blood vessels is known as the Seldinger Wire Technique. In some embodiments, the guidewire and catheter 430 are advanced within the lung using a modified Seldinger Wire Technique. It may be appreciated that when using a guidewire, the delivery system components may be configured to be delivered Over-The-Wire (OTW) or Rapid Exchange (RX). In an OTW design, the guidewire exits the delivery system at its proximal end so that the guidewire that tracks along the full length of the delivery device. In contrast, in the RX design, the guidewire exits the delivery system at a side port. Thus, the guidewire only tracks along a short section (about 25 cm) of the delivery device and then exists at the side port. This design saves time compared with advancing a guidewire through the full length of the delivery device.

It may be appreciated that the guidewire is configured to be compatible with advancement within lung tissue, particularly to contact lung tissue with minimal or no incident or injury. In some embodiments, the guidewire is comprised of a wire cable, wire bundles, continuous braid, twisted wire, or twisted wire bundle shaft structure with blunt tip (typically formed by crimping, gluing or welding the tip of the guidewire shaft structure). In some embodiments, the guidewire has a diameter in a range of 0.005 to 0.100 inches, preferably in a range of 0.018 to 0.070 inches. Typically, the guidewire fills the catheter lumen in a way that presents no gaps or very minimal gapping while the guidewire is curved or bent during delivery. In some embodiments, the guidewire is configured so that no portion of the guidewire which contacts tissue creates a gap which opens more than 0.030 inches, preferably in a range of 0 and 0.020 inches during bending around a radius that is 0.5 inches or smaller, to minimize catching tissue in the gaps. This is in contrast to conventional vascular guidewires made with a central core wire and a coiled spring outer jacket. When such vascular guidewires are used in the lung, the adjacent coils in the coil spring jacket tend to separate more than 0.030 inches which creates gaps that allow lung tissue to intrude and be caught during bending through lung passageways. Thus, when the vascular guidewire is retracted, the pulling/withdrawing motion straightens the wire and closes the gaps more than 0.001 inches smaller which causes the lung tissue to be pinched or caught in the coil spring jacket. Such outcomes are avoided with the specially configured guidewire embodiments described herein.

Once the distal tip of the catheter 430 is positioned near a target location for placement of the treatment device 400, the device 400 is deployed. If a guidewire was used, the guidewire is removed and the device 400 is inserted and advanced through the catheter 430 using a pusher, cable, or link, such as torqueing tool 408. In some embodiments, the torqueing tool 408 is attachable to the device 400 near the attachment end 406, and in other embodiments the torqueing tool 408 is attachable at a location between the tissue gathering element 402 and the attachment end 406.

Deployment from the catheter 430 may be achieved by a variety of methods or a combination of multiple methods. In some embodiments, the device 400 is self-expanding. In such instances, the catheter 430 may be retracted to expose the device 400. Once exposed, the device 400 self-expands, tending toward its pre-formed or natural configuration. Alternatively, the device 400 may be advanced beyond the distal tip of the catheter 430 allowing self-expansion, again due to release of tension or compression. In either case, the self-expanding device 400 is recovered to a programmed or pre-bent curved shape. When the device 400 is comprised of nitinol, the super-elastic or pseudo-elastic properties of nitinol force the curved shape to recover. When the device 400 is comprised of a memory shape alloy, the heat energy provided by the body temperature of the patient causes the device 400 to resume a pre-programmed curved shape. In other embodiments, the device 400 is not self-expanding. For example, in some embodiments the tissue gathering element 402 is bent into a deployed shape within the lung L by the user or the tissue gathering element is actuated into a deployed shape by use of a mechanical mechanism, such as a mechanism that bows the tissue gathering element 402 (e.g. by retracting a suture that is attached to the distal most tip of the tissue gathering element 402).

Deployment allows the distal tip of the tissue gathering element 402 to engage the surrounding tissue, curving through and/or against the tissue. Such deployment may be in an airway or beyond the natural airways into damaged tissue, parenchyma, alveoli, artificially created passageways, disease created passageways or other types of lung tissue. It may be appreciated that the distal tip of the tissue gathering element 402 may be sharp or blunt, including a ball tip or other shapes. The ability to pierce the tissue may be due to a combination of factors, including tissue type, tissue condition and tip shape, to name a few. Thus, in some embodiments, the tissue gathering element 402 pierces through lung tissue during deployment from the catheter 430 and in other embodiments the tissue gathering element 402 deploys within the tissue without piercing. And, in some embodiments, the tissue gathering element 402 pierces some tissue and not other tissue. In any case, the deployed tissue gathering element 402 has an expanded configuration within the lung L.

Figure 60:
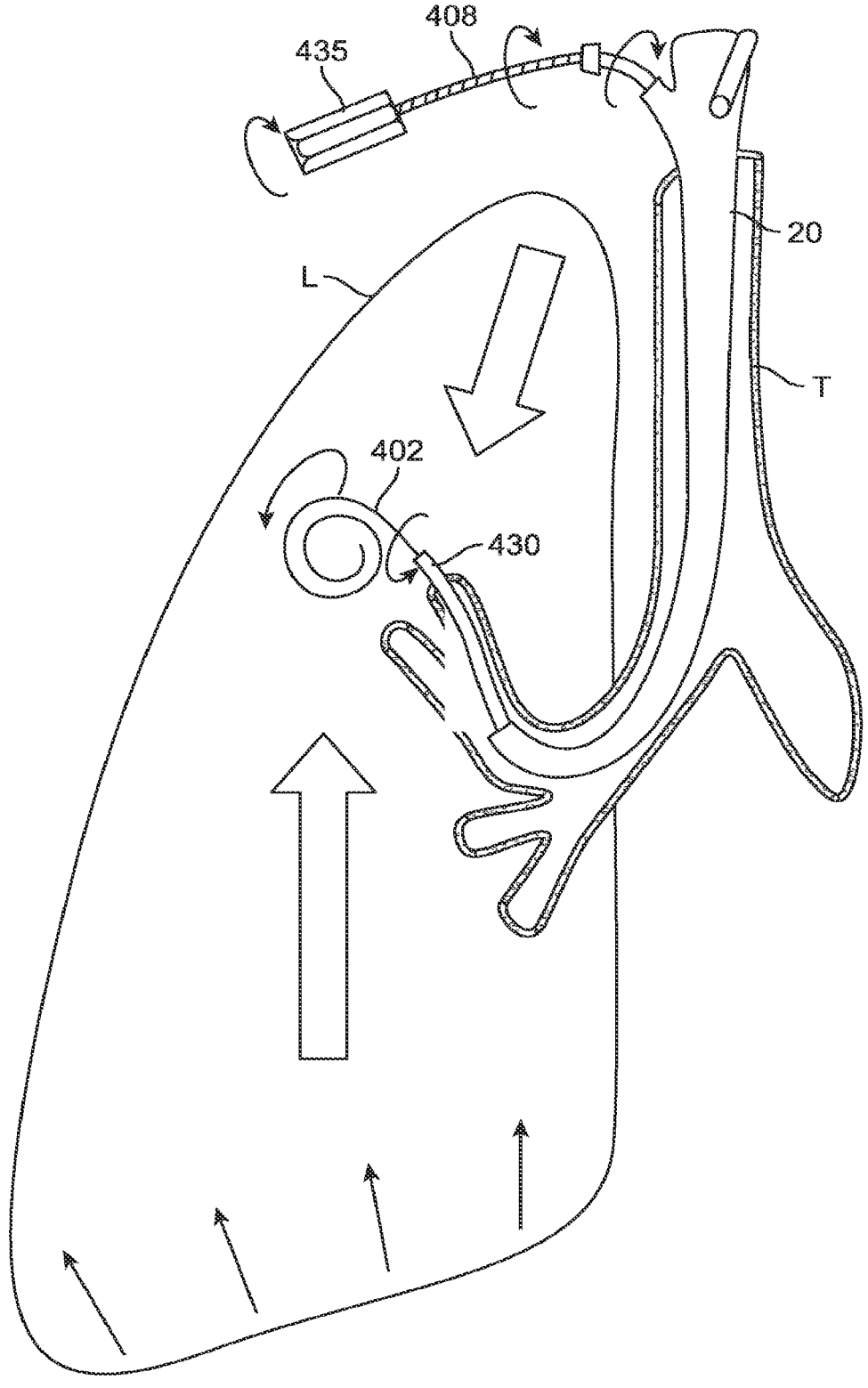
FIG. 60 illustrates a treatment device and delivery system whereas the treatment device is partially deployed in the lung and the tissue gathering end of the treatment device is being rotated to apply torque to lung tissue to tension the lung tissue

The device 400 is then rotated, as illustrated in FIG. 60. Rotation is achieved by applying torqueing, twisting or rotational force to at least a portion of the device 400 with the use of the torqueing tool 408 or other such device. In some embodiments, the torqueing tool 408 includes a handle 435 which is graspable by a user so as to manually applying the rotational force. Since the torqueing tool 408 is attached to the device 400, the device 400 (and therefore tissue gathering element 402) rotates as well. The arrows indicating rotation of the proximal and distal end of the torqueing tool 408 in FIG. 60 indicate that the torqueing tool 408 may be rotated both clock-wise or counter clock-wise directions. This gathers up the surrounding lung tissue onto and around the tissue gathering element 402 as the element 402 rotates, such as like twisting a fork in spaghetti to gather the spaghetti onto the fork. Thus, loose parenchyma, portions of blebs and bullae, damaged alveolar sacs and other distended, slackened or stretched tissue is pulled inwardly, twisted and/or gathered up by the tissue gathering element 402. Rotation continues, gathering the loose, slackened tissue, until tension is achieved in the tissue. With each additional rotation, the lung tissue will be increasingly strained or tensioned. Likewise, the diameter of tissue that is spooled up around the tissue gathering element 402 will grow to further improve the effectiveness of the device 400. In some instances, as lung parenchyma is gathered around the tissue gathering element 402, it is compressed around the tissue gathering element 402 and/or compressed between layers of tissue that is wrapped around the tissue gathering element 402. It may be appreciated that the device 400 may be effective at gathering, tensioning or compressing lung tissue even if there is no compression of tissue or lung volume reduction that is performed within the center of the distal tissue gathering element 402 or within coils of a helix shape.

Recall, it is the inward pulling tension of the lung tissue that lifts the diaphragm and is balanced by the outward recoil pressure or outward pulling of the chest wall. The lung is suspended in an expanded state due to negative pressure or vacuum between the chest wall and the exterior lining of the lung. This vacuum keeps the lung expanded and pinned to the chest wall. Because the lungs are held in a generally expanded state, applying torque with the device 400 in the interior of the lung L stresses and tensions diseased lung tissue (restoring lung elastic resistance to elongation, commonly referred to as lung elastic recoil). This tension, throughout the lung, pulls radially outward on the airways to hold these airways open and the tension helps to allow air to be squeezed out of the lungs during the expiration breathing cycle. Thus, the tissue gathering element 402 is rotated until re-tensioning of the lung is achieved to mimic the natural, healthy state of the lung.

In some embodiments, the device 400 is rotationally rigid so that rotational force that is applied to by the torqueing tool 408 is transmitted directly to the lung tissue. However, in other embodiments, at least a portion of the device 400 is designed to be intentionally less torque transmissive. This allows the portion to twist more easily so as to store rotational energy within the structure of the device 400. In some embodiments, the proximal end of the device 400 is rotatable up to 1000 degrees more than the tissue gathering element 402, preferably up to 720 degrees more than the tissue gathering element 402. In some embodiments, the tissue gathering element 402 and/or other portions of the device 400 are torqued sufficiently to be distorted and strained in a way that stores elastic spring energy. By storing this potential elastic energy using torque forces (e.g. rotation and twisting), the resulting lung tissue tensioning and lung elastic recoil restoration effects may be prolonged because chronic tensioning force is maintained on the lung tissue even if continued effects from the disease allow the tissue to elongate over time. As the tissue elongates, portions of the device 400 may be allowed to incrementally recover a small amount over a time period of months or years in a rotational recovery or strain relaxing orientation. However, if sufficient elastic strain energy is stored in the device 400, some residual chronic tension and restoration of lung elastic recoil will be maintained throughout this period and possibly for the remainder of the patient's lifetime. Thus, the stored elastic strain energy in the device 400 enhances the acute and chronic benefits to the patient. For example, the stored elastic strain energy provides chronic tension that is maintained even if the lung tissue continues to degrade and elongate. Thus, the stored rotational strain energy continues to provide benefit to the patient over time as the patient progresses with complications relating to COPD, even as the lung tissue slowly elongates into the future. In some embodiments, this time period is up to 10 years or up to a lifetime, but even a period of 3 years is considered a very acceptable time period.

Figure 61:
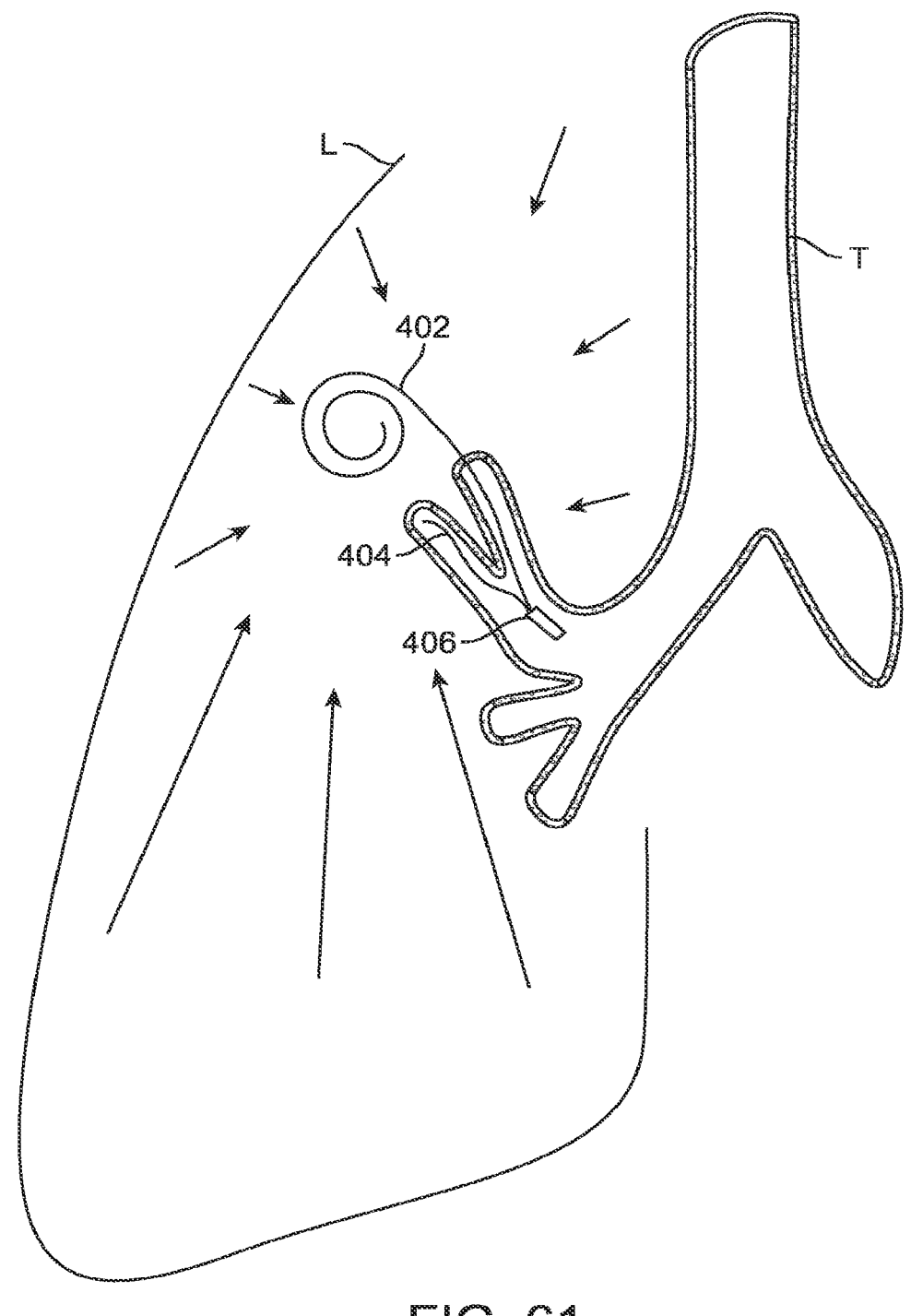
FIG. 61 illustrates the treatment device deployed in the lung after the tissue gathering end has been rotated to apply toque to tension lung tissue and the anchoring end has been deployed in another airway branch to maintain the torsion and lung tissue tension

Once the lung L is desirably re-tensioned, the device 400 is anchored to maintain the rotated arrangement. This is achieved by deployment of the anchoring element 404. In this embodiment, the anchoring element 404 is comprised of a shaft 420 which extends from the attachment end 406 in the same direction as the tissue gathering element 402, generally along a longitudinal axis 411. Thus, upon deployment, the shaft 420 of the anchoring element 420 bows outwardly, away from the longitudinal axis 411 and tissue gathering element 420, such as to form the shape of a bifurcation. The anchoring element 404 is then advanced into an adjacent or nearby airway, as illustrated in FIG. 61. In some embodiments, deployment is achieved by retracting the catheter 430 to expose the anchoring element 404, thereby allowing its deployment. Thus, the catheter 430 and device 400 are positioned so that such deployment of the anchoring element 404 is possible, such as in an airway, proximal to a bifurcation. This may involve pulling the proximal end of the device 400 in the proximal direction prior to deployment of the anchoring element 404. Likewise, in some embodiments, the device 400 is rotated an additional amount so that the anchoring element 404 is aligned with the direction that the bifurcation branches off. Visualization may be achieved with a variety of methods, including fluoroscopy and/or imaging through the bronchoscope camera. Once desirably positioned, the anchoring element 404 is deployed and advanced into an airway. For example, the tissue gathering element 402 resides in a first airway while the anchoring element is deployed and advanced into a second airway, adjacent or nearby the first airway. The rigidity and robustness of the airways minimizes or prevents rotation or unwinding of the device 400. This is maintained even after the torqueing tool 408 is removed.

The torque that is applied to the lung tissue is a function of the diameter of the distal tissue gathering element 402 or the width of any shape that is used as the tissue gathering element 402. If the tissue gathering element 402 is less than 0.5 inches wide or in diameter, a range of 0 to 2.0 inch-pounds of torque will be typically applied. If the width or diameter is greater than 0.5 inches, a range of torque between 0.3 and 3.0 inch-pounds is typically applied. It is advantageous that any loss of stored energy due to relaxation of the lung tissue after removing the torqueing tool 408 will be stored in the lung tissue through counter rotation and contact between the anchoring element 404 and the adjacent airway or other lung parenchyma or lung structure that the anchoring element 404 has been deployed into. As an example, if the torqueing tool 408, tissue gathering end 402, remainder of device 400 and the catheter is rotated 180 degrees in a clockwise direction to apply 1.0 inch ounce of torque to the distal tissue gathering element 402, while the remaining portion of the device 400 is still inside the catheter 430, the torque may be communicated to tissue effectively through portions of the tissue gathering element 402 bearing on the tissue and the tissue may present resistance and a propensity to unwind the device 400 with an equal amount of torque in the opposite counter clockwise direction. This unwinding may happen if the torqueing tool 408 were to be uncoupled and removed. To counter this, the anchoring element 404 is deployed and coupled to tissue to prevent this from happening in a gross way. However, after deploying the anchoring element 404, it is simply wedged against the tissue to hold the device fixed with respect to the airway or lung tissue it has been deployed into. The anchoring element 404 may not have been rotated to rotationally load the anchoring element 404 against the bifurcation branch or ostium it has been placed into to resist counter rotation of the device 400, as the torqueing tool 408 is removed. Also, the tissue may not have been conditioned to resist rotation such as being loaded in a rotated way to gather loose tissue to create rotational resistance. As such, removal of the torqueing tool 408 may allow up to 90 degrees of counter-rotation or unwinding of the entire device 400 in a counter clockwise direction until the anchoring element 404 rotationally loads the lung tissue it has been deployed into in this same counter clockwise direction. In this example, as much as 0.5 inch-pounds of torque may have been lost at the distal end when the tissue gathering element 404 was allowed to unwind 90 degrees in the counter clockwise direction. However, the tissue anchoring element 404 will be rotated 90 degrees in the counter clockwise direction which loads proximal lung tissue in a rotational direction which improves lung mechanics as previously described herein. The amount of rotational work energy that is potentially lost at the distal end of the device will be gained at the proximal end of the device, as the torqueing tool 408 is removed. It is possible that the 90 degrees that the tissue anchoring element 404 is counter rotated may apply as much as 0.5 inch-pounds of torque to tissue that is adjacent to the proximal end of the device 400 and adjacent to the anchoring element 404. The force rotational applied to tissue by the distal tissue gathering element 402 will be balanced by the forces that are applied by the anchoring element 404 to rotate the proximal lung tissue. The anchoring element 404 will be anchored into lung tissue that is structurally stiffer than the tissue that the tissue gathering element 402 will be anchored into because lung tissue that is closer to the trachea is normally reinforced by cartilage. As a result, the rotational torqueing loads that are applied to the tissue may be balanced but the angle of rotation experienced by the tissue may not be the same between the two regions of lung tissue.

It may be appreciated that the anchoring element 404 may be deployed to anchor the device 400 in many possible structures of the lung L to maintain the lung tension but it is often beneficial to deploy the anchoring element 404 in a bifurcation that can be accessed by a bronchoscope. This provides support to prevent the continued recovery of the tissue gathering element 402 from pulling the device into a more distal position, over time. By hooking the attachment end 406 of the device 400 around the carina of the airway bifurcation, there is strong support to keep the device 400 in a position to be later accessed, such as by using a bronchoscope, to remove the device 400 if the need arises. This is very advantageous to be nearly guaranteed that the implanted device 400 can be accessed with a bronchoscope, such with the use of a bronchoscope camera alone. This is in contrast to conventional lung volume reduction coils which tend to migrate so far distally that bronchoscopes, appropriately sized to guide recapture instrumentation, cannot be advanced far enough and cannot fit in the portion of the lung that the proximal coil eventually resides within.

In some instances, the device 400 is rotated further in the same direction that the torqueing tool 408 rotated the device 400 while the anchoring element 404 is being deployed from the bronchoscope 20 or delivery system catheter 430 or other delivery system component. If the anchoring element 404 is shaped in the form of a helix, removal of the constraining device, such as by retracting a catheter 430, in the proximal direction will drive rotation of device 400. The direction of spiral of the helix shape will dictate the direction that the device 400 will be rotated. Thus, the helix may be configured to add rotation and torque in the same direction that the torqueing tool 408 has been used to rotate device 400 further or the helix may be configured in the opposite direction to remove some rotation or torque to relieve some of the torque force during deployment of the anchoring element.

In some instances, the device 400 is pulled proximally (along its longitudinal axis) to further tension the lung tissue distal to the device 400 and/or to position the anchoring element 404 at a more proximal location. Thus, in some embodiments, the device 400 applies both radial re-tensioning within the lung and linear re-tensioning toward the trachea T. In some embodiments, the proximal pulling of the device 400 may be as much as 5 inches, but more preferably it will be 0.5 to 3 inches of linear proximal displacement. In these embodiments, the tissue gathering element 402 is strategically positioned within the lung L so that such pulling in the proximal direction is at least partially maintained after the anchoring element 404 is deployed so that the device 400 applies both radial re-tensioning within the lung and linear re-tensioning toward the trachea T.

Once desirably positioned and anchored, the device 400 is left in place as an implant. Thus, the torqueing tool 408 is detached from the attachment end 406 of the device 400 and withdrawn along with the catheter 430 and bronchoscope 20. Chronic tension is maintained on the tissue to restore lung elastic recoil. In some instances, the patient's COPD will progress and the device 400 may gradually unwind, releasing increments of stored energy, to maintain tensioning of the lung. And, in some advanced cases, the device 400 may ultimately fully untwist so that the device 400 has recovered to a zero-strain state due to continued elongation of tissue because of the progressive nature of the COPD disease. This can be easily detected, using common medical imaging techniques, by comparing the rotational position of the tissue gathering element 402 relative to the anchoring element 404 to determine if they are similar to an unconstrained device 400 before it is deployed in the patient. If the tissue has relaxed sufficiently that the twist in the device 400 has been substantially eliminated, additional devices 400 may be deployed to restore lung function back to the patient or the existing previously implanted device 400 may be accessed again with a torqueing system that can rotate the device 400 again to energize and restore the rotational strain back into the previously implanted device 400. Additionally, the anchoring element 404 may be pulled from its anchored position so rotation can be applied and then the anchoring element 404 may be advanced back into the same airway branch, a new airway branch or it may be anchored at another anatomical location in the lung to resist unwinding of the device 400.

Medical imaging techniques may be used to visualize device 400 delivery, the deployment of the device 400 from delivery system constraints, rotation or torqueing of device 400, deployment of the anchoring element 404, deployment of the tissue gathering element 402, decoupling of the torqueing tool 408 from the device 400, reattachment of the torqueing tool 408 to device 400, recapture of device 400 by attaching a recapture tool (e.g. a forceps instrument or suture or specialized recapture tool designed to couple to a feature of device 400), attaching a guide tool to device 400 to guide a catheter to be advanced to recapture device 400, to name a few. Likewise, other maneuvers may be used to visualize any of the measurable physiologic changes listed herein to improve breathing in COPD patients during the implantation procedure or after the procedure or in comparison to determine change in breathing function by comparing the physiologic difference in the patient as a result of placing one or more device 400 in the patient. Medical imaging may be used to assist in selecting a device 400 size before implantation and any other maneuver that would benefit from visualization while delivering device 400, recapturing device 400 or evaluating any of the outcome parameters. Medical imaging includes the use of all forms of equipment that allows for real time imaging, recording or computer processing that outputs an image of devices, organs or tissue within the human body without needing to expose the devices, organs or tissue to be visualized using a direct line of site by the human eye. These medical imaging techniques may typically benefit by the emission of low to high frequency electro-magnetic energy or sound energy which may include the use of one or more video cameras such as the ones bronchoscopes are equipped with, computed tomography, biplane imaging, fluoroscopy, ultrasound or standard planar x-ray machines.

Figures 62A, 62B, 62C, 62D:
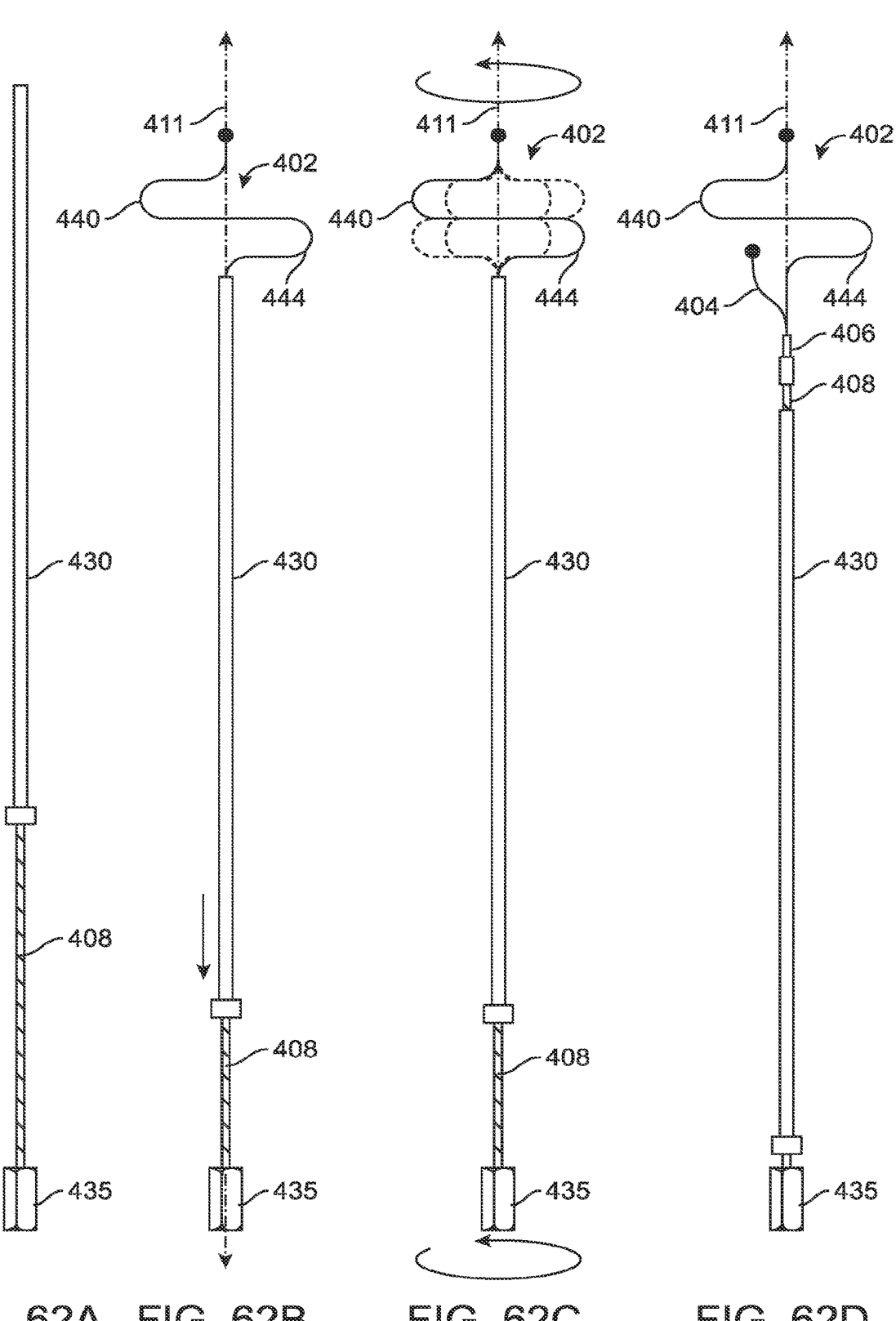
FIGS. 62A-62D illustrate the treatment device and delivery system with sequential deployment steps including rotation motions applied to the tissue gathering end and deployment of the anchoring end to maintain the tissue gathering, rotation and tensioning.

FIGS. 62A-62D additionally illustrate an embodiment of delivering a torque-based pulmonary treatment device 400. FIG. 62A illustrates the device 400 loaded within the catheter 430 which is advanceable through a lumen of a delivery device, such as a bronchoscope. Thus, the device 400 is constrained within the catheter 430 to allow for ease of movement. The anchoring element 404 and tissue gathering element 402 are drawn together and the tissue gathering element 402 is uncoiled and straightened. The device 400 remains within the catheter 430 until the distal tip of the catheter 430 is desirably positioned within the lung L. In this embodiment, the catheter 430 is then retracted, as illustrated in FIG. 62B, while the torqueing tool 408 remains in place. This exposes the tissue gathering element 402, allowing the element 402 to deploy. In this embodiment, the tissue gathering element 402 has a curved shape, particularly an S-shape, wherein a first wing 440 extends in a first direction (radially outwardly from a longitudinal axis 442 of the device 400 and joined torqueing tool 408) and a second wing 444 extends in a second direction (radially outwardly from the longitudinal axis 411). In this embodiment, the first and second directions are directly opposite to each other. However, it may be appreciated that the first and second directions may be at an angle to each other. Referring to FIG. 62C, the handle 435 is then twisted to rotate the tissue gathering element 402. This causes at least the wings 440, 444 to rotate around the longitudinal axis 411. This rotation draws the surrounding tissue toward the longitudinal axis 411, as the wings 440, 444 capture and pull the tissue. The tissue gathering element 402 is then anchored in place by deployment of the anchoring element 404, as illustrated in FIG. 62D. Here, the catheter 430 is further retracted exposing the more proximally positioned anchoring element 404 which curves or bows radially outwardly, away from the longitudinal axis 411. As mentioned, in some embodiments, additional torque is applied to the torqueing tool 408 in order to align the anchoring element 404 with an available airway branch so that the anchoring element 404 is advanceable into the airway branch so as to keep the device 400 from unwinding upon release of the torqueing tool 408. The torqueing tool 408 is then removed from the attachment end 406 and the device 400 is left behind.

A. Tissue Gathering Element

It may be appreciated that the tissue gathering element 402 may be comprised of a variety of materials, may take a variety of forms or shapes, and may include a variety of features.

In some embodiments, device 400 is formed from a single shaft (e.g. wire, cable, braid), wherein the shaft is curved or bent to form the tissue gathering element 402 and an anchoring element 404. In such embodiments, the attachment end 406 is created by a loop, bend, U shaped bend, coil or other feature of the shaft that allows for grasping or other mechanisms of attachment to a suitable delivery system. Examples of attachment include attachment to a pusher, grasper, forceps, suture, or catheter, to name a few.

FIGS. 63A-63C illustrate a variety of embodiments of torque-based pulmonary treatment devices 400. As illustrated, each device 400 includes at least one tissue gathering element 402 and at least one anchoring element 404 which meet at an attachment end 406. More than one tissue gathering elements 402 may be attached to a single device 400 to improve lung function. More than one anchoring element 404 may be attached to a single device 400 to improve lung function. It may also be appreciated that the embodiments illustrated in FIGS. 63A-63C may be formed from a single shaft to create the tissue gathering element 402 and anchoring element 404, as described above, or may be formed from multiple shafts, etc. It may also be appreciated that the tissue gathering elements 402 may include a distal tip 405, and the tip 405 is often not the distal-most portion of the tissue gathering element 402. For example, FIGS. 63A-63C illustrate devices 400 having tissue gathering elements 402 comprising a partial loop which curves radially outwardly from the longitudinal axis 411. In some embodiments, the loop extends such that the distal tip 405 is directed back toward the longitudinal axis 411 (e.g. FIG. 63A-63B). In other embodiments, the distal tip 405 is directed substantially parallel to the longitudinal axis 411 in the distal direction, such as extending around a full circle (e.g. FIG. 63C). In such embodiments, the tissue gathering element 402 may be described as having a radius R. As the radius R of the tissue gathering end is increased, the circumference of the loop is increased by a factor of $2\pi$ (i.e. $2 \times 3.1415$). Thus, increasing the size of the loop increases the volume of tissue that can be gathered, particularly by $\pi R^2$ (i.e. the area of a circle; the square of R times 3.1415). In some instances, it is desirable for the loop to extend as far as feasibly possible to create a maximum radius to increase effectiveness in gathering tissue. Such feasibility depends on a variety of factors, including shaft construction, loop design, and desired function, to name a few. In some instances, it is desired that the loop has increased torsional strength so as to more efficiently gather tissue.

In other embodiments, the tissue gathering element 402 may not be circular so the effective dimension may be described as having a width W. Looking at FIG. 63A, if the tissue gathering element 402 was not circular, what is shown as R would be described as W. Stated another way, W is the extreme maximum width of a non-circular tissue gathering element shape. As the width W of the tissue gathering element 402 is increased, the path length around the tissue gathering element 402 is increased by a factor of $2 \times W$ to describe the length of lung tissue that is pulled towards the longitudinal axis 411 by rotating the tissue gathering element 360 degrees. Thus, increasing the width W of the tissue gathering element 402 increases the length of tissue that can be gathered, particularly by 2 times the width W. In some instances, it is desirable for the tissue gathering element 402 width W to extend as far as feasibly possible to create a maximum width to increase effectiveness in gathering tissue. Such feasibility depends on a variety of factors, including shaft construction, tissue gathering element 402 design, and desired function, to name a few. In some instances, it is desired that the loop has increased torsional strength so as to more efficiently gather tissue. The tissue gathering width W may be produced in a range between 0.25 and 3 inches but a range between 0.5 and 1.0 inches is preferable. If ribbon is used to make the tissue gathering element 402, it's preferable to use ribbon between 0.005 and 0.030 inches thick if it's made from metallic material. The width of the ribbon is typically between 0.005 and 0.100 inches but preferably between 0.040 and 0.075 inches wide to withstand the torqueing forces and to resist deforming to such a degree that it no longer effectively gathers tissue.

Figure 64:
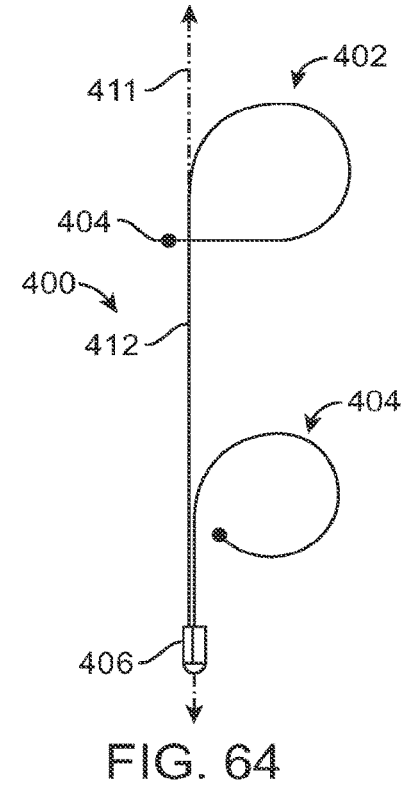
FIG. 64 illustrates an embodiment of a treatment device with a tissue gathering element that crosses over the longitudinal axis of the device.

In some embodiments, the loop shape is designed to increase strength during torsion. For example, in some embodiments, the loop has a "D" or "P" shape wherein the loop extends over the longitudinal axis 411, crossing the portion of the tissue gathering element 402 that extends along the longitudinal axis 411 (e.g. FIG. 64). By forming a shape in the shaft 412 that crosses over itself, the circular section of the "D" or "P" shape or other looping shape is stiffened to resist twist or torsional deformation. Stiffening is provided because the free end (distal tip 405) is stabilized at the crossing point, against the portion of the shaft that it crosses. These crossing points or points of contact may optionally be held together with a reinforcing element, such as a crimped tube connector, or they may be joined together, such as by brazing or welding (e.g. with an arc or using laser light or any combination), to geometrically stiffen the attachment end 406, the anchoring element 404 or the tissue gathering element 402.

When rotating the tissue gathering element 402 around the longitudinal axis 411 the direction of the cross-over, so that the tissue presses the shaft 412 against itself at the cross-over point, the cross-over resists deformation of the loop. By arresting the deformation in this way, the looped portion of the tissue gathering element 402 is made more effective to transmit torque or rotation energy directly to the tissue. When rotating the tissue gathering element 402 in the opposite direction, the tissue gathering element 402 will deform because the free distal tip 405 is not supported to prevent the deformation. In some instances, this may be beneficial because the deformation stores elastic strain energy in the device 400 that can continue to perform work on the lung L after the delivery system has been removed (like loading a spring and leaving it in the body to continue pulling on tissue).

It may be appreciated that the distal tip 405 may have a variety of forms. In some embodiments, the distal tip 405 is atraumatic and has a blunt shape, such as a ball or other rounded shape (e.g. FIG. 63A). In this configuration, the tissue gathering element 402 may be more inclined to track along the inside lumen of an airway if the airways are still preserved. However, in nearly all cases, they are not. If the distal tip includes a ball that is smaller than 0.060 inches diameter, it will still be capable of penetrating the wall of an airway to engage connective alveoli instead of manipulating airways alone. In other embodiments, the distal tip 405 has a sharp shape, configured to pierce and/or penetrate tissue (e.g. FIG. 63B). In other embodiments, the distal tip 405 has an anchoring shape, such as a fish-hook or other shape which is configured for piercing or penetrating tissue while resisting withdrawal from the tissue (FIG. 63C).

Figure 65:
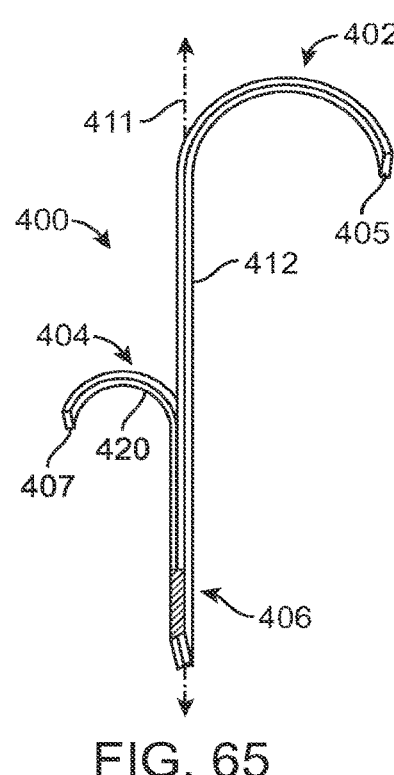
FIG. 65 illustrates an embodiment of a treatment device made from two ribbon strips that have been bonded together.

In some embodiments, the device 400 is made from round wire. It may be appreciated that in some embodiments the round wire has been flattened at the distal tip or any other portion of the tissue gathering element 402 to add bearing area. For example, FIG. 65 illustrates an embodiment of a device 400 formed from flattened wire. In this embodiment, the tissue gathering element 402 is formed from a shaft 412 and the anchoring element 404 is formed from a shaft 420, wherein the shafts 412, 420 are fixed together to form the attachment end 406. Each shaft 412, 420 has a flattened, broader surface, such as a ribbon, wherein the flattened surfaces are mated so as to increase contact for fixing to each other. Fixing the elements together may be accomplished by welding, gluing, thermally friction bonding, crimping, locking together using puzzle lock patterns, locking extrusion sections within each other, wrapping with a spring, riveting, locking together with threaded fasteners, by joining using locking hardware that is known in the art. In some embodiments, the flattened or broader surface is arranged to be perpendicular to the direction the shaft 412 contacts tissue to prevent the tissue gathering element 402 from cutting or migrating through tissue over time. Thus, the flattened or broader surface serves as the bearing area. In some instances, this is particularly useful along curved portions of the tissue gathering element 402 so as to prevent the curved portion of the tissue gathering element 402 from cutting or migrating through tissue over time.

Figure 66:
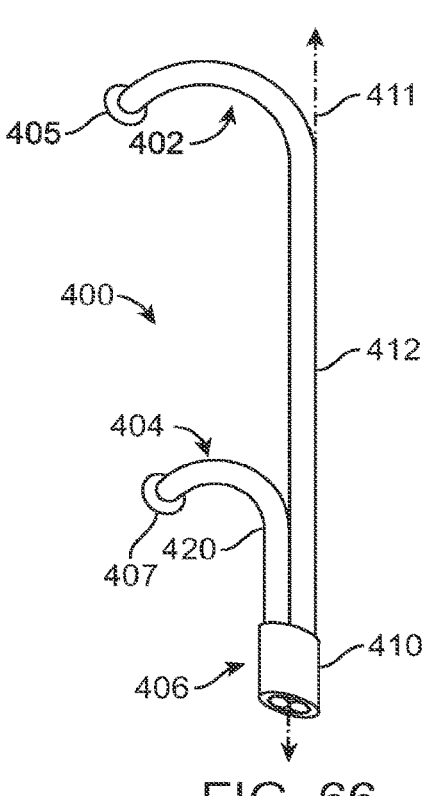
FIG. 66 illustrates an embodiment of a treatment device that has been crimped together.

FIG. 66 illustrates an embodiment of a device 400 formed from oval wire. In this embodiment, the tissue gathering element 402 is formed from a shaft 412 and the anchoring element 404 is formed from a shaft 420, wherein the shafts 412, 420 are fixed together with the use of an attachment element 410. The attachment element 410 assists in joining the shafts 412, 420 and forming a desired shape for attachment and torqueing. In this embodiment, the broader side of the oval wire is arranged to be perpendicular to the direction the shaft 412 contacts tissue to prevent the tissue gathering element 402 from cutting or migrating through tissue over time.

FIGS. 65-66 also illustrate tissue gathering elements 402 having a shape which is more similar to an arc or arch than a loop. In FIG. 65, the shaft 412 bends radially outwardly from the longitudinal axis 411 to form a curved arch wherein the distal tip 405 is parallel to the longitudinal axis 411 facing the proximal direction. In FIG. 66, the shaft 412 bends radially outwardly from the longitudinal axis 411 to form a curved arc wherein the distal tip 405 parallel to the longitudinal axis 411 facing the radially outwardly from the longitudinal axis 411.

Figure 67:
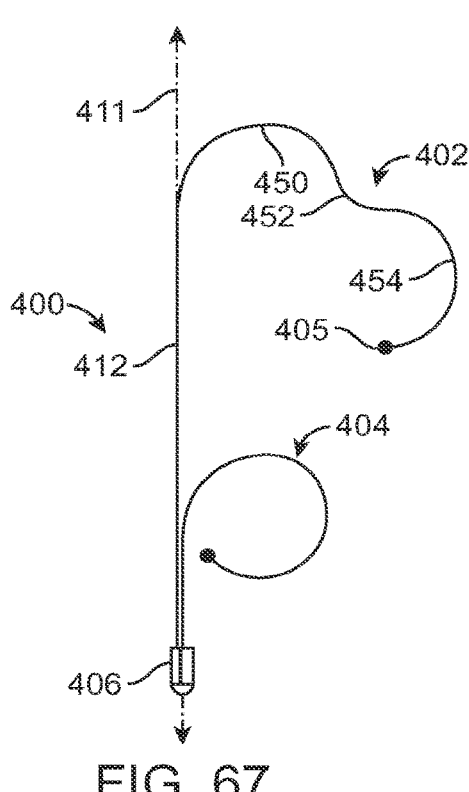
FIG. 67 illustrates an embodiment of a treatment device with a curvilinear tissue gathering element.

It may be appreciated that the tissue gathering element 402 may have irregular shapes or compound curvatures. For example, FIG. 67 illustrates a tissue gathering element 402 having a shape formed by the shaft 412 curving radially outwardly from the longitudinal axis 411 and forming a first curvature 450, a second curvature 452 and then a third curvature 454. The first curvature 450 has an arc shape which then transitions into an inverse arc shape for the second curvature 452. This then transitions into a semi-circle or arch shape which directs the distal tip 405 toward the longitudinal axis 411. This compound curvature (combination of curvatures 450, 452, 454) creates a hook shape which may be particularly beneficial for gathering tissue in both a twisting fashion and a pulling fashion. The partial loop shape extending radially outwardly from the longitudinal axis 411 assists in gathering tissue during torqueing, as described above. And, the hooking shape (distal tip 405 facing the longitudinal axis 411) assists in holding the tissue when pulling the device 400 in the proximal direction, such as along the longitudinal axis 411.

Figures 68, 69, 70A, 70B:
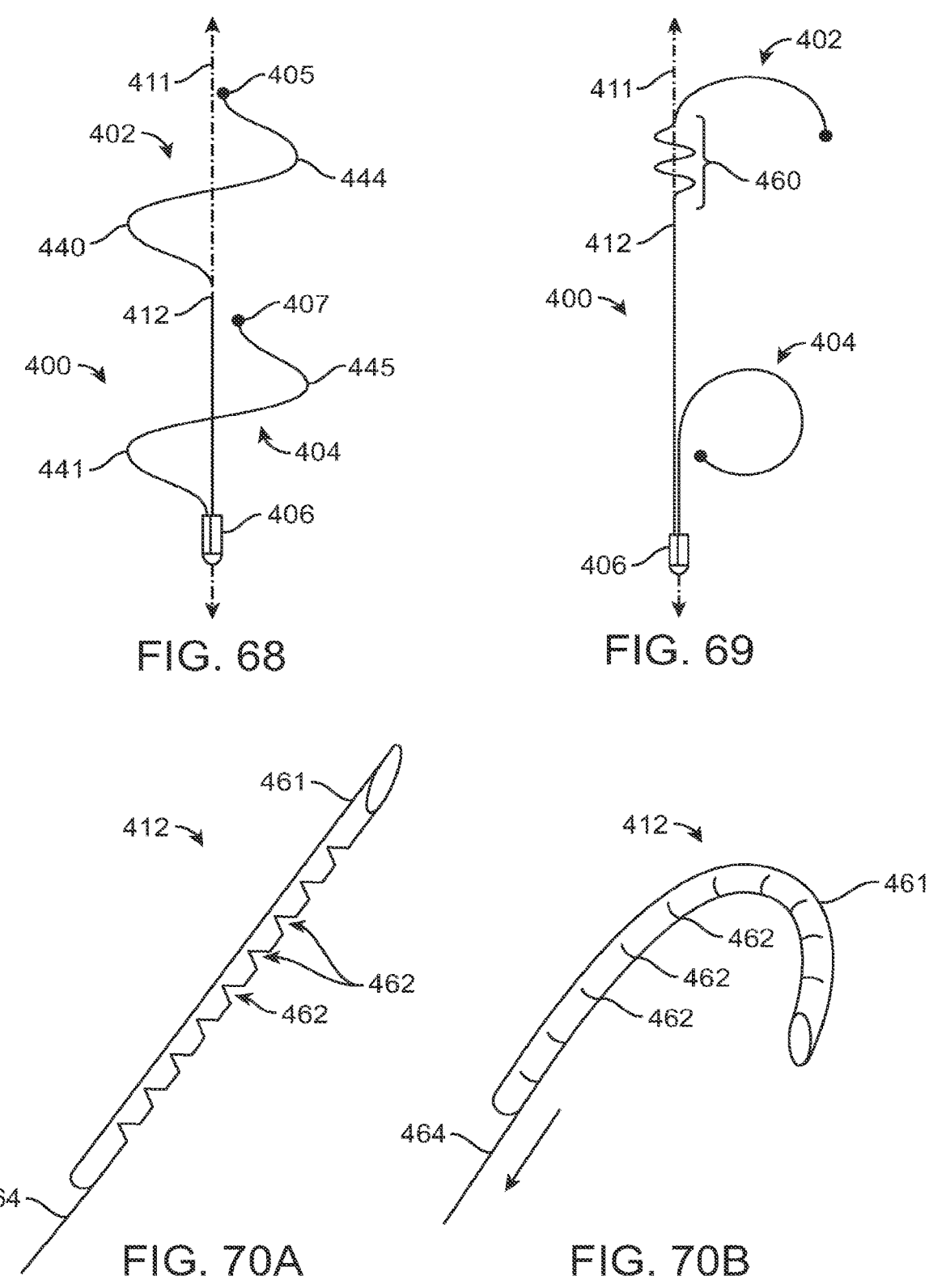
FIG. 68 illustrates an embodiment of a treatment device with matching tissue gathering and anchoring elements.
FIG. 69 illustrates an embodiment of a treatment device with strain relief sections that store energy during deployment.
FIGS. 70A-70B illustrates an embodiment of a treatment device comprised of a tube having slots or cuts along at least a portion of its length to increase bearing area against tissue.

It may also be appreciated that the tissue gathering element 402 may have a variety of other shapes, including bends and arcs which are rounded or angular, in the same direction or opposite directions, and in a variety of configurations. FIG. 68 illustrates a tissue gathering element 402 similar to that illustrated in FIGS. 62A-62D. In this embodiment, the tissue gathering element 402 has a curved shape, particularly an S-shape, wherein a first wing 440 extends in a first direction (radially outwardly from a longitudinal axis 411) and a second wing 444 extends in a second direction (radially outwardly from the longitudinal axis 411). In this embodiment, the first and second directions are directly opposite to each other. However, it may be appreciated that the first and second directions may be at an angle to each other. In addition, this embodiment illustrates the distal tip 405 aligned with the longitudinal axis 411, particularly facing in the distal direction.

It may be appreciated that the shaft 412 may include various additional bends or curvatures to provide particular features. For example, FIG. 69 illustrates an embodiment wherein the shaft 412 is configured to provide strain relief. Here, the shaft 412 has one or more bends, switchbacks or wings in succession configured to act as a strain relief while manipulating the device 400. In this embodiment, the strain relief portion 460 is disposed proximal to the tissue gathering end 404. Thus, pulling in the proximal direction, such as along the longitudinal axis 411, would expand the strain relief portion 460 leaving the tissue gathering end 404 in position. This may be desired in situations wherein it is preferred to maintain position of the tissue gathering end 404 when pulling the attachment end 406, such as when positioning the anchoring element 404.

It may be appreciated the shaft 412 of the tissue gathering end 404 may vary in terms of construction and materials so as to provide various features. In some embodiments, as illustrated in FIGS. 70A-70B, the shaft 412 is comprised of a tube 461 having slots or cuts 462 along at least a portion of its length. Such cuts 462 may be fabricated by laser cutting of the tube 461. In addition, a pull cord 464 is positioned within or along the tube 461 extending distal to the cuts 462. The cuts 462 are aligned along the tube 461 so as to allow flexibility of the tube 461 while the pull cord 464 is slack (FIG. 70A), and to allow curvature along a predetermined arc or arch when the pull cord 464 is pulled (FIG. 70B). Such pulling closes the slots or cuts 462, holding the shaft 412 in the curved formation. This construction provides increased torque strength and allows the tissue gathering end 404 to transmit higher levels of torque. It may be appreciated that although the shaft 412 is illustrated with a needle tip, any suitable tip shape may be used.

In other embodiments, the shaft 412 is comprised of a twisted pair of wires or a combination of more than 2 wires. In other embodiments, the shaft may be pressure cast or made from powder metal to form a near net shape that varies in dimension along its length. Near net shapes are limited only to the shape of a mold that is used to forge the powder metal together to form a high performance metalized composite material of nearly any shape. In another embodiment, the shaft 412 is made from a twisted pair of wires, the preferable direction of rotation that the user should use to rotate the tissue gathering element 402 within the lung is the same direction that was used to produce the twist in the twisted pair of wires. This same direction will further tighten the twist to maintain a reasonably small diameter of the tissue gathering element 402. This will also transmit the greatest amount of torque through the delivery system and the device 400 to the tissue. This is the direction that will transmit the maximum torque force to the lung tissue.

Figures 71A, 71B, 71C, 72, 73, 74:
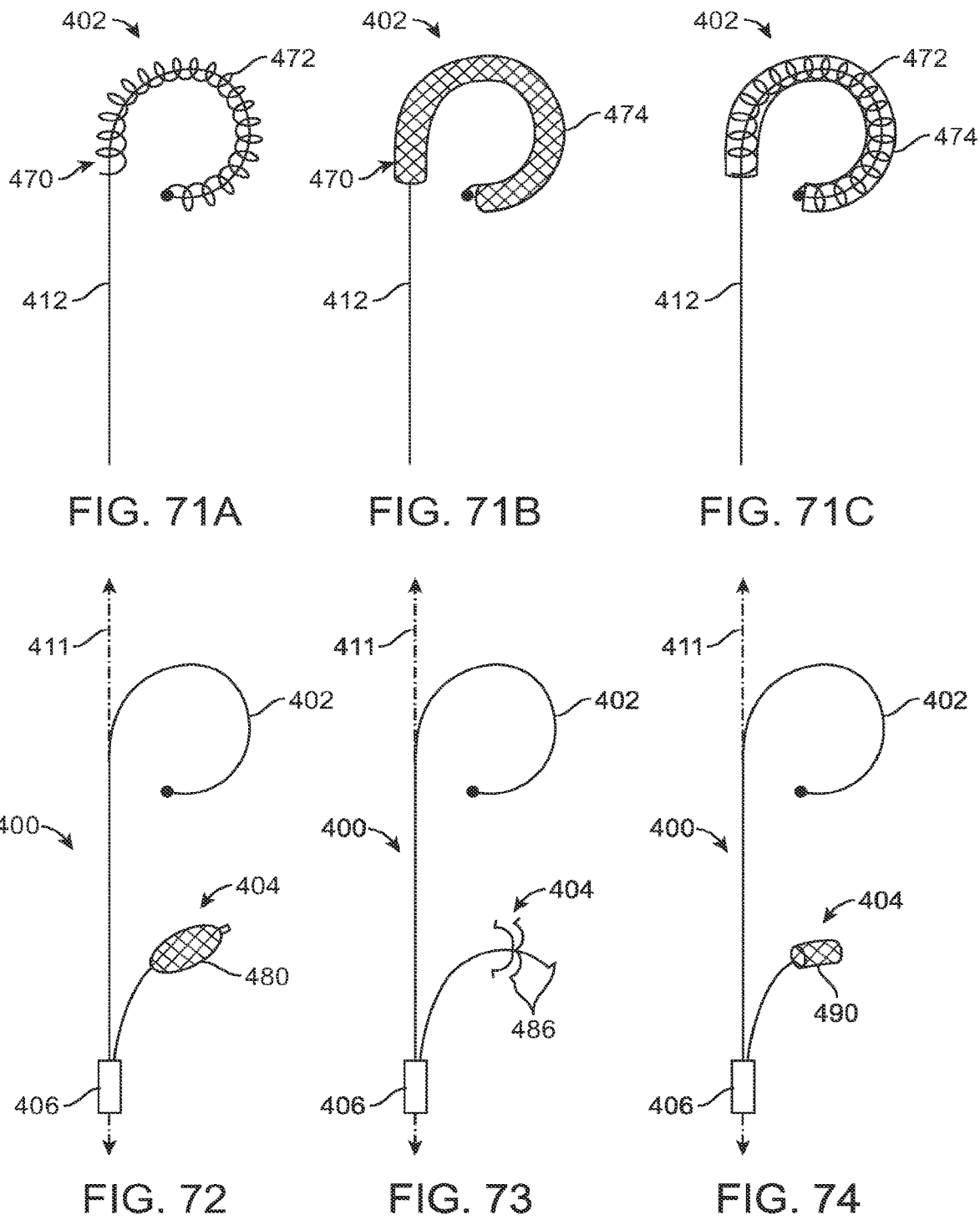
FIG. 71A-71C illustrates alternative designs to increase device bearing area on tissue.
FIG. 72 illustrates an embodiment of a treatment device with a expandable anchoring element design.
FIG. 73 illustrates an embodiment of a treatment device with hooks as anchoring elements.
FIG. 74 illustrates an embodiment of a treatment device with a stent as an anchoring element.

In some embodiments, the tissue gathering element 402 comprises a jacket which extends over at least a portion of the shaft 412 so as to increase gripping of the lung tissue and reduce cutting through lung tissue (i.e. "cheese wiring"). FIGS. 71A-71C illustrate example embodiments of jackets 470. FIG. 71A illustrates a jacket 470 comprising a coil 472 which extends over a portion of the shaft 412 to increase bearing area on the tissue. In some embodiments, the coil 472 comprises a spring coil that is tight wound to grip the shaft 412. In some embodiments, gaps between coil turns are spaced between 0.003 and 0.100 inches so as to increase friction between the tissue gathering element 402 and the tissue, therefore enhancing tissue gathering. In some embodiments, a suitable coil 472 outer diameter would be larger than 0.018" and smaller than 0.130" to be suitable to fit in a typical bronchoscope. FIG. 71B illustrates a jacket 470 comprising a flexible sleeve 474. In some embodiments, the flexible sleeve 474 comprises a woven material, such as Dacron or polyester. In other embodiments, the flexible sleeve 474 comprises a braided tube. In either case, the flexible sleeve 474 increases bearing area on the tissue and increases friction or gripping. In other embodiments, the flexible sleeve 474 comprises silicone. In other embodiments, the flexible sleeve 474 comprises shrink fit tubing. FIG. 71C illustrates a jacket 470 comprising a combination of a coil 472 and a sleeve 474. In this embodiment, the coil 472 extends over the shaft 412 and the sleeve 474 extends over the coil 472. Thus, the jacket 470 may be comprised of a coil 472 having shrink fit tubing thereover.

In some embodiments, the distal tip of the tissue gathering element 402 comprises a balloon expandable or self-expanding stent structure that grips an airway wall or that grips to lung tissue as the stent is dilated to minimize the distal tip from being pulled out of the tissue as the device 400 is rotated, to further increase the effectiveness of the tissue gathering.

B. Anchoring Element

It may be appreciated that the anchoring element 404 may be comprised of a variety of materials, may take a variety of forms or shapes, and may include a variety of features.

As mentioned previously, in some embodiments, the device 400 is formed from a single shaft (e.g. wire, ribbon, cable, braid), wherein the shaft is curved or bent to form the tissue gathering element 402 and the anchoring element 404. In such embodiments, the attachment end 406 is created by a loop, bend, U shaped bend, coil or other feature of the shaft that allows for grasping or other mechanisms of attachment to a suitable delivery system. Examples of attachment include attachment to a pusher, grasper, forceps, suture, or catheter, to name a few.

As mentioned previously, FIGS. 63A-63C illustrate a variety of embodiments of torque-based pulmonary treatment devices 400. As illustrated, each device 400 includes a tissue gathering element 402 and an anchoring element 404 which meet at an attachment end 406. It may be appreciated that the embodiments illustrated in FIGS. 63A-63C may be formed from a single shaft to create the tissue gathering element 402 and anchoring element 404 or may be formed from multiple shafts, etc. As shown in these embodiments, the anchoring element 404 is typically comprised of a shaft 420 which extends from the attachment end 406 in the same direction as the tissue gathering element 402, generally along a longitudinal axis 411. Thus, upon deployment, the shaft 420 of the anchoring element 420 bows outwardly, away from the longitudinal axis 411 and tissue gathering element 420, such as to form the shape of a bifurcation. The anchoring element 404 is then advanced into an adjacent or nearby airway to anchor the device 400.

FIG. 63A illustrates an anchoring element 404 comprising a loop which curves radially outwardly from the longitudinal axis 411. In some embodiments, the loop extends such that its distal tip 407 is directed back toward the longitudinal axis 411. In some embodiments, the distal tip 405 is directed so that the loop extends substantially around a full circle. In such embodiments, the anchoring element 404 may be described as having a radius R. Increasing R increases the moment on fixing the proximal end of the device 400. Torque resistance=R×F (friction in the tissue). By increasing R, less friction is needed to hold the device 400 from counter rotating. Some embodiments may include barbs or hooks that penetrate the airway wall and increase the R dimension to reinforce anchoring and resistance to counter rotating with respect to the torqueing force that had been applied to the tissue gathering element 402 and tissue.

FIG. 63B illustrates an anchoring element 404 which bows radially outwardly away from the longitudinal axis 411 and then curves back toward the longitudinal axis 411 and extends along the longitudinal axis 411 in the distal direction. In this embodiment, the proximal end of the tissue gathering element 402 similarly bows radially outwardly from the longitudinal axis 411, substantially symmetrical to the anchoring element 404.

FIG. 63C illustrates a plurality of anchoring elements 404 on a single device 400. In this embodiment, three anchoring elements 404 extend from the attachment end 406, however any number may be present including one, two, three, four, five, or more. In this embodiment, each anchoring element 404 extends in a different radial direction from the longitudinal axis. This provides the user with a variety of options when anchoring the device 400. In particular, the anchoring element 404 most suitably positioned for anchoring within the particular anatomy may be used to anchor the device 400. Or, more than one anchoring element 404 may be used in the same or differing airways for additional anchoring support.

It may be appreciated that in some embodiments, such as illustrated in FIGS. 65-66, the anchoring element 404 has a shape which is more similar to an arc or arch than a loop. In FIG. 65, the shaft 420 bends radially outwardly from the longitudinal axis 411 to form a curved arch wherein the distal tip 407 is parallel to the longitudinal axis 411 facing the proximal direction. In FIG. 66, the shaft 420 bends radially outwardly from the longitudinal axis 411 to form a curved arc wherein the distal tip 407 parallel to the longitudinal axis 411 facing the radially outwardly from the longitudinal axis 411.

It may also be appreciated that the anchoring element 404 may have a variety of other shapes, including bends and arcs which are rounded or angular, in the same direction or opposite directions, and in a variety of configurations. FIG. 68 illustrates an anchoring element 404 having a curved shape, particularly an S-shape, wherein a first wing 441 extends in a first direction (radially outwardly from a longitudinal axis 411) and a second wing 445 extends in a second direction (radially outwardly from the longitudinal axis 411). In this embodiment, the first and second directions are directly opposite to each other. However, it may be appreciated that the first and second directions may be at an angle to each other. In addition, this embodiment illustrates the distal tip 407 aligned with the longitudinal axis 411, particularly facing in the distal direction.

It may be appreciated that in any of the embodiments, the tissue gathering element 402 and anchoring element 404 may extend radially outwardly from the longitudinal axis 411 in the same or different directions. Likewise, it may be appreciated that in any of the embodiments, the tissue gathering element 402 and anchoring element 404 may have the same or similar shapes or different shapes.

It may be appreciated that in some embodiments the anchoring element 404 maintains position in an airway or area of the lung anatomy by simple entrapment of the anchoring element 404, such as insertion into an airway that is separate from the pathway to the tissue gathering element 402. In such instances, the anchoring element 404 may be "loose" within the airway yet pressed against a portion of the airway due to forces applied via the attachment end 406 so as to anchor the device 400. Such anchoring elements 404 may be easily removable by releasing the forces applied via the attachment end 406 or applying sufficient pulling force in the proximal direction. In other embodiments, the anchoring element 404 is actively anchored within the airway so as to maintain anchoring without relying on forces applied via the attachment end 406 for anchoring. FIG. 72 illustrates an embodiment of an anchoring element 404 comprising an expandable basket 480. In this embodiment, the expandable basket 480 is insertable into an airway or other anatomy and expandable so as to apply radial outward force upon the airway. This holds the basket 480 within the airway resisting movement within the airway. This, in turn, anchors the device 400 and holds the tissue gathering element 402 in place. FIG. 73 illustrates an embodiment of an anchoring element 404 comprising one or more anchoring hooks 486. In this embodiment, the one or more anchoring hooks 486 are insertable into an airway or other anatomy and expandable so as to puncture or penetrate the wall of the airway. This holds the one or more anchoring hooks 486 within the airway resisting movement within the airway. This, in turn, anchors the device 400 and holds the tissue gathering element 402 in place. FIG. 74 illustrates an embodiment of an anchoring element 404 comprising an expandable stent 490. The stent 490 may be comprised of a variety of materials, such as nitinol, steel, etc. Likewise, the stent 490 may be braided or laser cut, to name a few. In this embodiment, the expandable stent 490 is insertable into an airway or other anatomy (such as alone or with the use of a guidewire) and expandable so as to circumferentially expand against the inner walls of the airway. In some embodiments, the stent 490 is self-expanding and in other embodiments the stent 490 is expandable with assistance, such as by balloon inflation. This holds the stent 490 within the airway resisting movement within the airway. This, in turn, anchors the device 400 and holds the tissue gathering element 402 in place.

C. Attachment End

As mentioned previously, the torque-based pulmonary treatment device 400 typically comprises an attachment end 406 where the tissue gathering element 402 and an anchoring element 404 join. The attachment end 406 may be used to attach a delivery device thereto, such as a torqueing tool 408. Thus, the attachment end 406 typically has a non-round cross-section shape, such as a square, rectangular, polygonal or oval shape, to assist in maintaining rotational toque coupling and torque transmission during rotational or torqueing motion of the torqueing tool 408. It may be appreciated that in some embodiments the attachment end 406 is formed from portions of the tissue gathering element 402 and anchoring element 404 themselves, such the joining of their respective proximal ends. In other embodiments, the tissue gathering element 402 and anchoring element 404 are formed from a continuous shaft and the attachment end 406 is formed from a bend or crimp in the shaft therebetween. In some embodiments, the attachment end 406 includes an attachment element 410 to assist in joining and/or holding the elements 402, 404 and forming a desired shape for attachment and torqueing. And yet in other embodiments, the attachment end 406 resides at the proximal end of the tissue gathering element 402 or the anchoring element 404 and the elements 402, 404 are joined to each other distally of the attachment end 406.

As mentioned, in some embodiments, the attachment end 406 is formed from portions of the tissue gathering element 402 and anchoring element 404 themselves, such the joining of their respective proximal ends. FIG. 75 illustrates such an embodiment wherein the proximal ends of the tissue gathering element 402 and anchoring element 404 are bonded together by gluing or welding but they may also be joined by riveting, using threaded fasteners, crimping using a tubing or spring coupler, press fit together using a coupler or interlocking features such as threading a hitch pin, it may also be sutured together or tied using metal or plastic wire, cable, fibers, string, or they may be fused together by congealing biologic material they may be held adjacent to each other using magnetic attraction force with magnetic materials. Thus, FIG. 75 illustrates bonding material 510 between and optionally covering outer portions of the tissue gathering element 402 and anchoring element 404.

As mentioned, in some embodiments, the tissue gathering element 402 and anchoring element 404 are formed from a continuous shaft 412 and the attachment end 406 is formed from a bend or crimp in the shaft therebetween. FIG. 76A illustrates such an embodiment wherein the attachment end 406 has the form of a bend, in particular a loop-shaped bend. FIG. 76B illustrates an example of usage of the embodiment of FIG. 76A. Here, the attachment end 406 is connected with another device, such as a torqueing tool 408 or removal tool, using a hitch pin 503 with a ball end 505. The hitch pin 503 releasably attaches the devices together. Removal of the hitch pin 503 detaches the devices from each other. It may be appreciated that this design may also be used to pin the tissue gathering element 402 and the anchor element 404 together.

FIG. 77 illustrates a portion of an attachment end 406 of a device 400 having torqueing tool socket 507 that has been slipped thereover. The torqueing tool socket 507 has a shape that allows for a slip fit over the portion of the attachment end 406. The socket 507 is attached to or part of a torqueing tool 408 so that rotation of the torqueing tool 408 is transmitted through the torqueing tool socket 507 and translated to the attachment end 406. Likewise, the torqueing tool 408 is able to be translated longitudinally to be released from the device 400 without requiring any actuation of any mechanism to release the slip fit connection.

In some embodiments, the attachment end 406 is configured to mate with a torqueing tool 408 in a manner which temporarily locks the device 400 and tool 408 together. In some instances, this assists in positioning the device 400 wherein the device 400 can be easily advanced and retracted with the use of the tool 408. For example, in FIG. 78 the attachment end 406 has a threaded outer surface and the torqueing tool 408 includes threaded inner surface. This allows the attachment end 406 to join with a torqueing tool

Figures 79, 80:
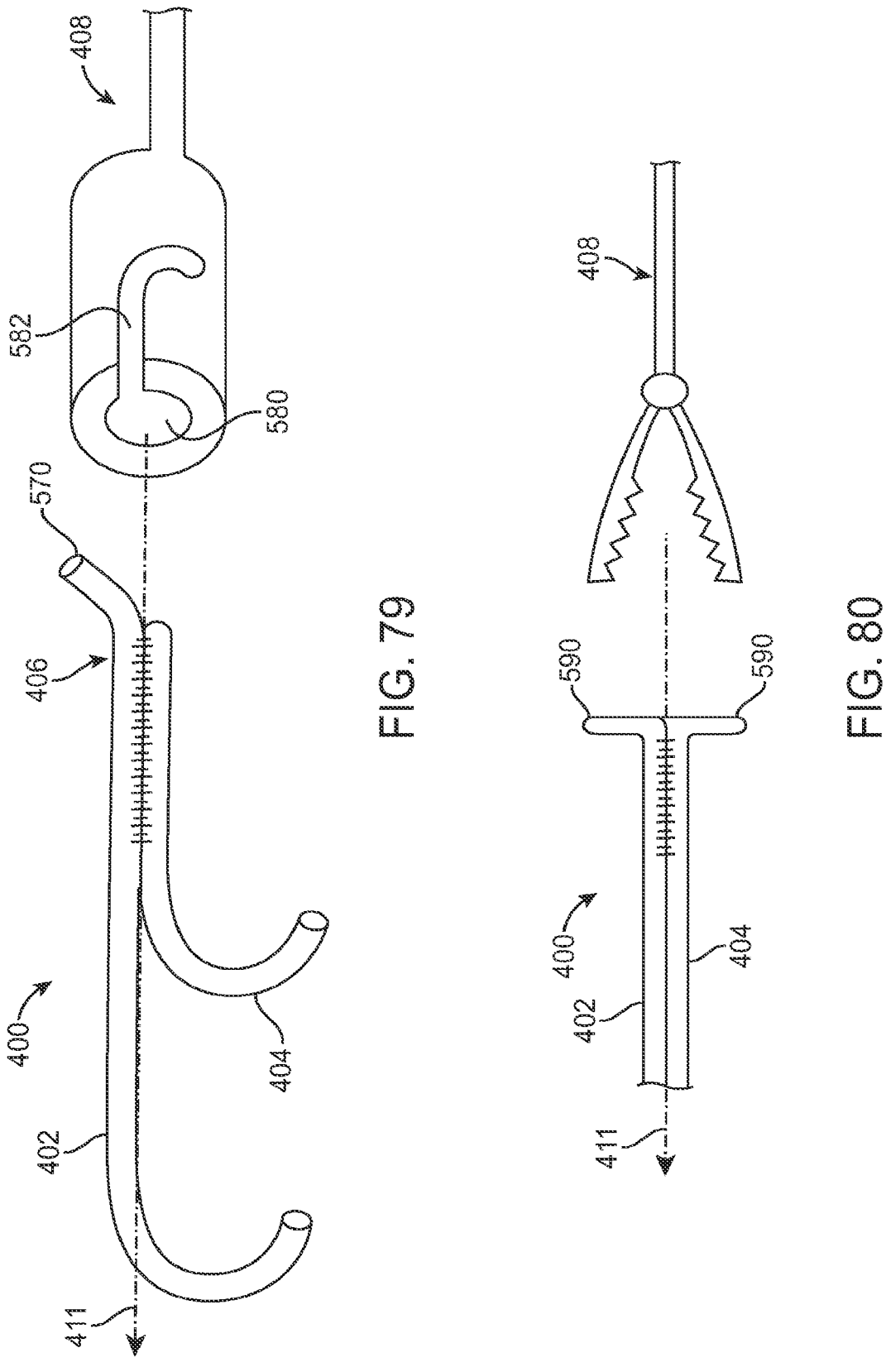
FIG. 79 illustrates an embodiment of a treatment device with an interlocking attachment end.
FIG. 80 illustrates an embodiment of a treatment device attachment end that is controlled by forceps.

408 in a screw-type manner. In this embodiment, the torqueing tool 408 has a threaded receptacle 550 configured to receive the attachment end 406 so as to mate the threading surfaces together. It may be appreciated that such joining may be achieved by rotation of the torqueing tool 408, wherein continued rotation in the same direction then rotates or torques the tissue gathering element 402. Once desired rotation has been achieved, the anchoring element 404 is actuated and the torqueing tool 408 is then unscrewed from the attachment end 406. FIG. 79 illustrates an attachment end 406 which keys into the torqueing tool 408. In this embodiment, the attachment end 406 includes an extension 570 which extends away from the longitudinal axis 411 of the device 400. The extension 570 may have any suitable shape including a rod, protrusion, bump, etc. In this embodiment, the torqueing tool 408 includes a receptacle 580 having a groove or cutaway 582 configured to receive the extension 570 upon mating of the attachment end 406 with the receptacle 580. Typically, the cutaway 582 extends along a first direction, such as along the longitudinal axis 411 and then extends along a second direction, such as angular or perpendicular to the longitudinal axis 411. As the attachment end 406 is joined with the torqueing tool 408, the extension 570 is advanced along the cutaway 582 (along the first and second directions) which typically involves rotating the torqueing tool 408 to allow advancement of the extension along the second direction. Positioning of the extension 570 within the cutaway 582 along the second direction temporarily locks the attachment end 406 to the torqueing tool 408 during pulling or pushing along the longitudinal axis 411. It may be appreciated that continued rotation of the torqueing tool 408 in the same direction rotates or torques the device 400. since the extension 570 is unable to slide out of the cutaway 582. Once desired rotation has been achieved, the anchoring element 404 is actuated and the torqueing tool 408 is then rotated in the reverse direction to release the extension 570 from the receptacle 580.

In other embodiments, the attachment end 406 includes one or more accessories configured to assist in rotation of the device 400. For example, FIG. 80 illustrates an embodiment of an attachment end 406 having at least one protrusion 590 which extends radially outwardly from the longitudinal axis 411. The at least one protrusion 590 provides a larger surface area for attachment to the torqueing tool 408. In this embodiment, the torqueing tool 408 comprises a grasper which grasps the at least one protrusion 590. Rotation of the torqueing tool 408 thus rotates the device 400. The torqueing tool 408 is then disengaged from the device 400 by releasing the grasper.

Figure 81:
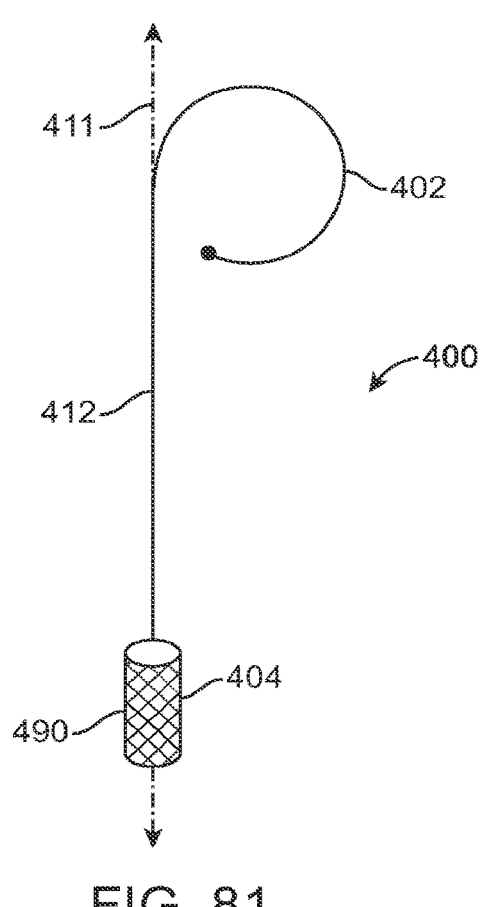
FIG. 81 illustrates an embodiment of a treatment device with a stent anchoring element.

In some embodiments, the anchoring element 404 is positionable within the same airway or passageway as the tissue gathering element 402 or within an airway or passageway which is proximal to that of the tissue gathering element 402. FIG. 81 illustrates an embodiment of such a device 400. Here, the anchoring element 404 is disposed in the opposite direction as the tissue gathering element 402, along the longitudinal axis 411. Here, the anchoring element 404 comprises an expandable stent 490. Thus, the tissue gathering element 402 may be advanced into an airway and desirably positioned. The device 400 is then anchored in place by expanding the stent 490 proximally of the tissue gathering element 402. This may be particularly useful in situations wherein a nearby airway is not available for anchoring due to anatomical configuration or lack of strength.

Figure 82A:
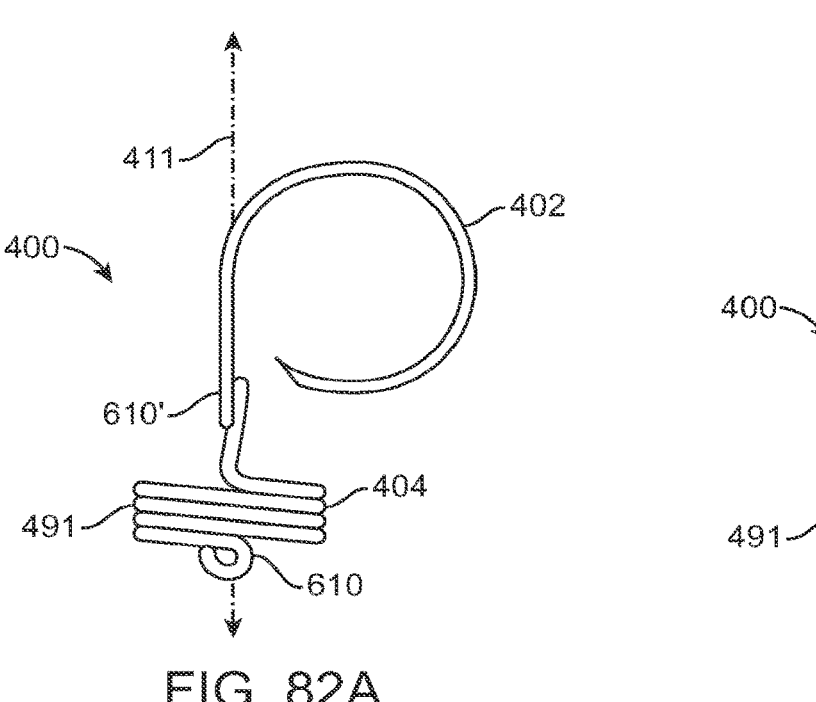
FIGS. 82A-82B illustrates an embodiment of a treatment device made from a single wire shaft.
Figure 82B:
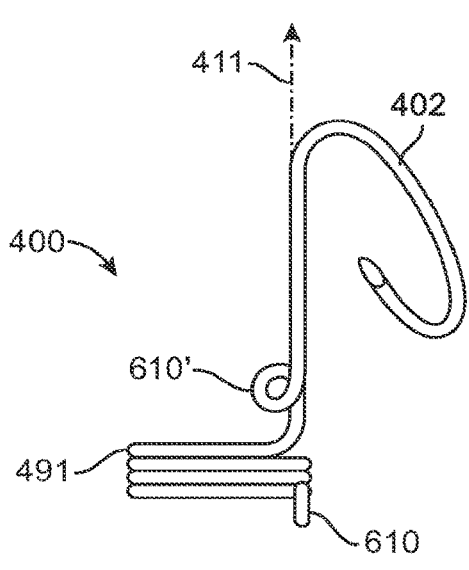

FIGS. 82A-82B illustrate another embodiment wherein the anchoring element 404 is positionable within the same airway or passageway as the tissue gathering element 402. Here, the anchoring element 404 is disposed in the opposite direction as the tissue gathering element 402, along the longitudinal axis 411. Here, the anchoring element 404 comprises a coil 491. Thus, the tissue gathering element 402 may be advanced into an airway or through the wall of the airway into destroyed fragile lung tissue and desirably positioned. The device 400 is then anchored in place by deploying the coil 491 which expands within a luminal passageway or airway proximally of the tissue gathering element 402. In this embodiment, the device 400 includes an attachment feature 610 near the proximal end of the coil 491 and an additional attachment feature 610' disposed between the tissue gathering element 402 and the anchoring element 404. Thus, the torqueing tool 408 may be attached to either attachment feature 610, 610' for the most desirable outcome. Alternatively, more than one torqueing tool 408 may be attached to device 400 to apply torque and to help deploy the anchoring element 404. One or both of the torqueing tools may also be used to remove the device 400 from the lung in a coordinated way if this is desirable. FIG. 82B illustrates the device 400 of FIG. 82A rotated 90 degrees about the longitudinal axis 411. In this embodiment, the tissue gathering element 402 has a hook or loop shape. It may be appreciated that the loop of the tissue gathering element 402 may curve within a single plane. However, in this embodiment, the loop of the tissue gathering element 402 curves within multiple planes, as illustrated in FIG. 82B. This may be beneficial when the tissue gathering element 402 is less rigid and therefore less capable of moving tissue. The out-of-plane curvature accounts for such flexibility wherein rotation of the tissue gathering element 402 causes the tissue to align the loop toward a single plane. The tissue gathering element 402 then has increased ability to move tissue.

Figure 82C:
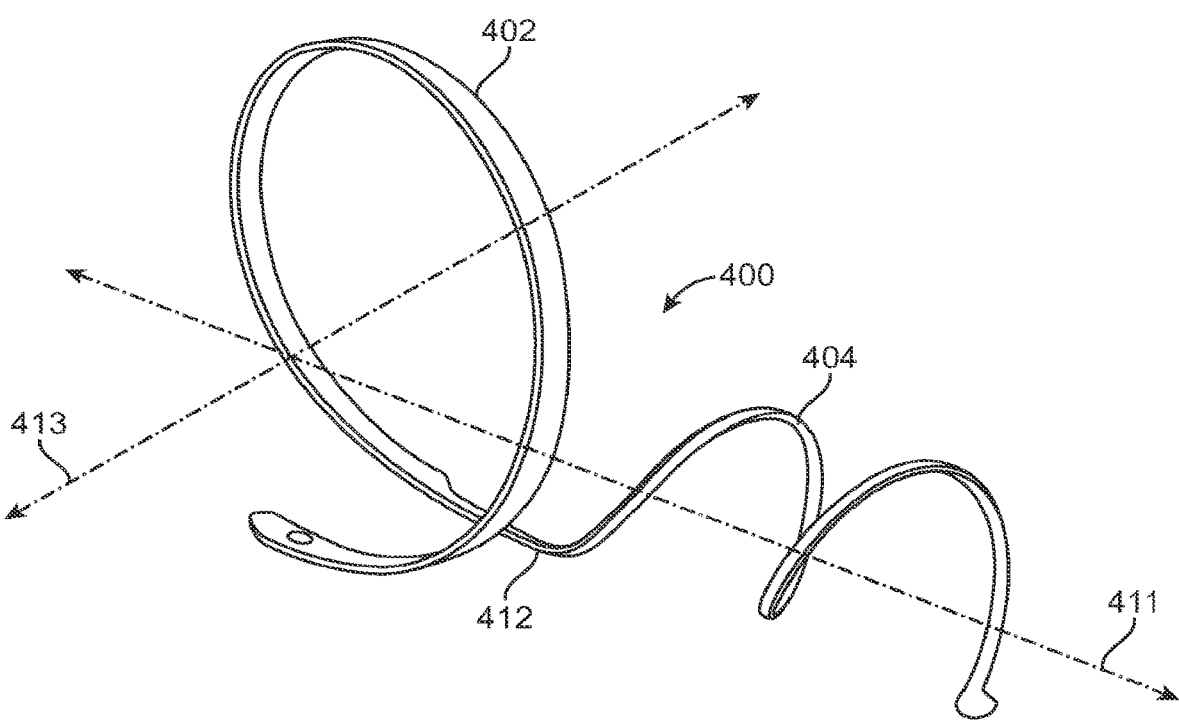
FIGS. 82C-82D illustrate additional embodiments of a pulmonary treatment device having a tissue gathering element and an anchoring element.

FIG. 82C illustrates another embodiment of a pulmonary treatment device 400 having a tissue gathering element 402 and an anchoring element 404. In this embodiment, the device 400 is formed from a continuous shaft 412 which bends to form the elements 402, 404. Here, the device 400 generally extends along a longitudinal axis 411. The tissue gathering element 402 is formed by the shaft 412 bending radially outwardly away from the longitudinal axis 411 forming a loop around an axis 413 that is perpendicular to the longitudinal axis 411. In some embodiments, the outer diameter of the loop that is formed around the axis 413 in the range of 0.400 inches to 3.0 inches in diameter or any size between. Most preferably, the loop may have an outer diameter in the range of 0.75 inches and 1.25 inches. In this embodiment, the loop continues into a full loop shape around the axis 413, however it may be appreciated that in other embodiments the loop is a partial loop forming an arc shape. In this embodiment, the anchoring element 404 is formed by the shaft 412 bending into a coiled shape, wherein each turn of the coil extends at least partially around the longitudinal axis 411. In this embodiment, the shaft 412 has a flattened, ribbon shape. In some embodiments, the ribbon shape is between 0.005 and 0.030 inches wide and between 0.005 and 0.030 inches thick in dimension. The ribbon may be blasted or tumbled in abrasive media to round the edges so it more closely appears like a round cross-section wire. Alternatively, the anchoring element 404 may be made from round cross section wire, for example having a diameter between 0.003 and 0.050 inches. The coiled shape may be configured to form a coil shaped stent or helix with an outer diameter of the helix that is between 5 mm and 17 mm in diameter but more preferably it is between 6 mm and 10 mm in diameter. Thus, the tissue gathering element 402 has a stiffness sufficient to move lung tissue, particularly to move lung tissue around the longitudinal axis 411. Thus, in such a situation the longitudinal axis 411 becomes a rotational axis.

Figure 82D:
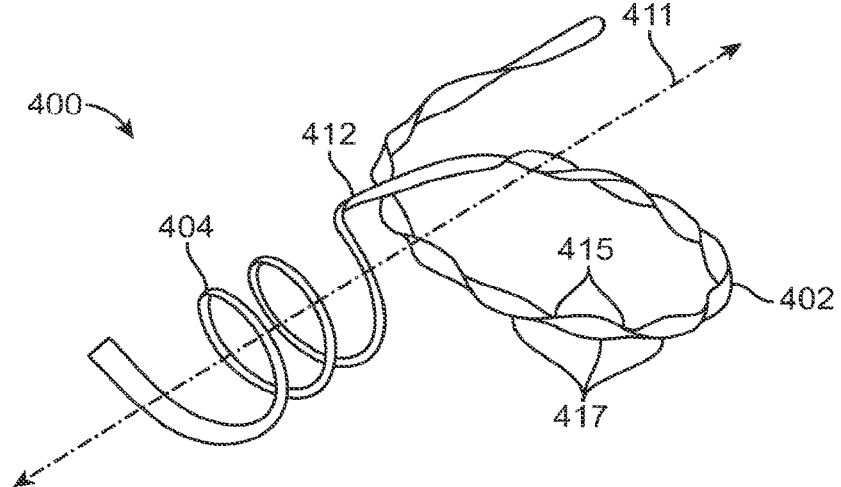

FIG. 82D illustrates another embodiment of a pulmonary treatment device 400 having a tissue gathering element 402 and an anchoring element 404. In this embodiment, the device 400 is formed from a continuous shaft 412 which bends to form the elements 402, 404 in a shape similar to that of FIG. 82C. Likewise, the tissue gathering element 402 has a flattened, ribbon shape. However, in this embodiment, the ribbon is twisted along its length in at least one location 415 so as to rotate at least one portion of a flat surface of the ribbon 417 toward an edge of the ribbon, as shown. In particular, the ribbon is twisted along its length at multiple locations 415 so as to rotate a series of portions of the flat surface 417 of the ribbon toward the edge of the ribbon. Thus, when the device 400 is rotated about the longitudinal axis 411, the series of portions of the flat surface of the ribbon are posed to engage the surrounding tissue. This adds 300-500% more bearing area against the tissue for engagement. This reduces the stress on the tissue to less than 20% compared to when the edge of the ribbon engages the tissue.

It may be appreciated that the anchoring elements 404 described herein may be positioned within an airway, lung passageway, blood vessel, parenchyma, or destroyed tissue, to name a few. The choice of design used for the anchoring element 404 is typically chosen based on the anatomy or environment within which the element 404 is to be positioned. For example, a stent 490 design may be more suitable for a luminal passageway while an anchoring hook 486 design may be more suitable for damaged tissue.

Figures 82E, 82F, 82G:
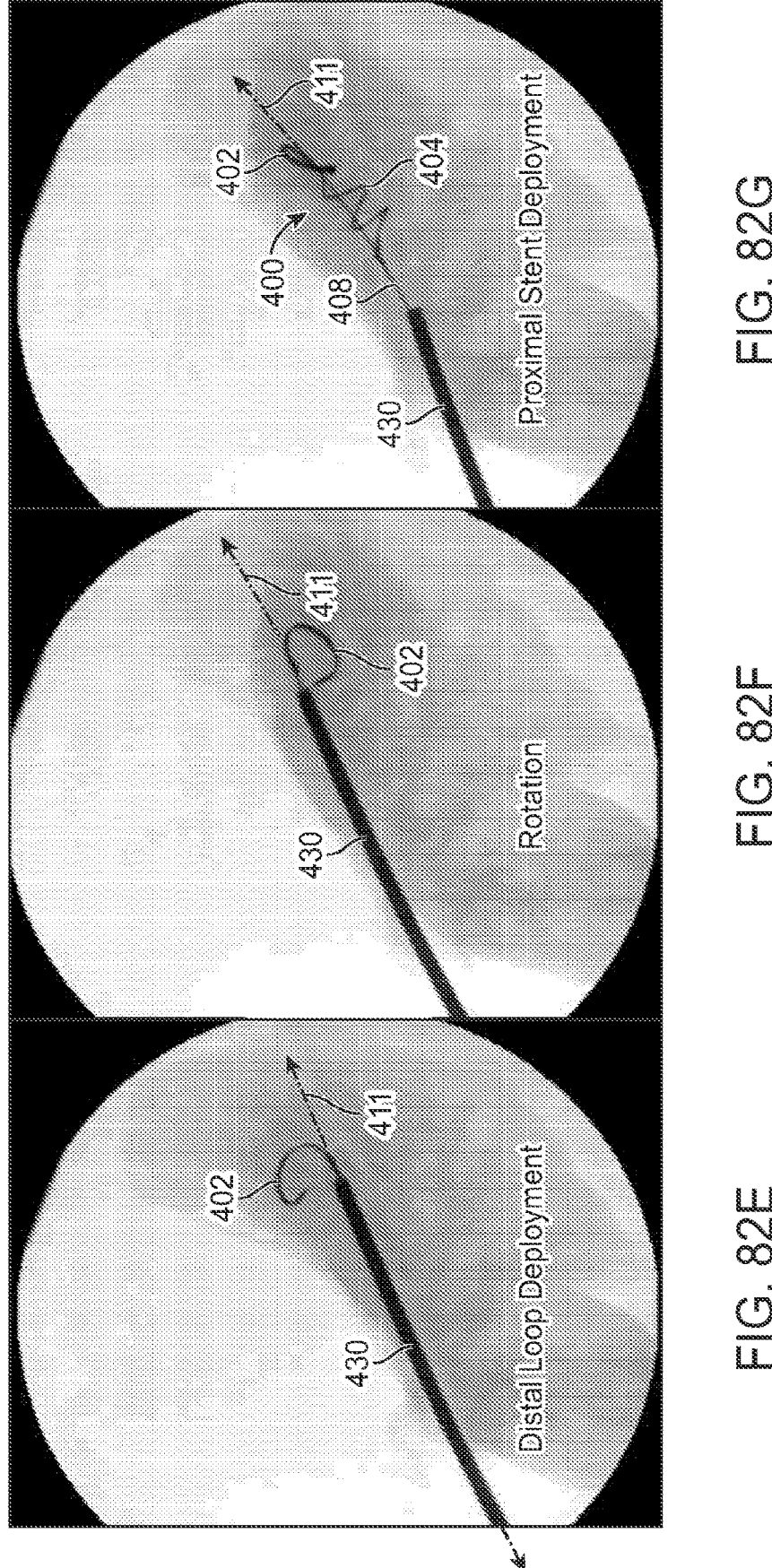
FIGS. 82E-82G illustrate steps in an example method of deploying a torque-based pulmonary treatment device such as illustrated in FIGS. 82A-82D.

FIGS. 82E-82G illustrate steps in an example method of deploying a torque-based pulmonary treatment device 400 such as illustrated in FIGS. 82A-82D. In this embodiment, deployment begins (FIG. 82E) by pushing the device 400 through a catheter 430 and out its distal end so that the tissue gathering element 402 extends from the distal end of the catheter 430 and curves radially outwardly from the longitudinal axis 411. As the tissue gathering element 402 is further advanced additional portions of the tissue gathering element 402 extend from the distal end of the catheter 430, curving around into a loop shape, as shown. FIG. 83F illustrates rotation of the device 400, such as by rotation of the catheter 430 around the longitudinal axis 411. The forces on the tissue adjacent the tissue gathering element 402 move the tissue around the longitudinal axis 411 into a torqued configuration. This tensions the surrounding tissue. Once the lung has been desirably tensioned, the device 400 is then anchored to maintain the tensioning or resist unwinding of the device from the torqued configuration. In this embodiment, this is achieved by deploying the anchoring element 404, as illustrated in FIG. 82G. In this embodiment, the anchoring element 404 had a coil shape and is concentrically aligned with the longitudinal axis 411. In this embodiment, deployment of the anchoring element 404 is achieved by retracting the catheter 430 so as to allow the coils of the anchoring element 404 to expand. In this embodiment, a torqueing tool 108 remains attached to the device 400 at this stage of delivery. The torqueing tool 408 is then removed from the device 400. The device 400 is then left in place as an implant while the catheter 430 is removed.

Figure 83A:
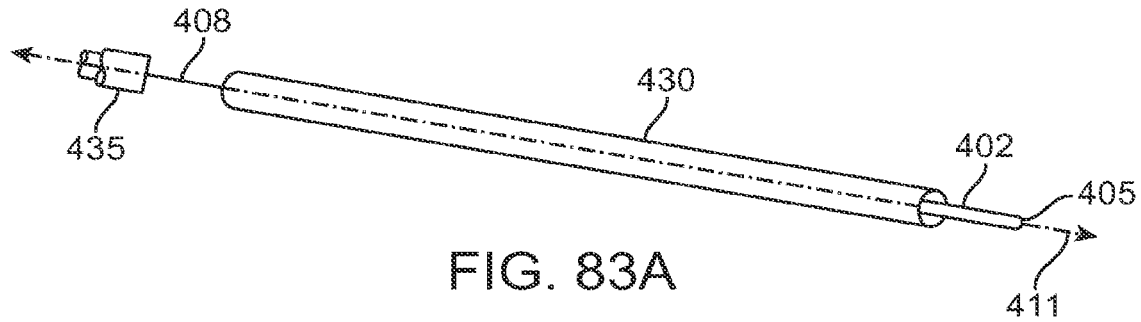
FIGS. 83A-83I illustrates an embodiment of a treatment device being deployed in lung tissue.
Figure 83B:
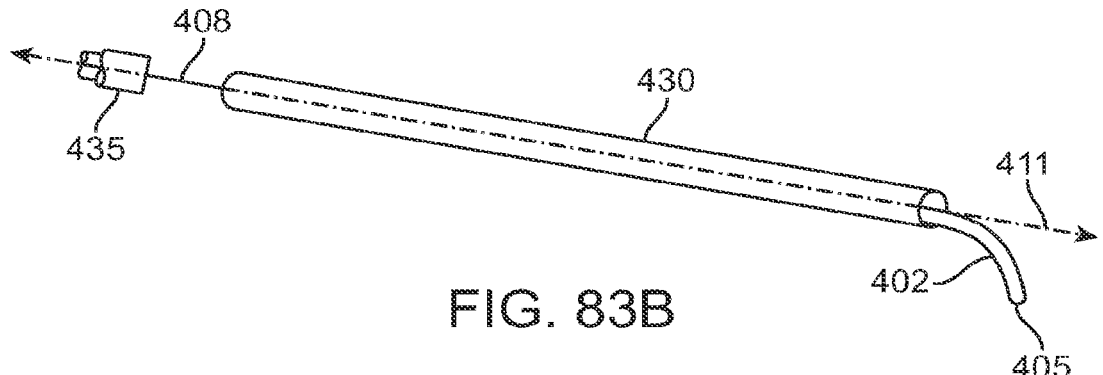
Figure 83C:
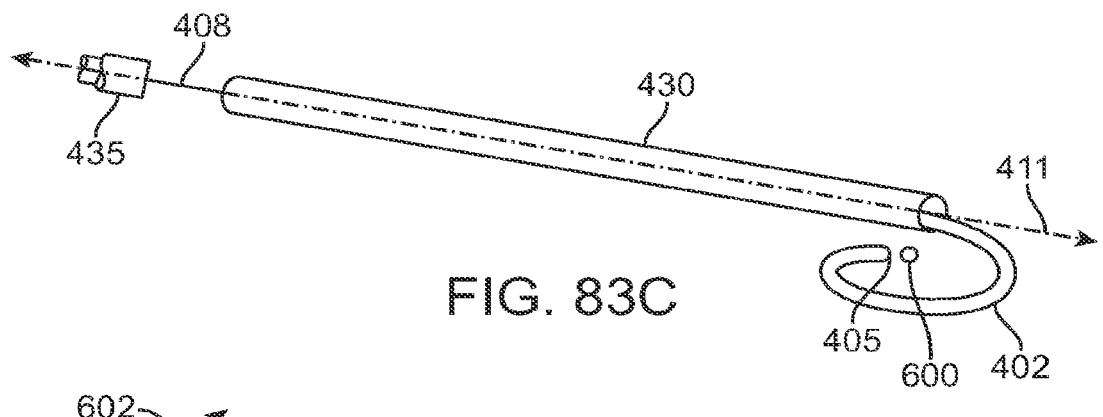
Figure 83D:
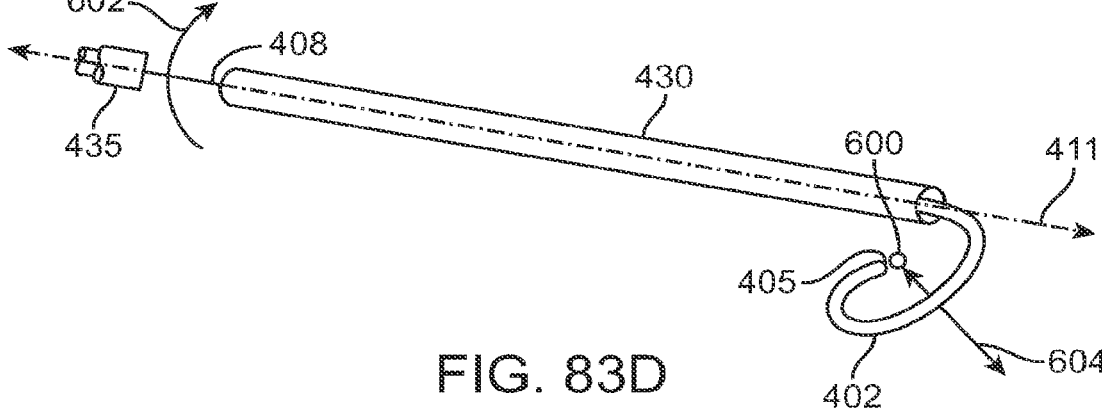
Figures 83E, 83F, 83G, 83H, 83I:
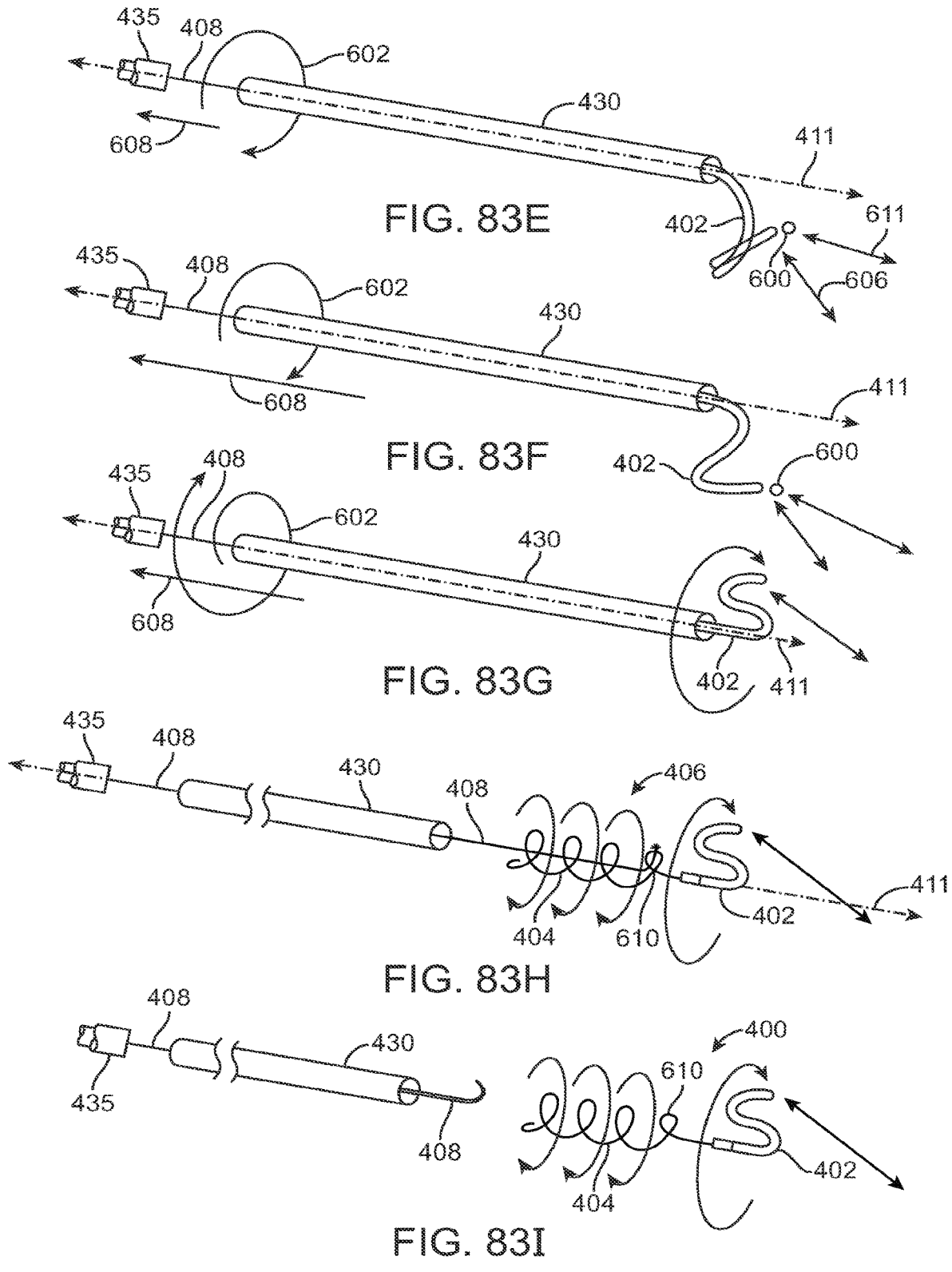

FIGS. 83A-83J provide a more detailed illustration of steps in an example method of deploying a torque-based pulmonary treatment device 400 such as illustrated in FIGS. 82A-82D. To begin (FIG. 83A), the device 400 is loaded within a catheter 430 or similar delivery device which is configured to be advanceable through a lumen in an endoscope, such as a bronchoscope 20. The device 400 is constrained within the catheter 430 (along longitudinal axis 411) to allow for ease of placement. The device 400 is attached to a torqueing tool 408 which extends from the distal end of the catheter 430. In this embodiment, the torqueing tool 408 includes a handle 435. In this embodiment, deployment begins by advancing the torqueing tool 408 into the catheter 430 so as to begin pushing the device 400 through the catheter 430 and out its distal end. FIG. 83A illustrates the distal tip 405 of the tissue gathering element 402 extending from the distal end of the catheter 430 along the longitudinal axis 411. As the torqueing tool 408 is additionally advanced, as illustrated in FIG. 83B, additional portions of the tissue gathering element 402 extend from the distal end of the catheter 430. Due to pre-curves set into the tissue gathering element 402 the distal tip 405 begins curving radially outwardly from the longitudinal axis 411. As the torqueing tool 408 is yet further advanced, as illustrated in FIG. 83C, additional portions of the tissue gathering element 402 extend from the distal end of the catheter 430, curving around into a loop shape. Here, the distal tip 405 is directed toward a sample tissue area 600 located off-set from the longitudinal axis 411. The sample tissue area 600 is demarked to illustrate how the sample tissue area 600 may move in response to torqueing the device 400. However, it may be appreciated that a larger mass of tissue surrounding the sample tissue area 600 is moved by rotation of the device 400.

FIG. 83D illustrates the start of rotating the torqueing tool 408; as indicated by arrow 602, the torqueing tool 408 is rotated in the counter-clockwise direction in this embodiment. It may be appreciated that in other embodiments, the torqueing tool 408 may be rotated in the clockwise direction. In this embodiment, slight resistance of the tissue is illustrated wherein the torqueing tool 408 rotates while the tissue gathering element 402 flexes. The forces on the sample tissue area 600 begin to pull the surrounding tissue creating tension, as illustrated by arrow 604. FIG. 83E illustrates further rotation of the torqueing tool 408. At this point the curved portion of the tissue gathering element 402 has rotated around the longitudinal axis 411 pulling the sample tissue area 600 along with it. This further tensions the surrounding tissue as illustrated by arrow 606. Additionally, in this embodiment, the torqueing tool 408 is pulled back, in the proximal direction along the longitudinal axis 411, as indicated by arrow 608. This additionally applies longitudinal force to the sample tissue area 600 as indicated by arrow 611. As illustrated in FIG. 83F, the torqueing tool 408 is then retracted further in this embodiment, as illustrated by arrow 608. Because the tissue gathering element 402 has been distorted due to the rotational and longitudinal motions illustrated in FIG. 83E, the tissue gathering element 402 has been interlocked into tissue to allow additional rotation and translation motions and applied forces to tissue that would not normally have been possible without pulling the tissue gathering element 402 out of tissue. Designing the tissue gathering element in a way that allows it to be rotated and translated so it is distorted to converge more closely to occupy a plane that is perpendicular to axis 411 locks it into tissue to allow more extreme torsion and translational forces to be applied to tissue. In this embodiment, the device 400 is then additionally rotated, as illustrated in FIG. 83G, so as to further wrap the surrounding tissue around the tissue gathering element 402. Thus, the sample tissue area 600 continues rotating around the longitudinal axis 411, applying further radial and longitudinal tension on the surrounding lung. Once the lung has been desirably tensioned, the device 400 is then anchored to maintain the tensioning. In this embodiment, this is achieved by deploying the anchoring element 404. In this embodiment, the anchoring element 404 had a coil shape and is concentrically aligned with the longitudinal axis 411. FIG. 83H illustrates deployment of the anchoring element 404 wherein the catheter 430 is retracted to allow the coils of the anchoring element 404 to expand. In this embodiment, the torqueing tool 108 remains attached to the device 400 at this stage of delivery. In particular, in this embodiment, the torqueing tool 408 has a curved distal tip (e.g. a 90 degree curvature away from the longitudinal axis) which passes through an attachment feature 610 (e.g. a loop) on the device 400, maintaining attachment. The torqueing tool 408 is then removed from the attachment feature 610 by retracting the torqueing tool with sufficient force as to straighten the curved end of the torqueing tool 408 to pull it out of the attachment feature 610, as illustrated in FIG. 83I. The device 400 is then left in place as an implant while the catheter 430 is removed. In some embodiments, the torqueing tool 408 is be made from a resilient material such as Nitinol or titanium in which the modulus of elasticity is less than 30E6 pounds per square inch. In other embodiments, the torqueing tool 408 is made from ferrous or non-ferrous metals with a cross section area less than 0.005 square inches. These dimensions allow for the wire to be deformed. In some embodiments, the torqueing tool 408 is made from stainless steel wire that has a dimension between 0.010 and 0.030 inches in diameter.

D. Alternative Embodiment

Figures 84A, 84B, 84C, 84D, 84E:
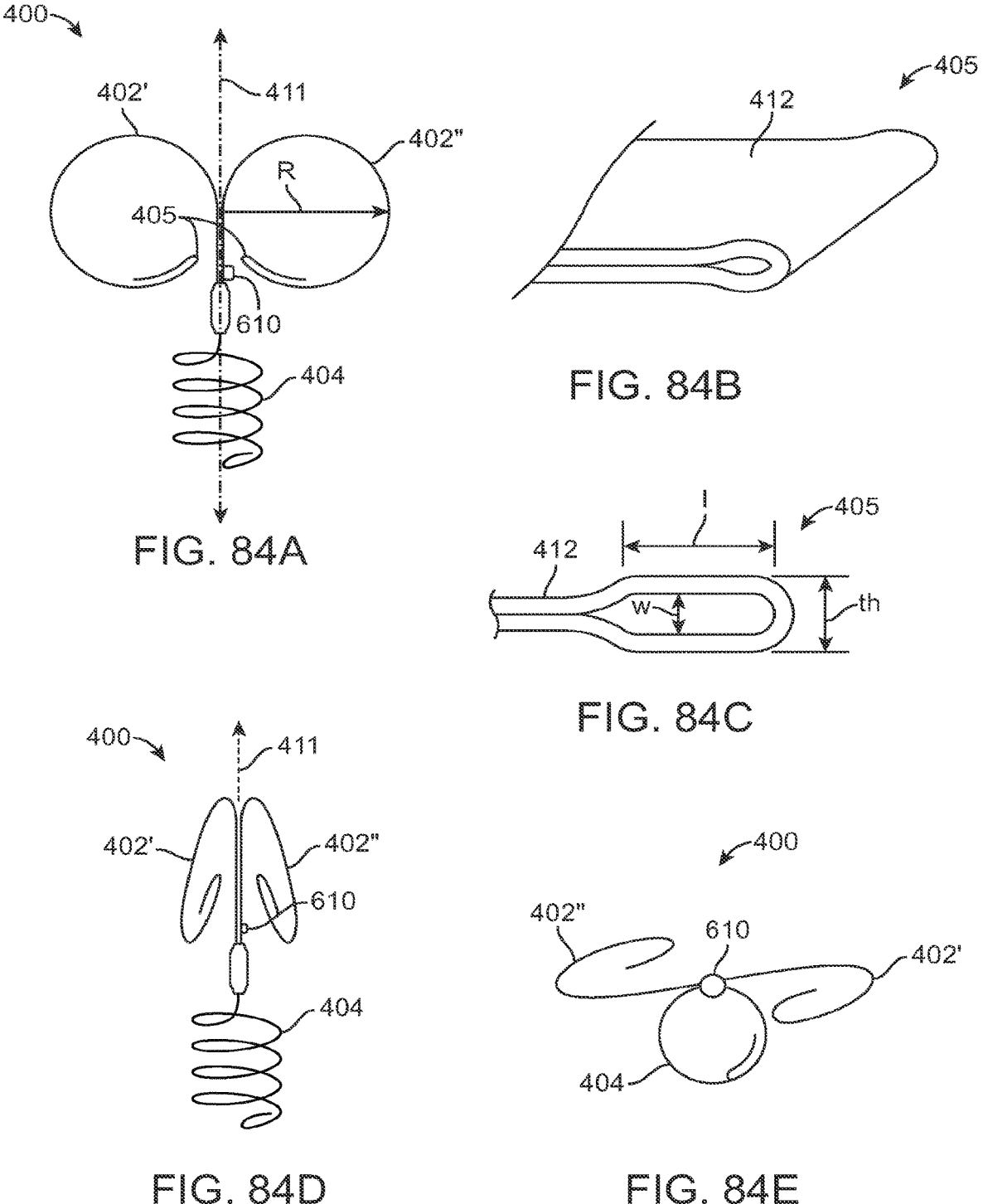
FIG. 84A-84E illustrates an embodiment of a dual tissue gathering element treatment device and components.

It may be appreciated that the torque-based pulmonary treatment device 400 may take a variety of forms and include a variety of features, such as those of the pulmonary treatment devices 10 described herein above which are applicable to torque-based methods and treatments. FIGS. 84A-84E illustrate another embodiment of a torque-based pulmonary treatment device 400. Here, the device 400 includes a plurality of tissue gathering elements 402. In particular, two tissue gathering elements 402 are shown, however it may be appreciated that additional tissue gathering elements 402 may be present including three, four, five, six or more. In this embodiment, the tissue gathering elements 402 extend radially outwardly away from the longitudinal axis 411, particularly in opposite directions from each other. Thus, in this embodiment, the device 400 includes a first tissue gathering element 402' and a second tissue gathering element 402", each extending outwardly from the longitudinal axis 411 and then curving around and back toward the longitudinal axis 411 in a loop shape. In this embodiment, each loop forms half of the diameter of the distal end of the device 400 which rotates within the tissue. Therefore, each loop may be considered as forming a radius R as indicated in FIG. 84A. In this embodiment, each loop forms a radius R wherein R=0.5 inches. It may be appreciated that in other embodiments radius R may vary including R values in the range of 0.3 to 3.0 inches.

Each tissue gathering element 402', 402" is comprised of shaft 412 made from a suitable material, such as nitinol wire, stainless steel wire, etc.). In this embodiment, the tissue gathering elements 402', 402" are comprised of 0.020 inch thick ribbon that is 0.020 to 0.100 inches wide. In particular, in this embodiment, each tissue gathering element 402', 402" is comprised of a wire ribbon. In addition, here each tissue gathering element 402', 402" terminates in a distal tip 405 which is formed by bending back and overlapping the ribbon to form a blunt end. FIG. 84B provides a closer view of a distal tip 405 of FIG. 84A. In this embodiment, the ribbon material is curved back upon itself forming a bend having an outer thickness of approximately 0.065 inches at its thickest location. FIG. 84C provides another embodiment of a distal tip 405 wherein the ribbon material is curved back upon itself forming a bullet-nose shape. In this embodiment, the folded material creates an opening 620 within the distal tip 405 that has a length l and width w. In some embodiments, the opening 620 has a length of l=5 mm. Likewise, in some embodiments, the distal tip 405 has a thickness th wherein the thickness has a maximum of 0.065 inches. It may be appreciated that the tissue gathering elements 402', 402" may be formed from separate shafts or from one continuous shaft.

Referring back to FIG. 84A, in this embodiment, the device 400 also includes an anchoring element 404. Here, the anchoring element 404 is disposed in the opposite direction as the tissue gathering element 402, concentrically along the longitudinal axis 411. Here, the anchoring element 404 comprises a coil 491. Thus, the tissue gathering element 402 may be advanced into an airway and desirably positioned. The device 400 is then anchored in place by deploying the coil 491 which expands within a luminal passageway or airway proximally of the tissue gathering element 402. In this embodiment, tissue gathering elements 402', 402" are joined therebetween by a crimp, weld, glue joint, rivet, threaded fastener, spring element that is wrapped around parts to clamp components together. In this embodiment, the device 400 includes an attachment feature 610. Thus, the torqueing tool 408 is attached to the attachment feature 610 as will be described in more detail herein below.

FIG. 84D illustrates a possible position of the tissue gathering elements 402', 402" during rotation and torqueing of the device 400. As shown, the resistance of the surrounding lung tissue may initially bend the elements 402', 402" as the device 400 rotates within the lung. Thus, the elements 402', 402" are somewhat flexible while imparting force on the tissue. The tissue gathering elements 402' and 402" are shaped with a twist so that the resistance of surrounding tissue deforms them to be more in-plane with respect to each other and along axis 411. If the tissue gathering elements 402' and 402" are shaped so they deform to a more vertical structure along axis 411, the tissue gathering elements 402' and 402" will present the greatest amount of contact and the greatest amount of bearing area on effected tissue possible as the device 400 is rotated.

FIG. 84E provides a top view of this embodiment of the device 400 as produced or once implanted. In this embodiment, the elements 402', 402" both curve downward toward the proximal end of the device 400. However, this view shows the elements 402', 402" out of plane (i.e. not in the same plane) which is a common position when advanced into tissue, particularly after rotation of the device 400. Thus, the first tissue gathering element 402' is shown set back from the second tissue gathering element 402". FIG. 84E also illustrates that the coil design of the anchoring element 404 leaves an open passageway therethrough once deployed. Thus, anchoring of the device 400 does not impinge upon or block airflow through the airway within which the device 400 is anchored.

Figure 85:
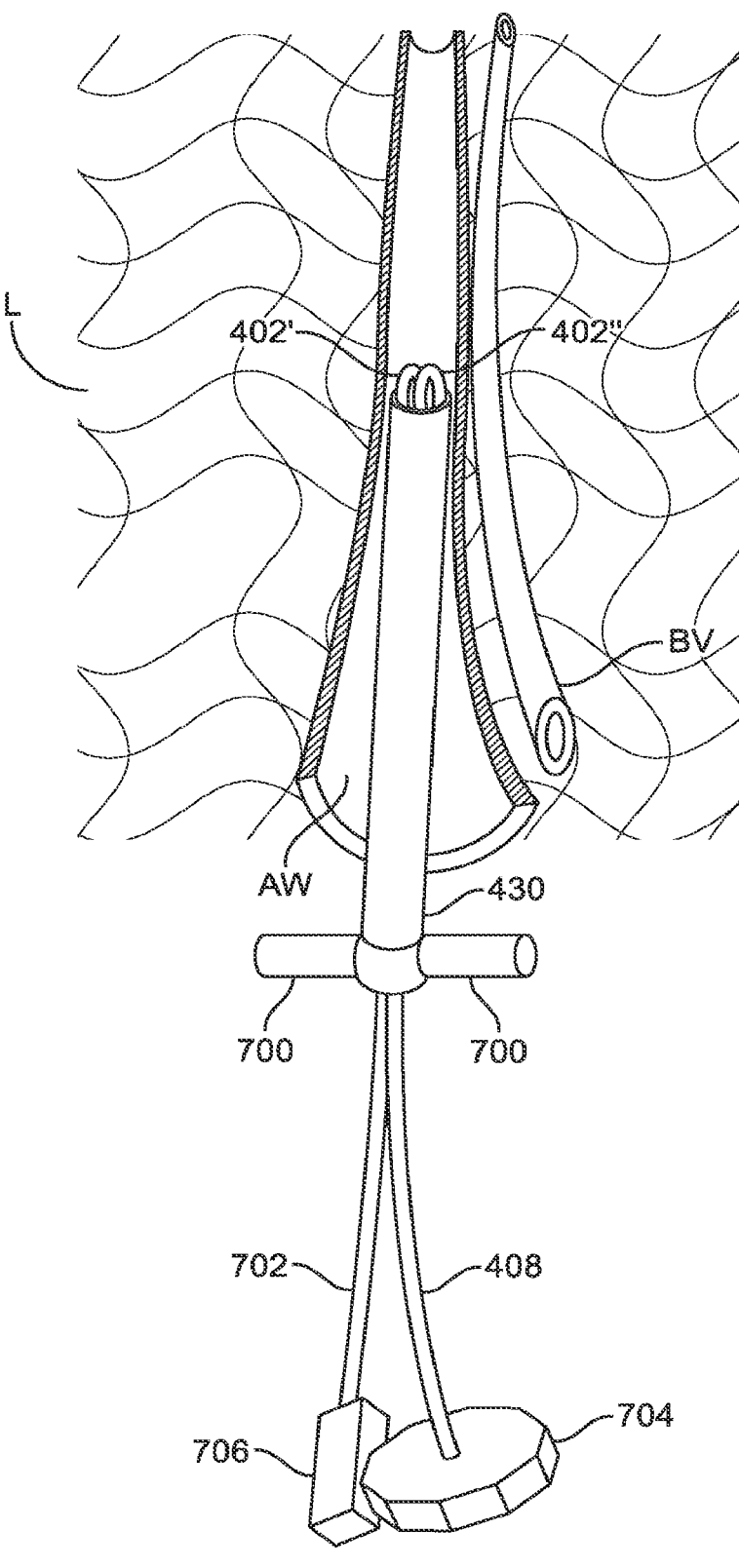
FIG. 85 illustrates an embodiment of a treatment device and delivery system inserted into an airway.

FIGS. 85-90 illustrate example method steps of delivering a device 400 having double tissue gathering elements 402', 402", such as in the device of FIG. 84A. Referring to FIG. 85, the device 400 is loaded within the catheter 430 or other suitable delivery device such as a loading cartridge so that the tissue gathering elements 402', 402" are positioned near the distal end of the catheter 430, ready for deployment. In this embodiment, the portion of device 400 that protrudes from the catheter forms a blunt tip that allows the catheter to be advanced through fragile airways or fragile lung tissue without causing trauma. In this embodiment, the catheter 430 includes at least one leverage element 700 which resides outside of the body when the distal end of the catheter 430 is positioned within the patient's body. The at least one leverage element 700 assist the user in manipulating the catheter 430, such as applying torque to the catheter 430 or moving the catheter 430 longitudinally in the proximal or distal direction. In this embodiment, the device 400 is attached to a torqueing tool 408 which extends through the catheter 430 and exits the proximal end of the catheter 430. In this embodiment, the torqueing tool 408 includes a torqueing handle 704 disposed near its proximal end to assist the user in grasping and applying torque to the torqueing tool 408. In this embodiment, the device 400 is also attached to a tether 702 (e.g. suture, metallic wire (such as comprised of stainless steel, titanium, nitinol or other nickel based alloy), monofilament or multifilament fiber, braid, polymer or ceramic or glass fiber (such as comprised of Kevlar®, carbon fiber, nylon, polyurethane, polypropylene or other durable material)). The tether 702 may be used to manipulate portions of the device 400, typically other than torqueing, such as pulling the anchoring element 404 in the proximal direction or removing the device 400, to name a few. Thus, in this embodiment, the tether 702 includes a tether handle 706 disposed near its proximal end to assist the user in grasping and manipulating the tether 702. The manipulating tether may also be a second torqueing tool that is located at proximal end of the anchoring element 404. FIG. 85 illustrates advancement of the distal end of the catheter 430 through at least one airway AW to a target location within a lung L. Thus, in this example, the distal-most end of the catheter 430 is disposed within an airway AW. Likewise, a blood vessel BV is shown residing nearby the airway AW along with alveolar or connective lung tissue surrounding the airway AW. It may be appreciated that FIGS. 85-90 are not drawn to scale; rather, the distal and proximal ends of the delivery devices are prominent for focus and detail. It may be appreciated that the catheter 430 is much longer than depicted to allow for advancement through the trachea to various airways, including advancement along airways past the 4$^{th}$ generation. Likewise, it may be appreciated that the airway AW is illustrated as bisected for the purpose of clear viewing of the device 400 and delivery devices disposed therein.

Figure 86:
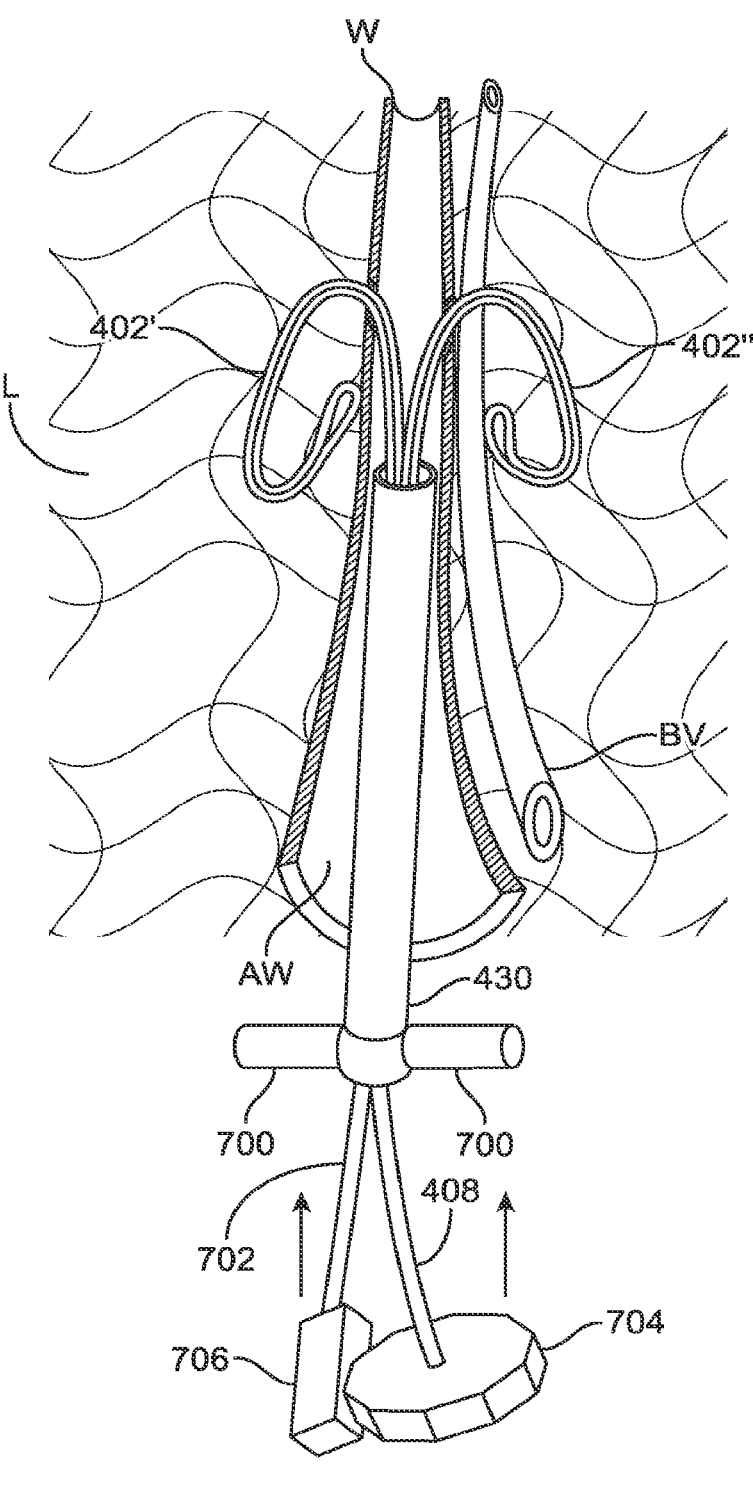
FIG. 86 illustrates an embodiment of a treatment device tissue gathering elements deployed through the airway wall.

FIG. 86 illustrates delivery of the tissue gathering elements 402', 402". Here, the tissue gathering elements 402', 402" are deployed by pushing the torqueing tool 408 in the distal direction which in turn pushes the device 400 toward the distal end of the catheter 430, revealing the tissue gathering elements 402', 402". This allows each element 402', 402" to extend radially outwardly, through the airway wall W, and curve around through the tissue surrounding the airway AW. In this example, the tissue gathering element 402" passes in front of the blood vessel BV.

Figure 87:
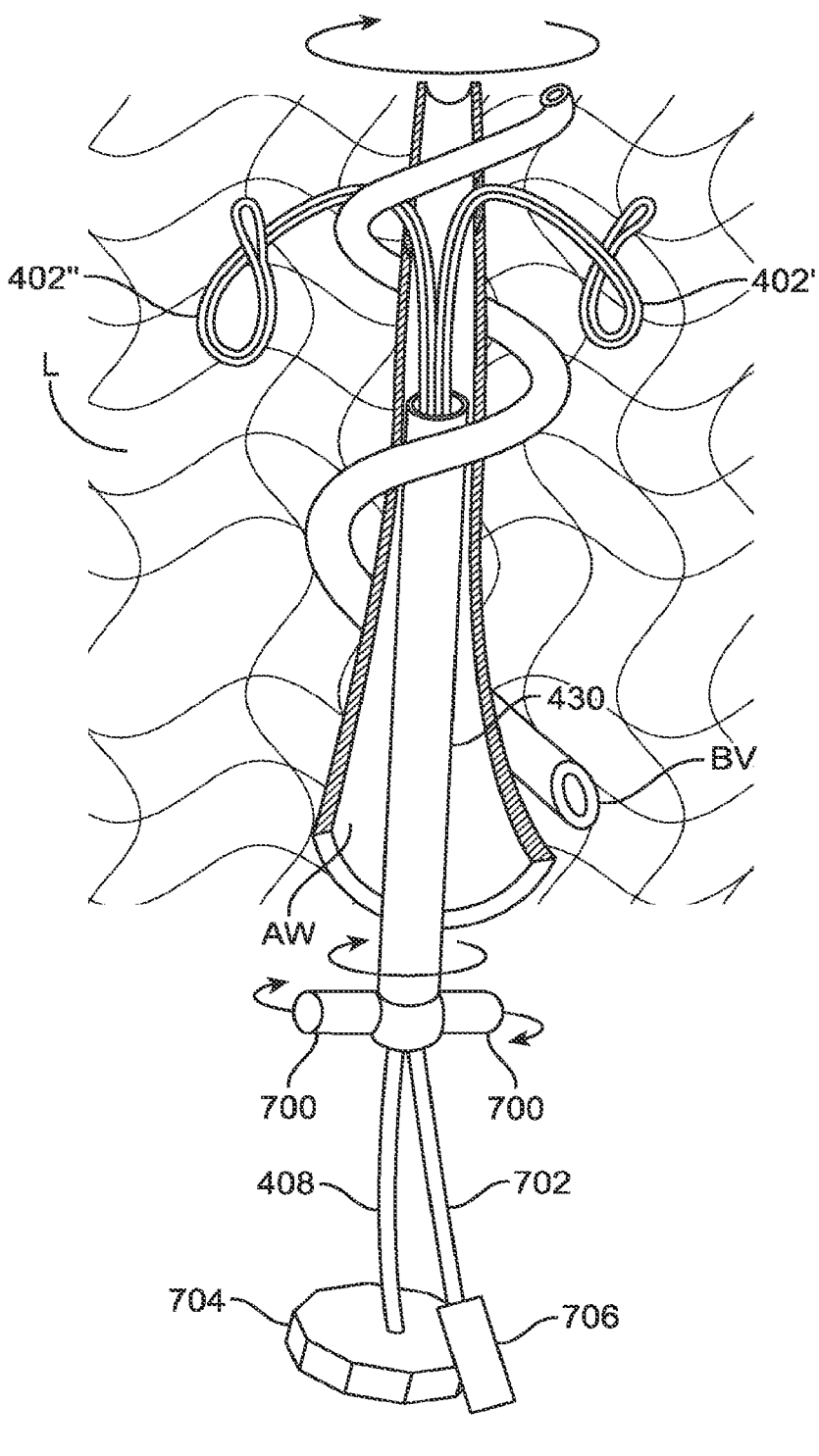
FIG. 87 illustrates an embodiment of a treatment device being rotated to rotate and tension tissue.
Figure 88:
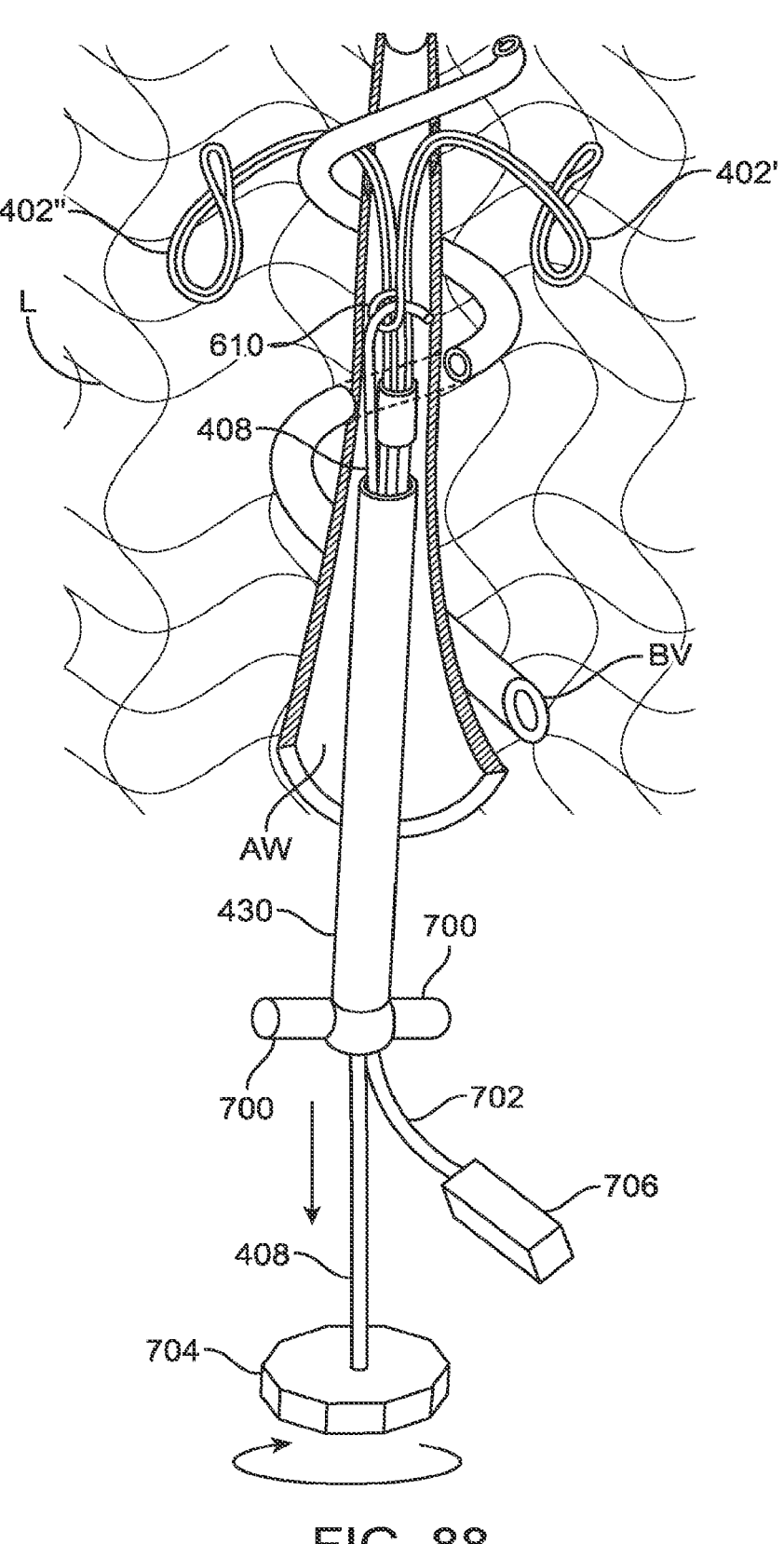
FIG. 88 illustrates an embodiment of a treatment device middle section being deployed from the catheter.

FIG. 87 illustrates torqueing steps of the method. In this embodiment, the catheter 430 and device 400 together are rotated or torqued, such as by grasping the at least one leverage element 700 and applying a torqueing force. As the device 400 rotates, the tissue gathering elements 402', 402" gather up the tissue surrounding the airway AW, along with the blood vessel BV which is now shown wrapping around the airway AW. This step tensions the tissue, as indicated by the diagonal orientation of the lines depicting the tissue, by drawing in the surrounding tissue toward the device 400. FIG. 88 illustrates further withdrawal of the catheter 430, such as by pulling the at least one leverage element 700 in the distal direction. Torque is maintained or adjusted with the use of the torqueing tool 408. The torqueing tool 408 is attached to device 400 at the location such as the attachment feature 610.

Figure 89:
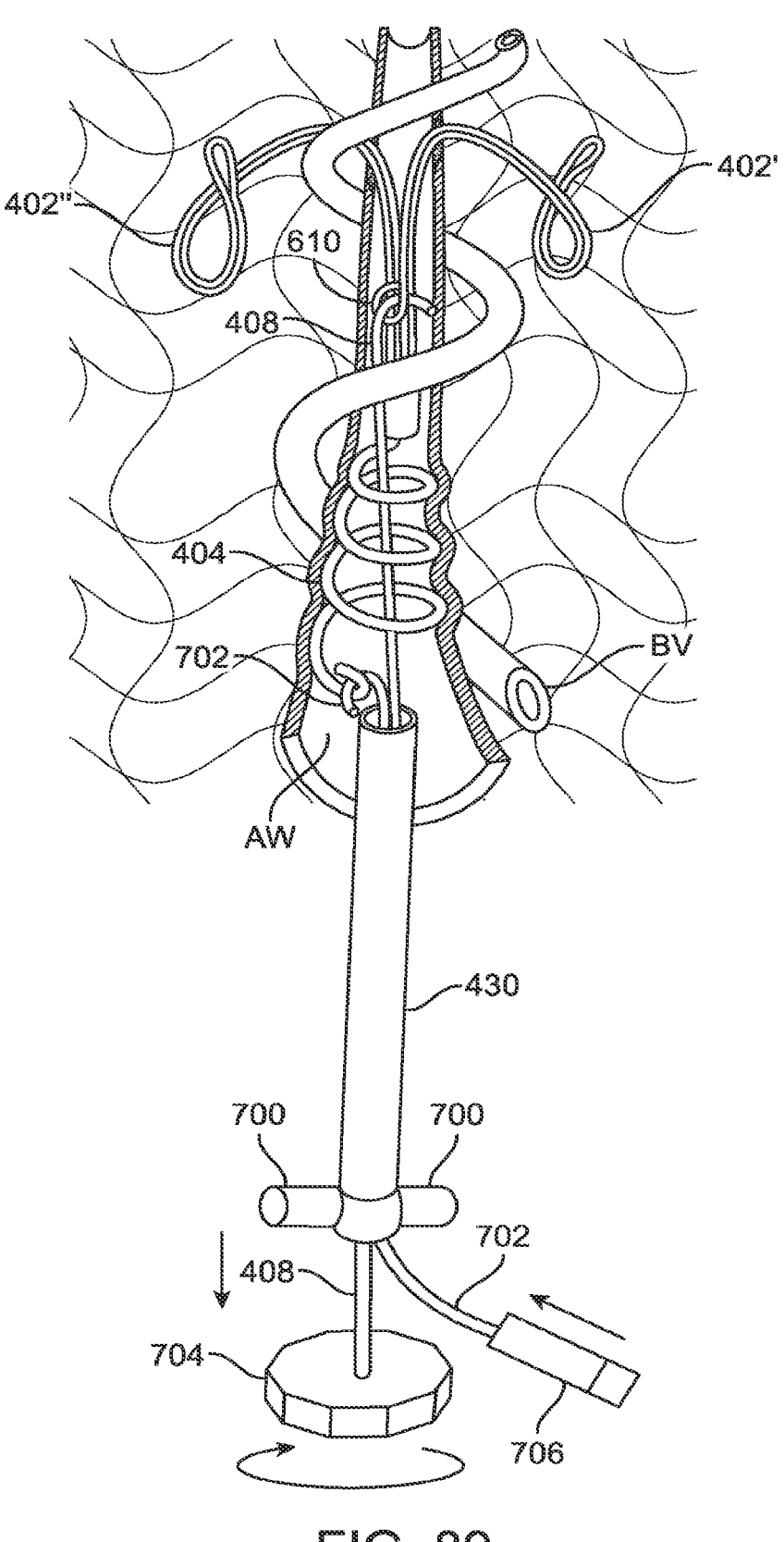
FIG. 89 illustrates an embodiment of a treatment device anchoring end being deployed to the airway ostium.
Figure 90:
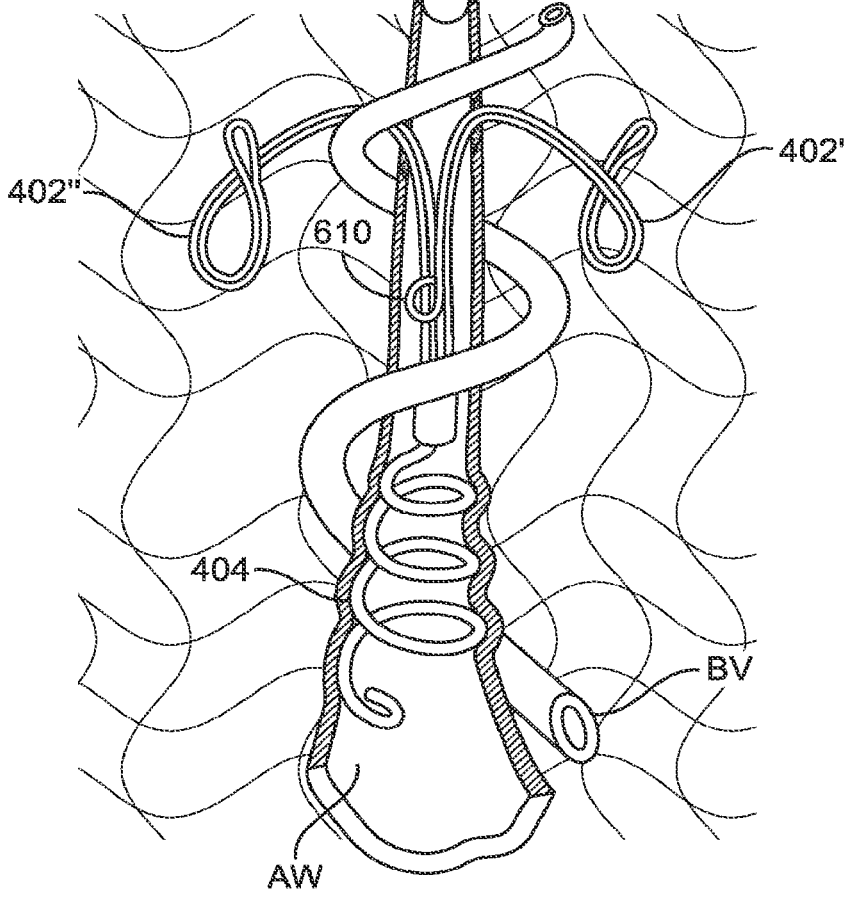
FIG. 90 illustrates an embodiment of a treatment device being decoupled from the delivery system control devices.

The device 400 is then anchored within the airway W, as illustrated in FIG. 89. In this embodiment, this is achieved by retracting the catheter 430 so as the expose the anchoring element 404 while maintaining position of the device 400 or pushing the anchoring element 404 in the distal direction by manipulation of the tether handle 706 to actuate the tether 702. In this embodiment, the anchoring element 404 comprises a coil which expands against the inner surface of the airway AW. It may be appreciated that in some embodiments the coil is wound in the opposite direction as the torqueing applied to the tissue gathering elements 402', 402". Thus, over time, any unwinding of the device 400 will cause the coil to expand, further anchoring the device 400. Referring to FIG. 90, the torqueing tool 408 and tether 702 are then disengaged from the device 400 and removed along with the catheter 430. Thus, the device 400 is left behind as an implant. It may be appreciated that the implant is typically so securely positioned that it is unable to move around sufficiently to cause coughing and other uncomfortable symptoms for the patient.

Figure 91A:
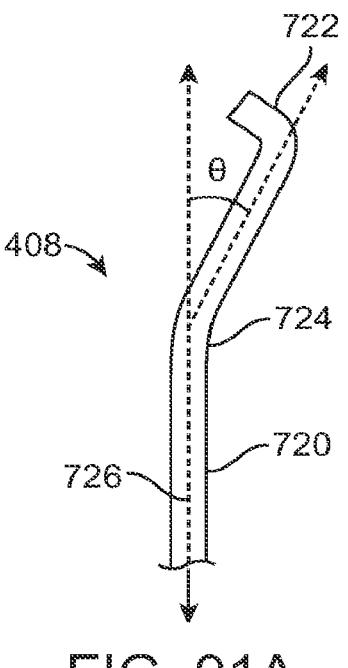
FIGS. 91A-91D illustrate design details of an embodiment of a torqueing tool and connection.
Figure 91B:
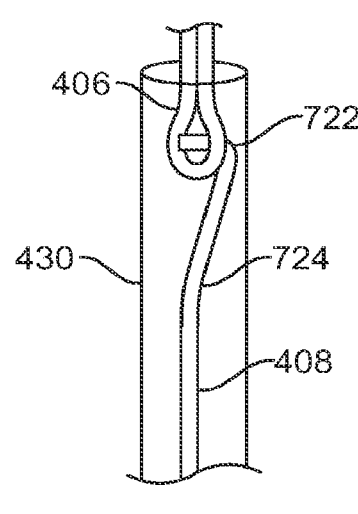
Figure 91C:
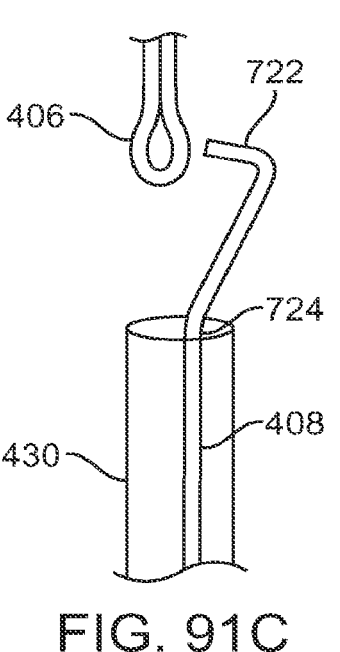

It may be appreciated that in some embodiments, the torqueing tool 408 is configured to assist in detachment from the device 400. FIGS. 91A-91C illustrate an embodiment of such a torqueing tool 408. FIG. 91A illustrates a torqueing tool 408 comprising a shaft 720 having a hooked end 722. The hooked end 722 is formed from an approximately 90 degree bend in the shaft 720 adjacent to its distal tip but the bend can range from 10 to 90 degrees to allow the hook to be easily pulled off the device 400 or it may range from 90 to 180 degrees to hook through and around the attachment end 406 (shown in FIG. 91C) of device 400 so traction is maintained. In addition, the shaft 720 has a curvature 724 set a distance proximally from the hooked end 722. In some embodiments, the curvature 724 is disposed 0.05 to 1.0 inches from the hooked end 722 of the tool 408. The curvature 724 bends the shaft 720 radially outwardly from a longitudinal axis 726 extending through the proximal end of the shaft 720. In some embodiments, the curvature 724 bends the shaft 720 radially outwards by 0 degrees, wherein 0 is in the range of 1 to 90 degrees. The torqueing tool 408 is comprised of a flexible or resilient material which allows the curvature 724 to straighten when retracted into a tube or catheter 430. FIG. 91B illustrates the tool 408 retracted within a catheter 430. The hooked end 722 is sized to maintain its hooked shape while retracted within the catheter 430. Thus, the length of the hooked end 722 (and therefore, overall width of the distal end of the torqueing tool 408) typically does not exceed 0.070 inches. Consequently, the torqueing tool 408 is able to remain attached to an attachment end 406 of a torque-based pulmonary treatment device 400 while the hooked end 722 resides within the catheter 430. This allows the tool 408 to torque the device 400 as desired. Once the desired torqueing has been achieved, the torqueing tool 408 may be removed from the attachment end 406 by simply advancing the tool 408. This allows the hooked end 722 to spring radially outwardly due to the preset curvature 724, as illustrated in FIG. 91C. This disengages the hooked end 722 from the attachment end 406. The tool 408 can then be retracted into the catheter 430 once again and removed, leaving the device 400 behind.

Figure 91D:
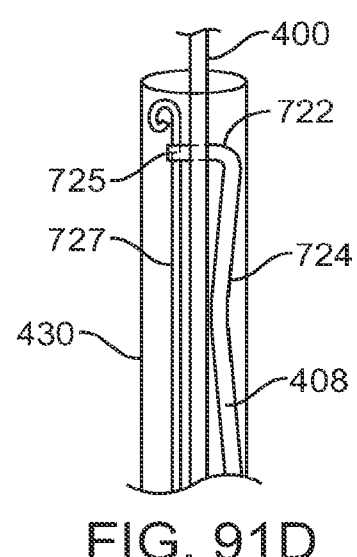

In some embodiments, as illustrated in FIG. 91D, the torqueing tool 408 includes a cross drilled end hole 725 which passes through the hooked end 722 of shaft 720, so a hitch wire 727 can be threaded through the hole 725. This holds the torqueing tool 408 in engagement with the device 400, such as to the attachment end 406 or to an attachment fixation feature 610. The end hole 725 may be drilled through the torqueing tool 408 in any orientation, relative to the axis along the length of the shaft 720 of the torqueing tool 408. FIG. 91D illustrates the torqueing tool 408 that has been inserted through hole or slot of an attachment feature 610. The hitch wire 727 has been threaded through the torqueing tool 408 end hole 725 to connect the torqueing tool 408 to the device 400. In some embodiments, the hitch wire 727 is made from metallic wire, nitinol, suture, polymer, monofilament line, braided material, glass, organic fiber or shape memory NiTi wire. The distal end of the hitch wire 727 is typically shaped to form a non-straight end shape, such as a curl or loop, that is designed to create drag or pulling resistance as it is pulled through the torqueing tool 408 end hole 725. This prevents the hitch wire 727 from accidentally being pulled out prematurely. In some embodiments, the hitch wire 727 is a suture that is threaded through the end hole 725 and tied to form a complete loop that is exposed outside the delivery system so as to be accessible to the user. By forming a loop, the hitch wire 727 cannot be accidentally removed. Alternatively, the user can easily cut the loop and withdraw the hitch wire 727 at any time the torqueing tool 408 needs to be removed from device 400.

Figure 92:
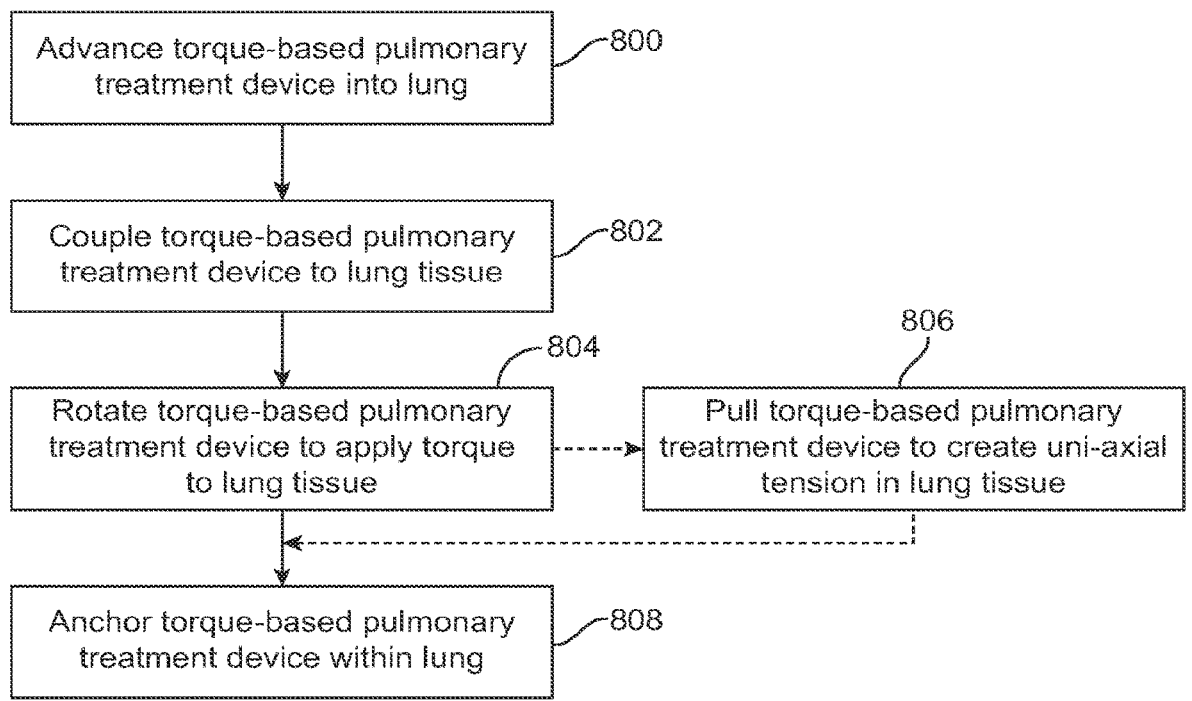
FIG. 92 illustrates steps of an embodiment of a method that includes basic treatment steps that utilize torque to affect tissue.

FIG. 92 outlines steps of an example method of treating a patient with a torque-based pulmonary treatment device 400. To begin, the first step 800 describes that the device 400 is advanced into a lung. It may be appreciated that in some embodiments such advancement is through the mediastinum, through the trachea, through an airway, through the chest wall, through an opening in the chest, through blood vessels, through wall or barriers that define the previously described structures in the body or between ribs, to name a few. Likewise, in some embodiments, such advancement is with the use of a trocar, guide introducer, catheter, endoscope or bronchoscope. The second step 802 describes coupling the device 400 to lung tissue. In some embodiments, such coupling includes pulling back to engage the lung tissue, advancing to engage the lung tissue, rotating to engage the lung tissue, unsheathing at least a portion of the device 400 to allow expansion of the device 400, unsheathing at least a portion of the device 400 to allow bending of the device 400, advancing at least a portion of the device 400 through an airway wall, removing a constraint to allow expansion of the device 400 (such as removing a sleeve, removing a pin, removing a hitch wire, cable or knot, melting a polymer, unzipping a seam, splitting a sheath wall, applying a current to melt a metal connection, etc.), deploying a balloon to expand at least a portion of the device 400, pulling a draw string to actuate at least a portion of the device 400, pushing a push rod to actuate at least a portion of the device 400, shortening a structure to radially expand at least a portion of the device 400, pulling a tether to pull at least a portion of device 400, bending or rotating a torqueing tool to rotate at least a portion or feature of device 400, barbing at least a portion of the device 400 into tissue, or allowing self-expansion of at least a portion of the device 400, to name a few. The third step 804 describes rotating the device 400 to apply torque to lung tissue. In some embodiments, such rotation includes twisting to apply torque, pulling tissue along tangent, pulling tissue in an arc direction, curvilinear pulling, creating tension along a perpendicular plane relative to a longitudinal axis of the device, non-uniaxial tensioning of tissue, lung volume reduction by rolling tissue around a hub or tissue gathering element 402 spooling tissue on the device, winding tissue around the device, shortening tissue in the lung by winding, compressing lung volume or reducing lung volume by compressing tissue around a tissue gathering element 402 or by compressing tissue by wrapping tissue over itself as it's wound around a tissue gathering element 402 to name a few. Optionally, a fourth step 806 is included which describes pulling the device 400 to create a uni-axial displacement, translation, stress, strain or tension in the lung. And the fifth step 808 describes anchoring the device 400 within the lung. In some embodiments, this includes releasing stored elastic energy to engage an anchoring element 404, hooking an anchoring element 404 into tissue, expanding the anchoring element 404 against lung tissue or otherwise coupling the anchoring element 404 to lung tissue so counter rotation of device 400 is resisted by the tissue the anchoring element 404 is coupled to.

Figure 93:
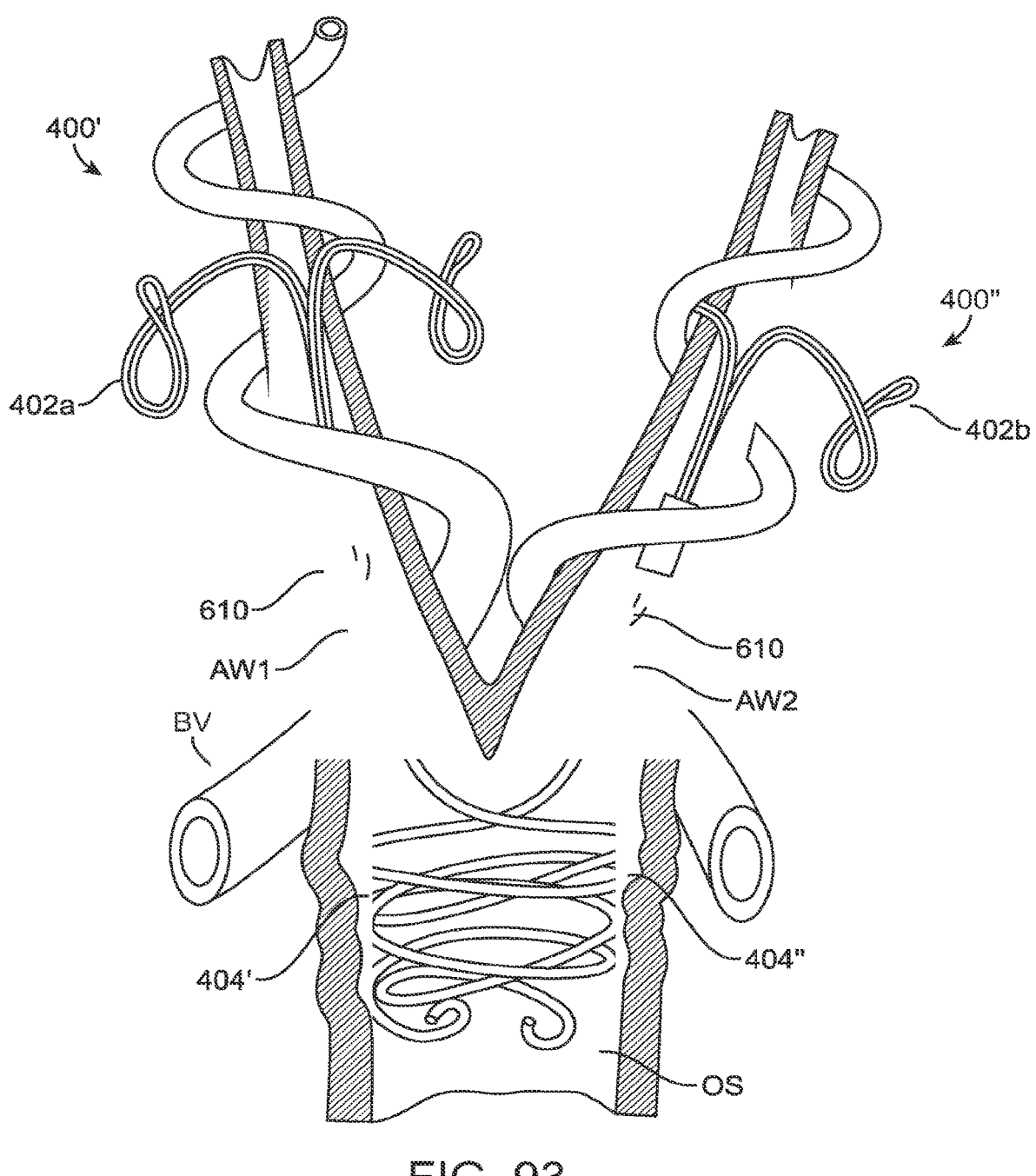
FIG. 93 illustrates an example of two treatment devices deployed into adjacent airways.

FIG. 93 illustrates an embodiment of the placement of two torque-related pulmonary treatment devices (a first torque-related pulmonary treatment device 400' and a second torque-related pulmonary treatment device 400"). In this embodiment, each device 400', 400" is comprised of a tissue gathering element 402a and another tissue gathering element 402b, each extending outwardly and then curving around and back in a loop shape, such as illustrated in FIG. 84A. Likewise, the first device 400' includes a first anchoring element 404' and the second device 400" includes a second anchoring element 404". Referring back to FIG. 93, the first torque-related pulmonary treatment device 400' is positioned so that its tissue gathering elements 402a, 402b are disposed within a first airway AW1. Similarly, the second torque-related pulmonary treatment device 400" is positioned so that its tissue gathering elements 402a, 402b are disposed within a second airway AW2. Torque is applied to each device 400', 400" either simultaneously or in series, so that their tissue gathering elements 402a, 402b to gather up the surrounding tissue (as indicated by the twisted configuration of the blood vessels BV). In some embodiments, torque is applied to the first device 400' in a first direction and torque is applied to the second device 400" in an opposite direction. In any case, torqueing re-tensions the lung, as described hereinabove. In this embodiment, the devices 400', 400" are then both anchored within a common airway proximal to the first and second airways AW1, AW2, such as in an ostium OS. In this embodiment, each anchoring element 404', 404" has the shape of a coil. In such embodiments, it is desirable that the coil is wound in a direction opposite to the direction of the torque/rotation of the tissue gathering elements 402a, 402b. Thus, any unwinding of the torque would further expand the corresponding anchoring element. In FIG. 93, the anchoring elements 404', 404" are positioned within the ostium OS so as to overlap with each other. In some embodiments, the anchoring elements 404', 404" are positionable so as to overlap and in other embodiments, the anchoring elements 404', 404" are manufactured as intertwined so as to be delivered in an intertwined configuration. In any case, the anchoring elements 404', 404" take up minimal space when positioned in the same or overlapping portions of the ostium OS or airway. Likewise, when the devices 400', 400" are torqued in opposite directions, the devices 400', 400" are able to counterbalance each other, thereby placing less load on the ostium OS or airway at the point of anchoring.

FIG. 94 outlines steps of an example method of treating a patient with two pulmonary treatment devices. The pulmonary treatment devices may be torque based or linear so as to lead to the following combinations: two linear pulmonary treatment devices 10, two torque-based pulmonary treatment devices 400 or one linear pulmonary treatment device 10 and one torque-based pulmonary treatment device 400. To begin, the first step 820 describes advancing a first pulmonary treatment device (torque-based on linear) into a lung at a first target location. The second step 822 describes advancing a second pulmonary treatment device (torque-based on linear) into the lung at a second target location. The third step 824 describes actuating the first and/or second pulmonary treatment devices to tension the lung. And, the fourth step 826 describes coupling the pulmonary treatment devices together to maintain tensioning of the lung.

Figure 95:
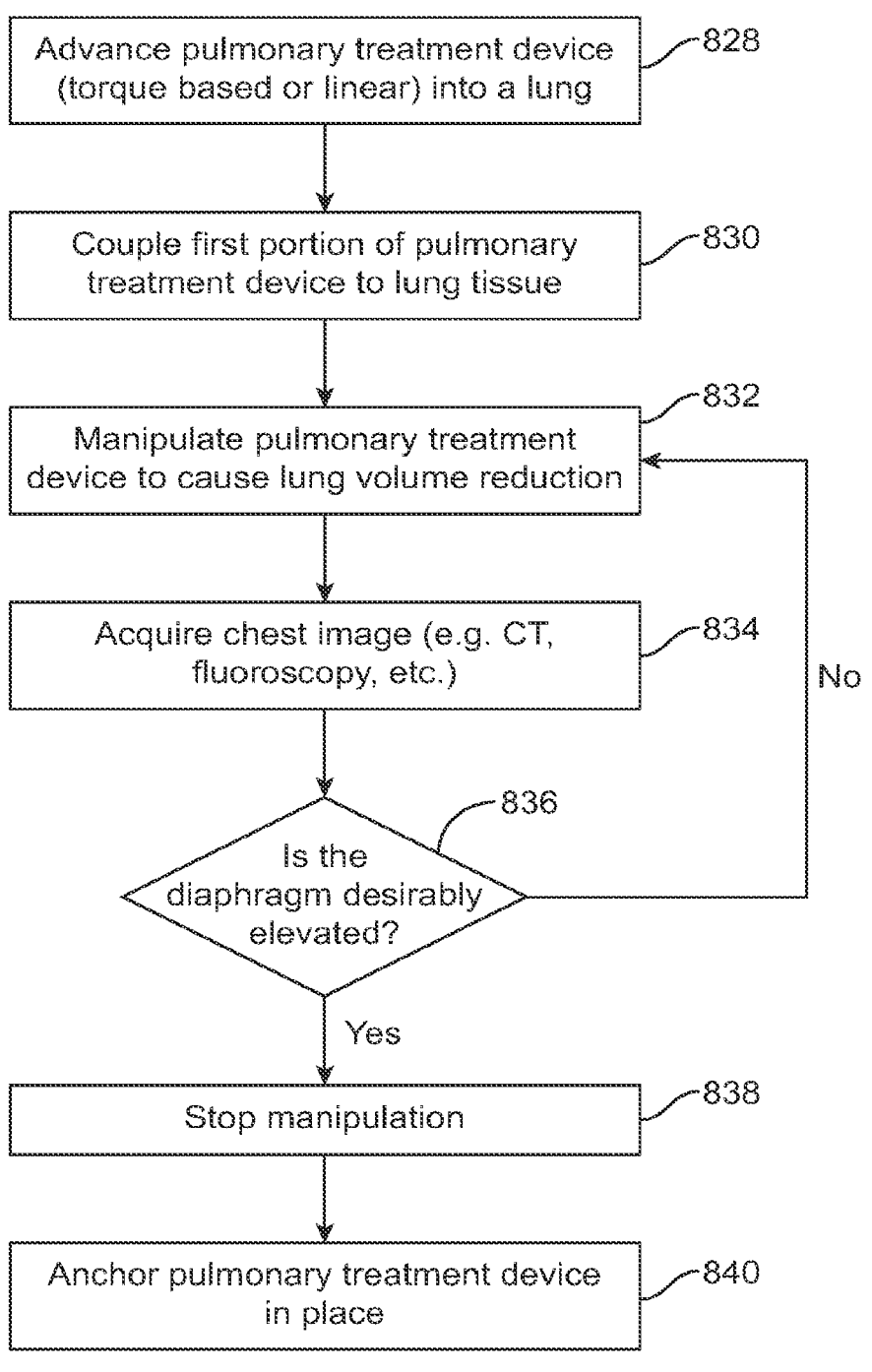
FIG. 95 illustrates steps of an embodiment of a method to deploy a treatment device while seeking anatomical feedback.

FIG. 95 outlines steps of an example method of treating a patient with a pulmonary treatment device while monitoring with imaging. The pulmonary treatment device may be linear or torque-based. To begin, the first step 828 describes advancing the pulmonary treatment device into a lung. The second step 830 describes coupling a first portion of the pulmonary treatment device to lung tissue. The third step 832 describes manipulating the pulmonary treatment device to cause lung volume reduction. The fourth step 834 describes acquiring a chest image, such as via computed tomography (CT), fluoroscopy or any other imaging method or modality that has been described herein or other data may be assessed such as any of the measurable physiologic changes listed herein that indicate improved breathing in COPD patients. The chest image or data is then analyzed to determine if the diaphragm is desirably elevated (as described in the fifth step 836) or to determine if any of the measurable physiologic changes listed herein that indicate improved breathing in COPD patients has been shown. If not, the method is then repeated from the third step 832 wherein the pulmonary treatment device is further manipulated. If so, then manipulation ceases, as indicated in the sixth step 838. The device is then anchored in place, as indicated in the seventh step 840.

Figure 96:
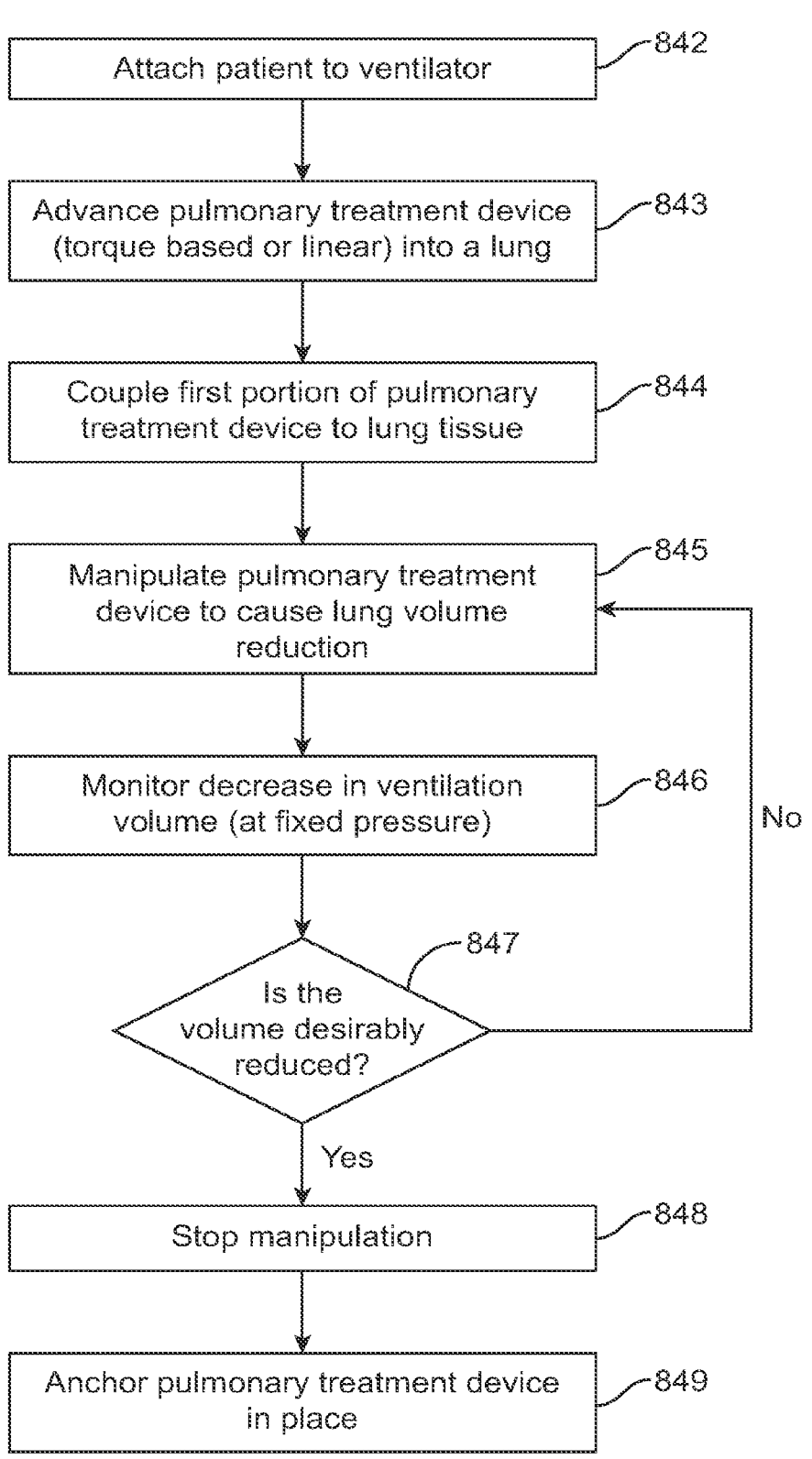
FIG. 96 illustrates steps of an embodiment of a method to deploy a treatment device while seeking physiologic feedback.

FIG. 96 outlines steps of an example method of treating a patient with a pulmonary treatment device while monitoring with the use of a ventilator. The pulmonary treatment device may be linear or torque-based. To begin, the first step 842 describes attaching the patient to the ventilator. The ventilator should be set to provide breathable gas into the patient until a constant peak pressure is achieved during each breathing cycle. The required volume of delivered breathable gas to achieve the constant peak pressure should be noted. The second step 843 describes advancing the pulmonary treatment device into a lung. The third step 844 describes coupling a first portion of the pulmonary treatment device to lung tissue. The fourth step 845 describes manipulating the pulmonary treatment device to cause lung volume reduction. The fifth step 846 describes monitoring a decrease in ventilation volume of breathable gas that is required to achieve the constant peak pressure. In some instances, a volume reduction of 20-1500 cc is desired, however, a volume reduction of 300-500 cc is typically considered desirable. The volume reduction is then analyzed to determine if it is sufficiently reduced (as described in the sixth step 847). If not, the method is then repeated from the fourth step 845 wherein the pulmonary treatment device is further manipulated. Alternatively, an additional device 400 may be installed to further reduce the volume of breathable gas that must be ventilated into the patient to achieve the constant peak pressure during each breathing cycle. If the volume reduction is sufficiently reduced (as described in the sixth step 847), then manipulation ceases, as indicated in the seventh step 848. The device is then anchored in place, as indicated in the eighth step 849.

In some embodiments, the torque-based pulmonary treatment device 400 is positioned in the lung by a surgical procedure, such as a minimally invasive video assisted portal procedure or an open procedure. In such embodiments, the device 400 is not anchored in place by stabilization within an ostium or airway. Rather, the device 400 is anchored within lung tissue by suturing or balancing torque forces. FIGS. 97A-97C illustrate an embodiment of a device 400 which may be positioned in the lung by a surgical procedure. Here, the device 400 has a first pair of tissue gathering elements 402a, 402b, each tissue gathering element 402a, 402b extending outwardly radially outwardly from a longitudinal axis 411 and then curving around and back toward the longitudinal axis 411 in a loop shape, such as illustrated in FIG. 84A. The device 400 also has a second pair of tissue gathering elements 402c, 402d. In this embodiment, these tissue gathering elements 402c, 402d mirror the first pair of tissue gathering elements 402a, 402b around an axis 850 which is perpendicular to the longitudinal axis 411. Thus, in this embodiment, both pairs of tissue gathering elements (402a, 402b) (402c, 402d) extend radially outwardly from the longitudinal axis 411 and then curve toward the axis 850 before curving back toward the longitudinal axis 411. In some embodiments, the device 400 includes a coupler 852 to connect the tissue gathering elements 401a and 402b and possibly the anchoring elements 402c and 402d. In some embodiments, the device 400 includes an attachment feature 854 which is used to attach a torqueing tool 408 to the device 400 to rotate the distal end of device 400 to apply torqueing loads to the surrounding lung tissue. A suture or other fixation device may be used to attach the attachment feature 854 to the lung tissue within the lung L.

Figure 98:
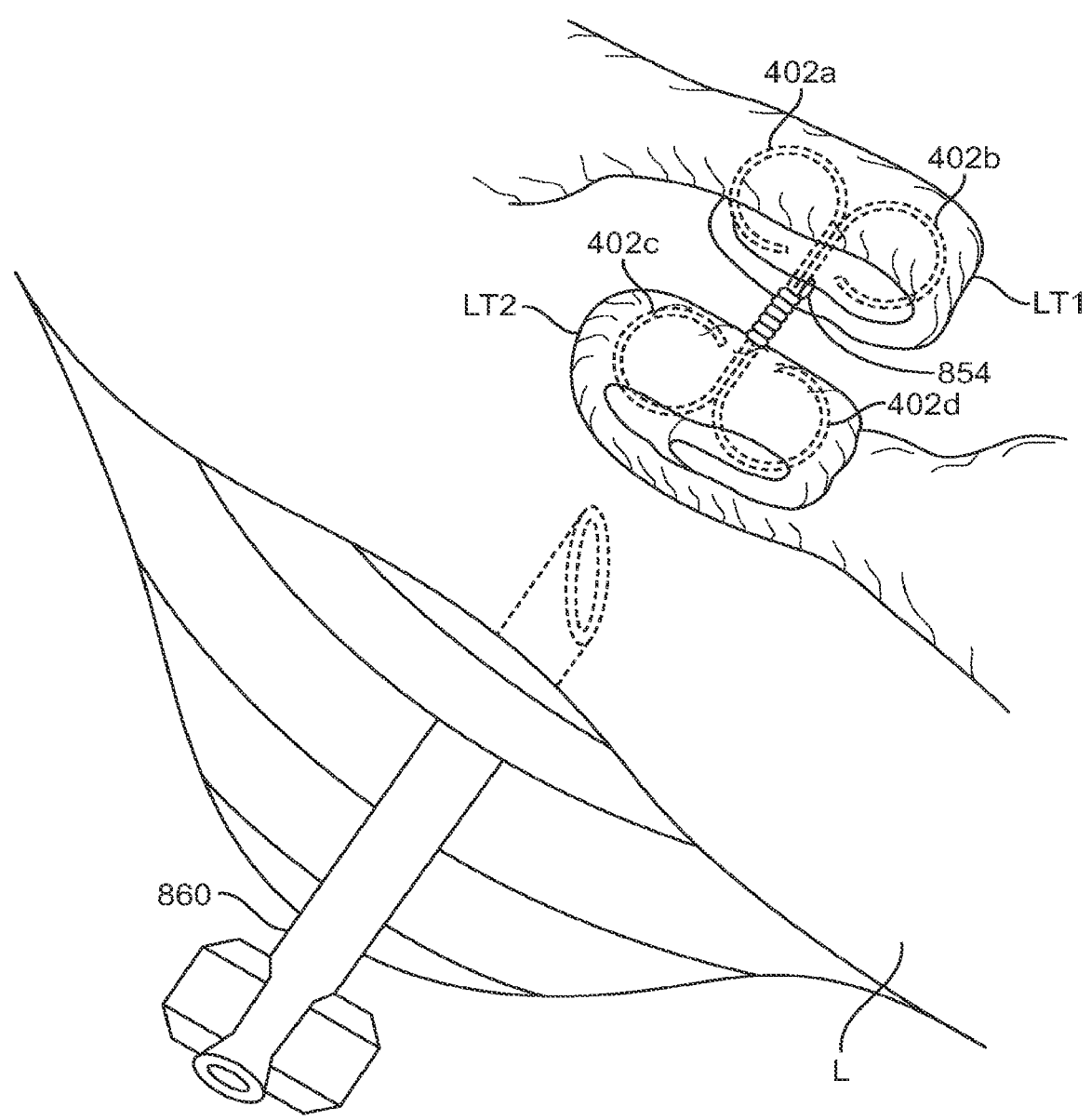
FIG. 98 illustrates the treatment device of FIG. 97A surgically installed.

FIG. 98 illustrates the device 400 of FIGS. 97A-97C in use. FIG. 96 shows access to lung tissue of the lung L with the use of a trocar or cannula 860. The device 400 loaded within a distal end of delivery catheter 430 and the distal end of the catheter 430 is advanced through the cannula 860 to a target location within the lung L. The first pair of tissue gathering elements 402a, 402b are then deployed and torqued so as to gather up a first portion of lung tissue LT1. The second pair of tissue gathering elements 402c, 402d are then deployed and torqued so as to gather up a second portion of lung tissue LT2. In this embodiment, the first portion of lung tissue LT1 and the second portion of lung tissue LT2 are torqued in opposite directions. Such torqueing in opposite directions creates a counter-balance, anchoring the device 400 in place. Alternatively or in addition, the device 400 may be anchored in place by joining the fixation feature 854 to the lung tissue with the use of a fixation element, such as a suture, staple, tissue glue, coagulated blood or by using other devices that are sufficiently biocompatible and designed to connect tissue and device components to tissue.

It may be appreciated that in some embodiments, one or more torque-based pulmonary treatment devices 400 may be used to "wad up" tissue, so as to close off airways, close communication of gas in diseased tissue or close off gas exchange in the lung. This may be utilized to tune where preferential filling occurs. Thus, it may be desired to block flow to severely diseased parts of the lung so that filling preferentially occurs in the less severe parts of the lung. Any devices described herein may be used to block the flow of gas in one or both directions to cause atelectasis or shrinkage of volumes of the lung. Ideally, portions of the lung can be completely blocked off to cause atelectasis. Such methods may also may be used to stop chronic air leaks in lung fistulas that are currently very difficult to treat effectively. Such small leaks in the pleura typically cause repeated pneumothorax incidents. Thus, the torque-based pulmonary treatment devices may be a minimally invasive treatment to block the leak by twisting tissue to block air flow.

Additionally, these devices and methods may be used to block, reduce or generally regulate the flow of blood through the lung so as to minimize the flow of insufficiently or minimally oxygenated blood that flows through areas of lung with severe damage. Patients will benefit by reducing the flow of blood that is under-oxygenated because mixing this blood with fully oxygenated blood, as the blood streams exit the lungs, allows for oxygen dilution that leads to reduced oxygen as a percentage of blood volume in the patient's vascular system. Blocking the flow of under-oxygenated blood before the blood exits the lungs actually increases the percentage of blood oxygen in the patient's system. The other benefit to blocking the flow of blood through areas in the lung that are severely damaged by emphysema is that the $CO_2$ that is normally not sufficiently transported out of the blood in these damage regions so it should not be allowed to be mixed with low $CO_2$ or normally conditioned blood where the blood streams combine and exit the lungs. By blocking blood flow in severe areas of the lung, the blood that does exit the lungs carries a higher percentage of oxygen and a lower percentage of $CO_2$ than the levels of these gases that would otherwise be present in typical emphysema or COPD patients.

E. Placement

Many of the pulmonary treatment devices (torque-based and linear) described herein may be placed in any lung, lobe, mainstem segment, segment, sub-segment or even farther down the airway tree. Likewise, many of the devices may be placed directly through the chest wall into the lung or through the wall of the main bronchi to access pockets of destroyed parenchyma. Many of the devices may be implanted via open chest procedure or with the use of any type of endoscope.

The number, type and placement location of the devices are chosen to best treat the disease type and disease state of the patient. Restoring tension and lung elastic recoil in the lung with these devices mitigates the symptoms typically experienced by COPD patients and patients suffering from other lung conditions. The devices described herein are capable of producing a tremendous amount of work to tension lung tissue. These lung treatments have been shown to induce biologic feedback in the lungs that further enhances the reduction of symptoms, restoration of lung elastic recoil, enhancement of the lifting displacement of the diaphragm and general restoration of breathing mechanics in patients. Treatment magnitude, during each device deployment, is controlled by controlling the amount of force that is placed on the tissue, the linear distance that the proximal or distal end of the device is translated or the amount of rotation that is applied to a treatment device that acts upon tissue with the application of torque. Additionally, linear force and linear translation as well as the application of torque may be combined with any of the embodiments provided herein to enhance the amount of work performed on the lung tissue. By controlling these forces, a patient may be treated with one or more devices in a single major lobe of the patient's lung, more than one major lobe or all of the major lobes. It may be appreciated that a patient has four major lobes in the lung. It may also be appreciated that major lobes may also include the middle lobe in the right lung and the Lingula in the left lung of a patient.

In some embodiments, the first treatments target the lobes with the maximum amount of tissue damage, as can be determined using quantitative computed tomography (CT) analysis (CT image file post processing) that analyzes the least dense portions of the lung. Any number of CT analyses may be studied to determine the most severe portions of each lobe and the magnitude and nature of the damage. Patients with heterogeneous lung damage typically present with severely damaged upper lobes and generally preserved lower lobes. These patients should be treated with implantation in the upper lobes and possibly not in the lower lobes during the initial treatments. If the patient doesn't respond adequately, additional devices may be implanted and those may be added to the upper lobes or they may be implanted in the lower lobes to balance the tensioning forces in the lungs.

Homogeneous patients generally present with mild to severe damage in all four major lobes. It is preferable to treat one, two or three lobes in a single lung during a single intervention or implantation event so that mucus, bacteria, fungus or other infectious contaminants are not transferred from one lung to the other during a treatment. That way bilateral infections are avoided. If all major lobes are to be treated, it is preferable to treat each lung during one of two total procedures. A single lobe may be treated during a single procedure or a combination of lobes may be treated during a series of treatments. If the delivery methods described herein may be used to deliver into a patient each device 400 in less than 10 minutes or with the use of 10 or less minutes of energized fluoroscope time, patient risk to x-ray exposure and risk of hypoxemia will be reduced. In homogeneous patients, it is important to treat at least all four major lobes. In order to uniformly lift the diaphragm, all patients preferably benefit by receiving treatment in at least one lobe in each of the patient's two lungs. Treatment success requires that the treatment gathers a threshold amount of relatively loose tissue to a slightly tightened condition that is approximately physiologically normal. If a patient does not respond positively to a treatment, this only indicates that the dose was not sufficient and more devices should be placed to transcend the threshold minimum tissue displacement to tension the loose elongated tissue, hold airways open to allow expiration of gas during exhale events and to lift the diaphragm enough to restore diaphragm pumping motion. The pulmonary function tests listed herein are excellent indicators of positive and adequate response.

It may be appreciated that the more severely affected patients may require treatments that are delivered in stages that progressively build a dose level to accomplish several possible outcomes. For these patients, low doses may result in some elimination of slack in the lung tissue but inadequate tensioning to lift the diaphragm enough or it may provide an inadequate dose to delay airway closure during exhalation. With implantation of additional devices, the patient may experience sufficient tensioning to lift the diaphragm and hold airways open enough to show positive reduction of symptoms described herein but not enough of a dose to adequately tension the majority of the lung volume. With implantation of additional devices, the patient may show positive reduction of symptoms on a large number of the symptoms listed herein. At this stage, the treatment may be successful, but the duration of the benefit may still be improved. Implantation of a larger number of devices or implantation with a higher degree of displacement, force, or torque (or higher level of a combination of displacement, force, and torque) will present such a high degree of stress and strain on the lung tissue that it responds in the same way that tissue responds to typical tissue injury. This can be quite beneficial to the patient.

The lung tissue is quite radio transparent using typical medical imaging such as fluoroscopy, computed tomography (CT), and X-ray imaging. However, if the lung tissue is stressed sufficiently, the tissue hydrates and this presents in images as consolidation with opacities that sometime present with local consolidates. The tissue goes into a wound healing cascade that manifests as opacities in the tissue between devices, between devices and the pleura, and between anatomical features of the lung. Wherever the tissue is stressed and strained sufficiently, bands of opaque shades present in the images that indicate that the treatment dose has been applied sufficiently to yield a maximum effect that is possible in these severe COPD and emphysema patients. As the wound healing cascade progresses, the end stage presents as tissue healing and contraction which further enhances the lifting of the diaphragm and tensioning of the lung tissue throughout the patient's lung. This contraction adds a high impact to boost the benefit of the treatment and the combination of slight scaring in the contracted tissue seems to reinforce the tissue in a way that allows the effect to be maintained for long periods of time such as 1 to 10 years but normally 3-5 years. The wound healing cascade can be managed using steroidal treatments to control the rate of healing, slightly alleviate contraction and the magnitude of effect. This also manages the pain that is sometime associated with the high degree of tensioning that this presents. In addition, this minimizes symptoms that often lead the attending physicians into erroneously believing that the patient suffers from pneumonia, such as elevated body temperature and flu symptoms. Additionally, because these patients already present with compromised immune mechanisms, they are more susceptible to the effects of infection and colonization of inherent fungus in the lung, so the use of steroid treatment to manage stress induced opacity, is recommended. Normally antibiotic treatments tend to mitigate the effect of steroids so a mix of antibiotic treatments may be prescribed but the major drug regimen should be dominated by steroids or some nonsteroidal anti-inflammatory drug such as the (NSAID) class that is commonly referred to as Ibuprofen.

After straining lung tissue, airway walls, blood vessels, pulmonary arteries, pulmonary veins, alveoli, alveolar ducts, smooth muscle, interstitial connective tissue, capillary beds, elastic fibers and collagen fibrils sufficiently to cause a wound healing response, the inflammatory phase is the first phase of healing and is characterized by hemostasis and inflammation. Hemostasis is initiated during the exposure of collagen during wound formation that activates the intrinsic and extrinsic clotting cascade in the available vasculature. In addition, the injury to tissue causes a release of thromboxane A2 and prostaglandin 2-alpha to the wound bed causing a potent vasoconstrictor response. Furthermore, the extravasation of blood constituents provides the formation of the blood clot reinforcing the hemostatic plug. This initial response helps to limit hemorrhage and provides an initial extracellular matrix for cell migration. Platelets are among the first response cells that play a key role in the formation of the hemostatic plug. They secrete several chemokines such as epidermal growth factor (EGF), fibronectin, fibrinogen, histamine, platelet-derived growth factor (PDGF), serotonin, and von Willebrand factor. These factors help stabilize the wound through clot formation and also attract and activate macrophages and fibroblasts. They also act to control bleeding and limit the extent of injury. Platelet degranulation activates the complement cascade, specifically C5, a potent neutrophils chemotactic protein. Vasoactive mediators and chemokines are released by the activated coagulation cascade, complement pathways, and parenchymal cells which play a key role in the recruitment of inflammatory leukocytes to injured skin.

After hemostasis is achieved, capillary vasodilatation and leakage result secondary to local histamine release by the activated complement cascade. The increased blood flow and altered vascular permeability allow for the migration of inflammatory cells to the wound bed. The presence of foreign organisms further stimulates the activation of the alternate complement pathway. Complement C3 activation results in a cascade of non-enzymatic protein cleavage and interactions that eventually stimulate inflammatory cells and the lysis of bacteria.

The second response cell to migrate to the wound after complement activation and platelet recruitment is the neutrophil. It is responsible for debris scavenging, complement-mediated opsonization and lysis of foreign organisms, and bacterial destruction via oxidative burst mechanisms (i.e., superoxide and hydrogen peroxide formation). Neutrophils kill bacteria and decontaminate the wound from foreign debris. These wastes are later extruded with the eschar or phagocytosed by macrophages. Macrophages are important phagocytic cells that play a key role in wound healing. They are formed from monocytes stimulated by fragments of the extracellular matrix protein, transforming growth factors and monocyte chemoattractant protein 1. In addition to direct phagocytosis of bacteria and foreign materials, macrophages secrete numerous enzymes and cytokines; collagenases, which debride the wound; interleukins and tumor necrosis factor (TNF), which stimulate fibroblasts and promote angiogenesis; and transforming growth factor (TGF), which stimulates keratinocytes. Macrophages also secrete platelet-derived growth factor and vascular endothelial growth factor which initiate the formation of granulation tissue and thus initiate the transition into the proliferative phase and tissue regeneration.

The proliferative phase is the second phase of wound healing and it is marked by epithelialization, angiogenesis, granulation tissue formation, and collagen deposition. Epithelialization occurs within hours after injury in wound repair. With an intact basement membrane, the epithelial cells migrate upwards in the normal pattern as occurs in a first-degree skin burn whereby the epithelial progenitor cells remain intact below the wound and the normal layers of epidermis are restored in 2-3 days. If the basement membrane has been damaged, then the wound periphery re-epithelializes the wound. Neovascularization is necessary to deliver nutrients to the wound and help maintain the granulation tissue bed. Angiogenesis has been attributed to many molecules including fibroblast growth factor, vascular endothelial growth factor, transforming growth factors, angiogenin, angiotropin, angiopoietin 1, tumor necrosis factor alpha, and thrombospondin. In emphysematous lung tissue where there is little to no vascularization, this critical nutrient supply by capillaries is insufficient to sustain the tissue deposition in the granulation phase and may result in a chronically unhealed wound in some portions of the patient's lungs. The proliferative phase ends with granulation tissue formation. This new stroma begins to invade the wound space close to four days after injury. The new blood vessels at this time have provided a facilitated entry point into the wound to cells such as macrophages and fibroblasts. Macrophages continue to supply growth factors stimulating further angiogenesis and fibroplasia. The secreted platelet-derived growth factor and transforming growth factors along with the extracellular matrix molecules stimulate fibroblasts differentiation to produce ground substance and then collagen. Fibroblasts are the key players in the synthesis, deposition, and remodeling of the extracellular matrix providing strength and substance to the wound.

The third and final phase of wound healing is the maturational phase. This is characterized by the transition from granulation tissue to scar formation. Close to two weeks after injury, the wound undergoes contraction, ultimately resulting in a smaller amount of apparent scar tissue. Collagen deposition by fibroblasts continues for a prolonged period with a net increase in collagen deposition reached after three weeks from tissue injury. The entire process is a dynamic continuum dictated by numerous growth factors and cells with an overlap of each of the three phases of wound healing to provide continued remodeling. The wound is estimated to reach its maximal strength at one year, with a maximal tensile strength that is 70% of normal lung parenchyma.

F. Implant Removal

It may be appreciated that in some instances the device 400 may need to be removed. It may be determined that the device 400 may need to be removed to be repositioned if the initial deployment isn't ideal or this may be determined after the deployment has been performed. If the initial deployment has been misplaced or too much torque has been applied to the tissue, it may be desired to recapture and adjust the device 400 to remove torque based stress on the lung tissue. Or it may be desired to recapture and adjust the device 400 to reduce linear or uniaxial tension that the device 400 is imparting on the lung tissue. It may also be appreciated that a torqueing tool 408 may be releasably coupled to the far proximal end of the device 400 at an attachment feature 610 near the proximal end that allows the user to control the deployment of the anchoring element 404 and to allow for the possibility of removing the device 400 in an orderly manner.

G. Torqueing Tool

It may be appreciated that in some instances the torqueing tool 408 is provided to the end user already attached to device 400. In some embodiments, one or more torqueing tools 408 are releasably attached to the device 400 during a manufacturing step to spare the end user from making the attachments during the procedure. In other embodiments, the tool 408 is attached by the user, such as just before delivering device 400 to the patient or while delivering device 400 to the patient. In some embodiments, the torqueing tool 408 is made from metal or organic materials such as carbon fiber, ceramic, plastic, glass or a combination of these materials. In some embodiments, the torqueing tool 408 is terminated with a handle or a wire form loop that can accommodate a finger or thumb to facilitate rotation. The distal end section of the torqueing tool 408 is resilient so as to pass through bends in human anatomy or common bends in a typical endoscope or bronchoscope. However, stiffness of the shaft 720 may vary to reliably transmit torque efficiently.

In some embodiments, torque transmission is such that a single turn at the control or user actuated end results in at least $\frac{1}{10}^{th}$ of a rotation or more at the device 400 end. The torqueing tool 408 may be inserted through a hole, slot or loop in the device 400 to retain the torqueing tool 408 so torque transmission may be communicated to device 400. The torqueing tool 408 may be snap fit, interference fit, or loosely fit through the device 400 attachment feature 6104 so that it may be easily removed during a desired time. As described previously, the distal tip of the torqueing tool 408 may be cross drilled to accept a hitch pin, wire or thread that locks the torqueing tool 408 engaged in the attachment feature 610 of device 400 until such time as the hitch pin, wire or thread has been pulled out or broken to allow the release of the torqueing tool 408.

H. Distal Tip

As mentioned previously, the distal tip 405 of the tissue gathering elements 402 may have a variety of forms. As previously shown in FIG. 63A, in some embodiments, the distal tip 405 is atraumatic and has a blunt shape, such as a ball or other rounded shape. In this configuration, the tissue gathering element 402 may be more inclined to track along the inside lumen of an airway if the airways are still preserved. However, in nearly all cases, they are not. If the distal tip includes a ball that is smaller than 0.060 inches diameter, it will still be capable of penetrating the wall of an airway to engage connective alveoli instead of manipulating airways alone. In other embodiments, as previously shown in FIG. 63B, the distal tip 405 has a sharp shape, configured to pierce and/or penetrate tissue. In other embodiments, as previously shown in FIG. 63C, the distal tip 405 has an anchoring shape, such as a fish-hook or other shape which is configured for piercing or penetrating tissue while resisting withdrawal from the tissue.

As mentioned previously, in some embodiments, the device 400 is made from round wire and in some embodiments the round wire has been flattened at the distal tip or any other portion of the tissue gathering element 402 to add bearing area. Likewise, in other embodiments, the device 400 is made from ribbon which already has a flattened shape. In such instances, the ribbon can optionally be twisted so as to form the distal tip 405. FIG. 99A illustrates such twisting of a ribbon 900. Here, the ribbon 900 is shown extending in a plane wherein its free end 902 is twisted 90 degrees so as to reside in a perpendicular plane.

FIGS. 99B-99D illustrate additional embodiments of distal tips 405 having twisted ends. FIG. 99B illustrates a portion of a tissue gathering element 402, particularly its distal tip 405. Here, the distal tip 405 is formed from a ribbon 900 that is twisted so that its free end 902 is flat forming a planar surface 903 that resides in a plane configured to maximize contact area with tissue when engaging the tissue gathering elements 402 with the tissue, such as during torqueing. In some embodiments, the twist is approximately 90 degrees, however it may be appreciated that any amount of twist may be used including various degrees up to 90 degrees or in a range of 1 to 90 degrees. In other embodiments, the twist is beyond 90 degrees. In addition, in this embodiment, the edge 904 of the free end 902 is blunt or rounded. This assists in smooth advancement of the distal tip 405 through delivery devices. FIG. 99C illustrates another embodiment of the distal tip 405 formed from a ribbon 900 that is twisted so that its free end 902 is flat forming a planar surface 903 that resides in a plane configured to maximize contact area with tissue when engaging the tissue gathering elements 402 with the tissue, such as during torqueing. In this embodiment, the edge 904 of the free end 902 has a point 906 to assist in forward penetration but has angled corners 908 straddling the point 906 so as to reduce any friction or digging into delivery devices during advancement. FIG. 99D illustrates another embodiment of the distal tip 405 formed from a ribbon 900 that is twisted so that its free end 902 is flat forming a planar surface 903 that resides in a plane configured to maximize contact area with tissue when engaging the tissue gathering elements 402 with the tissue, such as during torqueing. In this embodiment, the edge 904 of the free end 902 has an elongate taper ending in a ball 914. In some embodiments, this distal tip 405 is formed by putting a very slow long taper on the ribbon 900 and melting its tip back to form the ball 914.

Example System for Torque-Based Treatment

Both the pulmonary treatment device 10 and the torque-based pulmonary treatment device 400 are sized and configured to be delivered by a delivery device that is insertable into the lung, such as a steerable scope (e.g. bronchoscope 20), catheter or other delivery system. As described previously, such as in relation to FIGS. 31A-31B, an example delivery device is a bronchoscope 20. In this example, the bronchoscope 20 includes a bronchoscope body 200 and an insertion cord 202. The insertion cord 202 is advanced into the endobronchial tree of the patient and the bronchoscope body 200 remains outside of the patient, typically grasped by the operator's non-dominant hand. The insertion cord 202 contains a fiberoptic bundle for light and image transmission, tip bending control wires and a working channel. The working channel continues into the bronchoscope body 200, exiting at the working channel port 204. The working channel 210 extends through the tip 208, allowing delivery of the pulmonary treatment devices 10, 400 therefrom.

In some embodiments, the pulmonary treatment device 10 is loaded directly into the working channel port 204 and advanced through the working channel 210 for delivery from the insertion cord tip 208. However, in other embodiments, the device 10 is pre-loaded into an introducer which is advanceable into the working channel 210 for delivery therefrom.

FIG. 32 previously illustrated an embodiment of an introducer 220 having a pre-loaded pulmonary treatment device 10. In this embodiment, the introducer 220 comprises an elongate tube 222 having a first end 224 and a second end 226. The introducer 220 is typically strong enough to keep the device 10 from distorting from a straight configuration and hard enough that the device 10 cannot indent into the wall of the introducer 220, particularly during the sterilization process that involves heating to 130-180° C.

Figure 100:
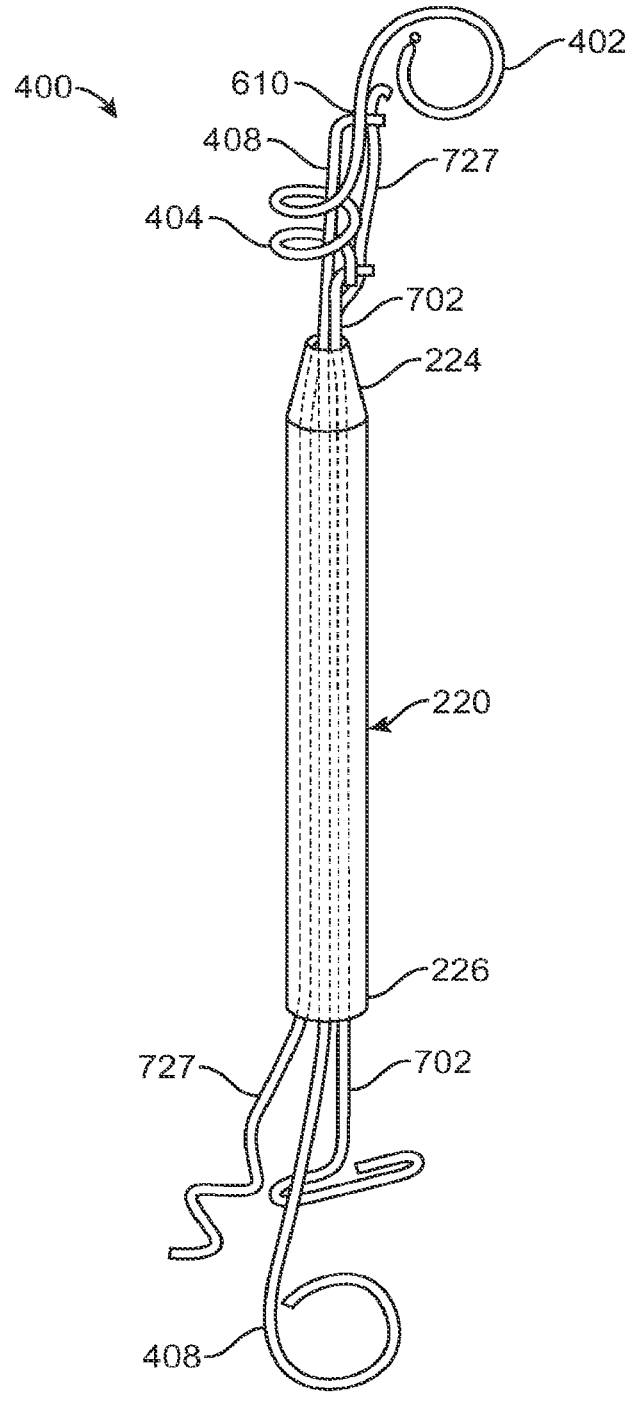
FIG. 100 illustrates an embodiment of a torque-based pulmonary treatment device prepared for pre-loading in an introducer.

FIG. 100 illustrates an embodiment of a torque-based pulmonary treatment device 400 prepared for pre-loading in an introducer 220. Here, the device 400 is prepared for pre-loading by having the torqueing tool 408, hitch wire 727 and tether 702 attached thereto. In particular, the torqueing tool 408 is attached to an attachment feature 610 on the device 400. Thus, the torqueing tool 408 is able to torque the device 400 by rotation of its handle. In this embodiment, its handle has a loop shape for easy grasping and rotational leverage. The hitch wire 727 is attached to the torqueing tool 408 to maintain its engagement as previously described in relation to FIG. 91D. In this embodiment, its handle has a T shape for ease of pulling and pushing the hitch wire 727. The tether 702 is attached to the anchoring element 404 and its handle is shaped for ease of use and to distinguish from the other handles. These tools (i.e. torqueing tool 408, hitch wire 727, tether 702) extend through the introducer 220 so that the device 400 resides beyond the first end 224 of the introducer 220 and the handles of the tools reside proximal to the second end 226 of the introducer 220. Thus, in this arrangement, the device 400 is not confined within the introducer 220 in a straightened configuration. In some instances, implantable materials, such as nitinol, can be damaged if they are stressed in packaging and then exposed to heat that exceeds 25 degrees C. during shipment as the stress on the device is elevated with the additional heat. In some embodiments, the device 400 is packaged in this manner so that any heating due to transit or sterilization will not introduce any potential damage or inadvertent shape setting while the device 400 is constrained in a straightened configuration. It is advantageous to ship the device 400 in an unstressed configuration. It is also advantageous to ship the device 400 in an unstressed configuration but already attached to the torqueing tool 408, tether 702 and the hitch wire 727 so the assembly does not have to be attached by the user and the device 400 may be quickly and easily be retracted into the introducer 220 by simply pulling on one or more of the attached tools to pull device 400 into the introducer 220 through the first end 224.

Figure 101:
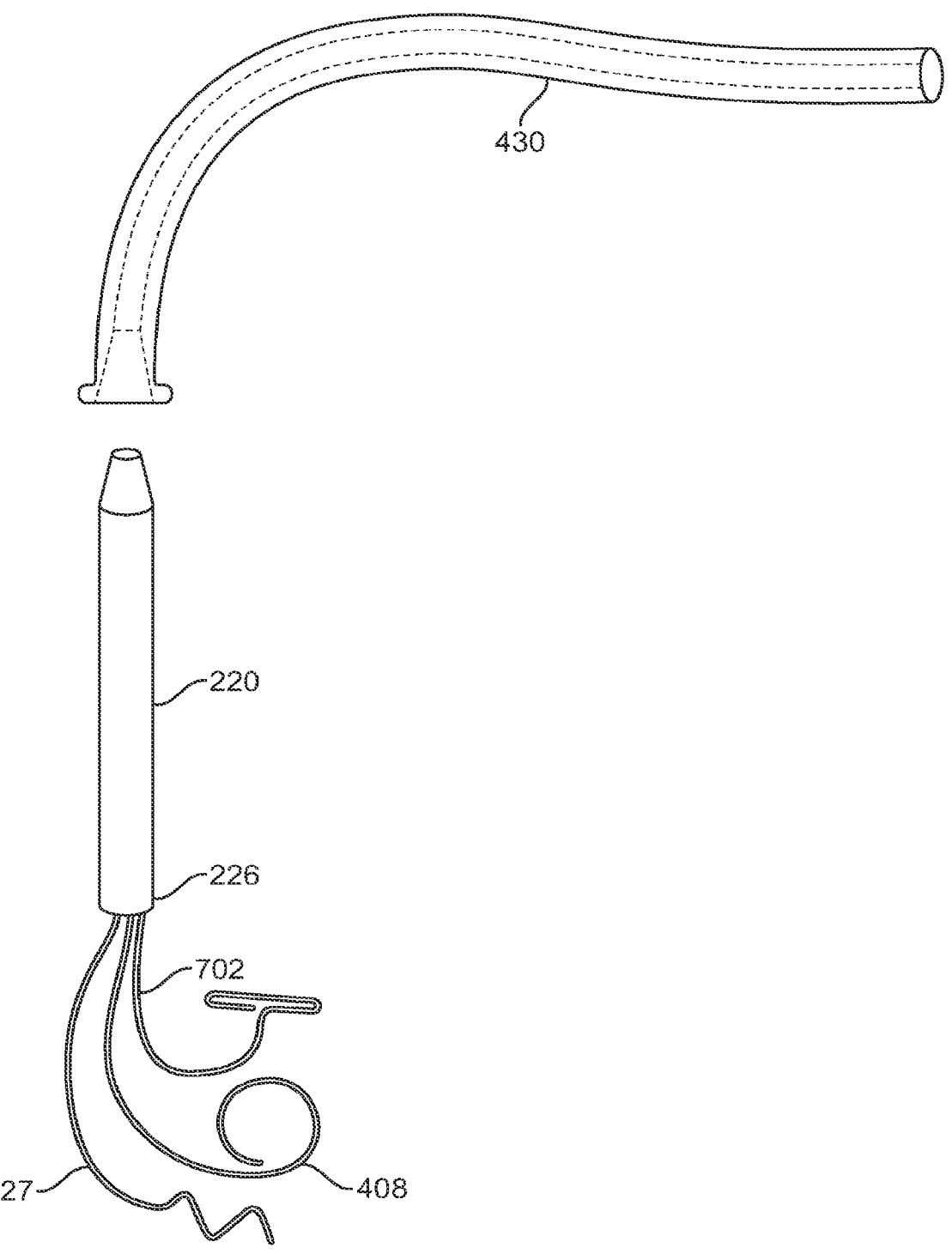
FIG. 101 illustrates the device of FIG. 100 preloaded into the introducer and prepared for advancement into a catheter.

FIG. 101 illustrates the device 400 preloaded into the introducer 220. This can be achieved by retracting the device 400 into the introducer 220 by pulling the tether 702. Alternatively, or in addition, the introducer may be advanced over the device 400. Finally, device 400 may be advanced into the introducer 220 by advancing the tissue gathering element 402 into the introducer 220 by inserting it into the second end 226 of the introducer 220. Thus, the device itself is disposed within the introducer 220 while the handles of the torqueing tool 408, hitch wire 727, tether 702 extend from the second end 226 of the introducer 220. The introducer 220 is then ready to be advanced into or coupled to a bronchoscope 20 working channel or a catheter 430 or similar delivery device which is advanceable through a lumen in the bronchoscope 20. The device 400 is constrained within the catheter 430 to allow for ease of advancement through the bronchoscope. The device 400 remains within the catheter 430 until the distal tip of the catheter 430 is desirably positioned within the lung L. Alternatively, a guidewire 313 may be used to guide the catheter 430 through and distal to the bronchoscope 20 to an optimal position within the lung L before the introducer 220 is coupled to it.

Figure 102:
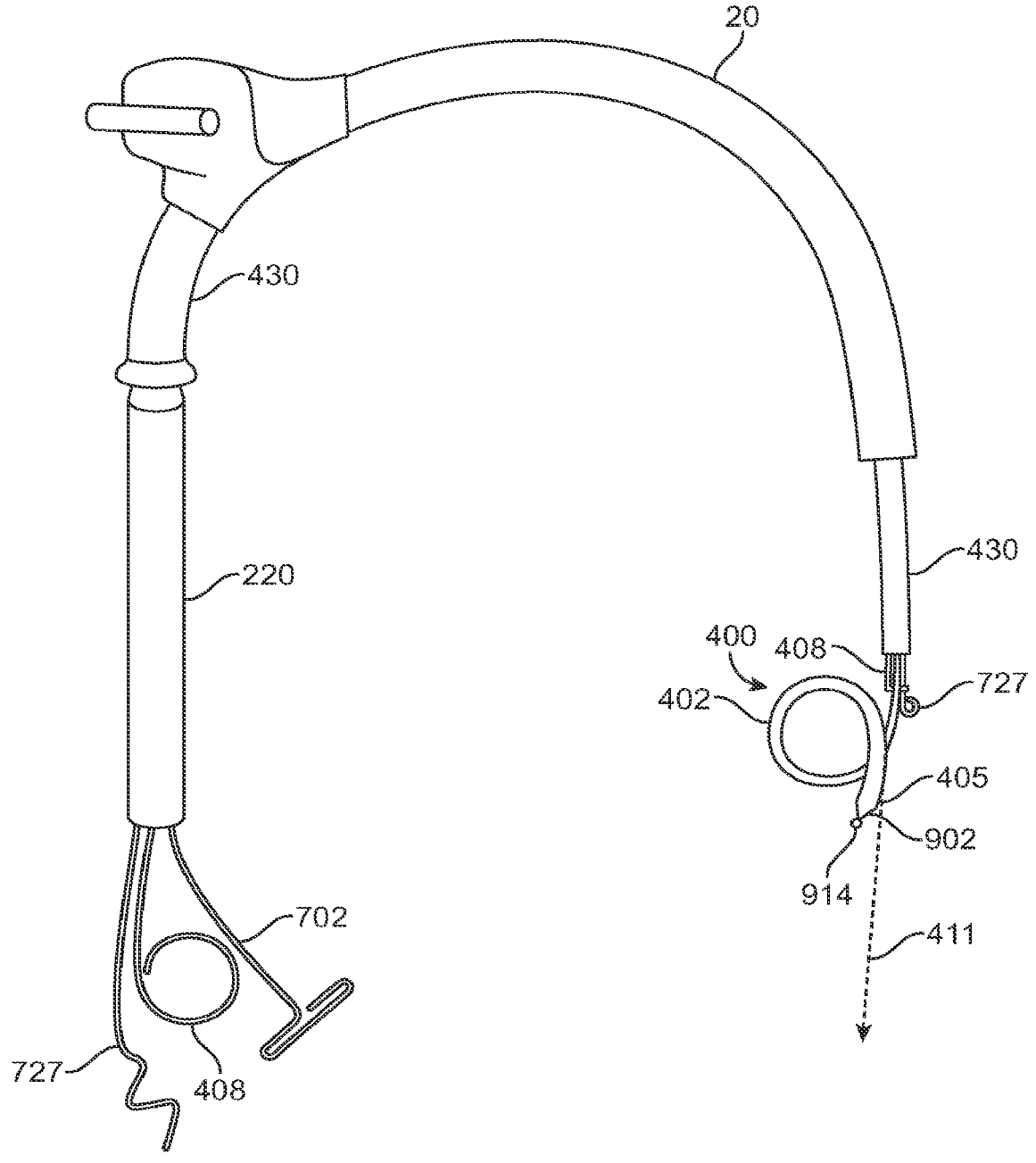
FIG. 102 illustrates the distal tip of the catheter of FIG. 101 advanced beyond the distal tip of the bronchoscope and the beginning steps of deployment of the device.

As illustrated in FIG. 102, the distal tip of the catheter 430 is advanced beyond the distal tip of the bronchoscope 20. This allows the catheter 430 to reach locations that are beyond the reach of the bronchoscope 20 due to size constraints (i.e. the smaller diameter of the catheter 430 can pass through small diameter or contorted passageways that the larger diameter bronchoscope is restricted from entering). Thus, in some instances, the catheter 430 is able to reach far distal portions of the lung L, such as the apical portions of the upper lobes and the lateral corners of the lower lobes, which are typically unreachable by the bronchoscope alone.

Once the distal tip of the catheter 430 is positioned near a target location for placement of the treatment device 400, the device 400 is deployed. Deployment from the catheter 430 may be achieved by a variety of methods or a combination of multiple methods. In this embodiment, the device 400 is pushed beyond the catheter 430, such as with the use of the torqueing tool 408, to allow the tissue gathering element 402 bend toward its pre-formed or natural configuration (e.g. radially outwardly and around into a loop shape as illustrated in FIG. 102). In this embodiment, the tissue gathering element 402 has a distal tip 405 having a free end 902 shaped as an elongate taper ending in a ball 914. Thus, deployment allows the distal tip of the tissue gathering element 402 to engage the surrounding tissue, curving through and/or against the tissue. Such deployment may be in an airway or beyond the natural airways into damaged tissue, parenchyma, alveoli, artificially created passageways, disease created passageways or other types of lung tissue.

The device 400 is then rotated by applying torqueing, twisting or rotational force to at least a portion of the device 400 with the use of the torqueing tool 408. As shown, the torqueing tool 408 includes a handle which is graspable by a user so as to manually applying the rotational force. Since the torqueing tool 408 is attached to the device 400, the device 400 (and therefore tissue gathering element 402) rotates as well. This gathers up the surrounding lung tissue onto and around the tissue gathering element 402 as the element 402 rotates. Thus, loose parenchyma, portions of blebs and bullae, damaged alveolar sacs and other distended, slackened or stretched tissue is pulled inwardly, twisted and/or gathered up by the tissue gathering element 402. Rotation continues, gathering the loose, slackened tissue, until desired tension is achieved in the tissue.

It may be appreciated that although such rotation is applied around the longitudinal axis 411, such rotation may occur in the tissue around other axes. Such other axes may be at a variety of angles to the longitudinal axis 411 and on either side of the longitudinal axis. This may occur due to bending of portions of the device 400, such as bending of the tissue gathering element 402, during advancement of the tissue gathering element 402 or during rotation itself. Such bending may cause the torque applied around the longitudinal axis 411 to be transmitted around one or more different axes. Such other axes are typically in the range of 1 to 90 degrees from the longitudinal axis 411.

It may be appreciated that the desired amount of torque imposed by the device may vary depending on the patient anatomy and disease state, to name a few. In some embodiments, the desired level of torque is determined by tactile feedback to the user. For example, in some instances, torque is applied until the user encounters desired resistance to rotation, ranging from minimal resistance to complete obstruction of further rotation. Such resistance may simply be felt by the user as manual rotation is attempted. Typically, torque is applied quite easily while slack tissue is gathered until a sudden increase in tension is reached. In some patients, a minimal amount of tension is desired wherein torque application is ceased as soon as the increase in tension is reached. In other embodiments, torque is measured by a torque measurement mechanism, such as a torque sensor, torque transducer or torque meter attached to or incorporated within the torqueing tool 408. In some instances, torque sensors or torque transducers use strain gauges applied to a rotating shaft. With this method, a mechanism to power a strain gauge bridge is present as well as a means to receive the signal from the rotating shaft. This can be accomplished using slip rings, wireless telemetry, or rotary transformers, to name a few. In some embodiments, SAW devices are attached to the shaft and remotely interrogated. The strain on these tiny devices as the shaft flexes are read remotely and output without the need for attached electronics on the shaft. In other embodiments, torque is measured by way of twist angle measurement or phase shift measurement, whereby the angle of twist resulting from applied torque is measured by using two angular position sensors and measuring the phase angle between them. In some embodiments, a predetermined level of torque is established wherein the torque measurement mechanism indicates when the predetermined level of torque has been reached, such as by a visual or auditory signal or by obstruction of further rotation. In some embodiments, the predetermined amount of torque is approximately 0 to 3 in-oz, preferably approximately 0.1 to 0.5 in-oz, more preferably approximately 0.1 to 0.3 in-oz.

In other embodiments, torque is applied until a predetermined amount of rotation has been achieved. In some instances, the amount of rotation is visually monitored such as by watching rotation of the tissue gathering element 402 by visualization with a variety of methods, including fluoroscopy and/or imaging through a bronchoscope camera. Typically, when the desired amount of rotation is observed, the user ceases rotation. In other instances, the amount of rotation is measured by a rotational measurement mechanism, such as attached to or incorporated within the torqueing tool 408. In some embodiments, a predetermined amount of rotation is established wherein the rotation measurement mechanism indicates when the predetermined level of rotation has been reached, such as by a visual or auditory signal or by obstruction of further rotation. In some embodiments, the predetermined amount of rotation is up to 10 degrees, up to 20 degrees, up to 30 degrees, up to 40 degrees, up to 45 degrees, up to 50 degrees, up to 60 degrees, up to 70 degrees, up to 80 degrees, up to 90 degrees, up to 100 degrees, up to 110 degrees, up to 120 degrees, up to 130 degrees, up to 135 degrees, up to 140 degrees, up to 150 degrees, up to 160 degrees, up to 170 degrees, up to 180 degrees, up to 225 degrees, up to 270 degrees, up to 315 degrees, up to 360 degrees, or over 360 degrees.

Figure 103:
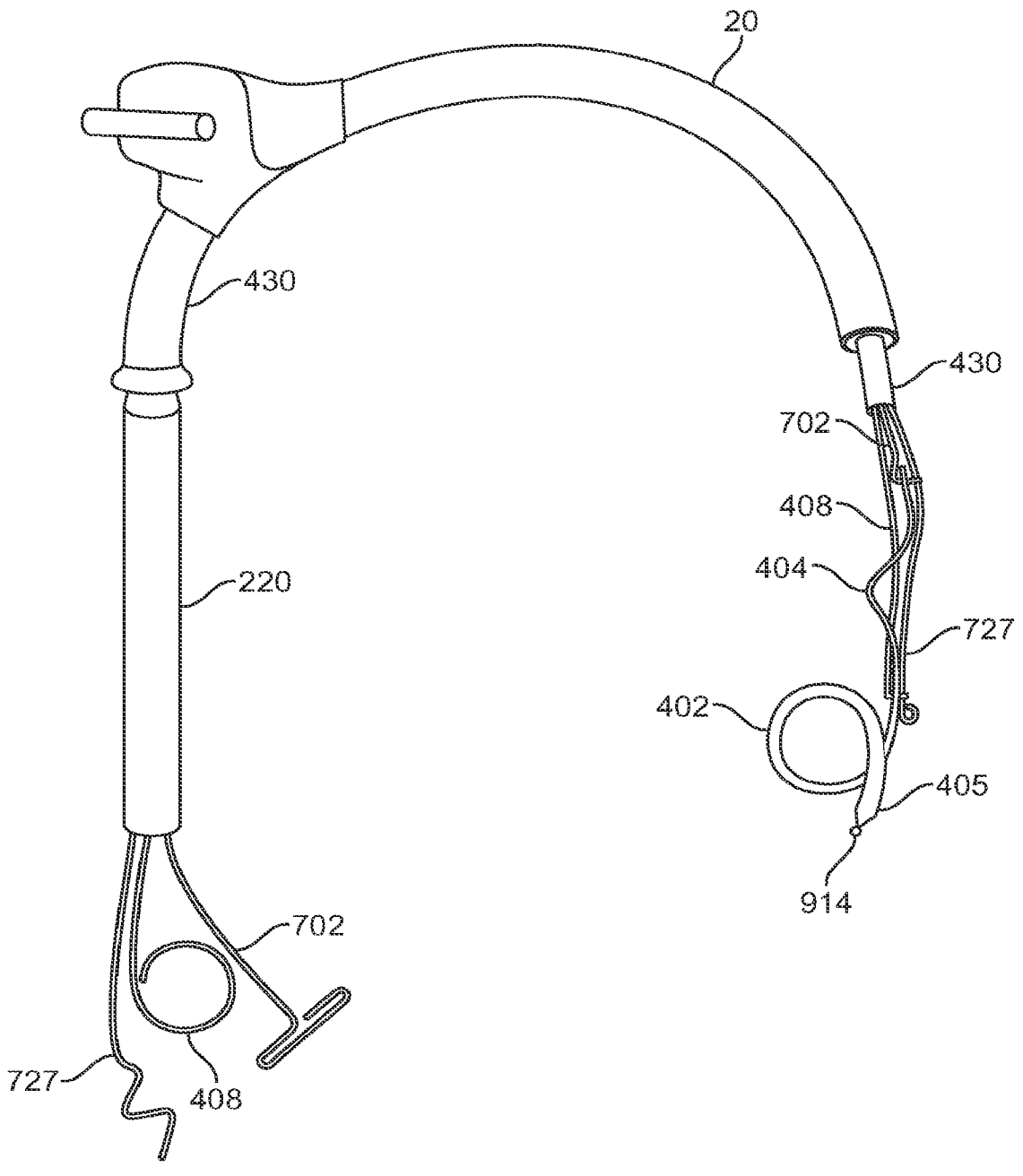
FIG. 103 illustrates exposure of the anchoring element for anchoring of the device.
Figure 104:
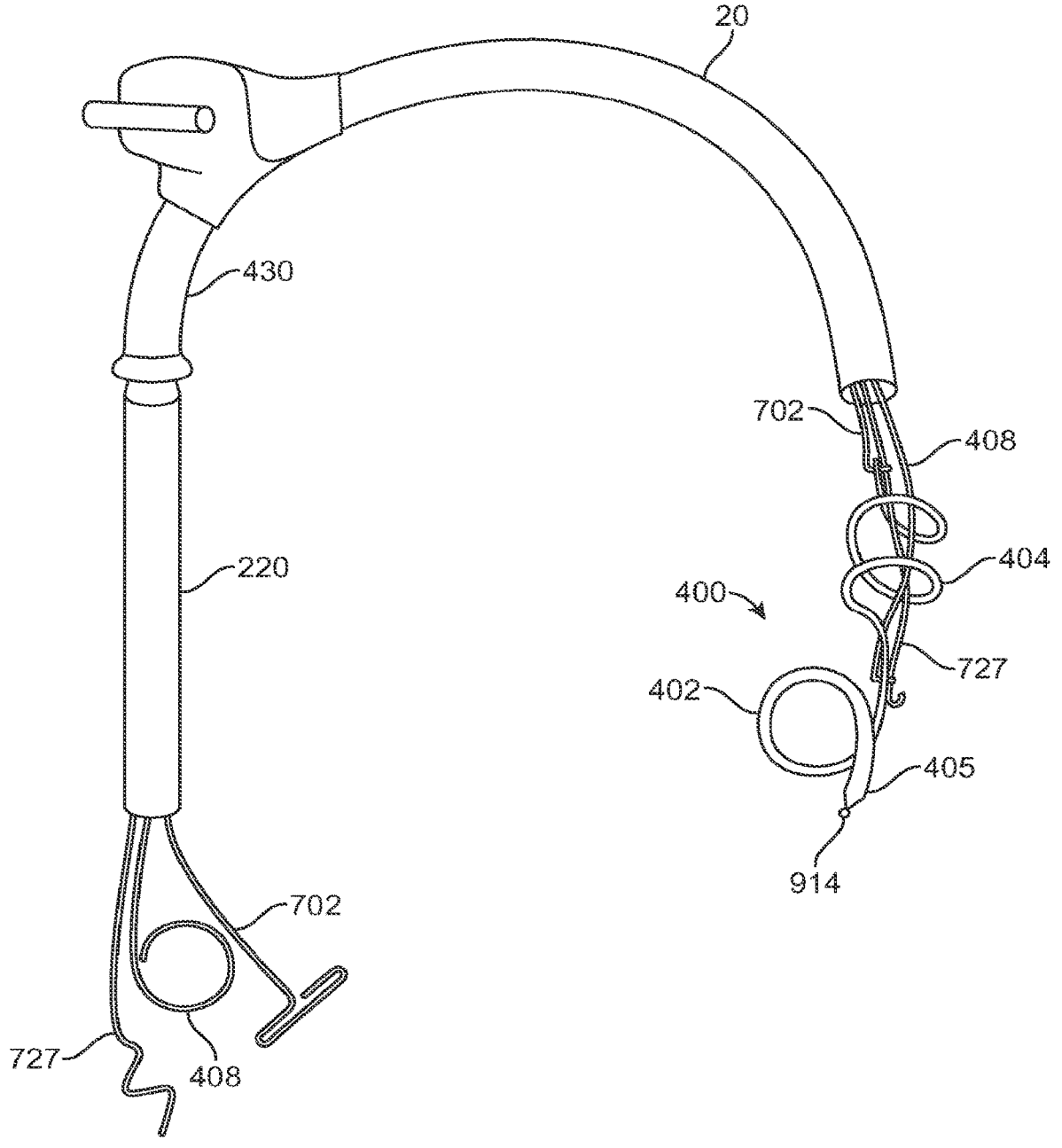
FIG. 104 illustrates expansion of the anchoring element.

Once the lung L is desirably re-tensioned, the device 400 is anchored to maintain the rotated arrangement. This is achieved by deployment of the anchoring element 404. FIG. 103 illustrates such deployment. Here the catheter 430 is retracted to expose the anchoring element 404. Here, the tether 702 is still attached to proximal end of the device 400, particularly to the anchoring element 404, and holds the anchoring element 404 in a stretched configuration. The anchoring element 404 is then expanded, such as by advancement of the tether 702 in relation to the torqueing tool 408. Alternatively, or in addition, the torqueing tool 408 may be retracted. This assists in shortening the anchoring element 404, allowing the coils to reform as illustrated in FIG. 104. It may be appreciated that anchoring may be verified by observation of any unwinding of the device 400. Typically, any unwinding of the device 400 pulls on the airway until the airway is unable to rotate any further. Thus, anchoring is established.

Figure 105:
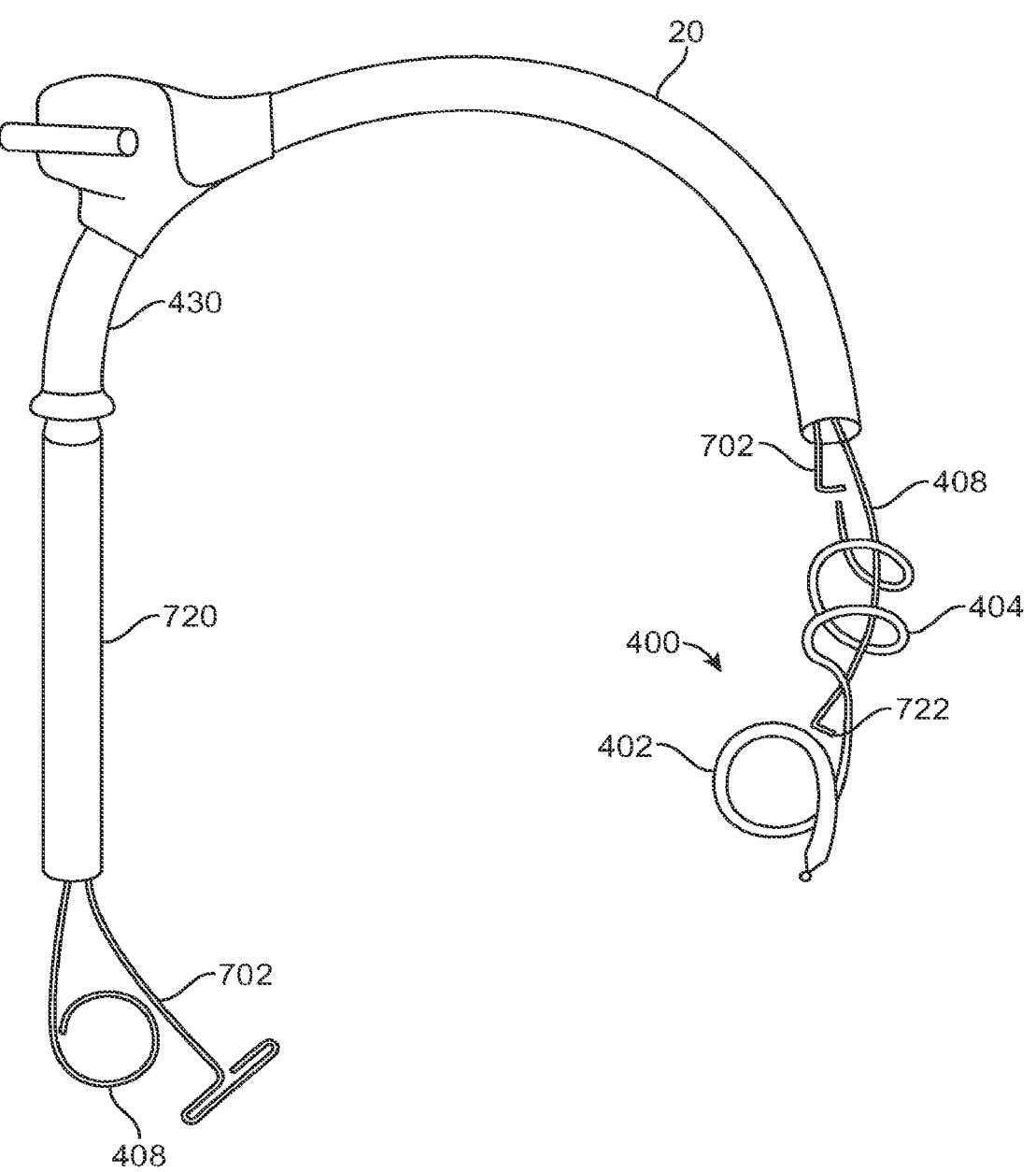
FIG. 105 illustrates release of the device to be left behind as an implant.

The device 400 is then released, as illustrated in FIG. 105. The torqueing tool 408 is released from the device 400 by removal of the hitch wire 727. Removal of the hitch wire 727 allows the hooked end 722 the torqueing tool 408 withdraw from the attachment feature 610. Likewise, the tether 702 is removed from the anchoring element 404. The tools (torqueing tool 408, hitch wire 727, tether 702) are then removed and the device 400 is left behind as an implant.

Patients suffering from severe COPD typically have a high chance of having an inflammatory response to implantation of the device 400. In such instances, the inflammatory response can be beneficial to implantation since it typically causes higher volume contraction, lung volume reduction and lung tensioning. For such patients, a lower level of torque may be applied in anticipation of the effects of the inflammatory response.

It may be appreciated that in some embodiments, a similar inflammatory response is actively induced in a patient so as to obtain similar benefits. In some embodiments, the tissue gathering element 402, or other portions of the device 400, includes sharp edges which cause a fibrotic reaction or thickening of the tissue. This in turn causes increased contraction. In other embodiments, fibrosis is achieved by increasing tissue tension because the wound healing and the formation of scar tissue is accelerated. In some embodiments, the tissue gathering element 402, or other portions of the device 400, are texturized to enhance epithelium adhesion and fibrotic reaction around the implanted device 400. For example, in some embodiments, the device 400 is texturized by etching lines along its surface, such as lines that are spaced 2-30 micrometers apart to help drive macrophage propulsion along the surface and to preserve macrophage health that minimizes collateral tissue growth formations that may occur in the airway. It may be appreciated that the tissue gathering element 402, or other portions of the device 400, may be coated to reduce infection. Examples of coating include silver plating, which is known to inhibit bacteria. Other coatings, coverings or plating materials may be applied to the device to inhibit colonization of bacteria, inhibit growth of granulation tissue, random collagen or other foreign growths that would compromise breathing. Coatings, coverings or plating materials may be provided to enhance epithelium attachment and health, cause fibrosis formation to enhance the structure of the emphysema lung tissue and to reduce friction between the device and delivery system components during delivery into the patient. It may be appreciated that any reduction of coating over time may be inconsequential since it may be most desired during and shortly after implantation.

In some embodiments, natural and/or induced inflammatory and wound healing responses are controlled with the use of agents, such as steroidal drugs. Coatings may be applied to the device to efficiently carry anti-inflammatory drugs to the lung airway in the form of a gel that rubs into the airway wall or lung tissue, in the form of a resorbable polymer that releases the drugs over time or in the form of film on the surface of the device. These drugs may include, for example, Sirolimus, Rapamune, Rapamycin, Paclitaxel, Taxol or a combination thereof. In some instances, such control may allow for more precise treatments, such as more precise levels of torque application depending on patient condition and anatomy.

In some embodiments, various therapies are used in combination with implantation of one or more devices 400. For example, in some instances, radiotherapy is used in combination with implantation of one or more devices 400. Radiotherapy or X-ray therapy cross-links and shrinks lung tissue so as to cause additional tissue contraction, tensioning the lung tissue which adds more elastic recoil and reduced compliance.

It may be appreciated that the methods, devices and systems provided herein may be used in combination with a variety of conventional treatments for COPD and other lung conditions. For example, in some instances, the methods, devices and systems provided herein may be used in combination with lung volume reduction surgery (LVRS). Likewise, in some instances, the methods, devices and systems provided herein may be used in combination with conventional implantable therapeutic devices, such as conventional endobronchial valves and conventional endobronchial coils. Example conventional endobronchial valves include those developed by Emphasys Medical (now Pulmonx—Redwood City, California) as a minimally invasive alternative to lung volume reduction surgery for emphysema. Emphasys was purchased by Pulmonx in 2009, and Pulmonx currently markets the Zephyr® endobronchial valve (developed by Emphasys). Other example conventional endobronchial valves include those developed by Spiration (Seattle, Washington) which was acquired by Olympus in 2010. Example conventional endobronchial coils include those developed by PnemRx (Mountain View, California) which has been acquired by BTG. Based in London, BTG is an international specialist healthcare company that is active in interventional medicine and specialty pharmaceuticals. BTG has since been acquired by Boston Scientific.

Likewise, the methods, devices and systems provided herein may be used in combination with conventional lung airway bypass products that cause venting of trapped air, such as conventional pulmonary stents. Example conventional pulmonary stents include the Ultraflex™ Tracheobronchial Stent System (Boston Scientific), the Polyflex™ Self-Expanding Silicone Airway Stent (Boston Scientific) and the Dynamic™ (Y) Stent Bifurcated Tracheobronchial Stent (Boston Scientific).

Likewise, the methods, devices and systems provided herein may be used in combination with conventional devices that inject steam to cause tissue trauma, scarring and cell death, such as the InterVapor® Bronchoscopic Thermal Vapor Ablation (BTVA®) system which has returned to the market after a brief hiatus as the asset sale of Uptake Medical Corporation was being completed to Broncus Holding Co. A new company, Uptake Medical Technology, Inc was formed in Seattle, WA, USA and has received a new CE Mark for the technology. Likewise, the methods, devices and systems provided herein may be used in combination with conventional sealants, such as the AeriSeal® System. The AeriSeal® System is foam-based lung sealant system wherein polymers are mixed and blown with air to create foam in the damaged regions of lung. The foam turns to a state like hard rubber blocking holes and damages in the lung and stays for several months while the lung shrinks in its normal size. The AeriSeal® System was developed by Aeris Therapeutics and was later acquired by Pulmonx®.

Clip Treatment Overview

In some instances, lung function may be improved by straightening airways at bifurcations or other branching locations within the lung. This is achieved by pulling the airways closer together along a length of the airways thereby creating a straightened flow path. In some embodiments, this is achieved with the use of one or more pulmonary treatment devices 10 having the form of a clip.

Figure 106:
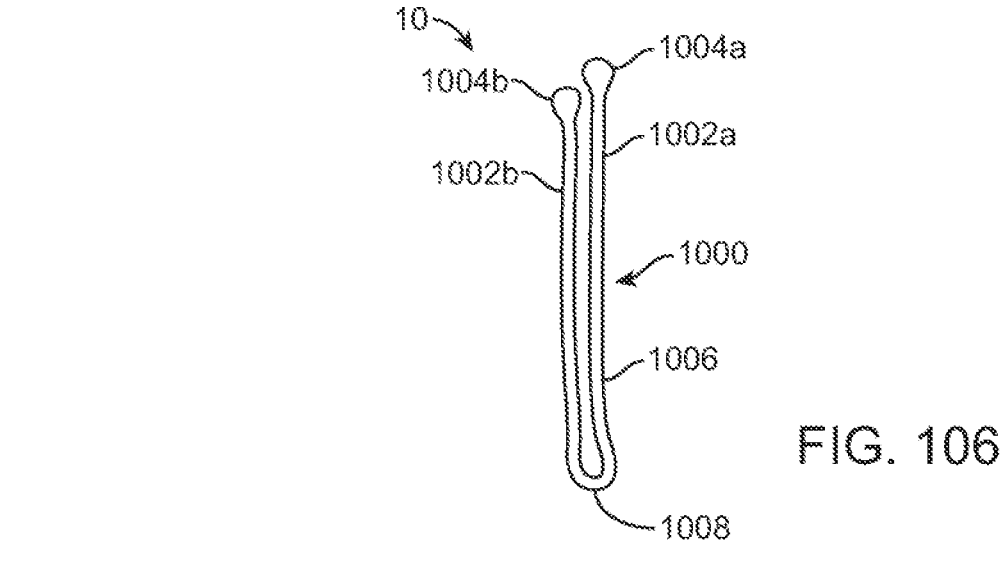
FIG. 106 illustrates an embodiment of such a pulmonary treatment device comprising a clip having a first arm and a second arm.

FIG. 106 illustrates an embodiment of such a pulmonary treatment device 10 of the present invention. In this embodiment, the device 10 comprises a clip 1000 having a first arm 1002a and a second arm 1002b, each having a free end with a respective tip 1004a, 1004b, such as an atraumatic tip. In this embodiment, the arms 1004a, 1004b are disposed substantially parallel when in a resting position so that the tips 1004a, 1004b are adjacent to each other. It may be appreciated that the clip 1000 may have greater than two arms 1002, such as three, four, five, or six arms, to name a few; however, clips 1000 having two arms 1002 will be depicted herein for simplicity. The features of the clips 1000 having greater than two aims may be extrapolated from these examples.

It may be appreciated that the clip 1000 may be comprised of any biocompatible material that can withstand conditions in an airway, such as metals, steels, titaniums, nitinols, plastics, or ceramics to name a few. The arms 1002a, 1002b can have a variety of forms, such as tube, wire, ribbon, sheet, machined, extruded or drawn, to name a few. Likewise, the arms 1002a, 1002b can be covered in a variety of materials, such as cloth, polytetrafluoroethylene (PTFE), or expanded polytetrafluoroethylene (ePTFE), to name a few. In some embodiments, the arms 1002a, 1002b are formed from a single shaft 1006 that is bent therebetween, as shown, thus forming a proximal end 1008 of the clip 1000 that is curved. In other embodiments, the clip 1000 has differing form and construction as will be described in later sections. In this embodiment, the arms 1002a, 1002b are of differing length. This may assist in placement wherein the longer arm is directed into position first, followed by the shorter arm. This allows attention to be focused on a single arm at a time during the initial directing phase of the placement. Once an arm has entered an airway it will typically naturally follow the airway.

Figure 107A:
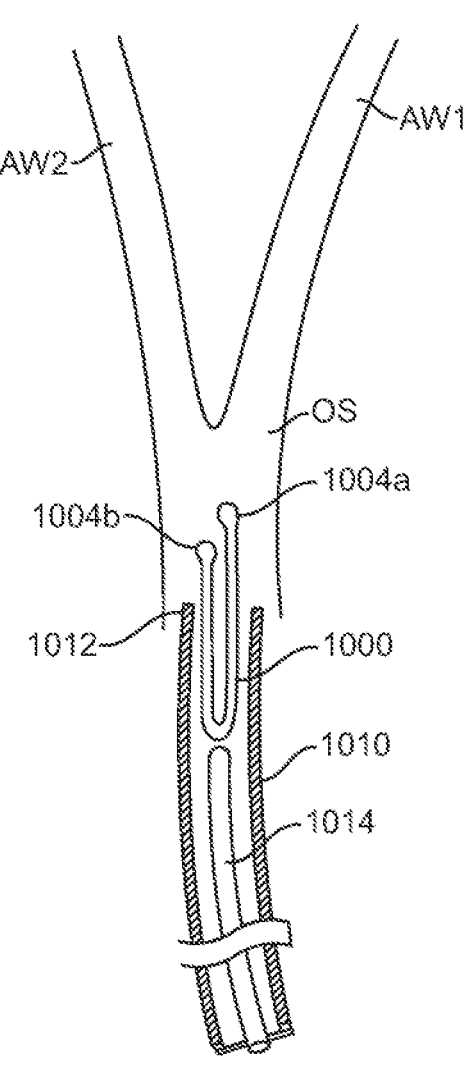
FIGS. 107A-107C illustrate an embodiment of the clip of FIG. 106 in use.
Figure 107B:
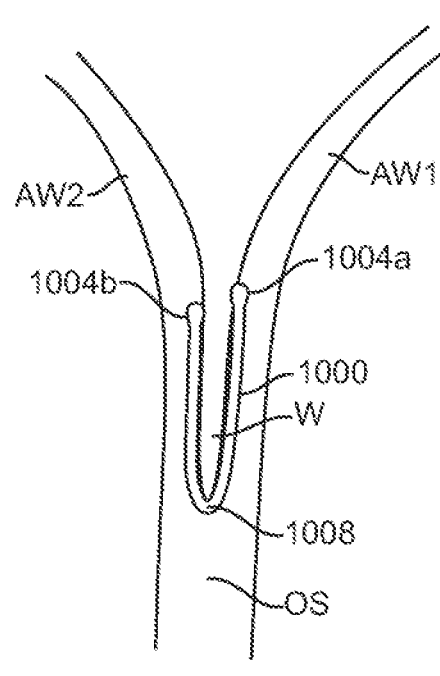
Figure 107C:
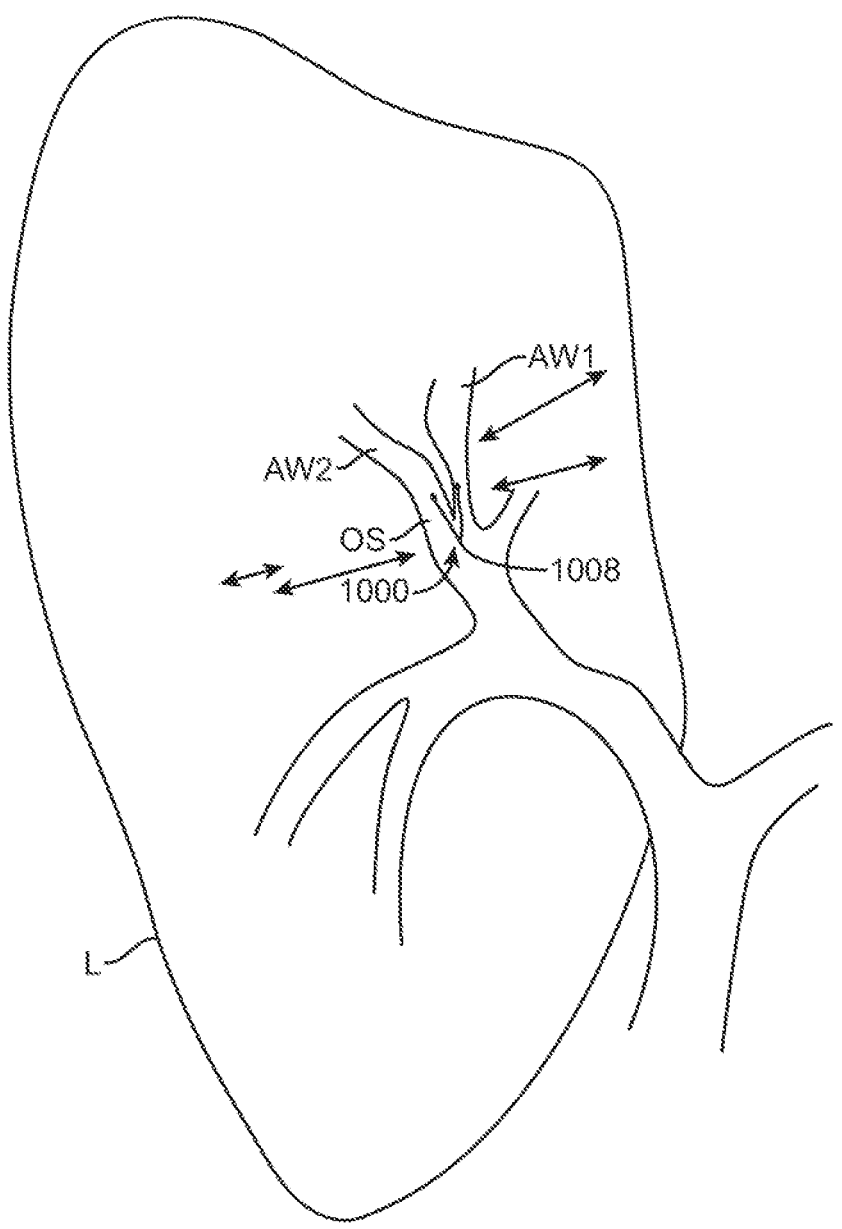

FIGS. 107A-107C illustrate an embodiment of the clip 1000 of FIG. 106 in use. Referring to FIG. 107A, the clip 1000 is loaded into a delivery device 1010 (e.g. catheter, endoscope, bronchoscope, etc) having a distal end 1012 from which it is delivered. In this embodiment, the clip 1000 is loaded into the delivery device 1010 so that the tips 1004a, 1004b face distally and are first to emerge from the distal end 1012 upon deployment. In this embodiment, the clip 1000 is not in a constrained position while within the delivery device 1010, however, it may be appreciated that other clip 1000 embodiments may be constrained therein. In some embodiments, the clip 1000 is configured to be loaded within and advanceable through a 1.3-3.2 mm channel within the delivery device 1010 or through a 1-10 French catheter.

The delivery device 1010 is advanced through the bronchial tree to a target location, such as an ostium OS which branches into a first airway AW1 and a second airway AW2. In this embodiment, the first airway AW1 and second airway AW2 are excessively diverging away from each other prior to treatment. This is because the tissue is distended so lung elastic recoil has been lost in the lung. The native airways are the most robust structures in the lung and they naturally diverge, so it is desired to return the airways to their natural state. The clip 1000 brings the airways AW1, AW2 closer together to cause lung volume reduction and enhanced treatment durability. The clip 1000 is advanced from the distal end 1012 of the delivery device 1010 by advancement of a deployment device 1014 which acts as a pusher or plunger. The deployment device 1014 may have a variety of forms, including a high torque tube, braided tube, rope, wire, rod, element tube, etc. The clip 1000 is deployed so that the first arm 1002a enters the first airway AW1 and the second arm 1002b enters the second airway AW2. Since, in this embodiment, the first arm 1002a is slightly longer then the second arm 1002b, the first arm 1002a will enter first, however the arms 1002a, 1002b typically enter the airways substantially simultaneously. In this embodiment, the clip 1000 is advanced so that the proximal end 1008 resides substantially near the wall W that connects the airways AW1, AW2, as illustrated in FIG. 107B. Due to the rigidity of the clip 1000 the arms 1002a, 1002b recoil toward each other, pushing the inner walls of the diverging airways AW1, AW2 toward each other, thereby straightening the airways AW1, AW2 in the vicinity. This is also shown in FIG. 107C which provides a larger overall view of the anatomy with an embodiment of the clip 1000 in place. Here, the clip 1000 is shown positioned so that the first arm 1002a enters the first airway AW1 and the second arm 1002b enters the second airway AW2. In this embodiment, the clip 1000 is advanced so that the proximal end 1008 resides substantially near the wall W that connects the airways AW1, AW2. Advancement of the clip 1000 draws two or more airways together to cause compression between them. By causing this lung volume reduction, the greater lung is tensioned and lung elastic recoil is restored.

It may be appreciated that the clip 1000 may be removed if desired. For example, the proximal end 1008 can be accessed and grasped, such as with forceps or a suitable tool. The proximal end 1008 can then be pulled in the proximal direction to withdraw the arms 1002a, 1002b from the airways AW1, AW2. The atraumatic tips 1004a, 1004b simply slide along the walls of the airways until they disengage from the airways. The clip 1000 can then be withdrawn from the body. Optionally, the clip 1000 can be repositioned in a similar manner. For example, the clip 1000 can be entirely removed from the airways and then reapplied while still near the target location, or the clip 1000 can be repositioned along the airways while the clip 1000 is at least partially engaged with one or more airways. This may entail pushing, pulling, raising, lowering, tilting or otherwise manipulating the clip 1000.

Figures 108, 109:
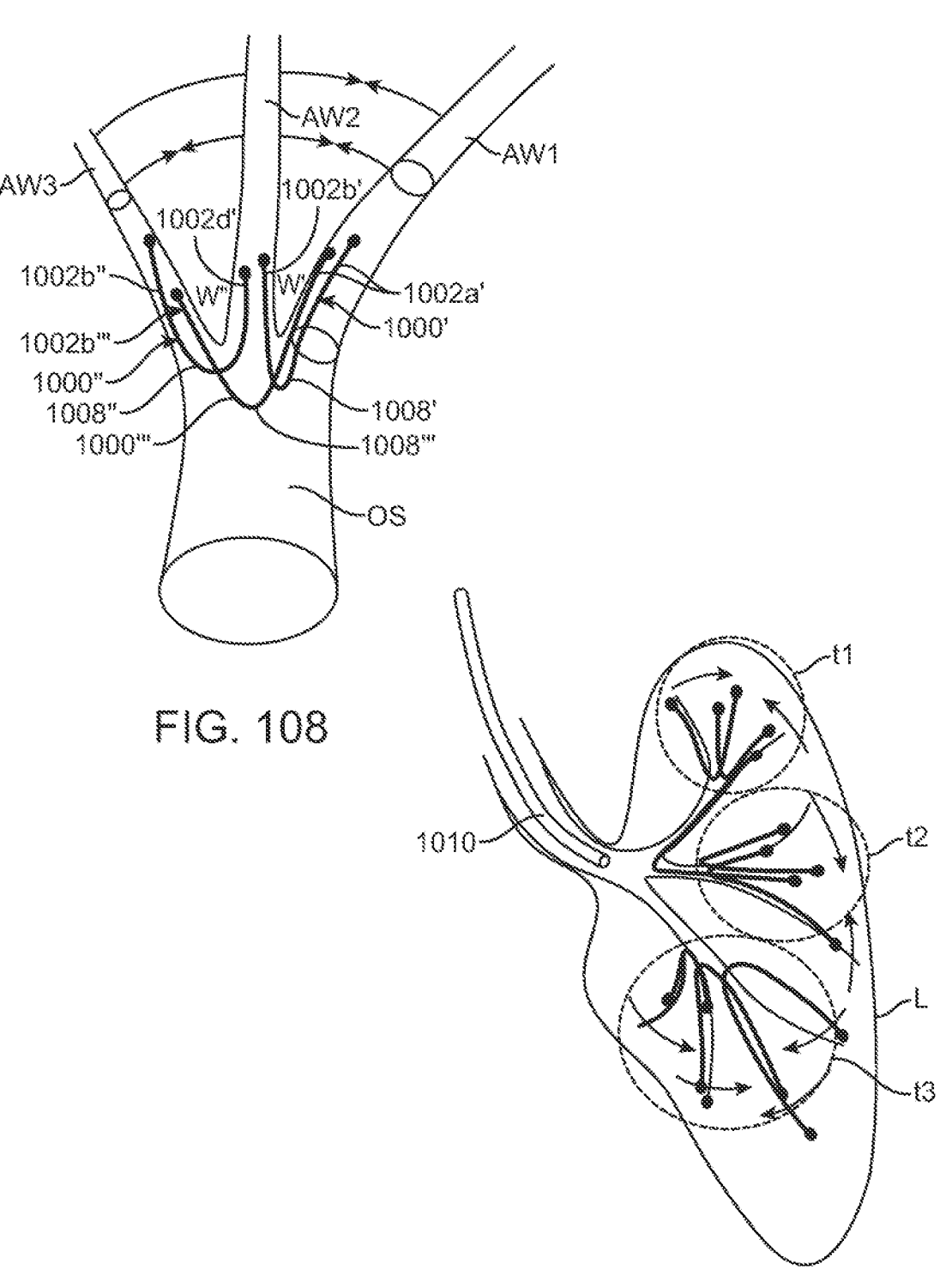
FIG. 108 illustrates a plurality of clips used to treat a target location having a plurality of airways branching from an ostium.
FIG. 109 illustrates example treatment of a plurality of target locations within a lung wherein each target location comprises a triple branching airway from a single ostium.

In some embodiments, one or more clips 1000 are used to treat a target location having a plurality of airways branching from an ostium OS. FIG. 108 illustrates a target location comprising a first airway AW1, a second airway AW2 and a third airway AW3, all branching from a single ostium OS and diverging away from each other. Here, three clips 1000 are deployed and positioned as follows. First, a first clip 1000' is positioned in a manner similar to FIGS. 107A-107C, wherein the first arm 1002a' of the first clip 1000' enters the first airway AW1 and the second arm 1002b' of the first clip 1000' enters the second airway AW2. In this embodiment, the first clip 1000' is advanced so that its proximal end 1008' resides substantially near the wall W' that connects the first and second airways AW1, AW2. Due to the rigidity of the first clip 1000' the arms 1002a', 1002b' recoil toward each other, pushing the inner walls of the diverging airways AW1, AW2 toward each other (indicated by arrows), thereby straightening the airways AW1, AW2 in the vicinity. Second, a second clip 1000" is positioned in a manner similar to FIGS. 107A-107C, wherein the first arm 1002a" of the second clip 1000" enters the second airway AW2 and the second arm 1002b" of the second clip 1000" enters the third airway AW3. In this embodiment, the second clip 1000" is advanced so that its proximal end 1008" resides substantially near the wall W" that connects the second and third airways AW2, AW3. Due to the rigidity of the second clip 1000", the arms 1002a", 1002b" recoil toward each other, pushing the inner walls of the diverging airways AW2, AW3 toward each other (indicated by arrows), thereby straightening the airways AW2, AW3 in the vicinity. In some embodiments, a third clip 1000''' is applied to reduce strain on the second airway AW2, reinforce the compression of the walls W',W" and maintain straightening of the airways AW1, AW2, AW3. As illustrated, the clip 1000''' is positioned so that the first arm 1002a''' of the third clip 1000''' enters the first airway AW1 and the second arm 1002b" of the third clip 1000''' enters the third airway AW3. In this embodiment, the third clip 1000''' is advanced so that its proximal end 1008''' resides substantially near the walls W', W" that connects the airways. Due to the rigidity of the third clip 1000''', the arms 1002a''', 1002b" recoil toward each other, pushing the inner walls of the first and third airways AW1, AW3 toward each other, thereby reducing strain on the second airway AW2, reinforcing the compression of the walls W',W" and maintaining straightening of the airways AW1, AW2, AW3.

In some embodiments, the airways AW1, AW2, AW3 reside in a triangle pattern rather than substantially along the same plane. For example, the second airway AW2 may reside at an angle tipping away from a plane within which the first and third airways AW1, AW3 reside. In such embodiments, the clips 1000', 1000", 1000''' may be placed similarly to FIG. 108, however the resulting compressing is a three dimensional compression. The volume within the triangular or pyramid shape (e.g. from the ostium OS outwardly in a distal direction) is compressed. By placing many clips at various angles and orientations within the lung, a larger volume can be compressed while still allowing gas to flow both ways. This allows functional lung tissue to still exchange gas.

FIG. 109 illustrates this concept by treating a plurality of target locations within a lung L wherein each target location comprises a triple branching airway from a single ostium. Here, three target locations t1, t2, t3 are shown as indicated by dashed circled outline. As shown, each target location t1, t2, t3 has a triple branching airway from a single ostium. Likewise, in this embodiment, three clips 1000', 1000", 1000''' are positioned at each target location according to FIG. 108. As shown, the three target locations t1, t2, t3 are accessible from a more proximal ostium. Therefore, a delivery device 1010 may be used to access each target location t1, t2, t3 from the same main branch leading thereto. Once the clips are placed, compression is achieved throughout the lung L (as indicated by arrows), raising the diaphragm and restoring airflow.

Figures 110, 111, 112A, 112B:
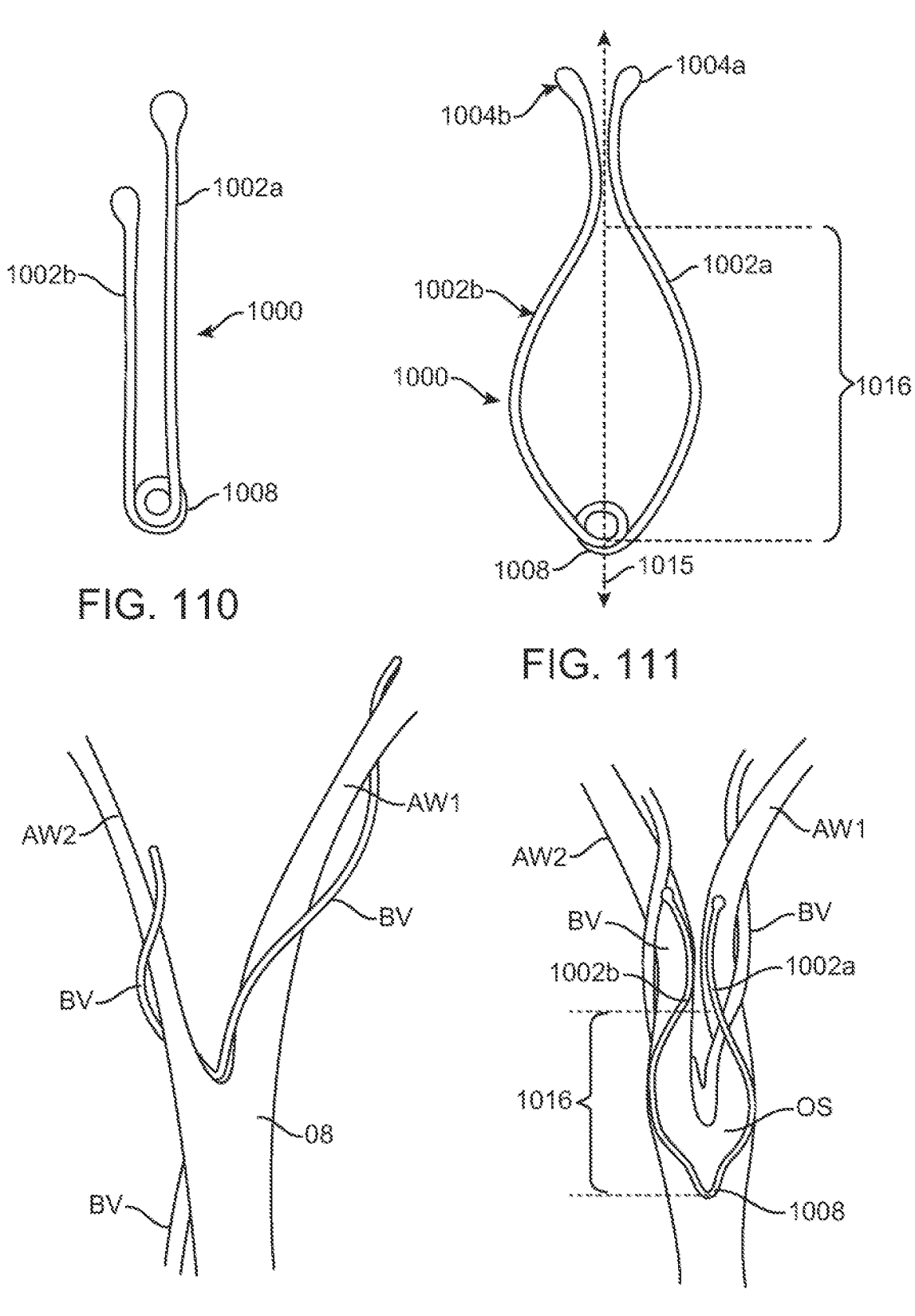
FIG. 110 illustrates an embodiment of a clip having a proximal end that includes a strain relieving loop.
FIG. 111 illustrates an embodiment of a clip having a proximal end that includes a strain relieving loop and arms that are curved rather than straight.
FIGS. 112A-112B illustrate a branched airway having an entwined blood vessel and an embodiment of a clip having a gap.

It may be appreciated that the clips 1000 may take a variety of forms and include a variety of features. As mentioned previously, in some embodiments, the arms 1002a, 1002b of the clip 1000 are formed from a single shaft 1006 that is bent therebetween, thus forming a proximal end 1008 of the clip 1000 that is curved. In some embodiments, the proximal end 1008 may include additional curves, bends or loops to impart particular features. For example, FIG. 110 illustrates an embodiment of a clip 1000 having a proximal end 1008 that includes a strain relieving loop. FIG. 111 illustrates another embodiment of a clip 1000 having a proximal end 1008 that includes a strain relieving loop. However, in this embodiment, the arms 1002a, 1002b are curved rather than straight. In particular, the arms 1002a, 1002b curve outwardly from a longitudinal axis 1015 that extends through the proximal end 1008 and then curve inwardly toward the longitudinal axis 1015 near the tips 1004a, 1004b, thereby creating a bulge. Such curvature of the arms 1002a, 1002b may be beneficial in particular situations, such as when compression of tissue or pulling of airways is desired at a location more distally from the proximal end 1008. Thus, a gap 1016 is provided between the proximal end 1008 and the force bearing surfaces (i.e. between the gaps and the tips 1004a, 1004b) of the arms 1002a, 1002b. This may be useful in a variety of situations. For example, FIGS. 112A-112B illustrate a branched airway having an entwined blood vessel BV. Such entwinement is often common. FIG. 112B illustrates an embodiment of a clip 1000 having a gap 1016 similar to the clip 1000 of FIG. 111. Thus, the clip 1000 is positioned so that a first arm 1002a enters a first airway AW1 and a second arm 1002b enters a second airway AW2 while the proximal end 1008 remains in the ostium OS. The bulge of the arms 1002a, 1002b creating the gap 1016 avoids pinching of the blood vessels BV which reside adjacent the ostium OS. Likewise, the force bearing surfaces of the arms 1002a, 1002b (which reside along the longitudinal axis 1015) are positionable further away from the ostium OS where the airways AW1, AW2 are more easily moved. At this more distal location, the airways AW1, AW2 may be drawn together a greater distance to create more compression of tissue and therefore more tension in the lung. Further, by oversizing the bulge, the walls of the ostium OS (and adjacent collagen and cartilage reinforced airways) may push the arms 1002*a*, 1002*b* into compression creating increased force.

It may be appreciated that the embodiment of the clip 1000 illustrated in FIG. 112B has a proximal end 1008 having the shape of a U-bend. The U-bend comprises a narrowed loop section that, in some instances, reduces strain and stress on the clip 1000 while loaded in the delivery device 1010.

Likewise, the U-bend provides an identifiable location upon which to grasp for easy removal if so desired. Further, when combined with bulged arms, the bulged arms keep the clip 1000 from being excessively spread at the U-bend. It may be appreciated that the U-bend may be present in a variety of variations such as a V-bend, W-bend or other types of bends.

Figures 113, 114, 115, 116:
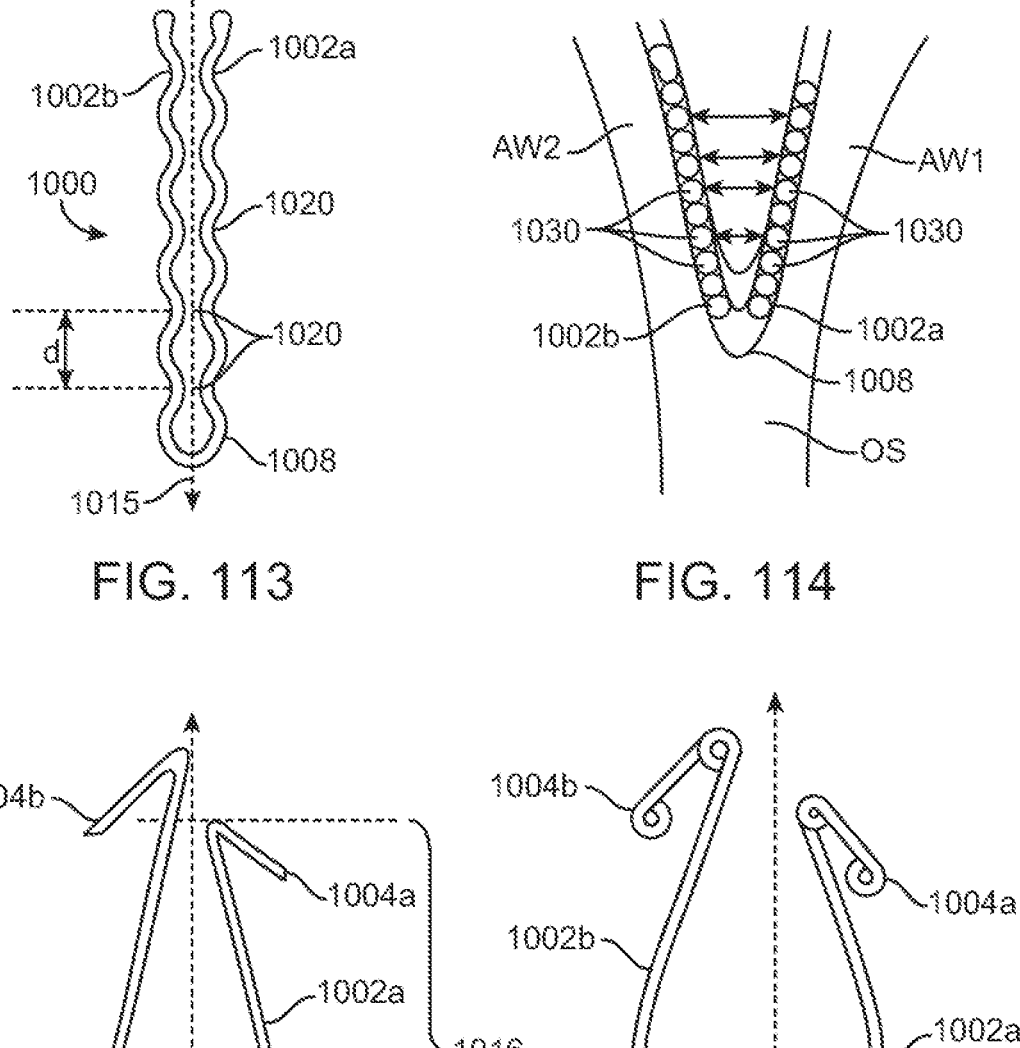
FIG. 113 illustrates an embodiment of a clip having arms with a variety of curves, some of which are symmetrical about a longitudinal axis and some of which are not.
FIG. 114 illustrates an embodiment of a clip having magnets.
FIG. 115 illustrates an embodiment of a clip having pointed tips at the ends of the arms.
FIG. 116 illustrates an embodiment of a clip having tips that are blunt and spring loaded for strain relief.

It may be appreciated that the clip 1000 may have a variety of shapes and sizes. The arms 1002*a*, 1002*b* may be symmetrical or non-symmetrical, of similar or differing length, of similar or differing cross-section, straight or curved, constructed of same or differing material, to name a few. Likewise, the arms 1002*a*, 1002*b* may be formed individually and joined together, either directly to each other (such as by bonding, e.g. metallurgical joining, welding, adhering, gluing) or to an intervening structure such as a connector. Or, the arms 1002*a*, 1002*b* may be formed from a continuous structure, such as described above. The arms 1002*a*, 1002*b* may have consistent or differing cross-section. FIG. 113 illustrates an embodiment of a clip 1000 having arms 1002*a*, 1002*b* with a variety of curves, some of which are symmetrical about a longitudinal axis 1015 and some of which are not. Here, the clip 1000 comprises a proximal end 1008 having a hoop or loop shape. Each arm 1002*a*, 1002*b* extends distally therefrom in a repetitive pattern (mirroring each other)—first bulging outwardly away from the longitudinal axis 1015 and then curving inwardly toward the longitudinal axis 1015—creating contact points 1020 along the longitudinal axis 1015. These contact points 1020 are separated by a distance d along the longitudinal axis 1015. The distance d between each of the contact points 1020 may be the same or may vary. By spacing the contact points 1020 farther apart, the clip 1000 is stronger and by spacing them closer together, the clip 1000 can be made to be more flexible. In preferred embodiments, the proximal end 1008 having the U-bend is strong and the distal free ends are flexible. In this embodiment, the aforementioned repetitive pattern ends near the tips 1004*a*, 1004*b* wherein the arms 1002*a*, 1002*b* then curve in a nesting arrangement. Thus, where the first arm 1002*a* bends toward the longitudinal axis 1015, the second arm 1002*b* bends away from the longitudinal axis 1015. Therefore, in this region, the arms 1002*a*, 1002*b* follow the shape of each other (nesting against each other) so as to create additional contact surface area. By nesting, the tissue contact is continuous and smooth. This may eliminate pinch points that can potentially pinch off blood vessels or tissue circulation.

It may be appreciated that the clip 1000, particularly the arms 1002*a*, 1002*b* may be coated, covered, jacketed, treated or otherwise surface modified so as to create beneficial results, such as increased gripping strength. For example, in some embodiments one or more portions of the clip 1000 covered with a metal or polymer structure (e.g. coil, weave, etc.). Optionally, one or more portions of the clip 1000 may be coated with or covered by a drug eluting substance or polymer, such as to reduce inflammation or to kill bacteria.

In some embodiments, the clip 1000 includes one or more magnets to increase gripping strength. Such magnets may be incorporated into a cover or jacket, or such magnets may be constructed in the arms 1002*a*, 1002*b* (or other portions of the clip 1000) themselves. FIG. 114 illustrates an embodiment of a clip 1000 having magnets. In this embodiment, a series of magnets 1030 are positioned along a first arm 1002*a* and a coordinating series of magnets 1030' are positioned along a second arm 1002*b*. Typically, the magnets 1030 and their coordinating magnets 1030' are disposed directly opposite each other so as to draw the magnets 1030, 1030' toward each other, however it may be appreciated that magnetic force may be varied by placement of the magnets 1030, 1030', type of magnets and size of magnets, to name a few. Positioning of the clip 1000 having magnets 1030, 1030' so that the first arm 1002*a* is within a first airway AW1 and the second arm 1002*b* is within a second airway AW2, as illustrated in FIG. 114) allows the magnets 1030, 1030' to naturally draw the arms 1002*a*, 1002*b* toward each other by magnetic force. First, the closest magnets 1030, 1030' are drawn together which then disposes the next closest magnets 1030, 1030' to be drawn together and so forth in a zipper fashion. As the arms 1002*a*, 1002*b* move closer together, the magnetic force increases (exponentially with reduced distance) until the maximum compression of the tissue therebetween occurs. During breathing, the distance between the magnets 1030, 1030' may vary, however, the magnetic force will then resume its resting arrangement. Magnets provide a beneficial result due to their ability to provide more force than many other mechanical solutions and they can be easily removed.

As mentioned previously, the clips 1000 typically include a first arm 1002*a* and a second arm 1002*b*, each having a free end with a respective tip 1004*a*, 1004*b*, such as an atraumatic (e.g. blunt) or traumatic (e.g. pointed) tip. In some embodiments, the tip (e.g. tip 1004*a*) is aligned with its respective arm (e.g. arm 1002*a*). In other embodiments, such as depicted in FIGS. 115-116, the tips 1004*a*, 1004*b* are located on a portion of their respective arms 1002*a*, 1002*b* which bend radially outward. In these embodiments, the arms 1002*a*, 1002*b* bulge away from a longitudinal axis 1015 throughout the gap 1016 and then bend toward the longitudinal axis 1015 and each other in the distal direction creating an area of contact and compression of tissue therebetween. More distally, arms 1002*a*, 1002*b* then bend away from the longitudinal axis 1015, such as at a downward angle, as shown so that the tips 1004*a*, 1004*b* are facing radially outward. Such angling allows the arms 1002*a*, 1002*b* to slide along the most inward walls of a bifurcated airway while the tips 1004*a*, 1004*b* prevent retraction. Such resistance may be traumatic, such as in FIG. 115 wherein the tips 1004*a*, 1004*b* are pointed, or atraumatic, such as in FIG. 116 wherein the tips 1004*a*, 1004*b* are blunt. In FIG. 116, the tips 1004*a*, 1004*b* are spring loaded for strain relief.

Figures 117, 118, 119, 120, 121:
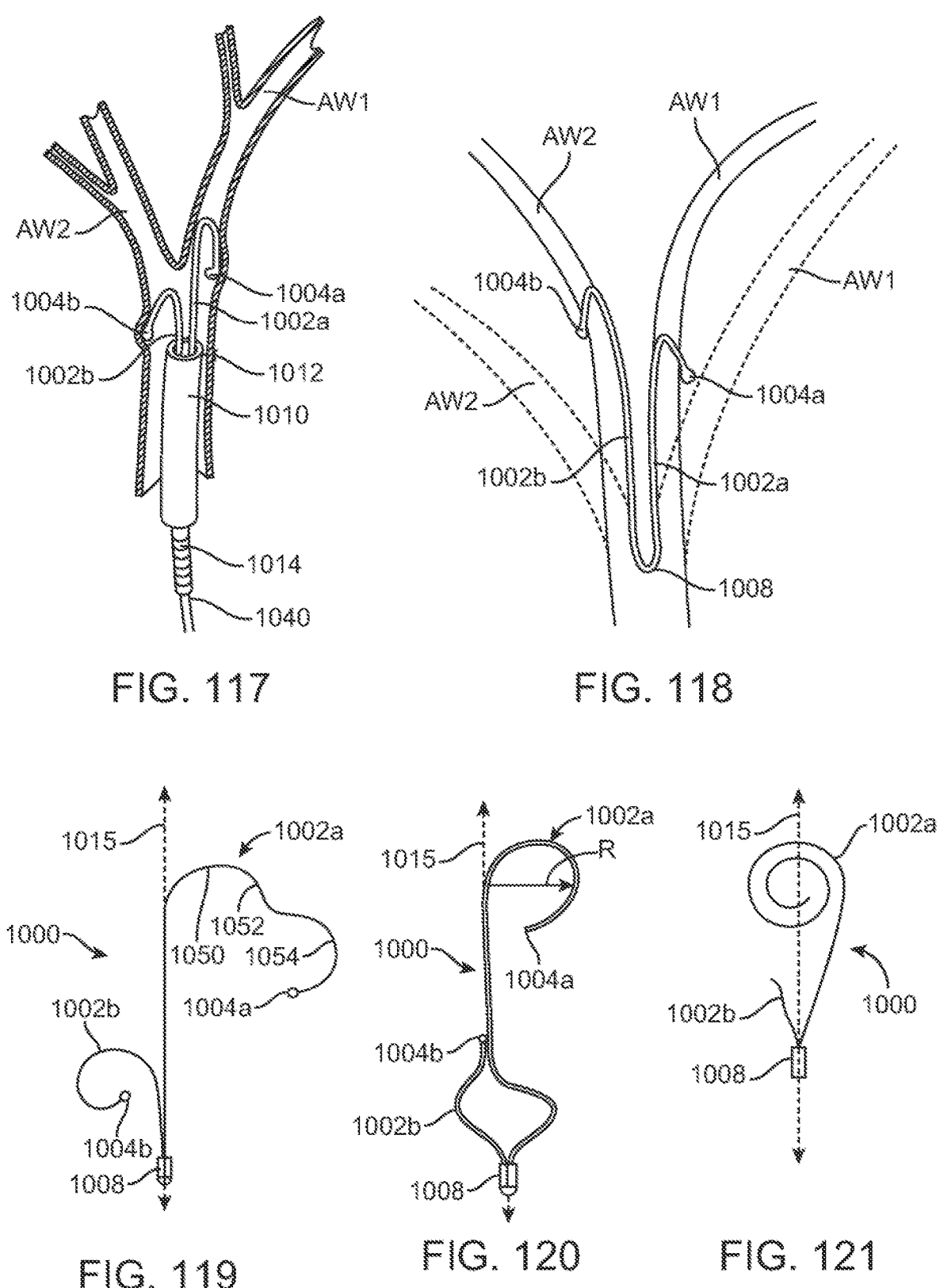
FIG. 117 illustrates the embodiment of the clip being delivered with the use of a delivery device.
FIG. 118 illustrates the clip of FIG. 117 fully deployed within the bifurcation.
FIGS. 119-121 illustrate embodiments of clips wherein the arms have differing lengths and/or shapes from each other.

FIGS. 117-118 illustrate an embodiment of a clip 1000 having proximal facing tips 1004*a*, 1004*b* positioned within a bifurcation. In particular, FIG. 117 illustrates the embodiment of the clip 1000 being delivered with the use of a delivery device 1010. Here, the distal tips 1004*a*, 1004*b* have been deployed from the distal end 1012 of the delivery device 1010, wherein a first arm 1002*a* is entering a first airway AW1 and a second arm 1002*b* is entering a second airway AW2, by advancement of a deployment device 1014 (e.g. pusher or plunger). The tips 1004*a*, 1004*b* are advanced along the airways AW1, AW2 engaging the walls as shown. Due to the strength of the arms 1002a, 1002b, the walls may bend at the areas of engagement creating points of purchase. Thus, retraction of the clip 1000 is resisted due to the points of purchase. However, in some embodiments, this resistance may be overcome with sufficient force. FIG. 117 illustrates a tether 1040 extending proximally from the delivery device 1010, wherein the tether 1040 is attached to the proximal end 1008 of the clip 1000 so as to allow such retraction of the clip 1000. FIG. 118 illustrates the clip 1000 of FIG. 117 fully deployed within the bifurcation. As shown, the first airway AW1 and the second airway AW2 are drawn together due to the recoil force of the arms 1002a, 1002b toward each other. Typically, the arms 1002a, 1002b are comprised of materials that can store strain energy, such as spring steel. The clip 1000 resists slipping out of position due to the frictional force of the tips 1004a, 1004b applying purchase to the airway walls. In some embodiments, the arms 1002a, 1002b are constructed so as to buckle or flip if sufficient force is applied in the proximal direction (i.e. causing the arms 1002a, 1002b to essentially straighten). This allows the clip 1000 to be removed while minimizing any trauma to the lung tissue.

It may be appreciated that each of the arms 1002 of the clip 1000 may have differing shapes, including irregular shapes or compound curvatures. For example, FIGS. 119-121 illustrate embodiments of clips 1000 wherein the arms 1002a, 1002b have differing lengths and/or shapes from each other. Referring to FIG. 119, the clip 1000 has a first arm 1002a which is longer than the second arm 1002b. Further, the first arm 1002a has a shape formed by curving radially outwardly from the longitudinal axis 1015 and forming a first curvature 1050, a second curvature 1052 and then a third curvature 1054. The first curvature 1050 has an arc shape which then transitions into an inverse arc shape for the second curvature 1052. This then transitions into a semi-circle or arch shape which directs the distal tip 1004a toward the longitudinal axis 1015. This compound curvature (combination of curvatures 1050, 1052, 1054) creates a hook shape which may be used for gathering diseased tissue (e.g. loose tissue), such as in a twisting fashion and a pulling fashion. The partial loop shape extending radially outwardly from the longitudinal axis 1015 may assist in gathering tissue during torqueing, as described previously. However, it may be appreciated that the compound curvature may be used for other purposes without twisting, torqueing or pulling. It may be appreciated that the hooking shape (distal tip 1004a facing the longitudinal axis 1015) may assist in holding tissue or creating purchase when pulling the clip 1000 in the proximal direction, such as along the longitudinal axis 1015. In this embodiment, the second arm 1002b curves radially outwardly from the longitudinal axis 1015 in a direction opposite the first arm 1002a. Again, a hooking shape is formed (distal tip 1004b facing the longitudinal axis 1015). Still, the arms 1002a, 1002b are constructed so as to compress tissue positioned between the arms 1002a, 1002b thereby straightening the airways as described above.

It may also be appreciated that the arms 1002 may have a variety of other shapes, including bends and arcs which are rounded or angular, in the same direction or opposite directions, and in a variety of configurations. FIG. 120 illustrates a clip 1000 similar to that illustrated in FIG. 111 but with an extended first arm 1002a. Here, the first arm 1002a comprises a partial loop which curves radially outwardly from the longitudinal axis 1015 and extends such that the tip 1004a is directed back toward the longitudinal axis 1015. In other embodiments, the distal tip 1004a is directed substantially parallel to the longitudinal axis 1015 in the distal direction, such as extending around a full circle. In such embodiments, the loop may be described as having a radius R. Such a loop shape may serve a variety of purposes. In some instances, the loop functions creates a hook shape which may be used for gathering diseased tissue (e.g. loose tissue), such as in a twisting fashion and a pulling fashion. The partial loop shape extending radially outwardly from the longitudinal axis 1015 may assist in gathering tissue during torqueing, as described previously. However, it may be appreciated that the partial loop shape may be used for other purposes without twisting, torqueing or pulling. It may be appreciated that the hooking or loop shape (distal tip 1004a facing the longitudinal axis 1015) may assist in holding tissue or creating purchase when pulling the clip 1000 in the proximal direction, such as along the longitudinal axis 1015. Still, the arms 1002a, 1002b are constructed so as to compress tissue positioned between the arms 1002a, 1002b thereby straightening the airways as described above.

FIG. 121 illustrates another embodiment of a clip 1000 having an extended first arm 1002a with a shape differing from its second arm 1002b. Here, the arms 1002a, 1002b are joined at the proximal end 1008. In this embodiment, the first arm 1002a extends in a first direction from the proximal end 1008 and then bends laterally outwardly in a second direction to form a circular, inwardly spiraled shape. In this embodiment, the second arm 1002b extends from the proximal end 1008 generally along a longitudinal axis 1015 but has a shorter length than the first arm 1002a. FIG. 121 illustrates the second arm 1002b bowed outwardly, away from the longitudinal axis 1015 as it would appear when implanted. However, it may be appreciated the arms 1002a, 1002b are configured recoil toward each other, compressing tissue therebetween.

Figure 122:
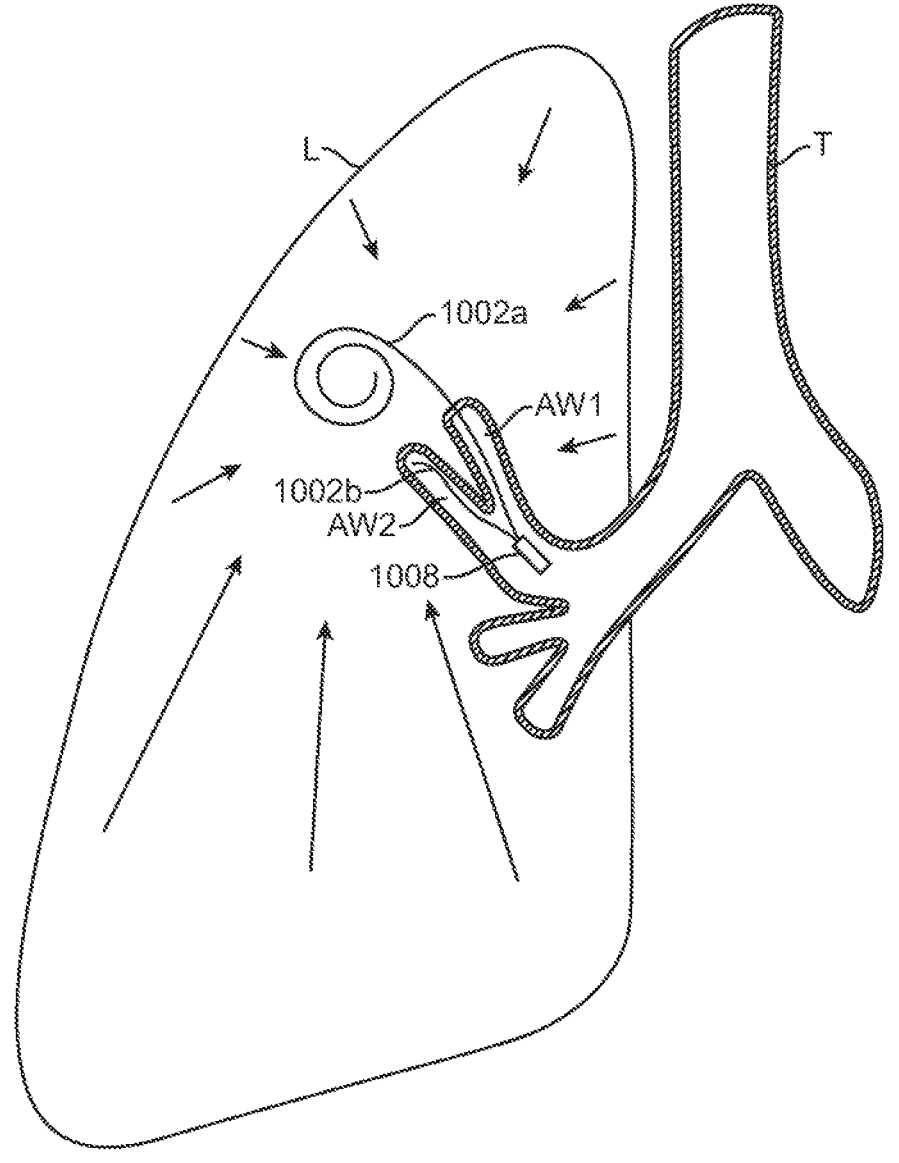
FIG. 122 illustrates the clip of FIG. 121 positioned at a bifurcation.

This is illustrated in FIG. 122 wherein the clip 1000 of FIG. 121 is shown positioned at a bifurcation. In some instances, the inwardly spiraled shape of the first arm 1002a may be used for gathering diseased tissue (e.g. loose tissue), such as in a twisting fashion and a pulling fashion. The spiral shape may assist in gathering tissue during torqueing, as described previously. However, it may be appreciated that the spiral shape may be used for other purposes without twisting, torqueing or pulling. It may be appreciated that the spiral shape may assist in holding tissue or creating purchase when pulling the clip 1000 in the proximal direction, such as along the longitudinal axis 1015. Still, the arms 1002a, 1002b are constructed so as to compress tissue positioned between the arms 1002a, 1002b thereby straightening the airways as described above.

In some embodiments, the delivery device 1010 is configured to rotate the clip 1000 during its delivery to assist in positioning the arms 1002 into the airways. FIG. 123 illustrates an embodiment of a delivery device 1010 having a deployment device 1014 that is coupleable to the clip 1000 in a manner that allows transmission of torque to the clip 1000 by rotation of the deployment device 1014. FIG. 124 provides a close-up view of an embodiment of such a deployment device 1014. In this embodiment, the deployment device 1014 has a blunt distal end 1060. In this embodiment the blunt distal end 1060 is closed, however it may be appreciated that it may alternatively be open to allow passage of tools or instruments therethrough. In this embodiment, the deployment device 1014 includes an indent, slot or window 1062 having a top edge 1064 and a bottom edge 1066. In this embodiment, the window 1062 has a flat bottom edge 1066. This provides a flat surface to apply direct force to the clip 1000 during advancement of the deployment device 1014. In this embodiment, the window 1062 has a slanted top edge 1064. This allows the clip 1000 to slide out of the window 1062 when the deployment device 1014 is retracted. However, the clip 1000 can be held within the window 1062 with the use of a hitch wire 1068 which is advanceable at least partially through the deployment device 1014 so as to cross through the window 1062, holding the proximal end 1008 of the clip 1000 within the window 1062, as depicted in FIG. 124. Retraction of the hitch wire 1068 allows the proximal end 1008 of the clip 1000 to slide along the slanted top edge 1064 and out of the window 1062. This is desired when the clip 1000 is released for implantation. It may be appreciated that the window 1062 may have a variety of shapes. In some embodiments the window 1062 has a slanted bottom edge 1066. This may assist in holding the proximal end 1008 of the clip 1000 in place during rotation. FIG. 125 illustrates an embodiment of a window 1062 having a spiral shape. This allows the clip 1000 to remain captured in the window 1062 when the deployment device 1014 is loaded in rotation but releases the clip 1000 when counter-rotation is applied. Thus, the window 1062 can be locking in clockwise rotation and releasing in counter-clockwise rotation or vice versa.

FIG. 126 illustrates an embodiment of a deployment device 1014 similar to FIG. 124, however here the hitch wire 1068 has a configured proximal end 1070 and distal end 1072. In this embodiment, the distal end 1072 has a loop shape which provides a blunt tip and is sized to resist retraction into the deployment device 1014. In such embodiments, the hitch wire 1068 is comprised of a compliant material which is able to plastically or elastically deform in shape to allow the distal end 1072 to be retracted into the deployment device 1014 with sufficient positive load in the proximal direction. This assists in avoiding accidental withdrawal of the hitch wire 1068 and release of the clip 1000. Continued pulling of the hitch wire 1068 in the proximal direction will allow the distal end 1072 to pass through the window 1062, releasing the clip 1000. In this embodiment, the proximal end 1070 of the hitch wire 1068 has a thumb-loop that assists in grasping for manipulation of the hitch wire 1068, such as pushing and pulling. It may be appreciated that the proximal end 1070 may have a variety of shapes and features to assist in manipulation.

Referring back to FIG. 123, the first arm 1002*a* is longer and is advanced into the first airway AW1 prior to positioning of the second arm 1002*b*. Once the first arm 1002*a* enters the first airway AW1, the clip 1000 is optionally rotated to angle and align the second arm 1002*b* with the second airway AW2. This is achieved by rotating the deployment device 1014. As depicted in FIG. 124, the position of the clip 1000 is fixed in relation to the deployment device 1014 because the proximal end 1008 of the clip 1000 is held within the window 1062 by the hitch wire 1068. Thus, rotation of the deployment device 1014 is transmitted to the clip 1000. Once the second arm 1002*b* is desirably rotated, the clip 1000 is further advanced so the arms 1002*a*, 1002*b* are advanced further into the airways AW1, AW2. Once the clip 1000 is desirably positioned (e.g. the proximal end 1008 is positioned within the ostium OS near the bifurcation), the hitch wire 1068 is retracted so as to open the window 1062. Retraction of the deployment device 1014 then allows the clip 1000 to slide along the top edge 1064 of the window 1062 and out of the window 1062. The deployment device 1014 and delivery device 1010 can then be removed, leaving the clip 1000 behind.

Invertible Pulmonary Treatment Device Embodiments

A variety of embodiments of invertible pulmonary treatment devices 2000 are provided. The devices 2000 are comprised of a shape memory material or one or more materials that can be strained more than 2% strain before plastic and permanent deformation. The devices 2000 are able to be expanded under tension, and then are able to recoil back toward an original relaxed or resting shape. Thus, each device 2000 is able to be strained, tensioned or expanded to store energy, wherein the energy is utilized to continually provide shape recovery which maintains tension on the lung tissue as the device 2000 relaxes, self-recovers and becomes less strained as it transitions toward its original shape. In these embodiments, a portion of the device 2000 is invertible. In some embodiments, the invertible portion inverts during expansion of the device 2000 and relaxes toward an uninverted orientation, tensioning the lung as it relaxes. However, it may be appreciated that in some embodiments the invertible portion relaxes toward an inverted orientation from an uninverted orientation. It may be appreciated that in some embodiments inversion comprises partial inversion and recovery of inversion comprises partial recovery. Thus, in some embodiments, the device 2000 fully inverts and partially recovers (i.e. uninverts) and in some embodiments the device 2000 partially inverts and fully recovers (i.e. univerts). In some embodiments, the invertibility, inversion ability or amount of inversion of the device 2000 provides a distinct visual indication to the user as to the changing tension in the lung tissue during placement of the device 2000 and after implantation. In some embodiments, while the device 2000 is in its relaxed configuration (prior to inversion), slacked tissue is being gathered with minimal or no tension applied to the lung. Inversion begins once slacked tissue is taut and force is continued to be applied to the device 2000. Such inversion can be achieved by extremely low forces allowing fine granularity of control while force is applied to the device 2000 and attached lung tissue. In some embodiments, the forces that deform the implant into the inverted position are approximately similar to normal lung tissue elastic recoil force (e.g. in a range between 0.001 pounds force per inch to 1.0 or more pounds force per inch). Thus, the invertible pulmonary treatment devices 2000 typically have a very low modulus of elasticity or spring constant. This allows the user to be able to manipulate the device 2000, particularly so as to apply tension to the lung L, without risking tearing the lung tissue or ripping the device 2000 from the lung tissue. Thus, the inversion acts as a clutch to prevent sudden failure of the extremely degraded lung tissue to which the device 2000 has attached or grasped. Example embodiments of invertible pulmonary treatment devices 2000 and example methods of delivery are provided herein.

FIG. 127 illustrates an embodiment of an invertible pulmonary treatment device 2000 emerged from a delivery device 2010, such as a catheter. FIG. 127 illustrates the device 2000 in its relaxed state, without inversion. For reference the device 2000 may be considered to be disposed within a three dimensional space defined by an x-axis (axis 2016), a y-axis (longitudinal axis 2012) and a z-axis (axis 2011). Thus, plane of the paper is considered to substantially correlate to the x-y plane. In this embodiment, the device 2000 includes at least one inversion element 2002 and at least one anchoring element 2004 which are disposed near opposite ends of the device 2000 along the longitudinal axis 2012. In particular, in this embodiment, the device includes a first inversion element 2002*a* and a second inversion element 2002*b*, each of which extend along the longitudinal axis 2012 and then curve radially outwardly away from the longitudinal axis 2012 forming a loop around an axis 2014 (i.e. the first inversion element 2002*a* forms a loop around a first axis 2014*a* and the second inversion element 2002*b* forms a loop around a second axis 2014*b*). Each of the first and second axis 2014*a*, 2014*b* are parallel to axis 2011 (z-axis) and therefore extend substantially out of the page. Typically, the first axis 2014*a* is spaced apart from the longitudinal axis 2012 and perpendicular to the plane of the loop of the first inversion element 2002*a*. In this embodiment, the first and second inversion elements 2002*a*, 2002*b* extend in opposite directions from the longitudinal axis. In some embodiments, the outer diameter of the loop of the first or second inversion elements 2002*a*, 2002*b* is in the range of 0.400 inches to 3.0 inches in diameter or any size between. Most preferably, the loop may have an outer diameter in the range of 0.75 inches to 1.25 inches. In this embodiment, each of the first and second inversion elements 2002*a*, 2002*b* curve to form a respective holding element or tissue gathering element 2006*a*, 2006*b* which will be used to capture and hold tissue during positioning of the device 2000. In this embodiment, each tissue gathering element 2006*a*, 2006*b* has a loop shape which terminates in its respective distal tip 2008*a*, 2008*b*. In some embodiments, the outer diameter of the loop of the first or second tissue gathering elements 2006*a*, 2006*b* is in the range of 0.1 inches to 0.9 inches in diameter or any size between. Most preferably, the loop may have an outer diameter in the range of 0.2 inches to 0.3 inches. In this embodiment, each tissue gathering element 2006*a*, 2006*b* extends around an axis 2016' which is parallel to and above axis 2016 so as to form a loop residing in the y-z plane. Thus, in this embodiment, the axis 2016' is perpendicular to the longitudinal axis 2012 so that the loops of the tissue gathering elements 2006*a*, 2006*b* lie in parallel planes, each of which are substantially perpendicular to the plane of the inversion elements 2002*a*, 2002*b*. Likewise, in this embodiment, the axis 2016' is offset from the longitudinal axis 2012 so that the tissue gathering elements 2006*a*, 2000*b* protrude upwardly (out of the page). In this embodiment, the tissue gathering elements 2006*a*, 2006*b* are disposed near the inversion elements 2002*a*, 2002*b*, such as aligned with the inversion elements 2002*a*, 2002*b*. For example, in this embodiment, if the loops of the tissue gathering elements 2008*a*, 2008*b* were bent down into the plane of the inversion elements 2002*a*, 2002*b*, the tissue gathering elements 2008*a*, 2008*b* would reside within the loops of the inversion elements 2002*a*, 2002*b*. It may be appreciated that the tissue gathering elements 2006*a*, 2006*b* may have a variety of shapes and may be positioned in a variety of orientations in relation to the inversion elements 2002*a*, 2002*b*.

In this embodiment, the invertible pulmonary treatment device 2000 includes an anchoring element 2004 positioned opposite the inversion elements 2002*a*, 2002*b* (i.e. spaced apart from the inversion elements 2002*a*, 2002*b* along the longitudinal axis 2012. In this embodiment, the anchoring element 2004 has a coiled shape, wherein each turn of the coil extends at least partially around the longitudinal axis 2012. The anchoring element 2004 is configured to be positioned within a lung passageway, such as an airway or ostium OS.

FIG. 128 illustrates an embodiment of an invertible pulmonary treatment device 2000 that is similar to that illustrated in FIG. 127. Here, the device 2000 is released from the delivery device so as to reveal the remainder of its proximal end. In this embodiment, the anchoring element 2004 comprises three turns of a coil and then dips down to form an attachment feature 2020. In this embodiment, the attachment feature 2020 has the form of a small loop that can be grasped, tethered or otherwise coupled to a portion of a delivery device 2010.

FIG. 129 illustrates another embodiment of an invertible pulmonary treatment device 2000. Here, the device 2000 is emerging from a delivery device 2010 and has inversion elements 2002*a*, 2002*b* and tissue gathering elements 2006*a*, 2006*b* similar to those of FIGS. 127-128. In this embodiment, the device 2000 has an anchoring element 2004 comprising a plurality of loops around the longitudinal axis 2012. Here, the anchoring element 2004 is formed from two portions of a shaft which extend around in a first loop shape and then cross to form an additional loop shape substantially concentric with the first loop shape below.

FIG. 130 illustrates another embodiment of an invertible pulmonary treatment device 2000. Here, the device 2000 is released from the delivery device so as to reveal the remainder of its proximal end. In this embodiment, the anchoring element 2004 comprises an arc shape extending at least partially around the longitudinal axis 2012. In this embodiment, the attachment feature 2020 has the form of a small loop that can be grasped, tethered or otherwise coupled to a portion of a delivery device 2010.

It may be appreciated that the invertible pulmonary treatment device 2000 may be formed from a single continuous shaft or from a combination of two or more elements acting as a continuous shaft that are fixed together, such as by welding, gluing, thermally friction bonding, crimping, locking together using puzzle lock patterns, locking extrusion sections within each other, wrapping with a spring, riveting, locking together with threaded fasteners, or by joining using locking hardware that is known in the art. The devices 2000 illustrated in FIGS. 127-130 are comprised from a single continuous shaft. Such single element designs enjoy the benefit of not comprising joints or links that may fail due to strain or bending during the high number of breathing cycles the device may encounter during the remainder of the patient's life. The single element may be made with varying diameter sections or it can be made from tapered diameter material as well as material that has totally non-uniform size or cross section along its length. In some embodiments, the shaft is comprised of wire, such as metal (e.g. nitinol, austenite or martensite nitinol, spring steel, stainless steel, cobalt steel alloys, titanium etc.) or polymeric compounds, ceramic, carbon fiber and/or other biocompatible materials. Such wire is typically extruded, drawn or sintered into near net shapes or wire form. A single component structure may be configured with tuned material properties in different locations of the single element. Nitinol material may be adjusted by using local heat treatment techniques to increase or decrease the stiffness or modulus of elasticity in local portions of the wire.

In some embodiments, the shaft has a flattened, ribbon shape. In some embodiments, the ribbon shape is between 0.005 and 0.030 inches wide and between 0.005 and 0.030 inches thick in dimension. The ribbon may be blasted or tumbled in abrasive media to round the edges so it more closely appears like a round cross-section wire. Alternatively, the shaft may be made from round cross section wire, for example having a diameter between 0.003 and 0.050 inches. In some embodiments, the anchoring element 2004 may be configured to form a coil shaped stent or helix with an outer diameter of the helix that is between 5 mm and 17 mm in diameter but more preferably it is between 6 mm and 10 mm in diameter.

One or more invertible pulmonary treatment devices 2000 may be positioned within the lungs L as will be described herein. It may be appreciated that a plurality of invertible pulmonary treatment devices 2000 may be positioned within a single airway, within multiple airways, within a single lung or within both lungs. Likewise, in some instances, the invertible pulmonary treatment devices 2000 may be used in combination with other pulmonary treatment devices described herein or in combination with conventional implantable therapeutic devices and treatment techniques.

FIG. 131 illustrates a branched lung passageway comprising a first airway AW1 that extends into damaged tissue DT in the area of alveoli. In such areas of damaged tissue DT, large portions of parenchyma are often unsupported, loose or missing, forming coalesced blebs and bullae. Thus, any existing tissue is sponge-like and very weak. FIG. 131 also illustrates airways A that have collapsed near the area of damaged tissue DT. In this embodiment, a bronchoscope 20 is advanced into the lung passageway and a delivery device 2010 is advanced through the bronchoscope 20 so that the distal end 2013 of the delivery device 2010 resides within the first airway AW1. In this embodiment, the invertible pulmonary treatment device 2000 is disposed within the distal end 2013. Therefore, the distal end 2013 is positioned at the target location within the first airway AW1 for deployment of the device 2000 therefrom. It may be appreciated that in some embodiments the target location is within damaged tissue DT or other tissue where airway walls are not present.

FIG. 132 illustrates an early step in this embodiment of the process of deployment of the device 2000. Here, the device 2000 is advanced within the delivery device 2010 (or the delivery device 2010 is retracted) so that the distal tips 2008a, 2008b emerge from the distal end 2013 of the delivery device 2010. Due to the precurvature of the tissue gathering elements 2006a. 2006b, the tips 2008a, 2008b begin to curve radially outwardly in opposite directions. In this step of this embodiment, the first distal tip 2008a penetrates the wall W of the first airway AW1 and extends into the damaged tissue DT. The second distal tip 2008a does not penetrate the wall W and begins to curve within the first airway AW1. It may be appreciated that these serve as examples and the tips 2008a, 2008b may act the same or differently, penetrating the wall W or not, advancing into the damaged tissue or not. In any situation, tissue (either wall tissue, damaged tissue or other tissue) is grasped, even if such grasping is by frictional force or denting into the wall to form a purchase area. Additional portions of the tissue gathering elements 2006a, 2006b are exposed to allow the inversion elements 2002a, 2002b to emerge. In some embodiments, as the inversion elements 2006a, 2006b form, the grasped tissue is more adequately held and/or additional tissue is grasped.

FIG. 133 illustrates an example of the inversion elements 2002a, 2002b fully deployed. Since the tissue gathering elements 2006a, 2006b are grasping and holding tissue, the remainder of the inversion elements 2002a, 2002b loop up and over the tissue gathering elements 2006a, 2006b. FIG. 133 illustrates the inversion elements 2002a, 2002b extending into the damaged tissue DT and the tissue gathering elements 2006a, 2006b grasping damaged tissue DT.

At this point in this embodiment of the deployment procedure, the device 2000 is partially deployed and able to start applying tension or significantly increase tension applied to the lung tissue. The portion of the device 2000 coupled to the catheter 2010 is then pulled in the proximal direction, either by applying pulling force to the proximal portion of the device 2000, applying pulling force to the catheter 2010 and/or applying pulling force to the bronchoscope 20. Since the tissue gathering elements 2006a, 2006b have grasped tissue, typically damaged tissue DT, the damaged tissue DT is pulled in the proximal direction as well. This continues until the tissue slack is gathered. At some point, the slacked tissue will become sufficiently gathered and tension will begin to develop in the lung tissue. It is at this point that the user is to be particularly diligent so as to not tear the tissue with excess pulling force. This is assisted by the invertible design of the device 2000. Once the lung tissue is sufficiently taut, additional pulling force serves to invert the device 2000. FIG. 134 illustrates a device 2000 that has been pulled so that the inversion elements 2002a, 2002b have inverted. Thus, the portions of the inversion elements 2002a, 2002b that were previously disposed above the tissue gathering elements 2006a, 2006b are now disposed below the tissue gathering elements 2006a, 2006b. As shown, the airways A that were previously collapsed are now open, becoming rounder and larger. The airways A are also shifted more proximally; in some instances, this tissue can be relocated quite substantially. FIG. 134 illustrates the nearby tissue being tensioned (straightened lines) and the damaged tissue DT is compressed (curved lines representing loose, floppy tissue) by the device 2000. The obvious deformation of the device 2000 gives the user a distinct visual indication as to how far to pull the system back. If the lung tissue is extremely slacked, the device 2000 may be shifted proximally 1 mm to 100 mm, in some instances, before tension is restored. Only after restoration of tension will the device 2000 begin to elongate and invert. By incorporating a curvilinear design with loops or other shapes that are non-straight, the deformation of the device 2000 may be accomplished with extremely low forces. In some instances, the forces used to deform the implant are approximately similar to normal lung tissue elastic recoil force, such as in a range between 0.001 pounds force per inch to 1.0 or more pounds force per inch. By providing a visual signal (implant deformation) that more than zero net tension has been generated in the tissue and by providing a deformable implantable device 2000 with a very low modulus of elasticity or spring constant, the user can pull the proximal end of the device 2000 without risking tearing the lung tissue and/or ripping the device 2000 from the tissue. Thus, the low force deformable device 2000 can act as a clutch to prevent suddenly ripping the inversion elements 2002a, 2002b out of even extremely degraded lung tissue.

The inverted arrangement of the device 2000 also stores potential energy or spring force to enhance lung elastic recoil. The inversion and extension of the inversion elements 2002a, 2002b stores potential energy to maximize duration of effect to provide chronic force to the lung to take up slack as the diseased tissue elongates over time.

The device 2000 is then anchored in place. This is achieved by deploying the anchoring element 2004. FIG. 135 illustrates an embodiment of the anchoring element 2004 deployed by retraction of the delivery device 2010 and optionally the bronchoscope 20. Here, the anchoring element 2004 bows outwardly within the first airway AW1 and anchors against the airway walls W. It may be appreciated that the anchoring element 2004 may anchor against the wall W by frictional force, creating an indent in the wall W and a tissue ledge which impedes movement or by penetrating the wall W. It may also be appreciated that the anchoring element 2004 may alternatively be deployed within the ostium OS.

FIG. 136 illustrates the device 2000 decoupled from the delivery device 2010, revealing the attachment feature 2020. Such decoupling allows the device 2000 to elastically recover to a shorter length. Thus, the inversion elements 2002*a*, 2002*b* and the anchoring element 2004 are drawn toward each other. In some instances, this includes partial or total reverse of the inversion, as illustrated in FIG. 136. The tissue distal to, proximal to and adjacent to the device 2000, and in some instances generally everywhere in the lung, is tensioned more and the lung elastic recoil is restored. The tissue immediately between the inversion elements 2002*a*, 2002*b* and the anchoring element 2004 is compressed and that relative volume is reduced (lung volume reduction) as shown by the squiggly lines representing compressed tissue. The cross-sections of the airways A are now large and round as the tensioned tissue provides radial outward suspension to hold them open. The delivery device 2010 and bronchoscope 20 are then removed and the device 2000 is left behind as an implant.

FIG. 137A illustrates another embodiment of an invertible pulmonary treatment device 2000. Here, the device 2000 is shown in its relaxed state, without inversion. In some embodiments, the overall length of the device 2000 in the relaxed state is from 5-250 mm, preferably 75-110 mm for short airways and 100-150 mm for long airways that are found in the lower lobes of the lung. The shortening ratio can be 2:1 up to 100:1 but typically 10:1 (distance between the tissue gathering elements 2006*a*, 2006*b* and the proximal anchoring element 2004 starts out 100 mm and ends up 10 mm).

In this view, the tissue gathering elements 2006*a*, 2006*b* are disposed below the inversion elements 2002*a*, 2002*b*. The inversion elements 2002*a*, 2002*b* reside in an x-y plane, defined by an x-axis (axis 2016) and a y-axis (longitudinal axis 2012). The first inversion element 2002*a* and the second inversion element 2002*b* both extend along the longitudinal axis 2012 and then curve radially outwardly away from the longitudinal axis 2012 forming a loop around an axis 2011 (z-axis). In some embodiments such a loop has a diameter of 0.2-3 inches, such as 0.4-1 inches. In this embodiment, the inversion elements 2002*a*, 2002*b* are shown both curving to the right of the longitudinal axis 2012, but it may be appreciated that both may curve to the left of the longitudinal axis 2012. In both cases, the inversion elements 2002*a*, 2002*b* are concentric with each other. It may be appreciated that in some embodiments each of the inversion elements 2002*a*, 2002*b* extend along the longitudinal axis 2012 and then curve radially outwardly away from the longitudinal axis 2012 and each other, each forming a loop around a separate axis (2011*a*, 2011*b*), as illustrated in FIG. 137B. However, in the examples shown herein below, the inversion elements 2002*a*, 2002*b* are described and illustrated as being concentric to create a more compact device design.

FIG. 138 provides a side view of the device 2000 of FIG. 137A. This shows that the tissue gathering elements 2006*a*, 2006*b* are disposed below the inversion elements 2002*a*, 2002*b*, extending downward in the negative direction of the axis 2011 (z-axis) and looping around an axis 2017 which is parallel to axis 2016 (x-axis) and perpendicular to both the longitudinal axis 2012 and the axis 2011 (z-axis). Thus, axis 2017 is parallel to the x-y plane. In some embodiments, the tissue gathering elements 2006*a*, 2006*b* loop around an axis 2017 forming a circle having a diameter of 1-18 mm, such as 6-8 mm. It may be appreciated that any suitable number of tissue gathering elements 2006*a*, 2006*b* may be formed by additionally looping around the axis 2017, such as 1-20 times, however 2-3 is preferred. Thus, the inversion elements 2002*a*, 2002*b* and the tissue gathering elements 2006*a*, 2006*b* reside in perpendicular planes and are adjacent to each other. This allows the elements 2002*a*, 2002*b*, 2006*a*, 2006*b* to recoil closely together (i.e. in close proximity) so as to minimize the space that they occupy in the lung when in the device 2000 is in the relaxed position.

In this embodiment, the device 2000 includes at least one anchoring element 2004. In this embodiment, the anchoring element 2004 loops over itself to create a circular portion that extends around an axis 2019 parallel to the longitudinal axis 2012. Typically, the axis 2019 is above the longitudinal axis 2012. Thus, the anchoring element 2004 extends upward in the positive direction of the z-axis. This allows the axis 2019 to be concentric with a central axis of an airway lumen while the inversion elements 2002*a*, 2002*b* and tissue gathering elements 2006*a*, 2006*b* are off to the side, leaving the airway lumen patent.

The devices 2000 illustrated in FIGS. 137A, 137B, 138 may be comprised from a single continuous shaft or from a combination of two or more elements acting as a continuous shaft. Single element designs enjoy the benefit of not comprising joints or links that may fail due to strain or bending during the high number of breathing cycles the device may encounter during the remainder of the patient's life. The single element may be made with varying diameter sections or it can be made from tapered diameter material as well as material that has totally non-uniform size or cross section along its length. In some embodiments, the shaft is comprised of wire, such as metal (e.g. nitinol, austenite or martensite nitinol, spring steel, stainless steel, cobalt steel alloys, titanium etc.) or polymeric compounds, ceramic, carbon fiber and/or other biocompatible materials. Such wire is typically extruded, drawn or sintered into near net shapes or wire form. A single component structure may be configured with tuned material properties in different locations of the single element. Nitinol material may be adjusted by using local heat treatment techniques to increase or decrease the stiffness or modulus of elasticity in local portions of the wire.

In some embodiments, the shaft has a flattened, ribbon shape. In some embodiments, the ribbon shape is between 0.005 and 0.030 inches wide and between 0.005 and 0.030 inches thick in dimension. The ribbon may be blasted or tumbled in abrasive media to round the edges so it more closely appears like a round cross-section wire. Alternatively, the shaft may be made from round cross section wire, for example having a diameter of 0.01-5 mm, preferably 0.25-0.5 mm. In some embodiments, this creates a bearing area of 0.05-3000 mm$^2$. In some embodiments, the shaft has a highly reflective finish to enhance endothelium attachment, so as to reduce the time to grow over with a biocompatible layer of tissue to reduce granular tissue formation.

Figures 139A, 139B, 139C, 139D:
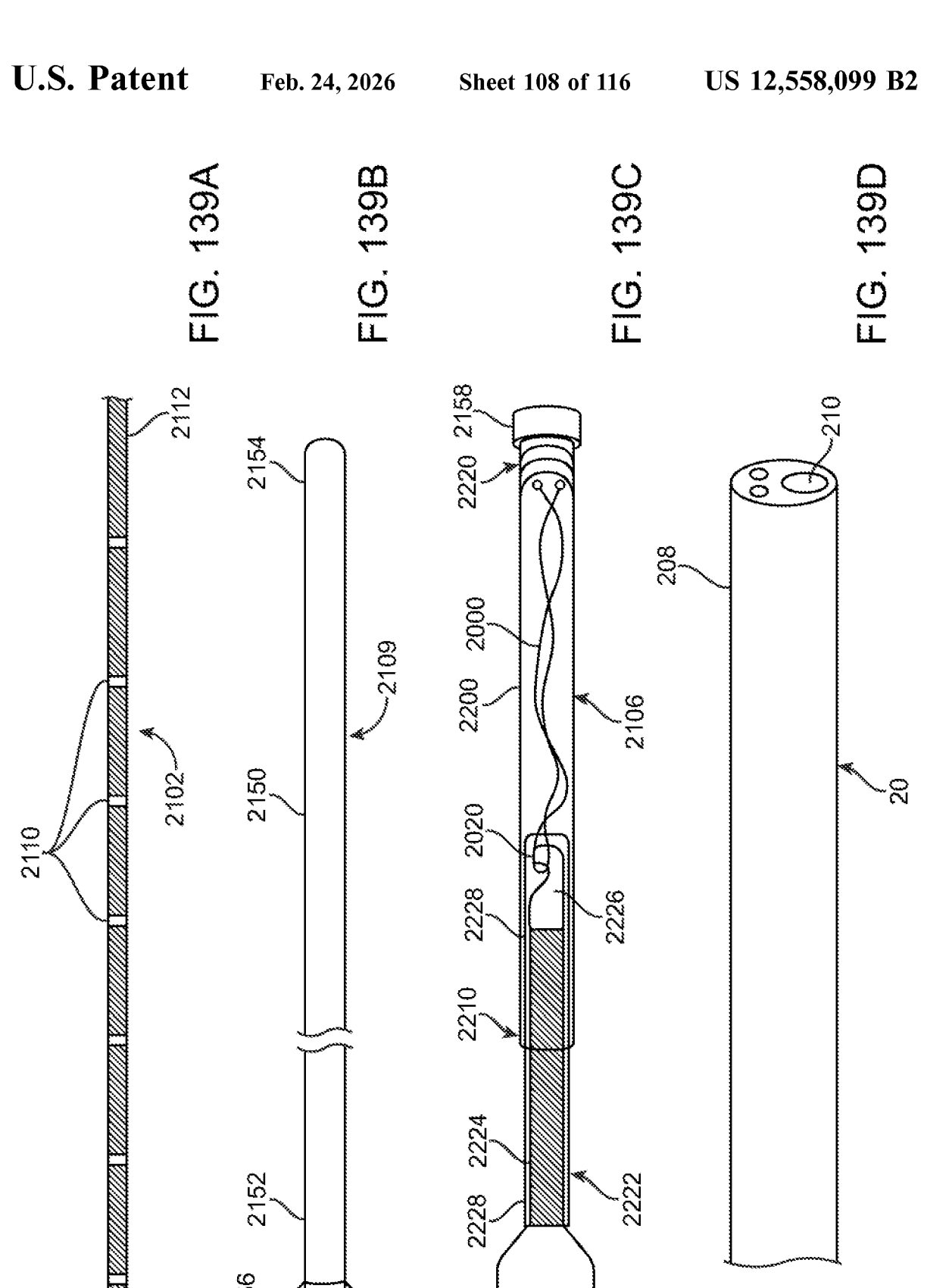

FIGS. 139A-139D illustrate an embodiment of a delivery system 2100 of an invertible pulmonary treatment device 2000. In this embodiment, the delivery system 2100 comprises a guidewire 2102, a catheter 2104, an introducer 2106 and a bronchoscope 20. FIG. 139A illustrates an embodiment of a guidewire 2102. The guidewire 2102 may be comprised of any suitable material to provide flexibility, strength and pushability. In some embodiments, the guidewire 2102 is comprised of wire rope stainless steel or titanium, such as having 1-2000 strands, more particularly 400 strands. This provides high flexibility while eliminating gaps in the wire rope during bending. In such embodiments, the strands are continuous from distal tip to proximal end, wherein the distal tip is welded. In some embodiments, the guidewire 2102 has a cross-sectional diameter of 0.05-5 mm, particularly 1.5 mm. In some embodiments, the guidewire 2102 includes a series of markers 2110, such as marker bands which extend around the circumference of the guidewire 2102. In this embodiment, the markers 2110 are spaced 0.1-3 inches apart (measured from the start of one marker 2110 to the start of the next marker 2110), preferably 0.45 inches mm apart. Typically, the markers 2110 extend along the length of the guidewire 2102, however it may be appreciated that the markers 2110 may be disposed only along the proximal end, only along the distal end or along any or all portions of the guidewire 2102. In some embodiments, visualization of the markers 2110 along the proximal end will allow the user to determine the position of the distal end relative to other components of the delivery system 2100, particularly the catheter 2104 through which it passes. Or, the position of the guidewire 2102 may be determined relative to the introducer 2106 as the introducer 2106 may be connected to and extending the effective length of the catheter 2104. In some embodiments, the markers 2110 are comprised of fluorescent paint so the markers 2110 are visible in a low light room (outside of the body) or under fluoroscopy (within the body). In other embodiments, the markers 2110 are comprised of white polymer that has fluorescent properties. In yet other embodiments, the markers 2110 are comprised of black laser markings which are generated from laser annealing the stainless steel wire to a black condition using a fiber laser. In some embodiments, the laser has a 1064 nm wavelength producing 1-100 watts and producing a long pulse width at 1-500 kHz frequency, such as a 2 kHz frequency. In some embodiments, the distal tip 2112 of the guidewire 2102 is plasma or TIG welded into a ball having diameter of 0.01-5, preferably 1.5 mm. In some embodiments, the proximal end of the guidewire 2102 has a hub, such as a polycarbonate hub.

FIG. 139B illustrates an embodiment of a catheter 2104. In some embodiments, the catheter 2104 comprises a shaft 2150 having a proximal end 2152 and a distal end 2154. The shaft 2150 is sized and configured to be advanced through a working lumen of a bronchoscope 20, particularly a bronchoscope having an inner diameter of 1.8-3.6 mm. Likewise, the shaft 2150 has an internal lumen sized and configured for passage of the guidewire 2102 therethrough. In some embodiments, the shaft 2150 is comprised of polyether block amide, such as known under the tradename of PEBAX® (Arkema). This allows the shaft 2150 to be electron beam or gamma sterilized. This is preferable to ethylene oxide sterilization which has environmental hazards. Conventional catheters often have polytetrafluoroethylene liners which require ethylene oxide sterilization. Therefore, in preferred embodiments the shaft 2150 is free of polytetrafluoroethylene. In some embodiments, Shore D 50-100 durometer, preferably 70 durometer, liner of polyether block amide or polyether ether ketone is utilized. In some embodiments, a lower durometer outer jacket is used. This allows the shaft 2150 to bend without kinking. In other embodiments, a stainless steel braided frame is provided as a jacket. In this embodiment, the catheter 2104 includes a proximal fitting 2156 which mates with a distal fitting 2158 disposed along the distal end of the introducer 2106. In this embodiment, the proximal fitting 2156 comprises a male luer fitting.

FIG. 139C illustrates an embodiment of an introducer 2106. The introducer 2106 is utilized to house the invertible pulmonary treatment device 2000 prior to and during delivery. Thus, the introducer 2106 is preloaded with the device 2000 so that the device is properly loaded and ready for delivery. In this embodiment, the introducer comprises a tube 2200 having a proximal end 2210 and a distal end 2220, wherein the invertible pulmonary treatment device 2000 is preloaded within the tube 2200 and disposed near the distal end 2220. In some embodiments, the tube 2200 is comprised of perfluoroalkoxy alkane (PFA). In this embodiment, the distal fitting 2158 comprises a female luer fitting so as to mate with the male luer fitting of the catheter 2104 in FIG. 139B. This allows the distal end 2220 of the introducer 2106 to connect with the proximal end of the catheter 2150. Ultimately, the device 2000 will be advanced from the introducer 2106 through the catheter 2150, as will be described in detail herein.

The introducer 2106 includes a plunger 2222 having an elongate member 2224 that extends into the proximal end 2210 of the tube 2200. The elongate member 2224 has a coupling element 2226 at its distal end. The coupling element 2226 is configured to couple with the invertible pulmonary treatment device 2000. In some embodiments, the elongate member 2224 is comprised of turned rope stainless steel cable. In some embodiments, the elongate member 2224 has a cross-sectional diameter of 0.05-5 mm, such as 0.75-1.25 mm. In some embodiments, the elongate member 2224 is 10-60 inches in length, such as 40-50 inches in length.

In this embodiment, the coupling element 2226 has a hook-shape wherein the attachment feature 2020 of the device 2000 slides over the hook of the hook-shape and rests in a cut-out. In some embodiments, the coupling element 2226 is comprised of stainless steel, titanium, plastic, ceramic, metal, etc. and is crimped on or glued with epoxy to the elongate member 2224. It may be appreciated that in other embodiments the coupling element 2226 is welded to the elongate member 2224. In some embodiments, the coupling element 2226 is 1-30 mm, such as 5 mm, in length. This allows the rigid coupling element 2226 to be short enough to pass through bends of the insertion cord tip 208 of the bronchoscope 20. In some embodiments, the cut-out has a cut depth of 0.01 to 3 mm, such as 0.5 mm. And, in some embodiments, coupling element 2226 has a thickness of 0.1-2 mm, such as 0.25 mm, in the area of the cut-out to allow the wire of the attachment feature 2020 of the device 2000 to slip around it and reside in the cut-out.

In some embodiments, the plunger 2222 includes a sheath 2228 which extends over the elongate member 2224 and retains the attachment feature 2020 of the device 2000 in the cut-out of the hook-shaped element. This keeps the device 2000 coupled to the plunger 2222. In some embodiments, the sheath 2228 is comprised of polyether ether ketone (PEEK). In some embodiments, the space within the introducer 2106, between the coupling element 2226 and the distal fitting 2158, is 20-500 mm, preferably 150-170 mm. This area within the introducer 2106 houses the pre-loaded device 2000 in its extended (tensioned) configuration.

The introducer 2106 further includes a handle 2230 at its proximal end. The handle 2230 is configured to actuate the coupling element 2226 so as to decouple the device 2000. In particular, the handle 2230 includes a push button 2232 that is coupled to the plunger 2222 so that depression of the push button 2232 advances the plunger 2222 so that the coupling element 2226 advances from the sheath 2228, revealing the hook-shaped element with cut-out. This allows the attachment feature 2020 to release from the cut-out, thereby releasing the device 2000 from the delivery system. Typically, the length of the push button 2232 is proportional to the distance that the plunger 2222 moves. In some embodiments, the push button 2232 extends 1-20 mm, such as 10 mm, from the handle 2230. In some embodiments, considerable force is used to push the push button 2232, such as 1-20 pounds of force, particularly 6 pounds of force, so as to avoid accidental release of the device 2000. In some embodiments, this is achieved with spring-loading. In some embodiments, the push button 2232 is able to be depressed so that the button 2232 is flush with the handle 2230 and is retained in this position. This ensures that the push button 2232 cannot be pulled back again and the introducer 2106 cannot be reused by the user. Such reuse may lead to inappropriate loading of the introducer 2106 with the device 2000.

FIG. 139D illustrates the insertion cord tip 208 of a bronchoscope 20. The bronchoscope 20 includes a light source which may be halogen, incandescent or LED, to name a few. As shown, the working channel 210 extends through the tip 208, allowing delivery of the guidewire 2102, catheter 2104 and introducer 2106 therethrough.

The delivery system 2100 is utilized to deliver the invertible pulmonary treatment device 2000 to the lung anatomy, particularly to an area of damaged tissue DT. The invertible pulmonary treatment devices 2000 described herein may be placed in any lung, lobe, mainstem bronchi, lobar bronchi, segmental bronchi, sub-segment bronchi or even farther down the airway tree. Typically, the device 2000 is advanced beyond a $4^{th}$ generation airway (e.g. $5^{th}$ generation, $6^{th}$ generation, $7^{th}$ generation, etc) into damaged tissue and anchored in a $4^{th}$ generation airway or lower generation airway. Although the methods and delivery devices described herein are endoscopic, it may be appreciated that many embodiments of the devices 2000 may be placed directly through the chest wall into the lung or through the wall of the main bronchi to access pockets of destroyed parenchyma. Many of the devices may be implanted via open chest procedure or with the use of any type of endoscope.

For endoscopic delivery, the insertion cord tip 208 of the bronchoscope 20 is typically advanced through the trachea T, a main stem bronchi, into a lobar airway and into a segmental airway. The guidewire 2102 and catheter 2106 are then removed from the packaging and inserted into the working channel 210 of the bronchoscope so that the guidewire 2102 passes through the catheter 2106. FIG. 140 illustrates the insertion cord tip 208 of the bronchoscope 20 inserted into a lung passageway. The distal end of the catheter 2104 extends a short distance from the bronchoscope 20 and the guidewire 2102 extends into the lung anatomy. Three locations are demarcated within the lung anatomy by dashed lines in FIG. 140: (A) the desired location of the anchoring element 2004 of the device 2000, (B) the initial desired location of the tissue gathering elements 2006a, 2006b of the device 2000, and (C) the location of the pleura or damaged tissue, such as bleb pockets or bullae pockets of damage. Location A is within a lung passageway having intact walls so as to allow anchoring therein. Location B is within damaged tissue, such as unsupported tissue, alveoli, loose tissue, tissue having bleb pockets or bullae, or may be within a lung passageway.

In some embodiments, the guidewire 2102 is advanced until its distal tip 2112 reaches the pleura (location C). The construction of the guidewire 2102 causes the guidewire 2018 to be advanced in a straight configuration (e.g. like a fishing pole) until it makes contact with tissue wherein it become flexible. Thus, when the guidewire 2102 reaches the pleura it curls into the pockets and cannot be advanced further. If the distal tip 2112 enters damaged tissue (e.g. appears as "swiss cheese holes") the distal tip will curl. In some embodiments, the distal tip 2112 of the guidewire 2102 extends 20-300 mm, typically 130-180 mm, from the distal end of the catheter 2104 (e.g. from location A to location C). The guidewire 2112 is then pulled back, such as 30-50 mm, so that the distal tip 2112 of the guidewire 2102 is at location B, as illustrated in FIG. 140. This provides a buffer distance between the initial desired location of the tissue gathering elements 2006a, 2006b of the device 2000 (i.e. furthest reach of the device 2000) and the pleura.

The distance between location A and location B is measured with the use of the markers 2110. As mentioned previously, the markers 2110 extend along the length of the guidewire 2102 or are disposed along the distal end and/or along the proximal end of the guidewire 2102 in a manner so that visualization of the markers along the proximal end will allow the user to determine the length of the distal end of the guidewire 2102 that is exposed. Alternatively or in addition, the distal markers 2110 may be visualized with the use of visualization techniques, such as fluoroscopy. Therefore, the distance between location A and location B can be calculated. This distance is utilized to determine the size of the device 2000 to be implanted. The more markers 2110 between location A and location B, the longer the device 2000 and the fewer markers between location A and location B, the shorter the device 2000. The introducer 2106 having the desired length pre-loaded device 2000 is then obtained.

The catheter 2106 is then advanced further into the working channel 210 of the bronchoscope 20 so that the distal end 2154 of the catheter 2104 is located at location B, as illustrated in FIG. 141. At this point the catheter 2106 is properly positioned for delivery of the device 2000. The introducer 2106 housing the desired device 2000 is then coupled to the proximal end of the catheter 2104 for delivery therethrough.

FIG. 142 illustrates the catheter 2104 inserted into the working channel 210 of the bronchoscope 20 so that its proximal end emerges from the working channel 210. As shown, the proximal fitting 2156 of the catheter 2104 is mated with the distal fitting 2158 of the introducer 2106. This allows the device 200 to be pushed through the introducer 2106 and into the catheter 2104. This is achieved by advancing the plunger 2222 so that the elongate member 2224 moves through the tube 2200 and into the catheter 2104. As the plunger 2222 is advanced, the elongate member 2224 pushes the device 2000 through the catheter 2104. This continues until the device 2000 reaches the distal end of the catheter 2104.

FIG. 143 illustrates the device 2000 reaching the distal end 2154 of the catheter 2104. Here, the distal end 2154 of the catheter 2104 is shown positioned within the damaged tissue DT at location B of FIG. 141. The device 2000 is collapsed in an extended (tensioned) position so that the distal tips 2008a, 2008b facing distally, poised to be the first portion of the device 2000 to be deployed from the catheter 2104. In some embodiments, the distal tips 2008a, 2008b are spaced apart by 0.5-10 mm, such as 1 mm, when the device 2000 is in the collapsed configuration. In some embodiments, such spacing is achieved by having inversion elements 2002a, 2002b and/or tissue gathering elements 2006a, 2006b that are of different lengths. This allows the catheter 2104 to have a small lumen size, such as an inner diameter of 5 mm, preferably 2 mm. This also allows the distal tips 2008a, 2008b to avoid entanglement or collision with each other during deployment. It may be appreciated that the distal tips 2008a, 2008b may have any suitable shape, including loops, ground ribbon, coils, strain reliefs or balls. In some embodiments, the distal tips 2008*a*, 2008*b* have a diameter of 0.25-2 mm, preferably 0.75 mm.

Deployment begins when the device 2000 is incrementally exposed at the distal end of the catheter 2104. In some embodiments, the catheter 2104 is retracted, as indicated by the arrow 2300. In other embodiments, the device 2000 is advanced such as by pushing with the plunger 2222. The speed in which the device 2000 is deployed is controlled by the speed in which the device 2000 is exposed, such as the speed in which the catheter 2014 is retracted. Thus, in some embodiments, deployment is achieved slowly and methodically. It may be appreciated that the device 2000 remains fixed to the coupling element 2226 of the plunger 2222 until the push button 2232 is depressed. Simply advancing or retracting the plunger 2222 or the catheter 2104 will not release the device 2000 from the plunger 2222.

FIG. 144 illustrates the device 2000 as it is emerged further from the catheter 2104. Here, the tissue gathering elements 2006*a*, 2006*b* are shown emerging from the distal end 2154 of the catheter 2104, splaying out in opposite directions from the longitudinal axis 2012 as indicated by arrows 2302. In some embodiments, the tissue gathering elements 2006*a*, 2006*b* have sufficient bearing area against the damaged tissue DT so that they do not "cheese wire" or cut through the damaged tissue DT. This allows the tissue gathering elements 2006*a*, 2006*b* to wind into the damaged tissue DT without cutting sideways through the tissue DT. Thus, the damaged tissue DT will be able to be wrapped up by the tissue gathering elements 2006*a*, 200*b*. In some embodiments, the ball-shaped distal tips 2008*a*, 2008*b* are large enough to keep from hanging up in the damaged tissue DT but small enough to push through lung tissue while winding into the tissue.

FIG. 145 illustrates further advancement of the tissue gathering elements 2006*a*, 2006*b* into the damaged tissue DT. As the tissue gathering elements 2006*a*, 2006*b* advance further, their pre-curvature bends distal tips 2008*a*, 2008*b* toward the proximal direction, as indicated by arrows 2304. In this embodiment, the radius curvature of the tissue gathering elements 2006*a*, 2006*b* is somewhat small, for example the distance d between the distal tip 2008*a* and the longitudinal axis 2012 of the device 2000 is 6-8 mm. However, it may be appreciated that in other embodiments, the distance d is 1-30 mm. Likewise, in this embodiment, a distance d1 (i.e. between the distal edge of the catheter 2104 and the peak of the curving tissue gathering element 2006*a*) is 2-5 mm, however it may be appreciated that in other embodiments the distance d1 is 0.05-10 mm. It may be appreciated that these measurements and characteristics also apply to tissue gathering element 2006*b*. Having somewhat tight curvatures (i.e. short forward deployment) avoids penetration of the lung wall when working in the farther reaches of the lung anatomy.

FIG. 146 illustrates still further advancement of the tissue gathering elements 2006*a*, 2006*b* into the damaged tissue DT. As the tissue gathering elements 2006*a*, 2006*b* advance further, their pre-curvature bends distal tips 2008*a*, 2008*b* back around toward the distal direction, as indicated by arrows 2306. Thus, the tissue gathering elements 2006*a*, 2006*b* have a "rams horn" shape. This helical shape corkscrews into the tissue upon deployment so as to grasp the lung tissue. It may be appreciated that a variety of shapes that wind into the lung tissue upon deployment may be used so as to grasp the lung tissue. At this point the tissue gathering elements 2006*a*, 2006*b* are nearly fully deployed allowing the arms of the tissue gathering elements 2006*a*,

2006*b* to curve around an axis 2016. In some embodiments, the arms of the tissue gathering elements 2006*a*, 2006*b* curve 180 degrees, 270 degrees, 360 degrees, 450 degrees, 540 degrees or more around the axis 2016. In some embodiments, the arms of the tissue gathering elements 2006*a*, 2006*b* make 1-20 full revolutions around the axis 2016, however in most embodiments the tissue gathering elements 2006*a*, 2006*b* make 0.75 to 1.5 revolutions around the axis 2016. In this embodiment, the radius of curvature of the tissue gathering elements 2006*a*, 2006*b* creates a diameter of the revolutions (distance d2) of 1-18 mm, such as 6-8 mm. In some embodiments, the distal tips 2008*a*, 2008*b* are 2-100 mm, such as 5-10 mm, apart as indicated by distance d3 in FIG. 146. Such curving of the "rams horn" shape weaves the tissue gathering elements 2006*a*, 2006*b* into the damaged tissues DT so as to create a reinforced grasp or grip on the loose damaged tissue DT. This grip will allow the damaged tissue T to be pulled in the proximal direction, tightening the tissue.

FIG. 147 illustrates still further advancement of the tissue gathering elements 2006*a*, 2006*b* into the damaged tissue DT. At this point the inversion elements 2002*a*, 2002*b* begin emerging from the distal end of the catheter 2104. The pre-curvature of the inversion elements 2002*a*, 2002*b* cause the tissue gathering elements 2006*a*, 2006*b* to move out of position, pulling the gripped damaged tissue DT along with them. This is the beginning of the inversion process. In particular, the inversion elements 2002*a*, 2002*b* curve around axis 2014 as indicated by arrow 2308, pushing the tissue gathering elements 2006*a*, 2006*b* up and around axis 2011 toward the proximal direction. In some embodiments, the inversion elements 2002*a*, 2002*b* curve at least partially around a circle having a diameter indicated by distance d4 in FIG. 147. In some embodiments, the distance d4 is 5-50 mm, such as 10-15 mm. It may be appreciated that rotating the tissue gathering elements 2006*a*, 2006*b* in the proximal direction (i.e. short forward deployment) avoids penetration of the lung wall when working in the farther reaches of the lung anatomy.

FIG. 148 illustrates the catheter 2106 and plunger 2222 having been pulled together in the proximal direction. This pulled the proximal portion of the device 2000, such as the anchoring element 2004, in the proximal direction while at least the tissue gathering elements 2006*a*, 2006*b* remained gripping the damaged tissue DT. The device 2000 is inverted so that the tissue gathering elements 2006*a*, 2006*b* are now located most distally and the inversion elements 2002*a*, 2002*b* are located between the tissue gathering elements 2006*a*, 2006*b* and the anchoring element 2004. Thus, the inversion elements 2002*a*, 2002*b* act as an elastic midsection. Under fluoroscopic visualization, the device 2000 can be pulled until the curved inversion elements 2002*a*, 2002*b* start to straighten. This indicates the slack in the damaged lung tissue has been fully removed, and local slack and net tension is starting to be generated. The strength of the inversion element 2002*a*, 2002*b* coils are so weak that the user is able to see that a tensioning effect is being created long before the tissue gathering elements 2006*a*, 2006*b* are pulled out of the tissue. This gives the user a lot of warning and safety margin so as to avoid contributing to damaging the lung tissue more than the disease itself. The loops of the tissue gathering elements 2006*a*, 2006*b* can be 0.1-5 times the loop diameter of the inversion elements 2002*a*, 2002*b*. However, it is preferred that the tissue gathering elements 2006*a*, 2006*b* are 0.4-0.75 times the inversion elements 2002*a*, 2002*b* in size, to keep them smaller so they are stronger than the inversion elements 2002a, 2002b and they stay anchored while the inversion elements 2002a, 2002b are extended.

Referring back to FIG. 148, the damaged tissue DT attached to the tissue gathering elements 2006a, 2006b, and optionally the inversion elements 2002a, 2002b, was pulled in the proximal direction, stretching and tensioning the tissue between the gripped tissue and the lung wall. This is typically continued until the slack in the diseased tissue DT is tensioned which causes overall tensioning of the lung. Deployment of the anchoring element 2004 allows the anchoring element 2004 to bend into its pre-curvatured shape, thereby anchoring itself within the lung passageway. Typically, the pre-curvature shape recovery self-expands portions of the anchoring element 2004 outwardly so as to rest against at least one wall of the lung passageway, such as in a ring surrounding the inner surface of the lumen of the lung passageway. This allows the anchoring element 2004 to anchor within the lung passageway while keeping the lung passageway patent. This can also assist in preventing collapse of the lumen and ensures that the device 2000 does not obstruct the lumen in any way which may collect mucus. In some embodiments, the loop stent design of the anchoring element 2004 is approximately the same size as the tissue gathering elements 2006a, 2006b so it is also stronger than the inversion elements 2002a, 2002b. This allows the inversion elements 2002a, 2002b to be deformed greatly and yet the anchoring element 2004 can overcome the tension to dilate in a transverse direction (toward the walls of the lung passageway) relative to the direction that the tension is being applied to the device 2000.

It may be appreciated that the device 2000 is still attached to the plunger 2222 even after the anchoring element 2004 has been deployed from the catheter 2106. After deploying the anchoring element 2004, the device 2000 can optionally be pulled back into the catheter 2106 to reposition the anchoring element 2004 or further tension the damaged tissue DT. The anchoring element 2004 can then be redeployed. It may be appreciated that, in a similar manner, the entire device 2000 can optionally be recovered and redeployed if desired. FIG. 149 illustrates the anchoring element 2004 released from the plunger 2222, leaving the anchoring element 2004 firmly anchored within the lung passageway. This is achieved by retracting the sheath 2228, thereby exposing the cutout of the coupling element 2226, by pressing the push button 2232. The push button 2232 is configured so that full depression of the push button 2332 advances the coupling element 2226 a predetermined distance so that the cutout clears the sheath 2228. This allows the attachment feature 2020 to release from the cutout of the coupling element 2226. It may be appreciated that the cut-out of the coupling element 2226 is angled so that the attachment feature 2020 easily slips out of the cutout, even if the coupling element 2226 is pinned against the wall of the lung passageway. The plunger 2222 and all parts of the delivery system can then be removed. In some embodiments, the anchoring element 2004 is configured so that the distance d5 is 2-30 mm, such as 10-15 mm or 12 mm. Likewise, in some embodiments, the attachment feature 2020 has a width shown as distance d6 of 0.5-5 mm, such as 2 mm. FIG. 149 illustrates how the device 2000 may appear 1-48 hours after deployment. Here, the inversion elements 2002a, 2002b are still extended which provides chronic tension to the device 2000. Thus, as the lung tissue relaxes, any slack will be taken up by the recoil force of the inversion elements 2002a, 2002b. In addition, the flexibility of the device 2000 allows the device 2000 to cycle in length during breathing to maintain tension.

FIG. 150 illustrates how the device 2000 may appear over time. Here, the inversion elements 2002a, 2002b have recovered toward its original pre-formed shape. Evolving slack, caused by continued effects of emphysema in the lung tissue, has been pulled toward the anchoring element 2004 as it develops. It may be appreciated that the strain recovery provides chronic force. This maintains tensioning in the lung, such as for 0.1 to 20 years.

FIG. 151 illustrates how the device 2000 may appear over a longer period of time. Here, the inversion elements 2002a, 2002b have fully retracted to its original pre-formed shape. Evolving slack in the lung tissue has been additionally pulled toward the anchoring element 2004 over time. This maintains tensioning in the lung over long periods of time.

It may be appreciated that various aspects of the above described pulmonary treatment devices may be combined in any combination. For example, the invertible pulmonary treatment devices 2000 may be configured to allow rotation or torqueing of tissue during placement. Likewise, the torque-based pulmonary treatment devices 400 may be configured to invert during placement. Further, any of the pulmonary treatment devices may be configured to act as a clip so as to draw airways together. Thus, elements of any pulmonary treatment devices may be combined with any others. Descriptive aspects applying to an element in one embodiment, such as a tissue gathering element, may be applied to another embodiment having the same element or an element configured to perform the same or similar function.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A pulmonary treatment device having a longitudinal axis for treating a lung, comprising:

an elongate shaft having shape-memory properties comprising a first end and a second end, wherein the elongate shaft has at least a constrained position aligned with the longitudinal axis configured for loading into a lumen of a delivery device and a deployed position wherein the elongate shaft relaxes toward a plurality of curves upon deployment from the lumen of the delivery device, wherein the deployed position of the elongate shaft has a proximal end, a distal end and the longitudinal axis, wherein the plurality of curves comprises two tissue gathering elements formed from the first and second ends of the elongate shaft, each of the two tissue gathering elements having a helical shape-memory shape configured to grasp tissue in the lung while deploying from the delivery device, wherein the helical shape-memory shape of each of the two tissue gathering elements is perpendicular to the longitudinal axis of the deployed position, an anchoring element disposed near the proximal end and formed from the elongate shaft between the first and second ends having a shape-memory shape configured to be positioned within a lung passageway of the lung so as to anchor the pulmonary treatment device proximally of the two tissue gathering elements by engagement with the lung passage way, and at least one inversion element formed from the elongate shaft having a shape-memory curvature configured to invert at least a portion of the pulmonary treatment device while deploying from the delivery device so that the inversion element draws the grasped tissue toward the anchoring element while inverting.

2. A pulmonary treatment device as in claim 1, wherein each of the two tissue gathering elements comprises at least one distal tip configured to move in rotation around a second axis as it deploys from the delivery device into the tissue of the lung so as to grasp the tissue due to its helically shape-memory shape.

3. A pulmonary treatment device as in claim 2, wherein continued deployment of each of the two tissue gathering elements from the delivery device allows the at least one inversion element to curve around a third axis.

4. A pulmonary treatment device as in claim 3, wherein continued deployment deploys the anchoring element from the delivery device into the lung passageway of the lung.

5. A pulmonary treatment device as in claim 1, wherein the helical shape-memory shape of each of the two tissue gathering elements is configured to wind into the tissue upon deployment by penetrating the tissue so as to grasp portions of the tissue.

6. A pulmonary treatment device as in claim 5, wherein the helical shape-memory shape of each of the two tissue gathering elements is configured to penetrate into the tissue upon deployment so as to grasp portions of the tissue.

7. A pulmonary treatment device as in claim 1, wherein the elongate shaft is formed from a continuous shaft.

8. A pulmonary treatment device as in claim 1, wherein the pulmonary treatment device is configured so that the two tissue gathering elements are deployable from the delivery device prior to deployment of the anchoring element.

9. A pulmonary treatment device as in claim 8, wherein the pulmonary treatment device is configured so that the two tissue gathering elements are deployable from the delivery device at the same time.

10. A pulmonary treatment device as in claim 1, wherein the at least one inversion element comprises two inversion elements, each of the two inversion elements formed from a portion of the elongated shaft adjacent to one of the two tissue gathering elements.

11. A pulmonary treatment device as in claim 10, wherein the anchoring element is formed from a portion of the elongated shaft between the two inversion elements.

12. A pulmonary treatment device as in claim 10, wherein each the two inversion elements have a lower modulus of elasticity than the two tissue gathering element.

13. A pulmonary treatment device as in claim 10, wherein the two inversion elements comprises at least two concentric loops.

14. A pulmonary treatment device as in claim 10, wherein each the two inversion elements are disposed between the two tissue gathering elements and the anchoring element when the pulmonary treatment device is positioned in the delivery device in the constrained position and wherein each of the two inversion elements moves at least a portion of the two tissue gathering elements between the two inversion elements and the anchoring element as the pulmonary treatment device is deployed from the delivery device and transitions toward the deployed position.

15. A pulmonary treatment device as in claim 1, wherein the pulmonary treatment device is configured to be loaded into the delivery device so as to extend along its longitudinal axis so that the anchoring element is deployable last from the delivery device.

16. A pulmonary treatment device for treating a lung, comprising:

an elongate body having a distal end, a proximal end and a longitudinal axis, wherein the elongate body has a shape-memory configuration that is configured to be loaded within a lumen of a delivery device so that the distal end and proximal end are positioned to exit the delivery device first so that together the distal end and the proximal end form two tissue gathering elements during simultaneous deployment, wherein each of the distal end and proximal end has a distal tip configured to move in rotation around at least one second axis during deployment from the lumen of the delivery device into tissue of the lung so as to gather at least a portion of the tissue, wherein continued deployment of each of the distal end and proximal end from the delivery device allows each of the distal end and proximal end to form at least one energy storage element which curves around at least one third axis, and wherein continued deployment deploys a remainder of the elongate body from the delivery device into a lung passageway of the lung which forms at least one loop configured to expand against walls of the lung passageway so as to anchors the pulmonary treatment device in the lung passageway.

17. A pulmonary treatment device as in claim 16, wherein the at least one energy storage element stores energy by inversion.

18. A pulmonary treatment device as in claim 16, wherein each of the distal end and proximal end forming the two tissue gathering elements are configured to rotate along a helical path during deployment away from each other.

19. A pulmonary treatment device as in claim 16, wherein the pulmonary treatment device is formed from a continuous shaft.

20. A pulmonary treatment device for treating a lung comprising:

an elongate body having a distal end, a proximal end and a longitudinal axis, wherein the elongate body is configured to be loaded within a lumen of a delivery device in a tensioned configuration so that the distal end and proximal end are adjacent to each other within the lumen, wherein the elongate body has a first tissue gathering element formed at the distal end, and a second tissue gathering element formed at the proximal end, each having a shape-memory shape configured to grasp lung tissue upon deployment from the lumen, and an anchoring element having a shape configured to anchor within a lung passageway of the lung, wherein the first and second tissue gathering elements are opposite the anchoring element along the longitudinal axis when the pulmonary treatment device is positioned in the delivery device in the tensioned configuration and after deployment from the lumen and wherein the first and second tissue gathering elements are perpendicular to the anchoring element after deployment, and at least one inversion element disposed between the first and the second tissue gathering elements and the anchoring element when the pulmonary treatment device is positioned in the delivery device in the tensioned configuration, wherein the at least one inversion element has a shape configured to move at least a portion of the first and second tissue gathering element between the at least one inversion element and the anchoring element as the pulmonary treatment device transitions toward a relaxed configuration upon release from the delivery device.

*    *    *    *    *